United States Patent
Bellenie et al.

(10) Patent No.: US 10,004,732 B2
(45) Date of Patent: Jun. 26, 2018

(54) AMINO PYRAZINE DERIVATIVES AS PHOSPHATIDYLINOSITOL 3-KINASE INHIBITORS

(71) Applicants: Benjamin Richard Bellenie, Horsham (GB); Graham Charles Bloomfield, Horsham (GB); Ian Bruce, Tyne and Wear (GB); Andrew James Culshaw, Greenford (GB); Edward Charles Hall, Cambridge, MA (US); Gregory John Hollingworth, Kent (GB); James Neef, Cambridge, MA (US); Matthew Spendiff, Horsham (GB); Simon James Watson, Horsham (GB)

(72) Inventors: Benjamin Richard Bellenie, Horsham (GB); Graham Charles Bloomfield, Horsham (GB); Ian Bruce, Tyne and Wear (GB); Andrew James Culshaw, Greenford (GB); Edward Charles Hall, Cambridge, MA (US); Gregory John Hollingworth, Kent (GB); James Neef, Cambridge, MA (US); Matthew Spendiff, Horsham (GB); Simon James Watson, Horsham (GB)

(73) Assignee: Novartis AG, Basel (CH)

(*) Notice: Subject to any disclaimer, the term of this patent is extended or adjusted under 35 U.S.C. 154(b) by 0 days. days.

(21) Appl. No.: 15/303,868

(22) PCT Filed: Apr. 24, 2014

(86) PCT No.: PCT/IB2014/060988
§ 371 (c)(1),
(2) Date: Oct. 13, 2016

(87) PCT Pub. No.: WO2015/162459
PCT Pub. Date: Oct. 29, 2015

(65) Prior Publication Data
US 2017/0042889 A1    Feb. 16, 2017

(51) Int. Cl.
| | | |
|---|---|---|
| *C07D 401/04* | (2006.01) |
| *C07D 401/14* | (2006.01) |
| *C07D 403/14* | (2006.01) |
| *C07D 405/04* | (2006.01) |
| *C07D 405/14* | (2006.01) |
| *C07D 409/04* | (2006.01) |
| *C07D 409/14* | (2006.01) |
| *C07D 413/04* | (2006.01) |
| *C07D 413/14* | (2006.01) |
| *C07D 417/04* | (2006.01) |
| *C07D 417/14* | (2006.01) |
| *A61K 31/497* | (2006.01) |

(Continued)

(52) U.S. Cl.
CPC ........ *A61K 31/497* (2013.01); *A61K 31/5377* (2013.01); *C07D 401/04* (2013.01); *C07D 401/14* (2013.01); *C07D 403/04* (2013.01); *C07D 403/14* (2013.01); *C07D 405/04* (2013.01); *C07D 405/14* (2013.01); *C07D 409/04* (2013.01); *C07D 409/14* (2013.01); *C07D 413/04* (2013.01); *C07D 413/14* (2013.01); *C07D 417/04* (2013.01); *C07D 417/14* (2013.01)

(58) Field of Classification Search
CPC .. C07D 401/04; C07D 401/14; C07D 403/04; C07D 403/14; C07D 405/04; C07D 405/14; C07D 409/04; C07D 409/14; C07D 413/04; C07D 413/14; C07D 417/04; C07D 417/14; A61K 31/5377; A61K 31/497
See application file for complete search history.

(56) References Cited

U.S. PATENT DOCUMENTS

| | | |
|---|---|---|
| 2009/0118305 A1 | 5/2009 | Barlaam et al. |
| 2009/0239847 A1 | 9/2009 | Bruce et al. |
| 2012/0071662 A1 | 3/2012 | Sander et al. |

(Continued)

FOREIGN PATENT DOCUMENTS

| | | |
|---|---|---|
| WO | WO2003077918 A1 | 9/2003 |
| WO | WO2003093297 A2 | 11/2003 |

(Continued)

OTHER PUBLICATIONS

International Search Report and Written Opinion for International Application No. PCT/IB2014/060988, dated Jun. 24, 2014 (8 pages).

(Continued)

*Primary Examiner* — Rebecca L Anderson
(74) *Attorney, Agent, or Firm* — Michelle Han

(57) ABSTRACT

The present invention provides compounds of formula (I) which inhibit the activity of PI 3-kinase gamma isoform, which are useful for the treatment of diseases mediated by the activation of PI 3-kinase gamma isoform.

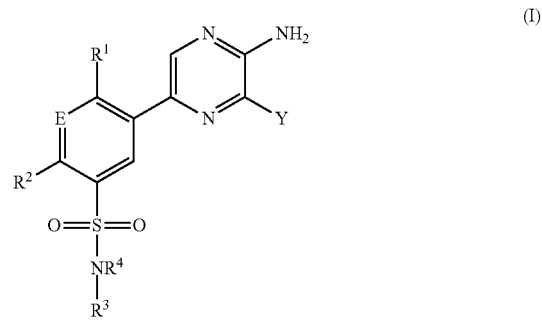

14 Claims, No Drawings

(51) Int. Cl.
*A61K 31/5377* (2006.01)
*C07D 403/04* (2006.01)

(56) References Cited

U.S. PATENT DOCUMENTS

2017/0029414 A1  2/2017  Bellenie et al.
2017/0037032 A1  2/2017  Bellenie et al.

FOREIGN PATENT DOCUMENTS

| WO | WO2006124874 A2 | 11/2006 |
| WO | WO2007110337 A1 | 10/2007 |
| WO | WO2007111904 A2 | 10/2007 |
| WO | WO2008006583 A1 | 1/2008 |
| WO | WO2008025820 A1 | 3/2008 |
| WO | WO2009007390 A2 | 1/2009 |
| WO | WO2009013348 A2 | 1/2009 |
| WO | WO2009053737 A2 | 4/2009 |
| WO | WO2009087212 A2 | 7/2009 |
| WO | 2009/115517 A2 | 9/2009 |
| WO | WO2010071837 A1 | 6/2010 |
| WO | WO2011086531 A2 | 7/2011 |
| WO | WO2015162456 A1 | 10/2015 |
| WO | WO2015162461 A1 | 10/2015 |

OTHER PUBLICATIONS

Leahy et al., "Discovery of a novel series of potent and orally bioavailable phosphoinositide 3-kinase γ inhibitors," J. Med Chem. Jun. 14, 2012;55(11):5467-82.

AMINO PYRAZINE DERIVATIVES AS PHOSPHATIDYLINOSITOL 3-KINASE INHIBITORS

TECHNICAL FIELD

The present invention relates to novel amino pyrazine derivatives which are PI 3-kinase gamma isoform selective inhibitors, processes for their preparation, pharmaceutical compositions and medicaments containing them and to their use in diseases and disorders mediated by the activation of PI 3-kinase gamma isoform, particularly asthma.

BACKGROUND

Phosphatidylinositol 3-kinases (PI 3-kinases), a family of enzymes which catalyse the phosphorylation of the 3'-OH of the inositol ring, play a central role in regulating a wide range of cellular processes including metabolism, survival, motility and cell activation (Vanhaesebroeck, B. et al., Annu. Rev. Biochem. 2001, 70, 535). These lipid kinases are divided into 3 major classes, I, II & III, according to their structure and in vitro substrate specificity (Wymann, M. et al.; Biochem. Biophys. Acta, 1998, 1436, 127). The most widely understood class I family is further subdivided into subclasses IA and IB. Class IA PI 3-kinases consist of an 85 kDa regulatory/adapter protein and three 110 kDa catalytic subunits (p110α, p110β and p110δ) which are activated in the tyrosine kinase system whilst class IB consists of a single p110γ isoform (PI 3-kinase gamma isoform) which is activated by G protein-coupled receptors. The three members of class II PI 3-kinases (C2α, C2β and C2γ) and single member of class III PI 3 kinases (Vps34) are less well understood. In addition there are also four PI 4-kinases and several PI 3-kinase related protein kinases (termed PIKK's or class IV) including DNA-PK, mTOR, ATM and ATR, all of which have a similar catalytic domain (Abraham R. T. et al.; DNA repair 2004, 3(8-9), 883).

A key role for PI 3-kinase gamma isoform in processes such as leukocyte activation, leukocyte chemotaxis and mast cell degranulation has been shown, thereby generating interest in this target for the treatment of autoimmune and inflammatory disorders (Ghigo et al., Bioessays, 2010, 32, p 185-196; Reif et al., J. Immunol., 2004, 173, p 2236-2240; Laffargue et al., Immunity, 2002, 16, p 441-451; Rommel et al, Nature Rev. Immunology, 2007, 7, p 191; Cushing et al J. Med. Chem., 2012, 55, p 8559; Bergamini et al, Nature Chem. Biol., 2012, 8, p 576). Specifically, numerous publications suggest the potential utility of PI3 Kinase gamma isoform inhibitors for the treatment of asthma (e.g. Thomas et al, Immunology, 2008, 126, p 413; Jiang et al, J. Pharm. Exp. Ther., 2012, 342, p 305; Takeda et al, Int. Arch. Allergy Immunol. 2010, 152 (suppl 1), p 90-95). There are also reports linking inhibition of the PI 3-kinase gamma isoform as having potential therapeutic value in numerous other indications such as cancer (Beagle and Fruman, Cancer Cell, 2011, 19, p 693; Schmid et al, Cancer Cell, 2011, 19, p 715; Xie et al, Biochem. Pharm., 2013, 85, p 1454; Subramaniam et al, Cancer Cell, 2012, 21, p 459), diabetes (Kobayashi et al, Proc. Nat. Acad. Sci, 2011, 108, p 5753; Azzi et al, Diabetes, 2012, 61, p 1509), cardiovascular disease (Fougerat et al, Clin. Sci., 2009, 116, p 791; Fougerat et al, Circulation, 2008, 117, p 1310; Chang et al, Proc. Nat. Acad. Sci., 2007, 104, p 8077; Fougerat et al, Br. J. Pharm., 2012, 166, p 1643), obesity (Becattini et al, Proc. Nat. Acad. Sci., 2011, 108, pE854), Alzheimer's disease (Passos et al, Brain, Behaviour and Immunity, 2010, 24, 493) and pancreatitis (Lupia et al, Am. J. Path, 2004, 165, p 2003). A recent review of PI 3-Kinase isoforms as drug targets is given in Blajecka et al, Current Drug Targets, 2011, 12, p 1056-1081.

WO2009/115517 (Novartis) describes amino pyrazine and pyridine derivatives as PI 3-kinase inhibitors.

WO2009/013348 (Novartis) describes amino pyrimidine derivatives as PI 3-kinase inhibitors.

WO2003/093297 (Exelixis) describes protein kinase modulators and methods of use of such modulators.

Leahy et al., J. Med. Chem., 2012, 55 (11), pp 5467-5482, describe PI 3-kinase gamma isoform inhibitors.

Hence, there is a need for potent, selective inhibitors of PI 3-kinase gamma isoform.

SUMMARY OF THE INVENTION

In a first aspect, the invention relates to a compound of formula (I)

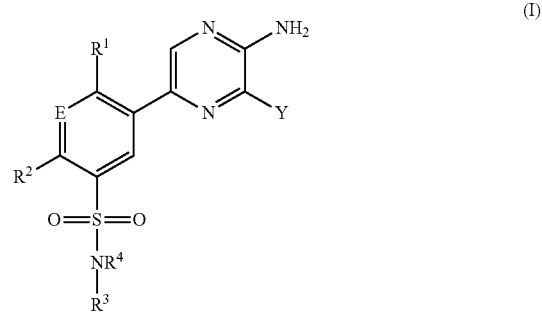

wherein
E is selected from N and $CR^E$;
$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy, $C_{1-4}$ hydroxyalkyl and $C_{3-7}$ cycloalkyl;
$R^3$ is selected from
(i) $C_{1-4}$ alkyl which is unsubstituted or substituted with 1 or more substituents, particularly 1 to 3 substituents, independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —$(C_{0-3}$ alkyl)-$NR^{3a}R^{3b}$, $C_{3-7}$ cycloalkyl and $C_{3-7}$ heterocyclyl, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —$(C_{0-3}$ alkyl)-$NR^{3a}R^{3b}$;
(ii) $C_{1-4}$ alkoxy which is unsubstituted or substituted with 1 or more substituents, particularly 1 to 3 substituents, independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —$(C_{0-3}$ alkyl)-$NR^{3a}R^{3b}$, $C_{3-7}$ cycloalkyl and $C_{3-7}$ heterocyclyl, and wherein the $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —$(C_{0-3}$ alkyl)-$NR^{3a}R^{3b}$;
(iii) —$C_{3-7}$ cycloalkyl or —O—$C_{3-7}$ cycloalkyl wherein the $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —$(C_{0-3}$ alkyl)-$NR^{3a}R^{3b}$;
(iv) a —$(C_{0-3}$ alkyl)-$C_{3-7}$ cycloalkyl or —O—$(C_{0-3}$ alkyl)-$C_{3-7}$ cycloalkyl wherein the $C_{3-7}$ cycloalkyl is spiro fused to a second $C_{3-7}$ cycloalkyl or $C_{3-7}$ heterocyclyl by one single carbon atom, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(v) a —($C_{0-3}$ alkyl)-$C_{3-7}$ heterocyclyl or —O—($C_{0-3}$ alkyl)-$C_{3-7}$ heterocyclyl, and wherein said $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vi) a —($C_{0-3}$ alkyl)-$C_{3-7}$ heterocyclyl or —(O—$C_{0-3}$ alkyl)-$C_{3-7}$ heterocyclyl, and wherein said $C_{3-7}$ heterocyclyl is spiro fused to a second $C_{3-7}$ heterocyclyl or a $C_{3-7}$ cycloalkyl by one single carbon atom, and wherein the $C_{3-7}$ heterocyclyl or $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vii) H;

$R^4$ is selected from H and $C_{1-4}$ alkyl; or $R^3$ and $R^4$ together with the nitrogen atom to which they are attached form a $C_{3-7}$ heterocyclyl, which $C_{3-7}$ heterocyclyl is optionally spiro fused to a second $C_{3-7}$ heterocyclyl or a $C_{3-7}$ cycloalkyl by one single carbon atom, and which $C_{3-7}$ heterocyclyl and $C_{3-7}$ cycloalkyl are unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

$R^{3a}$ and $R^{3b}$ are independently selected from H, $C_{1-4}$ alkyl and $C_{1-4}$ haloalkyl;

Y is a 5-6-membered heteroaryl, which heteroaryl is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy, halogen, $C_{1-4}$ hydroxyalkyl, —($C_{0-3}$ alkyl)-N'R", —($C_{0-3}$ alkyl)-$C_{3-7}$ cycloalkyl and —($C_{0-3}$ alkyl)-$C_{3-7}$ heterocyclyl, —(C=O)—$C_{3-7}$ heterocyclyl, —(C=O)—N'R", —($C_{0-3}$ alkyl)-phenyl and —($C_{0-3}$ alkyl)-5-6-membered heteroaryl;

R' and R" are independently selected from H and $C_{1-4}$ alkyl;

or a pharmaceutically acceptable salt thereof.

In other aspects, the invention relates to pharmaceutical compositions and combinations comprising compounds of the first aspect, and to the use of such compounds of the first aspect in the treatment of a disorder or disease mediated by the activation of PI 3-kinase gamma isoform.

DESCRIPTION OF THE EMBODIMENTS

In an embodiment 1 of the invention, there is provided a compound of formula (I)

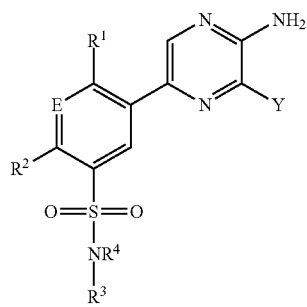

(I)

wherein

E is selected from N and $CR^E$;

$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy, $C_{1-4}$ hydroxyalkyl and $C_{3-7}$ cycloalkyl;

$R^3$ is selected from (i) $C_{1-4}$ alkyl which is unsubstituted or substituted with 1 or more substituents, particularly 1 to 3 substituents, independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(ii) $C_{1-4}$ alkoxy which is unsubstituted or substituted with 1 or more substituents, particularly 1 to 3 substituents, independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iii) —$C_{3-7}$ cycloalkyl or —O—$C_{3-7}$ cycloalkyl wherein the $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iv) a —($C_{0-3}$ alkyl)-$C_{3-7}$ cycloalkyl or —O—($C_{0-3}$ alkyl)-$C_{3-7}$ cycloalkyl wherein the $C_{3-7}$ cycloalkyl is spiro fused to a second $C_{3-7}$ cycloalkyl or $C_{3-7}$ heterocyclyl by one single carbon atom, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(v) a —($C_{0-3}$ alkyl)-$C_{3-7}$ heterocyclyl or —O—($C_{0-3}$ alkyl)-$C_{3-7}$ heterocyclyl, and wherein said $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vi) a —($C_{0-3}$ alkyl)-$C_{3-7}$ heterocyclyl or —(O—$C_{0-3}$ alkyl)-$C_{3-7}$ heterocyclyl, and wherein said $C_{3-7}$ heterocyclyl is spiro fused to a second $C_{3-7}$ heterocyclyl or a $C_{3-7}$ cycloalkyl by one single carbon atom, and wherein the $C_{3-7}$ heterocyclyl or $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vii) H;

$R^4$ is selected from H and $C_{1-4}$ alkyl; or $R^3$ and $R^4$ together with the nitrogen atom to which they are attached form a $C_{3-7}$ heterocyclyl, which $C_{3-7}$ heterocyclyl is optionally spiro fused to a second $C_{3-7}$ heterocyclyl or a $C_{3-7}$ cycloalkyl by one single carbon atom, and which $C_{3-7}$ heterocyclyl and $C_{3-7}$ cycloalkyl are unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

$R^{3a}$ and $R^{3b}$ are independently selected from H, $C_{1-4}$ alkyl and $C_{1-4}$ haloalkyl; Y is a 5-6-membered heteroaryl, which heteroaryl is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy, halogen, $C_{1-4}$ hydroxyalkyl, —$(C_{0-3}$ alkyl)-N'R", —$(C_{0-3}$ alkyl)-$C_{3-7}$ cycloalkyl and —$(C_{0-3}$ alkyl)-$C_{3-7}$ heterocyclyl, —(C=O)—$C_{3-7}$ heterocyclyl, —(C=O)—N'R", —$(C_{0-3}$ alkyl)-phenyl and —$(C_{0-3}$ alkyl)-5-6-membered heteroaryl; R' and R" are independently selected from H and $C_{1-4}$ alkyl;

or a pharmaceutically acceptable salt thereof.

In an embodiment 1.1 of the invention, there is provided a compound of formula (I)

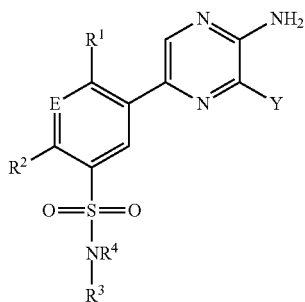

(I)

wherein
E is selected from N and $CR^E$;
$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy and $C_{3-6}$ cycloalkyl;
$R^3$ is selected from
(i) $C_{1-4}$ alkyl which is unsubstituted or substituted with 1 to 3 substituents independently selected from hydroxy, $C_{1-4}$ hydroxyalkyl, halogen, $C_{1-4}$ haloalkyl, $C_{1-4}$ alkoxy, $C_{1-4}$ alkyl, oxo, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl;
(ii) $C_{1-4}$ alkoxy which is unsubstituted or substituted with 1 to 3 substituents independently selected from hydroxy, $C_{1-4}$ hydroxyalkyl, halogen, $C_{1-4}$ haloalkyl, $C_{1-4}$ alkyl, $C_{1-4}$ alkoxy, oxo, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl;
(iii) —$C_{3-6}$ cycloalkyl or —O—$C_{3-6}$ cycloalkyl wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy, $C_{1-4}$ haloalkyl and —$(C_{0-3}$ alkyl)-$NR^{3a}R^{3b}$;
(iv) —$(C_{0-3}$ alkyl)-$C_{3-6}$ cycloalkyl or —(O—$C_{0-3}$ alkyl)-$C_{3-6}$ cycloalkyl spiro fused to a second $C_{3-6}$ cycloalkyl or $C_{3-6}$ heterocyclyl by one single carbon atom, wherein the $C_{3-6}$ cycloalkyl or $C_{3-6}$ heterocyclyl is unsubstituted or substituted with 1 to 3 substituents independently selected from hydroxy, $C_{1-4}$ hydroxyalkyl, halogen, $C_{1-4}$ alkoxy, $C_{1-4}$ haloalkyl and —$(C_{0-3}$ alkyl)-$NR^{3a}R^{3b}$;
(v) $(C_{0-3}$ alkyl)-$C_{3-6}$ heterocyclyl or —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —$(C_{0-3}$ alkyl)-$NR^{3a}R^{3b}$;
(vi) —$(C_{0-3}$ alkyl)-$C_{3-6}$ heterocyclyl or —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is spiro fused to a second $C_{3-6}$ heterocyclyl or a $C_{3-6}$ cycloalkyl by one single carbon atom, and wherein the $C_{3-6}$ heterocyclyl or $C_{3-6}$ cycloalkyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —$(C_{0-3}$ alkyl)-$NR^{3a}R^{3b}$;
$R^{3a}$ and $R^{3b}$ are independently selected from H, $C_{1-4}$ alkyl and $C_{1-4}$ haloalkyl;
$R^4$ is selected from H and $C_{1-4}$ alkyl; or
$R^3$ and $R^4$ together with the nitrogen atom to which they are attached form a $C_{3-6}$ heterocyclyl, which $C_{3-6}$ heterocyclyl is optionally spiro fused to a second $C_{3-6}$ heterocyclyl or a $C_{3-6}$ cycloalkyl by one single carbon atom, and which $C_{3-6}$ heterocyclyl and $C_{3-6}$ cycloalkyl are unsubstituted or substituted with 1 to 3 substituents independently selected from $C_{1-4}$ alkyl, hydroxy, $C_{1-4}$ hydroxyalkyl, halogen, $C_{1-4}$ alkoxy and $C_{1-4}$ haloalkyl;
Y is a 5-6-membered heteroaryl, which heteroaryl is unsubstituted or substituted with 1 to 3 substituents independently selected from $C_{1-4}$ alkyl, $C_{1-4}$ haloalkyl, $C_{1-4}$alkoxy$C_{1-4}$ alkyl, $C_{1-4}$hydroxyalkyl, $C_{1-4}$ alkoxy, $C_{1-4}$ haloalkoxy, halogen, —$(C_{0-3}$ alkyl)-$NR^{3a}R^{3b}$, —$(C_{0-3}$ alkyl)-$C_{3-6}$ cycloalkyl and —$(C_{0-3}$ alkyl)-$C_{3-6}$ heterocyclyl;
or a pharmaceutically acceptable salt thereof.

Definitions

"Halo" or "halogen", as used herein, may be fluoro, chloro, bromo or iodo.

"$C_{1-4}$ alkyl", as used herein, denotes straight chain or branched alkyl having 1-4 carbon atoms. If a different number of carbon atoms is specified, such as $C_6$ or $C_3$, then the definition is to be amended accordingly, such as "$C_1$-$C_4$ alkyl" will represent methyl, ethyl, propyl, isopropyl, butyl, isobutyl, sec-butyl and tert-butyl.

"$C_{1-4}$ alkoxy", as used herein, refers to an —O—$C_{1-4}$ alkyl group wherein $C_{1-4}$ alkyl is as defined herein. Examples of such groups include methoxy, ethoxy, propoxy, butoxy, pentoxy or hexoxy and the like. As for alkyl unless a particular structure is specified the terms propoxy, butoxy etc include all straight and branched chain forms having the appropriate number of carbon atoms e.g. propoxy includes n-propoxy and isopropoxy.

"$C_{1-4}$ haloalkoxy" as used herein refers to an —O—$C_{1-4}$ alkyl group wherein $C_{1-4}$ alkyl is as defined herein and substituted with one or more halogen groups, e.g. —O—$CF_3$.

"$C_{1-4}$ haloalkyl", as used herein, denotes straight chain or branched alkyl having 1-4 carbon atoms with at least one hydrogen substituted with a halogen. If a different number of carbon atoms is specified, such as $C_6$ or $C_3$, then the definition is to be amended accordingly, such as "$C_1$-$C_4$-Haloalkyl" will represent methyl, ethyl, propyl, isopropyl, butyl, isobutyl, sec-butyl and tert-butyl that have at least one hydrogen substituted with halogen, such as where the halogen is fluorine: $CF_3CF_2$—, $(CF_3)_2CH$—, $CH_3$—$CF_2$—, $CF_3CF_2$—, $CF_3$, $CF_2H$—, $CF_3CF_2CHCF_3$ or $CF_3CF_2CF_2CF_2$—.

"$C_{3-7}$ cycloalkyl" as used herein refers to a saturated monocyclic hydrocarbon ring of 3 to 7 carbon atoms. Examples of such groups include cyclopropyl, cyclobutyl, cyclopentyl and cyclohexyl. If a different number of carbon atoms is specified, then the definition is to be amended accordingly.

The term "hydroxy" or "hydroxyl" refers to —OH.

"$C_{1-4}$ hydroxyalkyl", as used herein, denotes a straight chain or branched alkyl having 1-4 carbon atoms with at least one hydrogen substituted with a hydroxy group. If a different number of carbon atoms is specified, such as $C_6$ or $C_3$, then the definition is to be amended accordingly, such as "$C_1$-$C_4$ hydroxyalkyl" will represent methyl, ethyl, propyl, isopropyl, butyl, isobutyl, sec-butyl and tert-butyl that have at least one hydrogen substituted with hydroxy.

"$C_{3-7}$ heterocyclyl ring" refers to a 3 to 7 membered saturated or partially unsaturated aliphatic ring system which contains 1 to 3 heteroatoms selected from oxygen, nitrogen and sulfur. Suitable examples of such ring systems include pyrrolidinyl, piperidinyl, piperazinyl, morpholinyl, tetrahydrofuranyl, tetrahydropyranyl, pyrrolinyl, thienyl or oxazolinyl.

"5-6 membered heteroaryl" refers to a 5-6 membered aromatic ring system which contains 1 to 3 heteroatoms selected from oxygen, nitrogen or sulfur. Examples of 5-membered heteroaryl rings in this instance include furanyl, pyrrolyl, oxazolyl, thiazolyl, imidazolyl, oxadiazolyl, thiadiazolyl, triazolyl, isothiazolyl, isoxazolyl, thiophenyl, or pyrazolyl. Examples of 6-membered heteroaryl rings include pyridinyl, pyridazinyl, pyrimidinyl, pyrazinyl, or triazinyl.

"Oxo" refers to =O.

The term "a," "an," "the" and similar terms used in the context of the present invention (especially in the context of the claims) are to be construed to cover both the singular and plural unless otherwise indicated herein or clearly contradicted by the context.

The term "treatment" as used herein refers to both to symptomatic and prophylactic treatment, particularly symptomatic.

As used herein, when one embodiment refers to several other embodiments by using the term "according to any one of", for example "according to any one of embodiments 1 to 5", then said embodiment refers not only to embodiments indicated by the integers such as 1 and 2 but also to embodiments indicated by numbers with a decimal component such as 1.1, 1.2 or 2.1, 2.2, 2.3. For example, "according to any one of embodiments 1 to 3" means according to any one of embodiments 1, 1.1, 2, 3, 3.1, 3.2, 3.3, 3.4, 3.5, 3.6, 3.7. The same applies when referring to exemplified compounds.

Various embodiments of the invention are described herein. It will be recognized that features specified in each embodiment may be combined with other specified features to provide further embodiments.

In an embodiment 2 of the invention, there is provided a compound of formula (Ia)

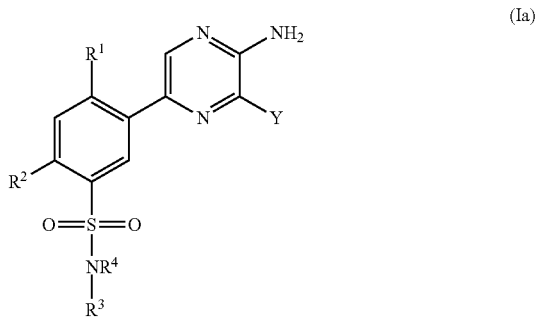

(Ia)

wherein $R^1$ is independently selected from H, halogen, $C_{1-4}$ alkyl, $C_{1-4}$ alkoxy, $C_{1-4}$ haloalkyl, $C_{1-4}$ haloalkoxy, $C_{1-4}$ hydroxyalkyl and $C_{3-7}$ cycloalkyl;

$R^2$ is selected from H, halogen, $CF_3$ and methyl;

$R^3$ is selected from (i) $C_{1-4}$ alkyl which is unsubstituted or substituted with 1 or more substituents, particularly 1 to 3 substituents, independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(ii) $C_{1-4}$ alkoxy which is unsubstituted or substituted with 1 or more substituents, particularly 1 to 3 substituents, independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iii) $C_{3-7}$ cycloalkyl or —O—$C_{3-7}$ cycloalkyl wherein the $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iv) a —($C_{0-3}$ alkyl)-$C_{3-7}$ cycloalkyl or —O—($C_{0-3}$ alkyl)-$C_{3-7}$ cycloalkyl wherein the $C_{3-7}$ cycloalkyl is spiro fused to a second $C_{3-7}$ cycloalkyl or $C_{3-7}$ heterocyclyl by one single carbon atom, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(v) a —($C_{0-3}$ alkyl)-$C_{3-7}$ heterocyclyl or —O—($C_{0-3}$ alkyl)-$C_{3-7}$ heterocyclyl, and wherein said $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vi) a —($C_{0-3}$ alkyl)-$C_{3-7}$ heterocyclyl or —(O—$C_{0-3}$ alkyl)-$C_{3-7}$ heterocyclyl, and wherein said $C_{3-7}$ heterocyclyl is spiro fused to a second $C_{3-7}$ heterocyclyl or a $C_{3-7}$ cycloalkyl by one single carbon atom, and wherein the $C_{3-7}$ heterocyclyl or $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vii) H;

$R^4$ is selected from H and $C_{1-4}$ alkyl; or $R^3$ and $R^4$ together with the nitrogen atom to which they are attached form a $C_{3-7}$ heterocyclyl, which $C_{3-7}$ heterocyclyl is optionally spiro fused to a second $C_{3-7}$ heterocyclyl or a $C_{3-7}$ cycloalkyl by one single carbon atom, and which $C_{3-7}$ heterocyclyl and $C_{3-7}$ cycloalkyl are unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

$R^{3a}$ and $R^{3b}$ are independently selected from H, $C_{1-4}$ alkyl and $C_{1-4}$ haloalkyl;

Y is selected from the group consisting of
thiazolyl,
thiadiazolyl, isothiazolyl,
pyrazolyl,
pyridyl,
triazolyl,
imidazolyl,
oxadiazolyl,
isoxazolyl,
oxazolyl,
pyrrolyl,
thienyl, and
furanyl;
each of which is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy, halogen, $C_{1-4}$ hydroxyalkyl, —($C_{0-3}$ alkyl)-N'R'', —($C_{0-3}$ alkyl)-$C_{3-7}$ cycloalkyl and —($C_{0-3}$ alkyl)-$C_{3-7}$ heterocyclyl, —(C=O)—$C_{3-7}$ heterocyclyl, —(C=O)—N'R'', —($C_{0-3}$ alkyl)-phenyl and —($C_{0-3}$ alkyl)-5-6-membered heteroaryl;
R' and R'' are independently selected from H and $C_{1-4}$ alkyl;
or a pharmaceutically acceptable salt thereof.

In an embodiment 2.1 of the invention, there is provided a compound according to embodiment 1.1, wherein
E is selected from N and $CR^E$;
$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy and $C_{3-6}$ cycloalkyl;
$R^3$ is selected from
(i) $C_{1-4}$ alkyl which is substituted with 1 to 3 substituents independently selected from hydroxy, $C_{1-4}$ hydroxyalkyl, halogen, $C_{1-4}$ haloalkyl, $C_{1-4}$ alkoxy, $C_{1-4}$ alkyl, oxo, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl;
(ii) $C_{1-4}$ alkoxy which is substituted with 1 to 3 substituents independently selected from hydroxy, $C_{1-4}$ hydroxyalkyl, halogen, $C_{1-4}$ haloalkyl, $C_{1-4}$ alkyl, $C_{1-4}$ alkoxy, oxo, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl;
(iii) $C_{3-6}$ cycloalkyl or —O—$C_{3-6}$ cycloalkyl wherein the $C_{3-6}$ cycloalkyl is substituted with 1 to 3 substituents independently selected from hydroxy, $C_{1-4}$ hydroxyalkyl, halogen, $C_{1-4}$ alkoxy, $C_{1-4}$ haloalkyl and —($C_{0-3}$ alkyl)-$NR^{3a}R^{3b}$;
(iv) a —($C_{0-3}$ alkyl)-$C_{3-6}$ cycloalkyl or —(O—$C_{0-3}$ alkyl)-$C_{3-6}$ cycloalkyl spiro fused to a second $C_{3-6}$ cycloalkyl or $C_{3-6}$ heterocyclyl by one single carbon atom, wherein the second $C_{3-6}$ cycloalkyl or $C_{3-6}$ heterocyclyl is substituted with 1 to 3 substituents independently selected from hydroxy, $C_{1-4}$ hydroxyalkyl, halogen, $C_{1-4}$ alkoxy, $C_{1-4}$ haloalkyl and —($C_{0-3}$ alkyl)-$NR^{3a}R^{3b}$;
(v) a —($C_{0-3}$ alkyl)-$C_{3-6}$ heterocyclyl or —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$;
(vi) a —($C_{0-3}$ alkyl)-$C_{3-6}$ heterocyclyl or —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is fused to a second $C_{3-6}$ heterocyclyl or a $C_{3-6}$ cycloalkyl by one single carbon atom, and wherein said second $C_{3-6}$ heterocyclyl or $C_{3-6}$ cycloalkyl is substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$;
$R^{3a}$ and $R^{3b}$ are independently selected from H, $C_{1-4}$ alkyl and $C_{1-4}$ haloalkyl;
$R^4$ is selected from H and $C_{1-4}$ alkyl; or
$R^3$ and $R^4$ together with the nitrogen atom to which they are attached form a $C_{3-6}$ heterocyclyl, which $C_{3-6}$ heterocyclyl is optionally spiro fused to a second $C_{3-6}$ heterocyclyl or a $C_{3-6}$ cycloalkyl by one single carbon atom, and which $C_{3-6}$ heterocyclyl and $C_{3-6}$ cycloalkyl are unsubstituted or substituted with 1 to 3 substituents independently selected from $C_{1-4}$ alkyl, hydroxy, $C_{1-4}$ hydroxyalkyl, halogen, $C_{1-4}$ alkoxy and $C_{1-4}$ haloalkyl;
Y is a 5-6-membered heteroaryl, which heteroaryl is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy, halogen, —($C_{0-3}$ alkyl)-$NR^{3a}R^{3b}$, —($C_{0-3}$ alkyl)-$C_{3-6}$ cycloalkyl and —($C_{0-3}$ alkyl)-$C_{3-6}$ heterocyclyl;
or a pharmaceutically acceptable salt thereof.

In an embodiment 2.2 of the invention, there is provided a compound of formula (Ia)

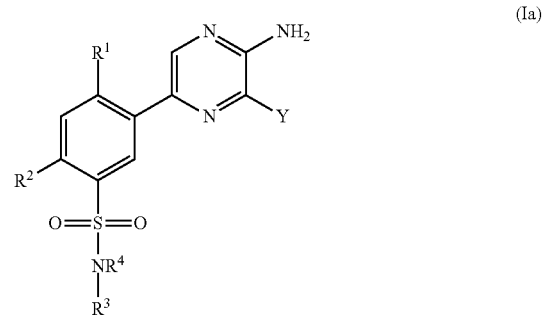

(Ia)

wherein
$R^1$ is independently selected from H, halogen, $C_{1-4}$ alkyl, $C_{1-4}$ alkoxy, $C_{1-4}$ haloalkyl, $C_{1-4}$ haloalkoxy, $C_{1-4}$ hydroxyalkyl and $C_{3-7}$ cycloalkyl;
$R^2$ is selected from H, halogen, $CF_3$ and methyl;
$R^3$ is selected from
(i) $C_{1-4}$ alkyl which is unsubstituted or substituted with 1 or more substituents, particularly 1 to 3 substituents, independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;
(ii) $C_{1-4}$ alkoxy which is unsubstituted or substituted with 1 or more substituents, particularly 1 to 3 substituents, independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;
(iii) —$C_{3-7}$ cycloalkyl or —O—$C_{3-7}$ cycloalkyl wherein the $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iv) a —($C_{0-3}$ alkyl)-$C_{3-7}$ cycloalkyl or —O—($C_{0-3}$ alkyl)-$C_{3-7}$ cycloalkyl wherein the $C_{3-7}$ cycloalkyl is spiro fused to a second $C_{3-7}$ cycloalkyl or $C_{3-7}$ heterocyclyl by one single carbon atom, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(v) a —($C_{0-3}$ alkyl)-$C_{3-7}$ heterocyclyl or —O—($C_{0-3}$ alkyl)-$C_{3-7}$ heterocyclyl, and wherein said $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vi) a —($C_{0-3}$ alkyl)-$C_{3-7}$ heterocyclyl or —(O—$C_{0-3}$ alkyl)-$C_{3-7}$ heterocyclyl, and wherein said $C_{3-7}$ heterocyclyl is spiro fused to a second $C_{3-7}$ heterocyclyl or a $C_{3-7}$ cycloalkyl by one single carbon atom, and wherein the $C_{3-7}$ heterocyclyl or $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(vii) H;

$R^4$ is selected from H and $C_{1-4}$ alkyl; or $R^3$ and $R^4$ together with the nitrogen atom to which they are attached form a $C_{3-7}$ heterocyclyl, which $C_{3-7}$ heterocyclyl is optionally spiro fused to a second $C_{3-7}$ heterocyclyl or a $C_{3-7}$ cycloalkyl by one single carbon atom, and which $C_{3-7}$ heterocyclyl and $C_{3-7}$ cycloalkyl are unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

$R^{3a}$ and $R^{3b}$ are independently selected from H, $C_{1-4}$ alkyl and $C_{1-4}$ haloalkyl;

Y is selected from the group consisting of
thiazolyl,
thiadiazolyl,
isothiazolyl,
pyrazolyl,
pyridyl,
triazolyl,
imidazolyl,
oxadiazolyl,
isoxazolyl,
oxazolyl,
pyrrolyl,
pyrimidinyl,
thienyl, and
furanyl;

each of which is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy, halogen, $C_{1-4}$ hydroxyalkyl, —($C_{0-3}$ alkyl)-N'R", —($C_{0-3}$ alkyl)-$C_{3-7}$ cycloalkyl and —($C_{0-3}$ alkyl)-$C_{3-7}$ heterocyclyl, —(C=O)—$C_{3-7}$ heterocyclyl, —(C=O)—N'R", —($C_{0-3}$ alkyl)-phenyl and —($C_{0-3}$ alkyl)-5-6-membered heteroaryl;

R' and R" are independently selected from H and $C_{1-4}$ alkyl; or a pharmaceutically acceptable salt thereof.

In an embodiment 3 of the invention, there is provided a compound according to embodiment 1 or 2, wherein $R^1$ is selected from H and $C_{1-4}$ alkyl;

$R^2$ is selected from H, halogen, $C_{1-4}$ haloalkyl and methyl;

$R^3$ is selected from (i) $C_{1-4}$ alkyl which is substituted with 1 or more substituents, particularly 1 to 3 substituents, independently selected from hydroxy, halogen, —$NR^{3a}R^{3b}$, $C_{1-4}$ alkyl, $C_{3-7}$ cycloalkyl and $C_{3-7}$ heterocyclyl;

(ii) $C_{1-4}$ alkoxy which is unsubstituted or substituted with 1 or more substituents, particularly 1 to 3 substituents, independently selected from hydroxy, halogen, —$NR^{3a}R^{3b}$, $C_{1-4}$ alkyl, $C_{3-7}$ cycloalkyl and $C_{3-7}$ heterocyclyl;

(iii) —O—($C_{0-3}$ alkyl)-$C_{3-7}$ heterocyclyl, and wherein said $C_{3-7}$ heterocyclyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, oxo and $C_{1-4}$ haloalkyl;

(iv) —O—($C_{0-3}$ alkyl)-$C_{3-7}$ cycloalkyl wherein the $C_{3-7}$ cycloalkyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, oxo and $C_{1-4}$ haloalkyl;

(v) —($C_{0-3}$ alkyl)-$C_{3-7}$ cycloalkyl wherein the $C_{3-7}$ cycloalkyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, oxo and $C_{1-4}$ haloalkyl;

(vi) ($C_{0-3}$ alkyl)-$C_{3-7}$ heterocyclyl, wherein said $C_{3-7}$ heterocyclyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, oxo and $C_{1-4}$ haloalkyl;

(vii) a —($C_{0-3}$ alkyl)-$C_{3-7}$ cycloalkyl or —O—($C_{0-3}$ alkyl)-$C_{3-7}$ cycloalkyl wherein the $C_{3-7}$ cycloalkyl is spiro fused to a second $C_{3-7}$ cycloalkyl or $C_{3-7}$ heterocyclyl by one single carbon atom, wherein the $C_{3-7}$ cycloalkyl or $C_{3-7}$ heterocyclyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, oxo and $C_{1-4}$ haloalkyl;

$R^4$ is selected from H and $C_{1-4}$ alkyl; or $R^3$ and $R^4$ together with the nitrogen atom to which they are attached form a $C_{3-7}$ heterocyclyl, which $C_{3-7}$ heterocyclyl is optionally spiro fused to a second $C_{3-7}$ heterocyclyl or a $C_{3-7}$ cycloalkyl by one single carbon atom, and which $C_{3-7}$ heterocyclyl and $C_{3-7}$ cycloalkyl are unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

$R^{3a}$ and $R^{3b}$ are independently selected from H and $C_{1-4}$ alkyl;

Y is selected from the group consisting of
thiazolyl,
thiadiazolyl,
isothiazolyl,
pyrazolyl,
pyridyl,
triazolyl,
imidazolyl,
oxadiazolyl,
isoxazolyl,
oxazolyl;
pyrrolyl,
thienyl, and
furanyl;

each of which is unsubstituted or substituted with 1 to 3 substituents independently selected from $C_{1-4}$ alkyl, $C_{1-4}$ haloalkyl, $C_{1-4}$hydroxyalkyl, —($C_{0-3}$ alkyl)-$C_{3-7}$ cycloalkyl, —(C=O)—C$_{3-7}$ heterocyclyl, —(C$_{0-3}$ alkyl)-N'R",
—(C=O)—N'R", —(C$_{0-3}$ alkyl)-phenyl and —(C$_{0-3}$ alkyl)-pyridyl;
R' and R" are independently selected from H and C$_{1-4}$ alkyl;
or a pharmaceutically acceptable salt thereof.

In an embodiment 3.1 of the invention, there is provided a compound or salt according to embodiment 1.1 or 2.1 wherein E is CR$^E$ and R$^E$ is H.

In an embodiment 4 of the invention, there is provided a compound according to any one of embodiments 1 to 3, wherein
Y is selected from the group consisting of
  oxazol-2-yl,
  oxazol-5-yl,
  oxazol-4-yl,
  thiazol-5-yl,
  thiazol-4-yl,
  1,3,4-thiadiazol-2-yl,
  isothiazol-5-yl,
  pyrazol-4-yl,
  pyrazol-3-yl,
  pyrazol-1-yl,
  pyrid-4-yl,
  pyrid-3-yl,
  pyrid-2-yl,
  1,2,4-triazol-1-yl,
  1,2,3-triazol-4-yl,
  imidazol-1-yl,
  1,2,4-oxadiazol-5-yl,
  1,3,4-oxadiazol-2-yl,
  1,2,4-oxadiazol-3-yl,
  isoxazol-5-yl,
  isoxazol-3-yl,
  isoxazol-4-yl,
  pyrrol-3-yl,
  thien-2-yl,
  thien-3-yl, and
  furan-3-yl,
each of which is unsubstituted or substituted with 1 to 3 substituents independently selected from C$_{1-4}$ alkyl, C$_{1-4}$ haloalkyl, C$_{1-4}$hydroxyalkyl, —(C$_{0-3}$ alkyl)-C$_{3-7}$ cycloalkyl, —(C=O)—C$_{3-7}$ heterocyclyl, —(C$_{0-3}$ alkyl)-N'R", —(C=O)—N'R", —(C$_{0-3}$ alkyl)-phenyl and —(C$_{0-3}$ alkyl)-pyridyl;
R' and R" are independently selected from H and C$_{1-4}$ alkyl;
or a pharmaceutically acceptable salt thereof.

In an embodiment 4.1 of the invention, there is provided a compound or salt according to any one of embodiments 1 to 3 wherein R$^1$ is selected from C$_{1-4}$ alkyl and H.

In an embodiment 5 of the invention, there is provided a compound according to any one of embodiments 1 to 4, wherein
Y is selected from the group consisting of

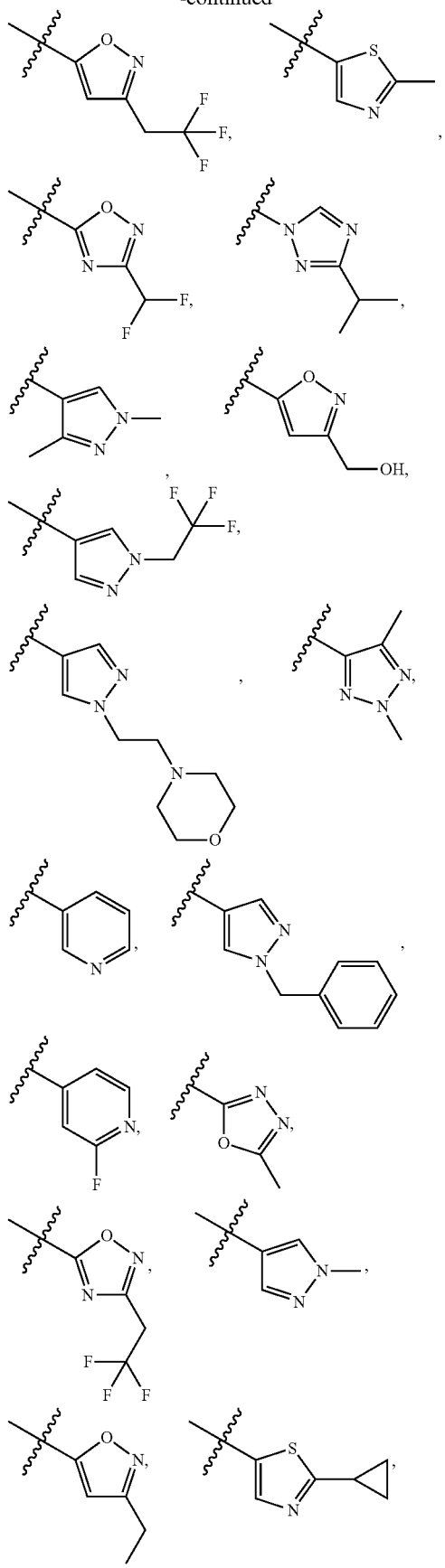

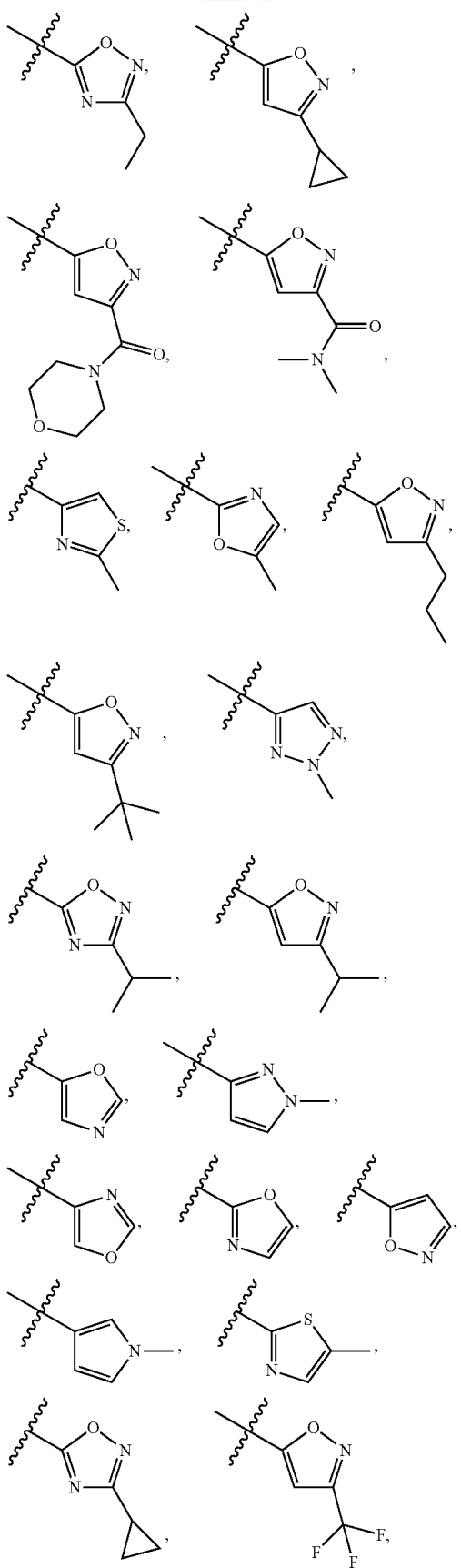
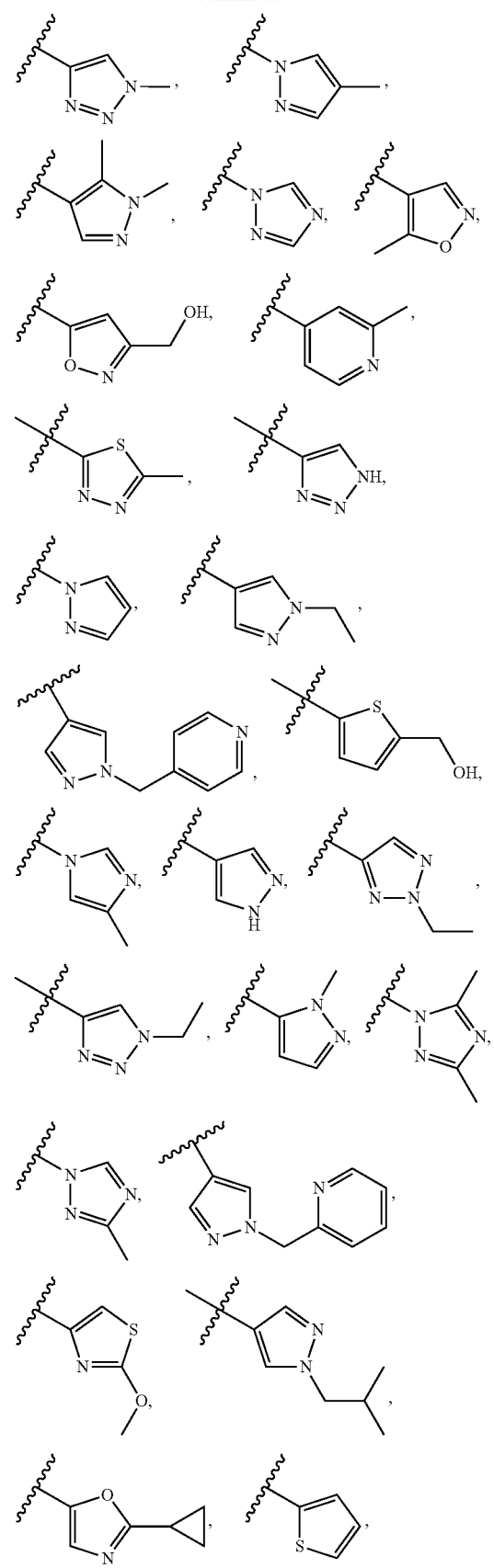

-continued

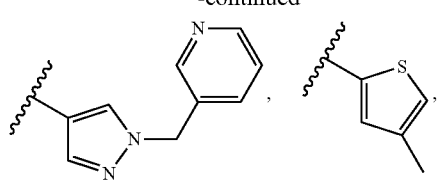
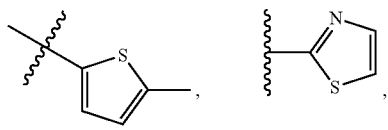
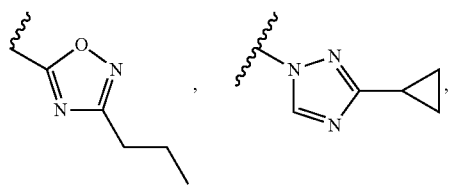
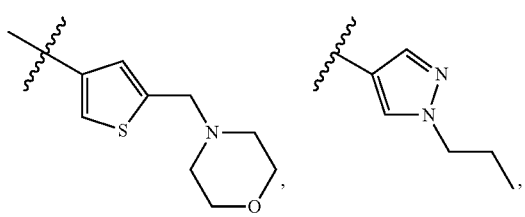
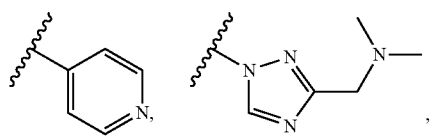
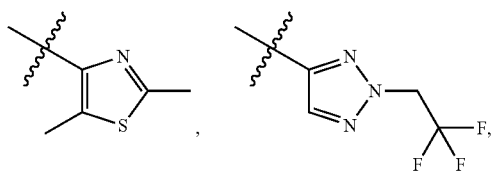
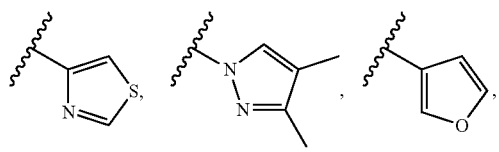
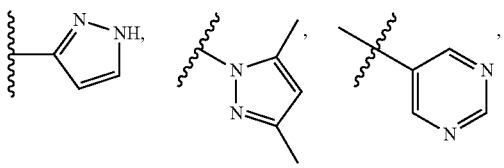
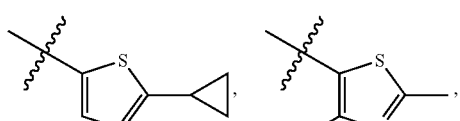
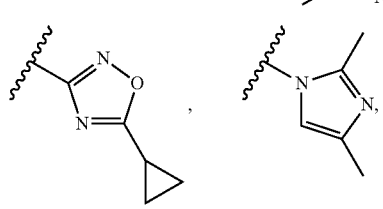

-continued

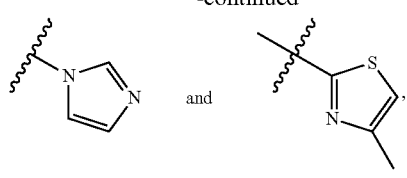  and or a pharmaceutically acceptable salt thereof.

In an embodiment 5.1 of the invention, there is provided a compound or salt according to embodiment 4.1, wherein $R^1$ is selected from methyl and H, particularly methyl.

In an embodiment 6 of the invention, there is provided a compound according to any one of embodiments 1 to 4, wherein Y is selected from the group consisting of

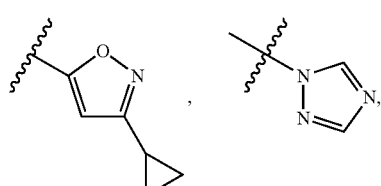
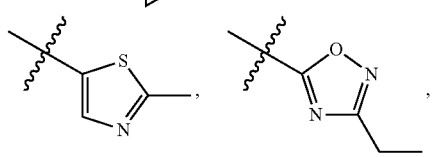
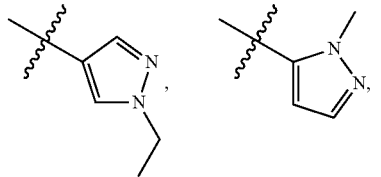
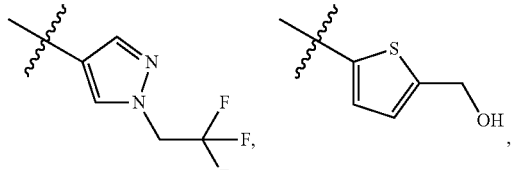
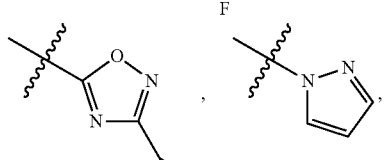
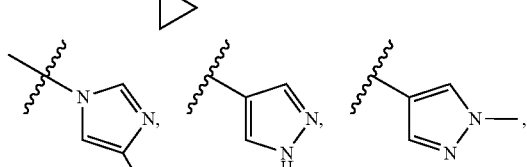
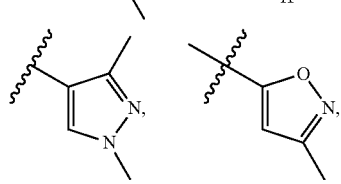

-continued
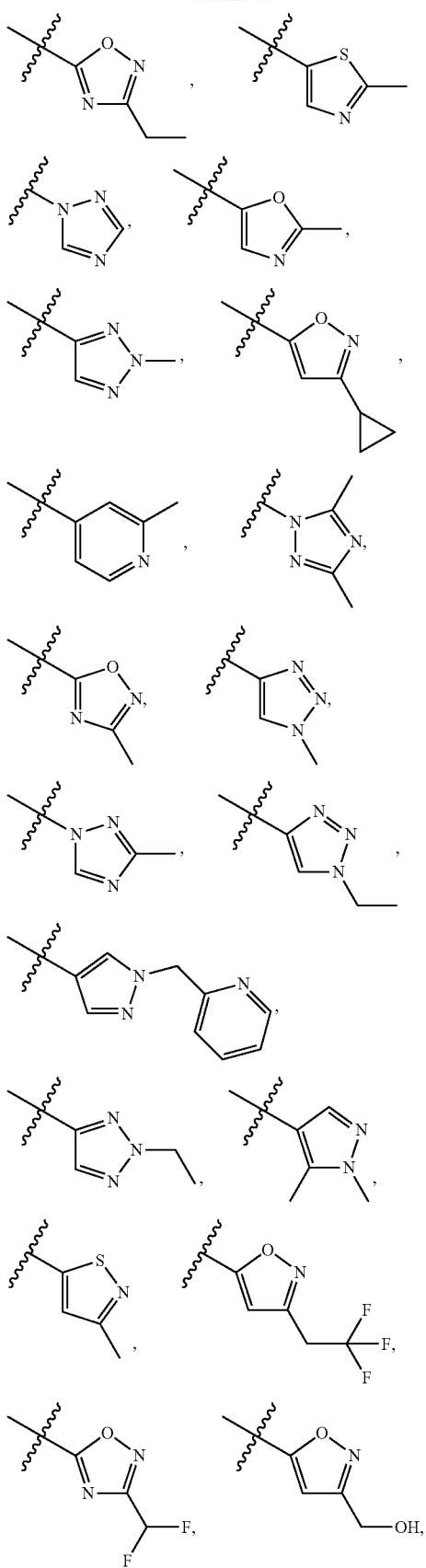
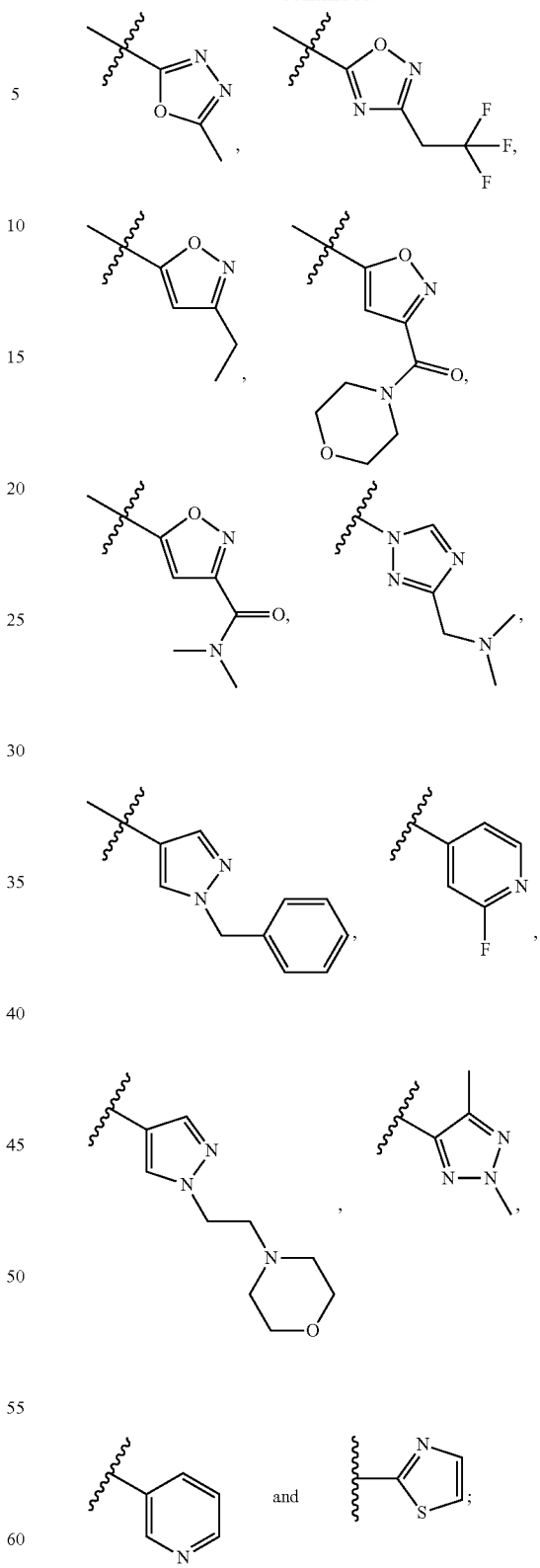
or a pharmaceutically acceptable salt thereof.
In an embodiment 6.1 of the invention, there is provided a compound or salt according to any one of embodiments 1 to 5, wherein $R^2$ is selected from H, $C_{1-4}$ alkyl and halogen.

In an embodiment 7 of the invention, there is provided a compound according to any one of embodiments 1 to 4, wherein
Y is selected from the group consisting of

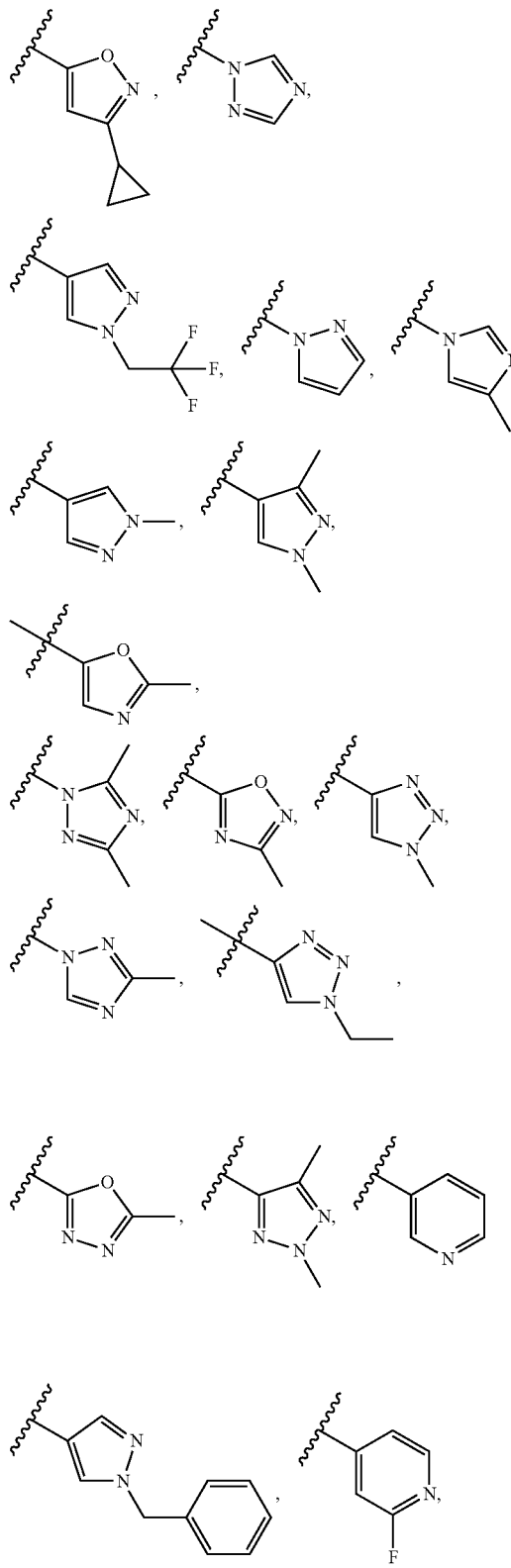

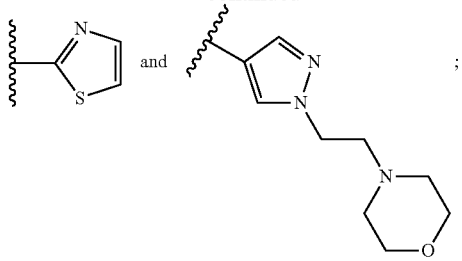

or a pharmaceutically acceptable salt thereof.

In an embodiment 7.1 of the invention, there is provided a compound or salt according to embodiment 6.1, wherein $R^2$ is selected from H, fluoro, chloro and methyl, particularly H and fluoro, more particularly H.

In an embodiment 8 of the invention, there is provided a compound according to any one of embodiments 1 to 7, wherein
$R^3$ is selected from
(i) $C_{1-4}$ alkyl which is substituted with 1 to 3 substituents independently selected from hydroxyl, halogen and $C_{1-4}$ alkyl;
(ii) $C_{1-4}$ alkoxy which is unsubstituted or substituted with 1 to 3 substituents independently selected from hydroxyl, halogen and $C_{1-4}$ alkyl;
(iii) —O—($C_{0-3}$ alkyl)-$C_{3-7}$ heterocyclyl wherein the $C_{3-7}$ heterocyclyl contains at least one heteroatom selected from O and N, and wherein said $C_{3-7}$ heterocyclyl is unsubstituted or substituted with 1 to 3 substituents independently selected from $C_{1-4}$ alkyl, hydroxy, $C_{1-4}$ hydroxyalkyl, halogen, oxo and $C_{1-4}$ haloalkyl;
(iv) —O—($C_{0-3}$ alkyl)-$C_{3-7}$ cycloalkyl wherein the $C_{3-7}$ cycloalkyl is unsubstituted or substituted with 1 to 3 substituents independently selected from $C_{1-4}$ alkyl, hydroxy, $C_{1-4}$ hydroxyalkyl, halogen, oxo and $C_{1-4}$ haloalkyl;
(v) —($C_{0-3}$ alkyl)-$C_{3-7}$ cycloalkyl wherein the $C_{3-7}$ cycloalkyl is unsubstituted or substituted with 1 to 3 substituents independently selected from $C_{1-4}$ alkyl, hydroxy, $C_{1-4}$ hydroxyalkyl, halogen, oxo and $C_{1-4}$ haloalkyl;
(vi) —($C_{0-3}$ alkyl)-$C_{3-7}$ heterocyclyl wherein the $C_{3-7}$ heterocyclyl contains at least one heteroatom selected from O and N, and wherein said $C_{3-7}$ heterocyclyl is unsubstituted or substituted with 1 to 3 substituents independently selected from $C_{1-4}$ alkyl, hydroxy, $C_{1-4}$ hydroxyalkyl, oxo, halogen and $C_{1-4}$ haloalkyl;
(vii) a —($C_{0-3}$ alkyl)-$C_{3-7}$ cycloalkyl or —(O—$C_{0-3}$ alkyl)-$C_{3-7}$ cycloalkyl where the $C_{3-7}$ cycloalkyl is spiro fused to a second $C_{3-7}$ cycloalkyl or $C_{3-7}$ heterocyclyl by one single carbon atom and wherein the $C_{3-7}$ cycloalkyl or $C_{3-7}$ heterocyclyl is unsubstituted or substituted with 1 to 3 substituents independently selected from $C_{1-4}$ alkyl, hydroxy, $C_{1-4}$ hydroxyalkyl, halogen, oxo and $C_{1-4}$ haloalkyl;
(viii) a —($C_{0-3}$ alkyl)-$C_{3-7}$ heterocyclyl or —(O—$C_{0-3}$ alkyl)-$C_{3-7}$ heterocyclyl wherein the $C_{3-6}$ heterocyclyl contains at least one heteroatom selected from O and N, and wherein said $C_{3-7}$ heterocyclyl is spiro fused to a second $C_{3-7}$ heterocyclyl or a $C_{3-7}$ cycloalkyl by one single carbon atom, and wherein the $C_{3-7}$ heterocyclyl or $C_{3-7}$ cycloalkyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, oxo and $C_{1-4}$ haloalkyl;
or a pharmaceutically acceptable salt thereof.

In an embodiment 8.1 of the invention, there is provided a compound or salt according to any one of embodiments 1 to 7, wherein $R^3$ is selected from (i) $C_{1-4}$ alkyl substituted with 1 to 3 substituents independently selected from hydroxy, $C_{1-4}$ alkyl, halogen, oxo, and —$NR^{3a}R^{3b}$;
(ii) $C_{1-4}$ alkoxy substituted with 1 to 3 substituents independently selected from hydroxy, halogen and $C_{1-4}$ alkyl;
(iii) —($C_{0-3}$ alkyl)-$C_{3-6}$ cycloalkyl wherein the $C_{3-6}$ cycloalkyl is substituted with 1 to 3 substituents independently selected from hydroxy, $C_{1-4}$ hydroxyalkyl and halogen;
(iv) —($C_{0-3}$ alkyl)-$C_{3-6}$ cycloalkyl spiro fused to a second $C_{3-6}$ cycloalkyl by one single carbon atom, wherein the second $C_{3-6}$ cycloalkyl is substituted with 1 to 3 substituents independently selected from hydroxy and halogen; and
(v) —($C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from hydroxy, $C_{1-4}$ alkyl and $C_{1-4}$ hydroxyalkyl;
(vi) a —($C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is spiro fused to a second $C_{3-6}$ heterocyclyl or a $C_{3-6}$ cycloalkyl by one single carbon atom, and wherein the $C_{3-6}$ heterocyclyl or $C_{3-6}$ cycloalkyl is unsubstituted or substituted with 1 to 3 substituents independently selected from $C_{1-4}$ alkyl, hydroxy and $C_{1-4}$ hydroxyalkyl;
$R^{3a}$ and $R^{3b}$ are independently selected from H and $C_{1-4}$ alkyl;
$R^4$ is selected from H and $C_{1-4}$ alkyl; or
$R^3$ and $R^4$ together with the nitrogen atom to which they are attached form a $C_{3-6}$ heterocyclyl, which $C_{3-6}$ heterocyclyl is unsubstituted or substituted with 1 to 3 substituents independently selected from hydroxy, $C_{1-4}$ hydroxyalkyl and $C_{1-4}$ alkyl.

In an embodiment 9 of the invention, there is provided a compound according to any one of embodiments 1 to 7, wherein
$R^3$ is selected from
(i) $C_{1-4}$ alkyl which is substituted with 1 to 3 substituents independently selected from hydroxyl, halogen and $C_{1-4}$ alkyl;
(ii) $C_{1-4}$ alkoxy which is unsubstituted or substituted with 1 to 3 substituents independently selected from hydroxyl, halogen and $C_{1-4}$ alkyl;
(iii) —O—($C_{0-3}$ alkyl)-$C_{3-7}$ heterocyclyl wherein the $C_{3-7}$ heterocyclyl contains at least one heteroatom selected from O and N, and wherein said $C_{3-7}$ heterocyclyl is unsubstituted or substituted with 1 to 3 substituents independently selected from $C_{1-4}$ alkyl, hydroxy, $C_{1-4}$ hydroxyalkyl, halogen, oxo and $C_{1-4}$ haloalkyl;
(iv) —O—($C_{0-3}$ alkyl)-$C_{3-7}$ cycloalkyl wherein the $C_{3-7}$ cycloalkyl is unsubstituted or substituted with 1 to 3 substituents independently selected from $C_{1-4}$ alkyl, hydroxy, $C_{1-4}$ hydroxyalkyl, halogen, oxo and $C_{1-4}$ haloalkyl;
(v) —($C_{0-3}$ alkyl)-$C_{3-7}$ cycloalkyl wherein the $C_{3-7}$ cycloalkyl is unsubstituted or substituted with 1 to 3 substituents independently selected from $C_{1-4}$ alkyl, hydroxy, $C_{1-4}$ hydroxyalkyl, halogen, oxo and $C_{1-4}$ haloalkyl;
(vi) —($C_{0-3}$ alkyl)-$C_{3-7}$ heterocyclyl wherein the $C_{3-7}$ heterocyclyl contains at least one heteroatom selected from O and N, and wherein said $C_{3-7}$ heterocyclyl is unsubstituted or substituted with 1 to 3 substituents independently selected from $C_{1-4}$ alkyl, hydroxy, $C_{1-4}$ hydroxyalkyl, oxo, halogen and $C_{1-4}$ haloalkyl;
(vii) a —($C_{0-3}$ alkyl)-$C_{3-7}$ cycloalkyl or —(O—$C_{0-3}$ alkyl)-$C_{3-7}$ cycloalkyl spiro fused to a second $C_{3-7}$ cycloalkyl or $C_{3-7}$ heterocyclyl by one single carbon atom, wherein the $C_{3-7}$ cycloalkyl or $C_{3-7}$ heterocyclyl is unsubstituted or substituted with 1 to 3 substituents independently selected from $C_{1-4}$ alkyl, hydroxy, $C_{1-4}$ hydroxyalkyl, oxo, halogen and $C_{1-4}$ haloalkyl; or a pharmaceutically acceptable salt thereof.

In an embodiment 9.1 of the invention, there is provided a compound or salt according to any one of embodiments 1 to 7, wherein $R^3$ is $C_{1-4}$ alkyl which is unsubstituted or substituted with 1 to 3 substituents independently selected from hydroxy, $C_{1-4}$ hydroxyalkyl, halogen, $C_{1-4}$ haloalkyl, $C_{1-4}$ alkoxy, $C_{1-4}$ alkyl, oxo, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl.

In an embodiment 10 of the invention, there is provided a compound according to any one of embodiments 1 to 7, wherein
$R^3$ is selected from
(i) $C_{1-4}$ alkyl which is substituted with 1 to 3 substituents independently selected from hydroxyl, halogen and $C_{1-4}$ alkyl;
(ii) $C_{1-4}$ alkoxy which is unsubstituted or substituted with 1 to 3 substituents independently selected from hydroxyl, halogen and $C_{1-4}$ alkyl;
(iii) —O—($C_{0-3}$ alkyl)-$C_{3-7}$ heterocyclyl wherein the $C_{3-7}$ heterocyclyl contains at least one heteroatom selected from O and N, and wherein said $C_{3-7}$ heterocyclyl is unsubstituted or substituted with 1 to 3 substituents independently selected from $C_{1-4}$ alkyl, hydroxy, $C_{1-4}$ hydroxyalkyl, halogen and $C_{1-4}$ haloalkyl;
(iv) —O—($C_{0-3}$ alkyl)-$C_{3-7}$ cycloalkyl wherein the $C_{3-7}$ cycloalkyl is unsubstituted or substituted with 1 to 3 substituents independently selected from $C_{1-4}$ alkyl, hydroxy, $C_{1-4}$ hydroxyalkyl, halogen and $C_{1-4}$ haloalkyl;
(v) ($C_{0-3}$ alkyl)-$C_{3-7}$ cycloalkyl wherein the $C_{3-7}$ cycloalkyl is unsubstituted or substituted with 1 to 3 substituents independently selected from $C_{1-4}$ alkyl, hydroxy, $C_{1-4}$ hydroxyalkyl, halogen and $C_{1-4}$ haloalkyl;
or a pharmaceutically acceptable salt thereof.

In an embodiment 10.1 of the invention, there is provided a compound or salt according to embodiment 9.1, wherein $R^3$ is selected from propyl, butyl and pentyl substituted with 1 to 3 substituents independently selected from hydroxy, $C_{1-4}$ alkyl, halogen, —$NR^{3a}R^{3b}$ and oxo.

In an embodiment 11 of the invention, there is provided a compound according to any one of embodiments 1 to 7, wherein $R^3$ is selected from
(i) $C_{1-4}$ alkyl which is substituted with 1 to 3 substituents independently selected from hydroxyl, halogen and $C_{1-4}$ alkyl;
(ii) $C_{1-4}$ alkoxy which is unsubstituted or substituted with 1 to 3 substituents independently selected from hydroxyl, halogen and $C_{1-4}$ alkyl;
(iii) —O—($C_{0-3}$ alkyl)-$C_{3-7}$ heterocyclyl wherein the $C_{3-7}$ heterocyclyl contains at least one heteroatom selected from O and N, and wherein said $C_{3-7}$ heterocyclyl is unsubstituted or substituted with 1 to 3 substituents independently selected from $C_{1-4}$ alkyl, hydroxy, $C_{1-4}$ hydroxyalkyl, halogen and $C_{1-4}$ haloalkyl;
(iv) —O—($C_{0-3}$ alkyl)-$C_{3-7}$ cycloalkyl wherein the $C_{3-7}$ cycloalkyl is unsubstituted or substituted with 1 to 3 substituents independently selected from $C_{1-4}$ alkyl, hydroxy, $C_{1-4}$ hydroxyalkyl, halogen and $C_{1-4}$ haloalkyl;
or a pharmaceutically acceptable salt thereof.

In an embodiment 11.1 of the invention, there is provided a compound or salt according to embodiment 9.1, wherein $R^3$ is selected from 3-hydroxypropyl-;
3-hydroxy-2,2-dimethylpropyl-;
3-hydroxy-3-methylbutyl-;
2-hydroxy-2-methylpropyl-;
4,4,4-trifluoro-3-hydroxybutyl-;
2,2-difluoroethyl-;
3,3-dimethyl-2-oxo-butyl; and
3,3,3-trifluoro-2-hydroxy-2-methylpropyl-.

In an embodiment 12 of the invention, there is provided a compound according to any one of embodiments 1 to 7, wherein
$R^3$ is selected from
(i) $C_{1-4}$ alkyl which is substituted with 1 to 3 substituents independently selected from hydroxyl, halogen and $C_{1-4}$ alkyl;
(ii) $C_{1-4}$ alkoxy which is unsubstituted or substituted with 1 to 3 substituents independently selected from hydroxyl and $C_{1-4}$ alkyl;
or a pharmaceutically acceptable salt thereof.

In an embodiment 12.1 of the invention, there is provided a compound or salt according to embodiment 11.1, wherein $R^3$ is selected from 3-hydroxypropyl-;
3-hydroxy-2,2-dimethylpropyl-;
2-hydroxy-2-methylpropyl; and
3-hydroxy-3-methylbutyl-.

In an embodiment 13 of the invention, there is provided a compound according to any one of embodiments 1 to 7, wherein
$R^3$ is selected from

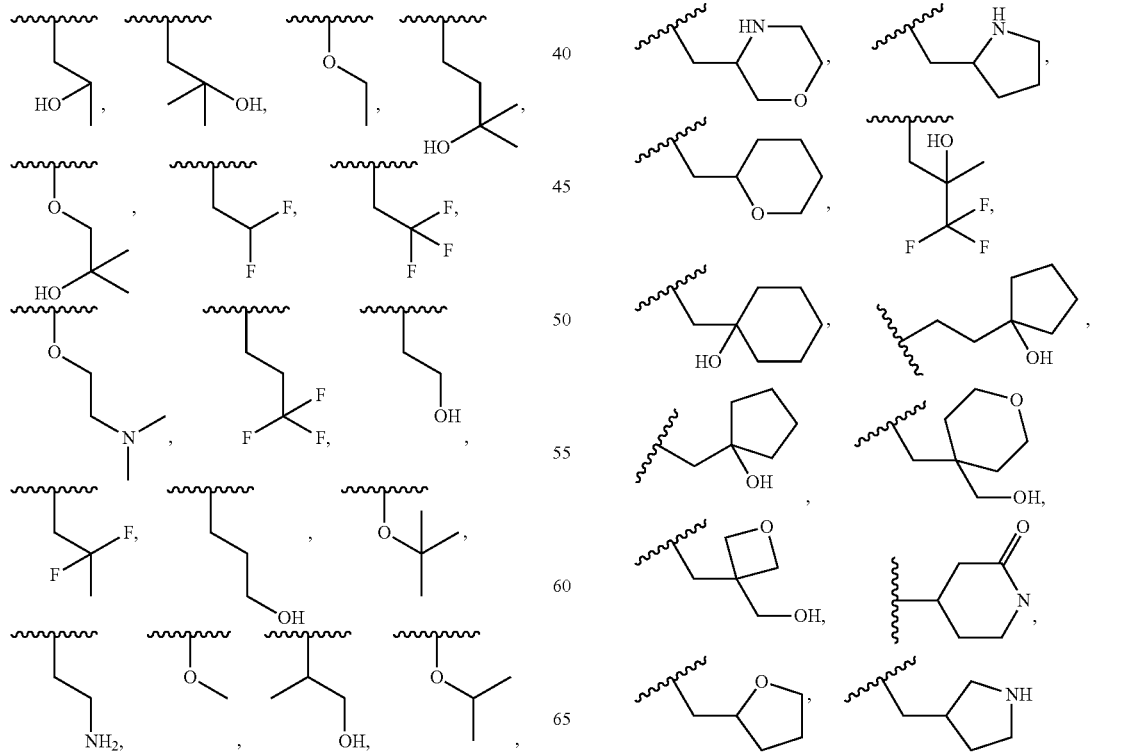

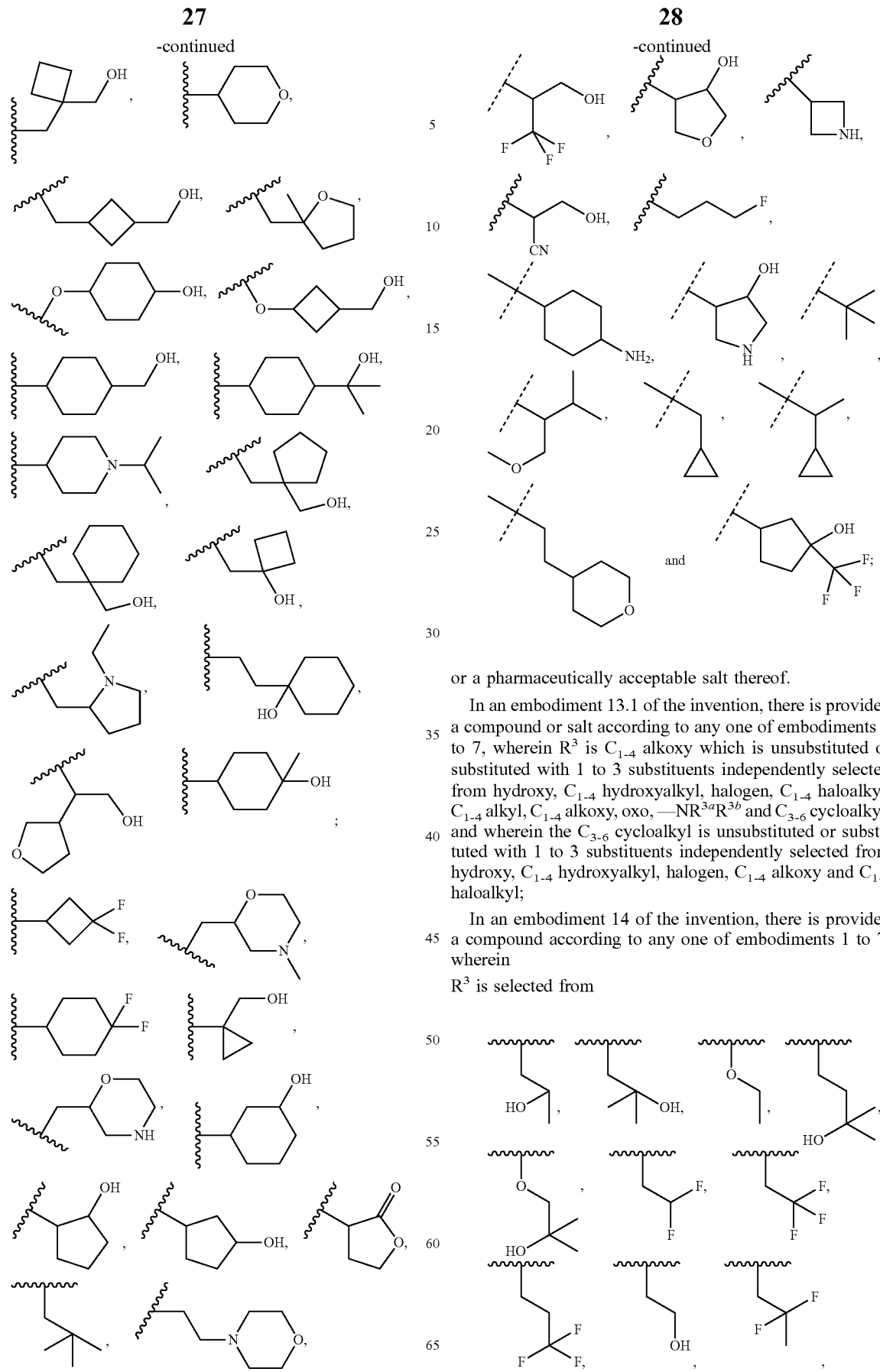

or a pharmaceutically acceptable salt thereof.

In an embodiment 13.1 of the invention, there is provided a compound or salt according to any one of embodiments 1 to 7, wherein $R^3$ is $C_{1-4}$ alkoxy which is unsubstituted or substituted with 1 to 3 substituents independently selected from hydroxy, $C_{1-4}$ hydroxyalkyl, halogen, $C_{1-4}$ haloalkyl, $C_{1-4}$ alkyl, $C_{1-4}$ alkoxy, oxo, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl;

In an embodiment 14 of the invention, there is provided a compound according to any one of embodiments 1 to 7, wherein $R^3$ is selected from

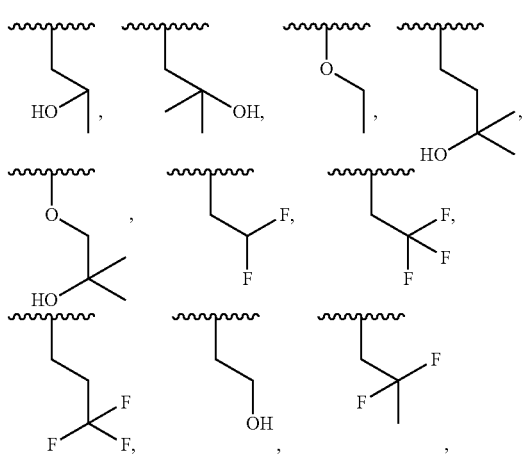

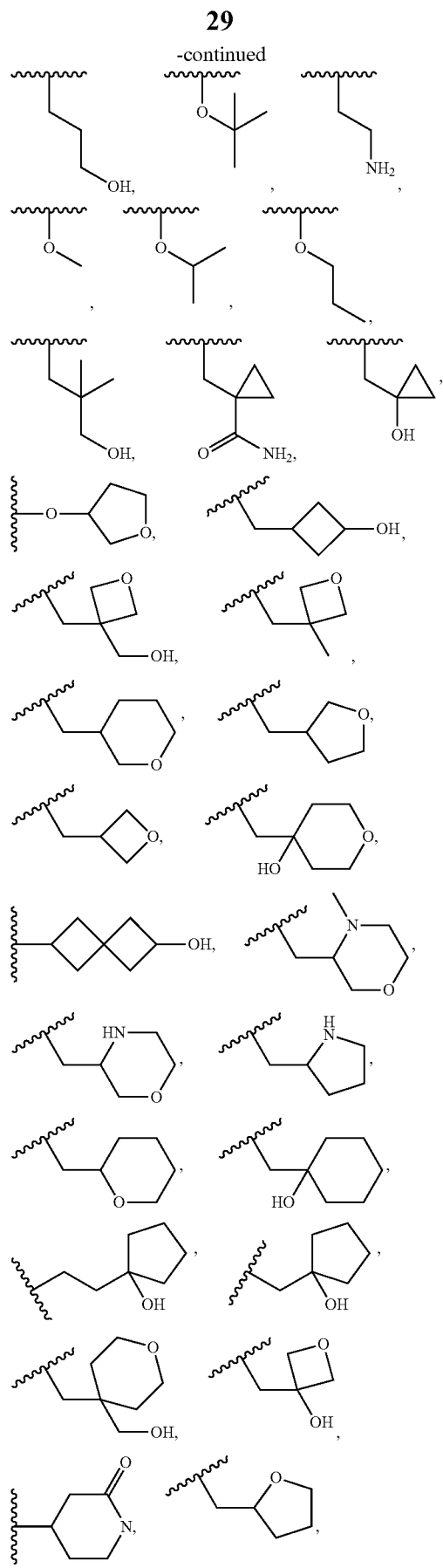
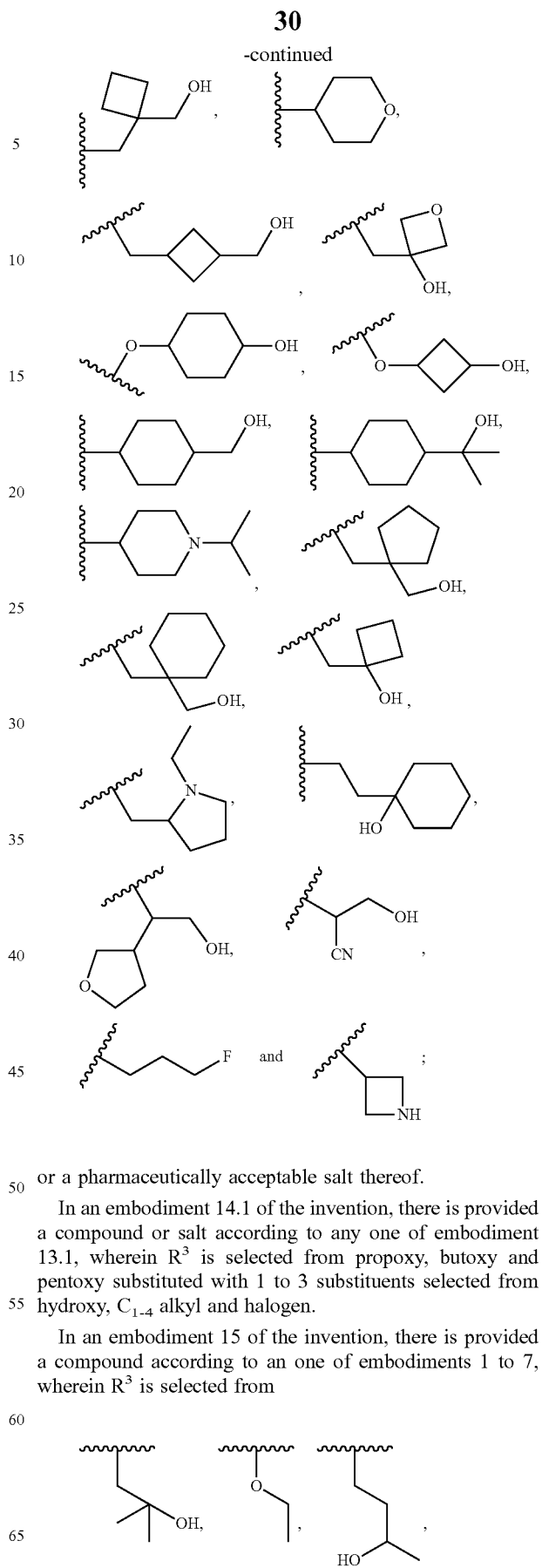

or a pharmaceutically acceptable salt thereof.

In an embodiment 14.1 of the invention, there is provided a compound or salt according to any one of embodiment 13.1, wherein $R^3$ is selected from propoxy, butoxy and pentoxy substituted with 1 to 3 substituents selected from hydroxy, $C_{1-4}$ alkyl and halogen.

In an embodiment 15 of the invention, there is provided a compound according to an one of embodiments 1 to 7, wherein $R^3$ is selected from -continued

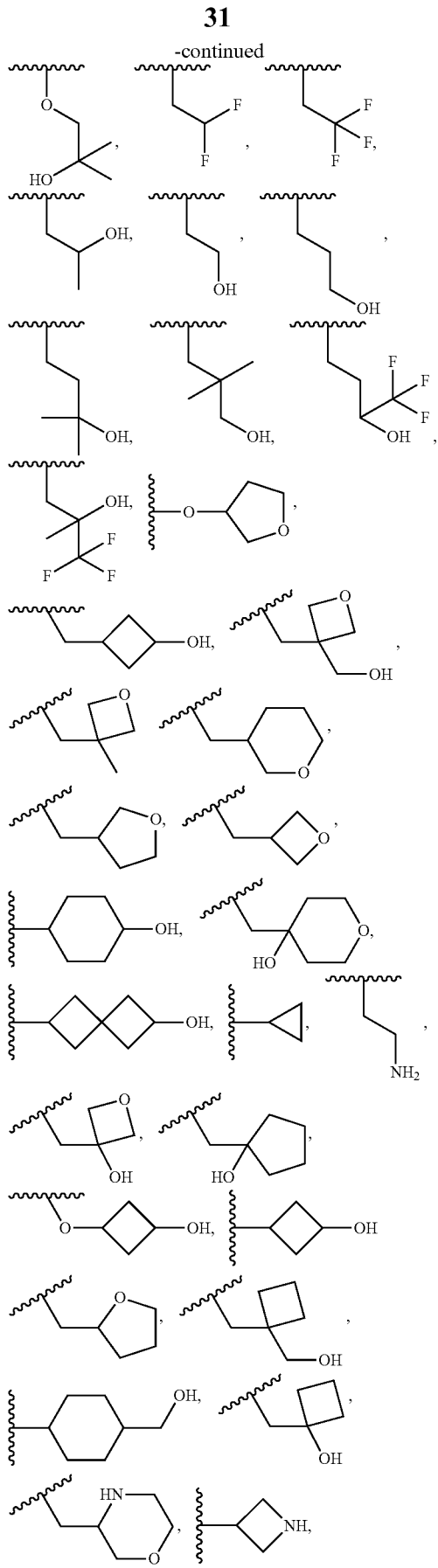

-continued

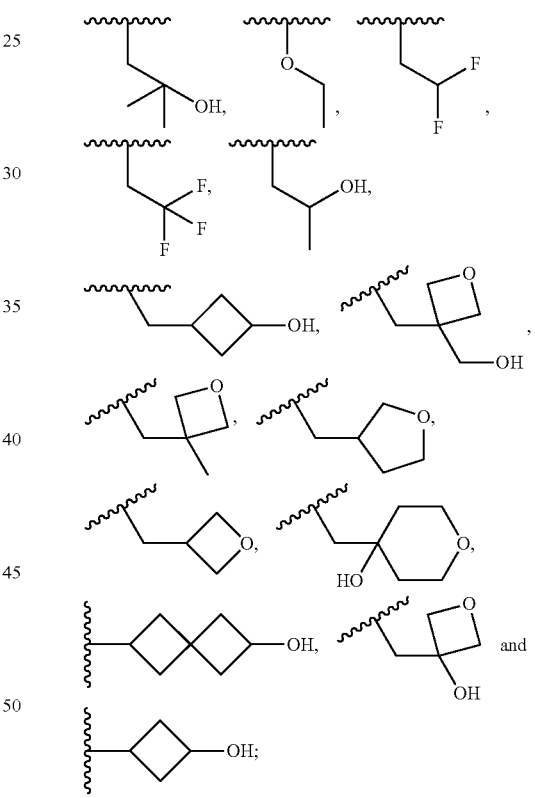

or a pharmaceutically acceptable salt thereof.

In an embodiment 15.1 of the invention, there is provided a compound or salt according to any one of embodiment 14.1, wherein $R^3$ is 2-hydroxy-2-methylpropoxy-.

In an embodiment 16 of the invention, there is provided a compound according to an one of embodiments 1 to 7, wherein $R^3$ is selected from or a pharmaceutically acceptable salt thereof.

In an embodiment 16.1 of the invention, there is provided a compound or salt according to any one of embodiments 1 to 7, wherein $R^3$ is $C_{3-6}$ cycloalkyl or —O—$C_{3-6}$ cycloalkyl wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy, $C_{1-4}$ haloalkyl and —($C_{0-3}$ alkyl)-$NR^{3a}R^{3b}$.

In an embodiment 17 of the invention, there is provided a compound according to any one of embodiments 1 to 7, wherein $R^3$ is selected from

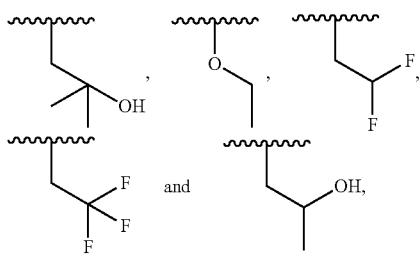

or a pharmaceutically acceptable salt thereof.

In an embodiment 17.1 of the invention, there is provided a compound or salt according to embodiment 16.1, wherein $R^3$ is selected from ($C_{0-3}$ alkyl)-cyclohexyl, —($C_{0-3}$ alkyl)-cyclobutyl and —($C_{0-3}$ alkyl)-cyclopropyl, and wherein the cyclohexyl, cyclobutyl and cyclopropyl are substituted with 1 or 2 substituents independently selected from hydroxy, $C_{1-4}$ hydroxyalkyl and halogen.

In an embodiment 18 of the invention, there is provided a compound according to any one of embodiments 1 to 7, wherein
$R^3$ is selected from

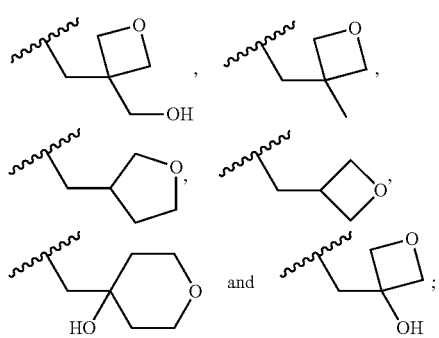

or a pharmaceutically acceptable salt thereof.

In an embodiment 18.1 of the invention, there is provided a compound or salt according to embodiment 17.1, wherein $R^3$ is selected from
4-hydroxycyclohexyl-;
3-hydroxycyclobutyl-methyl-;
1-hydroxycyclobutyl-methyl-;
1-(hydroxymethyl)cyclopropyl; and
1-hydroxycyclopropyl-methyl-.

In an embodiment 19 of the invention, there is provided a compound according to any one of embodiments 1 to 7, wherein
$R^3$ is selected from

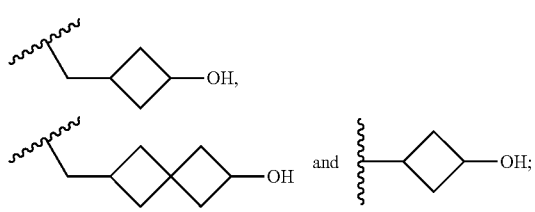

or a pharmaceutically acceptable salt thereof.

In an embodiment 19.1 of the invention, there is provided a compound or salt according to embodiment 17.1, wherein $R^3$ is selected from 4-hydroxycyclohexyl-.

In an embodiment 20 of the invention, there is provided a compound according to any one of embodiments 1 to 7, wherein
$R^3$ and $R^4$ together with the nitrogen atom to which they are attached form a ring selected from

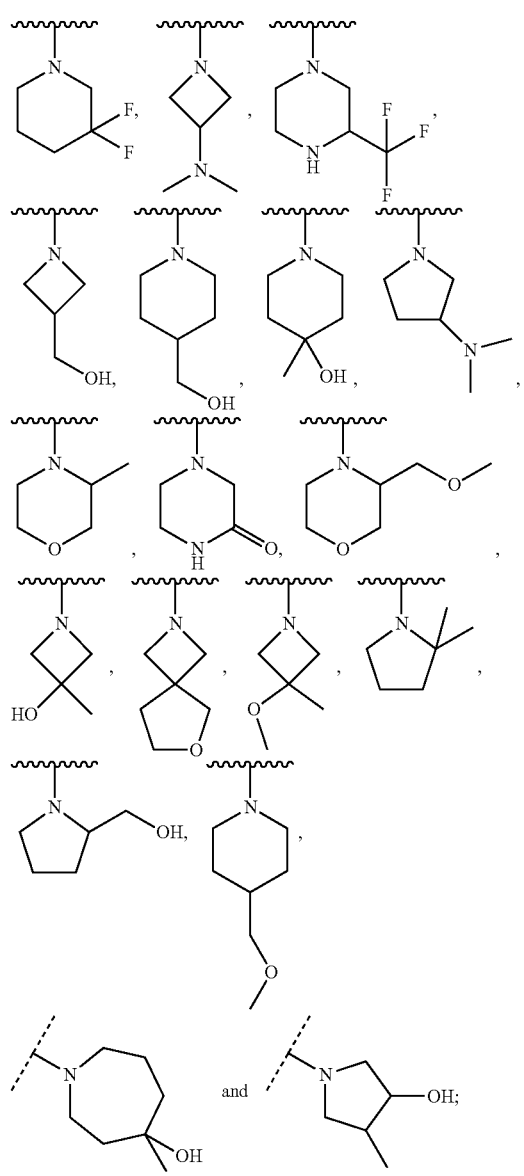

or a pharmaceutically acceptable salt thereof.

In an embodiment 20.1 of the invention, there is provided a compound or salt according to any one of embodiments 1 to 7, wherein $R^3$ is —($C_{0-3}$ alkyl)-$C_{3-6}$ cycloalkyl or —(O—$C_{0-3}$ alkyl)-$C_{3-6}$ cycloalkyl spiro fused to a second $C_{3-6}$ cycloalkyl or $C_{3-6}$ heterocyclyl by one single carbon atom, wherein the $C_{3-6}$ cycloalkyl or $C_{3-6}$ heterocyclyl is unsubstituted or substituted with 1 to 3 substituents independently selected from hydroxy, $C_{1-4}$ hydroxyalkyl, halogen, $C_{1-4}$ alkoxy, $C_{1-4}$ haloalkyl and —($C_{0-3}$ alkyl)-$NR^{3a}R^{3b}$.

In an embodiment 21 of the invention, there is provided a compound or salt according to embodiment 20.1, wherein R³ is selected from spiro[3.3]heptan-2-yl, spiro[3.4]octan-6-yl, spiro[4.4]nonan-2-yl and spiro[3.4]undecan-3-yl, which is substituted with 1 to 3 substituents selected from hydroxy and halogen.

In an embodiment 22 of the invention, there is provided a compound or salt according to embodiment 21, wherein R³ is 6-hydroxyspiro[3.3]heptan-2-yl.

In an embodiment 23 of the invention, there is provided a compound or salt according to any one of embodiments 1 to 7, wherein R³ is —($C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from hydroxy, $C_{1-4}$ alkyl and $C_{1-4}$ hydroxyalkyl;
or —($C_{0-3}$ alkyl)-$C_{3-6}$ heterocyclyl or —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is spiro fused to a second $C_{3-6}$ heterocyclyl or a $C_{3-6}$ cycloalkyl by one single carbon atom, and wherein the $C_{3-6}$ heterocyclyl or $C_{3-6}$ cycloalkyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$.

In an embodiment 24 of the invention, there is provided a compound or salt according to embodiment 23, wherein R³ is selected from a —($C_{0-3}$ alkyl)-tetrahydrofuranyl, —($C_{0-3}$ alkyl)-oxetanyl, —($C_{0-3}$ alkyl)-pyrrolidinyl, and —($C_{0-3}$ alkyl)-tetrahydropyranyl, each of which is unsubstituted or substituted with 1 to 3 substituents independently selected from hydroxy, 4 alkyl and $C_{1-4}$ hydroxyalkyl.

In an embodiment 25 of the invention, there is provided a compound or salt according to embodiment 24, wherein R³ is selected from
(1-ethylpyrrolidin-2-yl)methyl,
(tetrahydro-2H-pyran-4-yl,
(3-hydroxyoxetan-3-yl)methyl,
(3-methyloxetan-3-yl)methyl,
(4-hydroxy-tetrahydropyran)methyl,
(3-hydroxymethyl-oxetan-3-yl)methyl, and
(tetrahydrofuran-3-yl)methyl.

In an embodiment 26 of the invention, there is provided a compound or salt according to any one of embodiment 1 to 25, wherein R⁴ is H or methyl.

In an embodiment 27 of the invention, there is provided a compound or salt according to any one of embodiment 1 to 7, wherein R³ and R⁴ together with the nitrogen atom to which they are attached form a $C_{3-6}$ heterocyclyl, which heterocyclyl is unsubstituted or substituted with 1 to 3 substituents independently selected from $C_{1-4}$ alkyl, hydroxy, $C_{1-4}$ hydroxyalkyl, halogen, $C_{1-4}$ alkoxy and $C_{1-4}$ haloalkyl.

In an embodiment 28 of the invention, there is provided a compound or salt according to embodiment 27, wherein R³ and R⁴ together with the nitrogen atom to which they are attached form a piperazinyl, piperidinyl, or azetidinyl, which are unsubstituted or substituted with 1 to 3 substituents independently selected from hydroxy, $C_{1-4}$ hydroxyalkyl and $C_{1-4}$ alkyl.

In an embodiment 29 of the invention, there is provided a compound or salt according to embodiment 28, wherein R³ and R⁴ together with the nitrogen atom to which they are attached form a
3-(trifluoromethyl)piperazin-1-yl,
3,3-difluoropiperidin-1-yl, or
1-(hydroxymethyl)azetidin-3-yl.

In an embodiment 30 of the invention, there is provided a compound or salt according to any one of embodiment 1 to 29, wherein Y is selected from
thiazolyl,
pyrazolyl,
pyridyl,
triazolyl,
imidazolyl,
oxadiazolyl,
pyrimidinyl,
isoxazolyl,
oxazolyl, and
thienyl;
each of which is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy, halogen, —$NR^{3a}R^{3b}$, —($C_{0-3}$ alkyl)-$C_{3-6}$ cycloalkyl and —($C_{0-3}$ alkyl)-$C_{3-6}$ heterocyclyl.

In an embodiment 31 of the invention, there is provided a compound or salt according to embodiment 30, wherein Y is selected from
thiazol-5-yl,
pyrazol-4-yl,
pyrazol-5-yl,
pyrazol-1-yl,
pyrid-4-yl,
pyrid-3-yl,
1,2,4-triazol-1-yl,
1,2,3-triazol-4-yl,
imidazol-1-yl,
1,2,4-oxadiazol-5-yl,
1,3,4-oxadiazol-2-yl,
isoxazol-5-yl,
pyrimidin-5-yl,
thien-3-yl,
each of which is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy and —($C_{0-3}$ alkyl)-$C_{3-6}$ cycloalkyl.

In an embodiment 32 of the invention, there is provided a compound or salt according to embodiment 31, wherein Y is selected from
thiazol-5-yl,
pyrazol-4-yl,
pyrazol-5-yl,
pyrazol-1-yl,
pyrid-4-yl,
pyrid-3-yl,
1,2,4-triazol-1-yl,
1,2,3-triazol-4-yl,
imidazol-1-yl,
1,2,4-oxadiazol-5-yl,
isoxazol-5-yl,
pyrimidin-5-yl,
thien-3-yl,
each of which is unsubstituted or substituted with 1 to 3 substituents independently selected from methyl, ethyl, propyl, isopropyl, cyclopropyl, $CF_3$, hydroxyethyl, methoxyethyl and methoxy.

In an embodiment 33 of the invention, there is provided a compound or salt according to embodiment 30, wherein Y is selected from
5-morpholin-4-ylmethyl-thien-3-yl,
3-cyclopropyl-[1,2,4]triazol-1-yl,
2-cyclopropyl-thiazol-5-yl,
2,5-dimethyl-2H-[1,2,3]triazol-4-yl,
2-methylthiazol-5-yl, 1,3-dimethyl-1H-pyrazol-4-yl,
1,2,4-triazol-1-yl,
3-isopropyl-1,2,4-oxadiazol-5-yl,
1-methyl-1H-pyrazol-4-yl,
1H-pyrazol-1-yl,
3-ethyl-1,2,4-oxadiazol-5-yl,
2-methyl-2H-1,2,3-triazol-4-yl,
1H-pyrazol-4-yl,
3-methylisoxazol-5-yl,
2-methylpyridin-4-yl)pyrazin-2-yl,
1H-1,2,4-triazol-1-yl,
3-propyl-1,2,4-oxadiazol-5-yl,
pyrimidin-5-yl,
3-methyl-1H-1,2,4-triazol-1-yl,
5-methyl-1,3,4-oxadiazol-2-yl,
1-methyl-1H-pyrazol-5-yl,
pyrid-3-yl,
pyrid-4-yl,
2-methyl-pyrid-4-yl,
3-methyl-1,2,4-oxadiazol-5-yl,
2-methylthiazol-4-yl,
4-methyl-1H-imidazol-1-yl,
1-ethyl-1H-pyrazol-4-yl,
3,5-dimethyl-1H-pyrazol-1-yl,
3-cyclopropyl-1,2,4-oxadiazol-5-yl,
3-methylisoxazol-5-yl,
1-isopropyl-1H-pyrazol-4-yl,
1H-1,2,4-triazol-1-yl,
1-propyl-1H-pyrazol-4-yl,
4-methoxypyridin-3-yl,
pyrazol-3-yl,
3-methylisoxazol-5-yl, and
1-(2-methoxyethyl)-1H-pyrazol-4-yl.

In an embodiment 34 of the invention, there is provided a compound or salt according to any one of embodiment 1 to 29, wherein Y is selected from
thiazolyl,
pyrazolyl,
pyridyl, and
triazolyl,
each of which is unsubstituted or substituted with 1 to 3 substituents independently selected from $C_{1-4}$ alkyl, $C_{1-4}$ haloalkyl, $C_{1-4}$ alkoxy, $C_{1-4}$ haloalkoxy, —($C_{0-3}$ alkyl)-$C_{3-6}$ cycloalkyl and ($C_{0-3}$ alkyl)-$C_{3-6}$ heterocyclyl.

In an embodiment 35 of the invention, there is provided a compound or salt according to embodiment 34, wherein Y is selected from
thiazol-5-yl,
pyrazol-4-yl,
pyrazol-5-yl,
pyrazol-1-yl,
pyrid-4-yl,
pyrid-3-yl,
1,2,4-triazol-1-yl,
1,2,3-triazol-4-yl,
each of which is unsubstituted or substituted with 1 or 2 substituents independently selected from methyl, ethyl, propyl and isopropyl.

In an particular embodiment 36 of the invention, there is provided a compound of formula (I)

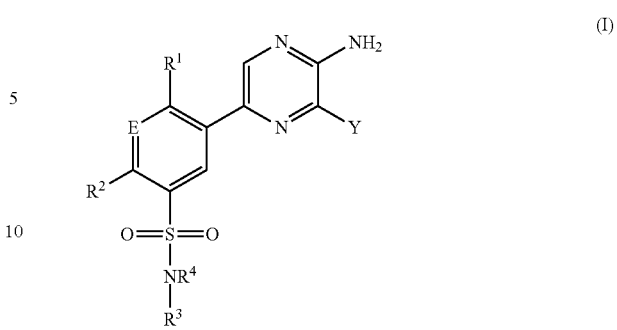

wherein

E is selected from N and $CR^E$;

$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy, $C_{1-4}$ hydroxyalkyl and $C_{3-7}$ cycloalkyl;

Y is selected from the group consisting of

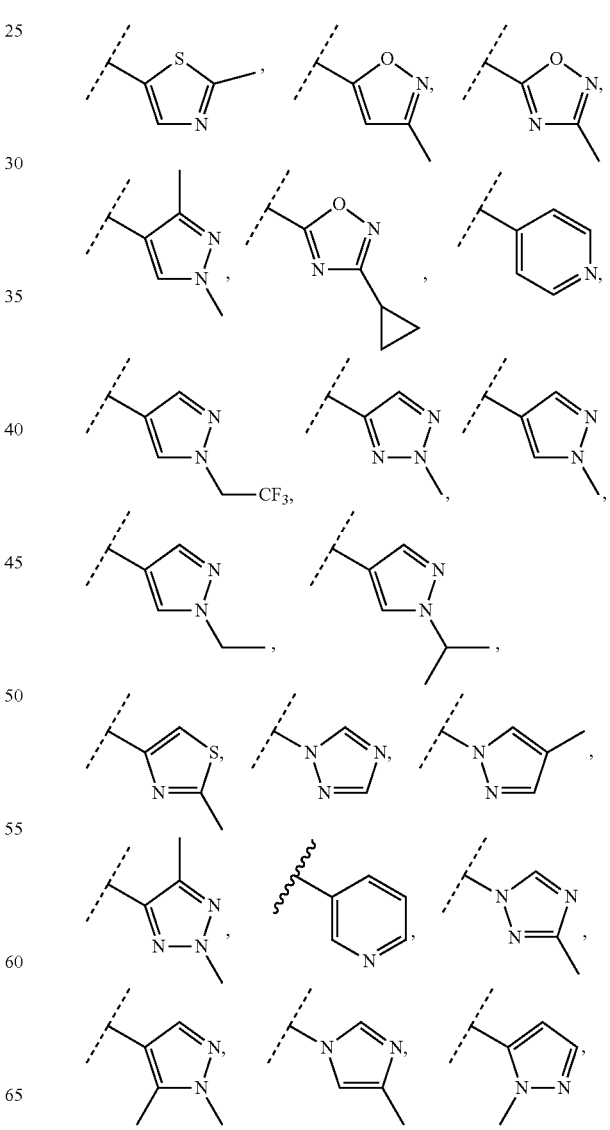

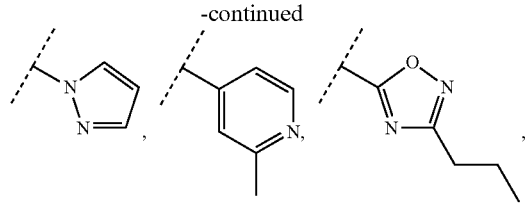
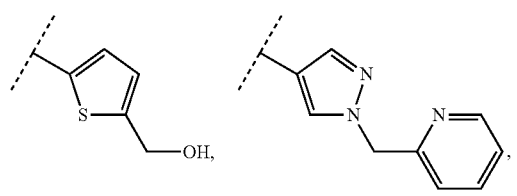
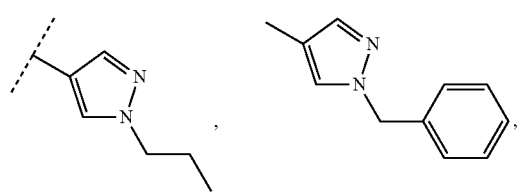
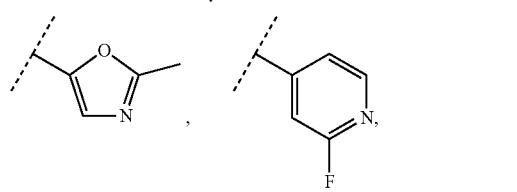
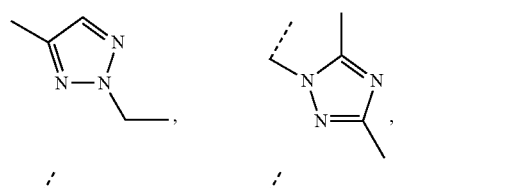
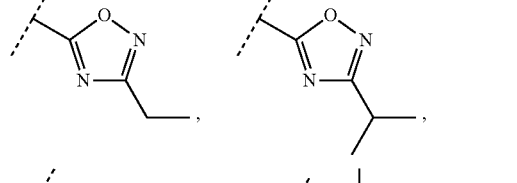
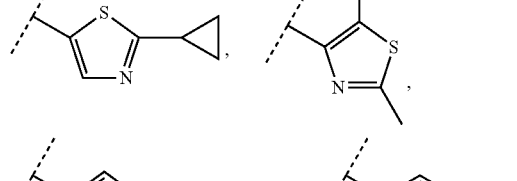
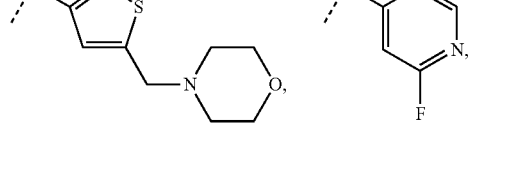
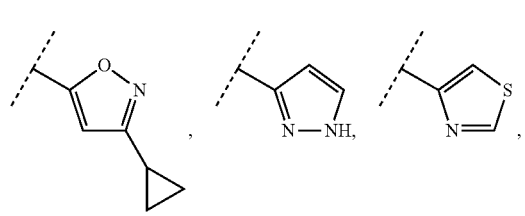
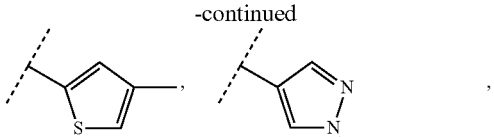
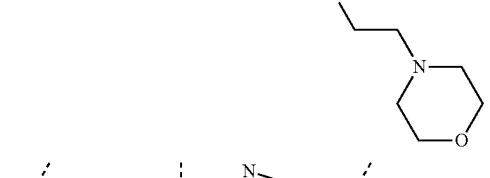
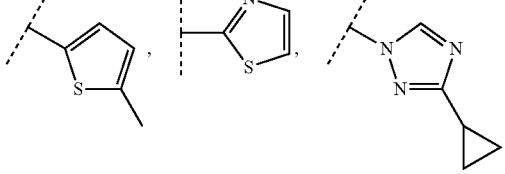
$R^4$ is H and $R^3$ is selected from the group consisting of
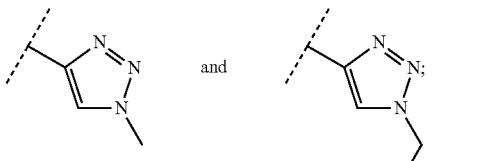
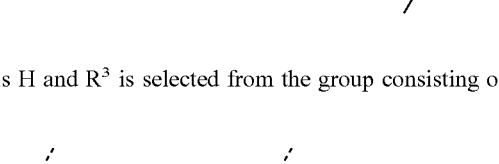
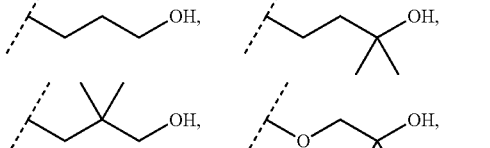

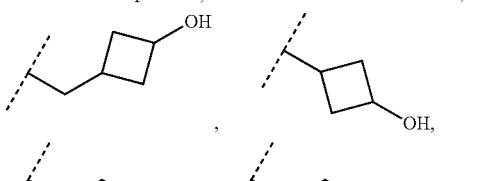
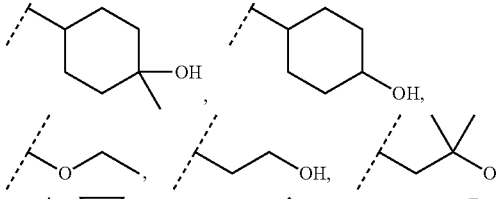
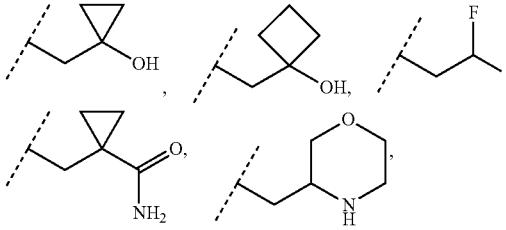

-continued

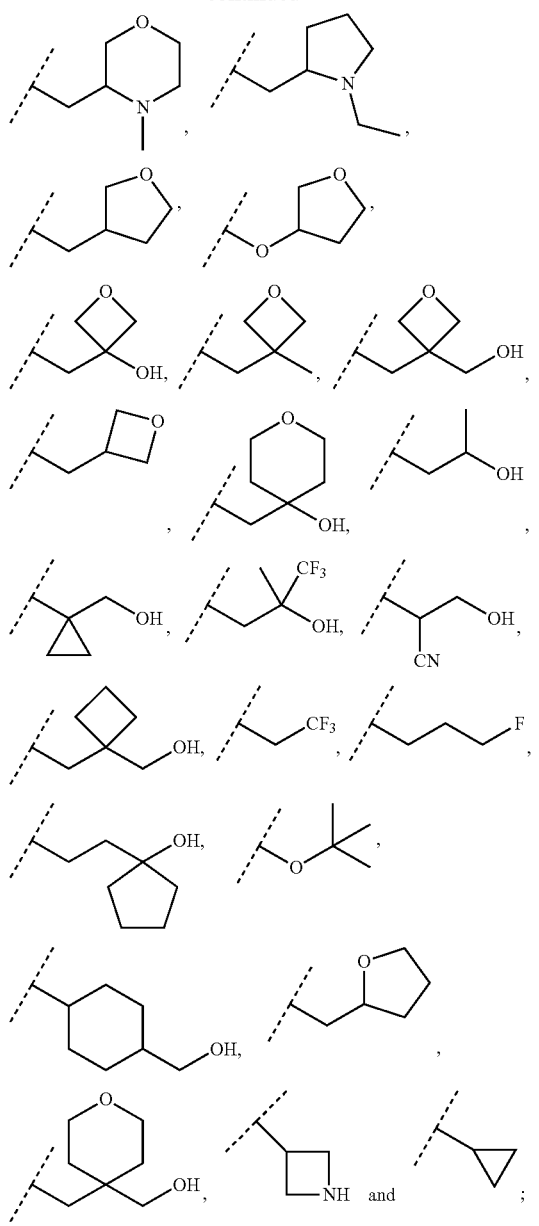

or R³ and R⁴ together with the nitrogen atom to which they are attached form a $C_{3-7}$ heterocyclyl selected from the group consisting of

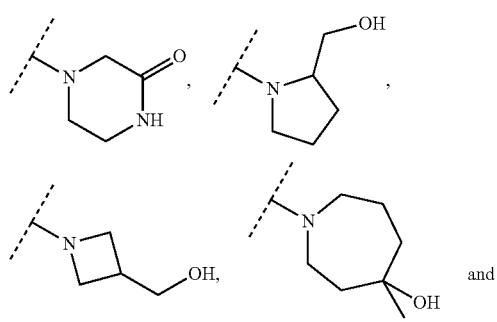

-continued

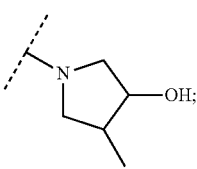

or a pharmaceutically acceptable salt thereof.

In a further particular embodiment 37 of the invention, there is provided a compound of formula (Ib)

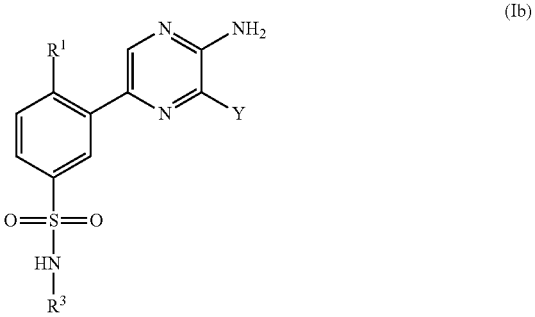

(Ib)

wherein

R¹ is H or $C_{1-4}$ alkyl, particularly $C_{1-4}$ alkyl, more particularly methyl;

Y is selected from the group consisting of

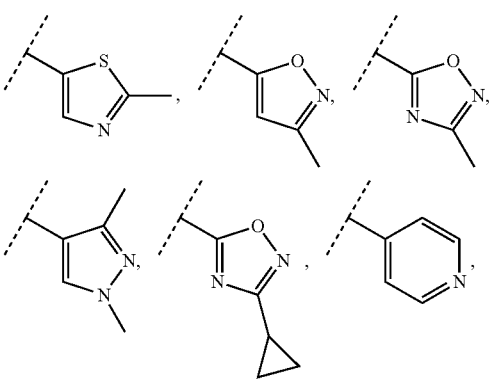

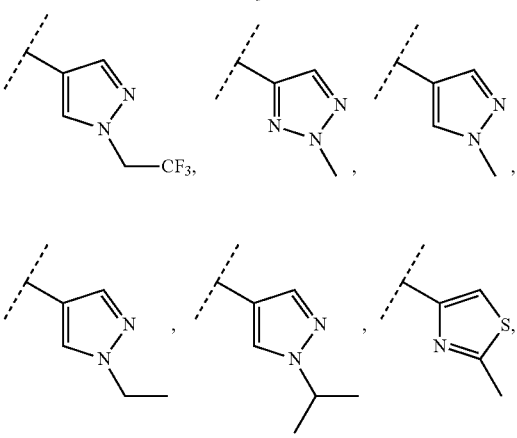

43
-continued
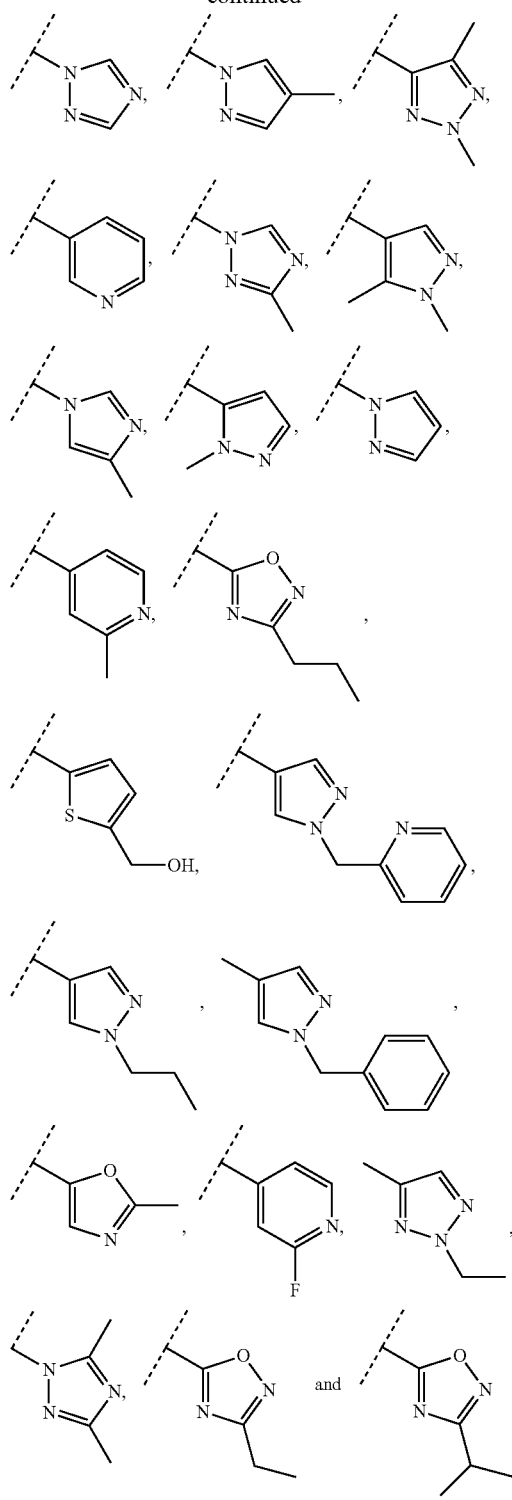
R³ is selected from the group consisting of
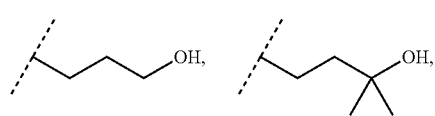
44
-continued
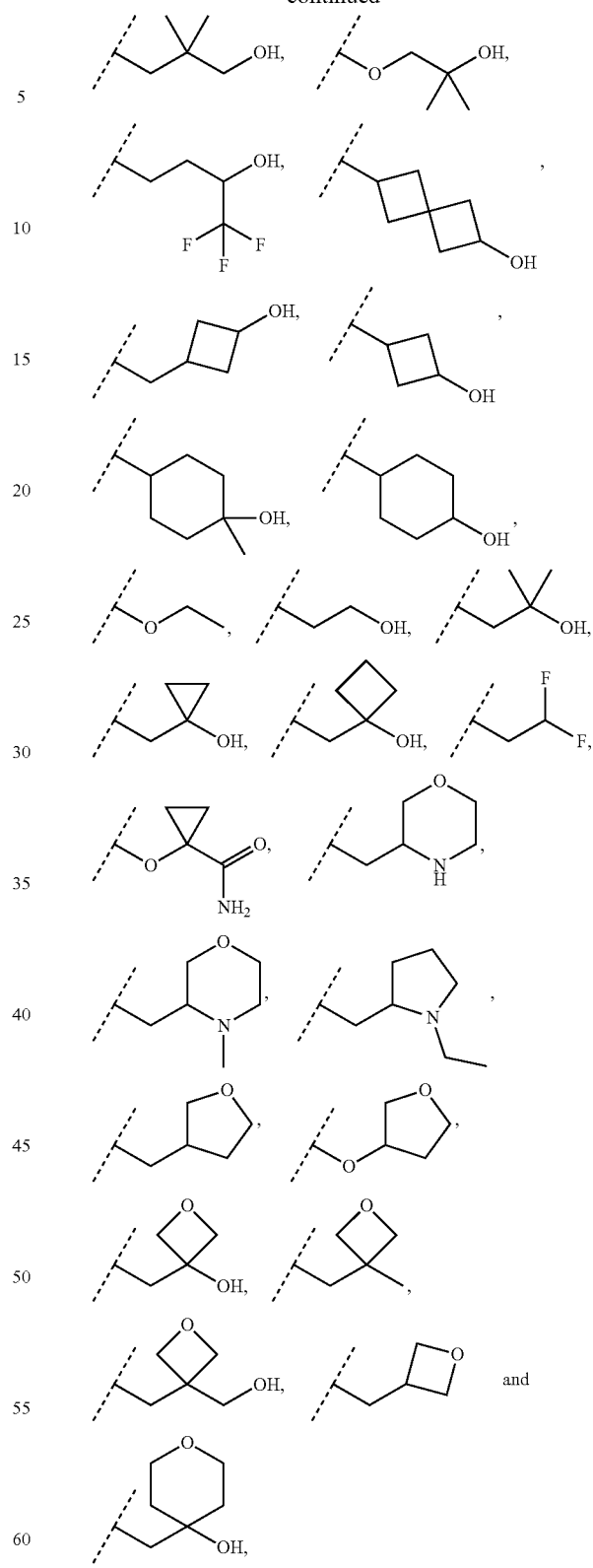
or a pharmaceutically acceptable salt thereof.
In a further particular embodiment 38 of the invention, there is provided a compound of formula (Ib)

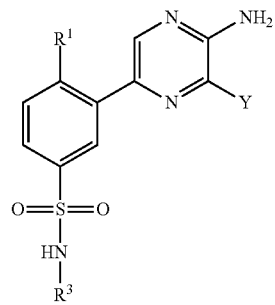
(Ib)
wherein
R[1] is H or C$_{1-4}$ alkyl, particularly C$_{1-4}$ alkyl, more particularly methyl;
Y is selected from the group consisting of
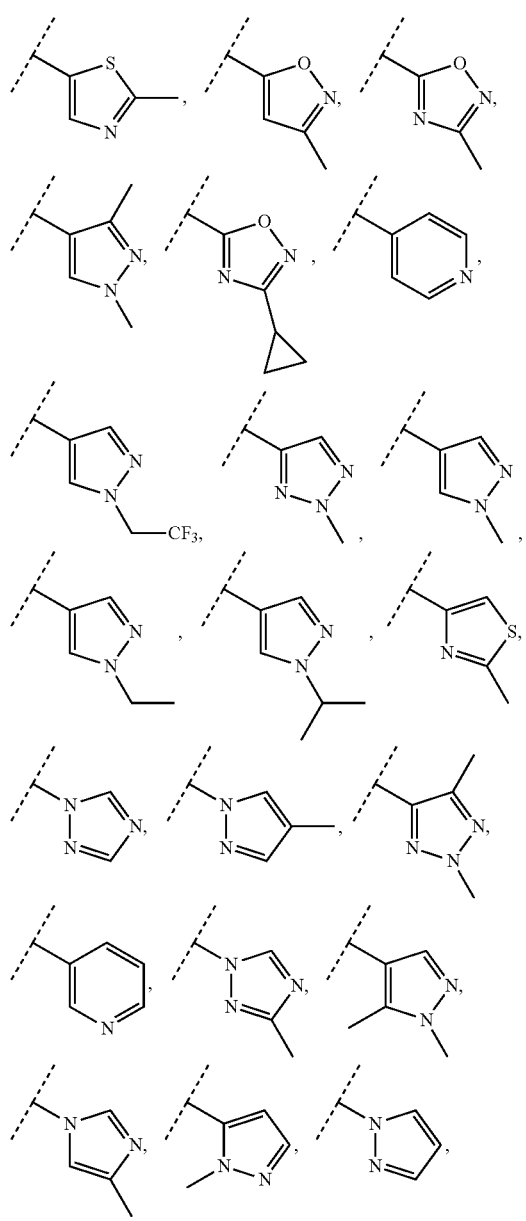
R[3] is selected from the group consisting of
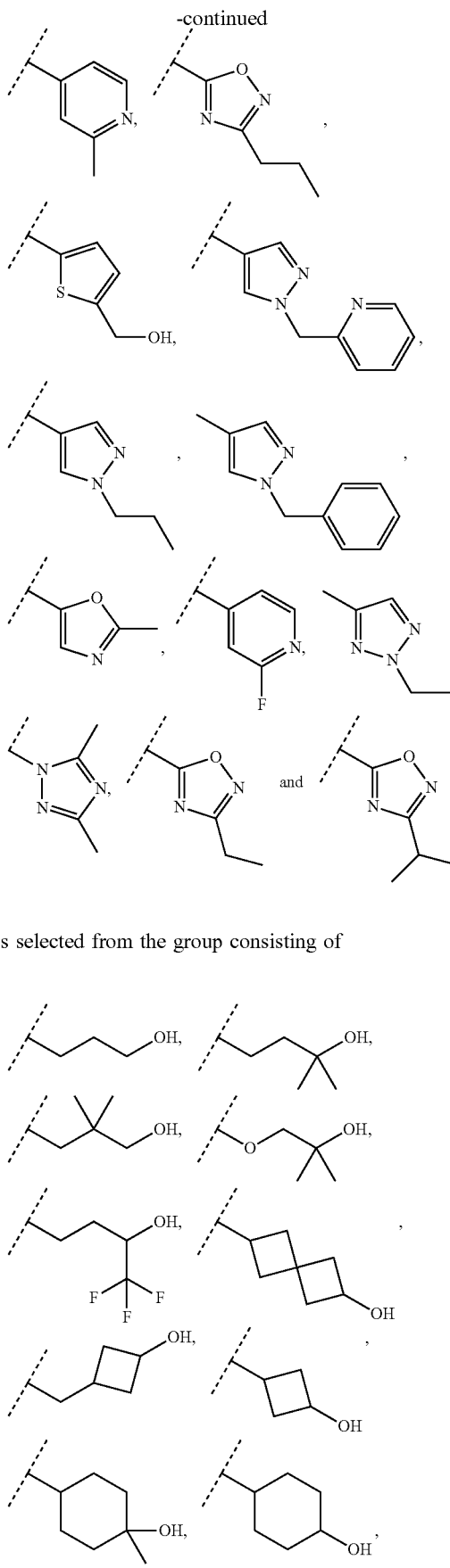

-continued
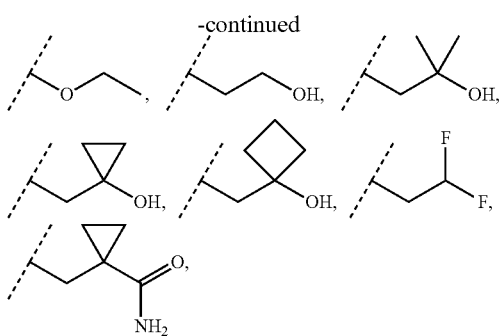
or a pharmaceutically acceptable salt thereof.
In another particular embodiment 39 of the invention, there is provided a compound of formula (Ib)
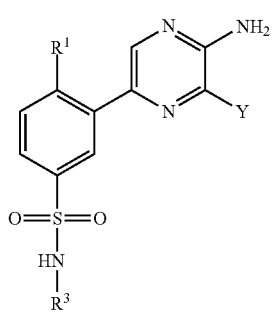
(Ib)
wherein
R¹ is H or $C_{1-4}$ alkyl, particularly $C_{1-4}$ alkyl, more particularly methyl;
Y is selected from the group consisting of
-continued
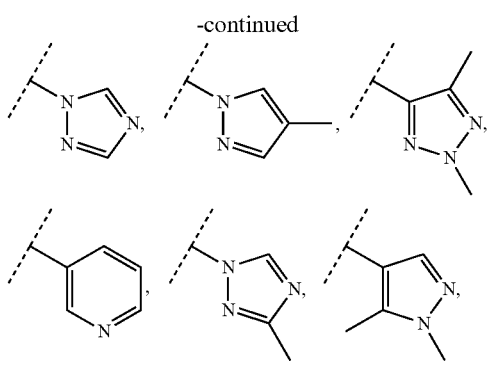
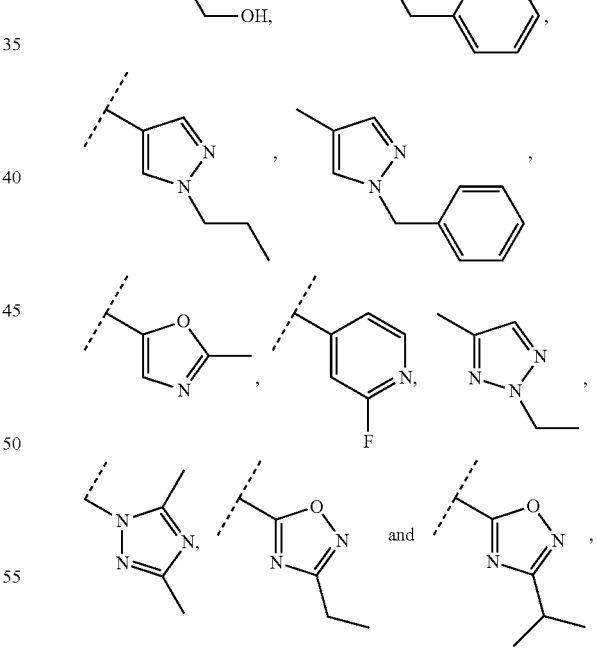
and
R³ is selected from the group consisting of
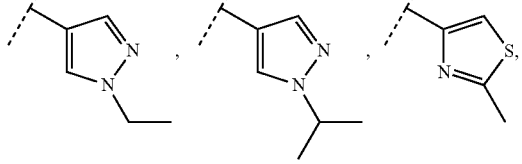

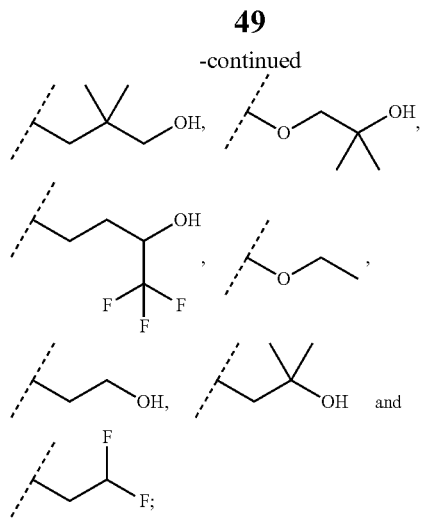
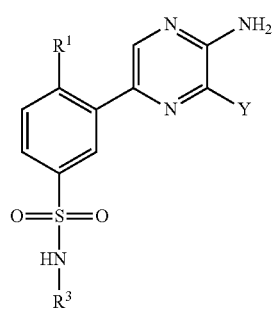
or a pharmaceutically acceptable salt thereof.
In another particular embodiment 40 of the invention, there is provided a compound of formula (Ib)
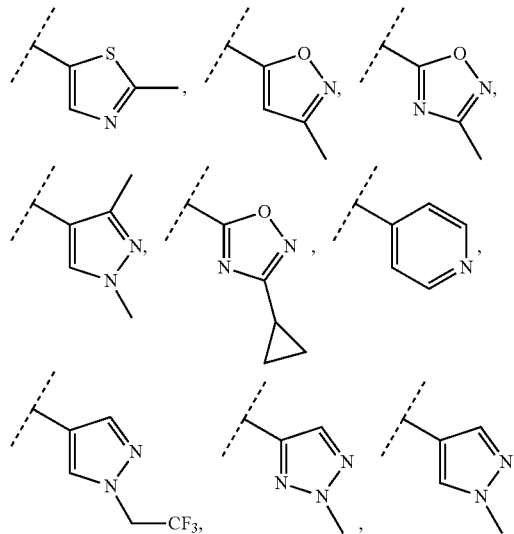
wherein
R[1] is H or $C_{1-4}$ alkyl, particularly $C_{1-4}$ alkyl, more particularly methyl;
Y is selected from the group consisting of
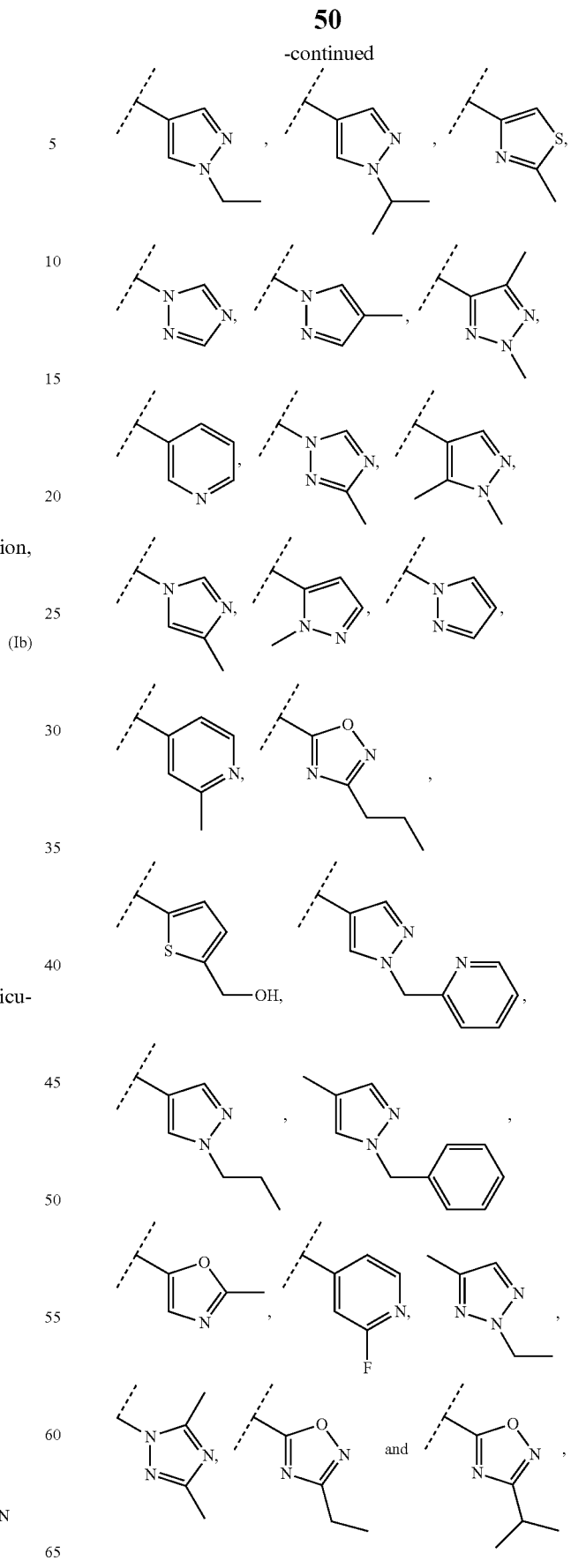

R³ is selected from the group consisting of
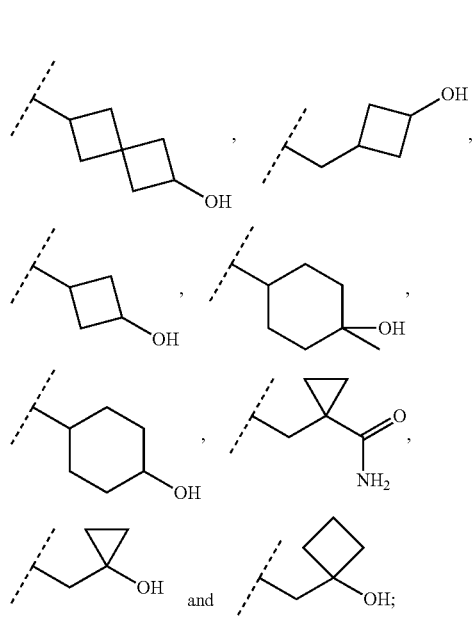
and
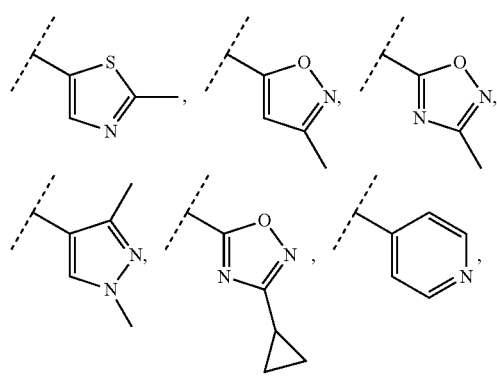
or a pharmaceutically acceptable salt thereof.
In another particular embodiment 41 of the invention, there is provided a compound of formula (Ib)
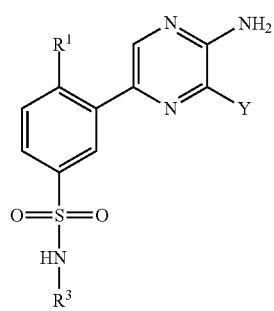
(Ib)
wherein
R¹ is H or $C_{1-4}$ alkyl, particularly $C_{1-4}$ alkyl, more particularly methyl;
Y is selected from the group consisting of
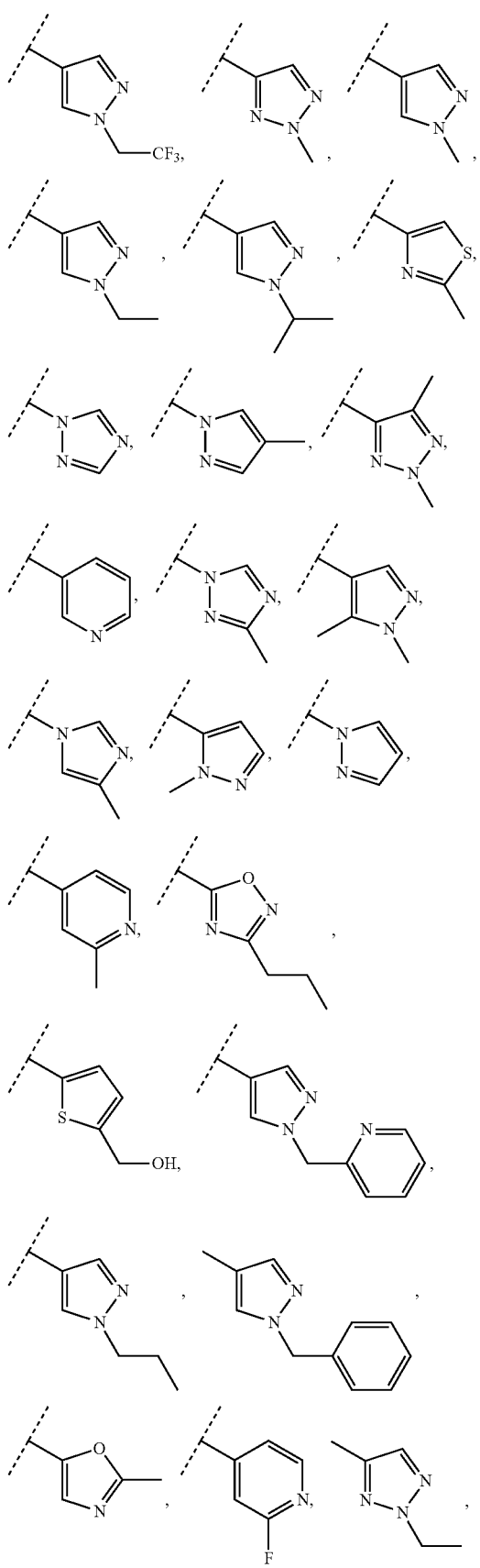

-continued

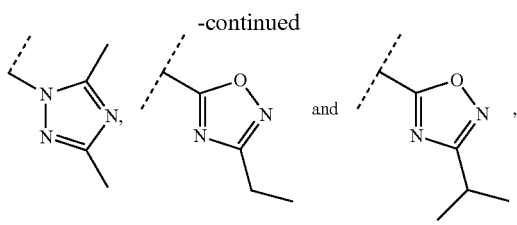

$R^3$ is selected from the group consisting of

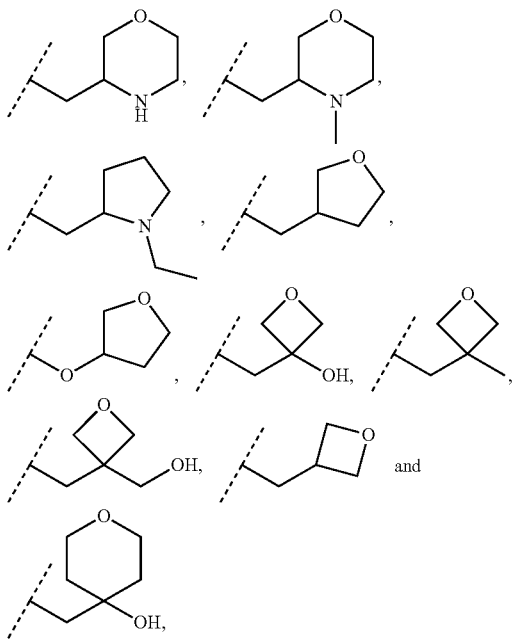

or a pharmaceutically acceptable salt thereof.

In an embodiment 42 of the invention, there is provided a compound according to embodiment 1 selected from 3-[5-Amino-6-(5-methyl-[1,3,4]oxadiazol-2-yl)-pyrazin-2-yl]-N-(4-hydroxy-cyclohexyl)-4-methyl-benzenesulfonamide;

3-[5-Amino-6-(3-methyl-[1,2,4]oxadiazol-5-yl)-pyrazin-2-yl]-N-(4-hydroxy-cyclohexyl)-4-methyl-benzenesulfonamide;

3-[5-Amino-6-(3-methyl-[1,2,4]oxadiazol-5-yl)-pyrazin-2-yl]-N-(3-hydroxy-3-methyl-butyl)-4-methyl-benzenesulfonamide;

3-[5-Amino-6-(3-methyl-isoxazol-5-yl)-pyrazin-2-yl]-N-(4-hydroxy-cyclohexyl)-4-methyl-benzenesulfonamide;

3-[5-Amino-6-(1-methyl-1H-pyrazol-4-yl)-pyrazin-2-yl]-4-methyl-N-(3-methyl-oxetan-3-ylmethyl)-benzenesulfonamide;

3-(5-Amino-6-(1H-1,2,4-triazol-1-yl)pyrazin-2-yl)-N-(2-hydroxy-2-methylpropyl)-4-methylbenzenesulfonamide;

3-(5-Amino-6-(2-methylthiazol-5-yl)pyrazin-2-yl)-N-(2-hydroxy-2-methylpropyl)-4-methylbenzenesulfonamide;

3-[5-Amino-6-(2-methyl-thiazol-5-yl)-pyrazin-2-yl]-N-(3-hydroxy-2,2-dimethyl-propyl)-4-methyl-benzenesulfonamide;

3-[5-Amino-6-(1,3-dimethyl-1H-pyrazol-4-yl)-pyrazin-2-yl]-N-(6-hydroxy-spiro[3.3]hept-2-yl)-4-methyl-benzenesulfonamide;

3-(5-Amino-6-(2-methylthiazol-5-yl)pyrazin-2-yl)-N-(3-hydroxypropyl)-4-methylbenzenesulfonamide;

3-(5-Amino-6-(pyridin-4-yl)pyrazin-2-yl)-N-(4-hydroxycyclohexyl)-4-methylbenzenesulfonamide;

3-(5-Amino-6-(1,3-dimethyl-1H-pyrazol-4-yl)pyrazin-2-yl)-N-(3-hydroxy-3-methylbutyl)-4-methylbenzenesulfonamide;

3-[5-Amino-6-(1,3-dimethyl-1H-pyrazol-4-yl)-pyrazin-2-yl]-N-(3-hydroxy-3-methyl-butyl)-4-methyl-benzenesulfonamide;

3-(5-Amino-6-(2-methylthiazol-5-yl)pyrazin-2-yl)-N-(4-hydroxycyclohexyl)-4-methylbenzenesulfonamide;

3-(5-Amino-6-(1H-1,2,4-triazol-1-yl)pyrazin-2-yl)-N-(4-hydroxycyclohexyl)-4-methylbenzenesulfonamide;

3-[5-Amino-6-(1,3-dimethyl-1H-pyrazol-4-yl)-pyrazin-2-yl]-4-methyl-N—[(R)-1-(tetrahydrofuran-3-yl)methyl]-benzenesulfonamide;

3-[5-Amino-6-(1,3-dimethyl-1H-pyrazol-4-yl)-pyrazin-2-yl]-4-methyl-N-(3-methyl-oxetan-3-ylmethyl)-benzenesulfonamide;

3-[5-Amino-6-(2-methyl-2H-[1,2,3]triazol-4-yl)-pyrazin-2-yl]-N-(2-hydroxy-2-methyl-propyl)-4-methyl-benzenesulfonamide;

3-[5-Amino-6-(2,5-dimethyl-2H-[1,2,3]triazol-4-yl)-pyrazin-2-yl]-N-(2-hydroxy-2-methyl-propyl)-4-methyl-benzenesulfonamide;

3-[5-Amino-6-(2-methyl-thiazol-5-yl)-pyrazin-2-yl]-N-(3-hydroxy-cyclobutylmethyl)-4-methyl-benzenesulfonamide;

3-[5-Amino-6-(2-cyclopropyl-thiazol-5-yl)-pyrazin-2-yl]-N-(2-hydroxy-2-methyl-propyl)-4-methyl-benzenesulfonamide;

3-(5-Amino-6-pyridin-3-yl-pyrazin-2-yl)-N-(4-hydroxy-cyclohexyl)-4-methyl-benzenesulfonamide;

3-[5-Amino-6-(3-isopropyl-[1,2,4]oxadiazol-5-yl)-pyrazin-2-yl]-N-(4-hydroxy-cyclohexyl)-4-methyl-benzene sulfonamide;

3-[5-Amino-6-(3-cyclopropyl-[1,2,4]oxadiazol-5-yl)-pyrazin-2-yl]-N-(4-hydroxy-cyclohexyl)-4-methyl-benzene sulfonamide;

3-[5-Amino-6-(3-methyl-[1,2,4]triazol-1-yl)-pyrazin-2-yl]-N-(2-hydroxy-2-methyl-propyl)-4-methyl-benzenesulfonamide;

3-[5-Amino-6-(3-cyclopropyl-[1,2,4]triazol-1-yl)-pyrazin-2-yl]-N-(3-hydroxy-3-methyl-butyl)-4-methyl-benzenesulfonamide;

3-[5-Amino-6-(1,3-dimethyl-1H-pyrazol-4-yl)-pyrazin-2-yl]-N—((R)-1-ethyl-pyrrolidin-2-ylmethyl)-4-methyl-benzenesulfonamide;

3-(5-Amino-6-[1,2,4]triazol-1-yl-pyrazin-2-yl)-N-(1-hydroxy-cyclopropylmethyl)-4-methyl-benzenesulfonamide;

3-(5-Amino-6-[1,2,4]triazol-1-yl-pyrazin-2-yl)-4-methyl-N-(3-methyl-oxetan-3-ylmethyl)-benzenesulfonamide;

3-[5-Amino-6-(5-morpholin-4-ylmethyl-thiophen-3-yl)-pyrazin-2-yl]-N-(3-hydroxy-3-methyl-butyl)-4-methyl-benzenesulfonamide;

3-(5-Amino-6-[1,2,4]triazol-1-yl-pyrazin-2-yl)-N-(2-hydroxy-2-methyl-propoxy)-4-methyl-benzenesulfonamide;

3-(5-Amino-6-[1,2,4]triazol-1-yl-pyrazin-2-yl)-N-(4-hydroxy-tetrahydropyran-4-ylmethyl)-4-methylbenzenesulfonamide;

N-(2-Amino-ethyl)-3-(5-amino-6-[1,2,4]triazol-1-yl-pyrazin-2-yl)-4-methyl-benzenesulfonamide;

3-(5-Amino-6-[1,2,4]triazol-1-yl-pyrazin-2-yl)-N-(2,2-difluoro-ethyl)-4-methyl-benzenesulfonamide;

3-(5-Amino-6-[1,2,4]triazol-1-yl-pyrazin-2-yl)-N-(3-hydroxymethyl-oxetan-3-ylmethyl)-4-methyl-benzenesulfonamide; and 3-(5-Amino-6-[1,2,4]triazol-1-yl-pyrazin-2-yl)-N-(3,3-dimethyl-2-oxo-butyl)-4-methyl-benzenesulfonamide;

or a pharmaceutically acceptable salt thereof.

In an embodiment 42.1 of the invention, there is provided a compound according to embodiment 1 selected from 3-[5-Amino-6-(5-methyl-[1,3,4]oxadiazol-2-yl)-pyrazin-2-yl]-N-(4-hydroxy-cyclohexyl)-4-methyl-benzenesulfonamide;

3-[5-Amino-6-(3-methyl-[1,2,4]oxadiazol-5-yl)-pyrazin-2-yl]-N-(4-hydroxy-cyclohexyl)-4-methyl-benzenesulfonamide;

3-[5-Amino-6-(3-methyl-[1,2,4]oxadiazol-5-yl)-pyrazin-2-yl]-N-(3-hydroxy-3-methyl-butyl)-4-methyl-benzenesulfonamide;

3-[5-Amino-6-(3-methyl-isoxazol-5-yl)-pyrazin-2-yl]-N-(4-hydroxy-cyclohexyl)-4-methyl-benzenesulfonamide;

3-[5-Amino-6-(1-methyl-1H-pyrazol-4-yl)-pyrazin-2-yl]-4-methyl-N-(3-methyl-oxetan-3-ylmethyl)-benzenesulfonamide;

3-(5-Amino-6-(1H-1,2,4-triazol-1-yl)pyrazin-2-yl)-N-(2-hydroxy-2-methylpropyl)-4-methylbenzenesulfonamide;

3-(5-Amino-6-(2-methylthiazol-5-yl)pyrazin-2-yl)-N-(2-hydroxy-2-methylpropyl)-4-methylbenzenesulfonamide;

3-[5-Amino-6-(2-methyl-thiazol-5-yl)-pyrazin-2-yl]-N-(3-hydroxy-2,2-dimethyl-propyl)-4-methyl-benzenesulfonamide;

3-[5-Amino-6-(1,3-dimethyl-1H-pyrazol-4-yl)-pyrazin-2-yl]-N-(6-hydroxy-spiro[3.3]hept-2-yl)-4-methyl-benzenesulfonamide;

3-(5-Amino-6-(2-methylthiazol-5-yl)pyrazin-2-yl)-N-(3-hydroxypropyl)-4-methylbenzenesulfonamide;

3-(5-Amino-6-(pyridin-4-yl)pyrazin-2-yl)-N-(4-hydroxycyclohexyl)-4-methylbenzenesulfonamide;

3-(5-Amino-6-(1,3-dimethyl-1H-pyrazol-4-yl)pyrazin-2-yl)-N-(3-hydroxy-3-methylbutyl)-4-methylbenzenesulfonamide;

3-[5-amino-6-(1,3-dimethyl-1H-pyrazol-4-yl)-pyrazin-2-yl]-N-(3-hydroxy-3-methyl-butyl)-4-methyl-benzenesulfonamide;

3-(5-Amino-6-(2-methylthiazol-5-yl)pyrazin-2-yl)-N-(4-hydroxycyclohexyl)-4-methylbenzenesulfonamide;

3-(5-Amino-6-(1H-1,2,4-triazol-1-yl)pyrazin-2-yl)-N-(4-hydroxycyclohexyl)-4-methylbenzenesulfonamide;

3-[5-Amino-6-(1,3-dimethyl-1H-pyrazol-4-yl)-pyrazin-2-yl]-4-methyl-N—[(R)-1-(tetrahydrofuran-3-yl)methyl]-benzenesulfonamide;

3-[5-Amino-6-(1,3-dimethyl-1H-pyrazol-4-yl)-pyrazin-2-yl]-4-methyl-N-(3-methyl-oxetan-3-ylmethyl)-benzenesulfonamide;

3-[5-Amino-6-(2-methyl-2H-[1,2,3]triazol-4-yl)-pyrazin-2-yl]-N-(2-hydroxy-2-methyl-propyl)-4-methyl-benzenesulfonamide;

3-[5-Amino-6-(2,5-dimethyl-2H-[1,2,3]triazol-4-yl)-pyrazin-2-yl]-N-(2-hydroxy-2-methyl-propyl)-4-methyl-benzenesulfonamide;

3-[5-Amino-6-(2-methyl-thiazol-5-yl)-pyrazin-2-yl]-N-(3-hydroxy-cyclobutylmethyl)-4-methyl-benzenesulfonamide;

3-[5-Amino-6-(2-cyclopropyl-thiazol-5-yl)-pyrazin-2-yl]-N-(2-hydroxy-2-methyl-propyl)-4-methyl-benzenesulfonamide;

3-(5-Amino-6-pyridin-3-yl-pyrazin-2-yl)-N-(4-hydroxy-cyclohexyl)-4-methyl-benzenesulfonamide;

3-[5-Amino-6-(3-isopropyl-[1,2,4]oxadiazol-5-yl)-pyrazin-2-yl]-N-(4-hydroxy-cyclohexyl)-4-methyl-benzene sulfonamide;

3-[5-Amino-6-(3-cyclopropyl-[1,2,4]oxadiazol-5-yl)-pyrazin-2-yl]-N-(4-hydroxy-cyclohexyl)-4-methyl-benzene sulfonamide;

3-[5-Amino-6-(3-methyl-[1,2,4]triazol-1-yl)-pyrazin-2-yl]-N-(2-hydroxy-2-methyl-propyl)-4-methyl-benzenesulfonamide;

3-[5-Amino-6-(3-cyclopropyl-[1,2,4]triazol-1-yl)-pyrazin-2-yl]-N-(3-hydroxy-3-methyl-butyl)-4-methyl-benzenesulfonamide;

3-[5-Amino-6-(1,3-dimethyl-1H-pyrazol-4-yl)-pyrazin-2-yl]-N—((R)-1-ethyl-pyrrolidin-2-ylmethyl)-4-methyl-benzenesulfonamide;

3-(5-Amino-6-[1,2,4]triazol-1-yl-pyrazin-2-yl)-N-(1-hydroxy-cyclopropylmethyl)-4-methyl-benzenesulfonamide;

3-(5-Amino-6-[1,2,4]triazol-1-yl-pyrazin-2-yl)-4-methyl-N-(3-methyl-oxetan-3-ylmethyl)-benzenesulfonamide;

3-[5-Amino-6-(5-morpholin-4-ylmethyl-thiophen-3-yl)-pyrazin-2-yl]-N-(3-hydroxy-3-methyl-butyl)-4-methyl-benzenesulfonamide;

3-(5-Amino-6-[1,2,4]triazol-1-yl-pyrazin-2-yl)-N-(2-hydroxy-2-methyl-propoxy)-4-methyl-benzenesulfonamide;

3-(5-Amino-6-[1,2,4]triazol-1-yl-pyrazin-2-yl)-N-(4-hydroxy-tetrahydropyran-4-ylmethyl)-4-methylbenzenesulfonamide;

N-(2-Amino-ethyl)-3-(5-amino-6-[1,2,4]triazol-1-yl-pyrazin-2-yl)-4-methyl-benzenesulfonamide;

3-(5-Amino-6-[1,2,4]triazol-1-yl-pyrazin-2-yl)-N-(2,2-difluoro-ethyl)-4-methyl-benzenesulfonamide;

3-(5-Amino-6-[1,2,4]triazol-1-yl-pyrazin-2-yl)-N-(3-hydroxymethyl-oxetan-3-ylmethyl)-4-methyl-benzenesulfonamide; and 3-(5-Amino-6-[1,2,4]triazol-1-yl-pyrazin-2-yl)-N-(3,3-dimethyl-2-oxo-butyl)-4-methyl-benzenesulfonamide;

3-(5-amino-6-(1H-1,2,4-triazol-1-yl)pyrazin-2-yl)-4-chloro-N-(2-hydroxy-2-methylpropyl)benzenesulfonamide;

3-(5-amino-6-(1H-1,2,4-triazol-1-yl)pyrazin-2-yl)-4-chloro-N-(3-hydroxy-3-methylbutyl)benzenesulfonamide;

3-(5-amino-6-(furan-3-yl)pyrazin-2-yl)-N-(2-hydroxy-2-methylpropyl)-4-methylbenzenesulfonamide;

3-(5-amino-6-(2,5-dimethylthiazol-4-yl)pyrazin-2-yl)-N-(2-hydroxy-2-methylpropyl)-4-methylbenzenesulfonamide;

(R)-3-(5-amino-6-(2-methylthiazol-5-yl)pyrazin-2-yl)-N-((1-ethylpyrrolidin-2-yl)methyl)-4-methylbenzenesulfonamide;

(R)-3-(5-amino-6-(2-methylthiazol-5-yl)pyrazin-2-yl)-4-methyl-N-((tetrahydrofuran-3-yl)methyl)benzenesulfonamide;

3-(5-amino-6-(2-methylthiazol-5-yl)pyrazin-2-yl)-N-(3-hydroxycyclobutyl)-4-methylbenzenesulfonamide;

3-(5-amino-6-(2-methylthiazol-5-yl)pyrazin-2-yl)-N-((3-(hydroxymethyl)oxetan-3-yl)methyl)-4-methylbenzenesulfonamide;

3-(5-amino-6-(2-methylthiazol-5-yl)pyrazin-2-yl)-N-(2-hydroxyethyl)-4-methylbenzenesulfonamide;

3-(5-amino-6-(2-methylthiazol-5-yl)pyrazin-2-yl)-4-methyl-N-(oxetan-3-ylmethyl)benzenesulfonamide;

3-(5-amino-6-(2-methylthiazol-5-yl)pyrazin-2-yl)-4-methyl-N-((tetrahydro-2H-pyran-4-yl)methyl)benzenesulfonamide;

3-(5-amino-6-(2-methylthiazol-5-yl)pyrazin-2-yl)-4-methyl-N-(tetrahydro-2H-pyran-4-yl)benzenesulfonamide;

3-(5-amino-6-(2-methylthiazol-5-yl)pyrazin-2-yl)-4-methyl-N-((tetrahydro-2H-pyran-2-yl)methyl)benzenesulfonamide;

3-(5-amino-6-(2-methylthiazol-5-yl)pyrazin-2-yl)-4-methyl-N-(2,2,2-trifluoroethyl)benzenesulfonamide;

3-(5-amino-6-(2-methylthiazol-5-yl)pyrazin-2-yl)-4-methyl-N-((tetrahydrofuran-2-yl)methyl)benzenesulfonamide;

3-(5-amino-6-(2-methylthiazol-5-yl)pyrazin-2-yl)-4-methyl-N-(tetrahydrofuran-3-yl)benzenesulfonamide;

(1-(3-(5-amino-6-(2-methylthiazol-5-yl)pyrazin-2-yl)-4-methylphenylsulfonyl)azetidin-3-yl)methanol;

3-(5-amino-6-(2-methylthiazol-5-yl)pyrazin-2-yl)-N-((4-(hydroxymethyl)tetrahydro-2H-pyran-4-yl)methyl)-4-methylbenzenesulfonamide;

3-(5-amino-6-(2-methylthiazol-5-yl)pyrazin-2-yl)-N-((4-hydroxytetrahydro-2H-pyran-4-yl)methyl)-4-methylbenzenesulfonamide;

3-(5-amino-6-(2-methylthiazol-5-yl)pyrazin-2-yl)-N-((3-hydroxyoxetan-3-yl)methyl)-4-methylbenzenesulfonamide;

3-(5-amino-6-(2-methylthiazol-5-yl)pyrazin-2-yl)-4-methyl-N-((4-methylmorpholin-3-yl)methyl)benzenesulfonamide;

3-(5-amino-6-(1,5-dimethyl-1H-pyrazol-4-yl)pyrazin-2-yl)-N-(2-hydroxy-2-methylpropyl)-4-methylbenzenesulfonamide;

3-(5-amino-6-(2,4-dimethylthiazol-5-yl)pyrazin-2-yl)-N-(2-hydroxy-2-methylpropyl)-4-methylbenzenesulfonamide;

3-(5-amino-6-(1-methyl-1H-pyrazol-4-yl)pyrazin-2-yl)-N-(2-hydroxy-2-methylpropyl)-4-methylbenzenesulfonamide;

3-(5-amino-6-(3,4-dimethyl-1H-pyrazol-1-yl)pyrazin-2-yl)-N-(2-hydroxy-2-methyl propyl)-4-methylbenzenesulfonamide;

3-(5-amino-6-(3,5-dimethyl-1H-pyrazol-1-yl)pyrazin-2-yl)-N-(2-hydroxy-2-methylpropyl)-4-methylbenzenesulfonamide;

3-(5-amino-6-(3,5-dimethyl-1H-1,2,4-triazol-1-yl)pyrazin-2-yl)-N-(2-hydroxy-2-methylpropyl)-4-methyl benzenesulfonamide;

3-(5-amino-6-(2,4-dimethyl-1H-imidazol-1-yl)pyrazin-2-yl)-N-(2-hydroxy-2-methylpropyl)-4-methylbenzenesulfonamide;

3-(5-amino-6-(1-methyl-1H-pyrazol-4-yl)pyrazin-2-yl)-4-methyl-N-(4,4,4-trifluoro-3-hydroxybutyl)benzenesulfonamide;

3-(5-amino-6-(1,3-dimethyl-1H-pyrazol-4-yl)pyrazin-2-yl)-4-methyl-N-(4,4,4-trifluoro-3-hydroxybutyl)benzenesulfonamide;

3-(5-amino-6-(1,3-dimethyl-1H-pyrazol-4-yl)pyrazin-2-yl)-4-methyl-N-(4,4,4-trifluoro-3-hydroxybutyl)benzenesulfonamide;

5-(5-amino-6-(1H-1,2,4-triazol-1-yl)pyrazin-2-yl)-N-(2-hydroxy-2-methylpropyl)-6-methylpyridine-3-sulfonamide;

3-(5-amino-6-(1-methyl-1H-pyrazol-4-yl)pyrazin-2-yl)-N-(4,4-difluorocyclohexyl)-4-methylbenzenesulfonamide;

3-(5-amino-6-(2-methylthiazol-5-yl)pyrazin-2-yl)-N-(4,4-difluorocyclohexyl)-4-methylbenzenesulfonamide;

3-(5-amino-6-(4-methyl-1H-imidazol-1-yl)pyrazin-2-yl)-N-((1r,4r)-4-hydroxycyclohexyl)-4-methylbenzenesulfonamide;

3-(5-amino-6-(4-methyl-1H-imidazol-1-yl)pyrazin-2-yl)-N-(3-hydroxypropyl)-4-methylbenzenesulfonamide;

3-(5-amino-6-(1-methyl-1H-pyrazol-4-yl)pyrazin-2-yl)-N-((1r,4r)-4-hydroxycyclohexyl)-4-methylbenzenesulfonamide;

3-(5-amino-6-(pyrimidin-5-yl)pyrazin-2-yl)-N-((1r,4r)-4-hydroxycyclohexyl)-4-methylbenzenesulfonamide;

3-(5-amino-6-(2-fluoropyridin-4-yl)pyrazin-2-yl)-N-((1r,4r)-4-hydroxycyclohexyl)-4-methylbenzenesulfonamide;

3-(5-amino-6-(1H-imidazol-1-yl)pyrazin-2-yl)-N-(3-hydroxy-3-methylbutyl)-4-methylbenzenesulfonamide;

3-(5-amino-6-(1H-pyrazol-1-yl)pyrazin-2-yl)-N-(3-hydroxy-3-methylbutyl)-4-methylbenzenesulfonamide;

3-(5-amino-6-(4-methyl-1H-imidazol-1-yl)pyrazin-2-yl)-N-(3-hydroxy-3-methylbutyl)-4-methylbenzenesulfonamide;

3-(5-amino-6-(1H-1,2,4-triazol-1-yl)pyrazin-2-yl)-N-(3-hydroxy-3-methylbutyl)-4-methylbenzenesulfonamide;

3-(5-amino-6-(3-methyl-1H-1,2,4-triazol-1-yl)pyrazin-2-yl)-N-(3-hydroxy-3-methylbutyl)-4-methylbenzenesulfonamide;

3-(5-amino-6-(3-isopropyl-1H-1,2,4-triazol-1-yl)pyrazin-2-yl)-N-(3-hydroxy-3-methylbutyl)-4-methylbenzenesulfonamide;

3-(5-amino-6-(1H-1,2,4-triazol-1-yl)pyrazin-2-yl)-N-(6-hydroxyspiro[3.3]heptan-2-yl)-4-methylbenzenesulfonamide;

3-(5-amino-6-(1H-1,2,4-triazol-1-yl)pyrazin-2-yl)-4-methyl-N-(tetrahydro-2H-pyran-4-yl)benzenesulfonamide;

3-(5-amino-6-(1H-1,2,4-triazol-1-yl)pyrazin-2-yl)-N-((1r,4r)-4-hydroxy-4-methylcyclohexyl)-4-methylbenzenesulfonamide;

3-(5-amino-6-(1H-1,2,4-triazol-1-yl)pyrazin-2-yl)-N-((1s,4s)-4-hydroxy-4-methylcyclohexyl)-4-methylbenzenesulfonamide;

3-(5-amino-6-(1H-1,2,4-triazol-1-yl)pyrazin-2-yl)-N-(6-hydroxyspiro[3.3]heptan-2-yl)-4-methylbenzenesulfonamide;

3-(5-amino-6-(1H-1,2,4-triazol-1-yl)pyrazin-2-yl)-N-(6-hydroxyspiro[3.3]heptan-2-yl)-4-methylbenzenesulfonamide;

3-(5-amino-6-(1H-1,2,4-triazol-1-yl)pyrazin-2-yl)-N-((1r,3r)-3-hydroxycyclobutyl)-4-methylbenzenesulfonamide;

3-(5-amino-6-(1H-1,2,4-triazol-1-yl)pyrazin-2-yl)-N-((1s,3s)-3-hydroxycyclobutyl)-4-methylbenzenesulfonamide;

3-(5-amino-6-(1H-1,2,4-triazol-1-yl)pyrazin-2-yl)-N-(((1s,3s)-3-hydroxycyclobutyl)methyl)-4-methylbenzenesulfonamide;

3-(5-amino-6-(1H-1,2,4-triazol-1-yl)pyrazin-2-yl)-N-(3-hydroxy-2,2-dimethylpropyl)-4-methylbenzenesulfonamide;

3-(5-amino-6-(1,3-dimethyl-1H-pyrazol-4-yl)pyrazin-2-yl)-N-(6-hydroxyspiro[3.3]heptan-2-yl)-4-methyl benzenesulfonamide;

3-(5-amino-6-(1-methyl-1H-pyrazol-4-yl)pyrazin-2-yl)-N-((1s,4s)-4-hydroxycyclohexyl)-4-methylbenzenesulfonamide;

3-(5-amino-6-(2-methylpyridin-4-yl)pyrazin-2-yl)-N-((1s,4s)-4-hydroxycyclohexyl)-4-methylbenzenesulfonamide;

3-(5-amino-6-(1-methyl-1H-pyrazol-5-yl)pyrazin-2-yl)-N-(3-hydroxy-3-methylbutyl)-4-methylbenzenesulfonamide;

3-(5-amino-6-(3-cyclopropylisoxazol-5-yl)pyrazin-2-yl)-N-(3-hydroxy-3-methylbutyl)-4-methylbenzenesulfonamide;

3-(5-amino-6-(3-cyclopropylisoxazol-5-yl)pyrazin-2-yl)-N-(2-hydroxy-2-methylpropyl)-4-methylbenzenesulfonamide;

3-(5-amino-6-(4-methylthiazol-2-yl)pyrazin-2-yl)-N-(2-hydroxy-2-methylpropyl)-4-methylbenzenesulfonamide;

3-(5-amino-6-(1-methyl-1H-1,2,3-triazol-4-yl)pyrazin-2-yl)-N-(2-hydroxy-2-methylpropyl)-4-methylbenzenesulfonamide;

3-(5-amino-6-(2-ethyl-2H-1,2,3-triazol-4-yl)pyrazin-2-yl)-N-(2-hydroxy-2-methylpropyl)-4-methylbenzenesulfonamide;

3-(5-amino-6-(1-ethyl-1H-1,2,3-triazol-4-yl)pyrazin-2-yl)-N-(2-hydroxy-2-methylpropyl)-4-methylbenzenesulfonamide;

3-(5-amino-6-(2-(2,2,2-trifluoroethyl)-2H-1,2,3-triazol-4-yl)pyrazin-2-yl)-N-(2-hydroxy-2-methylpropyl)-4-methylbenzenesulfonamide;

3-(5-amino-6-(2-methyl-2H-1,2,3-triazol-4-yl)pyrazin-2-yl)-N-(3-hydroxy-3-methylbutyl)-4-methylbenzenesulfonamide;

3-(5-amino-6-(2-methylthiazol-5-yl)pyrazin-2-yl)-N-((1s,4s)-4-hydroxycyclohexyl)-4-methylbenzenesulfonamide;

3-(5-amino-6-(3-methylisoxazol-5-yl)pyrazin-2-yl)-N-(2-hydroxy-2-methylpropyl)-4-methylbenzenesulfonamide;

3-(5-amino-6-(3-methylisoxazol-5-yl)pyrazin-2-yl)-N-(3-hydroxy-3-methylbutyl)-4-methylbenzenesulfonamide;

3-(5-amino-6-(5-methyl-1,3,4-oxadiazol-2-yl)pyrazin-2-yl)-N-(2-hydroxy-2-methylpropyl)-4-methylbenzenesulfonamide;

3-(5-amino-6-(5-cyclopropyl-1,2,4-oxadiazol-3-yl)pyrazin-2-yl)-N-(2-hydroxy-2-methyl propyl)-4-methyl benzenesulfonamide;

3-(5-amino-6-(3-methyl-1,2,4-oxadiazol-5-yl)pyrazin-2-yl)-N-(3-hydroxy-2,2-dimethylpropyl)-4-methyl benzenesulfonamide;

3-(5-amino-6-(3-cyclopropyl-1,2,4-oxadiazol-5-yl)pyrazin-2-yl)-N-(3-hydroxy-2,2-di methylpropyl)-4-methylbenzenesulfonamide;

3-(5-amino-6-(3-cyclopropyl-1,2,4-oxadiazol-5-yl)pyrazin-2-yl)-N-(((1s,3s)-3-hydroxycyclobutyl)methyl)-4-methylbenzenesulfonamide;

3-(5-amino-6-(3-cyclopropyl-1,2,4-oxadiazol-5-yl)pyrazin-2-yl)-N-(2-hydroxy-2-methyl propyl)-4-methyl benzenesulfonamide;

3-(5-amino-6-(3-methyl-1,2,4-oxadiazol-5-yl)pyrazin-2-yl)-N-(((1s,3s)-3-hydroxycyclobutyl)methyl)-4-methylbenzenesulfonamide;

3-(5-amino-6-(3-isopropyl-1,2,4-oxadiazol-5-yl)pyrazin-2-yl)-N-(2-hydroxy-2-methylpropyl)-4-methylbenzenesulfonamide;

3-(5-amino-6-(1H-1,2,4-triazol-1-yl)pyrazin-2-yl)-N-(1-(hydroxymethyl)cyclopropyl)-4-methylbenzenesulfonamide;

3-(5-amino-6-(3-cyclopropylisoxazol-5-yl)pyrazin-2-yl)-N-(3-hydroxy-2,2-dimethylpropyl)-4-methylbenzenesulfonamide;

3-(5-amino-6-(3-cyclopropylisoxazol-5-yl)pyrazin-2-yl)-N-(((1s,3s)-3-hydroxycyclobutyl)methyl)-4-methylbenzenesulfonamide;

2-(3-(5-amino-6-(1H-1,2,4-triazol-1-yl)pyrazin-2-yl)-4-methylphenylsulfonyl)-2-azaspiro[3.3]heptan-6-ol;

3-(1,3-dimethyl-1H-pyrazol-4-yl)-5-(5-(3-methoxy-3-methylazetidin-1-ylsulfonyl)-2-methylphenyl)pyrazin-2-amine;

3-(5-amino-6-(1H-pyrazol-1-yl)pyrazin-2-yl)-N-((1r,4r)-4-hydroxycyclohexyl)-4-methylbenzenesulfonamide;

(R)-3-(5-amino-6-(1,3-dimethyl-1H-pyrazol-4-yl)pyrazin-2-yl)-4-methyl-N-(pyrrolidin-2-ylmethyl)benzenesulfonamide;

3-(5-amino-6-(2-cyclopropylthiazol-5-yl)pyrazin-2-yl)-N-(3-hydroxy-3-methylbutyl)-4-methylbenzenesulfonamide;

3-(5-amino-6-(thiazol-4-yl)pyrazin-2-yl)-N-(3-hydroxy-3-methylbutyl)-4-methylbenzenesulfonamide;

3-(5-amino-6-(3-cyclopropyl-1H-1,2,4-triazol-1-yl)pyrazin-2-yl)-N-(2-hydroxy-2-methylpropyl)-4-methyl benzenesulfonamide;

3-(5-amino-6-(2-methoxythiazol-4-yl)pyrazin-2-yl)-N-(3-hydroxy-3-methylbutyl)-4-methylbenzenesulfonamide;

3-(5-amino-6-(4-methyl-1H-pyrazol-1-yl)pyrazin-2-yl)-N-((1r,4r)-4-hydroxycyclohexyl)-4-methylbenzenesulfonamide;

3-(5-amino-6-(1H-1,2,4-triazol-1-yl)pyrazin-2-yl)-N-ethoxy-4-methylbenzenesulfonamide;

3-(5-amino-6-(1H-1,2,4-triazol-1-yl)pyrazin-2-yl)-N-tert-butoxy-4-methylbenzenesulfonamide;

3-(5-amino-6-(1H-1,2,4-triazol-1-yl)pyrazin-2-yl)-N-(2-(dimethylamino)ethoxy)-4-methylbenzenesulfonamide;

3-(5-amino-6-(1H-1,2,4-triazol-1-yl)pyrazin-2-yl)-N-isopropoxy-4-methylbenzenesulfonamide;

3-(5-amino-6-(1H-1,2,4-triazol-1-yl)pyrazin-2-yl)-N-isobutoxy-4-methylbenzenesulfonamide;

3-(5-amino-6-(1H-1,2,4-triazol-1-yl)pyrazin-2-yl)-4-methyl-N-(tetrahydrofuran-3-yloxy)benzenesulfonamide;

5-(5-amino-6-(2-methylthiazol-5-yl)pyrazin-2-yl)-2-fluoro-N-(3-hydroxypropyl)-4-methylbenzenesulfonamide;

5-(5-amino-6-(1-methyl-1H-pyrazol-4-yl)pyrazin-2-yl)-2-fluoro-N-(3-hydroxypropyl)-4-methylbenzenesulfonamide;

5-(5-amino-6-(1-methyl-1H-pyrazol-4-yl)pyrazin-2-yl)-2-fluoro-N-(3-hydroxy-3-methylbutyl)-4-methylbenzenesulfonamide;

5-(5-amino-6-(1H-1,2,4-triazol-1-yl)pyrazin-2-yl)-2-fluoro-N-(3-hydroxy-3-methylbutyl)-4-methylbenzenesulfonamide;

3-(5-amino-6-(3-((dimethylamino)methyl)-1H-1,2,4-triazol-1-yl)pyrazin-2-yl)-N-(2-hydroxy-2-methylpropyl)-4-methylbenzenesulfonamide;

5-(2-methyl-5-(3-(trifluoromethyl)piperazin-1-ylsulfonyl)phenyl)-3-(2-methylthiazol-5-yl)pyrazin-2-amine;

3-(5-amino-6-(1-methyl-3-(trifluoromethyl)-1H-pyrazol-5-yl)pyrazin-2-yl)-N-(3-hydroxy-3-methylbutyl)-4-methylbenzenesulfonamide;

3-(5-amino-6-(2-fluoropyridin-3-yl)pyrazin-2-yl)-N-(3-hydroxy-3-methylbutyl)-4-methylbenzenesulfonamide;

3-(5-amino-6-(4-methoxypyridin-3-yl)pyrazin-2-yl)-N-(3-hydroxy-3-methylbutyl)-4-methylbenzenesulfonamide;

3-(5-amino-6-(2-methoxypyridin-4-yl)pyrazin-2-yl)-N-(3-hydroxy-3-methylbutyl)-4-methylbenzenesulfonamide;

3-(5-amino-6-(2-methoxypyridin-3-yl)pyrazin-2-yl)-N-(3-hydroxy-3-methylbutyl)-4-methylbenzenesulfonamide;

3-(5-amino-6-(pyridin-3-yl)pyrazin-2-yl)-N-(3-hydroxy-3-methylbutyl)-4-methylbenzenesulfonamide;

3-(5-amino-6-(2-chloropyridin-3-yl)pyrazin-2-yl)-N-(3-hydroxy-3-methylbutyl)-4-methylbenzenesulfonamide;

3-(5-amino-6-(5-methylpyridin-3-yl)pyrazin-2-yl)-N-(3-hydroxy-3-methylbutyl)-4-methylbenzenesulfonamide;

3-(5-amino-6-(5-chloro-2-fluoropyridin-3-yl)pyrazin-2-yl)-N-(3-hydroxy-3-methylbutyl)-4-methylbenzenesulfonamide;

3-(5-amino-6-(6-chloro-4-methylpyridin-3-yl)pyrazin-2-yl)-N-(3-hydroxy-3-methylbutyl)-4-methylbenzenesulfonamide;

3-(5-amino-6-(2-fluoropyridin-4-yl)pyrazin-2-yl)-N-(3-hydroxy-3-methylbutyl)-4-methylbenzenesulfonamide;

3-(5-amino-6-(3-fluoropyridin-4-yl)pyrazin-2-yl)-N-(3-hydroxy-3-methylbutyl)-4-methylbenzenesulfonamide;
3-(5-amino-6-(2-isopropoxypyridin-3-yl)pyrazin-2-yl)-N-(3-hydroxy-3-methylbutyl)-4-methylbenzenesulfonamide;
3-(5-amino-6-(6-ethoxypyridin-3-yl)pyrazin-2-yl)-N-(3-hydroxy-3-methylbutyl)-4-methylbenzenesulfonamide
3-(5-amino-6-(6-methoxy-2-methylpyridin-3-yl)pyrazin-2-yl)-N-(3-hydroxy-3-methyl butyl)-4-methylbenzenesulfonamide;
3-(5-amino-6-(furan-3-yl)pyrazin-2-yl)-N-(3-hydroxy-3-methylbutyl)-4-methylbenzenesulfonamide;
3-(5-amino-6-(1-methyl-1H-pyrazol-4-yl)pyrazin-2-yl)-N-(3-hydroxy-3-methylbutyl)-4-methylbenzenesulfonamide;
3-(5-amino-6-(6-(pyrrolidin-1-yl)pyridin-3-yl)pyrazin-2-yl)-N-(3-hydroxy-3-methylbutyl)-4-methylbenzenesulfonamide;
3-(5-amino-6-(6-fluoropyridin-3-yl)pyrazin-2-yl)-N-(3-hydroxy-3-methylbutyl)-4-methylbenzenesulfonamide;
3-(5-amino-6-(1,5-dimethyl-1H-pyrazol-4-yl)pyrazin-2-yl)-N-(3-hydroxy-3-methylbutyl)-4-methylbenzenesulfonamide;
3-(5-amino-6-(pyrimidin-5-yl)pyrazin-2-yl)-N-(3-hydroxy-3-methylbutyl)-4-methylbenzenesulfonamide;
3-(5-amino-6-(6-morpholinopyridin-3-yl)pyrazin-2-yl)-N-(3-hydroxy-3-methylbutyl)-4-methylbenzenesulfonamide;
3-(5-amino-6-(3-methyl-1H-pyrazol-4-yl)pyrazin-2-yl)-N-(3-hydroxy-3-methylbutyl)-4-methylbenzenesulfonamide;
3-(5-amino-6-(6-(piperidin-1-yl)pyridin-3-yl)pyrazin-2-yl)-N-(3-hydroxy-3-methylbutyl)-4-methylbenzenesulfonamide;
3-(5-amino-6-(6-(tetrahydro-2H-pyran-4-yloxy)pyridin-3-yl)pyrazin-2-yl)-N-(3-hydroxy-3-methylbutyl)-4-methylbenzenesulfonamide;
3-(5-amino-6-(1-propyl-1H-pyrazol-4-yl)pyrazin-2-yl)-N-(3-hydroxy-3-methylbutyl)-4-methylbenzenesulfonamide;
3-(5-amino-6-(1-isopentyl-1H-pyrazol-4-yl)pyrazin-2-yl)-N-(3-hydroxy-3-methylbutyl)-4-methylbenzenesulfonamide;
3-(5-amino-6-(pyridin-4-yl)pyrazin-2-yl)-N-(3-hydroxy-3-methylbutyl)-4-methylbenzenesulfonamide;
3-(5-amino-6-(2-methylpyridin-4-yl)pyrazin-2-yl)-N-(3-hydroxy-3-methylbutyl)-4-methylbenzenesulfonamide;
3-(5-amino-6-(2-methylthiazol-5-yl)pyrazin-2-yl)-N-(3-hydroxy-3-methylbutyl)-4-methylbenzenesulfonamide;
3-(5-amino-6-(2-methylthiazol-4-yl)pyrazin-2-yl)-N-(3-hydroxy-3-methylbutyl)-4-methylbenzenesulfonamide;
3-(5-amino-6-(1-isopropyl-1H-pyrazol-4-yl)pyrazin-2-yl)-N-(3-hydroxy-3-methylbutyl)-4-methylbenzenesulfonamide;
3-(5-amino-6-(1-isobutyl-1H-pyrazol-4-yl)pyrazin-2-yl)-N-(3-hydroxy-3-methylbutyl)-4-methylbenzenesulfonamide;
3-(5-amino-6-(1H-pyrazol-4-yl)pyrazin-2-yl)-N-(3-hydroxy-3-methylbutyl)-4-methylbenzenesulfonamide;
3-(5-amino-6-(1-ethyl-1H-pyrazol-4-yl)pyrazin-2-yl)-N-(3-hydroxy-3-methylbutyl)-4-methylbenzenesulfonamide;
3-(5-amino-6-(5-(hydroxymethyl)thiophen-2-yl)pyrazin-2-yl)-N-(3-hydroxy-3-methylbutyl)-4-methylbenzenesulfonamide;
3-(5-amino-6-(1,3-dimethyl-1H-pyrazol-5-yl)pyrazin-2-yl)-N-(3-hydroxy-3-methylbutyl)-4-methylbenzenesulfonamide;
3-(5-amino-6-(1-(pyridin-2-ylmethyl)-1H-pyrazol-4-yl)pyrazin-2-yl)-N-(3-hydroxy-3-methylbutyl)-4-methylbenzenesulfonamide;
3-(5-amino-6-(1-(pyridin-3-ylmethyl)-1H-pyrazol-4-yl)pyrazin-2-yl)-N-(3-hydroxy-3-methylbutyl)-4-methylbenzenesulfonamide;
3-(5-amino-6-(1-(pyridin-4-ylmethyl)-1H-pyrazol-4-yl)pyrazin-2-yl)-N-(3-hydroxy-3-methylbutyl)-4-methylbenzenesulfonamide;
3-(5-amino-6-(2-methyloxazol-5-yl)pyrazin-2-yl)-N-(3-hydroxy-3-methylbutyl)-4-methylbenzenesulfonamide;
3-(5-amino-6-(1-(2-morpholinoethyl)-1H-pyrazol-4-yl)pyrazin-2-yl)-N-(3-hydroxy-3-methylbutyl)-4-methylbenzenesulfonamide;
3-(5-amino-6-(1H-pyrazol-3-yl)pyrazin-2-yl)-N-(3-hydroxy-3-methylbutyl)-4-methylbenzenesulfonamide;
3-(5-amino-6-(4-methylthiophen-2-yl)pyrazin-2-yl)-N-(3-hydroxy-3-methylbutyl)-4-methylbenzenesulfonamide;
3-(5-amino-6-(5-methylthiophen-2-yl)pyrazin-2-yl)-N-(3-hydroxy-3-methylbutyl)-4-methylbenzenesulfonamide;
3-(5-amino-6-(thiophen-2-yl)pyrazin-2-yl)-N-(3-hydroxy-3-methyl butyl)-4-methylbenzenesulfonamide;
3-(5-amino-6-(5-cyclopropylthiophen-2-yl)pyrazin-2-yl)-N-(3-hydroxy-3-methylbutyl)-4-methylbenzenesulfonamide;
3-(5-amino-6-(2-methylthiazol-5-yl)pyrazin-2-yl)-4-methyl-N-((3-methyloxetan-3-yl)methyl)benzenesulfonamide;
5-(5-amino-6-(1H-1,2,4-triazol-1-yl)pyrazin-2-yl)-N-(2-hydroxy-2-methylpropyl)-2,4-di methylbenzenesulfonamide;
5-(5-amino-6-(1H-1,2,4-triazol-1-yl)pyrazin-2-yl)-2-fluoro-N-(2-hydroxy-2-methylpropyl)-4-methylbenzenesulfonamide;
3-(5-amino-6-(1H-1,2,4-triazol-1-yl)pyrazin-2-yl)-N-(2-hydroxy-2-methylpropyl)benzenesulfonamide;
5-(5-amino-6-(1H-1,2,4-triazol-1-yl)pyrazin-2-yl)-2-chloro-N-(2-hydroxy-2-methylpropyl)-4-methylbenzenesulfonamide;
3-(5-amino-6-(1,3-dimethyl-1H-pyrazol-4-yl)pyrazin-2-yl)-N-(2-hydroxy-2-methylpropoxy)-4-methylbenzenesulfonamide;
3-(5-amino-6-(2-methyloxazol-5-yl)pyrazin-2-yl)-N-(2-hydroxy-2-methylpropyl)-4-methylbenzenesulfonamide;
3-(5-amino-6-(1H-1,2,4-triazol-1-yl)pyrazin-2-yl)-4-methyl-N-(2,2,2-trifluoroethyl)benzenesulfonamide;
5-(5-(3,3-difluoropiperidin-1-ylsulfonyl)-2-methylphenyl)-3-(1H-1,2,4-triazol-1-yl)pyrazin-2-amine;
5-(5-(3-fluoropyrrolidin-1-ylsulfonyl)-2-methylphenyl)-3-(1H-1,2,4-triazol-1-yl)pyrazin-2-amine;
5-(5-(3,3-difluoropyrrolidin-1-ylsulfonyl)-2-methylphenyl)-3-(1H-1,2,4-triazol-1-yl)pyrazin-2-amine;
5-(5-(3,3-difluoroazetidin-1-ylsulfonyl)-2-methylphenyl)-3-(1H-1,2,4-triazol-1-yl)pyrazin-2-amine;
5-(5-(3-fluoroazetidin-1-ylsulfonyl)-2-methylphenyl)-3-(1H-1,2,4-triazol-1-yl)pyrazin-2-amine;
3-(5-amino-6-(1H-1,2,4-triazol-1-yl)pyrazin-2-yl)-N-(4-(hydroxymethyl)cyclohexyl)-4-methylbenzenesulfonamide;
3-(5-amino-6-(1H-1,2,4-triazol-1-yl)pyrazin-2-yl)-N-(3,3-difluorocyclobutyl)-4-methylbenzenesulfonamide;
5-(2-methyl-5-(3,3,4,4-tetrafluoropyrrolidin-1-ylsulfonyl)phenyl)-3-(1H-1,2,4-triazol-1-yl)pyrazin-2-amine;
3-(5-amino-6-(1H-1,2,4-triazol-1-yl)pyrazin-2-yl)-N-(5-hydroxypentyl)-4-methylbenzenesulfonamide;
3-(5-amino-6-(1H-1,2,4-triazol-1-yl)pyrazin-2-yl)-N-(3-methoxypropyl)-4-methylbenzenesulfonamide;

3-(5-amino-6-(1H-1,2,4-triazol-1-yl)pyrazin-2-yl)-N-((1-hydroxycyclohexyl)methyl)-4-methylbenzenesulfonamide;

(R)-3-(5-amino-6-(1H-1,2,4-triazol-1-yl)pyrazin-2-yl)-N-((1-ethylpyrrolidin-2-yl)methyl)-4-methylbenzenesulfonamide;

(R)-3-(5-amino-6-(1H-1,2,4-triazol-1-yl)pyrazin-2-yl)-N-(2-hydroxypropyl)-4-methylbenzenesulfonamide;

(R)-3-(5-amino-6-(1H-1,2,4-triazol-1-yl)pyrazin-2-yl)-4-methyl-N-((tetrahydrofuran-2-yl)methyl)benzenesulfonamide;

3-(5-amino-6-(1H-1,2,4-triazol-1-yl)pyrazin-2-yl)-N-((1-hydroxycyclobutyl)methyl)-4-methylbenzenesulfonamide;

3-(5-amino-6-(1H-1,2,4-triazol-1-yl)pyrazin-2-yl)-4-methyl-N-((tetrahydro-2H-pyran-2-yl)methyl)benzenesulfonamide;

3-(5-amino-6-(1H-1,2,4-triazol-1-yl)pyrazin-2-yl)-4-methyl-N-((1-methylpyrrolidin-3-yl)methyl)benzenesulfonamide;

3-(5-amino-6-(1H-1,2,4-triazol-1-yl)pyrazin-2-yl)-4-methyl-N-((tetrahydro-2H-pyran-3-yl)methyl)benzenesulfonamide;

(R)-3-(5-amino-6-(1H-1,2,4-triazol-1-yl)pyrazin-2-yl)-4-methyl-N-(tetrahydrofuran-3-yl)benzenesulfonamide;

(S)-3-(5-amino-6-(1H-1,2,4-triazol-1-yl)pyrazin-2-yl)-4-methyl-N-(tetrahydrofuran-3-yl)benzenesulfonamide;

(R)-3-(5-amino-6-(1H-1,2,4-triazol-1-yl)pyrazin-2-yl)-4-methyl-N-(3,3,3-trifluoro-2-hydroxy-2-methylpropyl)benzenesulfonamide;

(S)-3-(5-amino-6-(1H-1,2,4-triazol-1-yl)pyrazin-2-yl)-4-methyl-N-(3,3,3-trifluoro-2-hydroxy-2-methylpropyl)benzenesulfonamide;

3-(5-amino-6-(1H-1,2,4-triazol-1-yl)pyrazin-2-yl)-4-methyl-N-(4,4,4-trifluoro-3-hydroxy-3-methylbutyl)benzenesulfonamide;

3-(5-amino-6-(1H-1,2,4-triazol-1-yl)pyrazin-2-yl)-N-((1-(hydroxymethyl)cyclopentyl)methyl)-4-methylbenzenesulfonamide;

(S)-3-(5-amino-6-(1H-1,2,4-triazol-1-yl)pyrazin-2-yl)-4-methyl-N-((tetrahydrofuran-3-yl)methyl)benzenesulfonamide;

(R)-3-(5-amino-6-(1H-1,2,4-triazol-1-yl)pyrazin-2-yl)-4-methyl-N-((tetrahydrofuran-3-yl)methyl)benzenesulfonamide;

3-(5-amino-6-(1H-1,2,4-triazol-1-yl)pyrazin-2-yl)-N-(2-fluoroethyl)-4-methylbenzenesulfonamide;

3-(5-amino-6-(1H-1,2,4-triazol-1-yl)pyrazin-2-yl)-N-(3-fluoropropyl)-4-methylbenzenesulfonamide;

3-(5-amino-6-(1H-1,2,4-triazol-1-yl)pyrazin-2-yl)-4-methyl-N-(2-oxotetrahydrofuran-3-yl)benzenesulfonamide;

3-(5-amino-6-(1H-1,2,4-triazol-1-yl)pyrazin-2-yl)-4-methyl-N-(3,3,3-trifluoropropyl)benzenesulfonamide;

3-(5-amino-6-(1H-1,2,4-triazol-1-yl)pyrazin-2-yl)-4-methyl-N-(2-methyl-2-morpholinopropyl)benzenesulfonamide;

5-(5-(4,4-difluoropiperidin-1-ylsulfonyl)-2-methylphenyl)-3-(1H-1,2,4-triazol-1-yl)pyrazin-2-amine;

5-(5-(4-fluoropiperidin-1-ylsulfonyl)-2-methylphenyl)-3-(1H-1,2,4-triazol-1-yl)pyrazin-2-amine;

3-(5-amino-6-(1H-1,2,4-triazol-1-yl)pyrazin-2-yl)-N-((1-hydroxycyclopentyl)methyl)-4-methylbenzenesulfonamide;

3-(5-amino-6-(1H-1,2,4-triazol-1-yl)pyrazin-2-yl)-N-(2-(1-hydroxycyclopentyl)ethyl)-4-methylbenzenesulfonamide;

3-(5-amino-6-(1H-1,2,4-triazol-1-yl)pyrazin-2-yl)-N-(2-(1-hydroxycyclohexyl)ethyl)-4-methylbenzenesulfonamide;

3-(5-amino-6-(1H-1,2,4-triazol-1-yl)pyrazin-2-yl)-N-((1-(hydroxymethyl)cyclopropyl)methyl)-4-methylbenzenesulfonamide;

(S)-3-(5-amino-6-(1H-1,2,4-triazol-1-yl)pyrazin-2-yl)-N-((5,5-dimethyltetrahydrofuran-2-yl)methyl)-4-methylbenzenesulfonamide;

(R)-3-(5-amino-6-(1H-1,2,4-triazol-1-yl)pyrazin-2-yl)-N-((5,5-dimethyltetrahydrofuran-2-yl)methyl)-4-methylbenzenesulfonamide;

(S)-3-(5-amino-6-(1H-1,2,4-triazol-1-yl)pyrazin-2-yl)-N-(1-hydroxypropan-2-yl)-4-methylbenzenesulfonamide;

3-(5-amino-6-(1H-1,2,4-triazol-1-yl)pyrazin-2-yl)-N-(1-hydroxypropan-2-yl)-4-methylbenzenesulfonamide;

3-(5-amino-6-(1H-1,2,4-triazol-1-yl)pyrazin-2-yl)-N-(2,2-difluoropropyl)-4-methylbenzenesulfonamide;

3-(5-amino-6-(1H-1,2,4-triazol-1-yl)pyrazin-2-yl)-4-methyl-N-(3-methylbutan-2-yl)benzenesulfonamide;

(1-(3-(5-amino-6-(1H-1,2,4-triazol-1-yl)pyrazin-2-yl)-4-methylphenylsulfonyl)azetidin-3-yl)methanol;

1-(3-(5-amino-6-(1H-1,2,4-triazol-1-yl)pyrazin-2-yl)-4-methylphenylsulfonyl)-3-methylazetidin-3-ol;

3-(5-amino-6-(1H-1,2,4-triazol-1-yl)pyrazin-2-yl)-N-((3-hydroxyoxetan-3-yl)methyl)-4-methylbenzenesulfonamide;

(R)-3-(5-amino-6-(1H-1,2,4-triazol-1-yl)pyrazin-2-yl)-N-(1-cyano-2-hydroxyethyl)-4-methylbenzenesulfonamide;

3-(5-amino-6-(1H-1,2,4-triazol-1-yl)pyrazin-2-yl)-N-((1-(hydroxymethyl)cyclobutyl)methyl)-4-methylbenzenesulfonamide;

3-(5-amino-6-(1H-1,2,4-triazol-1-yl)pyrazin-2-yl)-N-((4-(hydroxymethyl)tetrahydro-2H-pyran-4-yl)methyl)-4-methylbenzenesulfonamide;

3-(5-amino-6-(1H-1,2,4-triazol-1-yl)pyrazin-2-yl)-4-methyl-N-(2-oxotetrahydrothiophen-3-yl)benzenesulfonamide;

3-(5-amino-6-(1H-1,2,4-triazol-1-yl)pyrazin-2-yl)-N-((1-(hydroxymethyl)cyclohexyl)methyl)-4-methylbenzenesulfonamide;

3-(5-amino-6-(1H-1,2,4-triazol-1-yl)pyrazin-2-yl)-N-cyclopropyl-4-methylbenzenesulfonamide;

3-(5-amino-6-(1H-1,2,4-triazol-1-yl)pyrazin-2-yl)-N-cyclobutyl-4-methylbenzenesulfonamide;

3-(5-amino-6-(1H-1,2,4-triazol-1-yl)pyrazin-2-yl)-N-cyclopentyl-4-methylbenzenesulfonamide;

1-((3-(5-amino-6-(1H-1,2,4-triazol-1-yl)pyrazin-2-yl)-4-methylphenylsulfonamido)methyl)cyclopropanecarboxamide;

(R)-3-(5-amino-6-(1H-1,2,4-triazol-1-yl)pyrazin-2-yl)-4-methyl-N-(pyrrolidin-3-ylmethyl)benzenesulfonamide;

(S)-3-(5-amino-6-(1H-1,2,4-triazol-1-yl)pyrazin-2-yl)-4-methyl-N-(pyrrolidin-3-ylmethyl)benzenesulfonamide;

3-(5-amino-6-(1H-1,2,4-triazol-1-yl)pyrazin-2-yl)-N-((3R,4R)-4-hydroxypyrrolidin-3-yl)-4-methylbenzenesulfonamide;

3-(5-amino-6-(1,3-dimethyl-1H-pyrazol-4-yl)pyrazin-2-yl)-N-((3-(hydroxymethyl)oxetan-3-yl)methyl)-4-methylbenzenesulfonamide;

(S)-3-(5-amino-6-(1,3-dimethyl-1H-pyrazol-4-yl)pyrazin-2-yl)-N-((1-ethylpyrrolidin-2-yl)methyl)-4-methylbenzenesulfonamide;

3-(5-amino-6-(1,3-dimethyl-1H-pyrazol-4-yl)pyrazin-2-yl)-4-methyl-N-((4-methylmorpholin-3-yl)methyl)benzenesulfonamide;

3-(5-amino-6-(1,3-dimethyl-1H-pyrazol-4-yl)pyrazin-2-yl)-4-methyl-N-((4-methyl morpholin-3-yl)methyl)benzenesulfonamide;

3-(5-amino-6-(1,3-dimethyl-1H-pyrazol-4-yl)pyrazin-2-yl)-4-methyl-N-((4-methylmorpholin-3-yl)methyl)benzenesulfonamide;

3-(5-amino-6-(1,3-dimethyl-1H-pyrazol-4-yl)pyrazin-2-yl)-4-methyl-N-((2-methyltetrahydrofuran-2-yl)methyl)benzenesulfonamide;

3-(5-amino-6-(1,3-dimethyl-1H-pyrazol-4-yl)pyrazin-2-yl)-4-methyl-N-((4-methylmorpholin-2-yl)methyl)benzenesulfonamide;

(R)-3-(5-amino-6-(1,3-dimethyl-1H-pyrazol-4-yl)pyrazin-2-yl)-4-methyl-N-(morpholin-3-ylmethyl)benzenesulfonamide;

(S)-3-(5-amino-6-(1,3-dimethyl-1H-pyrazol-4-yl)pyrazin-2-yl)-4-methyl-N-(morpholin-3-ylmethyl)benzenesulfonamide;

3-(5-amino-6-(1,3-dimethyl-1H-pyrazol-4-yl)pyrazin-2-yl)-4-methyl-N-(morpholin-2-ylmethyl)benzenesulfonamide;

(R)-3-(5-amino-6-(2-methylpyridin-4-yl)pyrazin-2-yl)-N-(2-hydroxypropyl)-4-methylbenzenesulfonamide;

3-(5-amino-6-(2-methylpyridin-4-yl)pyrazin-2-yl)-N-(4-(hydroxymethyl)cyclohexyl)-4-methylbenzenesulfonamide;

3-(5-amino-6-(2-methylpyridin-4-yl)pyrazin-2-yl)-N-(3,3-difluorocyclobutyl)-4-methylbenzenesulfonamide;

3-(5-amino-6-(2-methylpyridin-4-yl)pyrazin-2-yl)-N-(5-hydroxypentyl)-4-methylbenzenesulfonamide;

3-(5-amino-6-(2-methylpyridin-4-yl)pyrazin-2-yl)-N-((1-hydroxycyclohexyl)methyl)-4-methylbenzenesulfonamide;

3-(5-amino-6-(2-methylpyridin-4-yl)pyrazin-2-yl)-N-((1-hydroxycyclobutyl)methyl)-4-methylbenzenesulfonamide;

(S)-3-(5-amino-6-(2-methylpyridin-4-yl)pyrazin-2-yl)-N-(1-hydroxybutan-2-yl)-4-methylbenzenesulfonamide;

(R)-3-(5-amino-6-(2-methylpyridin-4-yl)pyrazin-2-yl)-N-(1-hydroxybutan-2-yl)-4-methylbenzenesulfonamide;

3-(5-amino-6-(2-methylpyridin-4-yl)pyrazin-2-yl)-N-(1-hydroxy-2-methylpropan-2-yl)-4-methylbenzenesulfonamide;

(S)-3-(5-amino-6-(2-methylpyridin-4-yl)pyrazin-2-yl)-N-(2-hydroxypropyl)-4-methylbenzenesulfonamide;

3-(5-amino-6-(2-methylpyridin-4-yl)pyrazin-2-yl)-4-methyl-N-(tetrahydro-2H-pyran-4-yl)benzenesulfonamide;

3-(5-amino-6-(2-methylpyridin-4-yl)pyrazin-2-yl)-N-(3-methoxypropyl)-4-methylbenzenesulfonamide;

(R)-3-(5-amino-6-(2-methylpyridin-4-yl)pyrazin-2-yl)-4-methyl-N-((tetrahydrofuran-2-yl)methyl)benzenesulfonamide;

3-(5-amino-6-(2-methylpyridin-4-yl)pyrazin-2-yl)-4-methyl-N-(4,4,4-trifluoro-3-hydroxy-3-methylbutyl)benzenesulfonamide;

3-(5-amino-6-(2-methylpyridin-4-yl)pyrazin-2-yl)-4-methyl-N-((tetrahydro-2H-pyran-3-yl)methyl)benzenesulfonamide;

3-(5-amino-6-(2-methylpyridin-4-yl)pyrazin-2-yl)-N-(2-methoxy-2-methylpropyl)-4-methylbenzenesulfonamide;

3-(5-amino-6-(2-methylpyridin-4-yl)pyrazin-2-yl)-4-methyl-N-((tetrahydro-2H-pyran-2-yl)methyl)benzenesulfonamide;

3-(5-amino-6-(2-methylpyridin-4-yl)pyrazin-2-yl)-4-methyl-N-((tetrahydrofuran-2-yl)methyl)benzenesulfonamide;

3-(5-amino-6-(2-methylpyridin-4-yl)pyrazin-2-yl)-4-methyl-N-((tetrahydrofuran-3-yl)methyl)benzenesulfonamide;

3-(5-amino-6-(2-methylpyridin-4-yl)pyrazin-2-yl)-N-(4-hydroxy-4-methylcyclohexyl)-4-methylbenzenesulfonamide;

(R)-3-(5-amino-6-(2-methylpyridin-4-yl)pyrazin-2-yl)-4-methyl-N-(3,3,3-trifluoro-2-hydroxy-2-methylpropyl)benzenesulfonamide;

3-(5-amino-6-(2-methylpyridin-4-yl)pyrazin-2-yl)-N-(1-isopropylpiperidin-4-yl)-4-methylbenzenesulfonamide;

3-(5-amino-6-(2-methylpyridin-4-yl)pyrazin-2-yl)-4-methyl-N-(1-methylpiperidin-4-yl)benzenesulfonamide;

3-(5-amino-6-(2-methylpyridin-4-yl)pyrazin-2-yl)-N-(3-(diethylamino)propyl)-4-methylbenzenesulfonamide;

3-(5-amino-6-(2-methylpyridin-4-yl)pyrazin-2-yl)-N-(3-(dimethylamino)-2,2-dimethylpropyl)-4-methylbenzenesulfonamide;

(R)-3-(5-amino-6-(2-methylpyridin-4-yl)pyrazin-2-yl)-N-((1-ethylpyrrolidin-2-yl)methyl)-4-methylbenzenesulfonamide;

3-(5-amino-6-(2-methylpyridin-4-yl)pyrazin-2-yl)-N-(2-(dimethylamino)ethyl)-4-methylbenzenesulfonamide;

3-(5-amino-6-(2-methylpyridin-4-yl)pyrazin-2-yl)-4-methyl-N-(2-(pyrrolidin-1-yl)ethyl)benzenesulfonamide;

3-(5-amino-6-(2-methylpyridin-4-yl)pyrazin-2-yl)-4-methyl-N-(2-morpholinoethyl)benzenesulfonamide;

3-(5-amino-6-(2-methylpyridin-4-yl)pyrazin-2-yl)-4-methyl-N-(2-methyl-2-morpholinopropyl)benzenesulfonamide;

3-(5-amino-6-(2-methylpyridin-4-yl)pyrazin-2-yl)-4-methyl-N-((1-methylpyrrolidin-3-yl)methyl)benzenesulfonamide;

4-((3-(5-amino-6-(2-methylpyridin-4-yl)pyrazin-2-yl)-4-methylphenylsulfonamido)methyl)tetrahydro-2H-pyran-4-carboxamide;

3-(5-amino-6-(2-methylpyridin-4-yl)pyrazin-2-yl)-N-((3-hydroxyoxetan-3-yl)methyl)-4-methylbenzenesulfonamide;

3-(5-amino-6-(2-methylpyridin-4-yl)pyrazin-2-yl)-4-methyl-N-(2-(methylamino)ethyl)benzenesulfonamide;

3-(5-amino-6-(2-methylpyridin-4-yl)pyrazin-2-yl)-N-(2-aminoethyl)-4-methylbenzenesulfonamide;

(R)-3-(5-amino-6-(2-methylpyridin-4-yl)pyrazin-2-yl)-4-methyl-N-(pyrrolidin-3-ylmethyl)benzenesulfonamide;

(S)-3-(5-amino-6-(2-methylpyridin-4-yl)pyrazin-2-yl)-4-methyl-N-(pyrrolidin-3-ylmethyl)benzenesulfonamide;

5-(5-(2,6-diazaspiro[3.3]heptan-2-ylsulfonyl)-2-methylphenyl)-3-(2-methylpyridin-4-yl)pyrazin-2-amine;

3-(5-amino-6-(2-methylpyridin-4-yl)pyrazin-2-yl)-N-((1S,2S)-2-aminocyclopentyl)-4-methylbenzenesulfonamide;

3-(5-amino-6-(2-methylpyridin-4-yl)pyrazin-2-yl)-N-((1R,2R)-2-aminocyclopentyl)-4-methylbenzenesulfonamide;

(R)-5-(5-(3-aminopyrrolidin-1-ylsulfonyl)-2-methylphenyl)-3-(2-methylpyridin-4-yl)pyrazin-2-amine;

5-(5-(4-aminopiperidin-1-ylsulfonyl)-2-methylphenyl)-3-(2-methylpyridin-4-yl)pyrazin-2-amine;

3-(5-amino-6-(2-methylpyridin-4-yl)pyrazin-2-yl)-N-(((1S,3R)-3-(aminomethyl)cyclohexyl)methyl)-4-methylbenzenesulfonamide;

3-(5-amino-6-(2-methylpyridin-4-yl)pyrazin-2-yl)-N-((1r,4r)-4-aminocyclohexyl)-4-methylbenzenesulfonamide;

3-(5-amino-6-(1-(2,2,2-trifluoroethyl)-1H-pyrazol-4-yl)pyrazin-2-yl)-N-(3-hydroxy-3-methylbutyl)-4-methylbenzenesulfonamide;

3-(5-amino-6-(1H-1,2,4-triazol-1-yl)pyrazin-2-yl)-4-methyl-N-(oxetan-3-ylmethyl)benzenesulfonamide;

3-(5-amino-6-(1-benzyl-1H-pyrazol-4-yl)pyrazin-2-yl)-N-(3-hydroxy-3-methylbutyl)-4-methylbenzenesulfonamide;
2-(3-(5-amino-6-(1H-1,2,4-triazol-1-yl)pyrazin-2-yl)-4-methylphenylsulfonamido)acetamide;
3-(5-amino-6-(2-methylpyridin-4-yl)pyrazin-2-yl)-4-methyl-N-(2-oxopiperidin-4-yl)benzenesulfonamide;
3-(5-amino-6-(2-methylpyridin-4-yl)pyrazin-2-yl)-N-((1r,4r)-4-hydroxycyclohexyl)-4-methylbenzenesulfonamide;
3-(5-amino-6-(3-ethyl-1,2,4-oxadiazol-5-yl)pyrazin-2-yl)-N-(3-hydroxy-3-methylbutyl)-4-methylbenzenesulfonamide;
3-(5-amino-6-(3-ethyl-1,2,4-oxadiazol-5-yl)pyrazin-2-yl)-N-(azetidin-3-yl)-4-methylbenzenesulfonamide;
3-(5-amino-6-(5-ethyl-1,3,4-oxadiazol-2-yl)pyrazin-2-yl)-N-((1r,4r)-4-hydroxycyclohexyl)-4-methylbenzenesulfonamide;
3-(5-amino-6-(3-ethyl-1,2,4-oxadiazol-5-yl)pyrazin-2-yl)-N-((1r,4r)-4-hydroxycyclohexyl)-4-methylbenzenesulfonamide;
3-(5-amino-6-(3-propyl-1,2,4-oxadiazol-5-yl)pyrazin-2-yl)-N-((1r,4r)-4-hydroxycyclohexyl)-4-methylbenzenesulfonamide;
(1-(3-(5-amino-6-(3-ethyl-1,2,4-oxadiazol-5-yl)pyrazin-2-yl)-4-methylphenylsulfonyl)piperidin-4-yl)methanol;
cis-3-(5-Amino-6-(2-methylthiazol-5-yl)pyrazin-2-yl)-N-(3-hydroxycyclobutyl)-4-methylbenzenesulfonamide;
trans-3-(5-Amino-6-(2-methylthiazol-5-yl)pyrazin-2-yl)-N-(3-hydroxycyclobutyl)-4-methylbenzenesulfonamide;
(R)-3-(5-Amino-6-(2-methylthiazol-5-yl)pyrazin-2-yl)-4-methyl-N-((tetrahydrofuran-2-yl)methyl)benzenesulfonamide;
(S)-3-(5-Amino-6-(2-methylthiazol-5-yl)pyrazin-2-yl)-4-methyl-N-((tetrahydrofuran-2-yl)methyl)benzenesulfonamide;
(R)-3-(5-Amino-6-(2-methylthiazol-5-yl)pyrazin-2-yl)-4-methyl-N-(tetrahydrofuran-3-yl)benzenesulfonamide;
(S)-3-(5-Amino-6-(2-methylthiazol-5-yl)pyrazin-2-yl)-4-methyl-N-(tetrahydrofuran-3-yl)benzenesulfonamide;
3-(5-Amino-6-(1-(2-(dimethylamino)ethyl)-1H-pyrazol-4-yl)pyrazin-2-yl)-N-(2-hydroxy-2-methylpropyl)-4-methylbenzenesulfonamide;
3-(5-Amino-6-(3-cyclopropyl-1,2,4-oxadiazol-5-yl)pyrazin-2-yl)-N-(3-hydroxy-3-methylbutyl)-4-methylbenzenesulfonamide;
or a pharmaceutically acceptable salt thereof.

In an embodiment 43 of the invention, there is provided a compound or salt according to any one of embodiments 1-42, or a pharmaceutically acceptable salt thereof, for use in medicine.

In an embodiment 44 of the invention, there is provided a compound or salt according to any one of embodiments 1-42 for use in the treatment of a disorder or disease mediated by the activation of PI 3-kinase gamma isoform (p110-γ).

In an embodiment 45 of the invention, there is provided a compound or salt according to any one of embodiments 1-42 for use in the treatment of inflammatory, obstructive or allergic conditions.

In an embodiment 46 of the invention, there is provided a compound or salt according to any one of embodiments 1-42 for use in the treatment of respiratory diseases, allergies, rheumatoid arthritis, osteoarthritis, rheumatic disorders, psoriasis, ulcerative colitis, Crohn's disease, septic shock, proliferative disorders such as cancer, atherosclerosis, allograft rejection following transplantation, diabetes, stroke, obesity and restenosis.

In an embodiment 47 of the invention, there is provided a compound or salt according to any one of embodiments 1-42 for use in the treatment of respiratory diseases, particularly asthma, COPD, COAD, COLD, chronic bronchitis, dyspnea or emphysema, more particularly asthma.

In an embodiment 48 of the invention, there is provided the use of a compound according to any one of embodiments 1-42, or a pharmaceutically acceptable salt thereof, in the manufacture of a medicament for the treatment of a disorder or disease mediated by the activation of PI 3-kinase gamma isoform (p110-γ).

In an embodiment 49 of the invention, there is provided the use of a compound according to any one of embodiments 1-42, or a pharmaceutically acceptable salt thereof, in the manufacture of a medicament for the treatment of respiratory diseases, allergies, rheumatoid arthritis, osteoarthritis, rheumatic disorders, psoriasis, ulcerative colitis, Crohn's disease, septic shock, proliferative disorders such as cancer, atherosclerosis, allograft rejection following transplantation, diabetes, stroke, obesity and restenosis.

In an embodiment 50 of the invention, there is provided the use of a compound according to any one of embodiments 1-42, or a pharmaceutically acceptable salt thereof, in the manufacture of a medicament for the treatment of respiratory diseases, particularly asthma, COPD, COAD, COLD, chronic bronchitis, dyspnea or emphysema, more particularly asthma.

In an embodiment 51 of the invention, there is provided the use of a compound according to any one of embodiments 1-42, or a pharmaceutically acceptable salt thereof, for the treatment of a disorder or disease mediated by the activation of PI 3-kinase gamma isoform (p110-γ).

In an embodiment 52 of the invention, there is provided the use of a compound according to any one of embodiments 1-43, or a pharmaceutically acceptable salt thereof, for the treatment of respiratory diseases, allergies, rheumatoid arthritis, osteoarthritis, rheumatic disorders, psoriasis, ulcerative colitis, Crohn's disease, septic shock, proliferative disorders such as cancer, atherosclerosis, allograft rejection following transplantation, diabetes, stroke, obesity and restenosis.

In an embodiment 53 of the invention, there is provided the use of a compound according to any one of embodiments 1-42, or a pharmaceutically acceptable salt thereof, for the treatment of respiratory diseases, particularly asthma, COPD, COAD, COLD, chronic bronchitis, dyspnea or emphysema, more particularly asthma.

In an embodiment 54 of the invention, there is provided a method of treating a disorder or disease mediated by the activation of PI 3-kinase gamma isoform (p110-γ), comprising administering to a subject in need thereof a therapeutically effective amount of a compound according to any one of embodiments 1-42, or a pharmaceutically acceptable salt thereof.

In an embodiment 55 of the invention, there is provided a method of treating respiratory diseases, allergies, rheumatoid arthritis, osteoarthritis, rheumatic disorders, psoriasis, ulcerative colitis, Crohn's disease, septic shock, proliferative disorders such as cancer, atherosclerosis, allograft rejection following transplantation, diabetes, stroke, obesity and restenosis, comprising
administering to a subject in need thereof a therapeutically effective amount of a compound according to any one of embodiments 1-36, or a pharmaceutically acceptable salt thereof.

In an embodiment 56 of the invention, there is provided a method of treating respiratory diseases, particularly asthma, COPD, COAD, COLD, chronic bronchitis, dyspnea or emphysema, more particularly asthma, comprising administering to a subject in need thereof a therapeutically effective amount of a compound according to any one of embodiments 1-42, or a pharmaceutically acceptable salt thereof.

In an embodiment 57 of the invention, there is provided a pharmaceutical composition comprising:

The term "compounds of the present invention" or "a compound of the present invention" refers to a compound as defined in any one of embodiments 1-42.

The compounds as defined in embodiments 1-42 may be synthesized by the general synthetic routes below, specific examples of which are described in more detail in the Examples.

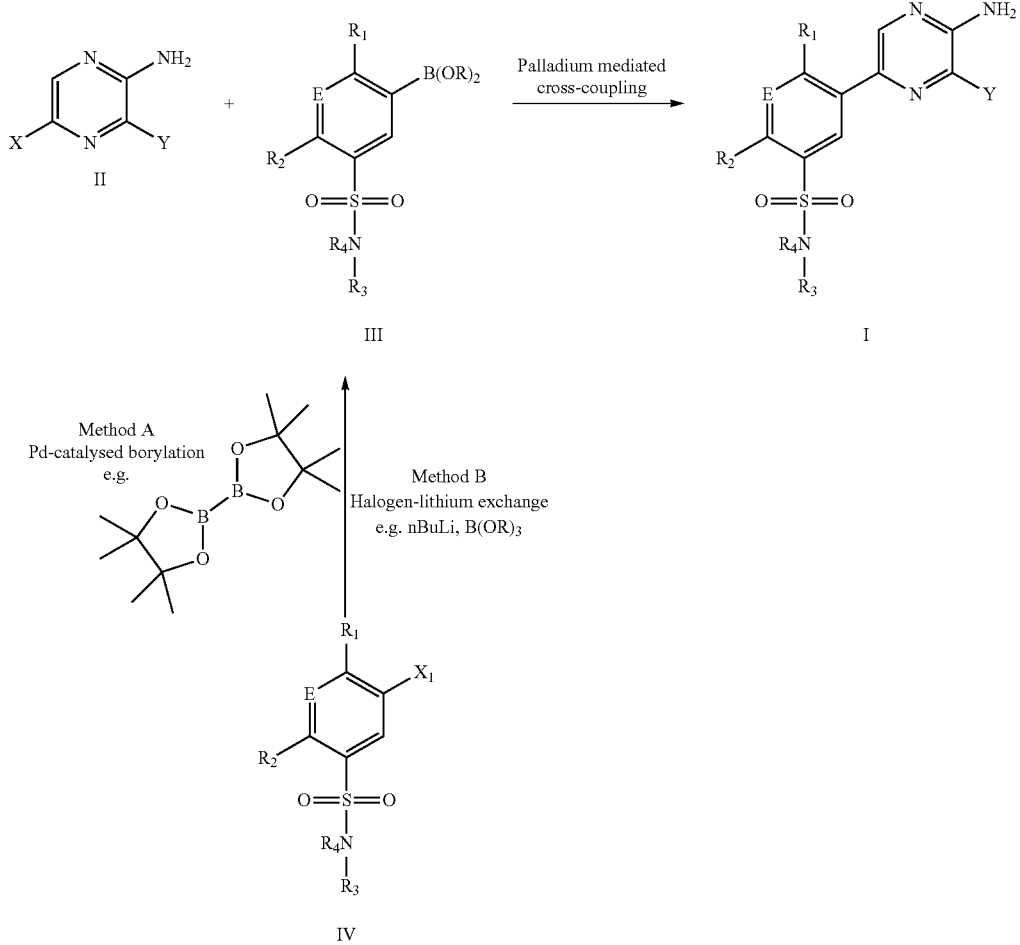

a therapeutically effective amount of the compound according to any one of embodiments 1-42, or a pharmaceutically acceptable salt thereof, and one or more pharmaceutically acceptable carriers.

In an embodiment 58 of the invention, there is provided a pharmaceutical combination, comprising:
a therapeutically effective amount of the compound according to any one of embodiments 1 to 42, or a pharmaceutically acceptable salt thereof, and a second active agent.

In an embodiment 59 of the invention, there is provided a pharmaceutical combination according to embodiment 58, wherein the second active agent is selected from an anti-inflammatory, bronchodilatory or antihistamine drug substance.

In another embodiment, individual compounds according to the invention are those listed in the Examples section below.

wherein $X_1$ is a halogen such as Br or I, Y, $R^1$, $R^2$, $R^3$, $R^4$ and E are as defined in embodiment 1, and X is a halogen such as I, Br or Cl.

The reaction between halopyrazine II and boronic acid or boronic ester III to form compounds of formula I as shown in Scheme 1 may be carried out using a suitable palladium catalyst, such as $Pd(PPh_3)_2Cl_2$, Pd-118 ($PdCl_2(dtbpf)$), $Pd(dppf)Cl_2$ or its adduct with dichloromethane, in a suitable solvent or mixture of solvents, such as 1,2-dimethoxyethane (DME), DME/ethanol, acetonitrile, 1,4-dioxane or toluene/ethanol. The reaction typically requires a base, such as aqueous sodium carbonate, aqueous potassium phosphate or in some cases potassium acetate and may be carried out at elevated temperatures, using conventional or microwave heating.

Compounds of formula II may be obtained from commercial suppliers, prepared as described in Schemes 2b, 3a, 6, 6a, 6b, 6c, 6d, 6e, 8 or 10 or by other methods known in the art. Compounds of formula III may be obtained from commercial suppliers or prepared by borylation of an aryl halide of formula IV with a boron source such as bis(pinacolato)diboron at elevated temperature using conventional or microwave heating (Method A). This reaction is typically catalysed by a palladium catalyst such as Pd(dppf)Cl$_2$.CH$_2$Cl$_2$, and utilises a suitable base such as potassium acetate in an appropriate solvent such as DME or dioxane. In a variation of scheme 1, this borylation of IV to form III may be followed without isolation of III by the subsequent coupling with compound II in a 'one-pot' procedure to form compound I. In a further variation of scheme 1, the 'one-pot' procedure can be carried out by borylation of II and subsequent coupling with IV.

Compounds of formula III may also be prepared by halogen-metal exchange, followed by reaction of the resulting organometallic with a boron source (Method B). Typically this reaction may be carried out by lithiation of a compound of formula IV using an appropriate organometallic species such as n-butyl lithium in an appropriate solvent such as THF, with cooling (for example to −78° C.). The resulting species can then be reacted in situ with an appropriate boron source such as triisopropyl borate.

Compounds of formula IV may be obtained from commercial suppliers, prepared as described in Schemes 4a and 9, or by other methods known in the art.

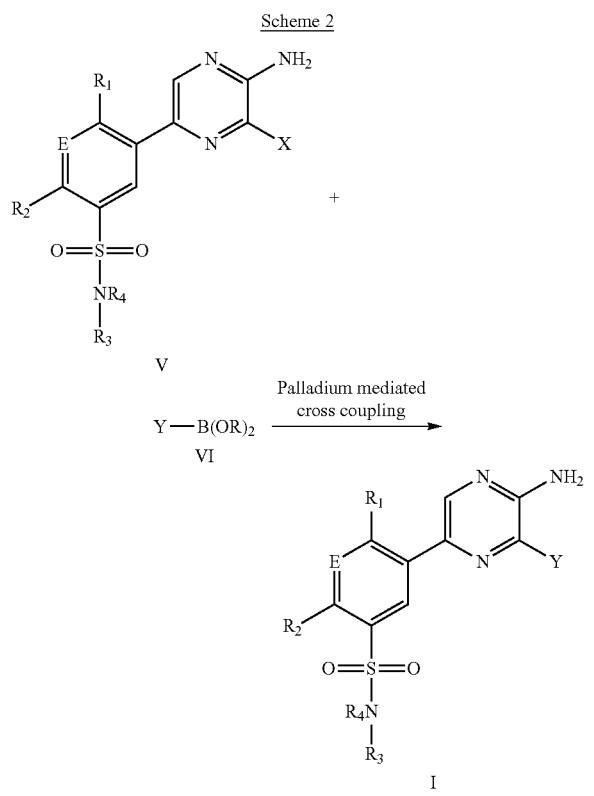

Scheme 2 wherein Y, R$^1$, R$^2$, R$^3$, R$^4$ and E are as defined in embodiment 1, and X is a halogen such as I, Br or Cl.

Where Y is attached to the pyrazine ring by a carbon-carbon bond, compounds of formula I may be prepared as shown in Scheme 2 via a reaction between compounds V and a boronic acid or ester VI. Appropriate conditions for Suzuki couplings such as this are known in the art and include those described in Scheme 1.

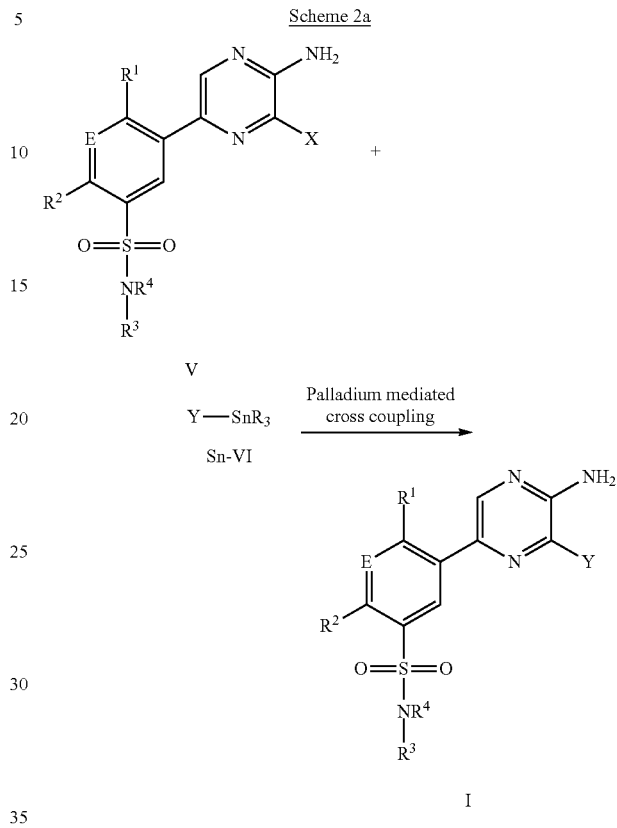

Scheme 2a wherein Y, R$^1$, R$^2$, R$^3$, R$^4$ and E are as defined in embodiment 1, and X is a halogen such as I, Br or Cl.

Where Y is attached to the pyrazine ring by a carbon-carbon bond, compounds of formula I may be prepared as shown in Scheme 2a via a reaction between compounds V and stannane Sn-VI (for example, optionally substituted 4-(tributylstannyl)thiazole). This may be carried out using a suitable palladium catalyst, such as Pd-118, in a suitable solvent such as THF at elevated temperature, optionally in the presence of an appropriate additive such as copper (I) iodide. Alternative conditions for Stille couplings such as this are known in the art.

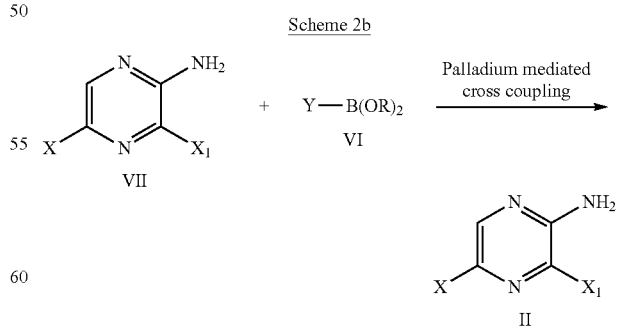

Scheme 2b wherein Y is as defined in embodiment 1, X$_1$ is a halogen such as I, Br or Cl, and X is hydrogen or a halogen.

Compounds of formula II, where Y is attached to the pyrazine ring by a carbon-carbon bond, may be prepared via a palladium mediated cross coupling reaction between a compound of formula VII, as shown in Scheme 2b. Appropriate conditions include those described in Scheme 1 or others known in the art. Where X=H, this can be converted to X=halogen by halogenation conditions. Various conditions for this reaction are known in the art, for example bromination by use of a halogenating agent such as NBS, in an appropriate solvent such as acetonitrile at elevated temperature. Compounds VII, such as 3-bromo-5-chloropyrazin-2-amine, are commercially available, or may be formed by known methods.

Scheme 2c

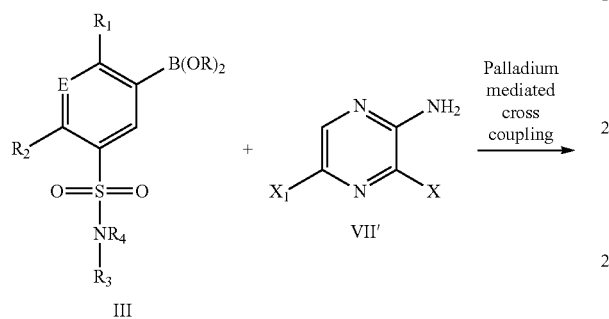

III wherein $R^1$, $R^2$, $R^3$, $R^4$ and E are selected from those in embodiment 1, $X_1$ is a halogen such as I, Br or Cl, and X is hydrogen or a halogen.

The same general method can be used to prepare compounds of formula V, via a reaction between a boronic acid or ester of formula III and a compound of formula VII' as shown in Scheme 2c. Where X=H, this can be converted to X=halogen by methods known in the art. Typically the halogenation could be carried out with a halogenating agent such as N-bromosuccinimide in an appropriate solvent such as DCM.

Compounds of formula VI, VII, VII' are commercially available or may be prepared according to known methods.

Scheme 3

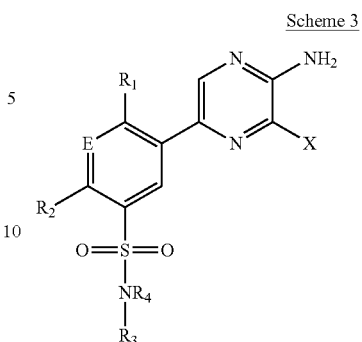

V

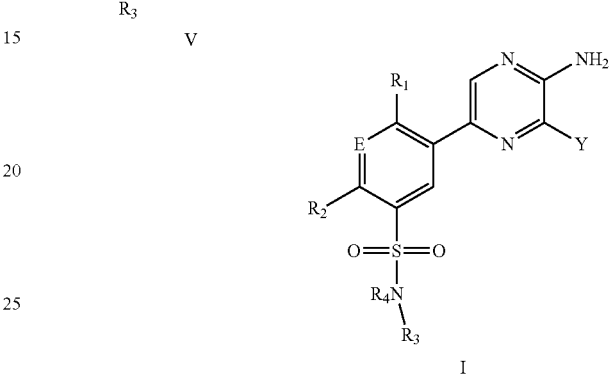

I wherein Y, $R^1$, $R^2$, $R^3$, $R^4$ and E are as defined in embodiment 1, and where Y can be attached to the pyrazine ring by a nitrogen-carbon bond, and X is a halogen.

Compounds of formula I where Y can be attached to the pyrazine ring by a nitrogen-carbon bond may be prepared by a reaction of compound V with an appropriate heteroaryl Y containing an NH group, such as (optionally substituted) 1,2,4-triazole, imidazole or pyrazole. This reaction is typically carried out in the presence of a suitable base (such as an amine, an alkali metal hydride or carbonate, e.g. sodium hydride or cesium carbonate), in a suitable solvent such as dimethyl acetamide (DMA), optionally in the presence of an appropriate catalyst system such as CuI and N,N-dimethylglycine, typically at an elevated temperature of up to 180° C. using, for example, microwave heating. Heteroaryls used may be commercially available or prepared by known methods.

Scheme 3a

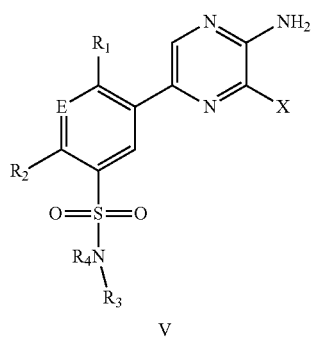

wherein Y is as defined in embodiment 1, where Y can be attached to the pyridine ring by a nitrogen-carbon bond, $X_1$ is a halogen such as I, Br or Cl, and X is hydrogen or a halogen.

Compounds of formula II may be prepared via reaction between a compound of formula VII, such as 5-bromo-3-chloropyrazin-2-amine and an appropriate heteroaryl containing an NH group, such as (optionally substituted) 1,2, 4-triazole, imidazole or pyrazole as shown in Scheme 3a. Typical conditions include the use of catalyst systems as described in Scheme 3, or direct reaction of compound VII with an appropriate heteroaryl, for example by heating in an appropriate solvent such as DMF in the presence of a base such as cesium carbonate. Where X=H, this can be converted to X=halogen by halogenation conditions known in the art.

Scheme 3b

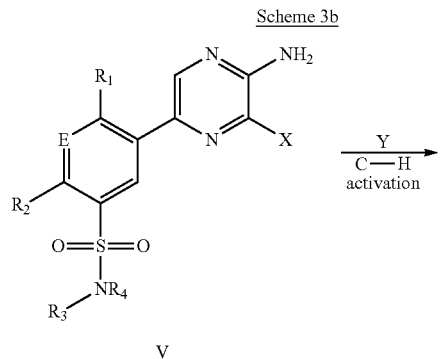

V

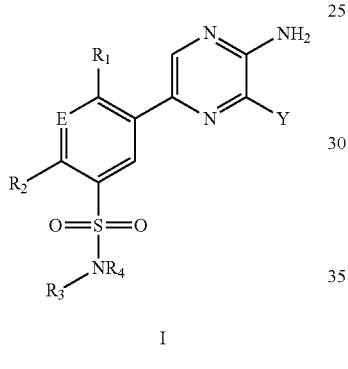

I wherein Y, $R^1$, $R^2$, $R^3$, $R^4$ and E are as defined in embodiment 1, and X is a halogen.

In certain cases compound I can be prepared directly from aminopyrazine halides V and heterocycles, such as oxazole (to give I where Y is oxazol-5-yl or oxazol-2-yl), using a palladium catalysed C—H activation protocol as shown in Scheme 3b. Suitable conditions are known in the art, such as the use of palladium acetate with an added ligand such as di(adamant-1-yl)-n-butyl phosphine, with a base such as potassium carbonate and an additive such as pivalic acid in a solvent such as dimethylacetamide, heating at elevated temperatures such as 110° C.

Scheme 4

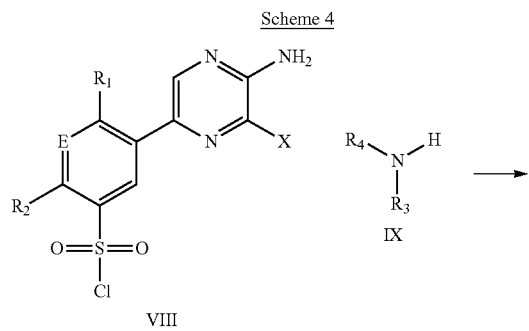

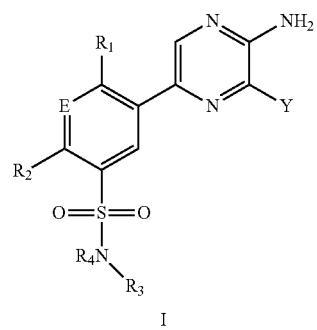

I wherein Y, $R^1$, $R^2$, $R^3$, $R^4$ and E are as defined in embodiment 1.

Compounds of formula I may be prepared by reacting sulfonyl chloride VIII with an amine IX in the presence of a suitable base such as pyridine, triethylamine or diisopropylethylamine, in a suitable solvent such as DCM, THF, pyridine or dimethylacetamide.

Scheme 4a wherein $X_1$ is a halogen such as Br or I, Y, $R^1$, $R^2$, $R^3$, $R^4$ and E are as defined in embodiment 1.

The same method can be used to prepare compounds of formula IV from sulfonyl chlorides VIII* as shown in Scheme 4a. Compounds of formula IX are commercially available or may be prepared by known methods.

Scheme 5

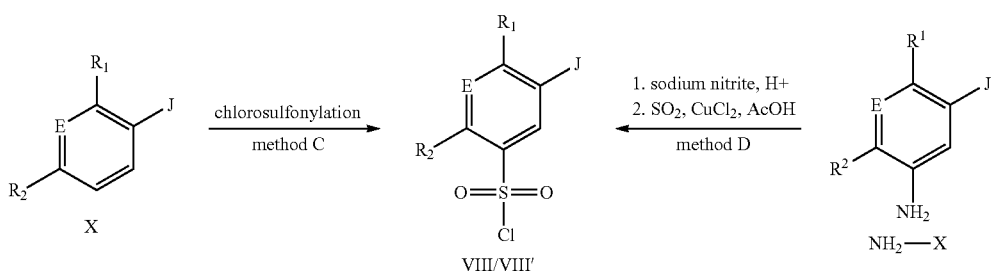

wherein J is a halogen such as Br or I, or

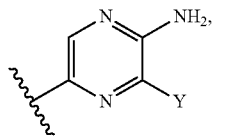

and wherein Y, $R^1$, $R^2$ and E are appropriate groups chosen from those in embodiment 1.

Compounds of formula VIII

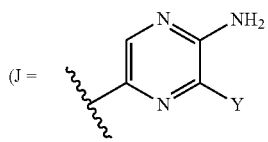

may be prepared according to Scheme 5 by chlorosulfonation of a compound of formula X (method C), typically using chlorosulfonic acid in an appropriate solvent such as chloroform, at ambient temperature or with cooling such as to 0° C. Sulfonyl chlorides VIII/VIII' formed may be reacted directly with amines IX without isolation or purification as described in Schemes 4 and 4a to form compounds I/IV. An alternative preparation of compound VIII is shown in Scheme 5 (method D), by a diazotisation/chlorosulfonation sequence (see, for example Meerwein, H. et al, Chem. Ber., 90: 841-852.) Example conditions include the reaction of compound $NH_2$—X with sodium nitrite in the presence of acid (for example, mixture of acetic acid and conc. HCl) in water with cooling (typically 0° C.), then the resulting mixture added to a stirring solution of the green supernatant of a mixture prepared by bubbling sulfur dioxide gas into glacial acetic acid followed by the addition of $CuCl_2$ in water. Compounds of formula VIII' are commercially available or may be prepared according to the same methods. Compounds of formula X or $NH_2$—X may be obtained from commercial suppliers or made by known methods.

Scheme 6

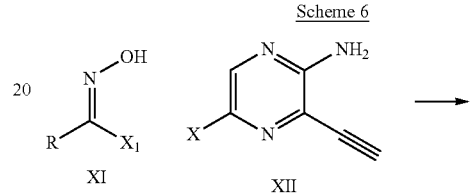

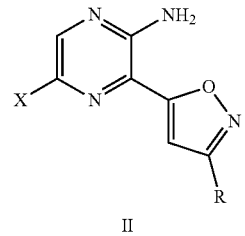

wherein R is an appropriate group chosen from the substitutents listed in the definition of Y in embodiment 1, $X_1$ is a halogen such as bromo, chloro or iodo, and X is a halogen or hydrogen.

Compounds of formula II where Y is 3-substituted-isoxazol-5-yl can be prepared according to the route shown in Scheme 6 by the reaction of a compound of formula XI with an alkyne of formula XII. Typical conditions for this transformation use copper (II) sulfate, sodium ascorbate and sodium bicarbonate in appropriate solvent mixtures such as t-BuOH and water, under a nitrogen atmosphere at ambient temperature. Compounds of formula XI are commercially available, or can be prepared by known methods, or prepared in situ. For example compounds of formula XI can be prepared by halogenation of aldehyde oximes. By adding chloramine-T, copper powder and copper (II) sulfate to the mixture of an aldehyde, hydroxylamine hydrochloride, and base (e.g. sodium hydroxide) in appropriate solvent mixture (e.g. t-butanol water), followed by addition of alkyne XII and heating, compound II can be formed. Where X=H, this can be converted to X=halogen by halogenation conditions known in the art.

Compounds of formula XII are commercially available or can be prepared by known methods, for example using Sonogashira coupling with TMS-acetylene followed by deprotection.

Scheme 6a

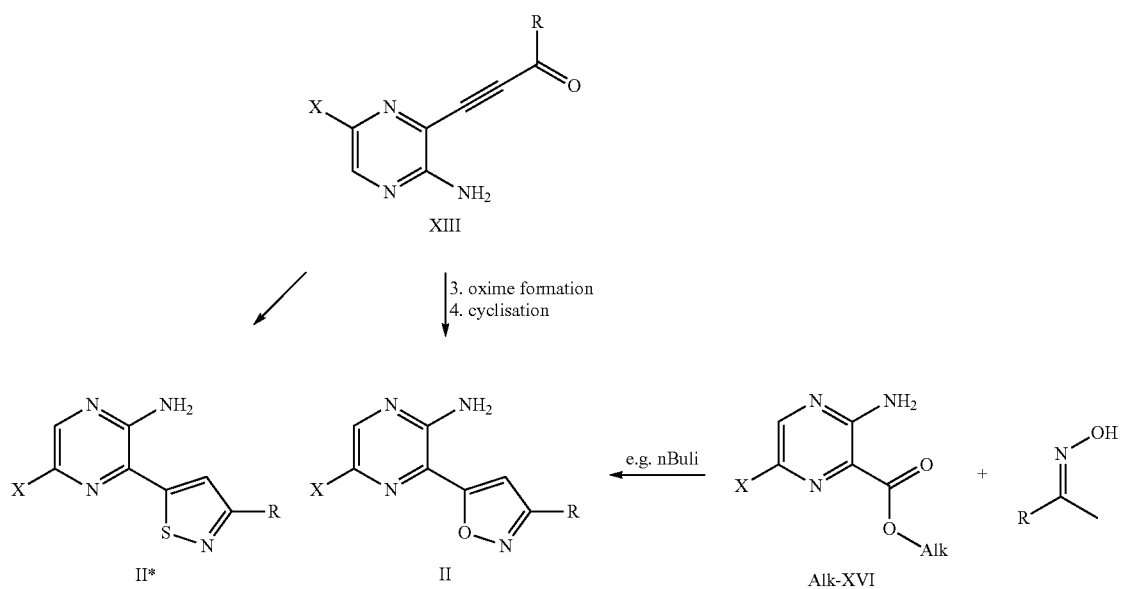

wherein R and X are as defined in Scheme 6, $X_1$ is bromo or iodo, Alk is an alkyl group such as methyl or ethyl.

Compounds of formula II where Y is 3-substituted-isoxazol-5-yl can also be formed by cycloisomerization of acetylenic oximes as shown in scheme 6a.

Following oxime formation from ketone XIII by known methods, the cyclisation in step 4 to form compound II is typically catalysed by acid (such as aqueous HCl in AcOH) or by gold catalysis as described in Synlett, 2010, No. 5, pp 0777-0781. Compounds of formula II* (compounds of formula II where Y is 3-substituted-isothiazol-5-yl) can also be formed from ketone XIII, for example by treatment with hydroxylamine-O-sulfonic acid, sodium bicarbonate and sodium hydrogen sulfide in an appropriate solvent mixture such as THF/water. Ketone XIII can be formed from a dihaloaminopyrazine such as 3-bromo-5-chloropyrazin-2-amine using known methods as shown in Scheme 6a, for example by Sonogashira coupling with propargylic alcohol XIV, followed by oxidation using an oxidising agent such as manganese dioxide.

A further alternative preparation of compound II where Y is 3-substituted-isoxazol-5-yl is shown in Scheme 6a, and utilises the reaction of ester Alk-XVI with the dianion of an oxime, (typically formed by treatment of oxime (such as acetone oxime) with 2 eq. of n-butyllithium in dry solvent such as THF with cooling), followed by dehydrative cyclisation (using, for example sulfuric acid) to give compound II. Where X=H, this can be converted to X=halogen by halogenation conditions known in the art.

Compounds of formula XIV are commercially available or can be prepared by known methods.

Scheme 6b

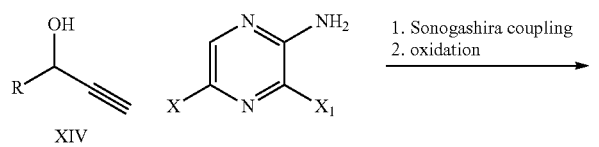

wherein R and X are as defined in Scheme 6.

Compounds of formula II where Y is 3-substituted-[1,2,4]oxadiazol-5-yl may be prepared by condensation and dehydration of amidoxime XV and acid XVI as shown in Scheme 6b. Where X=H, this can be converted to X=halogen by halogenation conditions known in the art. Suitable reagents for the condensation and dehydration are known in the art and include Ghosez' reagent, T3P®, DCC and HOBt, or HATU in an appropriate solvent such as DCM, THF or toluene, in the presence of an appropriate base such as DIPEA.

Scheme 6c

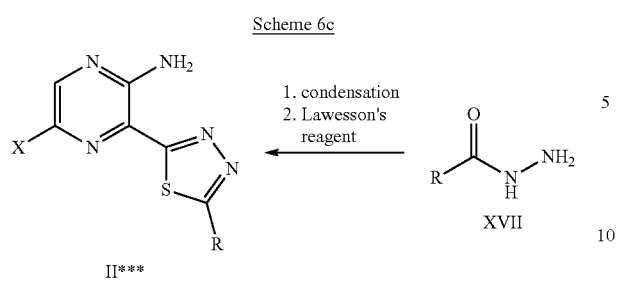

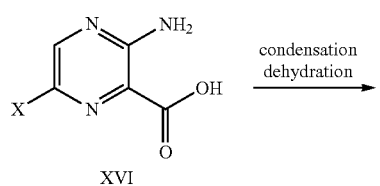

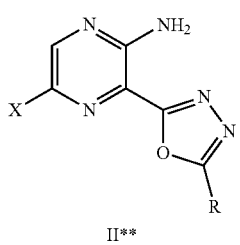

wherein R and X are as defined in Scheme 6.

In a related reaction shown in Scheme 6c, compounds of formula II (compounds of formula II where Y=5-substituted-1,3,4-oxadiazol-2-yl) are prepared by condensation and dehydration of compounds XVI and XVII using conditions known in the art. This can be carried out by a one or two step process, for example using an amide coupling reagent such as HATU or T3P in the presence of an appropriate base such as triethylamine, then dehydrative cyclisation using for example tosyl chloride in the presence of an appropriate base such as triethylamine, in a suitable solvent such as DCM. Other dehydrating agents are known in the art, such as POCl₃. Similarly, following amide formation/condensation, the resulting N-acylhydrazide may be treated with Lawesson's reagent to prepare compounds of formula II* (compounds of formula II where Y=5-substituted-1, 3,4-thiadiazol-2-yl). Where X=H, compounds II and II* can be converted to X=halogen by halogenation conditions known in the art. Compounds of formulae XV, XVI, Alk-XVI and XVII are commercially available or can be prepared by known methods.

Scheme 6d

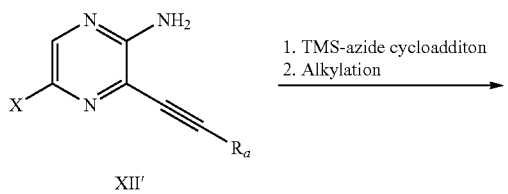

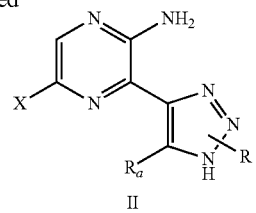

wherein R and X are as defined in Scheme 6, and R_a is hydrogen or an appropriate group chosen from the substitutents listed in the definition of Y in embodiment 1.

Compounds of formula II (where Y is 1,2,3-triazol-4-yl optionally substituted in the Sand 1 or 2 positions) are prepared by reaction of alkyne XII' with trimethylsilyl azide, followed by optional alkylation if 1 or 2 position substitution is required, as shown in Scheme 6d. Typical conditions for the first step of this transformation use copper (II) sulfate, sodium ascorbate and sodium bicarbonate in appropriate solvent mixtures such as t-BuOH and water, at elevated temperature such as 90° C. The resulting triazole (where R=H) can be alkylated using an alkylating agent (such as iodomethane, iodoethane, 2,2,2-trifluoroethyl trifluoromethanesulfonate or other alkyl halides or sulfonates) in the presence of an appropriate base/additive (such as TBAF or metal carbonates such as caesium carbonate), in an suitable solvent such as acetonitrile or THF, to give compounds of formula II as mixtures of N1 and N2 alkylated products, which may be separable by known methods. Where X=H, these can be converted to X=halogen by halogenation conditions known in the art. Compounds XII' may be obtained from commercial suppliers or prepared by methods known in the art, for example Sonogashira coupling.

Scheme 6e

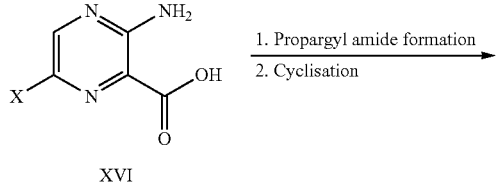

wherein X is a halogen or hydrogen.

Compounds of formula II (where Y=oxazol-2-yl) can be prepared from acid XVI by formation of a propargyl amide using known conditions, followed by cyclisation, for example using gold (III) chloride in a solvent such as DCM. Where X=H, this can be converted to X=halogen by halogenation conditions known in the art.

Scheme 7

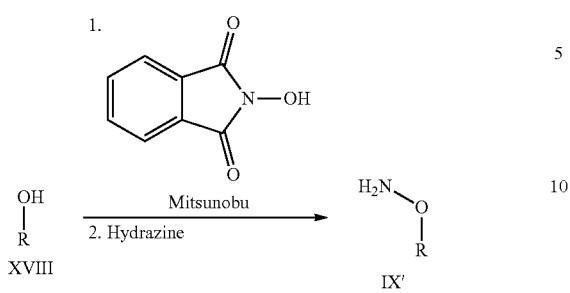

wherein R is an appropriate group chosen from the relevant list of substituents in embodiment 1.

Compounds of formula IX' can be prepared from alcohols XVIII (obtained commercially or prepared by known methods) by treatment with N-hydroxyphthalamide under Mitsunobu-type conditions known in the art (for example using PS-triphenylphosphine and di-tert-butyl azodicarboxylate in a solvent such as THF), followed by deprotection of the phthalamide group using known consitions, typically by treatment with hydrazine.

Scheme 8

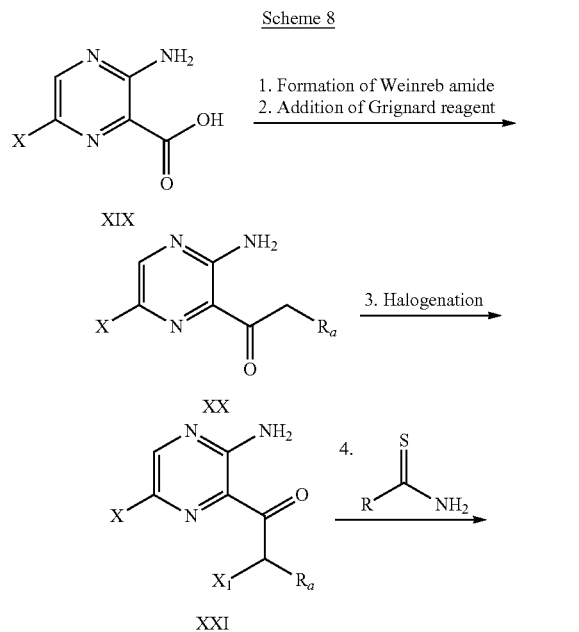

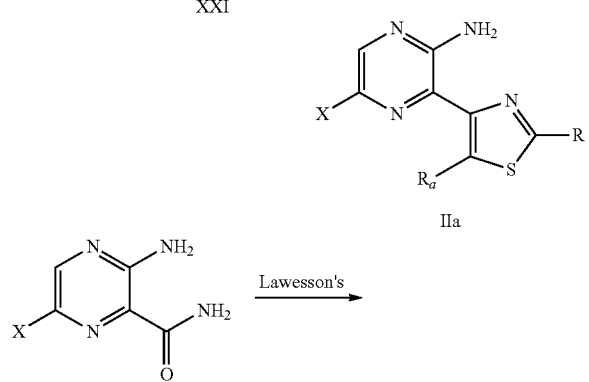

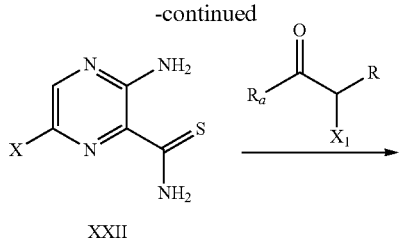

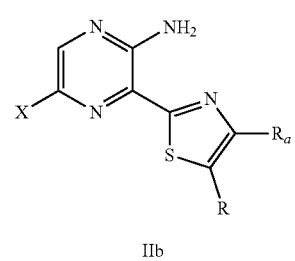

wherein X is hydrogen or halogen, R, $R_a$ are as defined in embodiment 1, $X_1$ is halogen.

Compounds of formula IIa (compounds of formula II where Y=2 or 2,5-substituted-thiazol-4-yl) can be prepared according to Scheme 8 from alpha-halo ketone XXI by reaction with a thioamide in a suitable solvent such as ethanol at elevated temperature such as 50-70° C. Similarly, compounds of formula IIb (compounds of formula II where Y=5 or 4,5-substituted-thiazol-2-yl) can be prepared from thioamide XXII and alpha-halo ketones (prepared by known methods or obtained commercially). Compound XXI can be prepared by halogenation of ketone XX by conditions known in the art, such as treatment with pyridinium tribromide (optionally on polymer support) and HBr in acetic acid at elevated temperature. Ketone XX can be prepared from commercially available starting materials by formation of the Weinreb amide from acid XIX (obtained commercially or prepared by known methods), followed by addition of a Grignard reagent. Thioamide XXII can be prepared by methods known in the art, such as treatment of the appropriate primary amide (obtained commercially or prepared by known methods), with Lawesson's reagent. Where X=H, IIa or IIb can be converted to the corresponding compound where X=halogen by halogenation conditions known in the art.

Scheme 9

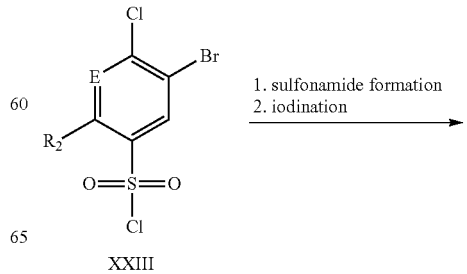

Scheme 11

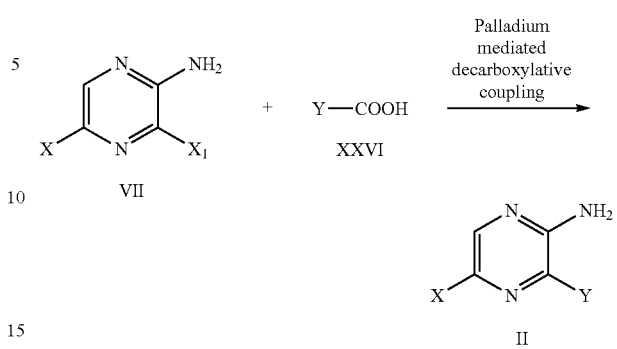

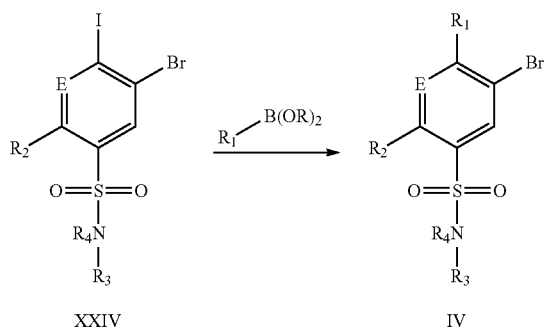

wherein E, $R^1$, $R^2$, $R^3$, $R^4$ are as defined in embodiment 1.

Certain compounds of formula IV may be prepared by a cross coupling reaction of compound XXIV with an appropriate boronic acid (such as methyl boronic acid), in the presence of a base (for example aqueous sodium carbonate), an appropriate catalyst (for example bis(triphenylphosphine) palladium dichloride) and in an appropriate solvent such as 1,4-dioxane under elevated temperature. Compound XXIV (where E=N) can be prepared in two steps from compound XXIII by sulfonamide formation (for conditions, see Scheme 4) followed by iodination, which typically can be carried out by treatment with an iodide source such as trimethylsilyliodide (or trimethylsilyl chloride plus sodium iodide) in an appropriate solvent such as acetonitrile. Compounds XXIII are commercially available or can be made by known methods.

Scheme 10

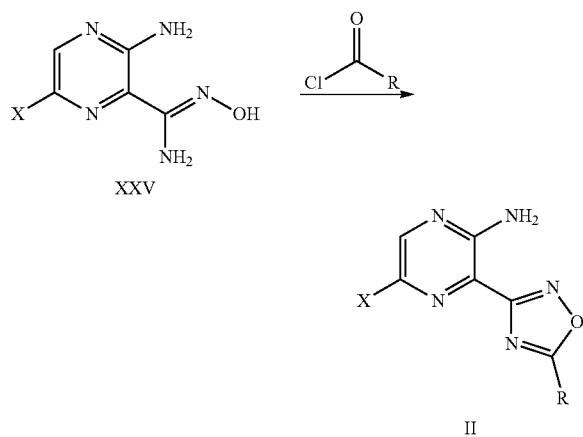

wherein X=hydrogen or halogen, R is what

Compounds of formula II (where Y is 5-substituted-1,2,4-oxadiazol-3-yl) may be prepared by reaction of amidoxime XXV with an acid chloride using known conditions, followed by dehydrative cyclisation. Conditions for this sort of cyclisation are known in the art, and include the use of hexachloroethane in acetic acid at elevated temperature. Compound XXV can be formed by known methods, for example the reaction of commercially available 3-amino-6-bromopyrazine-2-carbonitrile with hydroxylamine hydrochloride, in the presence of a base (such as triethylamine) and in an appropriate solvent such as methanol.

wherein Y is an appropriate group selected from the groups defined in embodiment 1, $X_1$ is halogen such as I, Br or Cl and X is H or halogen.

Compounds of formula II may be prepared by a decarboxylative cross-coupling of carboxylic acid XXVI (obtained from commercial suppliers or prepared by known methods) with compound VII. Reagents for the coupling are known in the art and include a suitable palladium catalyst, such as $Pd(PPh_3)_2Cl_2$ and a base (preferentially a silver salt such as silver carbonate) in an appropriate solvent such as NMP at elevated temperature. Where X=H, this can be converted to X=halogen by halogenation using known conditions.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the present invention and intermediates can also be converted into each other according to methods generally known to those skilled in the art.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter. All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds of the present invention, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

The term "an optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line.

Certain compounds described herein contain one or more asymmetric centers or axes and may thus give rise to enantiomers, diastereomers, and other stereoisomeric forms that may be defined, in terms of absolute stereochemistry, as (R)- or (S)—.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

As used herein, the terms "salt" or "salts" refers to an acid addition or base addition salt of a compound of the present invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds of the present invention. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$Cl, $^{125}$I respectively. The invention includes various isotopically labeled compounds of the present invention, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F labeled compound of the present invention may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the present invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

The compounds of the present invention are potent inhibitors of the PI 3-kinase gamma isoform. This is shown in Table 4, assay E. Furthermore and importantly, the compounds of the present invention are selective for the PI 3-kinase gamma isoform over the other class 1 PI 3-kinase isoforms alpha, beta and delta, which is shown in Table 4, assays A, B and F, and over related lipid kinases Vps34 and PI 4-kinase beta, which is shown in Table 4, assays C and D, and also over the PI 3-kinase related protein kinases such as mTOR (Table 4, assay G). Selectivity for PI 3-kinase gamma isoform is preferred in order to avoid possible unwanted side effects when treating patients. Particularly, selectivity for the PI 3-kinase gamma isoform over the PI 3-kinase alpha isoform is preferred as the PI 3-kinase alpha isoform is widely expressed in the body and has shown to be important in insulin receptor signalling.

The target enzyme of the compounds of the present invention, i.e. PI 3-kinase gamma isoform, is an intracellular target. Thus, compounds of the present invention which retain their activity in a cellular environment are preferred. The compounds of the present invention have thus been tested in cellular assays (see Table 5, assays H1, H2, I1, I2, J1, J2, K1 and K2). In assays K1 and K2, the compounds were tested for their ability to inhibit the production of phosphorylated AKT (Protein Kinase B) generated in a PI 3-kinase gamma isoform-dependent process in a U937 human cell line. Activity of a particular compound in a cellular assay depends on a variety of different factors such as potency of that compound at the target (see Table 4), solubility of the compound, Log P and permeability. Thus, good cellular activity of compounds of the present invention results from the combination of structural features conveying a good overall balance of molecular properties. Generally, preferred compounds of the present invention have high potency at the target (see Table 4) and show good activity in the cellular assays (Table 5).

In order to effectively inhibit the PI 3-kinase gamma isoform target (present in leukocytes) in an in vivo system, a drug compound will preferably need to show sufficient activity in whole blood. Hence, compounds of the present invention have been tested for their ability to inhibit neutrophil shape change in response to the chemotactic factor interleukin-8 (IL-8), which is a PI 3-kinase gamma isoform-dependent event, in human whole blood (Table 5, assay L). Activity in whole blood is dependent on additional factors such as plasma protein binding and plasma stability of a particular compound. Preferred compounds of the present invention thus have besides of potency at the PI 3-kinase gamma isoform target (Table 4) and sufficient cellular potency (Table 5) also sufficient activity in human whole blood as tested in assay L. More preferably, compounds of the present invention have IC50 values of in this human whole blood assay of <1 µM.

Additionally to the on-target potency (Table 4, assay E)), selectivity (Table 4, assays A, B, C, D, F and G), activity in cellular assays (Table 5, assays H1, H2, I1, I2, J1, J2, K1 and K2) and human whole blood assay (Table 5, assay L), the maintenance of sufficient drug concentration in vivo after oral administration to inhibit the target is required. Such pharmacokinetic properties are dependent on a variety of factors such as Log P, permeability, aqueous solubility and stability against oxidative metabolism. Compounds of the present invention have been tested for stability against oxidative metabolism using an in vitro microsomal stability assay (Table 5, assay M). Preferred compounds of the present invention show sufficient stability in this liver microsomal assay. Furthermore, preferred compounds of the present invention also have sufficient aqueous solubility.

Thus, the compounds of the present invention may be useful in the treatment of conditions which are mediated by the activation of PI 3-kinase gamma isoform, particularly inflammatory or allergic conditions.

Compounds of the present invention are useful in the treatment of inflammatory or obstructive airways diseases, resulting, for example, in reduction of tissue damage, airways inflammation, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome")

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, compounds of the present invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the present invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Compounds of the present invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, leishmaniasis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Other diseases or conditions which may be treated with compounds of the present invention include thrombosis, hypertension, heart ischaemia and pancreatitis, (Nature review November 2006 Vol 5), treatment of anaemia including haemolytic anaemia, aplastic anaemia and pure red cell anaemia (WO 2006/040318), septic shock, rheumatoid arthritis, osteoarthritis, proliferative diseases such as cancer, atherosclerosis, allograft rejection following transplantation, stroke, obesity, restenosis, diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, and conditions characterised by elevated intraocular pressure or secretion of ocular aqueous humor, such as glaucoma.

Agents of the present invention may be useful in the treatment or prevention of heart failure such as (acute and chronic) congestive heart failure, left ventricular dysfunction including impaired cardiac contractility, hypertrophic cardiomyopathy, diabetic cardiac myopathy and other types of detrimental cardiac dysfunction and remodelling.

The compounds of the present invention may also be useful in the treatment of visceral disorders, inflammatory bowel disease, inflammatory bowel disorder, cystitis, e.g. interstitial cystitis and urinary incontinence including bladder detrusor hyper-reflexia and bladder hypersensitivity.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, *J. Immunol. Methods* (1997) 202:49-57; Renzi et al, *Am. Rev. Respir. Dis.* (1993) 148:932-939; Tsuyuki et al., *J. Clin. Invest.* (1995) 96:2924-2931; and Cernadas et al (1999) *Am. J. Respir. Cell Mol. Biol.* 20:1-8.

The compounds of the present invention are also useful as co-therapeutic agents for use in combination with PI 3-Kinase delta inhibitors, for example in allergic asthma or in immune-mediated inflammatory diseases, such as rheumatoid arthritis or multiple sclerosis. Such an effect could be potentially achieved through co-administration of a selective inhibitor of PI 3-kinase gamma isoform with a selective inhibitor of PI 3-kinase delta isoform.

The compounds of the present invention are also useful as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosage or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory or antihistamine drug substance, said agent of the invention and said drug substance being in the same or different pharmaceutical composition.

Useful combinations of PI 3-kinase inhibitors with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]amino]phenyl]-methyl]tetrahydro-N,N-dimethyl-2H-pyran-4-amin-ium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, in particular, glucocorticosteroids, such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists, such as montelukast and zafirlukast; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ 00-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine A2B receptor antagonists such as those described in WO 02/42298; and beta-2 adrenoceptor agonists, such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula (I) of WO 0075114, which document is incorporated herein by reference, preferably compounds of the Examples thereof, especially a compound of formula:

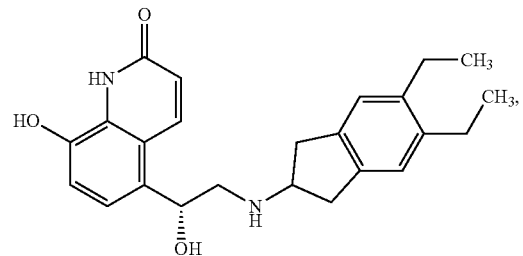 [SMILES: CCc1cc2c(cc1CC)CC(NC[C@H](O)c1ccc(O)c3[nH]c(=O)ccc13)C2]

corresponding to indacaterol and pharmaceutically acceptable salts thereof, as well as compounds (in free or salt or solvate form) of formula (I) of WO 04/16601, and also compounds of EP 1440966, JP 05025045, WO 93/18007, WO 99/64035, USP 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618, WO 04/46083, WO 04/80964, WO 04/108765 and WO 04/108676.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285.

Suitable dual anti-inflammatory and bronchodilatory drugs include dual beta-2 adrenoceptor agonist/muscarinic antagonists such as those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841

Pi3 kinase inhibitors, e.g. those compounds of the invention, may be combined with an angiotensin receptor blocker, e.g. valsartan (an angiotensin receptor blocker) and achieve greater therapeutic effect than the administration of valsartan alone. The combination regimen also surprisingly reduces the rate of progression of cardiac, renal and cerebral end-organ damage. The combination elicits enhanced antihypertensive effects (whether malignant, essential, reno-vascular, diabetic, isolated systolic, or other secondary type of hypertension) and lessening of pulse pressure. The combination is also effective in treating supraventricular and ventricular arrhythmias, atrial fibrillation, atrial flutter or detrimental vascular remodeling. It can further be shown that the combination is beneficial in the treatment and prevention of myocardial infarction and its sequelae, and is useful in treating atherosclerosis, angina (whether stable or unstable), renal insufficiency (diabetic and non-diabetic), peripheral vascular disease, cognitive dysfunction, and stroke. Furthermore, the improvement in endothelial function with the combination therapy provides benefit in diseases in which normal endothelial function is disrupted such as heart failure, angina pectoris and diabetes. Furthermore, the combination may be used for the treatment or prevention of primary and secondary pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, peripheral vascular disease, Raynaud's disease, luminal hyperplasia, cognitive dysfunction (such as Alzheimer's), glaucoma and stroke.

Compounds of the present invention may also be useful in the treatment of diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, Graves ophthalmopathy, alopecia areata and others, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis and further eczematous dermatitises, seborrhoeic dermatitis, cutaneous manifestations of immunologically-mediated disorders, inflammatory eye disease, myocarditis or hepatitis, gut ischemia, traumatic shock, cancer, e.g. breast cancer, T cell lymphomas or T cell leukemias, infectious diseases, e.g. toxic shock (e.g. superantigen induced), septic shock, adult respiratory distress syndrome or viral infections, e.g. AIDS, viral hepatitis, chronic bacterial infection, or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus.

Compounds of the present invention may be administered in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders. For example, the compounds of formula I may be used in combination with a calcineurin inhibitor, e.g. cyclosporin A or FK 506; a mTOR inhibitor, e.g. rapamycin, 40-O-(2-hydroxyethyl)-rapamycin, CCI779, ABT578, AP23573, biolimus-7 or biolimus-9; an ascomycin having immuno-suppressive properties, e.g. ABT-281 or ASM981; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-cyanoacetamide-cyano-(3,4-dihydroxy)-]N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxylphenyl)-amino-6,7-dimethoxyquinazoline] (WHI-P154), [4-(3',5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550), or a compound as disclosed in WO 04/052359 or WO 05/066156; a S1P receptor agonist or modulator, e.g. FTY720 optionally phosphorylated or an analog thereof, e.g. 2-amino-2-[4-(3-benzyloxyphenylthio)-2-chlorophenyl]ethyl-1,3-propanediol optionally phosphorylated or 1-{4-[1-(4-cyclohexyl-3-trifluoromethyl-benzyloxyimino)-ethyl]-2-ethyl-benzyl}-azetidine-3-carboxylic acid or its pharmaceutically acceptable salts; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists.

The compounds of the present invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

Thus, in a further aspect, there is provided a compound of the present invention for use in therapy. In a further embodiment, the therapy is selected from a disease or disorder which is mediated by the activation of PI 3-kinase gamma isoform. In a further embodiment, the therapy is selected from a disease which may be treated by inhibiting of PI 3-kinase gamma isoform. In another embodiment, the therapy is selected from a disease which may be treated by inhibiting of PI 3-kinase gamma isoform selectively over PI 3-kinase delta isoform.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by the activation of PI 3-kinase, particularly the gamma isoform, or (ii) associated with PI 3-kinase gamma isoform activity, or (iii) characterized by activity (normal or abnormal) of PI 3-kinase gamma isoform; or (2) reducing or inhibiting the activity of PI 3-kinase gamma isoform. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of PI 3-kinase gamma isoform.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The compounds of the present invention may be useful as pharmaceuticals and are thus usually formulated in the form of a pharmaceutical composition.

Hence, in another aspect, the present invention provides a pharmaceutical composition comprising a compound of the present invention and a pharmaceutically acceptable carrier.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art. Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in a mixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Where the inhalable form of the active ingredient is an aerosol composition, the inhalation device may be an aerosol vial provided with a valve adapted to deliver a metered dose, such as 10 to 100 µl, e.g. 25 to 50 µl, of the composition, i.e. a device known as a metered dose inhaler. Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, sometimes referred to as a soft mist or soft spray inhaler, for example an electronically controlled device such as an AERx (Aradigm, US) or Aerodose (Aerogen), or a mechanical device such as a RESPIMAT (Boehringer Ingelheim) nebulizer which allows much smaller nebulized volumes, e.g. 10 to 100 µl, than conventional nebulizers. Where the inhalable form of the active ingredient is the finely divided particulate form, the inhalation device may be, for example, a dry powder inhalation device adapted to deliver dry powder from a capsule or blister containing a dry powder comprising a dosage unit of (A) and/or (B) or a multidose dry powder inhalation (MDPI) device adapted to deliver, for example, 3-25 mg of dry powder comprising a dosage unit of (A) and/or (B) per actuation. The dry powder composition preferably contains a diluent or carrier, such as lactose, and a compound that helps to protect against product performance deterioration due to moisture e.g. magnesium stearate. Suitable such dry powder inhalation devices include devices disclosed in U.S. Pat. No. 3,991,761 (including the AEROLIZER™ device), WO 05/113042, WO 97/20589 (including the CERTIHALER™ device), WO 97/30743 (including the TWISTHALER™ device) and WO 05/37353 (including the GYROHALER™ device).

Hence, the invention also includes (A) an agent of the invention, or a pharmaceutically acceptable salt or solvate thereof, in inhalable form; (B) an inhalable medicament comprising a compound of the present invention in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages of compounds of the present invention employed in practicing the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compound of the present invention may be administered either simultaneously with, or before or after, one or more other therapeutic agent. The compound of the present invention may be administered separately, by the same or different route of administration, or together in the same pharmaceutical composition as the other agents.

In a further aspect, there is provided a pharmaceutical combination comprising a compound of the present invention and at least one other therapeutic agent, for example for simultaneous, separate or sequential use in therapy. In one embodiment, the therapy is the treatment of a disease or disorder mediated by the activation of PI 3-kinase, particularly the gamma isoform. Products provided as a pharmaceutical combination include a composition comprising the compound of the present invention and the other therapeutic agent(s) together in the same pharmaceutical composition, or the compound of the present invention and the other therapeutic agent(s) in separate form, e.g. in the form of a kit.

In one embodiment, the invention provides a pharmaceutical combination comprising a compound of the present invention and another therapeutic agent(s). Optionally, the pharmaceutical composition may comprise a pharmaceutically acceptable excipient, as described above.

In one embodiment, there is provided a kit comprising two or more separate pharmaceutical compositions, at least one of which contains a compound of the present invention. In one embodiment, the kit comprises means for separately retaining said compositions, such as a container, divided bottle, or divided foil packet. An example of such a kit is a blister pack, as typically used for the packaging of tablets, capsules and the like.

The kit may be used for administering different dosage forms, for example, oral and parenteral, for administering the separate compositions at different dosage intervals, or for titrating the separate compositions against one another. To assist compliance, the kit of the invention typically comprises directions for administration.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound of the present invention, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

PI 3-kinase antagonists such as the compounds of the present invention are also useful as co-therapeutic agents for use in combination with a second active agent such as for example an organic nitrate and NO-donors, such as sodium nitroprusside, nitroglycerin, isosorbide mononitrate, isosorbide dinitrate, molsidomine or SIN-1, and inhalational NO; compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors such as sildenafil, vardenafil and tadalafil; NO-independent, but haem-dependent stimulators of guanylate cyclase, such as in particular the compounds described in WO 00/06568, WO 00/06569, WO 02/42301 and WO 03/095451; NO— and haem-independent activators of guanylate cyclase, such as in particular the compounds described in WO 01/19355, WO 01/19776, WO 01/19778, WO 01/19780, WO 02/070462 and WO 02/070510; compounds which inhibit human neutrophilic elastase, such as sivelestat or DX-890 (Reltran); compounds inhibiting the signal transduction cascade, such as tyrosine kinase and/or serine/threonine kinase inhibitors, in particular imatinib, gefitinib, erlotinib, sorafenib and sunitinib; compounds influencing the energy metabolism of the heart, for example and preferably etomoxir, dichloroacetate, ranolazine or trimetazidine; antithrombotic agents, for example and preferably from the group comprising platelet aggregation inhibitors, anticoagulants or profibrinolytic substances; active substances for lowering blood pressure, for example and preferably from the group comprising calcium antagonists, angiotensin II antagonists, ACE inhibitors, endothelin antagonists, renin inhibitors, aldosterone synthase inhibitors, alpha receptor blockers, beta receptor blockers, mineralocorticoid receptor antagonists, Rho-kinase inhibitors and diuretics; and/or active substances that modify lipid metabolism, for example and preferably from the group comprising thyroid receptor agonists, inhibitors of cholesterol synthesis, for example and preferably HMG-CoA-reductase inhibitors or inhibitors of squalene synthesis, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein (a) antagonists, particularly in the treatment of PAH or diseases and disorders such as those mentioned hereinbefore, e.g., as potentiators of therapeutic activity of such drugs or as a means of reducing required dosaging or potential side effects of such drugs.

In a particular embodiment, there is provided a pharmaceutical combination comprising the compounds of the present invention and a second agent wherein the second agent is a PDE 5 inhibitor or neutral endopeptidase inhibitor.

The compounds of the present invention may be mixed with a second agent in a fixed pharmaceutical composition or it may be administered separately, before, simultaneously with or after the other drug substance.

Particularly, the invention includes in a further aspect a combination of a PI 3-kinase inhibitor such a compound of the present invention with osmotic agents (hypertonic saline, dextran, mannitol, Xylitol), ENaC blockers, an anti-inflammatory, bronchodilatory, antihistamine, anti-tussive, antibiotic and/or DNase drug substance, wherein the TPH1 antagonist and the further drug substance may be in the same or different pharmaceutical composition.

Suitable antibiotics include macrolide antibiotics, e.g., tobramycin (TOBI™).

Suitable DNase drug substances include dornase alfa (Pulmozymen™), a highly-purified solution of recombinant human deoxyribonuclease I (rhDNase), which selectively cleaves DNA. Dornase alfa is used to treat cystic fibrosis.

Accordingly, the invention includes as a further aspect a combination of PI 3-kinase inhibitors such the compounds of the present invention with second agents that are IP receptor agonist, particularly the compounds disclosed in WO2012/007539.

Accordingly, the invention includes as a further aspect a combination of PI 3-kinase inhibitors such the compounds of the present invention with second agents that are multi-kinase inhibitors, such as imatinib mysilate, Gleevec. Imatinib functions as a specific inhibitor of a number of tyrosine kinase enzymes. It occupies the TK active site, leading to a decrease in activity. TK enzymes in the body, include the insulin receptor. Imatinib is specific for the TK domain in the Abelson proto-oncogene, c-kit and PDGF-R (platelet-derived growth factor receptor).

In a particular embodiment, there is provided a pharmaceutical combination comprising a compound of the present invention and a second active agent selected from phosphodiesterase V inhibitors, neutral endopeptidase 1 inhibitors, ALK-5 inhibitors, rho-kinase inhibitors, TPH1 inhibitors, multi-kinase inhibitors, endothelin antagonist, diuretic, aldosteron receptor blocker, and endothelin receptor blocker.

In another embodiment, there is provided a pharmaceutical combination comprising a compound of the present invention and a second active agent selected from phosphodiesterase V inhibitors, neutral endopeptidase 1 inhibitors, ALK-5 inhibitors, rho-kinase inhibitors, TPH1 inhibitors, multi-kinase inhibitors.

Compounds according to any one of embodiments 1-42 where both $R^3$ and $R^4$ are H have been found to be metabolites of the compounds of the present invention.

EXPERIMENTAL

The present invention is illustrated by the following examplified compounds.

From the foregoing it will be appreciated that, although specific embodiments of the invention have been described herein for purposes of illustration, various modifications may be made without deviating from the spirit and scope of the invention. Accordingly, the invention is not limited except as by the appended claims.

General Conditions:

Mass spectra were run on LCMS systems using electrospray ionization. These were either Agilent 1100 HPLC/Micromass Platform Mass Spectrometer combinations or Waters Acquity UPLC with SQD Mass Spectrometer. [M+H]$^+$ refers to mono-isotopic molecular weights. NMR spectra were run on Bruker AVANCE 400 MHz or 500 MHz NMR spectrometers using ICON-NMR. Spectra were measured at 298K and were referenced using the solvent peak.

As a person skilled in the art understands, when running a $^1$H NMR in deuterated DMSO for compounds according to any one of embodiments 1-42 with $R^1$=methyl, the signal of said methyl protons is often obscured due to the DMSO solvent peak at δ of around 2.5 ppm.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 30 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. If not defined, the terms have their generally accepted meanings.

Abbreviations:
AcOH acetic acid
ACN acetonitrile
aq. aqueous
br broad
BuOH butanol
conc. concentrated
doublet
dd double doublet
DCM dichloromethane
DCC N,N'-dicyclohexylcarbodiimide
DOE 1,2-dichloroethane
DEAD diethyl azodicarboxylate
DIPEA diisopropylethylamine
DMA dimethylacetamide
DME 1,2-dimethoxyethane
DMF N,N-dimethylformamide
DMSO dimethylsulfoxide
Et$_2$O diethyl ether
EtOAc ethyl acetate
EtOH ethanol
h hour(s)
HATU 0-(7-azabenzotriazol-1-yl)-N,N,N,N-tetramethyluronium hexafluorophosphate
Hex hexane
HOBt.H$_2$O 1-Hydroxybenzotriazole hydrate
HPLC High Performance Liquid Chromatography
IPA iso-propyl alcohol
KOAc Potassium acetate
KOtBu Potassium tert-butoxide
LCMS liquid chromatography and mass spectrometry
MeOH methanol
MeCN acetonitrile
MS mass spectrometry
m multiplet
min minute
ml milliliter(s)
m/z mass to charge ratio
NBS N-bromosuccinimide
NMR nuclear magnetic resonance
NOESY nuclear Overhauser effect spectroscopy
Pd-118 Dichloro [1,1' bis(di-tert-butylphosphino)]ferrocene palladium (II)
PdCl$_2$(dppf).CH$_2$Cl$_2$ adduct [1,1-Bis(diphenylphosphino)ferrocene]dichloropalladium (II) dichloromethane adduct.
Pd(PPh$_3$)$_2$Cl$_2$ Bis(triphenylphosphine)palladium(II) dichloride
ppm parts per million
PS polymer supported
PS-TBD 1,5,7-triazabicyclo[4.4.0]dec-5-ene polystyrene
Rt retention time
RT room temperature
singlet
sat. saturated
SCX-2 strong cation exchange (e.g. Isolute® SCX-2 columns from Biotage)
SFC supercritical fluid chromatography
Si-TMT Si-TMT is the silica bound equivalent of 2,4,6-trimercaptotriazine, commercially available e.g. from Biotage
t triplet
TBME methyl-tert-butyl ether
TEA triethylamine
TFA trifluoroacetic acid
THF tetrahydrofuran
TLC thin layer chromatography
T3P® propylphosphonic anhydride Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

Where microwave heating was employed, this was carried out using a Biotage Initiator Sixty microwave in dedicated reaction vials at the temperature shown and for the time indicated.

If not indicated otherwise, the analytical LCMS conditions are as follows:
Method A
Column: Cynergi 2.5 uMMax-RP100A (20×4.0) mm.
Mobile Phase: A: Water +0.1% Formic Acid B:Acetonitrile
Gradient 0.0-0.5 min 20% B, 2.5-4.5 mins 95% B, 5.0 min 20% B
Method 2minLC_v003
Column Waters BEH C18 50×2.1 mm, 1.7 m
Column Temperature 50° C.
Eluents A: H$_2$O, B: acetonitrile, both containing 0.1% TFA
Flow Rate 0.8 ml/min
Gradient 0.20 min 5% B; 5% to 95% B in 1.30 min, 0.25 min 95% B
Method 2minLowpH
Column: Waters Acquity CSH 1.7 μm, 2.1×50 mm
Temperature: 50° C.
Mobile Phase: A: Water +0.1% Formic Acid B: Acetonitrile +0.1% Formic Acid
Flow rate: 1.0 mL/min
Gradient: 0.0 min 5% B, 0.2-1.3 min 5-98% B, 1.3-1.55 min 98% B, 1.55-1.6 min 98-5% B
Method 2minLowpHv01
Column: Waters Acquity CSH 1.7 μm, 2.1×50 mm
Temperature: 50° C.
Mobile Phase: A: Water +0.1% Formic Acid B: Acetonitrile +0.1% Formic Acid
Flow rate: 1.0 mL/min
Gradient: 0.0 min 5% B, 0.2-1.55 min 5-98% B, 1.55-1.75 min 98% B, 1.75-1.8 min 98-5% B
Method 2minLowpHv02
Column: Acquity CSH C18 50×2.1 mm
Temperature: 50° C.
Eluents A: Water B: Acetonitrile both with +0.1% TFA
Flow Rate: 1.0 mL/min
Gradient: 0.0 min 5% B, 0.2-1.55 min 5-98% B, 1.55-1.75 min 98% B, 1.75-1.8 min 98-5% B
Method 2minLowpHv03:
Column: Waters Acquity CSH 1.7 μm, 2.1×50 mm
Temperature: 50° C.
Mobile Phase: A: Water +0.1% Formic Acid B: Acetonitrile +0.1% Formic Acid
Flow rate: 1.0 mL/min
Gradient: 0.0 min 5% B, 0.2-1.8 min 5-98% B, 1.8-2.1 min 98% B, 2.1-2.3 min 98% B
Method 10minLowpH
Column: Waters Acquity CSH 1.7 μm, 2.1×100 mm
Temperature: 50° C.
Mobile Phase: A: Water +0.1% Formic Acid B: Acetonitrile +0.1% Formic Acid
Flow rate: 0.7 mL/min
Gradient: 0.0 min 2% B, 0.58-8.0 min 2-98% B, 8.0-9.0 min 98% B, 9.0-9.1 min 98-2% B
Method 10minLowpHv01:
Column: Waters Acquity CSH 1.7 μm, 2.1×100 mm
Temperature: 50° C.
Mobile Phase: A: Water +0.1% Formic Acid B: Acetonitrile +0.1% Formic Acid
Flow rate: 0.7 mL/min
Gradient: 0.0 min 2% B, 0.5-8.0 min 2-98% B, 8.0-9.0 min 98% B, 9.0-9.1 min 98-2% B
Method10minHighpH
Column: Waters Acquity CSH 1.7 μm, 2.1×100 mm
Temperature: 50° C.
Mobile Phase: A: Water +0.1% Ammonia B: Acetonitrile +0.1% Ammonia
Flow rate: 0.7 mL/min
Gradient: 0.0 min 2% B, 0.5-8.0 min 2-98% B, 8.0-9.0 min 98% B, 9.0-9.1 min 98-2% B
Method 2minLowpH_TFA
Column: Waters Acquity CSH 1.7 μm, 2.1×50 mm
Temperature: 50° C.
Mobile Phase: A: Water +0.1% Formic Acid B: Acetonitrile +0.1% TFA
Flow rate: 1.0 mL/min
Gradient: 0.0 min 5% B, 0.2-1.3 min 5-98% B, 1.3-1.55 min 98% B, 1.55-1.6 min 98-5% B
Method LowpH_v002
Column Phenomenex Gemini C18 50×4.6 mm, 3.0 μm
Column Temperature 50° C.
Eluents A: H$_2$O, B: methanol, both containing 0.1% TFA
Flow Rate 1.0 mL/min
Gradient 5% to 95% B in 2.0 min, 0.2 min 95% B
Method 8minLowpHv01:
Column: Waters Acquity CSH 1.7 μm, 2.1×100 mm
Temperature: 50° C.
Mobile Phase: A: Water +0.1% Formic Acid B: Acetonitrile +0.1% Formic Acid
Flow rate: 0.7 mL/min
Gradient: 0.0 min 2% B, 0.3-6.5 min 2-98% B, 6.5-7.5 min 98% B, 7.5-8.0 min 5-98% B
Method 2minHighpHv03:
Column: Waters Acquity CSH 1.7 μm, 2.1×50 mm
Temperature: 50° C.
Mobile Phase: A: Water +0.1% Ammonia B: Acetonitrile +0.1% Ammonia
Flow rate: 1.0 mL/min
Gradient: 0.0 min 5% B, 0.2-1.8 min 5-98% B, 1.8-2.1 min 98% B, 2.1-2.3 min 98-5% B Unless indicated otherwise, preparative HPLC was carried out using an appropriate column and a mobile phase of 0.1% TFA in acetonitrile and 0.1% aqueous TFA with an appropriate gradient.

Example 1

Trans-3-[5-Amino-6-(5-methyl-[1,3,4]oxadiazol-2-yl)-pyrazin-2-yl]-N-(4-hydroxy-cyclohexyl)-4-methyl-benzenesulfonamide

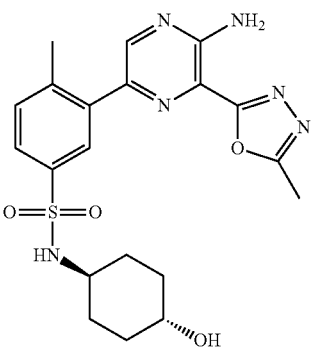 [SMILES: Cc1nnc(-c2nc(-c3cc(S(=O)(=O)N[C@H]4CC[C@H](O)CC4)ccc3C)cnc2N)o1]

A stirred mixture of trans-N-(4-hydroxy-cyclohexyl)-4-methyl-benzenesulfonamide 3-boronic acid (Intermediate B5a) (0.15 g, 0.47 mmol), 5-bromo-3-(5-methyl-[1,3,4]oxadiazol-2-yl)-pyrazin-2-ylamine (Intermediate C1) (0.122 g, 0.47 mmol) and potassium acetate (0.14 g, 1.43 mmol) in dioxane (10 ml) was degassed by bubbling argon through the mixture for 10 mins. After adding bis(diphenylphosphinoferrocene) dichloropalladium (39 mg, 0.047 mmol) and further degassing with argon the mixture was heated to 110° C. for 5 h. Cool water (50 ml) was added and the mixture was extracted with ethyl acetate (2×50 ml). The organic extract was dried over sodium sulphate and concentrated under reduced pressure. Purification by preparative TLC using silicagel (GF 254) as stationary phase and 70% EtOAc in petroleum ether as the mobile phase afforded the title compound as a yellow coloured solid;

LC-MS: [M+H]+=445.2 Method A

¹H NMR (400 MHz, DMSO-d6) δ 8.45 (1H, s), 7.83 (1H, s), 7.75 (1H, d), 7.70 (2H, m), 7.55 (1H, d), 4.50 (1H, m), 3.30 (1H, m), 2.90 (1H, m), 2.60 (3H, s), 2.42 (3H, s), 1.70 (2H, m), 1.58 (2H, m), 1.00-1.23 (4H, m). One proton not visible, may be obscured by DMSO and/or water peaks.

Example 2

Trans-3-[5-Amino-6-(3-methyl-[1,2,4]oxadiazol-5-yl)-pyrazin-2-yl]-N-(4-hydroxy-cyclohexyl)-4-methyl-benzenesulfonamide

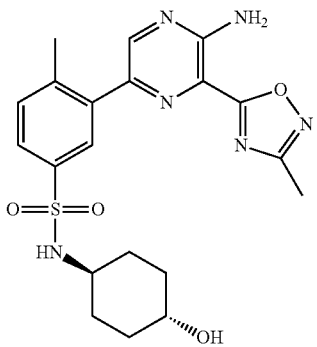 [SMILES: Cc1noc(-c2nc(-c3cc(S(=O)(=O)N[C@H]4CC[C@H](O)CC4)ccc3C)cnc2N)n1]

The title compound was prepared using 5-bromo-3-(3-methyl-[1,2,4]oxadiazol-5-yl)-pyrazin-2-ylamine (Intermediate C2a) and trans-N-(4-hydroxy-cyclohexyl)-4-methyl-benzenesulfonamide 3-boronic acid (Intermediate B5a) under analogous conditions to those of Example 1.

LCMS: Rt 1.79 mins MS m/z 445 [M+H]+: Method A

¹H NMR (400 MHz, CDCl₃) δ 8.49 (1H, s), 8.00 (1H, s), 7.83 (1H, d), 7.49 (1H, d), 6.5-7.5 (2H, br s), 4.36 (1H, m), 3.59 (1H, br mult), 3.22 (1H, br mult), 2.55 (6H, 2xs), 1.95 (4H, mult.) 1.2-1.4 (4H, mult). One proton not visible, may be broad or obscured by water peaks.

Example 3

3-[5-Amino-6-(3-methyl-[1,2,4]oxadiazol-5-yl)-pyrazin-2-yl]-N-(3-hydroxy-3-methyl-butyl)-4-methyl-benzenesulfonamide

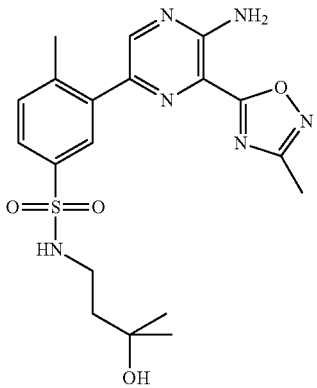 [SMILES: Cc1noc(-c2nc(-c3cc(S(=O)(=O)NCCC(C)(C)O)ccc3C)cnc2N)n1]

The title compound was prepared using 5-bromo-3-(3-methyl-[1,2,4]oxadiazol-5-yl)-pyrazin-2-ylamine (Intermediate C2a) and N-(3-Hydroxy-3-methyl-butyl)-4-methyl-benzenesulfonamide-3-boronic acid (Intermediate B3a) under analogous conditions to those of Example 1

¹H NMR (400 MHz, DMSO-d6) δ 8.59 (1H, s), 7.88 (1H, s), 7.80 (2H, br s), 7.75 (1H, d), 7.59 (1H, d), 7.45 (1H, m), 4.25 (1H, s), 2.85 (2H, mult.), 2.52 (3H, s), 2.49 (3H, s), 1.54 (2H, mult.), 1.03 (6H, s).

Example 4

Trans-3-[5-Amino-6-(3-methyl-isoxazol-5-yl)-pyrazin-2-yl]-N-(4-hydroxy-cyclohexyl)-4-methyl-benzenesulfonamide

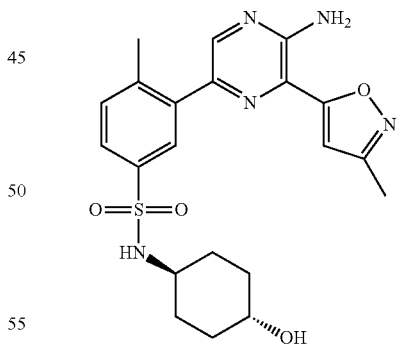

The title compound was prepared from trans-N-(4-hydroxy-cyclohexyl)-4-methyl-benzenesulfonamide 3-boronic acid (Intermediate B5a) and 5-bromo-3-(3-methyl-isoxazol-5-yl)-pyrazin-2-ylamine (Intermediate C3) using analogous conditions to those of Example 5.

LCMS MS m/z 444.2 [M+H]+: Method A

¹H NMR (400 MHz, DMSO-d6) δ 8.39 (1H, s), 7.90 (1H, s), 7.73 (1H, d), 7.60 (1H, d), 7.52 (1H, d), 6.95 (1H, s), 6.92 (2H, br s), 4.45 (1H, s), 3.31 (1H, m), 2.90 (1H, m), 2.48 (3H, s), 2.35 (3H, s), 1.55-1.75 (4H, m), 1.00-1.25 (4H, m).

Example 5

3-[5-Amino-6-(1-methyl-1H-pyrazol-4-yl)-pyrazin-2-yl]-4-methyl-N-(3-methyl-oxetan-3-ylmethyl)-benzenesulfonamide

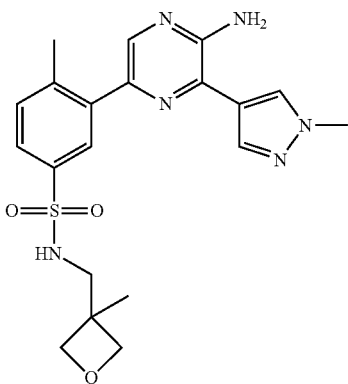 [SMILES: Cc1ccc(S(=O)(=O)NCC2(C)COC2)cc1-c1cnc(N)c(-c2cnn(C)c2)n1]

To a solution of 4-methyl-N-((3-methyloxetan-3-yl)methyl)-3-(4,4,5,5-tetramethyl-1,3,2-dioxaborolan-2-yl)benzenesulfonamide (Intermediate B4) (116 mg, 0.303 mmol) and 5-bromo-3-(1-methyl-1H-pyrazol-4-yl)pyrazin-2-amine (Intermediate C4) (70 mg, 0.275 mmol) in DME (2 ml) was added $PdCl_2(dppf)$-$CH_2Cl_2$ adduct (11.25 mg, 0.014 mmol) and the vial was degassed with $N_2$ several times before adding 2M aqueous $Na_2CO_3$ (0.413 ml, 0.826 mmol). The mixture was stirred at 100° C. for 20 min in a microwave. The mixture was diluted with DCM then washed with brine. The organic phase was separated, using a phase separator. The solvent was removed under reduced pressure. The crude product was purified by flash column chromatography, eluting in a 0% to 100% i-hex:EtOAc gradient on a 4 g silica cartridge to give the titled compound;

LCMS: RT 0.86 mins; MS m/z 429.3 [M+H]+; Method 2minLowpHv01

$^1$H NMR (400 MHz, CDCl$_3$) δ 8.08 (1H, s), 8.04 (1H, s), 7.98 (2H, s), 7.80 (1H, d), 7.45 (1H, d), 4.98 (2H, br s), 4.83 (1H, t), 4.39 (4H, dd), 4.02 (3H, s), 3.18 (2H, dd), 2.53 (3H, s), 1.33 (3H, s).

Example 6

3-(5-Amino-6-(1H-1,2,4-triazol-1-yl)pyrazin-2-yl)-N-(2-hydroxy-2-methylpropyl)-4-methylbenzenesulfonamide

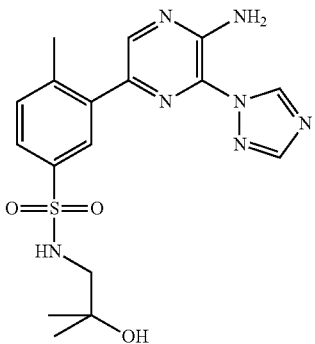 [SMILES: Cc1ccc(S(=O)(=O)NCC(C)(C)O)cc1-c1cnc(N)c(-n2cncn2)n1]

A mixture comprising of 3-bromo-N-(2-hydroxy-2-methylpropyl)-4-methylbenzenesulfonamide (Intermediate A2) (164 mg, 0.509 mmol), KOAc (74.9 mg, 0.763 mmol), $PdCl_2(dppf)$·$CH_2Cl_2$ adduct (20.77 mg, 0.025 mmol) and bis(pinacolato)diboron (129 mg, 0.509 mmol) in DME (2543 μL) under $N_2$ was heated at 90° C. for 3 hours. 5-Chloro-3-(1H-1,2,4-triazol-1-yl)pyrazin-2-amine (Intermediate C5)(100 mg, 0.509 mmol), 2M aqueous $Na_2CO_3$ (763 μl, 1.526 mmol) and $PdCl_2(dppf)$·$CH_2Cl_2$ adduct (20.77 mg, 0.025 mmol) were added and reaction mixture was heated using microwave irradiation at 120° C. for 40 mins. The resulting mixture was added to water (50 ml) and extracted with EtOAc (2×50 ml). The organic phases were washed with brine, dried over $MgSO_4$ and treated with Si-TMT to remove Pd. This mixture was swirled occasionally over 1 hour. The solids were removed by filtration and the resulting organic mixture was concentrated under reduced pressure. Purification by chromatography on silica gel eluting with a gradient of 0-10% [2M $NH_3$ in MeOH] in DCM afforded the title compound as a solid. The solid was recrystallised from hot EtOAc (~1 ml)/$Et_2O$ and allowed to stand overnight at RT to afford the title compound;

LCMS: Rt=0.81 mins; MS m/z 404.3 [M+H]+; Method 2minLowpH $^1$H NMR (400 MHz, DMSO-d6) δ 9.33 (1H, s), 8.41 (1H, s), 8.39 (1H, s), 7.92 (1H, d), 7.71 (1H, dd), 7.53 (1H, d), 7.48 (1H, t), 7.37 (2H, br s), 4.51 (1H, s), 2.61 (2H, d), 2.50 (3H, s), 1.05 (6H, s).

Example 7

3-(5-Amino-6-(2-methylthiazol-5-yl)pyrazin-2-yl)-N-(2-hydroxy-2-methylpropyl)-4-methylbenzenesulfonamide

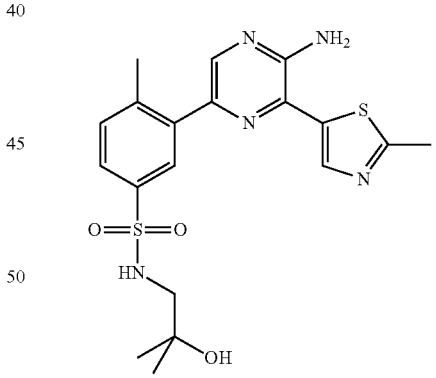

The title compound was prepared using 3-bromo-N-(2-hydroxy-2-methylpropyl)-4-methylbenzenesulfonamide (Intermediate A2) and 5-chloro-3-(2-methylthiazol-5-yl)pyrazin-2-amine (Intermediate C6) under analogous conditions to those of Example 6.

LCMS: Rt=0.87 mins; MS m/z 434.2 [M+H]+; Method 10minLowpH $^1$H NMR (400 MHz, DMSO-d6) δ 8.28 (1H, s), 8.22 (1H, s), 7.87 (1H, s), 7.70 (1H, d), 7.52 (1H, d), 7.45 (1H, t), 6.74 (2H, s), 4.40 (1H, s), 2.69 (3H, s), 2.65 (2H, d), 2.50 (3H, s), 1.07 (6H, s).

Example 8

3-[5-Amino-6-(2-methyl-thiazol-5-yl)-pyrazin-2-yl]-N-(3-hydroxy-2,2-dimethyl-propyl)-4-methyl-benzenesulfonamide

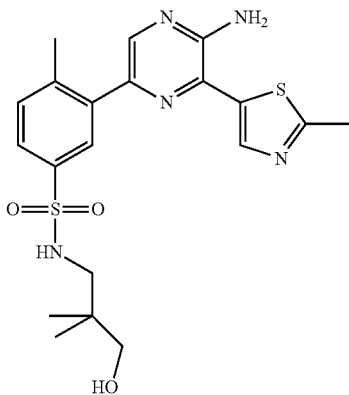 [SMILES: Cc1ncc(-c2nc(-c3cc(S(=O)(=O)NCC(C)(C)CO)ccc3C)cnc2N)s1]

The title compound was prepared using 3-bromo-N-(3-hydroxy-2,2-dimethylpropyl)-4-methylbenzenesulfonamide (Intermediate A9) and 5-chloro-3-(2-methylthiazol-5-yl)pyrazin-2-amine (Intermediate C6) under analogous conditions to those of Example 6

LCMS: R t 0.92 mins; MS m/z 448.2 [M+H]+; Method 2minLowpH.

$^1$H NMR (400 MHz, DMSO-d6) δ 8.28 (1H, s), 8.23 (1H, s), 7.86 (1H, d), 7.70 (1H, dd), 7.53 (1H, d), 7.38 (1H, t), 6.74 (2H, s), 4.44 (1H, t), 3.10 (2H, d), 2.49 (3H, s), 2.69 (3H, s), 2.59 (2H, d), 0.79 (6H, s).

Example 9a and Example 9b (R)- and (S)-3-[5-Amino-6-(1,3-dimethyl-1H-pyrazol-4-yl)-pyrazin-2-yl]-N-(6-hydroxy-spiro[3.3]hept-2-yl)-4-methyl-benzenesulfonamide

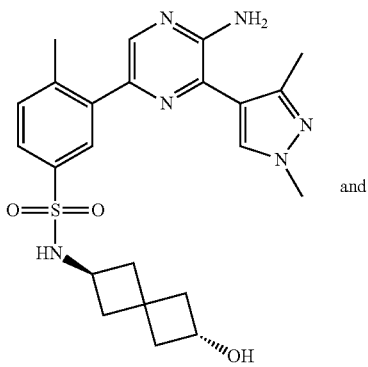

and

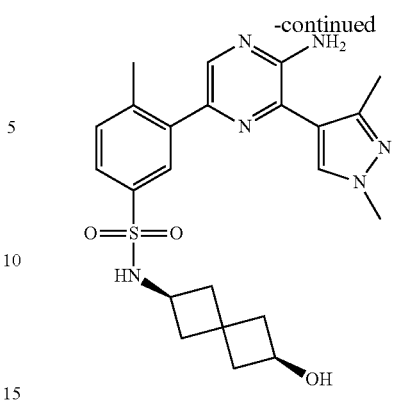

Racemic 3-[5-amino-6-(1,3-dimethyl-1H-pyrazol-4-yl)-pyrazin-2-yl]-N-(6-hydroxy-spiro[3.3]hept-2-yl)-4-methyl-benzenesulfonamide was prepared from 3-bromo-N-(6-hydroxy-spiro[3.3]hept-2-yl)-4-methyl-benzenesulfonamide (Intermediate A8) and 5-bromo-3-(1,3-dimethyl-1H-pyrazol-4-yl)-pyrazin-2-ylamine (Intermediate C7) under analogous conditions to those of Example 6.

The racemic mixture was separated by chiral separation to afford the individual isomers:

Column: 2× Chiralpak AD-H, 250×10 mm, 5 um @ 35 deg C.,
Mobile phase: 35% Isopropanol+0.1% v/v DEA/65% $CO_2$,
Flow: 10 ml/min,
Detection: UV @ 220 nm,
Instrument: Berger Minigram SF01)

Example 9a

First Eluting Compound

SFC Retention Time=7.14 (R)-3-[5-Amino-6-(1,3-dimethyl-1H-pyrazol-4-yl)-pyrazin-2-yl]-N-(6-hydroxy-spiro[3.3]hept-2-yl)-4-methyl-benzenesulfonamide or (S)-3-[5-Amino-6-(1,3-dimethyl-1H-pyrazol-4-yl)-pyrazin-2-yl]-N-(6-hydroxy-spiro[3.3]hept-2-yl)-4-methyl-benzenesulfonamide LCMS: Rt 0.87 mins; MS m/z 469.6 [M+H]+; Method: 2minLowpHv01

$^1$H NMR (400 MHz, DMSO-d6) δ 8.09 (1H, s), 8.06 (1H, s), 7.82 (2H, m), 7.64 (1H, dd), 7.49 (1H, d), 6.28 (2H, s), 4.82 (1H, d), 3.84 (1H, m), 3.83 (3H, s), 3.50 (1H, m),2.47 (3H, s), 2.30 (3H, s), 2.20 (1H, m), 2.02 (2H, m), 1.89 (1H, m), 1.71 (4H, m).

Example 9b

Second Eluting Compound

SFC Retention Time=7.93 mins (R)-3-[5-Amino-6-(1,3-dimethyl-1H-pyrazol-4-yl)-pyrazin-2-yl]-N-(6-hydroxy-spiro[3.3]hept-2-yl)-4-methyl-benzenesulfonamide or (S)-3-[5-Amino-6-(1,3-dimethyl-1H-pyrazol-4-yl)-pyrazin-2-yl]-N-(6-hydroxy-spiro[3.3]hept-2-yl)-4-methyl-benzenesulfonamide LCMS: Rt 0.87 mins; MS m/z 469.2 [M+H]+; Method: 2minLowpHv01

$^1$H NMR (400 MHz, DMSO-d6) δ 8.09 (1H, s), 8.06 (1H, s), 7.84-7.79 (2H, m), 7.63 (1H, dd), 7.49 (1H, d), 6.28 (2H, s), 4.82 (1H, d), 3.84 (1H, m), 3.83 (3H, s), 3.50 (1H, m), 2.47 (3H, s), 2.30 (3H, s), 2.20 (1H, m), 2.02 (2H, m), 1.89 (1H, m), 1.70 (4H, m).

Example 10

3-(5-Amino-6-(2-methylthiazol-5-yl)pyrazin-2-yl)-N-(3-hydroxypropyl)-4-methylbenzenesulfonamide

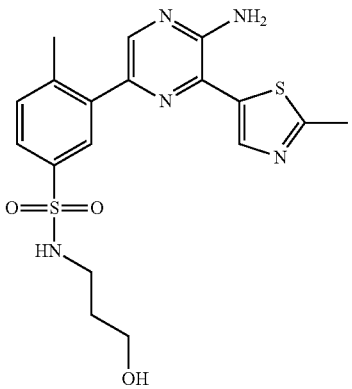 [SMILES: Cc1ncc(-c2nc(-c3cc(S(=O)(=O)NCCCO)ccc3C)cnc2N)s1]

To a solution of N-(3-hydroxypropyl)-4-methyl-3-(4,4,5,5-tetramethyl-1,3,2-dioxaborolan-2-yl)benzenesulfonamide (Intermediate B1) (62.7 mg, 0.176 mmol) in MeCN (882 μL) was added 5-chloro-3-(2-methylthiazol-5-yl)pyrazin-2-amine (Intermediate C6) (40 mg, 0.176 mmol), bis(triphenylphosphine)palladium(II) chloride (6.19 mg, 8.82 μmol) and 2M Na$_2$CO$_3$ (265 μl, 0.529 mmol). The reaction mixture was heated using microwave radiation at 150° C. for 30 minutes. The resulting mixture was added to water (50 ml) and extracted with EtOAc (2×40 ml). The combined organic extracts were washed with brine, dried over MgSO$_4$ and concentrated under reduced pressure. Purification by chromatography on silica eluting with 0-10% [2M NH$_3$ in MeOH] in DCM afforded a green solid which was sonicated in TBME (2 ml) and filtered to afford the title compound;

LCMS; Rt 0.82 mins; MS m/z 420.2 [M+H]+; Method 2minLowpH $^1$H NMR (400 MHz, DMSO-d6) δ 8.28 (1H, s), 8.22 (1H, s), 7.83 (1H, s), 7.69 (1H, d), 7.53 (1H, d), 7.49 (1H, t), 6.73 (2H, s), 4.41 (1H, t), 3.37 (2H, q), 2.81 (2H, q), 2.68 (3H, s), 2.48 (3H, s), 1.54 (2H, m).

Example 11

Trans-3-(5-Amino-6-(pyridin-4-yl)pyrazin-2-yl)-N-(4-hydroxycyclohexyl)-4-methylbenzenesulfonamide

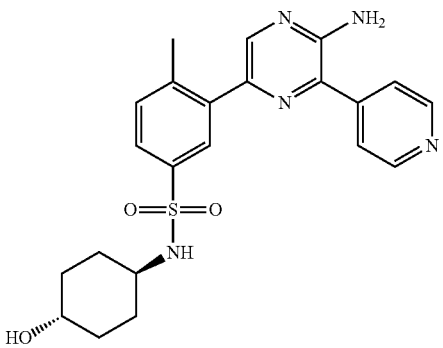 [SMILES: Cc1ccc(S(=O)(=O)N[C@H]2CC[C@H](O)CC2)cc1-c1cnc(N)c(-c2ccncc2)n1]

To a solution of trans-3-(5-amino-6-chloropyrazin-2-yl)-N-(4-hydroxycyclohexyl)-4-methylbenzenesulfonamide (Intermediate D1) (40 mg, 0.101 mmol) was added 4-(4,4,5,5-tetramethyl-1,3,2-dioxaborolan-2-yl)pyridine (24.80 mg, 0.121 mmol), bis(triphenylphosphine)palladium(II) chloride (3.54 mg, 5.04 μmol) and 2M Na$_2$CO$_3$ aq. (151 μL, 0.302 mmol). The reaction was heated using microwave radiation at 150° C. for 30 minutes. The resulting mixture was added to sat. Na$_2$CO$_3$ (40 ml) and extracted with EtOAc (2×40 ml). The organic extracts were washed with brine, dried over MgSO$_4$ and concentrated under reduced pressure. Purification by chromatography on silica gel eluting with 0-100% EtOAc in iso-hexane afforded the title compound as yellow solid;

LCMS: Rt=0.74 mins; MS m/z 440.0 [M+H]+; Method 2minLC_v003.

$^1$H NMR (400 MHz, DMSO-d6) δ 8.71 (2H, d), 8.29 (1H, s), 7.89 (1H, d), 7.77 (2H, d), 7.71 (1H, dd), 7.59 (1H, d), 7.51 (1H, d), 6.67 (2H, s), 4.48 (1H, d), 3.34-3.25 (1H, m), 2.97-2.86 (1H, m), 2.49 (3H, s), 1.73-1.58 (4H, m), 1.23-1.02 (4H, m).

Example 12

3-(5-Amino-6-(1,3-di methyl-1H-pyrazol-4-yl)pyrazin-2-yl)-N-(3-hydroxy-3-methyl butyl)-4-methyl benzenesulfonamide

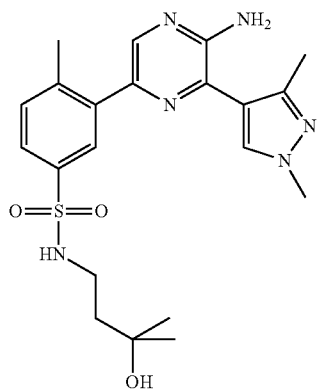 [SMILES: Cc1ccc(S(=O)(=O)NCCC(C)(C)O)cc1-c1cnc(N)c(-c2cn(C)nc2C)n1]

The title compound was prepared from 3-(5-amino-6-chloropyrazin-2-yl)-N-(3-hydroxy-3-methylbutyl)-4-methyl benzenesulfonamide (Intermediate D3) and 3-dimethyl-4-(4,4,5,5-tetramethyl-1,3,2-dioxaborolan-2-yl)-1H-pyrazole under analogous conditions to those of Example 11 (using DME/EtOH as solvent instead of MeCN).

LC-MS: Rt. 0.81 min; m/z 445.2 [M+H]+; Method 2minLowpH $^1$H NMR (400 MHz, DMSO-d6) δ 8.08 (1H, s); 8.06 (1H, s); 7.84 (1H, d); 7.66 (1H, dd); 7.51 (1H, d); 7.39 (1H, t); 6.27 (2H, s); 4.26 (1H, s); 3.82 (3H, s); 2.82 (2H, m); 2.47 (3H, s, partially overlapping with solvent); 2.29 (3H, s); 1.49 (2H, m); 1.00 (6H, s).

Example 13

3-[5-Amino-6-(1,3-dimethyl-1H-pyrazol-4-yl)-pyrazin-2-yl]-N-(3-hydroxy-3-methyl-butyl)-4-methyl-benzenesulfonamide

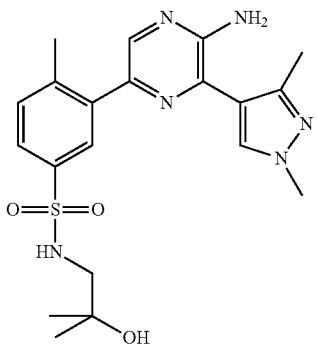 [SMILES: Cc1ccc(S(=O)(=O)NCC(C)(C)O)cc1-c1cnc(N)c(-c2cn(C)nc2C)n1]

The title compound was prepared from 3-(5-amino-6-chloro-pyrazin-2-yl)-N-(2-hydroxy-2-methyl-propyl)-4-methyl-benzenesulfonamide (Intermediate D2) and 3-dimethyl-4-(4,4,5,5-tetramethyl-1,3,2-dioxaborolan-2-yl)-1H-pyrazole under analogous conditions to those of Example 11 (using DME as solvent instead of MeCN).

LCMS: Rt 3.24 min; m/z 431.5 [M+H]+; Method 10min-LowpHv01

$^1$H NMR (400 MHz, DMSO-d6) δ 8.09 (1H, s); 8.06 (1H, s); 7.87 (1H, d); 7.68 (1H, dd); 7.50 (1H, d); 7.44 (1H, t); 6.33 (2H, br); 3.82 (3H, s); 3.17 (1H, s); 2.62 (2H, d); 2.47 (3H, s, partially overlapping solvent peak); 2.30 (3H, s); 1.05 (6H, s).

Example 14

Trans-3-(5-Amino-6-(2-methylthiazol-5-yl)pyrazin-2-yl)-N-(4-hydroxycyclohexyl)-4-methylbenzenesulfonamide

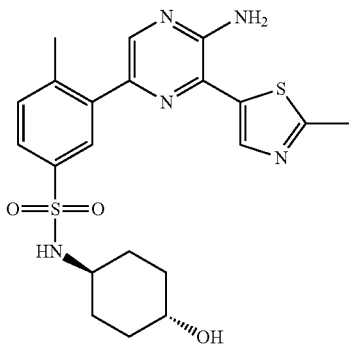 [SMILES: Cc1ncc(-c2nc(-c3cc(S(=O)(=O)N[C@H]4CC[C@H](O)CC4)ccc3C)cnc2N)s1]

The title compound was prepared from trans-3-(5-amino-6-chloropyrazin-2-yl)-N-(4-hydroxycyclohexyl)-4-methyl-benzenesulfonamide (Intermediate D1) and 2-Methyl-5-(4,4,5,5-tetramethyl-[1,3,2]dioxaborolan-2-yl)-thiazole under analogous conditions to those of Example 11.

LCMS: Rt 0.87 mins; MS m/z 460.2 [M+H]+; Method 2minLC_v003

$^1$H NMR (400 MHz, DMSO-d6) δ 8.28 (1H, s), 8.21 (1H, s), 7.87 (1H, d), 7.71 (1H, dd), 7.59 (1H, d), 7.51 (1H, d), 6.73 (2H, s), 4.48 (1H, d), 3.35-3.25 (1H, m), 2.98-2.87 (1H, m), 2.68 (3H, s), 2.48 (3H, s), 1.77-1.58 (4H, m), 1.24-1.03 (4H, m).

Example 15

Trans-3-(5-Amino-6-(1H-1,2,4-triazol-1-yl)pyrazin-2-yl)-N-(4-hydroxycyclohexyl)-4-methylbenzenesulfonamide

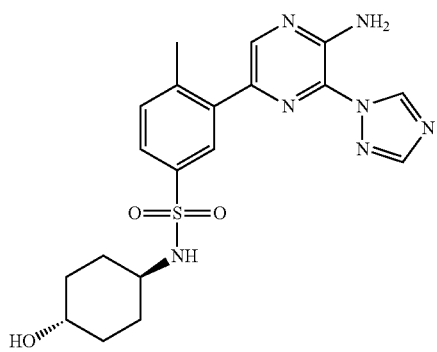 [SMILES: Cc1ccc(S(=O)(=O)N[C@H]2CC[C@H](O)CC2)cc1-c1cnc(N)c(-n2cncn2)n1]

A mixture comprising trans-3-(5-amino-6-chloropyrazin-2-yl)-N-(4-hydroxycyclohexyl)-4-methyl benzenesulfonamide (Intermediate D1) (50 mg, 0.126 mmol), 1H-[1,2,4] triazole (52.2 mg, 0.756 mmol), N,N-dimethylglycine (1.299 mg, 0.013 mmol), Cs$_2$CO$_3$ (123 mg, 0.378 mmol) and CuI (2.399 mg, 0.013 mmol) in DMA (1260 μl) was heated using microwave radiation at 180° C. for 2 hours. The resulting mixture was added to saturated Na$_2$CO$_3$ (50 ml) and extracted with EtOAc (2×50 ml). The organic extracts were washed with brine, dried over MgSO$_4$ and concentrated under reduced pressure. Purification by chromatography on silica eluting with 0-10% [2M NH$_3$ in MeOH] in DCM afforded an oil. To this oil was added Et$_2$O (2 ml) and the mixture sonicated until a fine was precipitate was produced. The excess Et$_2$O was removed and the solid was dried to afford the title compound;

LCMS: Rt 0.86 mins; MS m/z 430.3 [M+H]+; Method 2minLC_v003

$^1$H NMR (400 MHz, DMSO-d6) δ 9.33 (1H, s), 8.43 (1H, s), 8.40 (1H, s), 7.94 (1H, d), 7.74 (1H, dd), 7.63 (1H, d), 7.53 (1H, d), 7.38 (2H, s), 4.47 (1H, d), 3.30 (1H, m), 2.92 (1H, m), 2.51 (3H, s overlapping DMSO peak), 1.68 (4H, m), 1.12 (4H, m).

Example 16

3-[5-Amino-6-(1,3-dimethyl-1H-pyrazol-4-yl)-pyrazin-2-yl]-4-methyl-N—[(R)-1-(tetrahydrofuran-3-yl)methyl]-benzenesulfonamide

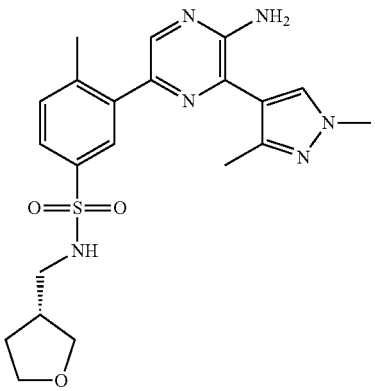 [SMILES: Cc1ccc(S(=O)(=O)NC[C@H]2CCOC2)cc1-c1cnc(N)c(-c2cn(C)nc2C)n1]

To a solution of (R)-4-methyl-N-((tetrahydrofuran-3-yl)methyl)-3-(4,4,5,5-tetramethyl-1,3,2-dioxaborolan-2-yl)benzenesulfonamide (Intermediate B7) (60 mg, 0.157 mmol) in EtOH/Toluene (1.5 ml; 1:2) was added 5-bromo-3-(1,3-dimethyl-1H-pyrazol-4-yl)-pyrazin-2-ylamine (Intermediate C7) (35.2 mg, 0.157 mmol) followed by Pd(PPh$_3$)$_2$Cl$_2$ (5.52 mg, 7.87 μmol) and 2M Na$_2$CO$_3$ (0.236 ml, 0.472 mmol). The reaction was heated in the microwave at 100° C. for 30 minutes. A further 0.05 equivalent of catalyst was added and the reaction heated in the microwave at 100° C. for a further 1 hour. More catalyst (5.52 mg, 7.87 μmol) was added and the reaction heated in the microwave at 100° C. for a further 2 hours. The reaction was diluted with ethyl acetate, washed with water and the organic layer dried (MgSO$_4$), filtered and concentrated. The product was purified by flash chromatography on silica gel (12 g) eluting with TBME/MeOH gradient (0-10%) to give the title compound;

LCMS Rt 0.86, 100%, MS m/z 443.5 [M+H]+; Method 2minLowpHv01

$^1$H NMR (400 MHz, DMSO-d6) δ (ppm) 8.09 (1H, s), 8.07 (1H, s), 7.85 (1H, s), 7.68 (2H, m), 7.52 (1H, d), 6.28 (2H, s), 3.82 (3H, s), 3.60 (3H, m), 3.32 (1H, m, partially obscured by water signal), 2.72 (2H, t), 2.48 (3H, s), 2.29 (3H, s), 2.27 (1H, m), 1.88 (1H, m), 1.48 (1H, m).

Example 17

3-[5-Amino-6-(1,3-dimethyl-1H-pyrazol-4-yl)-pyrazin-2-yl]-4-methyl-N-(3-methyl-oxetan-3-ylmethyl)-benzenesulfonamide

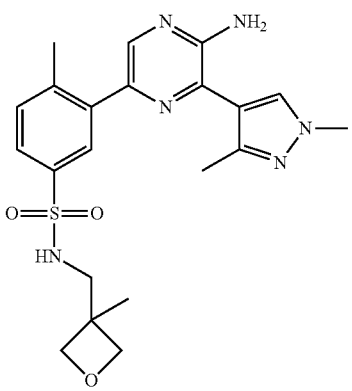 [SMILES: Cc1ccc(S(=O)(=O)NCC2(C)COC2)cc1-c1cnc(N)c(-c2cn(C)nc2C)n1]

To a solution of 4-Methyl-N-(3-methyl-oxetan-3-ylmethyl)-3-(4,4,5,5)tetramethyl-[1,3,2]dioxaborolan-2-yl)-benzenesulfonamide (Intermediate B4) (511 mg, 1.341 mmol) and 5-chloro-3-(1,3-dimethyl-1H-pyrazol-4-yl)-pyrazin-2-ylamine (Intermediate C7) (200 mg, 0.894 mmol) in DME (8 ml) was added PdCl$_2$(dppf) CH$_2$Cl$_2$ adduct (36.5 mg, 0.045 mmol) and the vial was degassed with N$_2$ several times before adding 2N aqueous sodium carbonate (1.34 ml, 2.68 mmol). The mixture was stirred at 120° C. for 30 min in the microwave. The mixture was diluted with DCM then washed with brine. The organic layer was stirred with the Pd scavenger resin (polymer supported trimercaptotriazine). The organic phase was separated, using a phase separator. Solvent was removed under reduced pressure to give the crude product. Purification by flash column chromatography eluting in a 0% to 15% TBME/MeOH gradient on a 12 g silica cartridge to afford the title compound;

LCMS: Rt 0.86, 100%, MS m/z 443.5 [M+H]+; Method 2minLowpHv01

$^1$H NMR (400 MHz, DMSO-d6) δ 8.09 (1H, s), 7.96 (1H, s), 7.78 (1H, d), 7.75 (1H, s), 7.45 (1H, d), 4.89 (2H, br s), 4.75 (1H, t), 4.37 (4H, dd), 3.93 (3H, s), 3.16 (2H, d), 2.52 (3H, s), 2.14 (3H, s), 1.30 (3H, s).

Example 18

3-[5-Amino-6-(2-methyl-2H-[1,2,3]triazol-4-yl)-pyrazin-2-yl]-N-(2-hydroxy-2-methyl-propyl)-4-methyl-benzenesulfonamide

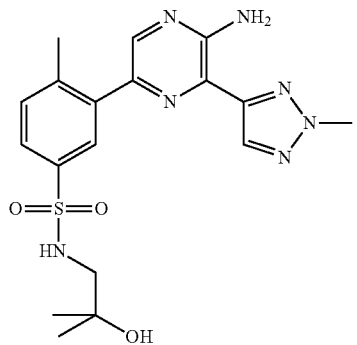

To 0.5-2 ml microwave vial was added N-(2-hydroxy-2-methylpropyl)-4-methyl-3-(4,4,5,5-tetramethyl-1,3,2-dioxaborolan-2-yl)benzenesulfonamide (Intermediate B2) (87 mg, 0.235 mmol), 5-bromo-3-(2-methyl-2H-1,2,3-triazol-4-yl)pyrazin-2-amine (Intermediate C8)(60 mg, 0.235 mmol), and PdCl$_2$(dppf)-CH$_2$Cl$_2$ adduct (9.60 mg, 0.012 mmol) and 2M aqueous sodium carbonate (0.372 ml, 0.745 mmol) in DME (1.5 ml). The reaction was heated in a biotage initiator microwave at 120° C. for 2 hours. The reactions were combined, extracted into ethyl acetate, washed with water, brine, the organic layer separated, dried over MgSO$_4$, filtered and the solvent removed under reduced pressure. The crude product was loaded onto silica and purified by flash column chromatography, elution with TBME:methanol (0-10%) on a 12 g silica cartridge. The required fractions were combined and the solvent removed under reduced pressure to yield a brown oil. The residue was taken up in hot ethanol and recrystallised to yield the title compound as a light brown solid;

LCMS Rt 0.98 mins m/z 418.1 [M+H]+; Method 2min-LowpH $^1$H NMR (400 MHz, DMSO-d6) δ (ppm) 8.32 (1H, s), 8.29 (1H, s), 7.90 (1H, d), 7.70 (1H, dd), 7.52 (1H, d), 7.47 (1H, t), 7.30 (2H, broad s), 4.40 (1H, s), 4.30 (3H, s), 2.62 (2H, d), 2.50 (3H, s), 1.06 (6H, s).

Example 19

3-[5-Amino-6-(2,5-dimethyl-2H-[1,2,3]triazol-4-yl)-pyrazin-2-yl]-N-(2-hydroxy-2-methyl-propyl)-4-methyl-benzenesulfonamide

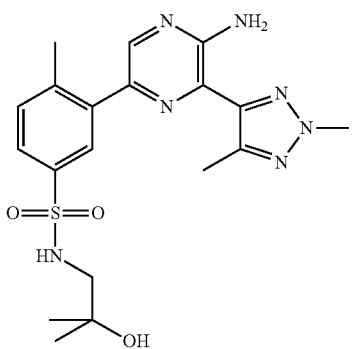 [SMILES: Cc1ccc(S(=O)(=O)NCC(C)(C)O)cc1-c1cnc(N)c(-c2nn(C)nc2C)n1]

A mixture of N-(2-hydroxy-2-methylpropyl)-4-methyl-3-(4,4,5,5-tetramethyl-1,3,2-dioxaborolan-2-yl)benzenesulfonamide (Intermediate B2) (240 mg, 0.650 mmol), 5-bromo-3-(2,5-dimethyl-2H-1,2,3-triazol-4-yl)pyrazin-2-amine (Intermediate C9) (175 mg, 0.325 mmol), and bis(triphenylphosphine)palladium(II) chloride (11.41 mg, 0.016 mmol) and 2M aqueous sodium carbonate (0.406 ml, 0.813 mmol) in DME (4 ml) was heated in the microwave at 120° C. for 90 mins. Further N-(2-hydroxy-2-methylpropyl)-4-methyl-3-(4,4,5,5-tetramethyl-1,3,2-dioxaborolan-2-yl)benzenesulfonamide (Intermediate B2) (120 mg, 0.325 mmol, 0.5 eq) was added and the reaction heated in the microwave at 120° C. for a further 2 hours. The reactions were combined, extracted into ethyl acetate, washed with water, brine, the organic layer separated, dried over MgSO$_4$, filtered and the solvent removed under reduced pressure. The crude product was loaded onto silica and purified by flash column chromatography, elution with iso hexane:ethyl acetate (0-100%) on a 12 g silica cartridge. The required fractions were combined and the solvent removed under reduced pressure to yield a yellow oil. The residue was taken up in DMSO and purified by mass directed preparative chromatography. The required fractions were combined and the product extracted into DCM, washed with sat. NaHCO$_3$ to remove all traces of TFA, the organic layer separated, dried over MgSO$_4$, filtered and the solvent removed under reduced pressure. The product was recrystallised from the minimum of hot ethanol to afford the title compound; LCMS: Rt 1.01 mins MS m/z 432.2 [M+H]+; Method 2minLowpHv01.

$^1$H NMR (400 MHz, DMSO-d6) δ 8.25 (1H, s), 7.93 (1H, d), 7.70 (1H, dd), 7.52 (1H, d), 7.46 (1H, broad), 7.34 (2H, broad), 4.41 (1H, broad), 4.21 (3H, s), 2.62 (2H, broad), 2.56 (3H, s), 2.49 (3H, s), 1.05 (6H, s).

Example 20a cis-3-[5-Amino-6-(2-methyl-thiazol-5-yl)-pyrazin-2-yl]-N-(3-hydroxy-cyclobutylmethyl)-4-methyl-benzenesulfonamide and Example 20b trans-3-[5-Amino-6-(2-methyl-thiazol-5-yl)-pyrazin-2-yl]-N-(3-hydroxy-cyclobutylmethyl)-4-methyl-benzenesulfonamide

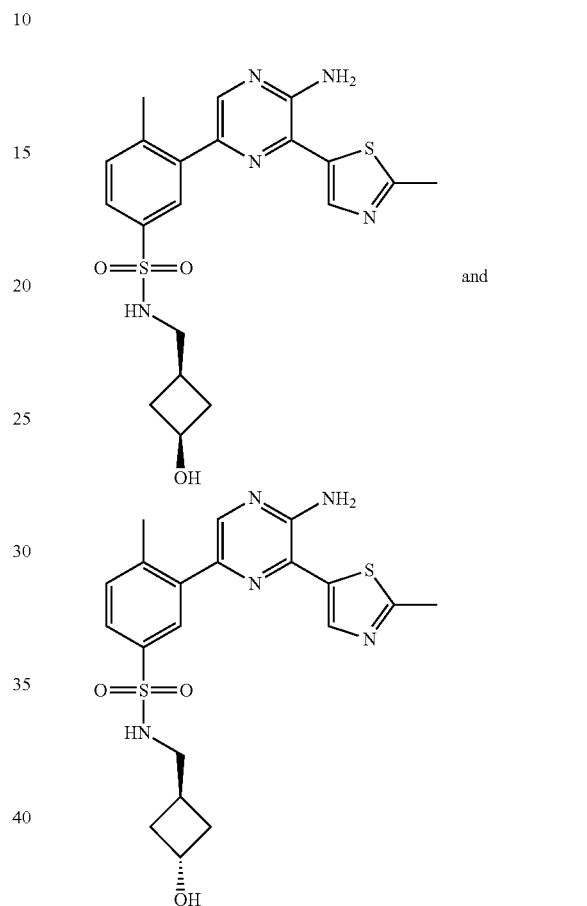

Racemic 3-[5-amino-6-(2-methyl-thiazol-5-yl)-pyrazin-2-yl]-N-(3-hydroxy-cyclobutylmethyl)-4-methyl-benzenesulfonamide was prepared from 5-chloro-3-(2-methylthiazol-5-yl)pyrazin-2-amine (Intermediate C6) and 3-bromo-N-(3-hydroxy-cyclobutylmethyl)-4-methyl-benzenesulfonamide (Intermediate A10) under analogous conditions to those of Example 6. Stereoisomers were separated using chiral SFC.

First Eluted Peak:

Example 20a cis-3-[5-Amino-6-(2-methyl-thiazol-5-yl)-pyrazin-2-yl]-N-(3-hydroxy-cyclobutylmethyl)-4-methyl-benzenesulfonamide LCMS: Rt 0.85 mins; MS m/z 446.3 [M+H]+; Method: 2minLowpH $^1$H NMR (500 MHz, DMSO-d6) δ 8.28 (1H, s), 8.22 (1H, s), 7.83 (1H, d), 7.68 (1H, dd), 7.54 (2H, m), 6.73 (2H, br s), 4.89 (1H, d), 3.84 (1H, m), 2.74 (2H, t), 2.68 (3H, s), 2.48 (3H, s), 2.17 (2H, m), 1.75 (1H, m), 1.41 (2H, m).

Second Eluted Peak:

Example 20b trans-3-[5-Amino-6-(2-methyl-thiazol-5-yl)-pyrazin-2-yl]-N-(3-hydroxy-cyclobutylmethyl)-4-methyl-benzenesulfonamide LCMS: Rt 0.85 mins; MS m/z 446.3 [M+H]+; Method: 2minLowpH $^1$H NMR (500 MHz, DMSO-d6) δ 8.28 (1H, s), 8.22 (1H, s), 7.83 (1H, d), 7.68 (1H, dd), 7.60 (1H, t), 7.52 (1H, d), 6.73 (2H, br s), 4.90 (1H, d), 4.09 (1H, m), 2.78 (2H, t), 2.68 (3H, s), 2.48 (3H, s), 2.12 (1H, m), 1.92 (2H, m), 1.82 (2H, m).

The assignment of compounds as cis or trans was carried out using 2D NMR experiments including NOESY.

Example 21

3-[5-Amino-6-(2-cyclopropyl-thiazol-5-yl)-pyrazin-2-yl]-N-(2-hydroxy-2-methyl-propyl)-4-methyl-benzenesulfonamide

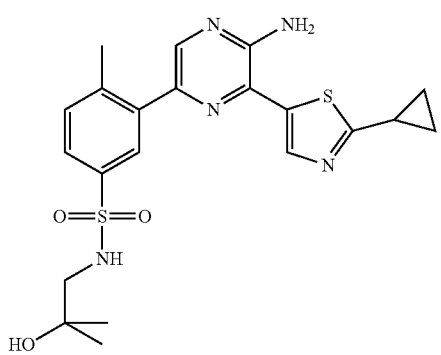 [SMILES: Cc1ccc(S(=O)(=O)NCC(C)(C)O)cc1-c1cnc(N)c(-c2cnc(C3CC3)s2)n1]

The title compound was prepared using N-(2-Hydroxy-2-methyl-propyl)-4-methyl-3-(4,4,5,5-tetramethyl[1,3,2]dioxaborolan-2-yl)benzenesulfonamide (Intermediate B2) and 5-Chloro-3-(2-cyclopropyl-thiazol-5-yl)-pyrazin-2-ylamine (Intermediate C10) under analogous conditions to those of Example 25.

LCMS: Rt 1.03 mins; MS m/z 460.2 [M+H]+; Method 2minLowpHv01.

$^1$H NMR (400 MHz, DMSO-d6) δ (ppm) 8.07 (1H, s), 8.06 (1H, s), 7.84 (1H, d), 7.68 (1H, t), 7.65 (1H, dd), 7.50 (1H, d), 6.27 (2H, br s), 3.81 (3H, s), 3.59 (3H, m), 3.34 (1H, m), 2.71 (1H, t), 2.46 (3H, s), 2.28 (3H, s), 2.25 (1H, m), 1.85 (1H, m), 1.47 (1H, m).

Example 22

Trans-3-(5-Amino-6-pyridin-3-yl-pyrazin-2-yl)-N-(4-hydroxy-cyclohexyl)-4-methyl benzenesulfonamide

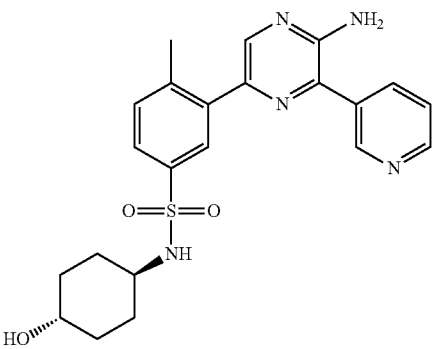 [SMILES: Cc1ccc(S(=O)(=O)N[C@H]2CC[C@H](O)CC2)cc1-c1cnc(N)c(-c2cccnc2)n1]

The title compound was prepared from trans-3-(5-Amino-6-chloropyrazin-2-yl)-N-(4-hydroxycyclohexyl)-4-methyl-benzene sulfonamide (Intermediate D1) and 3-(4,4,5,5-tetramethyl-[1,3,2]dioxaborolan-2-yl)-pyridine using analogous conditions to those of Example 11.

LCMS: Rt 0.74 mins; MS m/z 440.2 [M+H]+; Method 2minLC_v003

$^1$H NMR (400 MHz, DMSO-d6) δ 8.94 (1H, d); 8.65 (1H, dd); 8.25 (1H, s); 8.15 (1H, dt); 7.90 (1H, d); 7.70 (1H, dd); 7.60 (1H, d); 7.55-7.49 (2H, m); 6.60 (2H, s); 4.46 (1H, d); 3.28 (1H, br m); 2.90 (1H, br m); 2.49 (3H, s); 1.74-1.58 (4H, m); 1.23-1.00 (4H, m)

Example 23

3-[5-Amino-6-(3-isopropyl-[1,2,4]oxadiazol-5-yl)-pyrazin-2-yl]-N-(4-hydroxy-cyclohexyl)-4-methyl-benzene sulfonamide

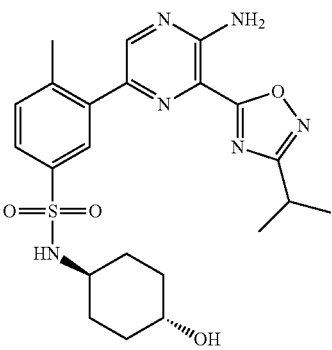 [SMILES: Cc1ccc(S(=O)(=O)N[C@H]2CC[C@H](O)CC2)cc1-c1cnc(N)c(-c2nc(C(C)C)no2)n1]

The title compound was prepared analogously to Example 2 using trans-N-(4-hydroxy-cyclohexyl)-4-methyl-benzenesulfonamide 3-boronic acid (Intermediate B5a) and 5-bromo-3-(3-isopropyl-[1,2,4]oxadiazol-5-yl)-pyrazin-2-ylamine (Intermediate C2b).

LCMS: Rt 1.94 mins; MS m/z 473 [M+H]+: Method A $^1$H NMR (400 MHz, DMSO-d6) δ 8.61 (1H, s), 7.94 (1H, s), 7.83 (2H, br s), 7.77 (1H, d), 7.65 (1H, d), 7.57 (1H, d), 4.48 (1H, s), 3.32 (1H, mult.) 3.20 (1H, m), 2.95 (1H, br s), 2.45 (3H, s), 1.68 (4H, mult.), 1.37 (6H, d), 1.15 (4H, mult).

Example 24

Trans-3-[5-Amino-6-(3-cyclopropyl-[1,2,4]oxadiazol-5-yl]-pyrazin-2-yl]-N-(4-hydroxy-cyclohexyl)-4-methyl-benzene sulfonamide 1

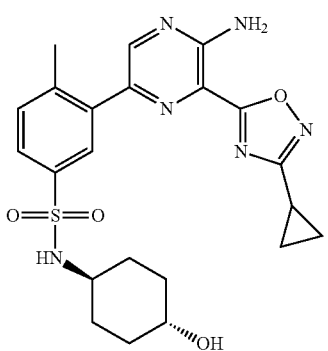 [SMILES: Cc1ccc(S(=O)(=O)N[C@H]2CC[C@H](O)CC2)cc1-c1cnc(N)c(-c2nc(C3CC3)no2)n1]

The title compound was prepared analogously to Example 2 using trans-N-(4-hydroxy-cyclohexyl)-4-methyl-benzenesulfonamide 3-boronic acid (Intermediate B5a) and 5-bromo-3-(3-cyclopropyl-[1,2,4]oxadiazol-5-yl)-pyrazin-2-ylamine (Intermediate C2c).

LCMS: Rt 1.94 mins; MS m/z 471.1 [M+H]+: Method A $^1$H NMR (400 MHz, DMSO-d6) δ 8.60 (1H, s), 7.90 (1H, s), 7.75 (1H, d), 7.65 (2H, br s), 7.55 (1H, d), 4.48 (1H, s), 3.32 (1H, m), 2.95 (1H, m), 2.49 (3H, s), 2.25 (1H, m), 1.93 (1H, s), 1.68 (4H, m), 1.1 (8H, m).

Example 25

3-[5-Amino-6-(3-methyl-[1,2,4]triazol-1-yl)-pyrazin-2-yl]-N-(2-hydroxy-2-methyl-propyl)-4-methyl-benzenesulfonamide

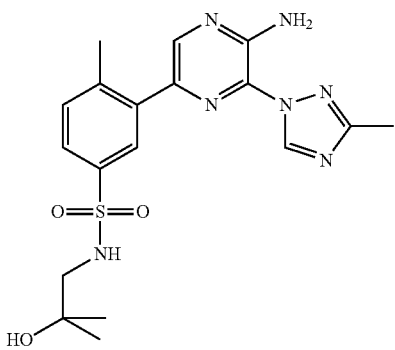 [SMILES: Cc1ncn(-c2nc(-c3cc(S(=O)(=O)NCC(C)(C)O)ccc3C)cnc2N)n1]

To a solution of N-(2-hydroxy-2-methylpropyl)-4-methyl-3-(4,4,5,5-tetramethyl-1,3,2-dioxaborolan-2-yl) benzenesulfonamide (Intermediate B2) (319 mg, 0.862 mmol) in DME (3920 μL) was added 5-bromo-3-(3-methyl-1H-1,2,4-triazol-1-yl)pyrazin-2-amine (Intermediate C12, 200 mg, 0.784 mmol), bis(triphenylphosphine)palladium(II) chloride (27.5 mg, 0.039 mmol) and Na$_2$CO$_3$ (aq. 2.0M) (1176 μL, 2.352 mmol). The reaction was heated in a microwave oven at 120° C. for 30 mins. The reaction was added to water (50 ml), and the product extracted into EtOAc (2×60 ml). The organic phase was washed with brine, dried over MgSO$_4$ and Si-TMT to remove Pd. The mixture was swirled occasionally over 1 hour. The solids were removed by filtration, washed with EtOAc and concentrated under vacuo. The crude product was purified by flash column chromatography, eluting with 0-10% gradient of (2M NH$_3$ in MeOH) in DCM on a 12 g Si-column, loading with DCM to give a solid which was recrystalised from hot EtOAc (~3 ml). Upon cooling the product crystallised as a yellow solid;

LCMS: Rt 0.90 mins; MS m/z 418.6 [M+H]+; Method 2minLowpHv01.

$^1$H NMR (400 MHz, DMSO-d6) δ9.19 (1H, s); 8.37 (1H, s); 7.93 (1H, s); 7.72 (1H, d); 7.53 (1H, d); 7.49 (1H, m); 7.42 (2H, s); 4.41 (1H, s); 2.63 (2H, d); 2.50 (3H, s), 2.45 (3H, s); 1.07 (6H, s)

Example 26

3-[5-Amino-6-(3-cyclopropyl-[1,2,4]triazol-1-yl)-pyrazin-2-yl]-N-(3-hydroxy-3-methyl-butyl)-4-methyl-benzenesulfonamide

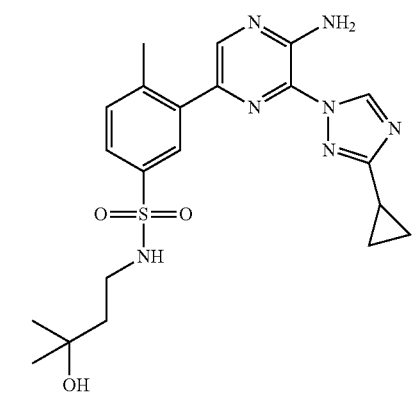 [SMILES: Cc1ccc(S(=O)(=O)NCCC(C)(C)O)cc1-c1cnc(N)c(-n2cnc(C3CC3)n2)n1]

A mixture of 3-(5-amino-6-chloropyrazin-2-yl)-N-(3-hydroxy-3-methylbutyl)-4-methylbenzenesulfonamide (Intermediate D3) (250 mg, 0.650 mmol), 3-cyclopropyl-1H-1,2,4-triazole (213 mg, 1.949 mmol), N,N-dimethylglycine (6.70 mg, 0.065 mmol), Cs$_2$CO$_3$ (635 mg, 1.949 mmol), and CuI (12.37 mg, 0.065 mmol) in DMA (3248 μL) was heated in a microwave at 150° C. for 2 hours. The reaction was added to saturated Na$_2$CO$_3$ (50 ml), and product extracted into EtOAc (2×40 ml). The organic phases were washed with brine, dried over MgSO$_4$, and concentrated under reduced pressure. The crude product was purified by automated flash chromatography using a 12 g silica column eluting with a gradient (0-10% of 2M methanolic NH$_3$ in dichloromethane). The product was crystallised from EtOAc to give the title compound as an off-white solid;

LCMS: Rt 0.95 mins; MS m/z 458.5[M+H]+; Method 2minLC_v003

$^1$H NMR (400 MHz, DMSO-d6) δ9.13 (1H, s); 8.35 (1H, s); 7.87 (1H, d); 7.71 (1H, dd); 7.55 (1H, d); 7.44 (1H, br); 7.41 (2H, s); 4.28 (1H, s); 2.83 (2H, br m); 2.50 (3H, s, partially obscured by DMSO), 2.18 (1H, m): 1.51 (2H, m); 1.03 (2H, m) overlapping with 1.02 (6H, s); 0.95 (2H, m).

Example 27

3-[5-Amino-6-(1,3-dimethyl-1H-pyrazol-4-yl)-pyrazin-2-yl]-N—((R)-1-ethyl-pyrrolidin-2-ylmethyl)-4-methyl-benzenesulfonamide hydrochloride

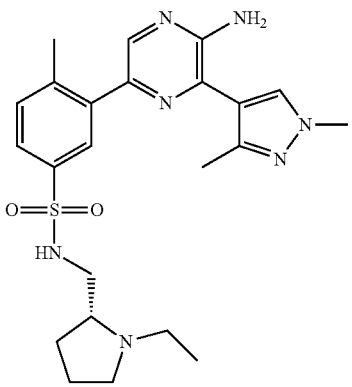 [SMILES: CCN1CCC[C@@H]1CNS(=O)(=O)c1ccc(C)c(-c2cnc(N)c(-c3cn(C)nc3C)n2)c1]

The title compound was prepared from N—((R)-1-Ethyl-pyrrolidin-2-ylmethyl)-4-methyl-3-(4,4,5,5-tetramethyl-[1,3,2]dioxaborolan-2-yl)-benzenesulfonamide (Intermediate B6) and 5-chloro-3-(1,3-dimethyl-1H-pyrazol-4-yl)-pyrazin-2-ylamine (Intermediate C7) using analogous conditions to those of Example 16. HCl salt formed using methanolic HCl.

LCMS: RT 0.64 mins; MS m/z 470.4 [M+H]+; Method 2minLowpHv01

$^1$H NMR (400 MHz, DMSO-d6) (HCl Salt) δ 10.1 (1H br s), 8.15 (2H, mult), 7.89 (1H, s), 7.72 (1H, d), 7.55 (1H, d), 6.55 (1H, br s), 3.82 (3H, s), 3.50 (2H, mult), 3.47 (1H, mult), 3.20 (1H, mult), 3.15 (3H, s), 3.12 (1H, mult), 3.05 (2H, mult), 2.49 (2H, s), 2.29 (3H, s), 2.12 (1H, mult), 1.95 (1H, mult), 1.85 (1H, mult), 1.78 (1H, mult), 1.23 (3H, t).

Example 28

3-(5-Amino-6-[1,2,4]triazol-1-yl-pyrazin-2-yl)-N-(1-hydroxy-cyclopropylmethyl)-4-methyl-benzenesulfonamide

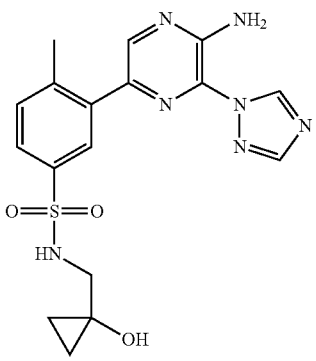 [SMILES: Cc1ccc(S(=O)(=O)NCC2(O)CC2)cc1-c1cnc(N)c(-n2cncn2)n1]

In a microwave vial, a mixture of 5-bromo-3-(1H-1,2,4-triazol-1-yl)pyrazin-2-amine (Intermediate C11, 100 mg, 0.415 mmol), bis(pinacolato)diboron (116 mg, 0.456 mmol), PdCl$_2$(dppf).CH$_2$Cl$_2$ adduct (33.9 mg, 0.041 mmol) and potassium acetate (61 mg, 0.622 mmol) in DME (1.5 ml) was heated at 120° C. for 60 mins. To the reaction was then added 2M Na$_2$CO$_3$ solution (0.519 ml, 1.037 mmol), PdCl$_2$ (dppf).CH$_2$Cl$_2$ adduct (17 mg, 0.02 mmol) and 3-bromo-N-(1-hydroxy-cyclopropylmethyl)-4-methyl-benzenesulfonamide (Intermediate A11, 133 mg, 0.415 mmol). The reaction was heated using microwave radiation at 90° C. for 60 mins, then at 100° C. for a further 60 mins. The reaction was diluted with ethyl acetate and the organic phase washed with water, then brine. The organic layer was dried over MgSO4, and the solvent removed under reduced pressure. The residue was purified by automated flash column chromatography eluting with a gradient of MeOH (0-10%) in TBME over 15 mins using a 12 g silica cartridge. The product was dried in a vacuum oven at 40° C. overnight to yield a yellow solid (51 mg) which was further purified using preparative LCMS to afford the title compound;

LCMS: Rt 0.90 mins; MS m/z 402.2 [M+H]+; Method LowpH_v002

$^1$H NMR (400 MHz, DMSO-d6) δ (ppm) 9.34 (1H, s), 8.42 (1H, s), 8.40 (1H, s), 7.93 (1H, d,), 7.73-7.71 (1H, dd), 7.67-7.64 (1H, m), 7.54-7.52 (1H, d), 7.38 (2H, broad s), 5.32 (1H, s), 2.87-2.86 (2H, d), 2.50 (3H, s), 0.50 (2H, m), 0.46 (2H, m).

Example 29

3-(5-Amino-6-[1,2,4]triazol-1-yl-pyrazin-2-yl)-4-methyl-N-(3-methyl-oxetan-3-ylmethyl)-benzenesulfonamide

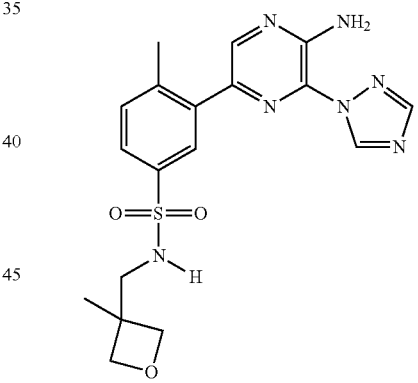

To a solution of 3-(5-amino-6-(1H-1,2,4-triazol-1-yl)pyrazin-2-yl)-4-methylbenzene-1-sulfonyl chloride (Intermediate E1, 100 mg, 0.285 mmol) in THF (5 ml) was added DIPEA (100 μl, 0.57 mmol) and (3-methyl-oxetan-3-yl)-methylamine (29 mg, 0.285 mmol) and the reaction mixture stirred for 2 h. The reaction was diluted into DCM, then washed with citric acid, then brine. The organic layer was separated, dried over MgSO$_4$, filtered and the solvent removed under reduced pressure to provide the title compound as a solid which required no further purification;

LCMS: Rt 0.84 mins; MS m/z 416.2 [M+H]+: Method LowpH_v002

$^1$H NMR (400 MHz, DMSO-d6) δ 9.33 (1H, s), 8.42 (2H, mult), 7.93 (1H, d), 7.83 (1H, mult), 7.74 (1H, dd), 7.56 (1H, d), 7.38 (2H, br), 4.31 (2H, d), 4.16 (2H, d), 2.92 (2H, d), 2.50 (3H, s), 1.20 (3H, s).

Example 30

3-[5-Amino-6-(5-morpholin-4-ylmethyl-thiophen-3-yl)-pyrazin-2-yl]-N-(3-hydroxy-3-methyl-butyl)-4-methyl-benzenesulfonamide

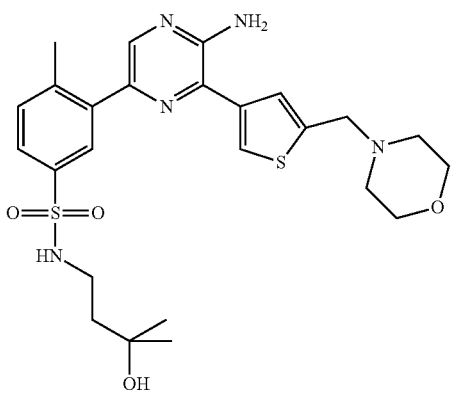 [SMILES: Cc1ccc(S(=O)(=O)NCCC(C)(C)O)cc1-c1cnc(N)c(-c2csc(CN3CCOCC3)c2)n1]

Prepared from 3-(5-Amino-6-chloropyrazin-2-yl)-N-(3-hydroxy-3-methylbutyl)-4-methyl benzenesulfonamide (Intermediate D3) and 4-((4-(4,4,5,5-tetramethyl-1,3,2-dioxaborolan-2-yl)thiophen-2-yl)methyl)morpholine using analogous conditions to those of Example 11.

LCMS: Rt 0.63 mins; MS m/z 532.3 [M+H]+: Method 2minLowpH $^1$H NMR (400 MHz, DMSO-d6) δ 8.15 (1H, s), 7.98 (1H, m), 7.83 (1H, m), 7.69 (1H, dd), 7.53 (1H, d), 7.47 (1H, s), 7.43 (1H, t), 6.47 (2H, br s), 4.27 (1H, s), 3.72 (2H, s), 3.59 (4H, m), 2.83 (2H, m), 2.48 (3H, s), 2.44 (4H, m), 1.51 (2H, m), 1.02 (6H, s).

Example 31

3-(5-Amino-6-[1,2,4]triazol-1-yl-pyrazin-2-yl)-N-(2-hydroxy-2-methyl-propoxy)-4-methyl-benzenesulfonamide

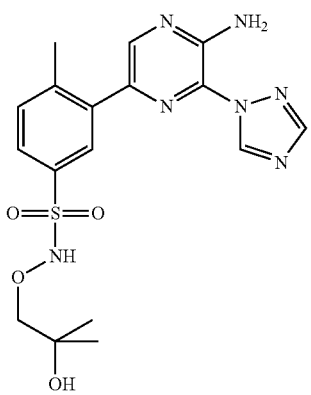 [SMILES: Cc1ccc(S(=O)(=O)NOCC(C)(C)O)cc1-c1cnc(N)c(-n2cncn2)n1]

A mixture of 3-(5-amino-6-(1H-1,2,4-triazol-1-yl)pyrazin-2-yl)-4-methylbenzene-1-sulfonyl chloride (Intermediate E1, 200 mg, 0.570 mmol) and 1-(aminooxy)-2-methylpropan-2-ol (200 mg, 1.90 mmol) in DCM (5 ml) was stirred at room temperature for 3 days. Pyridine (1 mL) was added and the reaction mixture stirred for 2 hours. The mixture was then evaporated under reduced pressure and partitioned between ethyl acetate and 5% citric acid. The aqueous phase was extracted with further ethyl acetate, then DCM and the combined organic phases were dried by passing through a phase separator and then evaporated under reduced pressure. The product was crystallised from ethyl acetate and dried under vacuum to give 100 mg of an off white solid. Recrystallisation from ethanol afforded the title compound as an off-white solid;

LC-MS: Rt 0.92 min; MS m/z 420.3 [M+H]+: Method 2minLowpHv01

$^1$H NMR (400 MHz, DMSO-d6) δ 10.44 (1H, s), 9.32 (1H, s), 8.42 (1H, s), 8.39 (1H, s), 7.95 (1H, br s), 7.78 (1H, br d), 7.61 (1H, d), 7.40 (2H, s), 4.47 (1H, s), 3.73 (2H, s), 2.54 (3H, s), 1.04 (6H, s).

Example 32

3-(5-Amino-6-[1,2,4]triazol-1-yl-pyrazin-2-yl)-N-(4-hydroxy-tetrahydropyran-4-ylmethyl)-4-methylbenzenesulfonamide

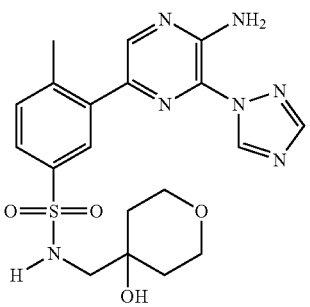 [SMILES: Cc1ccc(S(=O)(=O)NCC2(O)CCOCC2)cc1-c1cnc(N)c(-n2cncn2)n1]

4-Aminomethyl-tetrahydro-pyran-4-ol (20 mg, 0.15 mmol) was dissolved in DMA (1 ml) and a solution of 3-(5-amino-6-(1H-1,2,4-triazol-1-yl)pyrazin-2-yl)-4-methylbenzene-1-sulfonyl chloride (Intermediate E1, 35 mg, 0.1 mmol) in DMA (2 ml) was added, followed by DIPEA (0.035 ml, 0.2 mmol). The reaction was shaken at room temperature for 2 hrs, then the solvent was removed under reduced pressure to yield the crude product as a brown solid. The crude material was then recrystallised from methanol to give the title compound as an off white solid;

LCMS: Rt 0.87 mins MS m/z 428 [M—OH]+: Method 2minLowpHv02

$^1$H NMR (400 MHz, DMSO-d6) δ 9.35 (1H, s), 8.40 (2H, d), 7.93 (1H, s), 7.72 (1H, m), 7.54 (2H, d), 7.40 (2H, br), 3.56 (2H, d), 2.66 (2H, d), 2.52 (3H, s), 1.54 (2H, m), 1.32 (2H, m)

Example 33

N-(2-Amino-ethyl)-3-(5-amino-6-[1,2,4]triazol-1-yl-pyrazin-2-yl)-4-methyl-benzenesulfonamide trifluoroacetic acid salt

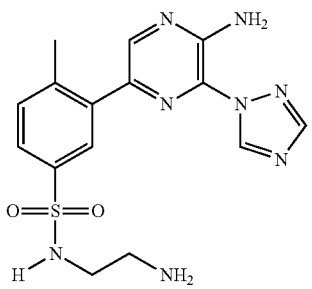 [SMILES: Cc1ccc(S(=O)(=O)NCCN)cc1-c1cnc(N)c(-n2cncn2)n1]

Tert-butyl (2-aminoethyl)carbamate (21 mg, 0.128 mmol) was dissolved in DMA (1 ml) and a solution of 3-(5-amino-6-(1H-1,2,4-triazol-1-yl)pyrazin-2-yl)-4-methylbenzene-1-sulfonyl chloride (Intermediate E1.30 mg, 0.086 mmol) in DMA (1.5 ml) was added, followed by DIPEA (0.030 ml, 0.171 mmol). The reaction was shaken at room temperature for 2 hrs, then the solvent was removed under reduced pressure to yield the crude product as a brown solid. The crude material was then suspended in DCM (2 ml) and TFA (0.15 ml, 1.97 mmol) added and the mixture shaken at room temperature for 3 hrs. The solvent was then removed under reduced pressure. The crude material was then purified via preparative HPLC using acetonitrile and water as the eluents with 0.1% TFA as a modifier, to give the title compound as an off white solid;

LCMS: Rt 0.60 mins MS m/z 375.2 [M+H]+: Method 2minLowpHv01

$^1$H NMR (400 MHz, DMSO-d6) δ 9.35 (1H, s), 8.40 (2H, d), 7.90 (2H, m), 7.80 (2H, br), 7.74 (1H, d), 7.60 (1H, d), 7.40 (2H, br), 2.95 (2H, m), 2.87 (2H, m), 2.52 (3H, s)

Example 34

3-(5-Amino-6-[1,2,4]triazol-1-yl-pyrazin-2-yl)-N-(2,2-difluoro-ethyl)-4-methyl-benzenesulfonamide

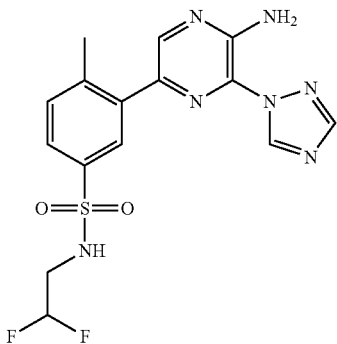 [SMILES: Cc1ccc(S(=O)(=O)NCC(F)F)cc1-c1cnc(N)c(-n2cncn2)n1]

The title compound was prepared from 3-(5-amino-6-(1H-1,2,4-triazol-1-yl)pyrazin-2-yl)-4-methylbenzene-1-sulfonyl chloride (Intermediate E1) and 2,2-difluoroethanamine using conditions analogous to those of Example 32. In this case, purification was carried out using preparative HPLC with an acetonitrile/0.1% aqueous TFA solvent gradient.

LCMS: Rt 1.0 mins MS m/z 396.0 [M+H]+: Method 2minLowpHv01

$^1$H NMR (400 MHz, DMSO-d6) δ 9.30 (1H, s), 8.41 (2H, d), 8.22 (1H, m), 7.92 (1H, s), 7.75 (1H, m), 7.55 (1H, d), 7.40 (2H, br), 6.00 (1H, t), 3.23 (2H, t), 2.51 (3H, s).

Example 35

3-(5-Amino-6-[1,2,4]triazol-1-yl-pyrazin-2-yl)-N-(3-hydroxymethyl-oxetan-3-ylmethyl)-4-methyl-benzenesulfonamide

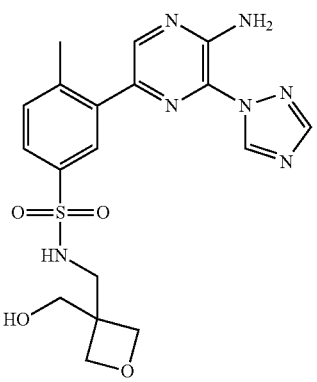 [SMILES: Cc1ccc(S(=O)(=O)NCC2(CO)COC2)cc1-c1cnc(N)c(-n2cncn2)n1]

The title compound was prepared from 3-(5-amino-6-(1H-1,2,4-triazol-1-yl)pyrazin-2-yl)-4-methylbenzene-1-sulfonyl chloride (Intermediate E1) and (3-aminomethyl-oxetan-3-yl)-methanol using conditions analogous to those of Example 32. In this case, purification was carried out using preparative HPLC with acetonitrile/0.1% aqueous TFA solvent gradient.

LCMS: Rt 0.83 mins MS m/z 432.2 [M+H]+: Method 2minLowpHv02

$^1$H NMR (400 MHz, DMSO-d6) δ 9.35 (1H, s), 8.40 (2H, d), 7.94 (1H, s), 7.80 (1H, m), 7.75 (1H, m), 7.57 (1H, d), 7.40 (2H, br), 4.30 (2H, d), 4.25 (2H, d), 3.52 (2H, m), 2.29 (2H, d), 2.51 (3H, s). One exchangable not clearly observed.

Example 36

3-(5-Amino-6-[1,2,4]triazol-1-yl-pyrazin-2-yl)-N-(3,3-dimethyl-2-oxo-butyl)-4-methyl-benzenesulfonamide

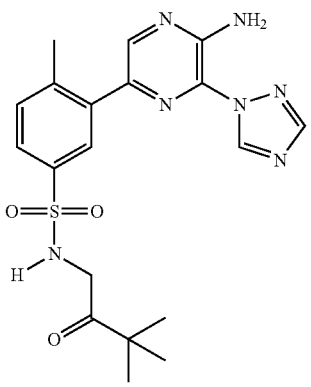 [SMILES: Cc1ccc(S(=O)(=O)NCC(=O)C(C)(C)C)cc1-c1cnc(N)c(-n2cncn2)n1]

The title compound was prepared from 3-(5-amino-6-(1H-1,2,4-triazol-1-yl)pyrazin-2-yl)-4-methylbenzene-1-sulfonyl chloride (Intermediate E1) and 1-amino-3,3-dimethyl-butan-2-one using conditions analogous to those of Example 32. In this case, purification was carried out using preparative HPLC with acetonitrile/0.1% aqueous TFA solvent gradient.

LCMS: Rt 1.06 mins MS m/z 430.2 [M+H]+: Method 2minLowpHv02

$^1$H NMR (400 MHz, DMSO-d6) δ 9.35 (1H, s), 8.40 (2H, dd), 7.92 (1H, s), 7.80 (1H, m), 7.73 (1H, d), 7.52 (1H, d), 7.40 (2H, br), 4.00 (2H, d), 2.52 (3H, s), 1.00 (9H, s).

Example 37

3-(5-Amino-6-(1H-1,2,4-triazol-1-yl)pyrazin-2-yl)-4-chloro-N-(2-hydroxy-2-methylpropyl)benzenesulfonamide

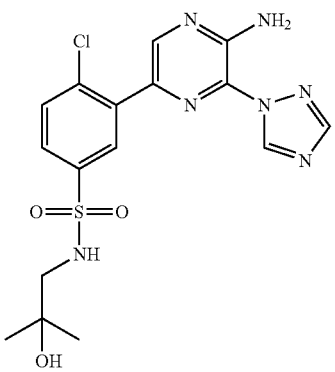 [SMILES: CC(C)(O)CNS(=O)(=O)c1ccc(Cl)c(-c2cnc(N)c(-n3cncn3)n2)c1]

Step 1: 3-Bromo-4-chlorobenzene-1-sulfonyl chloride

The chlorosulfonylation reagent was prepared by bubbling 74 g of sulfur dioxide gas into 740 mL of glacial acetic acid followed by the addition of 30 g of CuCl$_2$ in 35-40 mL of water. This mixture was allowed to settle and the green supernatant is used for the reaction.

Procedure:

To a stirred suspension of 3-bromo-4-chloroaniline (1 g, 4.84 mmol) in acetic acid (8 mL) and conc hydrochloric acid (8 mL) at 0° was added, dropwise, a cooled (0° C.) solution of sodium nitrite (368 mg, 5.33 mmol) in water (5 mL). The mixture was stirred at 0° C. for one hour and then added, dropwise while still cold, to a flask containing cooled (0° C.), stirred chlorosulfonylation reagent (40 mL). The mixture turned black/brown and was then allowed to warm to room temp and stirred at room temp overnight, by which time it had become a yellow/green solution. Crushed ice was added and when this had melted, the precipitate that was formed was recovered by filtration and dried at the pump. It was dissolved in EtOAc (50 mL), dried (MgSO$_4$), filtered and evaporated to give the title compound as a colourless oil. This material was used in the next step without further purification;

$^1$H NMR (400 MHz, CDCl$_3$) δH 8.32 (1H, d), 7.95 (1H, dd), 7.73 (1H, d).

Step 2: 3-Bromo-4-chloro-N-(2-hydroxy-2-methylpropyl)benzenesulfonamide

To a stirred solution of 3-bromo-4-chlorobenzene-1-sulfonyl chloride (step 1) (500 mg, 1.72 mmol) and triethylamine (0.385 mL, 2.76 mmol) in dry THF (10 mL) at room temp was added a solution of 4-amino-2-methylbutan-2-ol (231 mg, 2.6 mmol) in dry THF (5 mL). The mixture was stirred at room temp for 1 hour. The mixture was quenched by the addition of 50% aq. ammonium chloride (20 mL) and extracted with EtOAc (3×20 mL). The EtOAc extracts were combined and washed with sat. brine (20 mL), dried (MgSO$_4$), filtered and evaporated to give the title compound as a colourless solid. This material was used in the next step without further purification;

$^1$H NMR (400 MHz, DMSO-d6) δ 8.14 (1H, d), 7.86 (1H, d), 7.80 (1H, dd), 7.72 (1H, br s), 4.45 (1H, br s), 2.65 (2H, s), 1.05 (6H, s).

Step 3: 3-(5-Amino-6-(1H-1,2,4-triazol-1-yl)pyrazin-2-yl)-4-chloro-N-(2-hydroxy-2-methylpropyl)benzenesulfonamide A mixture of 5-bromo-3-(1H-1,2,4-triazol-1-yl)pyrazin-2-amine (Intermediate C11) (200 mg, 0.83 mmol), bis(pinacolato)diboron (263 mg, 1.04 mmol), potassium acetate (122 mg, 1.25 mmol) and PdCl2(dppf).CH$_2$Cl$_2$ adduct (34 mg, 0.041 mmol) was dissolved in DME (5 mL) and heated at 90° C. for 5 hours before addition of 3-bromo-4-chloro-N-(2-hydroxy-2-methylpropyl)benzenesulfonamide (step 2) (284 mg, 0.83 mmol), 2M aq. sodium carbonate (1.25 mL, 2.5 mmol) and further PdCl$_2$(dppf).CH$_2$Cl$_2$ adduct (34 mg, 0.041 mmol) and the mixture was stirred at 90° C. for 16 hours. The mixture was cooled to room temp, diluted with water (20 mL) and extracted with EtOAc (3×20 mL). The EtOAc extracts were combined, washed with brine (20 mL), dried (MgSO$_4$), filtered and absorbed directly onto silica gel for dry loading onto a column. The mixture was purified by chromatography on silica gel (24 g column) eluting with 0-100% EtOAc in isohexane over 20 min, then maintaining 100% EtOAc for a further 3 min. The product fractions were combined and evaporated. Trituration with EtOAc and filtration gave the title compound as a pale yellow powder;

¹H NMR (400 MHz, DMSO-d6) δH 9.33 (1H, s), 8.57 (1H, s), 8.43 (1H, s), 8.11 (1H, m), 7.82 (2H, m), 7.71 (1H, br s), 7.49 (2H, br s), 4.45 (1H, br s), 2.67 (2H, s), 1.06 (6H, s).

LCMS: Rt 0.86 mins; MS m/z 424/426[M+H]+: Method 2minLowpH

Example 38

3-(5-Amino-6-(1H-1,2,4-triazol-1-yl)pyrazin-2-yl)-4-chloro-N-(3-hydroxy-3-methylbutyl)benzenesulfonamide

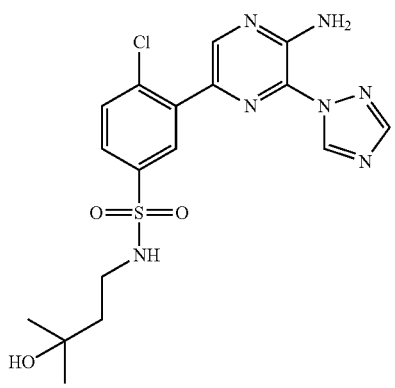 [SMILES: CC(C)(O)CCNS(=O)(=O)c1ccc(Cl)c(-c2cnc(N)c(-n3cncn3)n2)c1]

The title compound was prepared using analogous conditions to those used for the synthesis of Example 37.

¹H NMR (400 MHz, DMSO-d6) δ 9.31 (1H, s), 8.58 (1H, s), 8.43 (1H, s), 8.08 (1H, d), 7.85 (1H, d), 7.81 (1H, dd), 7.67 (1H, br s), 7.49 (2H, br s), 4.28 (1H, br s), 2.87 (2H, m), 1.52 (2H, m), 1.02 (6H, s).

LCMS: Rt 0.87 mins; MS m/z 438/440[M+H]+: Method 2minLowpH

Example 39

3-(5-Amino-6-(furan-3-yl)pyrazin-2-yl)-N-(2-hydroxy-2-methylpropyl)-4-methylbenzenesulfonamide

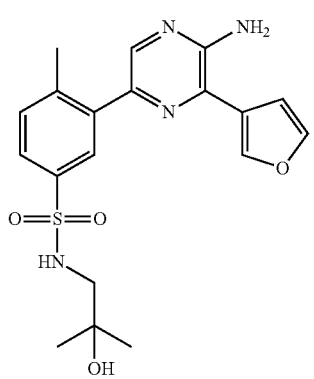 [SMILES: Cc1ccc(S(=O)(=O)NCC(C)(C)O)cc1-c1cnc(N)c(-c2ccoc2)n1]

To a stirred mixture of 3-(5-amino-6-chloro-pyrazin-2-yl)-N-(2-hydroxy-2-methyl-propyl)-4-methyl-benzenesulfonamide (Intermediate D2) (200 mg, 0.54 mmol), furan-3-ylboronic acid (78 mg, 0.7 mmol) and PdCl₂(dppf).CH₂Cl₂ adduct (22 mg, 0.027 mmol) in DME (3 mL) was added sodium carbonate (0.81 mL of a 2M aq. solution, 1.62 mmol). The mixture was heated at 90° C. for 2 hours then cooled to room temp, diluted with 10% aq. potassium hydrogen phosphate (5 mL) and extracted with EtOAc (3×15 mL). The EtOAc extracts were combined, washed with sat. brine (10 mL), dried (MgSO₄), filtered and absorbed directly onto silica gel prior to chromatography. The crude product was purified by chromatography on silica gel (24 g) eluting with 0-100% EtOAc in isohexane over 10 min as eluant. The product peak eluted at 100% EtOAc. The product fractions were combined and the solvent removed under reduced pressure to give the title compound as a pale yellow solid;

¹H NMR (400 MHz, DMSO-d6) δ 8.40 (1H, m), 8.17 (1H, s), 7.89 (1H, d), 7.82 (1H, m), 7.69 (1H, dd), 7.52 (1H, d), 7.47 (1H, t), 7.04 (1H, m), 6.42 (2H, br s), 4.39 (1H, s), 2.63 (2H, d), 2.49 (3H, s, partially obscured by DMSO-d6 peak), 1.06 (6H, s).

LC-MS: Rt 0.98 mins; MS m/z 403.6 MH+; Method 2minLowpHv01

Example 40

3-(5-Amino-6-(2,5-dimethylthiazol-4-yl)pyrazin-2-yl)-N-(2-hydroxy-2-methylpropyl)-4-methylbenzenesulfonamide

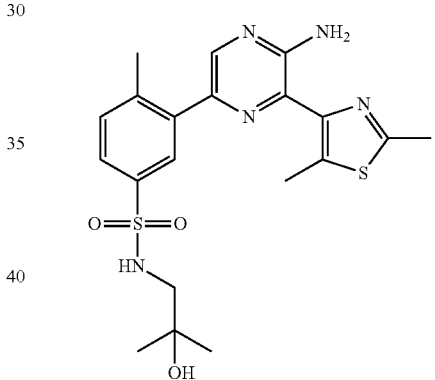

Step 1: 3-Amino-6-bromo-N-methoxy-N-methyl-pyrazine-2-carboxamide

To a stirred suspension of 3-amino-6-bromopyrazine-2-carboxylic acid (45 g, 206 mmol) and O,N-dimethylhydroxylamine hydrochloride (20.13 g, 206 mmol) in DMF (295 mL) at RT was added triethylamine (115 mL, 826 mmol) under N₂ supply. The resulting mixture was cooled to 0° C. and to this yellow suspension T3P® (50% in EtOAc) (151 g, 237 mmol) was added dropwise over 5 min (keeping T below 10° C.—exotherm). The mixture was allowed to warm to RT and stirred for 2-3 hours. During the reaction the contents had set solid into a gel. The flask was diluted with a further 200 ml of DMF and was warmed to 40° C. and was left overnight. Further triethylamine (50 mL, 0.4 equiv), O,N-dimethylhydroxylamine hydrochloride (10 g, 0.5 equiv) and T3P® (80 g, 0.5 equiv) were added and the reaction mixture was warmed to 40° C. and was allowed to stir for 2-3 hours. The mixture was allowed to cool to RT and then stirred for three days. The mixture was worked up by the addition of 2M HCl (100 mL) and was diluted with ethyl acetate (1 L) and water (500 mL). The biphasic mixture was separated. The aqueous layer was basified with 2M NaOH (~150 mL), organic extract was added back and the biphasic mixture was shaken. The organic was extracted, washed with brine, dried over MgSO$_4$, filtered and dried under vacuum to give a yellow oil. The crude yellow oil was loaded directly onto a 750 g column (in DCM ~20 mL) and was eluted with iso-Hex/EtOAc (0-70% gradient). The fractions containing pure product were combined and evaporated to give a yellow oil. Diethyl ether (50 mL) was added and this was evaporated under vacuum to give a pale yellow solid;

LC-MS: Rt 0.88 mins; MS m/z 263.1 MH+; Method 2minLC_v003

Step 2:
1-(3-Amino-6-bromopyrazin-2-yl)propan-1-one

To a stirred solution of 3-amino-6-bromo-N-methoxy-N-methylpyrazine-2-carboxamide (step 1) (4 g, 15.32 mmol) in dry THF (50 ml), cooled on an ice bath under nitrogen, was added dropwise 1M ethylmagnesium bromide in THF (46.0 ml, 46.0 mmol). The mixture was slowly warmed to room temperature. The reaction was cooled on an ice bath and quenched by dropwise addition of water. The reaction was diluted with ethyl acetate, washed with water and the aqueous back extracted with further ethyl acetate. The organics were combined, dried (MgSO$_4$), filtered and concentrated. The brown residue was triturated in diethyl ether, filtered under vacuum and dried.

LC-MS: Rt 1.06 mins; MS m/z 230.0/232.0 [M+H]+ Method 2minLowpHv01

Step 3: 1-(3-Amino-6-bromopyrazin-2-yl)-2-bromopropan-1-one

To a solution of 1-(3-amino-6-bromopyrazin-2-yl)propan-1-one (step 2) (3.04 g, 13.2 mmol) in glacial acetic acid (75 mL) at room temp was added polymer supported pyridinium tribromide (14.2 g of loading 2 mmol/g, 28.4 mmol) followed by 33% HBr in acetic acid (4.35 mL, 26.4 mmol). The mixture was heated at 70° C. for 1 hour. LCMS showed approx 4:1 product to starting material. Heating was continued at 70° C. for a further 30 min. Once cooled, the volatiles (including AcOH) were removed under reduced pressure. The dark brown syrup that remained was dissolved in EtOAc (ca. 150 mL) and washed with sat. sodium bicarbonate (150 mL). The EtOAc extracts were separated, washed with brine (100 mL), dried (MgSO$_4$) filtered and evaporated to give a brown oil. The oil was triturated in Et$_2$O (50 mL) and isohexane (200 mL) was added to give a brown solid which was recovered by filtration and dried.

$^1$H NMR (400 MHz, DMSO-d6) δ 8.53 (1H, s), 8.05 (2H, br s), 5.86 (1H, q), 1.77 (3H, d); approx 90% purity.

Step 4: 5-Bromo-3-(2,5-dimethylthiazol-4-yl)pyrazin-2-amine

A stirred mixture of 1-(3-amino-6-bromopyrazin-2-yl)-2-bromopropan-1-one (step 3) (782 mg, 2.53 mmol) and thioacetamide (399 mg, 5.32 mmol) in EtOH (25 mL) was heated at 50° C. for 30 mins. The mixture was cooled to RT and allowed to stir overnight. The volatiles were removed under reduced pressure. The residue was partitioned between EtOAc (30 mL) and water (30 mL) and extracted with further EtOAc (3×30 mL). The EtOAc extracts were combined, washed with sat brine (50 mL), dried (MgSO$_4$), filtered and evaporated to give a brown oil. The crude product was absorbed onto silica gel and purified by flash chromatography on silica gel using 40 g column and 0-100% EtOAc in isohexane as eluant. The desired compound was the first to elute at approx 35% EtOAc. Evaporation of product-containing fractions gave a pale yellow solid;

LC-MS: Rt 1.24 mins; MS m/z 285.4/287.4 [M+H]+; Method 2minLowpH_v01

$^1$H NMR (400 MHz, CDCl$_3$) δ 7.97 (1H, s), 6.57 (2H, br s), 2.76 (3H, s), 2.68 (3H, s).

Step 5: 3-(5-Amino-6-(2,5-dimethylthiazol-4-yl)pyrazin-2-yl)-N-(2-hydroxy-2-methylpropyl)-4-methylbenzenesulfonamide To a mixture of N-(2-hydroxy-2-methylpropyl)-4-methyl-3-(4,4,5,5-tetramethyl-1,3,2-dioxaborolan-2-yl)benzenesulfonamide (Intermediate B2) (95 mg, 0.26 mmol), 5-bromo-3-(2,5-dimethylthiazol-4-yl)pyrazin-2-amine (step 4) (67 mg, 0.24 mmol) and PdCl$_2$(dppf).CH$_2$Cl$_2$ adduct (19 mg, 0.023 mmol) in DME (2 mL) in a 5 mL tube equipped with stirrer bar was added sodium carbonate (352 μL of a 2M aq solution, 0.705 mmol). The mixture was heated at 90° C. for 2 hours. The mixture was cooled to room temp, diluted with EtOAc (10 mL) and water (10 mL) and extracted with further EtOAc (3×10 mL). The EtOAc extracts were combined, washed with sat. brine (20 mL), dried (MgSO$_4$), filtered and evaporated to give a brown oil. The crude product was dissolved in the minimum amount of DCM and applied to a 4 g silica gel column and purified by chromatography eluting with 0-100% EtOAc in isohexane as eluant. The fractions containing desired product were combined and evaporated to give a pale yellow oil which was triturated using DCM:Et$_2$O (1:10). The yellow powder obtained was recovered by filtration and dried to afford the title compound;

LC-MS: Rt 1.07 mins; MS m/z 448.3 [M+H]+; Method 2minLowpHv01

$^1$H NMR (400 MHz, CDCl$_3$) δ 8.09 (1H, s), 7.99 (1H, d), 7.77 (1H, dd), 7.44 (1H, d), 6.73 (2H, br s), 5.01 (1H, t), 2.94 (2H, d), 2.78 (3H, s), 2.73 (3H, s), 2.53 (3H, s), 1.27 (6H, s). OH proton missing due to exchange.

Example 41

(R)-3-(5-Amino-6-(2-methylthiazol-5-yl)pyrazin-2-yl)-N-((1-ethylpyrrolidin-2-yl)methyl)-4-methylbenzenesulfonamide

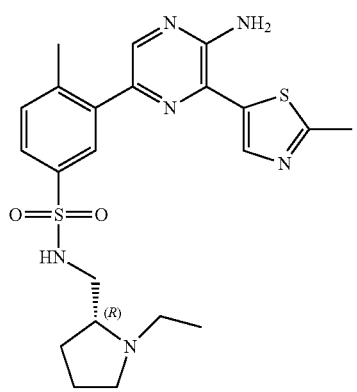

Pd-118 (13.58 mg, 0.022 mmol) was added to a mixture of 5-chloro-3-(2-methylthiazol-5-yl)pyrazin-2-amine (Intermediate C6) (100 mg, 0.441 mmol), N—((R)-1-ethyl-pyrrolidin-2-ylmethyl)-4-methyl-3-(4,4,5,5-tetramethyl-[1,3,2]dioxaborolan-2-yl)-benzenesulfonamide (Intermediate B6) (198 mg, 0.485 mmol), potassium phosphate (187 mg, 0.882 mmol), 1,4-dioxane (1765 μl) and water (441 μl). The reaction mixture was heated in a microwave reactor for 90 minutes at 120° C. The reaction mixture was added to water (50 ml) and extracted with EtOAc (50 ml). The organic phase was washed with brine (50 ml) and dried over MgSO$_4$. The solid was filtered off, washed with EtOAc and the solvent was concentrated under reduced pressure. The residue was purified by flash column chromatography, eluting with a gradient of 0-10% MeOH in DCM using a 4 g silica column, loading with DCM. The resulting oil was triturated with Et$_2$O to give a solid, which was filtered off, washed with Et$_2$O and dried overnight in a vacuum oven at 50° C. to give the title compound as a beige solid;

LCMS: Rt 0.74 mins; MS m/z 473.6 [M+H]+; Method 2minLowpHv03.

$^1$H NMR (400 MHz, DMSO-d6) δ 8.27 (1H, s), 8.21 (1H, s), 7.85 (1H, s), 7.70 (1H, d), 7.52 (1H, d), 7.48 (1H, br s), 6.73 (2H, br s), 2.94 (1H, m), 2.84 (1H, m), 2.67 (3H, s), 2.61-2.57 (2H, m), 2.48 (3H, s), 2.39 (1H, m), 2.14 (1H, m), 2.05 (1H, m), 1.76 (1H, m), 1.59-1.54 (3H, m), 0.92 (3H, t).

Example 42

(R)-3-(5-Amino-6-(2-methylthiazol-5-yl)pyrazin-2-yl)-4-methyl-N-((tetrahydrofuran-3-yl)methyl)benzenesulfonamide

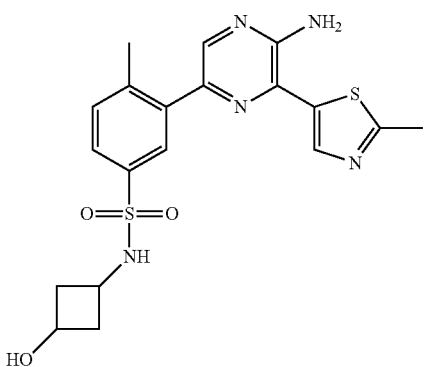 [SMILES: Cc1ncc(-c2nc(-c3cc(S(=O)(=O)NC4CC(O)C4)ccc3C)cnc2N)s1]

The title compound was prepared using 5-chloro-3-(2-methylthiazol-5-yl)pyrazin-2-amine (Intermediate C6) and (R)-4-methyl-N-((tetrahydrofuran-3-yl)methyl)-3-(4,4,5,5-tetramethyl-1,3,2-dioxaborolan-2-yl)benzenesulfonamide (Intermediate B7) under analogous conditions to those of Example 41;

LCMS: Rt 1.07 mins; MS m/z 446.5 [M+H]+; Method 2minLowpHv03.

Example 43

3-(5-Amino-6-(2-methylthiazol-5-yl)pyrazin-2-yl)-N-(3-hydroxycyclobutyl)-4-methylbenzenesulfonamide The title compound was prepared using 5-chloro-3-(2-methylthiazol-5-yl)pyrazin-2-amine (Intermediate C6) and N-(3-hydroxycyclobutyl)-4-methyl-3-(4,4,5,5-tetramethyl-1,3,2-dioxaborolan-2-yl)benzenesulfonamide (prepared analogously to Intermediate B1, starting from 3-aminocyclobutanol) under analogous conditions to those of Example 41;

LCMS: Rt 1.02 mins; MS m/z 432.3 [M+H]+; Method 2minLowpHv03.

Example 43a cis-3-(5-Amino-6-(2-methylthiazol-5-yl)pyrazin-2-yl)-N-(3-hydroxycyclobutyl)-4-methylbenzenesulfonamide and Example 43b: trans-3-(5-Amino-6-(2-methylthiazol-5-yl)pyrazin-2-yl)-N-(3-hydroxycyclobutyl)-4-methylbenzenesulfonamide

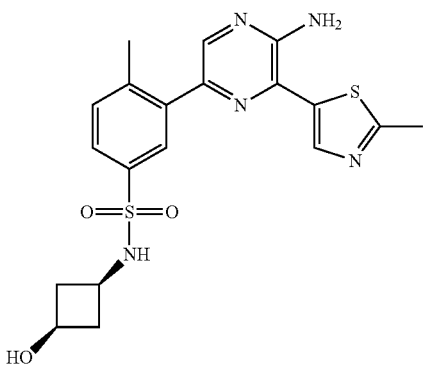

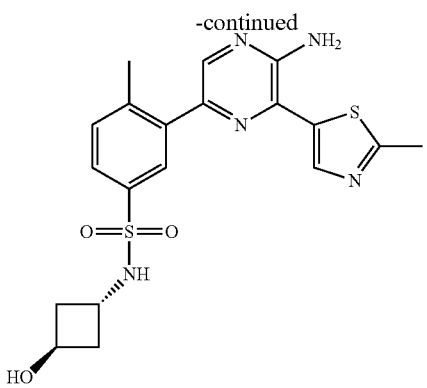

The diastereomeric mixture of 3-(5-amino-6-(2-methylthiazol-5-yl)pyrazin-2-yl)-N-(3-hydroxycyclobutyl)-4-methylbenzenesulfonamide (Example 43) was separated by chiral SFC under the following conditions:

Method Details:

Column: Phenomenex LUX A2 250×100 mm 5 um @ 35 deg C.

Mobile phase: 45% IPA+0.1% DEA/55% CO2

Flow rate: 10 ml/min

The two separated fractions were concentrated under reduced pressure. The residues were dissolved in MeOH and left to stand at room temperature and then dried in a vacuum oven at 50° C. over the weekend to afford the title compounds.

Example 43a cis-3-(5-Amino-6-(2-methylthiazol-5-yl)pyrazin-2-yl)-N-(3-hydroxycyclobutyl)-4-methylbenzenesulfonamide Peak 1:

SFC retention time=8.36 mins

LCMS: Rt=0.97 mins, MS m/z 432.2 [M+H]+; Method 2minLowpHv03.

Example 43b trans-3-(5-Amino-6-(2-methylthiazol-5-yl)pyrazin-2-yl)-N-(3-hydroxycyclobutyl)-4-methylbenzenesulfonamide Peak 2:

SFC retention time=10.73 mins

LCMS: Rt=0.97 mins, MS m/z 432.3 [M+H]+; Method 2minLowpHv03

1H NMR—AV81762-(400 MHz, MeOD)—Is consistent with proposed structure.

The cis/trans assignments were confirmed by NMR analysis.

Example 44

3-(5-Amino-6-(2-methylthiazol-5-yl)pyrazin-2-yl)-N-((3-(hydroxymethyl)oxetan-3-yl)methyl)-4-methylbenzenesulfonamide

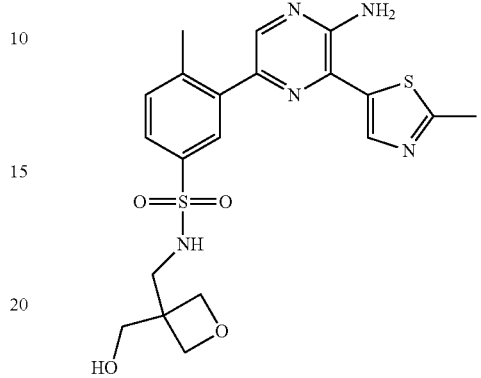

The title compound was prepared using 5-chloro-3-(2-methylthiazol-5-yl)pyrazin-2-amine (Intermediate C6) and N-((3-(hydroxymethyl)oxetan-3-yl)methyl)-4-methyl-3-(4,4,5,5-tetramethyl-1,3,2-dioxaborolan-2-yl)benzenesulfonamide (prepared analogously to Intermediate B1 starting from (3-(aminomethyl)oxetan-3-yl)methanol) under analogous conditions to those of Example 41;

LCMS: Rt 1.00 mins; MS m/z 462.3 [M+H]+; Method 2minLowpHv03.

Example 45

3-(5-Amino-6-(2-methylthiazol-5-yl)pyrazin-2-yl)-N-(2-hydroxyethyl)-4-methylbenzenesulfonamide

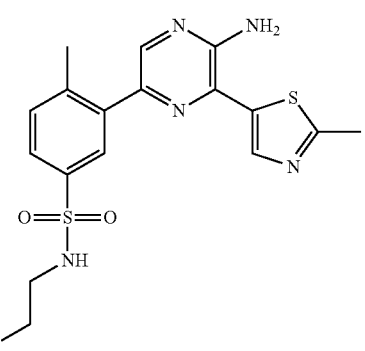

To a stirring solution of ethanolamine (11.89 µl, 0.197 mmol), DIPEA (57.3 µl, 0.328 mmol) in DMA (656 µl) was added 3-(5-amino-6-(2-methylthiazol-5-yl)pyrazin-2-yl)-4-methylbenzene-1-sulfonyl chloride (Intermediate E) (50 mg, 0.131 mmol). The reaction mixture was stirred overnight at RT and then added to water (50 ml) and extracted with EtOAc (50 ml). The organic phase was washed with brine (50 ml) and dried over MgSO4. The solid was filtered off, washed with EtOAc and the solvent was concentrated under reduced pressure. The crude material was purified by flash column chromatography, eluting with a gradient of 0-10% MeOH in DCM on a 4 g silica column, loading with DCM and MeOH. The resulting oil was triturated with Et$_2$O to give a solid which was filtered off, washed with Et$_2$O and dried in a vacuum oven at 50° C. overnight to give the title compound as a beige solid;

LCMS: Rt 0.99 mins; MS m/z 406.3 [M+H]+; Method 2minLowpHv03.

$^1$H NMR (400 MHz, DMSO-d6) δ 8.27 (1H, s), 8.22 (1H, s), 7.85 (1H, d), 7.70 (1H, dd), 7.57 (1H, t), 7.53 (1H, d), 6.73 (2H, br s), 4.67 (1H, t), 3.38 (2H, q), 2.81 (2H, q), 2.68 (3H, s), 2.48 (3H, s).

The following examples were prepared in an analogous manner to Example 45 from 3-(5-amino-6-(2-methylthiazol-5-yl)pyrazin-2-yl)-4-methylbenzene-1-sulfonyl chloride (Intermediate E) and the appropriate commercially available amine:

Example 45.1

3-(5-Amino-6-(2-methylthiazol-5-yl)pyrazin-2-yl)-4-methyl-N-(oxetan-3-ylmethyl)benzenesulfonamide

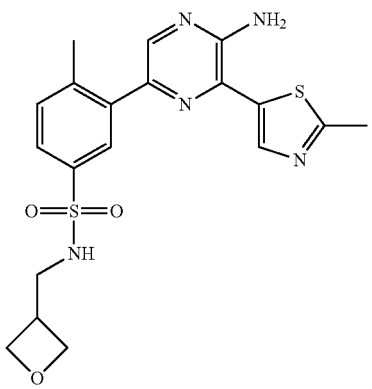 [SMILES: Cc1ncc(-c2nc(-c3cc(S(=O)(=O)NCC4COC4)ccc3C)cnc2N)s1]

LCMS: Rt 1.06 mins; MS m/z 432.3 [M+H]+; Method 2minLowpHv03.

Example 45.2

3-(5-Amino-6-(2-methylthiazol-5-yl)pyrazin-2-yl)-4-methyl-N-((tetrahydro-2H-pyran-4-yl)methyl)benzenesulfonamide

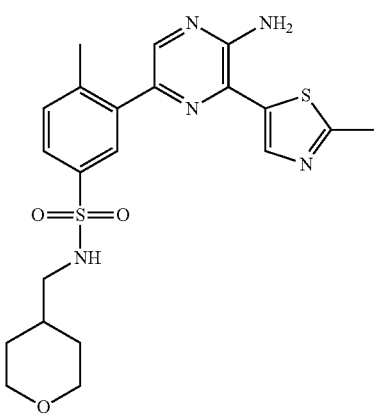 [SMILES: Cc1ncc(-c2nc(-c3cc(S(=O)(=O)NCC4CCOCC4)ccc3C)cnc2N)s1]

LCMS: Rt 1.15 mins; MS m/z 460.3 [M+H]+; Method 2minLowpHv03.

Example 45.3

3-(5-Amino-6-(2-methylthiazol-5-yl)pyrazin-2-yl)-4-methyl-N-(tetrahydro-2H-pyran-4-yl)benzenesulfonamide

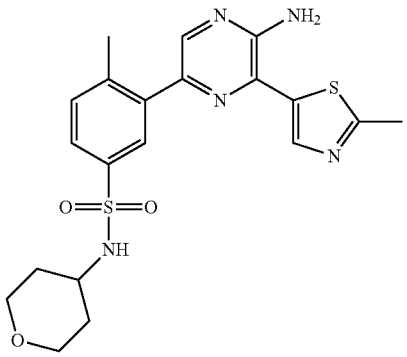 [SMILES: Cc1ncc(-c2nc(-c3cc(S(=O)(=O)NC4CCOCC4)ccc3C)cnc2N)s1]

LCMS: Rt 1.06 mins; MS m/z 446.2 [M+H]+; Method 2minLowpHv03.

Example 45.4

3-(5-Amino-6-(2-methylthiazol-5-yl)pyrazin-2-yl)-4-methyl-N-((tetrahydro-2H-pyran-2-yl)methyl)benzenesulfonamide

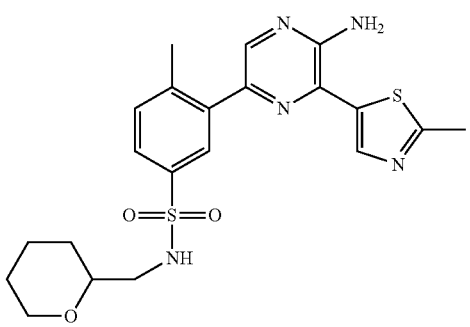 [SMILES: Cc1ncc(-c2nc(-c3cc(S(=O)(=O)NCC4CCCCO4)ccc3C)cnc2N)s1]

LCMS: Rt 1.20 mins; MS m/z 460.3 [M+H]+; Method 2minLowpHv03.

Example 45.5

3-(5-Amino-6-(2-methylthiazol-5-yl)pyrazin-2-yl)-4-methyl-N-(2,2,2-trifluoroethyl)benzenesulfonamide

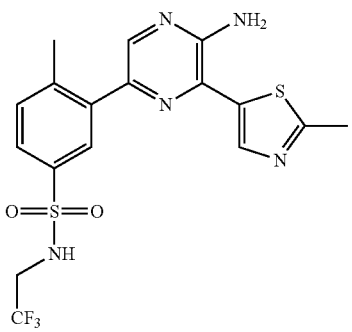 [SMILES: Cc1ncc(-c2nc(-c3cc(S(=O)(=O)NCC(F)(F)F)ccc3C)cnc2N)s1]

LCMS: Rt 1.22 mins; MS m/z 444.8 [M+H]+; Method 2minLowpHv03.

Example 45.6

3-(5-Amino-6-(2-methylthiazol-5-yl)pyrazin-2-yl)-4-methyl-N-((tetrahydrofuran-2-yl)methyl)benzenesulfonamide

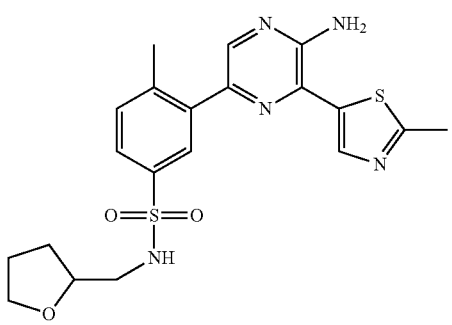 [SMILES: Cc1ncc(-c2nc(-c3cc(S(=O)(=O)NCC4CCCO4)ccc3C)cnc2N)s1]

LCMS: Rt 1.14 mins; MS m/z 446.2 [M+H]+; Method 2minLowpHv03.

Examples 45.6a and 45.6b (R)-3-(5-Amino-6-(2-methylthiazol-5-yl)pyrazin-2-yl)-4-methyl-N-((tetrahydrofuran-2-yOmethyl)benzenesulfonamide and (S)-3-(5-Amino-6-(2-methylthiazol-5-yl)pyrazin-2-yl)-4-methyl-N-((tetrahydrofuran-2-yl)methyl)benzenesulfonamide

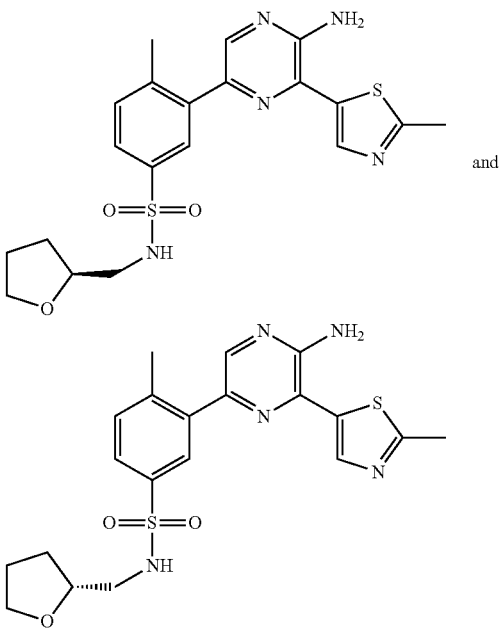

and

In this case, the racemic mixture was separated by chiral separation to afford the individual isomers:

Column: Chiralpak AS-H, 250×10 mm, 5 um @ 35 deg C.,

Mobile phase: 50% Isopropanol+0.1% v/v DEA/50% CO$_2$,

Flow: 10 ml/min,

Detection: UV @ 220 nm,

Instrument: Berger Minigram SFC1

Example 45.6a

First Eluting Compound

SFC Retention Time=7.00 mins. (R)-3-(5-Amino-6-(2-methylthiazol-5-yl)pyrazin-2-yl)-4-methyl-N-((tetrahydrofuran-2-yl)methyl)benzenesulfonamide or (S)-3-(5-Amino-6-(2-methylthiazol-5-yl)pyrazin-2-yl)-4-methyl-N-((tetrahydrofuran-2-yl)methyl) benzenesulfonamide LCMS: Rt 1.13 mins; MS m/z 446.1 [M+H]+; Method 2minLowpHv03.

Example 45.6b

Second Eluting Compound

SFC Retention Time=8.73 mins. (R)-3-(5-Amino-6-(2-methylthiazol-5-yl)pyrazin-2-yl)-4-methyl-N-((tetrahydrofuran-2-yl)methyl)benzenesulfonamide or (S)-3-(5-Amino-6-(2-methylthiazol-5-yl)pyrazin-2-yl)-4-methyl-N-((tetrahydrofuran-2-yl)methyl)benzenesulfonamide LCMS: Rt 1.15 mins; MS m/z 446.3 [M+H]+; Method 2minLowpHv03.

Example 45.7

3-(5-Amino-6-(2-methylthiazol-5-yl)pyrazin-2-yl)-4-methyl-N-(tetrahydrofuran-3-yl)benzenesulfonamide

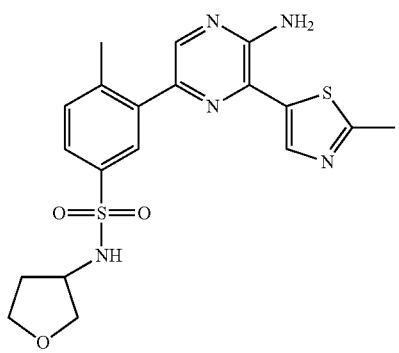

LCMS: Rt 1.09 mins; MS m/z 432.2 [M+H]+; Method 2minLowpHv03.

Examples 45.7a and 45.7b (R)-3-(5-Amino-6-(2-methylthiazol-5-yl)pyrazin-2-yl)-4-methyl-N-(tetrahydrofuran-3-yl)benzenesulfonamide and (S)-3-(5-Amino-6-(2-methylthiazol-5-yl)pyrazin-2-yl)-4-methyl-N-(tetrahydrofuran-3-yl)benzenesulfonamide

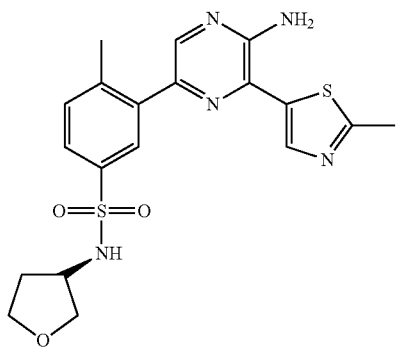 [SMILES: Cc1ncc(-c2nc(-c3cc(S(=O)(=O)NC4CCOC4)ccc3C)cnc2N)s1]

and

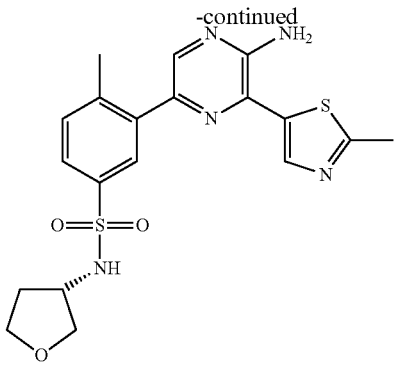

In this case, the racemic mixture was separated by chiral separation to afford the individual isomers:

Column: Chiralpak IC, 250×10 mm, 5 um @ 35 deg C.,

Mobile phase: 50% Methanol+0.1% v/v DEA/50% $CO_2$,

Flow: 10 ml/min,

Detection: UV @ 220 nm,

Instrument: Berger Minigram SFC1

Example 45.7a

First Eluting Compound

SFC Retention Time=11.74 mins. (R)-3-(5-Amino-6-(2-methylthiazol-5-yl)pyrazin-2-yl)-4-methyl-N-(tetrahydrofuran-3-yl)benzenesulfonamide or (S)-3-(5-Amino-6-(2-methylthiazol-5-yl)pyrazin-2-yl)-4-methyl-N-(tetrahydrofuran-3-yl)benzenesulfonamide LCMS: Rt 1.06 mins; MS m/z 432.3 [M+H]+; Method 2minLowpHv03.

Example 45.7b

Second Eluting Compound

SFC Retention Time=13.42 mins. (R)-3-(5-Amino-6-(2-methylthiazol-5-yl)pyrazin-2-yl)-4-methyl-N-(tetrahydrofuran-3-yl)benzenesulfonamide or (S)-3-(5-Amino-6-(2-methylthiazol-5-yl)pyrazin-2-yl)-4-methyl-N-(tetrahydrofuran-3-yl)benzenesulfonamide LCMS: Rt 1.06 mins; MS m/z 432.2 [M+H]+; Method 2minLowpHv03.

Example 45.8

(1-((3-(5-Amino-6-(2-methylthiazol-5-yl)pyrazin-2-yl)-4-methylphenyl)sulfonyl)azetidin-3-yl)methanol

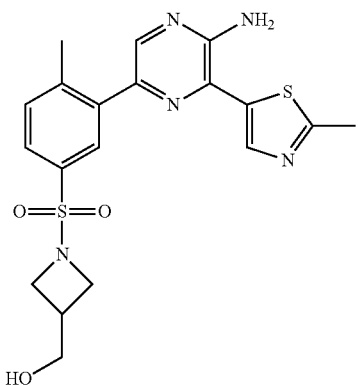 [SMILES: Cc1ncc(-c2nc(-c3cc(S(=O)(=O)N4CC(CO)C4)ccc3C)cnc2N)s1]

LCMS: Rt 1.00 mins; MS m/z 432.1 [M+H]+; Method 2minLowpHv03.

Example 45.9

3-(5-Amino-6-(2-methylthiazol-5-yl)pyrazin-2-yl)-N-((4-(hydroxymethyl)tetrahydro-2H-pyran-4-yl)methyl)-4-methylbenzenesulfonamide

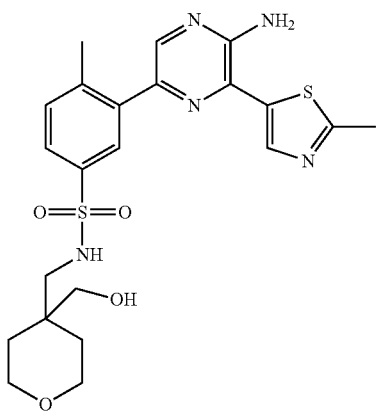 [SMILES: Cc1ncc(-c2nc(-c3cc(S(=O)(=O)NCC4(CO)CCOCC4)ccc3C)cnc2N)s1]

LCMS: Rt 1.05 mins; MS m/z 490.3 [M+H]+; Method 2minLowpHv03.

Example 45.10

3-(5-Amino-6-(2-methylthiazol-5-yl)pyrazin-2-yl)-N-((4-hydroxytetrahydro-2H-pyran-4-yl)methyl)-4-methylbenzenesulfonamide

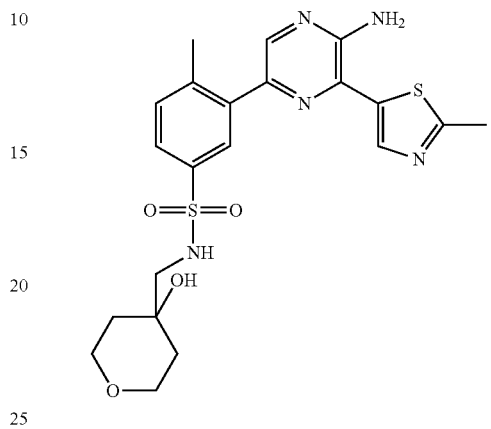

LCMS: Rt 1.03 mins; MS m/z 476.3 [M+H]+; Method 2minLowpHv03.

Example 45.11

3-(5-Amino-6-(2-methylthiazol-5-yl)pyrazin-2-yl)-N-((3-hydroxyoxetan-3-yl)methyl)-4-methylbenzenesulfonamide

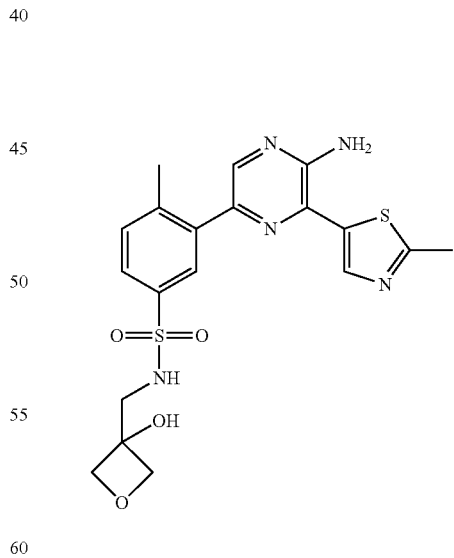

LCMS: Rt 1.00 mins; MS m/z 448.2 [M+H]+; Method 2minLowpHv03.

Example 45.12

3-(5-Amino-6-(2-methylthiazol-5-yl)pyrazin-2-yl)-4-methyl-N-((4-methylmorpholin-3-yl)methyl)benzenesulfonamide

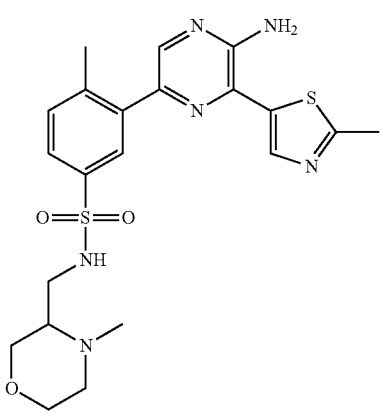 [SMILES: Cc1ncc(-c2nc(-c3cc(S(=O)(=O)NCC4COCCN4C)ccc3C)cnc2N)s1]

LCMS: Rt 0.71 mins; MS m/z 475.2 [M+H]+; Method 2minLowpHv03.

Example 46

3-(5-Amino-6-(1,5-dimethyl-1H-pyrazol-4-yl)pyrazin-2-yl)-N-(2-hydroxy-2-methylpropyl)-4-methylbenzenesulfonamide

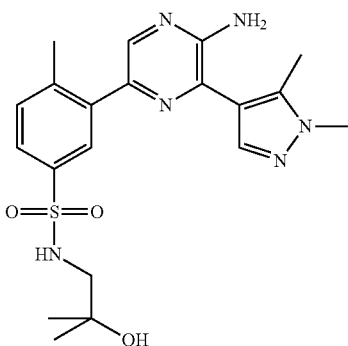 [SMILES: Cc1ccc(S(=O)(=O)NCC(C)(C)O)cc1-c1cnc(N)c(-c2cnn(C)c2C)n1]

A mixture of 3-(5-amino-6-chloro-pyrazin-2-yl)-N-(2-hydroxy-2-methyl-propyl)-4-methyl-benzenesulfonamide (Intermediate D2) (60 mg, 0.162 mmol), 1,5-dimethyl-4-(4,4,5,5-tetramethyl-1,3,2-dioxaborolan-2-yl)-1H-pyrazole (40 mg, 0.180 mmol), bis(triphenylphosphine) palladium dichloride (5 mg, 7.12 µmol) in DME (0.75 ml) and 2M aqueous sodium carbonate (0.25 mL, 0.500 mmol) was heated in the microwave to 130° C. for 1 hour. The resulting mixture was diluted with 10% methanol in DCM and filtered through 1 g Celite® washing with further 10% methanol in DCM. The crude product was purified by flash column chromatography (12 g silica, radient 0-20% methanol in TBME). The product fractions were evaporated under reduced pressure and dried in a vacuum oven to give the title compound as a brown-orange solid;

$^1$H NMR (400 MHz, DMSO-d6) δ 8.08 (1H, s); 7.86 (1H, s); 7.72 (1H, s); 7.67 (1H, dd); 7.49 (1H, d); 7.44 (1H, br m); 6.23 (2H, s); 4.38 (1H, s); 3.80 (3H, s); 2.61 (2H, d); 2.46 (3H, s); 2.36 (3H, s); 1.05 (6H, s)

LCMS: Rt 0.89 min; MS m/z 431.2 [M+H]+; Method: 2minLowpHv01

Example 46.1

3-(5-Amino-6-(2,4-dimethylthiazol-5-yl)pyrazin-2-yl)-N-(2-hydroxy-2-methylpropyl)-4-methylbenzenesulfonamide

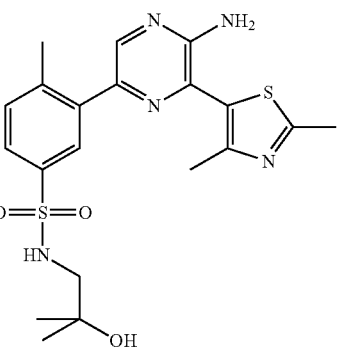

The title compound was prepared by an analogous method to that used for the preparation of Example 46 starting from 2,4-dimethyl-5-(4,4,5,5-tetramethyl-1,3,2-dioxaborolan-2-yl)thiazole;

LCMS: Rt 0.91 min; MS m/z 448.0 [M+H]+; 446.2 [M−H]−; Method: 2minLowpHv01

Example 46.2

3-(5-Amino-6-(1-methyl-1H-pyrazol-4-yl)pyrazin-2-yl)-N-(2-hydroxy-2-methylpropyl)-4-methylbenzenesulfonamide

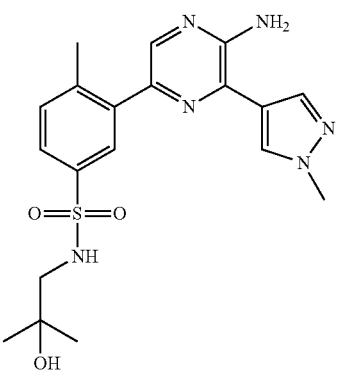 [SMILES: Cc1ccc(S(=O)(=O)NCC(C)(C)O)cc1-c1cnc(N)c(-c2cnn(C)c2)n1]

The title compound was prepared by an analogous method to that used for the preparation of Example 46 starting from 1-methyl-4-(4,4,5,5-tetramethyl-1,3,2-dioxaborolan-2-yl)-1H-pyrazole.

LCMS: Rt 0.87 min; MS m/z 417.3 [M+H]+; Method: 2minLowpHv01

$^1$H NMR (400 MHz, MeOD-d4) δ 8.26 (1H, s); 8.07 (1H, s); 8.00 (1H, s); 7.93 (1H, d, J 2 Hz); 7.80 (1H, dd, J~8 and 2 Hz); 7.53 (1H, d, J~8 Hz); 4.01 (3H, s); 2.81 (2H, s); 2.51 (3H, s); 1.19 (6H, s)

Example 47

3-(5-Amino-6-(3,4-di methyl-1H-pyrazol-1-yl)pyrazin-2-yl)-N-(2-hydroxy-2-methyl propyl)-4-methyl benzenesulfonamide

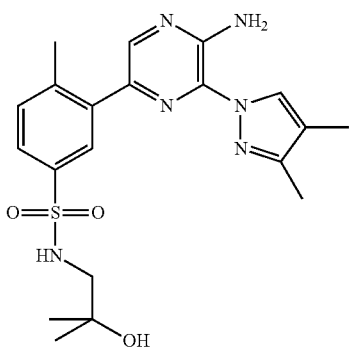 [SMILES: Cc1ccc(S(=O)(=O)NCC(C)(C)O)cc1-c1cnc(N)c(-n2cc(C)c(C)n2)n1]

The title compound was prepared from 3,4-dimethyl-1H-pyrazole and 3-(5-amino-6-chloro-pyrazin-2-yl)-N-(2-hydroxy-2-methyl-propyl)-4-methyl-benzenesulfonamide (Intermediate D2) by an analogous method to that used for the preparation of Example 15.

LCMS: Rt 1.16 min; MS m/z 431.2 [M+H]+; Method: 2minLowpHv01

Example 48

3-(5-Amino-6-(3,5-di methyl-1H-pyrazol-1-yl)pyrazin-2-yl)-N-(2-hydroxy-2-methyl propyl)-4-methyl benzenesulfonamide

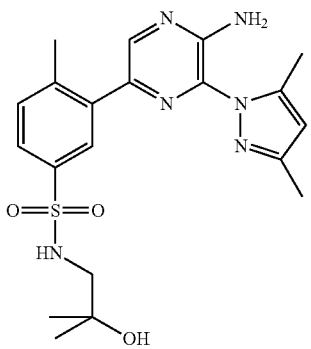 [SMILES: Cc1cc(C)n(-c2nc(-c3cc(S(=O)(=O)NCC(C)(C)O)ccc3C)cnc2N)n1]

The title compound was prepared from 3,5-dimethyl-1H-pyrazole and 3-(5-amino-6-chloro-pyrazin-2-yl)-N-(2-hydroxy-2-methyl-propyl)-4-methyl-benzenesulfonamide (Intermediate D2) by an analogous method to that used for the preparation of Example 15.

$^1$H NMR (400 MHz, MeOD-d4) δ 8.19 (1H, s); 7.94 (1H, d, J~2 Hz); 7.78 (1H, dd, J~8 and 2 Hz); 7.52 (1H, d, J~8 Hz); 6.15 (1H, s); 2.81 (2H, s); 2.51 (3H, s); 2.46 (3H, s); 2.31 (3H, s); 1.18 (6H, s)

LCMS: Rt 1.06 min; MS m/z 431.3 [M+H]+; Method: 2minLowpHv01

Example 49

3-(5-Amino-6-(3,5-dimethyl-1H-1,2,4-triazol-1-yl)pyrazin-2-yl)-N-(2-hydroxy-2-methylpropyl)-4-methylbenzenesulfonamide

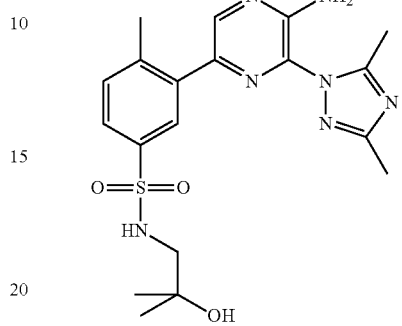

The title compound was prepared from 3,5-dimethyl-1H-1,2,4-triazole and 3-(5-amino-6-chloro-pyrazin-2-yl)-N-(2-hydroxy-2-methyl-propyl)-4-methyl-benzenesulfonamide (Intermediate D2) by an analogous method to that used for the preparation of Example 15.

LCMS: Rt 0.88 min; m/z 430.2 [M−H]−; Method: 2minLowpHv01.

$^1$H NMR (400 MHz, DMSO-d6) δ 8.38 (1H, s); 7.86 (1H, d, J~2 Hz); 7.71 (1H, dd, J~8 and 2 Hz); 7.53 (1H, d, J~8 Hz); 7.47 (1H, t, J~6.5 Hz); 6.98 (2H, br); 2.62 (2H, d, J 6.5 Hz); 2.47 (3H, s); 2.33 (3H, s); 1.05 (6H, s). OH not seen (under water peak/exchanged?) and one methyl group not seen (this is often hidden by solvent peak in related compounds) Non-identical methyl groups on triazole suggest product as drawn rather than attached through the N between the methyl groups.

Example 50

3-(5-Amino-6-(2,4-dimethyl-1H-imidazol-1-yl)pyrazin-2-yl)-N-(2-hydroxy-2-methylpropyl)-4-methylbenzenesulfonamide

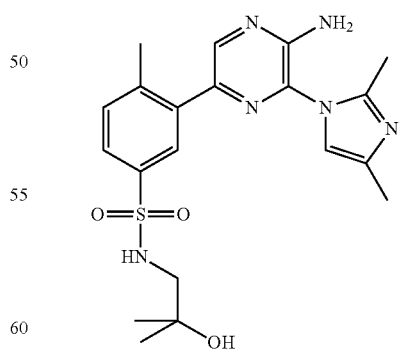

The title compound was prepared from 2,4-dimethyl-1H-imidazole and 3-(5-amino-6-chloro-pyrazin-2-yl)-N-(2-hydroxy-2-methyl-propyl)-4-methyl-benzenesulfonamide (Intermediate D2) by an analogous method to that used for the preparation of Example 15.

LCMS: Rt 0.64 min; MS m/z 431.3 [M+H]+; Method: 2minLowpHv01

Example 51

3-(5-Amino-6-(1-methyl-1H-pyrazol-4-yl)pyrazin-2-yl)-4-methyl-N-(4,4,4-trifluoro-3-hydroxybutyl)benzenesulfonamide

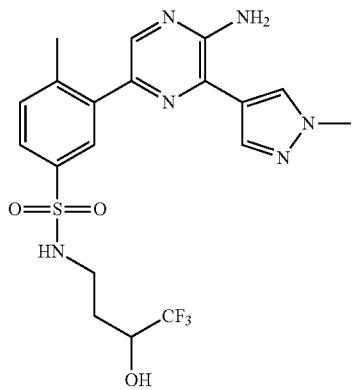 [SMILES: Cc1ccc(S(=O)(=O)NCCC(O)C(F)(F)F)cc1-c1cnc(N)c(-c2cnn(C)c2)n1]

A mixture of 1-methyl-4-(4,4,5,5-tetramethyl-1,3,2-dioxaborolan-2-yl)-1H-pyrazole (45 mg, 0.216 mmol), bis(triphenylphosphine)palladium dichloride (14 mg, 0.020 mmol), 3-(5-amino-6-chloropyrazin-2-yl)-4-methyl-N-(4,4,4-trifluoro-3-hydroxybutyl)benzenesulfonamide (Intermediate D4) (85 mg, 0.200 mmol), 2M sodium carbonate (0.300 ml, 0.600 mmol), 1,2-dimethoxyethane (1 ml) was heated in the microwave to 120° C. for 1 hour, then partitioned between DCM and water and separated using a phase separator column. The organic phase was evaporated under reduced pressure to give a brown gum, which was redissolved in ethyl acetate and bound to silica, then purified by flash column chromatography (2 g silica, 0-10% methanol in TBME). Appropriate fractions were combined and evaporated to give an orange gum. This was crystallised from ethyl acetate/diethyl ether to give a reddish solid; $^1$H NMR (400 MHz, MeOD-d4) δ 8.21 (1H, s); 8.05 (1H, s); 8.03 (1H, s); 7.90 (1H, d); 7.78 (1H, dd); 7.53 (1H, d); 4.02 (1H, br m) overlapping with 4.00 (3H, s); 3.07 (2H, m); 2.51 (3H, s); 1.83 (1H, m); 1.68 (1H, m).

LC-MS: Rt 0.83 min; MS m/z 471.4 [M+H]+; Method: 2minLowpH

Example 52a (R)-3-(5-Amino-6-(1,3-dimethyl-1H-pyrazol-4-yl)pyrazin-2-yl)-4-methyl-N-(4,4,4-trifluoro-3-hydroxybutyl)benzenesulfonamide or (S)-3-(5-Amino-6-(1,3-dimethyl-1H-pyrazol-4-yl)pyrazin-2-yl)-4-methyl-N-(4,4,4-trifluoro-3-hydroxybutyl)benzenesulfonamide

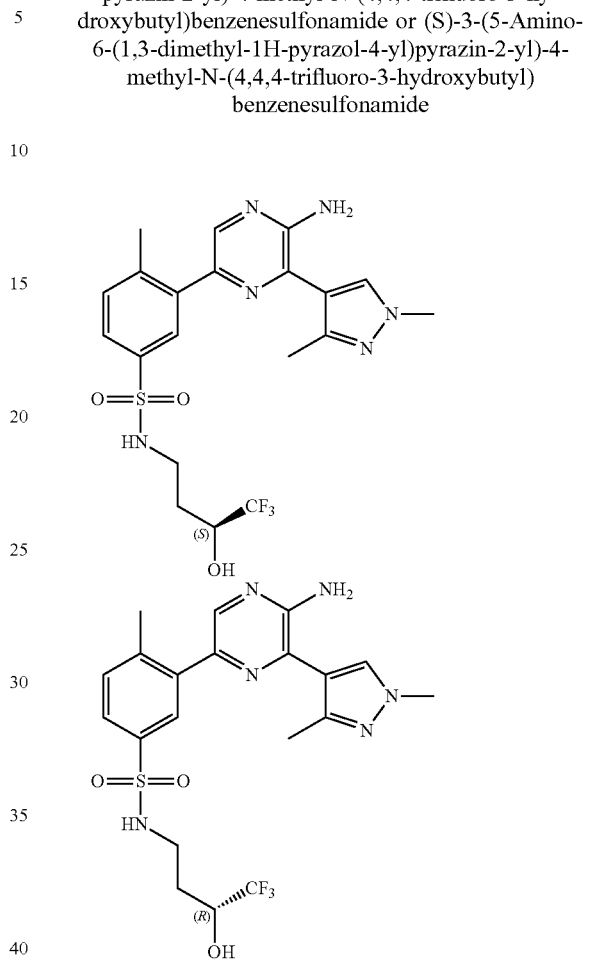

A mixture of 3-(5-amino-6-chloropyrazin-2-yl)-4-methyl-N-(4,4,4-trifluoro-3-hydroxybutyl)benzenesulfonamide (single enantiomer of unknown configuration, Intermediate D4a) (45 mg, 0.106 mmol), 1,3-dimethyl-4-(4,4,5,5-tetramethyl-1,3,2-dioxaborolan-2-yl)-1H-pyrazole (25 mg, 0.113 mmol) and bis(triphenylphosphine)palladium dichloride (4 mg, 5.70 μmol) in 1,2-dimethoxyethane (0.5 ml) and 2M sodium carbonate (150 μL, 0.300 mmol) was heated in the microwave to 130° C. for 1 hour. The resulting mixture was diluted with 10% methanol in DCM and filtered through 1 g Celite® washing with further 10% methanol in DCM, then purified by flash column chromatography (12 g silica, 0-20% methanol in TBME) to give 35 mg of orange glassy solid;

$^1$H NMR (400 MHz, DMSO-d6) δ 8.08 (1H, s); 8.06 (1H, s); 7.85 (1H, d, J-2 Hz); 7.67 (1H, dd, ~2 and 8 Hz) overlapping with 7.72-7.59 (approx, 1H, v broad); 7.52 (1H, d, J-8 Hz); 6.28 (2H, s); 6.17 (1H, v broad); 3.99 (1H, broad m); 3.82 (3H, s); 2.90 (2H, m); 2.47 (3H, s); 2.29 (3H, s); 1.69 (1H, broad m); 1.57 (1H, broad m).

LCMS: Rt 0.98 min; MS m/z 485.5 [M+H]+; Method: 2minLowpHv01

Chiral SFC: Rt 5.51 min; 100% purity by DAD;

Method: Chiralpak AD-3, 150×2.1 mm 3 urn @ 400, 0.7 ml/min, UV @ 220 nm and 254 nm A=CO2, B=Methanol+

0.1% v/v DEA; Gradient: 0-1.5 min 5% B; 1.5-6.0 min 5-50% B; 6.0-9.0 min 50% B

Example 52b (R)-3-(5-Amino-6-(1,3-dimethyl-1H-pyrazol-4-yl)pyrazin-2-yl)-4-methyl-N-(4,4,4-trifluoro-3-hydroxybutyl)benzenesulfonamide or (S)-3-(5-Amino-6-(1,3-dimethyl-1H-pyrazol-4-yl)pyrazin-2-yl)-4-methyl-N-(4,4,4-trifluoro-3-hydroxybutyl)benzenesulfonamide

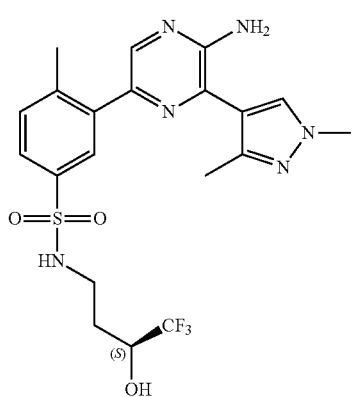

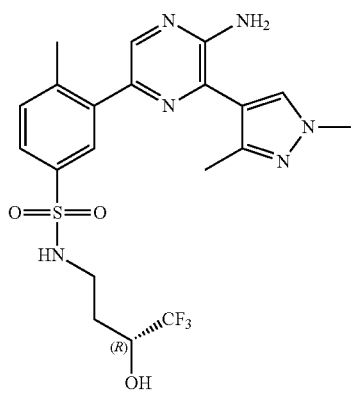

The title compound was prepared analogously to Example 52a from Intermediate D4b;

$^1$H NMR (400 MHz, DMSO-d6) δ 8.08 (1H, s); 8.06 (1H, s); 7.85 (1H, d, J-2 Hz); 7.69-7.60 (2H, m); 7.52 (1H, d, J-8 Hz); 6.28 (2H, s); 6.16 (1H, d, J-6.5 Hz); 3.98 (1H, m); 3.81 (3H, s); 2.89 (2H, m); 2.47 (3H, s); 2.29 (3H, s); 1.73-1.51 (2H, m).

LCMS: Rt 0.93 min; m/z 485.2 [M+H]+; Method: 2minLowpHv01

Chiral SFC: Rt 5.15 min; 97.4% purity by DAD (hence ~95% ee);

Method: Chiralpak AD-3, 150×2.1 mm 3 um @ 400, 0.7 ml/min, UV @ 220 nm and 254 nm A=CO2, B=Methanol+ 0.1% v/v DEA; Gradient: 0-1.5 min 5% B; 1.5-6.0 min 5-50% B; 6.0-9.0 min 50% B.

Example 53

5-(5-Amino-6-(1H-1,2,4-triazol-1-yl)pyrazin-2-yl)-N-(2-hydroxy-2-methylpropyl)-6-methylpyridine-3-sulfonamide

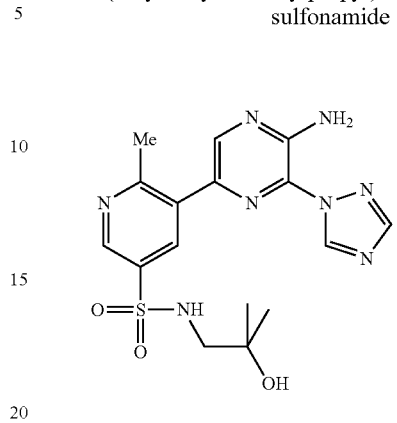

Step 1: 5-Bromo-6-chloro-N-(2-hydroxy-2-methylpropyl)pyridine-3-sulfonamide

To a solution of 1-amino-2-methylpropan-2-ol (0.306 g, 3.44 mmol) and DIPEA (0.62 mL, 3.55 mmol) in THF (6 mL) cooled in an ice bath was added dropwise a solution of 5-bromo-6-chloropyridine-3-sulfonyl chloride (1 g, 3.44 mmol) in THF (6 mL). The resulting mixture was stirred at room temperature overnight, then water (30 mL) was added, the mixture adjusted to pH 4-5 with 1M HCl/1M sodium bicarbonate as necessary and extracted with ethyl acetate (3×25 mL). The combined organic extracts were washed with brine (25 mL), dried over magnesium sulfate, filtered and evaporated under reduced pressure to give a pale yellow solid which was dried in the vacuum oven to give the title compound;

LCMS: Rt 1.03 min; MS m/z 345.0 and 343.0 (Br isotopes) [M+H]+; Method: 2minLowpHv03

Step 2: 5-Bromo-N-(2-hydroxy-2-methylpropyl)-6-iodopyridine-3-sulfonamide

To a solution of 5-bromo-6-chloro-N-(2-hydroxy-2-methylpropyl)pyridine-3-sulfonamide (from step 1) (500 mg, 1.455 mmol) in acetonitrile (40 mL) was added trimethylsilylchloride (375 µL, 2.93 mmol). After 15 mins, sodium iodide (1 g, 6.67 mmol) was added in two portions. The resulting orange cloudy mixture was stirred at room temperature for two days, then poured into ice water (~50 g). Sodium hydroxide (1M solution, 5 mL), was added, the pH adjusted to pH7 using 1M HCl (reached pH 3) then 1M sodium bicarbonate, and the mixture extracted with dichloromethane. The organic phase was washed with water and brine, dried by passing through a hydrophobic membrane and evaporated under reduced pressure. Trituration with ethyl acetate/hexane gave an off-white solid;

LCMS: Rt 1.08 min; MS m/z 435.1 and 437.2 [M+H]+; Method: 2minLowpHv03

Step 3: 5-Bromo-N-(2-hydroxy-2-methylpropyl)-6-methylpyridine-3-sulfonamide

To a mixture of methylboronic acid (9 mg, 0.150 mmol), 5-bromo-N-(2-hydroxy-2-methylpropyl)-6-iodopyridine-3-sulfonamide (from Step 2) (60 mg, 0.138 mmol), bis(triphenylphosphine) palladium dichloride (5 mg, 7.12 µmol) in 1,4-dioxane (1.3 mL) was added sodium carbonate 2M (44 mg, 0.415 mmol) and the resulting mixture heated under a nitrogen atmosphere at 50° C. for 90 minutes, at 80° C. for 1 hour, then at 100° C. for 1 hour. Additional methylboronic acid (9 mg) was added and the mixture stirred at 100° C. overnight. Further methylboronic acid (9 mg) was added, and the resulting mixture stirred for a further 5.5 hours at 100° C., with an additional portion of methylboronic acid (20 mg) added after 3 hours. After cooling to room temperature, the reaction mixture was diluted with methanol and passed through a Isolute® Si-TMT column (1 g) washing with further methanol and DCM. Combined organics were evaporated under reduced pressure, bound to silica gel and purified by flash column chromatography (4 g silica, 0-100% ethyl acetate in isohexane) to give the title compound as a yellow gum;

LCMS: Rt 0.94 min; MSm/z 323.4 [M+H]+; Method: 2minLowpHv03

Step 4: 5-(5-Amino-6-(1H-1,2,4-triazol-1-yl) pyrazin-2-yl)-N-(2-hydroxy-2-methylpropyl)-6-methylpyridine-3-sulfonamide A mixture of 5-bromo-N-(2-hydroxy-2-methylpropyl)-6-methylpyridine-3-sulfonamide (from step 3) (30 mg, 0.093 mmol), 5-Amino-6-(1H-1,2,4-triazol-1-yl)pyrazin-2-ylboronic acid (see Step 1 from the preparation of Example 121) (20 mg, 0.097 mmol), [1,1'-bis(di-tert-butylphosphino)ferrocene] dichloropalladium(11) (3 mg, 4.60 μmol) and potassium phosphate (40 mg, 0.188 mmol) in 1,4-dioxane (1 mL) and Water (0.25 mL) was heated to reflux for 30 minutes then cooled to room temperature, diluted with methanol: DCM (~1:2) and filtered through a 500 mg Isolute® Si-TMT column. The mixture was evaporated under reduced pressure and purified by flash column chromatography (4 g silica, 0-10% 7M methanolic ammonia in DCM). Product eluted at ~7%, and was collected and evaporated under reduced pressure to give a pale beige solid;

LCMS: Rt 0.83 min; MS m/z 405.3 [M+H]+; Method: 2minLowpHv03

¹H NMR (400 MHz, DMSO-d6) δ 9.39 (1H, s), 8.83 (1H, s), 8.49 (1H, s), 8.44 (1H, s), 8.29 (1H, s), 7.73 (1H, br. s.), 7.50 (2H, br. s.), 4.45 (1H, br. s.), 2.74 (3H, s), 2.69 (2H, s), 1.07 (6H, s)

Example 54

3-(5-Amino-6-(1-methyl-1H-pyrazol-4-yl)pyrazin-2-yl)-N-(4,4-difluorocyclohexyl)-4-methylbenzenesulfonamide

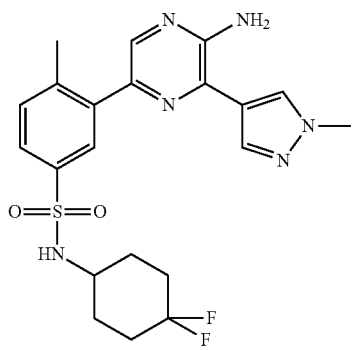 [SMILES: Cc1ccc(S(=O)(=O)NC2CCC(F)(F)CC2)cc1-c1cnc(N)c(-c2cnn(C)c2)n1]

The title compound was prepared by an analogous method to that used for the preparation of Example 11, using 1-methyl-4-(4,4,5,5-tetramethyl-1,3,2-dioxaborolan-2-yl)-1H-pyrazole and 3-(5-amino-6-chloropyrazin-2-yl)-N-(4,4-difluorocyclohexyl)-4-methylbenzenesulfonamide (prepared analogously to Intermediate D1);

LC-MS: Rt 4.18 mins; MS m/z 463.3 [M+H]+; Method 10minLowpH

Example 55

3-(5-Amino-6-(2-methylthiazol-5-yl)pyrazin-2-yl)-N-(4,4-difluorocyclohexyl)-4-methylbenzenesulfonamide

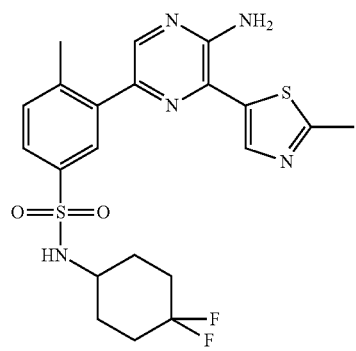 [SMILES: Cc1ncc(-c2nc(-c3cc(S(=O)(=O)NC4CCC(F)(F)CC4)ccc3C)cnc2N)s1]

The title compound was prepared by an analogous method to that used for the preparation of Example 11, using 2-methyl-5-(4,4,5,5-tetramethyl-1,3,2-dioxaborolan-2-yl) thiazole and 3-(5-amino-6-chloropyrazin-2-yl)-N-(4,4-difluorocyclohexyl)-4-methylbenzenesulfonamide (prepared analogously to Intermediate D1);

LC-MS: Rt 4.65 mins; MS m/z 480.2 [M+H]+; Method 10minLowpH

Example 56

Trans-3-(5-Amino-6-(4-methyl-1H-imidazol-1-yl) pyrazin-2-yl)-N-(-4-hydroxycyclohexyl)-4-methylbenzenesulfonamide

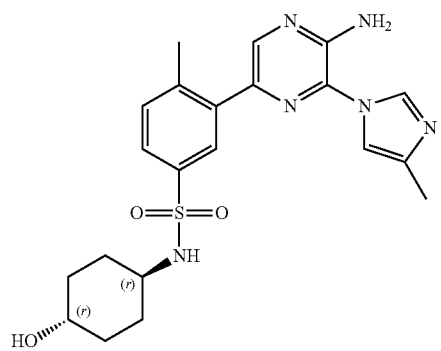 [SMILES: Cc1cn(-c2nc(-c3cc(S(=O)(=O)N[C@H]4CC[C@H](O)CC4)ccc3C)cnc2N)cn1]

The title compound was prepared analogously to Example 15 using 4-methyl-1H-imidazole.

LCMS: Rt 0.75 mins; MS m/z 443.3 [M+H]+; Method: 2minLC_v003

¹H NMR (400 MHz, DMSO-d6) δ 8.29 (1H, s), 8.03 (1H, s), 8.87 (1H, d), 7.71 (1H, dd), 7.60 (1H, d), 7.51 (1H, d), 7.34 (1H, s), 6.71 (2H, s), 4.46 (1H, d), 3.29 (1H, m), 2.90 (1H, m), 2.47 (3H, s), 2.20 (3H, s), 1.70 (2H, m), 1.61 (2H, m), 1.23-1.00 (4H, m).

Example 57

3-(5-Amino-6-(4-methyl-1H-imidazol-1-yl)pyrazin-2-yl)-N-(3-hydroxypropyl)-4-methylbenzenesulfonamide

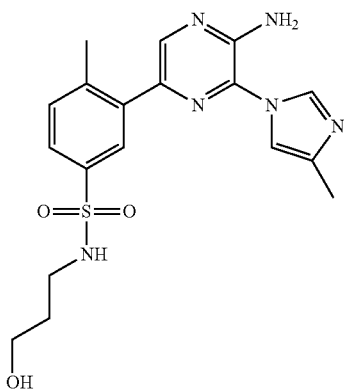 [SMILES: Cc1cn(-c2nc(-c3cc(S(=O)(=O)NCCCO)ccc3C)cnc2N)cn1]

Prepared by analogy to Example 15 using 4-methyl-1H-imidazole and 3-(5-amino-6-chloropyrazin-2-yl)-N-(3-hydroxypropyl)-4-methylbenzenesulfonamide (prepared by analogy to Intermediate D1, using Intermediate B1).
LCMS: Rt 0.54 mins; MS m/z 403.2 [M+H]+; Method: 2minLC_v003
¹H NMR (400 MHz, DMSO-d6) δ 8.29 (1H, s), 8.02 (1H, s), 7.82 (1H, s), 7.68 (1H, dd), 7.53 (1H, s), 7.31 (1H, s), 7.34 (1H, s), 6.70 (2H, s), 4.40 (1H, s), 3.35 (2H, m), 2.78 (2H, t), 2.46 (3H, s), 2.19 (3H, s), 1.52 (2H, m).

Example 58

Trans-3-(5-Amino-6-(1-methyl-1H-pyrazol-4-yl)pyrazin-2-yl)-N-(-4-hydroxycyclohexyl)-4-methyl-benzenesulfonamide

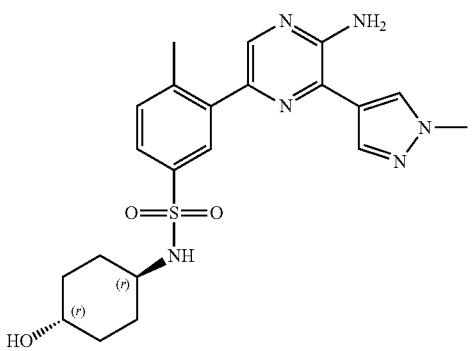 [SMILES: Cc1ccc(S(=O)(=O)N[C@H]2CC[C@H](O)CC2)cc1-c1cnc(N)c(-c2cnn(C)c2)n1]

Prepared using analogous conditions to those of Example 22, using 1-methylpyrazole-4-boronic acid pinacol ester.
LCMS: Rt 0.81 mins; MS m/z 443.0 [M+H]+; Method: 2minLC_v003

¹H NMR (400 MHz, DMSO-d6) δ 8.32 (1H, s), 8.08 (1H, s), 8.00 (1H, s), 7.87 (1H, d), 7.69 (1H, dd), 7.60 (1H, d), 7.50 (1H, d), 6.32 (2H, s), 4.47 (1H, d), 3.92 (3H, s), 3.29 (1H, m), 2.91 (1H, m), 2.48 (3H, s), 1.71 (2H, m), 1.63 (2H, m), 1.24-1.01 (4H, m).

Example 59

Trans-3-(5-Amino-6-(pyrimidin-5-yl)pyrazin-2-yl)-N-(-4-hydroxycyclohexyl)-4-methylbenzenesulfonamide

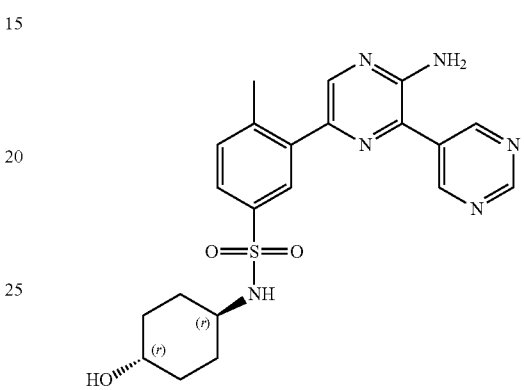

Prepared using analogous conditions to those of Example 22, using pyrimidin-5-ylboronic acid.
LCMS: Rt 0.80 mins; MS m/z 441.3 [M+H]+; Method: 2minLC_v003

Example 60

Trans-3-(5-Amino-6-(2-fluoropyridin-4-yl)pyrazin-2-yl)-N-(-4-hydroxycyclohexyl)-4-methylbenzenesulfonamide

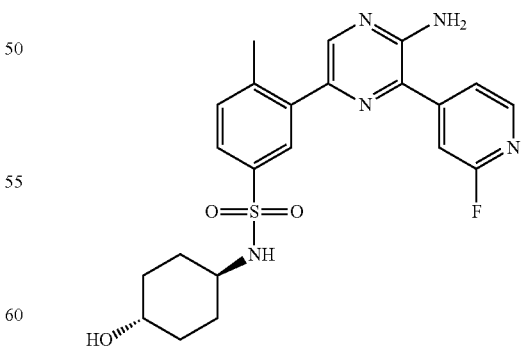

Prepared using analogous conditions to those of Example 22 using 2-fluoropyridine-4-boronic acid pinacol ester.
LCMS: Rt 0.90 mins; MS m/z 458.3 [M+H]+; Method: 2minLC_v003

Example 61

3-(5-Amino-6-(1H-imidazol-1-yl)pyrazin-2-yl)-N-(3-hydroxy-3-methylbutyl)-4-methylbenzenesulfonamide

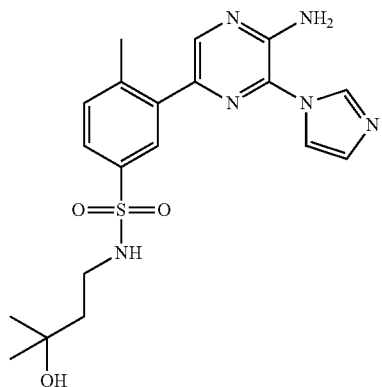 [SMILES: Cc1ccc(S(=O)(=O)NCCC(C)(C)O)cc1-c1cnc(N)c(-n2ccnc2)n1]

Prepared using analogous conditions to those of Example 26, using 1H-imidazole.

LCMS: Rt 0.62 mins; MS m/z 417.4 [M+H]+; Method: 2minLC_v003

Example 62

3-(5-Amino-6-(1H-pyrazol-1-yl)pyrazin-2-yl)-N-(3-hydroxy-3-methylbutyl)-4-methylbenzenesulfonamide

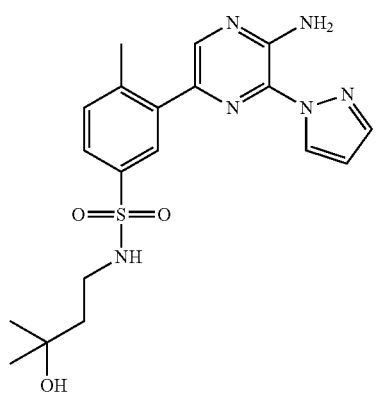 [SMILES: Cc1ccc(S(=O)(=O)NCCC(C)(C)O)cc1-c1cnc(N)c(-n2cccn2)n1]

Prepared using analogous conditions to those of Example 26, using 1H-pyrazole.

LCMS: Rt 0.97 mins; MS m/z 417.2 [M+H]+; Method: 2minLowpH

Example 63

3-(5-Amino-6-(4-methyl-1H-imidazol-1-yl)pyrazin-2-yl)-N-(3-hydroxy-3-methylbutyl)-4-methylbenzenesulfonamide

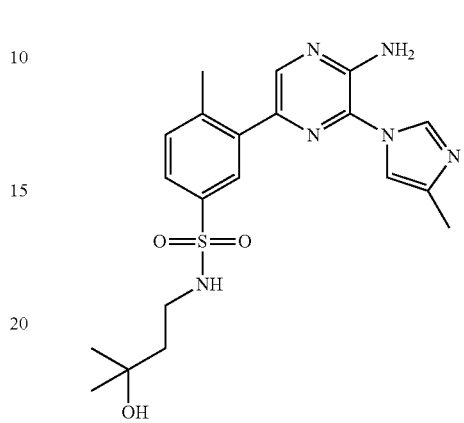

Prepared using analogous conditions to those of Example 26, using 4-methyl-1H-imidazole.

LCMS: Rt 0.61 mins; MS m/z 431.3 [M+H]+; Method: 2minLC_v003

Example 64

3-(5-Amino-6-(1H-1,2,4-triazol-1-yl)pyrazin-2-yl)-N-(3-hydroxy-3-methylbutyl)-4-methylbenzenesulfonamide

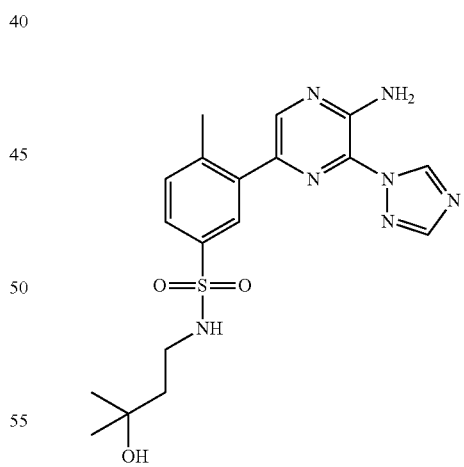

Prepared using analogous conditions to those of Example 26, using 1H-1,2,4-triazole.

LCMS: Rt 0.83 mins; MS m/z 418.3 [M+H]+; Method: 2minLC_v003

$^1$H NMR (400 MHz, DMSO-d6) δ 9.33 (1H, s), 8.42 (1H, s), 8.40 (1H, s), 7.89 (1H, d), 7.72 (1H, dd), 7.56 (1H, d), 7.45 (1H, t), 7.38 (2H, d), 4.27 (1H, s), 2.83 (2H, m), 2.51 (3H, s under DMSO), 1.51 (2H, m), 1.02 (6H, s).

Example 65

3-(5-Amino-6-(3-methyl-1H-1,2,4-triazol-1-yl)pyrazin-2-yl)-N-(3-hydroxy-3-methyl butyl)-4-methylbenzenesulfonamide

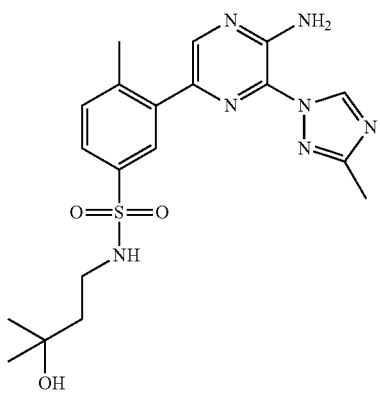 [SMILES: Cc1ncn(-c2nc(-c3cc(S(=O)(=O)NCCC(C)(C)O)ccc3C)cnc2N)n1]

Prepared using analogous conditions to those of Example 26, using 3-methyl-1H-1,2,4-triazole.

LCMS: Rt 0.87 mins; MS m/z 432.3 [M+H]+; Method: 2minLC_v003.

Example 66

3-(5-Amino-6-(3-isopropyl-1H-1,2,4-triazol-1-yl)pyrazin-2-yl)-N-(3-hydroxy-3-methylbutyl)-4-methylbenzenesulfonamide

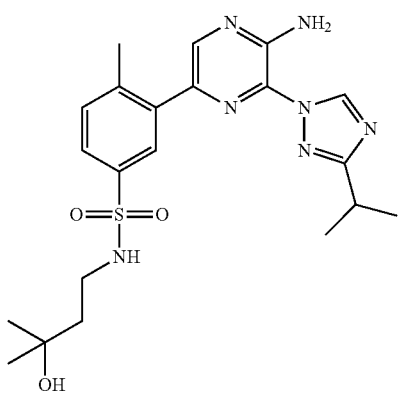 [SMILES: Cc1ccc(S(=O)(=O)NCCC(C)(C)O)cc1-c1cnc(N)c(-n2cnc(C(C)C)n2)n1]

Prepared using analogous conditions to those of Example 26, using 3-isopropyl-1H-1,2,4-triazole.

LCMS: Rt 0.99 mins; MS m/z 460.3 [M+H]+; Method: 2minLC_v003

Example 67

3-(5-Amino-6-(1H-1,2,4-triazol-1-yl)pyrazin-2-yl)-N-(6-hydroxyspiro[3.3]heptan-2-yl)-4-methylbenzenesulfonamide

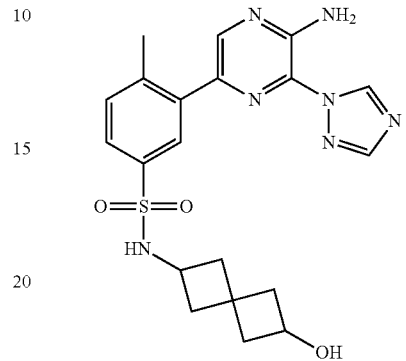

Prepared using analogous conditions to those of Example 29, using 6-aminospiro[3.3]heptan-2-ol.HCl, which was prepared by deprotection of commercially available tert-butyl (6-hydroxyspiro[3.3]heptan-2-yl)carbamate using 1.25M HCl in MeOH.

LCMS: Rt 0.90 mins; MS m/z 442.3 [M+H]+; Method: 2minLowpHv01

$^1$H NMR (400 MHz, DMSO-d6) δ 9.33 (1H, s), 8.43 (1H, s), 8.40 (1H, s), 7.88 (2H, m), 7.69 (1H, dd), 7.53 (1H, d), 7.38 (2H, d), 4.82 (1H, d), 3.85 (1H, m), 3.53 (1H, m), 2.51 (3H, s, under DMSO), 2.21 (1H, m), 2.03 (2H, m), 1.91 (1H, m), 1.76 (2H, m), 1.68 (2H, m).

Example 68

3-(5-Amino-6-(1H-1,2,4-triazol-1-yl)pyrazin-2-yl)-4-methyl-N-(tetrahydro-2H-pyran-4-yl)benzenesulfonamide

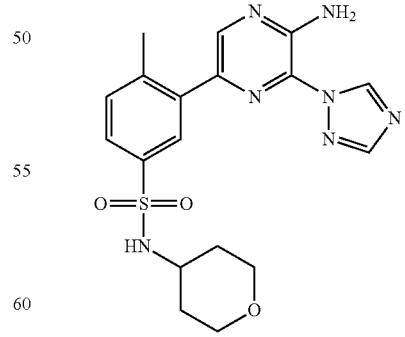

Prepared using analogous conditions to those of Example 29, using tetrahydro-2H-pyran-4-amine.

LCMS: Rt 0.92 mins; MS m/z 416.3 [M+H]+; Method: 2minLowpHv01

Example 69a 3-(5-Amino-6-(1H-1,2,4-triazol-1-yl)pyrazin-2-yl)-N-(trans-4-hydroxy-4-methylcyclohexyl)-4-methyl-benzenesulfonamide and Example 69b: 3-(5-amino-6-(1H-1,2,4-triazol-1-yl)pyrazin-2-yl)-N-(cis-4-hydroxy-4-methylcyclohexyl)-4-methylbenzenesulfonamide

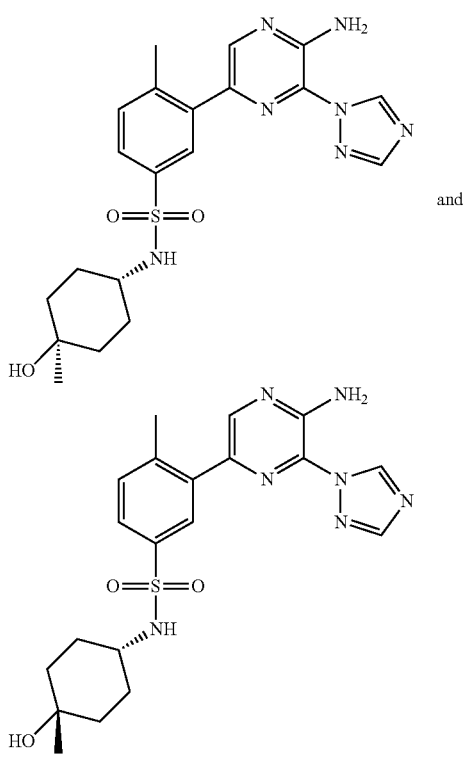

Prepared using analogous conditions to those of Example 29, using 4-amino-1-methylcyclohexanol. The resulting stereomeric mixture was separated by Chiral SFC.

Method Details:

Column: Chiralpak IC 250×10 mm, 5 um;

Mobile phase: 50% MeOH+0.1% v/v DEA/50% OO$_2$;

Flow: 10 ml/min; Detection: UV @ 220 nm; System: Berger Minigram SFC 2

Example 69a

First eluting peak at RT 6.2 mins as 3-(5-amino-6-(1H-1,2,4-triazol-1-yl)pyrazin-2-yl)-N-((1r,4r)-4-hydroxy-4-methylcyclohexyl)-4-methylbenzenesulfonamide LCMS: Rt 0.87 mins; MS m/z 444.5 [M+H]+; Method: 2minLowpHv01

$^1$H NMR (400 MHz, DMSO-d6) δ 9.33 (1H, s), 8.42 (1H, s), 8.40 (1H, s), 7.95 (1H, d), 7.73 (1H, dd), 7.59 (1H, d), 7.53 (1H, d), 7.38 (2H, s), 4.11 (1H, s), 3.06 (1H, m), 2.51 (3H, s, under DMSO), 1.60 (2H, m), 1.50 (2H, m), 1.32-1.20 (4H, m), 1.06 (3H, s).

Example 69a

Second eluting peak at RT 10.67 mins as 3-(5-amino-6-(1H-1,2,4-triazol-1-yl)pyrazin-2-yl)-N-((1s,4S)-4-hydroxy-4-methylcyclohexyl)-4-methylbenzenesulfonamide LCMS: Rt 0.94 mins; MS m/z 426.5 (minus OH) [M+H]+; Method: 2minLowpHv01

$^1$H NMR (400 MHz, DMSO-d6) δ 9.33 (1H, s), 8.41, (1H, s), 8.39 (1H, s), 7.94 (1H, s), 7.73 (1H, d), 7.60 (1H, d), 7.53 (1H, d), 7.38 (2H, s), 3.98 (1H, s), 2.93 (1H, m), 2.51 (3H, s, under DMSO), 1.53 (2H, m), 1.40 (2H, m), 1.25-1.12 (4H, m), 1.01 (3H, s).

Cis/Trans Stereochemistry Confirmed by NOESY NMR Spectroscopy

Example 70a (R)- or (S)-3-(5-Amino-6-(1H-1,2,4-triazol-1-yl)pyrazin-2-yl)-N-(6-hydroxyspiro[3.3]heptan-2-yl)-4-methylbenzenesulfonamide and Example 70b (R)- or (S)-3-(5-amino-6-(1H-1,2,4-triazol-1-yl)pyrazin-2-yl)-N-(6-hydroxyspiro[3.3]heptan-2-yl)-4-methylbenzenesulfonamide

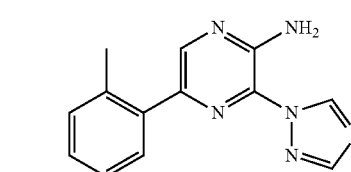
and
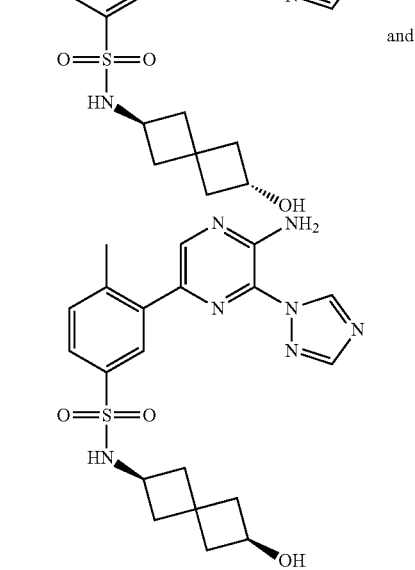

3-(5-Amino-6-(1H-1,2,4-triazol-1-yl)pyrazin-2-yl)-N-(6-hydroxyspiro[3.3]heptan-2-yl)-4-methylbenzenesulfonamide (Example 67) was separated into its isomers by chiral SFC. METHOD DETAILS: Column: Chiralpak AD-H 250× 10 mm, Sum @ 35 deg C.; Mobile phase: 40%; Isopropanol+0.1% v/v DEA/60% CO2; Flow: 10 ml/min; Detection: UV @ 220 nm; Instrument: Berger Minigram SF01

Example 70a

First Eluting Peak at 11.87 Mins (S)-3-(5-Amino-6-(1H-1,2,4-triazol-1-yl)pyrazin-2-yl)-N-(6-hydroxyspiro[3.3]heptan-2-yl)-4-methylbenzenesulfonamide or (R)-3-(5-Amino-6-(1H-1,2,4-triazol-1-yl)pyrazin-2-yl)-N-(6-hydroxyspiro[3.3]heptan-2-yl)-4-methylbenzenesulfonamide LCMS: Rt 0.88 mins; MS m/z 442.5 [M+H]+; Method: 2minLowpHv01

$^1$H NMR (400 MHz, DMSO-d6) δ 9.33 (1H, s), 8.43 (1H, s), 8.40 (1H, s), 7.90-7.85 (2H, m), 7.69 (1H, dd), 7.53 (1H, d), 7.39 (2H, s), 4.82 (1H, d), 3.84 (1H, m), 3.53 (1H, m) 2.51 (3H, s, under DMSO), 2.21 (1H, m), 2.03 (2H, m), 1.92 (1H, m), 1.76 (2H, m), 1.69 (2H, s).

Example 70b

Second Eluting Peak at 14.41 Mins (S)-3-(5-Amino-6-(1H-1,2,4-triazol-1-yl)pyrazin-2-yl)-N-(6-hydroxyspiro[3.3]heptan-2-yl)-4-methylbenzenesulfonamide or (R)-3-(5-Amino-6-(1H-1,2,4-triazol-1-yl)pyrazin-2-yl)-N-(6-hydroxyspiro[3.3]heptan-2-yl)-4-methylbenzenesulfonamide LCMS: Rt 0.90 mins; MS m/z 442.3 [M+H]+; Method: 2minLowpHv01

$^1$H NMR (400 MHz, DMSO-d6) δ 9.33 (1H, s), 8.43 (1H, s), 8.40 (1H, s), 7.91-7.86 (2H, m), 7.69 (1H, dd), 7.53 (1H, d), 7.38 (2H, s), 4.82 (1H, d), 3.85 (1H, m), 3.53 (1H, m) 2.51 (3H, s, under DMSO), 2.21 (1H, m), 2.03 (2H, m), 1.92 (1H, m), 1.76 (2H, m), 1.69 (2H, s)

Example 71a 3-(5-Amino-6-(1H-1,2,4-triazol-1-yl)pyrazin-2-yl)-N-((1r,3r)-3-hydroxycyclobutyl)-4-methylbenzenesulfonamide and Example 71b: 3-(5-amino-6-(1H-1,2,4-triazol-1-yl)pyrazin-2-yl)-N-((1s,3s)-3-hydroxycyclobutyl)-4-methylbenzenesulfonamide

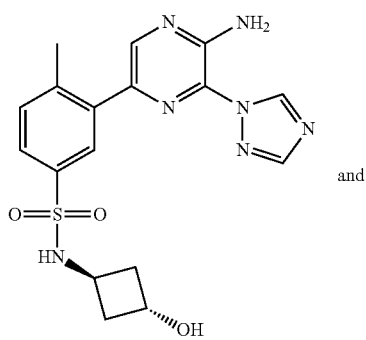

and

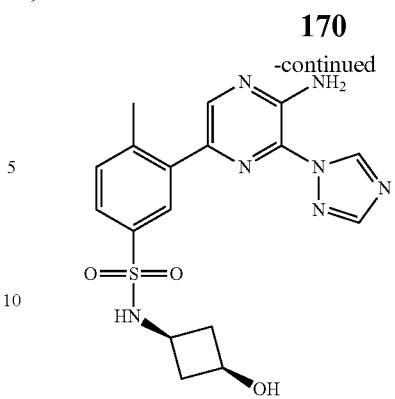

Prepared using analogous conditions to those of Example 29, using 3-aminocyclobutanol. The mixture of stereoisomers was separated by chiral SFC.

METHOD DETAILS: Column: Chiralpak AD-H, 250×10 mm, 5 um @ 35 deg C.; Mobile phase: 50% Methanol+0.1% v/v DEA/50% CO2; Flow: 10 ml/min; Detection: UV @ 220 nm; Instrument: Berger Minigram SFC1

Example 71a

First Eluting Peak at RT 4.41 Mins 3-(5-Amino-6-(1H-1,2,4-triazol-1-yl)pyrazin-2-yl)-N-((1r,3r)-3-hydroxycyclobutyl)-4-methylbenzenesulfonamide or 3-(5-amino-6-(1H-1,2,4-triazol-1-yl)pyrazin-2-yl)-N-((1s,3S)-3-hydroxycyclobutyl)-4-methylbenzenesulfonamide LCMS: Rt 0.83 mins; MS m/z 402.4 [M+H]+; Method: 2minLowpHv01

$^1$H NMR (400 MHz, DMSO-d6) δ 9.34 (1H, s), 8.43 (1H, s), 8.40 (1H, s), 7.90 (1H, br s), 7.88 (1H, s), 7.69 (1H, d), 7.54 (1H, d), 7.39 (2H, s), 4.92 (1H, d), 4.14 (1H, m), 3.75 (1H, m), 2.51 (3H, s, under DMSO), 1.98 (2H, m), 1.89 (2H, m).

Example 71b

Second Eluting Peak at RT 5.88 Mins 3-(5-Amino-6-(1H-1,2,4-triazol-1-yl)pyrazin-2-yl)-N-((1r,3r)-3-hydroxycyclobutyl)-4-methylbenzenesulfonamide or 3-(5-amino-6-(1H-1,2,4-triazol-1-yl)pyrazin-2-yl)-N-((1s,3s)-3-hydroxycyclobutyl)-4-methylbenzenesulfonamide LCMS: Rt 0.82 mins; MS m/z 402.5 [M+H]+; Method: 2minLowpHv01

$^1$H NMR (400 MHz, DMSO-d6) δ 9.34 (1H, s), 8.43 (1H, s), 8.40 (1H, s), 7.89 (1H, s), 7.86 (1H, br s), 7.70 (1H, dd), 7.54 (1H, d), 7.39 (2H, s), 4.99 (1H, d), 3.66 (1H, m), 3.13 (1H, m), 2.51 (3H, s, under DMSO), 2.24 (2H, m), 1.60 (2H, m).

Cis/Trans Stereochemistry Confirmed by NOESY NMR Spectroscopy

Example 72

3-(5-Amino-6-(1H-1,2,4-triazol-1-yl)pyrazin-2-yl)-N-(((1s,3s)-3-hydroxycyclobutyl)methyl)-4-methyl-benzenesulfonamide

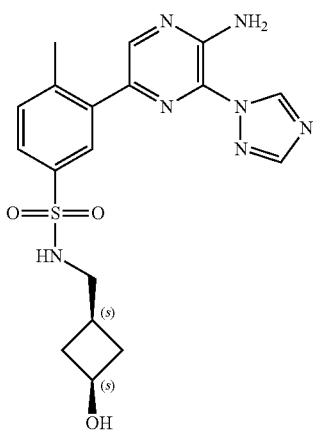 [SMILES: Cc1ccc(S(=O)(=O)NC[C@H]2C[C@@H](O)C2)cc1-c1cnc(N)c(-n2cncn2)n1]

Prepared using analogous conditions to those of Example 6 using cis-3-bromo-N-(3-hydroxy-cyclobutylmethyl)-4-methyl-benzenesulfonamide (Intermediate A10) and 5-Chloro-3-(1H-1,2,4-triazol-1-yl)pyrazin-2-amine (Intermediate C5).

LCMS: Rt 0.80 mins; MS m/z 416.3 [M+H]+; Method: 2minLowpH $^1$H NMR (400 MHz, DMSO-d6) δ 9.34 (1H, s), 8.42 (1H, s), 8.40 (1H, s), 7.89 (1H, s), 7.71 (1H, d), 7.60-7.52 (2H, m), 7.39 (2H, s), 4.89 (1H, s), 3.84 (1H, m), 2.74 (2H, t), 2.51 (3H, s, under DMSO), 2.17 (2H, m), 1.75 (1H, m), 1.41 (2H, m).

Example 73

3-(5-Amino-6-(1H-1,2,4-triazol-1-yl)pyrazin-2-yl)-N-(3-hydroxy-2,2-dimethylpropyl)-4-methylbenzenesulfonamide

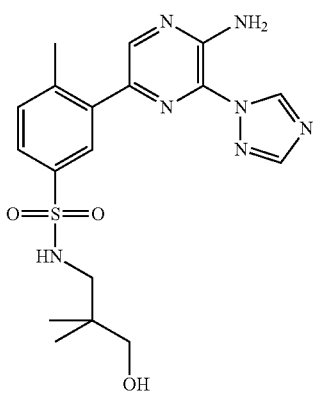 [SMILES: Cc1ccc(S(=O)(=O)NCC(C)(C)CO)cc1-c1cnc(N)c(-n2cncn2)n1]

Prepared using analogous conditions to those of Example 6 using 3-bromo-N-(3-hydroxy-2,2-dimethylpropyl)-4-methylbenzenesulfonamide (Intermediate A9) and 5-chloro-3-(1H-1,2,4-triazol-1-yl)pyrazin-2-amine (Intermediate C5).

LCMS: Rt 0.86 mins; MS m/z 418.2 [M+H]+; Method: 2minLowpH $^1$H NMR (400 MHz, DMSO-d6) δ 9.33 (1H, s), 8.42 (1H, s), 8.39 (1H, s), 7.91 (1H, s), 7.72 (1H, s), 7.55 (1H, d), 7.43-7.35 (3H, m), 4.45 (1H, t), 3.10 (2H, d), 2.57 (2H, d), 2.51 (3H, s, under DMSO), 0.77 (6H, s).

Example 74

3-(5-Amino-6-(1,3-dimethyl-1H-pyrazol-4-yl)pyrazin-2-yl)-N-(6-hydroxyspiro[3.3]heptan-2-yl)-4-methylbenzenesulfonamide

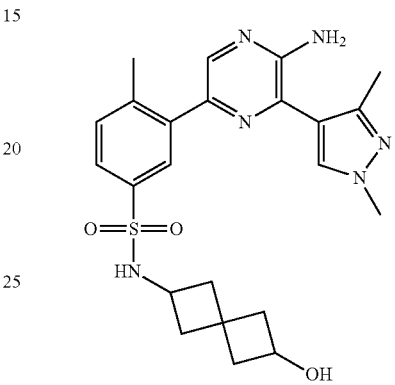

Prepared using analogous conditions to those of Example 6 using 3-Bromo-N-(6-hydroxy-spiro[3.3]hept-2-yl)-4-methyl-benzenesulfonamide (Intermediate A8) and 5-bromo-3-(1,3-dimethyl-1H-pyrazol-4-yl)-pyrazin-2-ylamine (Intermediate C7).

LCMS Rt 0.87 mins; MS m/z 469.2 [M+H]+; Method: 2minLowpHv01

$^1$H NMR (400 MHz, DMSO-d6) δ 8.08 (1H, s), 8.05 (1H, s), 7.82 (1H, s), 7.80 (1H, s), 7.63 (1H, d), 7.48 (1H, d), 6.28 (2H, s), 4.82 (1H, d), 3.84 (1H, m), 3.82 (3H, s), 3.50 (1H, m), 2.46 (3H, s), 2.29 (3H, s), 2.18 (1H, m), 2.00 (2H, m), 1.88 (1H, m), 1.69 (4H, m).

Example 75

3-(5-Amino-6-(1-methyl-1H-pyrazol-4-yl)pyrazin-2-yl)-N-((1s,4s)-4-hydroxycyclohexyl)-4-methylbenzenesulfonamide

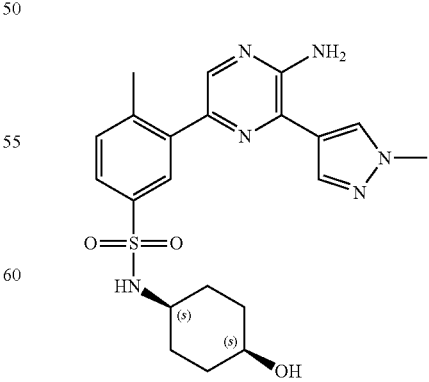

Prepared by conditions analogous to those used for the preparation of Example 18 using N-((cis)-4-hydroxycyclohexyl)-4-methyl-3-(4,4,5,5-tetramethyl-1,3,2-dioxaborolan-2-yl)benzenesulfonamide (Intermediate B8) and 5-chloro-3-(1-methyl-1H-pyrazol-4-yl)pyrazin-2-amine (prepared by analogy to Intermediate C6, starting from 1-methyl-4-(4,4,5,5-tetramethyl-1,3,2-dioxaborolan-2-yl)-1H-pyrazole).

LCMS: Rt 0.80 mins MS m/z 443.3 [M+H]+; Method 2minLowpH.

$^1$H NMR (400 MHz, DMSO-d6) δ 8.32 (1H, s), 8.07 (1H, s), 7.99 (1H, s), 7.99 (1H, s), 7.88 (1H, d, J=1.7 Hz), 7.70-7.68 (1H, dd, J=1.8, 8.0 Hz), 7.59-7.57 (1H, d, J=6.7 Hz), 7.50-7.48 (1H, d, J=8.0 Hz), 8.32 (2H, broad s), 3.91 (3H, s), 3.56 (1H, broad m), 2.97 (1H, broad m), 2.48 (3H, s), 1.58-1.49 (4H, m), 1.38-1.32 (4H, m).

Example 76

3-(5-Amino-6-(2-methylpyridin-4-yl)pyrazin-2-yl)-N-((1s,4s)-4-hydroxycyclohexyl)-4-methylbenzenesulfonamide

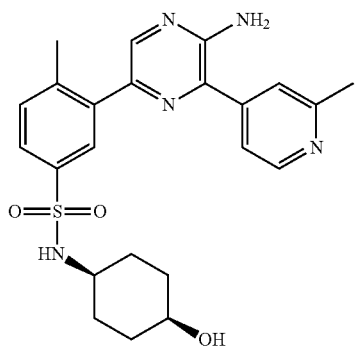 [SMILES: Cc1cc(-c2nc(-c3cc(S(=O)(=O)N[C@H]4CC[C@@H](O)CC4)ccc3C)cnc2N)ccn1]

Prepared by conditions analogous to those used for the preparation of Example 18 using N-((cis)-4-hydroxycyclohexyl)-4-methyl-3-(4,4,5,5-tetramethyl-1,3,2-dioxaborolan-2-yl)benzenesulfonamide (Intermediate B8) and 5-chloro-3-(2-methylpyridin-4-yl)pyrazin-2-amine (prepared by analogy to Intermediate C6, starting from 2-methyl-4-(4,4,5,5-tetramethyl-1,3,2-dioxaborolan-2-yl)pyridine);

LCMS: Rt 0.63 mins MS m/z 454.3 [M+H]+; Method 2minLowpH.

$^1$H NMR (400 MHz, DMSO-d6) δ 8.57-8.56 (1H, d, J=5.2 Hz), 8.26 (1H, s), 7.89 (1H, d, J=1.8 Hz), 7.72-7.69 (1H, dd, J=1.8, 8.0 Hz), 7.63 (1H, s), 7.59-7.55 (2H, m), 7.51-7.49 (1H, d, J=8.0 Hz), 6.64 (2H, s), 4.32 (1H, broad s), 3.55 (1H, m), 2.96 (1H, m), 2.55 (3H, s), 2.47 (3H, s), 1.55-1.50 (4H, m), 1.37-1.31 (4H, m).

Example 77

3-(5-Amino-6-(1-methyl-1H-pyrazol-5-yl)pyrazin-2-yl)-N-(3-hydroxy-3-methylbutyl)-4-methylbenzenesulfonamide

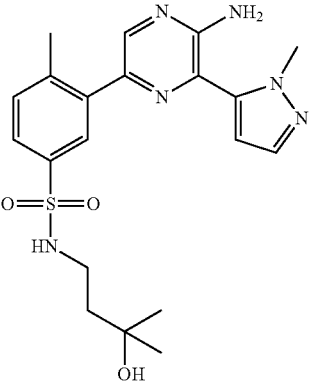 [SMILES: Cc1ccc(S(=O)(=O)NCCC(C)(C)O)cc1-c1cnc(N)c(-c2ccnn2C)n1]

Prepared by conditions analogous to those used for the preparation of Example 18 using N-(3-Hydroxy-3-methylbutyl)-4-methyl-3-(4,4,5,5-tetramethyl-1,3,2-dioxaborolan-2-yl)benzenesulfonamide (Intermediate B3) and 5-chloro-3-(1-methyl-1H-pyrazol-5-yl)pyrazin-2-amine), (prepared by analogy to Intermediate C6, starting from 1-methyl-5-(4,4,5,5-tetramethyl-1,3,2-dioxaborolan-2-yl)-1H-pyrazole)

LCMS: Rt 0.83 mins MS m/z 431.2 [M+H]+; Method 2minLowpH.

$^1$H NMR (400 MHz, DMSO-d6) δ 8.27 (1H, s), 7.84 (1H, d, J=2.0 Hz), 7.70-7.67 (1H, dd, J=2.0, 8.0 Hz), 7.57 (1H, d, J=2.0 Hz), 7.54-7.52 (1H, d, J=8.10 Hz), 7.44-7.41 (1H, m), 6.70 (1H, d), 6.50 (2H, s), 4.26 (1H, s), 3.91 (3H, s), 2.85-2.79 (2H, m), 2.48 (3H, s), 1.51-1.47 (2H, m), 1.00 (6H, s).

Example 78

3-(5-Amino-6-(3-cyclopropylisoxazol-5-yl)pyrazin-2-yl)-N-(3-hydroxy-3-methylbutyl)-4-methylbenzenesulfonamide

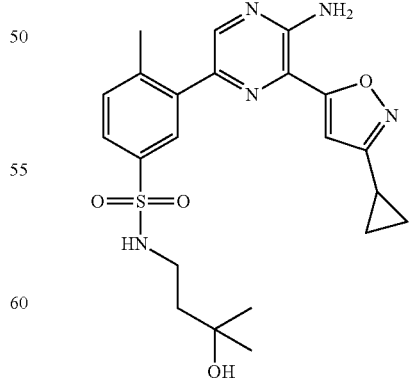

Prepared by conditions analogous to those used for the preparation of Example 18 using N-(3-Hydroxy-3-methylbutyl)-4-methyl-3-(4,4,5,5-tetramethyl-1,3,2-dioxaborolan- 2-yl)benzenesulfonamide (Intermediate B3) and 5-chloro-3-(3-cyclopropylisoxazol-5-yl)pyrazin-2-amine (Intermediate C13)

LCMS: Rt 0.98 mins MS m/z 458.4 [M+H]+; Method 2minLowpH.

$^1$H NMR (400 MHz, DMSO-d6) δ 8.37 (1H, s), 7.83 (1H, d), 7.71 (1H, dd), 7.55 (1H, d), 7.44 (1H, t), 6.91 (2H, br s), 6.81 (1H, s), 4.25 (1H, very broad s), 2.83 (2H, mult), 2.47 (3H, s), 2.09 (1H, mult), 1.51 (2H, mult), 1.06 (2H, mult), 1.02 (6H, s), 0.89 (2H, mult).

Example 79

3-(5-Amino-6-(3-cyclopropylisoxazol-5-yl)pyrazin-2-yl)-N-(2-hydroxy-2-methylpropyl)-4-methylbenzenesulfonamide

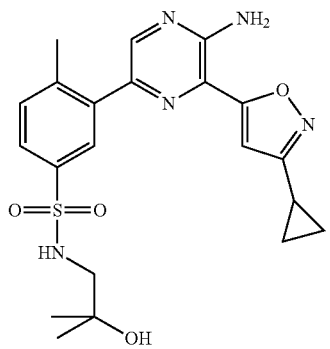 [SMILES: Cc1ccc(S(=O)(=O)NCC(C)(C)O)cc1-c1cnc(N)c(-c2cc(C3CC3)no2)n1]

Prepared by conditions analogous to those used for the preparation of Example 18, using N-(2-hydroxy-2-methyl propyl)-4-methyl-3-(4,4,5,5-tetramethyl-1,3,2-dioxaborolan-2-yl)benzenesulfonamide (Intermediate B2) and 5-chloro-3-(3-cyclopropylisoxazol-5-yl)pyrazin-2-amine (Intermediate C)

LCMS: Rt 1.06 mins MS m/z 444.4 [M+H]+; Method 2minLowpHv01.

$^1$H NMR (400 MHz, DMSO-d6) δ 8.37 (1H, s), 7.86 (1H, d), 7.72 (1H, dd), 7.53 (1H, d), 7.47 (1H, t), 6.91 (2H, br s), 6.81 (1H, s), 4.39 (1H, s), 2.62 (2H, d), 2.46 (3H, s), 2.09 (1H, mult), 1.06 (6H, s), 1.05 (2H, mult), 0.90 (2H, mult).

Example 80

3-(5-Amino-6-(4-methylthiazol-2-yl)pyrazin-2-yl)-N-(2-hydroxy-2-methylpropyl)-4-methylbenzenesulfonamide

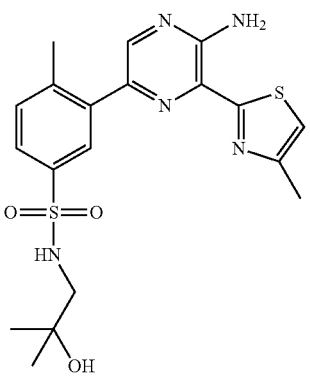 [SMILES: Cc1csc(-c2nc(-c3cc(S(=O)(=O)NCC(C)(C)O)ccc3C)cnc2N)n1]

Step 1:
3-Amino-6-bromopyrazine-2-carbothioamide

To a 100 ml flask was added 3-amino-6-bromopyrazine-2-carboxamide (1.5 g, 6.91 mmol) and Lawesson's Reagent (4.19 g, 10.37 mmol) in THF (30 ml). The reaction mixture was heated to 70° C. for 2 hours. The mixture was concentrated under reduced pressure and purified by flash column chromatography elution with Hex/EtOAc (0-40%) over 30 mins on a 24 g silica column. The required fractions were combined and concentrated under reduced pressure to yield a yellow solid; LCMS: Rt 0.88 mins MS m/z 233.2 [M+H]+; Method 2minLowpHv01.

Step 2:
5-Bromo-3-(4-methylthiazol-2-yl)pyrazin-2-amine

To a 10 ml flask was added 3-amino-6-bromopyrazine-2-carbothioamide (step 1) (300 mg, 1.287 mmol) and 1-chloropropan-2-one (0.154 ml, 1.931 mmol) in EtOH (7 ml) and stirred at 70° C. overnight. The reaction was extracted into EtOAc (10 ml), washed with sat. Na$_2$CO$_3$ (10 ml), brine (10 ml), dried over MgSO$_4$ and concentrated under reduced pressure. The mixture was purified by flash column chromatography, eluting with Hex/EtOAc (0-60%) over 15 mins on a 12 g silica cartridge. The required fractions were concentrated under reduced pressure to yield a yellow solid;

LCMS: Rt 1.23 mins MS m/z 273.2 [M+H]+; Method 2minLowpHv01.

$^1$H NMR (400 MHz, DMSO-d6), δ 8.27 (1H, s), 7.99 (2H, br s), 7.50 (1H, m), 2.48 (3H, s)

Step 3: 3-(5-Amino-6-(4-methylthiazol-2-yl)pyrazin-2-yl)-N-(2-hydroxy-2-methylpropyl)-4-methylbenzenesulfonamide Prepared by conditions analogous to those used for the preparation of Example 18 using N-(2-hydroxy-2-methylpropyl)-4-methyl-3-(4,4,5,5-tetramethyl-1,3,2-dioxaborolan-2-yl)benzenesulfonamide (Intermediate B2) and 5-bromo-3-(4-methylthiazol-2-yl)pyrazin-2-amine (Step 2)

LCMS: Rt 1.17 mins MS m/z 434.1 [M+H]+; Method 2minLowpHv01.

$^1$H NMR (400 MHz, CDCl$_3$), δ 8.24 (1H, s), 7.98 (1H, d), 7.81 (1H, dd), 7.49 (1H, d), 7.05 (1H, s), 4.90 (1H, t), 2.97 (2H, d), 2.59 (3H, s), 2.57 (3H, s), 1.29 (6H, s). Three exchangable protons not seen.

Example 81

3-(5-Amino-6-(1-methyl-1H-1,2,3-triazol-4-yl)pyrazin-2-yl)-N-(2-hydroxy-2-methylpropyl)-4-methylbenzenesulfonamide

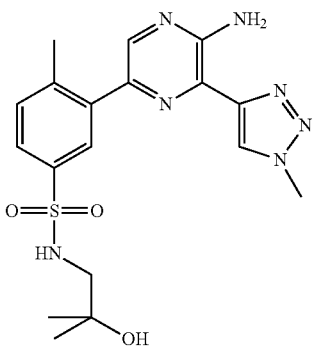 [SMILES: Cc1ccc(S(=O)(=O)NCC(C)(C)O)cc1-c1cnc(N)c(-c2cn(C)nn2)n1]

Step 1: 5-Bromo-3-(1-methyl-1H-1,2,3-triazol-4-yl)pyrazin-2-amine

To a suspension of 5-bromo-3-(1H-1,2,3-triazol-4-yl)pyrazin-2-amine (see Intermediate C8 synthesis, step 3) (1 g, 4.15 mmol) and potassium carbonate (1.720 g, 12.45 mmol) in THF (20 ml) was added iodomethane (778 μl, 12.45 mmol) and the reaction stirred at room temperature for 1 hour. The resulting mixture was extracted into ethyl acetate, washed with brine, the organic layer separated, dried over MgSO$_4$, filtered and the solvent removed under reduced pressure. The crude mixture was dissolved in DMSO (10 ml) and purified by mass directed preparative HPLC to afford the title compound;

LCMS: Rt 0.87 mins MS m/z 255.3 [M+H]+; Method 2minLowpHv01.

$^1$H NMR (400 MHz, DMSO-d6), δ 8.73 (1H, s), 8.12 (1H, s), 7.54 (2H, br s), 4.15 (3H, s).

Step 2: 3-(5-Amino-6-(1-methyl-1H-1,2,3-triazol-4-yl)pyrazin-2-yl)-N-(2-hydroxy-2-methylpropyl)-4-methylbenzenesulfonamide To 0.5-2 ml microwave vial was added N-(2-hydroxy-2-methylpropyl)-4-methyl-3-(4,4,5,5-tetramethyl-1,3,2-dioxaborolan-2-yl)benzenesulfonamide (Intermediate B2) (57.9 mg, 0.157 mmol), 5-bromo-3-(1-methyl-1H-1,2,3-triazol-4-yl)pyrazin-2-amine (from Step 1) (40 mg, 0.157 mmol), and bis(triphenylphosphine)palladium dichloride (5.50 mg, 7.84 μmol) and sodium carbonate (0.196 ml, 0.392 mmol) in DME (1.5 ml). The reaction was heated in the Biotage initiator microwave at 120° C. for 2 hours. The reaction was extracted into ethyl acetate, washed with water, brine, the organic layer separated, dried over MgSO$_4$, filtered and the solvent removed under reduced pressure. The crude product was loaded onto silica and purified by flash column chromatography, elution with TBME:methanol (0-10%) on a 12 g silica cartridge. The required fractions were combined and the solvent removed under reduced pressure to yield a pale yellow solid;

LCMS: Rt 0.92 mins MS m/z 418.6 [M+H]+; Method 2minLowpHv01.

$^1$H NMR (400 MHz, DMSO-d6) δ 8.70 (1H, s), 8.22 (1H, s), 7.87 (1H, d), 7.69 (1H, dd), 7.52 (3H, mult), 7.45 (1H, broad), 4.40 (1H, s), 4.16 (3H, s), 2.62 (2H, s), 2.49 (3H, s), 1.06 (6H, s).

Example 82

3-(5-Amino-6-(2-ethyl-2H-1,2,3-triazol-4-yl)pyrazin-2-yl)-N-(2-hydroxy-2-methylpropyl)-4-methylbenzenesulfonamide

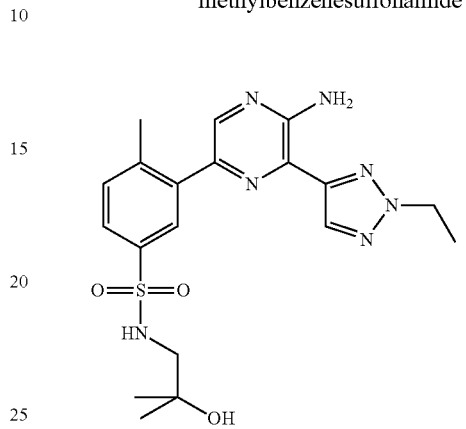

Prepared by conditions analogous to those for the preparation of Example 81 starting from 5-bromo-3-(2-ethyl-2H-1,2,3-triazol-4-yl)pyrazin-2-amine (Intermediate C8b) and N-(2-hydroxy-2-methylpropyl)-4-methyl-3-(4,4,5,5-tetramethyl-1,3,2-dioxaborolan-2-yl)benzenesulfonamide (Intermediate B2)

LCMS: Rt 1.05 mins MS m/z 432.6 [M+H]+; Method 2minLowpHv01.

$^1$H NMR (400 MHz, DMSO-d6) δ 8.34 (1H, s), 8.29 (1H, s), 7.90 (1H, d), 7.71 (1H, dd), 7.53 (1H, d), 7.47 (1H, broad), 7.31 (2H, broad), 4.59 (2H, q), 4.40 (1H, s), 2.63 (2H, broad), 2.51 (3H, s), 1.54 (3H, t), 1.07 (6H, s).

Example 83

3-(5-Amino-6-(1-ethyl-1H-1,2,3-triazol-4-yl)pyrazin-2-yl)-N-(2-hydroxy-2-methylpropyl)-4-methylbenzenesulfonamide

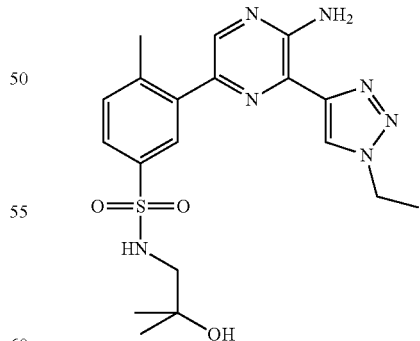

Prepared by conditions analogous to those for the preparation of Example 81 starting from 5-bromo-3-(1-ethyl-1H-1,2,3-triazol-4-yl)pyrazin-2-amine (Intermediate C8a) and N-(2-hydroxy-2-methylpropyl)-4-methyl-3-(4,4,5,5-tetramethyl-1,3,2-dioxaborolan-2-yl)benzenesulfonamide (Intermediate B2)

LCMS: Rt 0.98 mins MS m/z 432.6 [M+H]+; Method 2minLowpHv01.

¹H NMR (400 MHz, DMSO-d6) δ 8.76 (1H, s), 8.21 (1H, s), 7.86 (1H, d), 7.70 (1H, dd), 7.54 (3H, mult), 7.45 (1H, broad), 4.50 (2H, q), 4.40 (1H, s), 2.62 (2H, broad), 2.48 (3H, s), 1.50 (3H, t), 1.06 (6H, s).

Example 84

3-(5-Amino-6-(2-(2,2,2-trifluoroethyl)-2H-1,2,3-triazol-4-yl)pyrazin-2-yl)-N-(2-hydroxy-2-methylpropyl)-4-methyl benzenesulfonamide

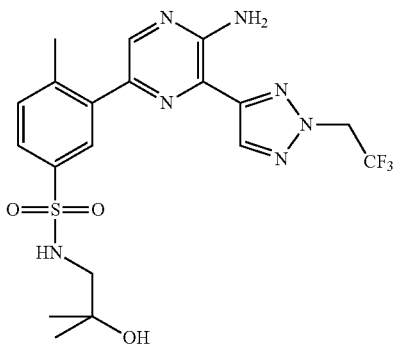 [SMILES: Cc1ccc(S(=O)(=O)NCC(C)(C)O)cc1-c1cnc(N)c(-c2cnn(CC(F)(F)F)n2)n1]

Prepared by conditions analogous to those used for the preparation of Example 18 using N-(2-hydroxy-2-methylpropyl)-4-methyl-3-(4,4,5,5-tetramethyl-1,3,2-dioxaborolan-2-yl)benzenesulfonamide (Intermediate B2) and 5-bromo-3-(2-(2,2,2-trifluoroethyl)-2H-1,2,3-triazol-4-yl)pyrazin-2-amine (Intermediate C8c);

LCMS: Rt 1.11 mins MS m/z 486.6 [M+H]+; Method 2minLowpHv01.

¹H NMR (400 MHz, DMSO-d6) δ 8.53 (1H, s), 8.35 (1H, s), 7.90 (1H, d), 7.71 (1H, dd), 7.53 (1H, d), 7.47 (1H, broad), 7.33 (2H, broad), 5.73 (2H, q), 4.40 (1H, s), 2.63 (2H, broad), 2.50 (3H, s), 1.06 (6H, s).

¹⁹F NMR (400 MHz, DMSO-d6) δ−69.51 (CF3).

Example 85

3-(5-Amino-6-(2-methyl-2H-1,2,3-triazol-4-yl)pyrazin-2-yl)-N-(3-hydroxy-3-methylbutyl)-4-methylbenzenesulfonamide

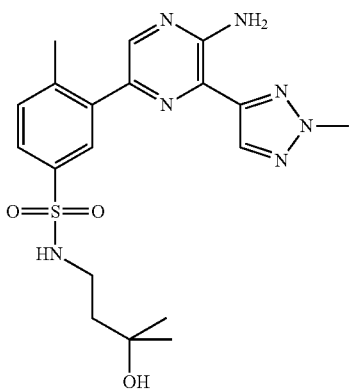 [SMILES: Cc1ccc(S(=O)(=O)NCCC(C)(C)O)cc1-c1cnc(N)c(-c2cnn(C)n2)n1]

Prepared by conditions analogous to those used for the preparation of Example 18, using N-(3-hydroxy-3-methylbutyl)-4-methyl-3-(4,4,5,5-tetramethyl-1,3,2-dioxaborolan-2-yl)benzenesulfonamide (Intermediate B3) and 5-bromo-3-(2-methyl-2H-1,2,3-triazol-4-yl)pyrazin-2-amine (Intermediate C8);

LCMS: Rt 0.98 mins MS m/z 432.3 [M+H]+; Method 2minLowpHv01.

¹H NMR (400 MHz, DMSO-d6) δ 8.32 (1H, s), 8.28 (1H, s), 7.86 (1H, d), 7.70 (1H, dd), 7.54 (1H, d), 7.43 (1H, mult), 7.30 (2H, broad), 4.30 (3H, s), 4.27 (1H, s), 2.83 (2H, mult), 2.50 (3H, s), 1.51 (2H, mult), 1.02 (6H, s).

Example 87

3-(5-Amino-6-(2-methylthiazol-5-yl)pyrazin-2-yl)-N-((1s,4s)-4-hydroxycyclohexyl)-4-methylbenzenesulfonamide

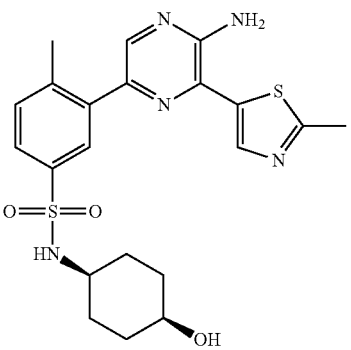 [SMILES: Cc1ncc(-c2nc(-c3cc(S(=O)(=O)N[C@H]4CC[C@@H](O)CC4)ccc3C)cnc2N)s1]

Prepared by conditions analogous to those used for the preparation of Example 18, using N-cis-4-hydroxycyclohexyl)-4-methyl-3-(4,4,5,5-tetramethyl-1,3,2-dioxaborolan-2-yl)benzenesulfonamide (Intermediate B8) and 5-chloro-3-(2-methylthiazol-5-yl)pyrazin-2-amine (Intermediate C6);

LCMS: Rt 0.88 mins MS m/z 460.2 [M+H]+; Method 2minLowpHv01.

Example 88

3-(5-Amino-6-(3-methylisoxazol-5-yl)pyrazin-2-yl)-N-(2-hydroxy-2-methylpropyl)-4-methylbenzenesulfonamide

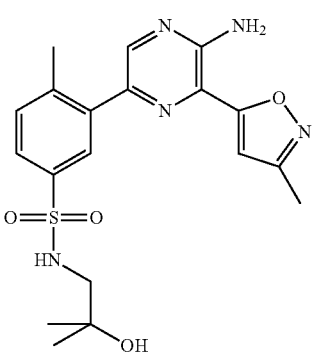 [SMILES: Cc1cc(-c2nc(-c3cc(S(=O)(=O)NCC(C)(C)O)ccc3C)cnc2N)on1]

Prepared by conditions analogous to those used for the preparation of Example 18, using N-(2-hydroxy-2-methylpropyl)-4-methyl-3-(4,4,5,5-tetramethyl-1,3,2-dioxaborolan-2-yl)benzenesulfonamide (Intermediate B2) and 5-bromo-3-(3-methyl-isoxazol-5-yl)-pyrazin-2-ylamine (Intermediate C3);

LCMS: Rt 0.98 mins MS m/z 418.4 [M+H]+; Method 2minLowpHv01.

$^1$H NMR (400 MHz, DMSO-d6) δ 8.39 (1H, s), 7.89 (1H, d), 7.72 (1H, dd), 7.53 (1H, d), 7.47 (1H, t), 6.96 (1H, s), 6.93 (2H, br s), 4.39 (1H, s), 2.63 (2H, d), 2.48 (3H, s), 2.33 (3H, s), 1.06 (6H, s).

Example 89

3-(5-Amino-6-(3-methylisoxazol-5-yl)pyrazin-2-yl)-N-(3-hydroxy-3-methylbutyl)-4-methylbenzenesulfonamide

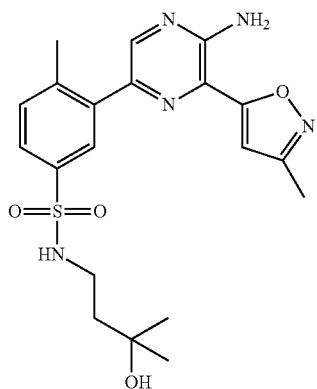 [SMILES: Cc1cc(-c2nc(-c3cc(S(=O)(=O)NCCC(C)(C)O)ccc3C)cnc2N)on1]

Prepared by conditions analogous to those used for the preparation of Example 18, using N-(3-Hydroxy-3-methylbutyl)-4-methyl-3-(4,4,5,5-tetramethyl-1,3,2-dioxaborolan-2-yl)benzenesulfonamide (Intermediate B3) and 5-bromo-3-(3-methyl-isoxazol-5-yl)-pyrazin-2-ylamine (Intermediate C3);

LCMS: Rt 1.00 mins MS m/z 432.4 [M+H]+; Method 2minLowpHv01.

$^1$H NMR (400 MHz, DMSO-d6) δ 8.39 (1H, s), 7.85 (1H, d), 7.71 (1H, dd), 7.55 (1H, d), 7.44 (1H, t), 6.96 (1H, s), 6.93 (2H, br s), 4.27 (1H, s), 2.84 (2H, mult), 2.49 (3H, s), 2.33 (3H, s), 1.51 (2H, mult), 1.02 (6H, s).

Example 90

3-(5-Amino-6-(5-methyl-1,3,4-oxadiazol-2-yl)pyrazin-2-yl)-N-(2-hydroxy-2-methylpropyl)-4-methylbenzenesulfonamide

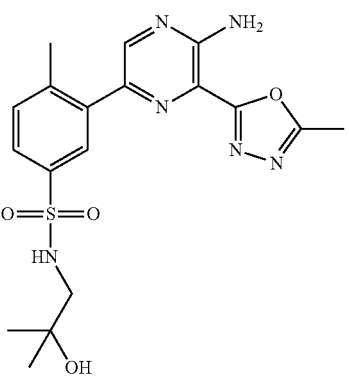 [SMILES: Cc1nnc(-c2nc(-c3cc(S(=O)(=O)NCC(C)(C)O)ccc3C)cnc2N)o1]

Prepared by conditions analogous to those used for the preparation of Example 18, using N-(2-hydroxy-2-methyl propyl)-4-methyl-3-(4,4,5,5-tetramethyl-1,3,2-dioxaborolan-2-yl)benzenesulfonamide (Intermediate B2) and 5-bromo-3-(5-methyl-[1,3,4]oxadiazol-2-yl)-pyrazin-2-ylamine (Intermediate C1);

LCMS Rt 0.89 mins MS m/z 419.5 [M+H]+; Method 2minLowpHv01.

$^1$H NMR (400 MHz, DMSO-d6), δ 8.50 (1H, s), 7.86 (1H, m), 7.75 (1H, dd), 7.71 (2H, br s), 7.55 (1H, d), 7.48 (1H, t), 4.39 (1H, s), 2.63 (3H, s), 2.62 (2H, m), 2.46 (3H, s), 1.06 (6H, s). Three exchangable protons not observed.

Example 91

3-(5-Amino-6-(5-cyclopropyl-1,2,4-oxadiazol-3-yl)pyrazin-2-yl)-N-(2-hydroxy-2-methylpropyl)-4-methylbenzenesulfonamide

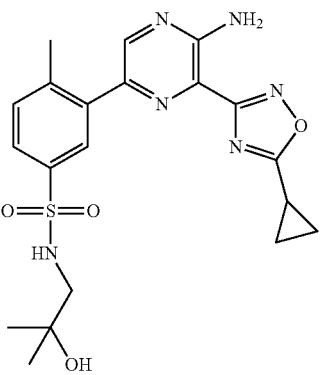 [SMILES: Cc1ccc(S(=O)(=O)NCC(C)(C)O)cc1-c1cnc(N)c(-c2noc(C3CC3)n2)n1]

Step 1: 3-Amino-6-bromo-N'-hydroxypyrazine-2-carboximidamide

To a 20 ml flask was added 3-amino-6-bromopyrazine-2-carbonitrile (600 mg, 3.01 mmol) in MeOH (12 ml) and cooled to 0° C. To the reaction mixture was added hydroxylamine hydrochloride (210 mg, 3.01 mmol) and triethylamine (0.420 ml, 3.01 mmol) and the mixture was allowed to warm to room temperature as a precipitate formed. The precipitate was filtered off and washed with MeOH. The filtrate was concentrated under reduced pressure and the resulting solid triturated in MeOH to give a second crop of product. The solid was triturated in MeOH again and sonicated for 15 mins until a suspension formed. The solid was filtered off and dried in a vacuum oven at 40° C. for 3 hours to afford the title compound;

$^1$H NMR (400 MHz, DMSO-d6), δ 10.38 (1H, s), 8.15 (1H, s), 7.64 (2H, br s), 5.88 (2H, s).

Step 2: 5-Bromo-3-(5-cyclopropyl-1,2,4-oxadiazol-3-yl)pyrazin-2-amine

To a 10 ml flask was added 3-amino-6-bromo-N'-hydroxypyrazine-2-carboximidamide (from Step 1) (290 mg, 1.250 mmol) and triethylamine (0.192 ml, 1.375 mmol) in DCM (7 ml) and cooled to <5° C. To this stirring mixture was added cyclopropanecarbonyl chloride (0.113 ml, 1.250 mmol) dropwise. The reaction mixture was allowed to warm to room temperature and stirred for 1 hour. To the mixture was added cyclopropanecarbonyl chloride (0.028 ml, 0.312 mmol) and continued at room temperature overnight. The resulting mixture was concentrated under reduced pressure to remove the solvent and the resulting residue was triturated in MeOH. The solid was collected by filtration, dried in a vacuum oven at 40° C. for 3 hours, then combined with hexachloroethane (483 mg, 2.039 mmol) in AcOH (6 ml) and heated to 100° C. for 1 hour in the biotage initiator microwave. To the reaction mixture was added hexachloroethane (241 mg, 1.020 mmol) and the reaction heated again in the microwave at 100° C. for 1 hour. The reaction was neutralised by addition of NaOH (1M) and extracted into EtOAc. The organic extracts were combined, washed with brine and dried over MgSO$_4$ and concentrated under reduced pressure. The resulting pale orange solid was dried in a vacuum oven at 40° C. for 3 hours to afford the title compound;

LCMS: Rt 0.93 mins MS m/z 282.0 [M+H]+; Method 2minLowpH.

$^1$H NMR (400 MHz, DMSO-d6), δ 8.37 (1H, s), 7.34 (2H, br s), 2.46 (1H, m), 1.35 (2H, m), 1.25 (2H, m)

Step 3: 3-(5-Amino-6-(5-cyclopropyl-1,2,4-oxadiazol-3-yl)pyrazin-2-yl)-N-(2-hydroxy-2-methylpropyl)-4-methylbenzenesulfonamide To a 0.5-2 ml microwave vial was added N-(2-hydroxy-2-methylpropyl)-4-methyl-3-(4,4,5,5-tetramethyl-1,3,2-dioxaborolan-2-yl)benzenesulfonamide (Intermediate B2) (131 mg, 0.354 mmol), 5-bromo-3-(5-cyclopropyl-1,2,4-oxadiazol-3-yl)pyrazin-2-amine (from step 2) (100 mg, 0.354 mmol), PdCl$_2$(dppf)-CH$_2$Cl$_2$ Adduct (14.47 mg, 0.018 mmol) and Na$_2$CO$_3$ (0.532 ml, 1.063 mmol) in DME (1.4 ml). The reaction mixture was heated at 120° C. for 45 mins in the Biotage initiator microwave. The reaction was combined with water (10 ml) and extracted into EtOAc (10 ml). The combined organic extracts were then washed with brine (10 ml) before being dried over magnesium sulfate and concentrated under reduced pressure. The reaction was purified by flash column chromatography elution with hexane/EtOAc (0-100%) over 15 mins on a 12 g silica cartridge. The required fractions were combined and concentrated under reduced pressure before being dried in a vacuum oven at 40° C. for 3 hours to afford the title compound;

LCMS: Rt 1.04 mins MS m/z 445.4[M+H]+; Method 2minLowpHv01.

$^1$H NMR (400 MHz, DMSO-d6), δ 8.46 (1H, s), 7.86 (1H, d), 7.73 (1H, dd), 7.54 (1H, d), 7.48 (1H, t), 7.30 (2H, s), 4.39 (1H, s), 2.63 (2H, d), 2.47 (1H, m), 2.45 (3H, s), 1.32 (2H, m), 1.25 (2H, m), 1.06 (6H, s).

Example 92

3-(5-Amino-6-(3-methyl-1,2,4-oxadiazol-5-yl)pyrazin-2-yl)-N-(3-hydroxy-2,2-dimethylpropyl)-4-methylbenzenesulfonamide

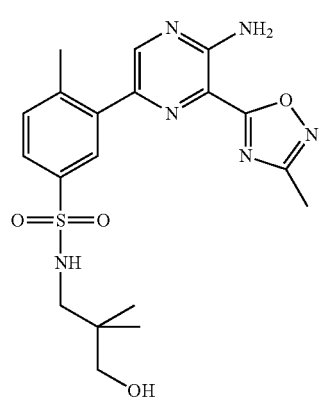 [SMILES: Cc1noc(-c2nc(-c3cc(S(=O)(=O)NCC(C)(C)CO)ccc3C)cnc2N)n1]

The title compound was prepared using 3-bromo-N-(3-hydroxy-2,2-dimethylpropyl)-4-methylbenzenesulfonamide (Intermediate A9) and 5-bromo-3-(3-methyl-[1,2,4]oxadiazol-5-yl)-pyrazin-2-ylamine (Intermediate C2a) under analogous conditions to those of Example 28 LCMS: Rt 0.95 mins MS m/z 433.2[M+H]+; Method 2minLowpH.

$^1$H NMR (400 MHz, DMSO-d6), δ 8.61 (1H, s), 7.90 (1H, d), 7.81 (2H, br s), 7.74 (1H, dd), 7.56 (1H, d), 7.42 (1H, t), 4.44 (1H, t), 3.10 (2H, d), 2.58 (2H, d), 2.49 (3H, s), 0.77 (6H, s). One methyl group not observed; likely obscured by solvent peak.

Example 93

3-(5-Amino-6-(3-cyclopropyl-1,2,4-oxadiazol-5-yl)pyrazin-2-yl)-N-(3-hydroxy-2,2-dimethylpropyl)-4-methylbenzenesulfonamide

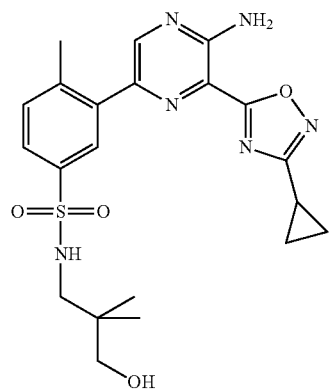 [SMILES: Cc1ccc(S(=O)(=O)NCC(C)(C)CO)cc1-c1cnc(N)c(-c2nc(C3CC3)no2)n1]

The title compound was prepared using 3-bromo-N-(3-hydroxy-2,2-dimethylpropyl)-4-methylbenzenesulfonamide (Intermediate A9) and 5-bromo-3-(3-cyclopropyl-[1,2,4]oxadiazol-5-yl)-pyrazin-2-ylamine (Intermediate C2c) under analogous conditions to those of Example 28.

LCMS: Rt 0.96 min; MS m/z=457.2 [M+H]+; Method 2minLowpH

¹H NMR (400 MHz, DMSO-d6), δ 8.60 (1H, s), 7.89 (1H, d), 7.75 (1H, dd), 7.72 (2H, br s), 7.56 (1H, d), 7.41 (1H, t), 4.44 (1H, t), 3.10 (2H, d), 2.58 (2H, d), 2.48 (3H, s), 2.27 (1H, m), 1.14 (4H, m), 0.77 (6H, s).

Example 94

3-(5-Amino-6-(3-cyclopropyl-1,2,4-oxadiazol-5-yl)pyrazin-2-yl)-N-(((1s,3s)-3-hydroxycyclobutyl)methyl)-4-methylbenzenesulfonamide

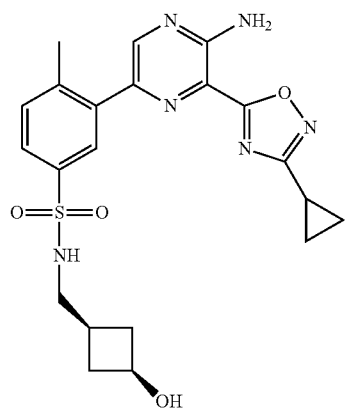 [SMILES: Cc1ccc(S(=O)(=O)NC[C@H]2C[C@@H](O)C2)cc1-c1cnc(N)c(-c2nc(C3CC3)no2)n1]

The title compound was prepared using cis-3-bromo-N-(3-hydroxy-cyclobutylmethyl)-4-methyl-benzenesulfonamide (Intermediate A10) and 5-bromo-3-(3-cyclopropyl-[1,2,4]oxadiazol-5-yl)-pyrazin-2-ylamine (Intermediate C2c) under analogous conditions to those of Example 28;

LCMS: Rt 0.96 min; MS m/z=457.2 [M+H]+; Method 2minLowpH

¹H NMR (400 MHz, DMSO-d6), δ 8.60 (1H, s), 7.87 (1H, d), 7.73 (1H, dd), 7.71 (2H, br s), 7.57 (1H, d), 4.89 (1H, d), 3.84 (1H, m), 2.74 (2H, m), 2.48 (3H, s), 2.26 (1H, m), 2.17 (2H, m), 1.74 (2H, m), 1.41 (2H, m), 1.13 (4H, m).

Example 95

3-(5-Amino-6-(3-cyclopropyl-1,2,4-oxadiazol-5-yl)pyrazin-2-yl)-N-(2-hydroxy-2-methylpropyl)-4-methylbenzenesulfonamide

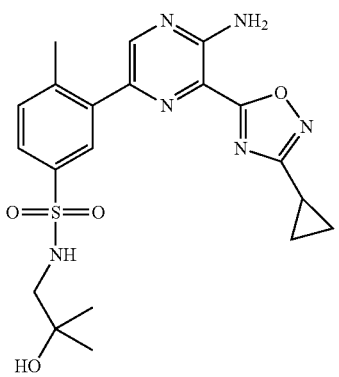 [SMILES: Cc1ccc(S(=O)(=O)NCC(C)(C)O)cc1-c1cnc(N)c(-c2nc(C3CC3)no2)n1]

The title compound was prepared using N-(2-hydroxy-2-methyl-propyl)-4-methyl-3-(4,4,5,5-tetramethyl[1,3,2]dioxaborolan-2-yl)benzenesulfonamide (Intermediate A2) and 5-bromo-3-(3-cyclopropyl-[1,2,4]oxadiazol-5-yl)-pyrazin-2-ylamine (Intermediate C2c) under analogous conditions to those of Example 28;

LCMS: Rt 0.98 mins MS m/z 445.4[M+H]+; Method 2minLowpH.

¹H NMR (400 MHz, DMSO-d6), δ 8.60 (1H, s), 7.90 (1H, s), 7.75 (1H, d), 7.73 (2H, br, s), 7.55 (1H, d), 7.49 (1H, t), 4.39 (1H, s), 2.63 (2H, d), 2.48 (3H, s), 2.26 (1H, m), 1.14 (4H, m), 1.06 (6H, s).

Example 96

3-(5-Amino-6-(3-methyl-1,2,4-oxadiazol-5-yl)pyrazin-2-yl)-N-(((1s,3s)-3-hydroxycyclobutyl)methyl)-4-methylbenzenesulfonamide

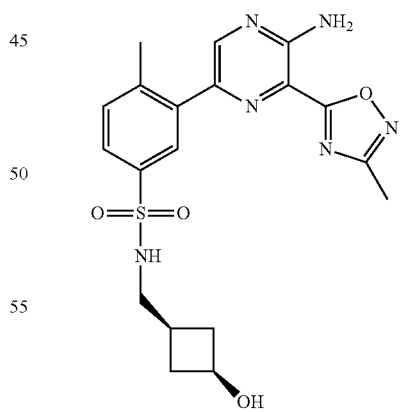

The title compound was prepared using cis-3-bromo-N-(3-hydroxy-cyclobutylmethyl)-4-methyl-benzenesulfonamide (Intermediate A10) and 5-bromo-3-(3-methyl-[1,2,4]oxadiazol-5-yl)-pyrazin-2-ylamine (Intermediate C2a) under analogous conditions to those of Example 28;

LCMS: Rt 0.97 mins MS m/z 431.4 [M+H]+; Method 2minLowpHv01.

¹H NMR (400 MHz, DMSO-d6) δ 8.62 (1H, s), 7.88 (1H, s), 7.81 (2H, br s), 7.73 (1H, dd), 7.58 (2H, m), 4.89 (1H, d), 3.84 (1H, m), 2.75 (2H, t), 2.49 (3H, s), 2.16 (2H, m), 1.75 (1H, m), 1.41 (2H, m). One methyl group not observed in NMR; likely under solvent peak.

Example 97

3-(5-Amino-6-(3-isopropyl-1,2,4-oxadiazol-5-yl)pyrazin-2-yl)-N-(2-hydroxy-2-methylpropyl)-4-methylbenzenesulfonamide

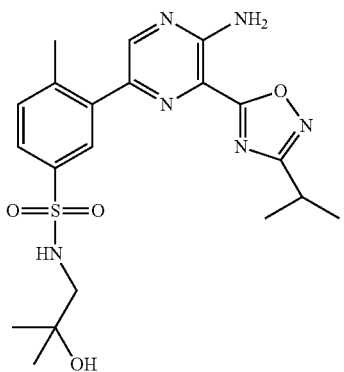 [SMILES: Cc1ccc(S(=O)(=O)NCC(C)(C)O)cc1-c1cnc(N)c(-c2nc(C(C)C)no2)n1]

The title compound was prepared using N-(2-Hydroxy-2-methyl-propyl)-4-methyl-3-(4,4,5,5-tetramethyl[1,3,2]dioxaborolan-2-yl)benzenesulfonamide (Intermediate B2) and 5-bromo-3-(3-isopropyl-[1,2,4]oxadiazol-5-yl)-pyrazin-2-ylamine (Intermediate C2b) under analogous conditions to those of Example 18;

LCMS: Rt 1.14 mins MS m/z 445.3[M+H]+; Method 2minLowpHv01.

¹H NMR (400 MHz, DMSO-d6) δ 8.62 (1H, s), 7.91 (1H, d), 7.82 (2H, br s), 7.75 (1H, dd), 7.56 (1H, d), 7.49 (1H, t), 4.40 (1H, s), 3.22 (1H, m), 2.64 (2H, d), 2.49 (3H, s), 1.37 (6H, d), 1.06 (6H, s).

Example 98

3-(5-Amino-6-(1H-1,2,4-triazol-1-yl)pyrazin-2-yl)-N-(1-(hydroxymethyl)cyclopropyl)-4-methylbenzenesulfonamide

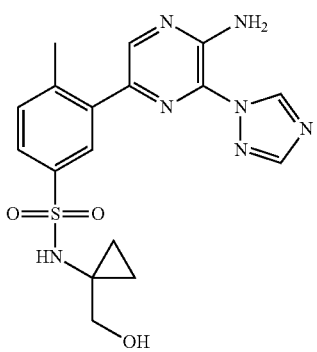 [SMILES: Cc1ccc(S(=O)(=O)NC2(CO)CC2)cc1-c1cnc(N)c(-n2cncn2)n1]

The title compound was prepared using N-(1-(hydroxymethyl)cyclopropyl)-4-methyl-3-(4,4,5,5-tetramethyl-1,3,2-dioxaborolan-2-yl)benzenesulfonamide (itself prepared in two steps by analogous conditions to those use for preparation of intermediate B1) and 5-bromo-3-(1H-1,2,4-triazol-1-yl)pyrazin-2-amine (Intermediate C11) under analogous conditions to those of Example 18.

LCMS: Rt 0.88 mins MS m/z 424.1 [M+Na]+; Method LowpH_v002

¹H NMR (400 MHz, DMSO-d6) δ 9.34 (1H, s), 8.43 (1H, s), 8.39 (1H, s), 8.18 (1H, s), 7.91 (1H, d), 7.72-7.69 (1H, dd), 7.54-7.52 (1H, d), 7.41 (2H, broad s), 4.67-4.64 (1H, m), 3.30-3.28 (2H, d), 2.52 (3H, s), 0.60-0.57 (2H, m), 0.53-0.50 (2H, m).

Example 99

3-(5-Amino-6-(3-cyclopropylisoxazol-5-yl)pyrazin-2-yl)-N-(3-hydroxy-2,2-dimethylpropyl)-4-methyl-benzenesulfonamide

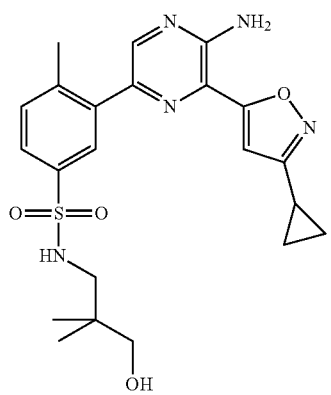 [SMILES: Cc1ccc(S(=O)(=O)NCC(C)(C)CO)cc1-c1cnc(N)c(-c2cc(C3CC3)no2)n1]

The title compound was prepared using 3-Bromo-N-(3-hydroxy-2,2-dimethylpropyl)-4-methylbenzenesulfonamide (Intermediate A9) and 5-chloro-3-(3-cyclopropylisoxazol-5-yl)pyrazin-2-amine (Intermediate C13) under analogous conditions to those of Example 28; LCMS: Rt 1.11 mins MS m/z 458.5 [M+H]+; Method 2minLowpH.

¹H NMR (400 MHz, DMSO-d6) δ 8.37 (1H, s), 7.85 (1H, d), 7.71 (1H, dd), 7.53 (1H, d), 7.38 (1H, t), 6.91 (2H, br s), 6.81 (1H, s), 4.44 (1H, mult), 3.09 (2H, d), 2.56 (2H, d), 2.46 (3H, s), 2.08 (1H, mult), 1.06 (2H, mult), 0.89 (2H, mult), 0.77 (6H, s).

Example 100

3-(5-Amino-6-(3-cyclopropylisoxazol-5-yl)pyrazin-2-yl)-N-(((1s,3s)-3-hydroxycyclobutyl)methyl)-4-methylbenzenesulfonamide

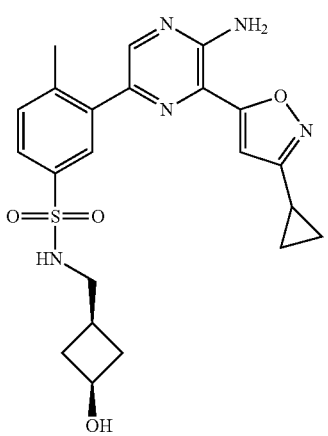 [SMILES: Cc1ccc(S(=O)(=O)NC[C@H]2C[C@@H](O)C2)cc1-c1cnc(N)c(-c2cc(C3CC3)no2)n1]

The title compound was prepared using cis-3-Bromo-N-(3-hydroxy-cyclobutylmethyl)-4-methyl-benzenesulfonamide (Intermediate A10) and 5-chloro-3-(3-cyclopropylisoxazol-5-yl)pyrazin-2-amine (Intermediate C13) under analogous conditions to those of Example 28

LCMS: Rt 0.94 mins MS m/z 456.4 [M+H]+; Method 2minLowpH.

$^1$H NMR (400 MHz, DMSO-d6) δ 8.37 (1H, s), 7.83 (1H, d), 7.70 (1H, dd), 7.57 (1H, t), 7.53 (1H, d), 6.91 (2H, br s), 6.81 (1H, s), 4.88 (1H, d), 3.84 (1H, mult), 2.74 (2H, t), 2.46 (3H, s), 2.16 (2H, mult), 2.09 (1H, mult), 1.74 (1H, mult), 1.40 (2H, mult), 1.06 (2H, mult), 0.89 (2H, mult).

Example 101

2-(3-(5-Amino-6-(1H-1,2,4-triazol-1-yl)pyrazin-2-yl)-4-methyl phenylsulfonyl)-2-azaspiro[3.3]heptan-6-ol

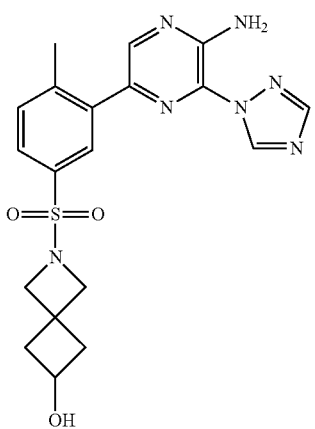 [SMILES: Cc1ccc(S(=O)(=O)N2CC3(CC(O)C3)C2)cc1-c1cnc(N)c(-n2cncn2)n1]

Step 1: 2-Azaspiro[3.3]heptan-6-one

To a 25 mL round-bottomed flask was added tert-butyl 6-oxo-2-azaspiro[3.3]heptane-2-carboxylate (600 mg, 2.84 mmol) and 4M HCl in dioxane (10 ml) to give a colorless solution. The reaction was stirred at room temperature for 1 hour. A thick white suspension formed. The crude reaction was filtered under reduced pressure to afford a white solid which was used without further purification;

Step 2: 2-(3-(5-Amino-6-(1H-1,2,4-triazol-1-yl)pyrazin-2-yl)-4-methylphenylsulfonyl)-2-azaspiro[3.3]heptan-6-one To a 50 mL round-bottomed flask was added 3-(5-amino-6-(1H-1,2,4-triazol-1-yl)pyrazin-2-yl)-4-methylbenzene-1-sulfonyl chloride (Intermediate E1) (200 mg, 0.570 mmol) and TEA (0.167 ml, 1.197 mmol) in DCM (15 ml) to give a yellow suspension. To the stirring solution was added 2-azaspiro[3.3]heptan-6-one (from Step 1) (84 mg, 0.570 mmol). The reaction mixture was stirred at room temperature for 30 mins after which time it became homogeneous. The reaction was diluted with DCM, washed with citric acid, brine, the organic layer separated, dried over MgSO$_4$, filtered and the solvent removed under reduced pressure. The product was purified by mass directed preparative chromatography. The product fractions were combined and extracted into DCM, washed with sat. sodium bicarbonate solution, the organic layer separated, dried over MgSO$_4$, filtered and the solvent removed under reduced pressure. The resulting oil was diluted with the minimum volume of ethyl acetate and allowed to evaporate at RT overnight to yield the title compound as white solid;

LCMS: Rt 0.94 mins MS m/z 426.3 [M+H]+; Method 2minLowpH.

$^1$H NMR (400 MHz, DMSO-d6) δ 9.32 (1H, s), 8.45 (1H, s), 8.42 (1H, s), 7.85 (1H, d), 7.76 (1H, dd), 7.65 (1H, d), 7.40 (2H, br s), 3.94 (4H, s), 3.12 (4H, s), 2.55 (3H, s).

Step 3: 2-(3-(5-Amino-6-(1H-1,2,4-triazol-1-yl)pyrazin-2-yl)-4-methylphenylsulfonyl)-2-azaspiro[3.3]heptan-6-ol To a 10 mL round-bottomed flask was added 2-(3-(5-amino-6-(1H-1,2,4-triazol-1-yl)pyrazin-2-yl)-4-methylphenylsulfonyl)-2-azaspiro[3.3]heptan-6-one (40 mg, 0.094 mmol) and sodium borohydride (5.34 mg, 0.141 mmol) in THF (2 ml) to give a white suspension. After 5 mins the mixture was extracted into ethyl acetate, washed with brine, the organic layer separated, dried over MgSO$_4$, filtered and the solvent removed under reduced pressure. The resulting yellow residue was dissolved in DMSO and purified by mass-directed preparative chromatography.

The required fraction was extracted into ethyl acetate, washed with sodium bicarbonate solution, the organic layer separated, dried over MgSO$_4$, filtered and the solvent removed under reduced pressure. The residue was dried in the oven at 40° C. overnight to yield a white solid;

LCMS: Rt 0.89 mins MS m/z 428.4 [M+H]+; Method 2minLowpH.

$^1$H NMR (400 MHz, DMSO-d6) δ 9.31 (1H, s), 8.44 (1H, s), 8.42 (1H, s), 7.83 (1H, d), 7.73 (1H, dd), 7.64 (1H, d), 7.40 (2H, br s), 4.97 (1H, d), 3.84 (1H, mult), 3.71 (2H, s), 3.66 (2H, s), 2.55 (3H, s), 2.14 (2H, mult), 1.76 (2H, mult).

Example 102

3-(1,3-Dimethyl-1H-pyrazol-4-yl)-5-(5-(3-methoxy-3-methylazetidin-1-ylsulfonyl)-2-methylphenyl)pyrazin-2-amine

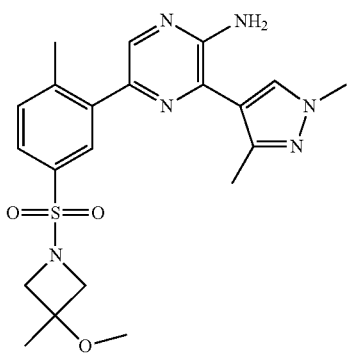 [SMILES: COC1(C)CN(S(=O)(=O)c2ccc(C)c(-c3cnc(N)c(-c4cn(C)nc4C)n3)c2)C1]

To a solution of 3-(5-amino-6-(1,3-dimethyl-1H-pyrazol-4-yl)pyrazin-2-yl)-4-methylbenzene-1-sulfonyl chloride (Intermediate E3) (165 mg, 0.437 mmol), and TEA (0.183 ml, 1.310 mmol) in DCM (5 ml) was added 3-methoxy-3-methylazetidine hydrochloride (60 mg, 0.437 mmol) and the mixture was stirred at room temperature for 30 mins. The resulting mixture was extracted with DCM, washed with water, brine, the organic layer separated, dried over MgSO₄, filtered and the solvent removed under reduced pressure. The crude product was loaded onto silica and purified by flash column chromatography elution with TBME:methanol (0-10%) on a 12 g silica cartridge. The product fractions were combined and the solvent removed under reduced pressure to yield a yellow oil;

LCMS: Rt 0.95 mins MS m/z 443.5 [M+H]+; Method 2minLowpHv01.

¹H NMR (400 MHz, DMSO-d6) δ 8.12 (1H, s), 8.10 (1H, s), 7.84 (1H, d), 7.70 (1H, dd), 7.61 (1H, d), 6.31 (2H, br s), 3.82 (3H, s), 3.60 (2H, d), 3.55 (2H, d), 2.94 (3H, s), 2.53 (3H, s), 2.30 (3H, s).

Example 103

3-(5-Amino-6-(1H-pyrazol-1-yl)pyrazin-2-yl)-N-((1r,4r)-hydroxycyclohexyl)-4-methylbenzenesulfonamide

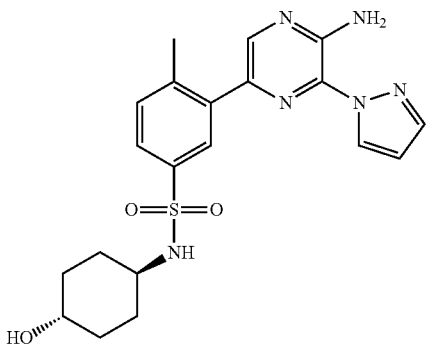 [SMILES: Cc1ccc(S(=O)(=O)N[C@H]2CC[C@H](O)CC2)cc1-c1cnc(N)c(-n2cccn2)n1]

The title compound was prepared analogously to Example 15 starting from pyrazole.

LCMS: Rt 0.92 mins; MS m/z 429.4 [M+H]+; Method: 2minLC_v003

Example 106

(R)-3-(5-Amino-6-(1,3-dimethyl-1H-pyrazol-4-yl)pyrazin-2-yl)-4-methyl-N-(pyrrolidin-2-ylmethyl)benzenesulfonamide hydrochloride

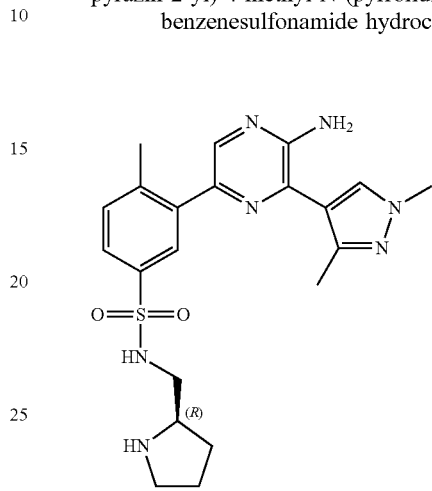

The title compound was prepared analogously to Example 128 starting from 3-(5-amino-6-(1,3-dimethyl-1H-pyrazol-4-yl)pyrazin-2-yl)-4-methylbenzene-1-sulfonyl chloride (Intermediate E3) and (R)-tert-butyl 2-(aminomethyl)pyrrolidine-1-carboxylate. The resulting product was stirred in DCM:TFA 3:1 v/v at room temperature for 4 hours to afford the title compound. Following purification the hydrochloride salt was prepared by treatment with 4N HCl in dioxane.

LCMS: Rt 0.65 mins; MS m/z 442.3 [M+H]+; Method: 2minLowpHv03

Example 107

3-(5-Amino-6-(2-cyclopropylthiazol-5-yl)pyrazin-2-yl)-N-(3-hydroxy-3-methylbutyl)-4-methylbenzenesulfonamide

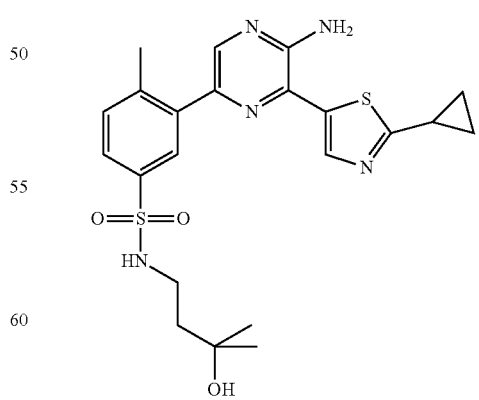

A mixture of 5-bromo-2-cyclopropylthiazole (80 mg, 0.390 mmol), KOAc (57.4 mg, 0.585 mmol), PdCl₂(dppf)·CH₂Cl₂ adduct (15.91 mg, 0.019 mmol) and bis(pinicolato)

diboron (109 mg, 0.429 mmol) in DME (1949 µL), under N$_2$, was heated at 90° C. for 14 hours. 3-(5-Amino-6-chloropyrazin-2-yl)-N-(3-hydroxy-3-methylbutyl)-4-methyl benzenesulfonamide (Intermediate D3) (150 mg, 0.390 mmol) was added to the reaction mixture followed by Na$_2$CO$_3$ (585 µL, 1.169 mmol) and PdCl$_2$(dppf).CH$_2$Cl$_2$ adduct (15.91 mg, 0.019 mmol). The resulting mixture was microwaved at 120° C. for 45 mins. The mixture was added to sat. Na$_2$CO$_3$ (50 ml) and the product extracted into EtOAc (2×50 ml). The organic extracts were washed with brine, dried over MgSO$_4$, and concentrated under reduced pressure. The crude product was purified by flash column chromatography, eluting with a modified 0-10% gradient of (2M NH$_3$ in MeOH) in DCM on a 12 g Si-column, followed by mass directed reverse phase prep chromatography to give the title compound;

LCMS: Rt 0.97 mins; MS m/z 472.3 [M–H]–; Method: 2minLowpH

Example 108

3-(5-Amino-6-(thiazol-4-yl)pyrazin-2-yl)-N-(3-hydroxy-3-methylbutyl)-4-methylbenzenesulfonamide

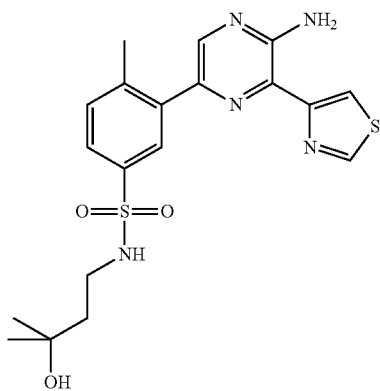 [SMILES: Cc1ccc(S(=O)(=O)NCCC(C)(C)O)cc1-c1cnc(N)c(-c2cscn2)n1]

To a solution of 3-(5-amino-6-chloropyrazin-2-yl)-N-(3-hydroxy-3-methylbutyl)-4-methyl benzenesulfonamide (Intermediate D3) (100 mg, 0.260 mmol) in THF (1299 µl) was added 4-(tributylstannyl)thiazole (146 mg, 0.390 mmol), CuI (2.474 mg, 0.013 mmol) and Pd-118 (8.47 mg, 0.013 mmol). The reaction mixture was heated in the microwave 1 hour at 100° C. Further 4-(tributylstannyl)thiazole (146 mg, 0.390 mmol), Pd-118 (8.47 mg, 0.013 mmol) and CuI (2.474 mg, 0.013 mmol) were added and reaction mixture microwaved at 150° C. for 3 hours. The resulting mixture was added to water (50 ml) and the product extracted into EtOAc (2×40 ml). The organic extracts were washed with brine, dried over MgSO$_4$ and Isolute® Si-TMT resin to remove Pd. The solids were removed by filtration, washed with EtOAc and the filtrate concentrated under reduced pressure. The crude product was purified by flash column chromatography, eluting with 0-10% gradient of (2M NH$_3$ in MeOH) in DCM on a 12 g Si-column, followed by mass directed reverse phase prep chromatography to give the title compound as a white solid;

LCMS: Rt 1.04 mins; MS m/z 432.2[M–H]–; Method: 2minLowpHv01

Example 109

3-(5-Amino-6-(3-cyclopropyl-1H-1,2,4-triazol-1-yl)pyrazin-2-yl)-N-(2-hydroxy-2-methylpropyl)-4-methyl benzenesulfonamide

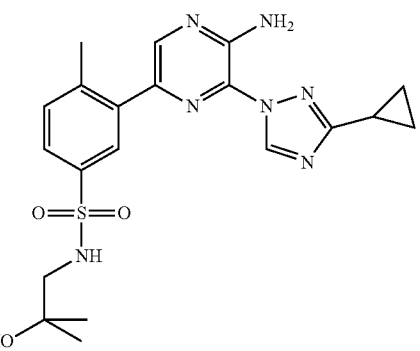

To a solution of N-(2-hydroxy-2-methylpropyl)-4-methyl-3-(4,4,5,5-tetramethyl-1,3,2-dioxaborolan-2-yl)benzenesulfonamide (Intermediate B2) (318 mg, 0.861 mmol) in DME (3913 µL) was added 5-bromo-3-(3-cyclopropyl-1H-1,2,4-triazol-1-yl)pyrazin-2-amine (prepared by analogy to intermediate C11 starting from 3-cyclopropyl-1H-1,2,4-triazole) (220 mg, 0.783 mmol), bis(triphenylphosphine)palladium(II) chloride (27.5 mg, 0.039 mmol) and Na$_2$CO$_3$ (aq. 2.0M) (1174 µL, 2.348 mmol). The reaction mixture was microwaved at 120° C. for 30 mins.

The mixture was added to water (50 ml) and the product extracted into EtOAc (2×60 ml). The organic extracts were washed with brine, dried over MgSO$_4$ and Si-TMT resin to remove Pd. The solids were removed by filtration, washed with EtOAc and concentrated under reduced pressure. The crude product was purified by flash column chromatography, eluting with 0-10% gradient of (2M NH$_3$ in MeOH) in DCM on a 12 g Si-column. The resulting solid was recrystallized from hot EtOAc (~3 ml). TBME was added slowly while hot (~3 ml). Upon cooling a yellow solid crystallized. This was collected by filtration and dried to give the title compound as a pale yellow solid;

LCMS: Rt 1.00 mins; MS m/z 444.6 [M+H]+; Method: 2minLowpHv01

Example 110

3-(5-Amino-6-(2-methoxythiazol-4-yl)pyrazin-2-yl)-N-(3-hydroxy-3-methylbutyl)-4-methylbenzenesulfonamide

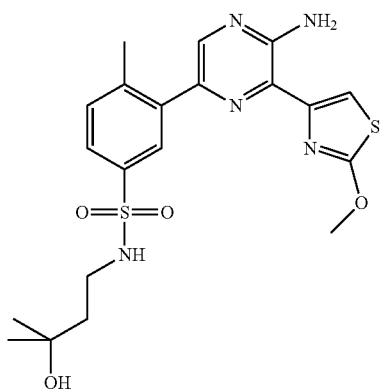 [SMILES: COc1nc(-c2nc(-c3cc(S(=O)(=O)NCCC(C)(C)O)ccc3C)cnc2N)cs1]

Prepared by analogy to Example 108 starting from 2-methoxy-4-(tributylstannyl)thiazole; LCMS: Rt 1.13 mins; MS m/z 464.5 [M+H]+; Method 2minLowpHv01

Example 111

3-(5-Amino-6-(4-methyl-1H-pyrazol-1-yl)pyrazin-2-yl)-N-((1r,4r)-4-hydroxycyclohexyl)-4-methylbenzenesulfonamide

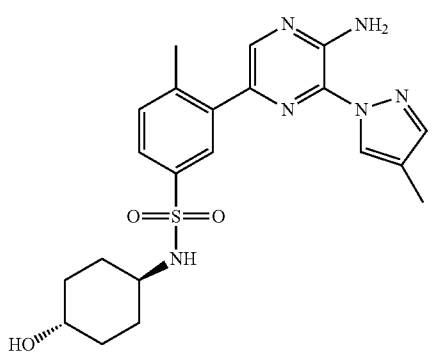 [SMILES: Cc1cnn(-c2nc(-c3cc(S(=O)(=O)N[C@H]4CC[C@H](O)CC4)ccc3C)cnc2N)c1]

The title compound was prepared analogously to Example 15 starting from 4-methyl-1H-pyrazole.

LCMS: Rt 1.06 mins; MS m/z 443.3 [M+H]+; Method: 2minLC_v003

Example 112

3-(5-Amino-6-(1H-1,2,4-triazol-1-yl)pyrazin-2-yl)-N-ethoxy-4-methylbenzenesulfonamide

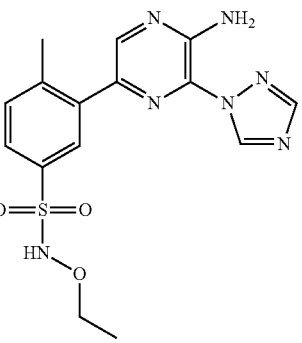

A mixture of 3-(5-amino-6-(1H-1,2,4-triazol-1-yl)pyrazin-2-yl)-4-methylbenzene-1-sulfonyl chloride (Intermediate E1) 100 mg, 0.285 mmol) and O-ethylhydroxylamine hydrochloride (83 mg, 0.855 mmol) in DCM (5 ml). Pyridine (1 ml, 12.36 mmol) was added to the reaction mixture and this was stirred at room temperature for 1 hr. The reaction mixture was washed with 1M HCl, brine and dried over MgSO4. The solvent was removed under reduced pressure. The crude product was dissolved in MeOH and water was added until the product precipitated out. This was filtered washing through with water and hexane to afford the title compound;

LCMS: Rt 3.96 min; MS m/z 376.4 [M+H]+; Method 10minLowpHv01

$^1$H NMR (400 MHz, DMSO-d6) δ 10.36 (1H, s), 9.33 (1H, s), 8.43 (1H, s), 8.40 (1H, s), 7.93 (1H, m), 7.76 (1H, m), 7.59 (1H, m), 7.40 (2H, s), 3.92 (2H, q), 2.53 (3H, s), 1.10 (3H, t).

The following examples were prepared analogously to Example 112 from 3-(5-amino-6-(1H-1,2,4-triazol-1-yl)pyrazin-2-yl)-4-methylbenzene-1-sulfonyl chloride (Intermediate E1) and an appropriate amine (commercially available unless otherwise stated).

Example 112.1

3-(5-Amino-6-(1H-1,2,4-triazol-1-yl)pyrazin-2-yl)-N-(tert-butoxy)-4-methylbenzenesulfonamide

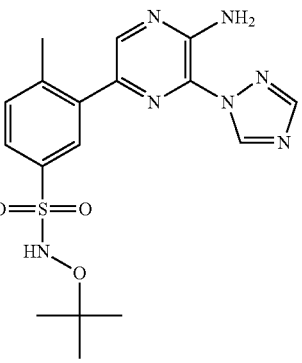

LCMS: Rt 4.48 min; MS m/z 404.5 [M+H]+; Method 10minLowpHv01

¹H NMR (400 MHz, DMSO-d6) δ 9.81 (1H, s), 9.32 (1H, s), 8.42 (1H, s), 8.39 (1H, s), 7.92 (1H, m), 7.75 (1H, m), 7.57 (1H, m), 7.39 (2H, s), 2.53 (3H, s), 1.16 (9H, s).

Example 112.2

3-(5-Amino-6-(1H-1,2,4-triazol-1-yl)pyrazin-2-yl)-N-(2-(dimethylamino)ethoxy)-4-methylbenzenesulfonamide

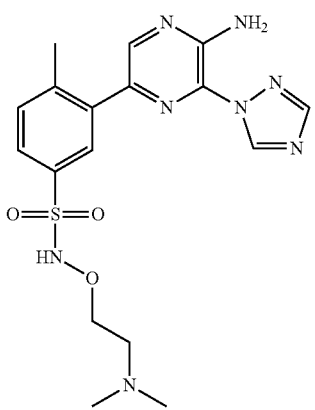 [SMILES: Cc1ccc(S(=O)(=O)NOCCN(C)C)cc1-c1cnc(N)c(-n2cncn2)n1]

LCMS: Rt 2.24 min; MS m/z 419.7 [M+H]+; Method 10minLowpHv01

¹H NMR (400 MHz, MeOD-d4) δ ppm 9.35 (1H, s), 8.33 (2H, s), 8.02 (1H, d), 7.86 (1H, dd), 7.57 (1H, d), 4.14 (2H, t), 2.68 (2H, t), 2.58 (3H, s), 2.30 (6H, s).

Example 112.3

3-(5-Amino-6-(1H-1,2,4-triazol-1-yl)pyrazin-2-yl)-N-isopropoxy-4-methylbenzenesulfonamide

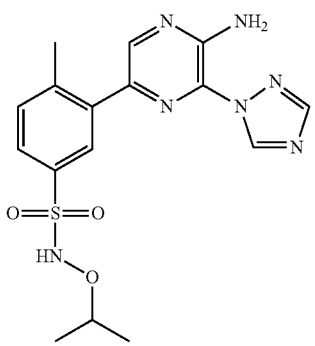 [SMILES: Cc1ccc(S(=O)(=O)NOC(C)C)cc1-c1cnc(N)c(-n2cncn2)n1]

LCMS: Rt 4.23 min; MS m/z 390.5 [M+H]+; Method 10minLowpHv01

¹H NMR (400 MHz, DMSO-d6) δ 10.16 (1H, s), 9.32 (1H, s), 8.42 (1H, s), 8.39 (1H, s), 7.92 (1H, d), 7.77 (1H, dd), 7.59 (1H, d), 7.40 (2H, s), 4.11 (1H, m), 2.53 (3H, s), 1.11 (6H, d).

Example 112.4

3-(5-Amino-6-(1H-1,2,4-triazol-1-yl)pyrazin-2-yl)-N-isobutoxy-4-methylbenzenesulfonamide

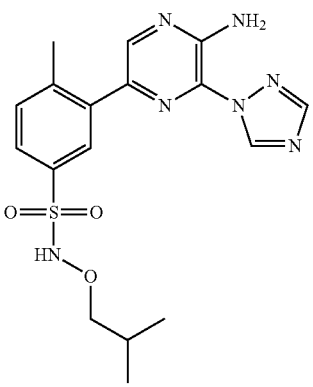 [SMILES: Cc1ccc(S(=O)(=O)NOCC(C)C)cc1-c1cnc(N)c(-n2cncn2)n1]

LCMS: Rt 4.62 min; MS m/z 404.5 [M+H]+; Method 10minLowpHv01

¹H NMR (400 MHz, DMSO-d6) δ 10.37 (1H, s), 9.32 (1H, s), 8.42 (1H, s), 8.39 (1H, s), 7.93 (1H, d), 7.77 (1H, dd), 7.60 (1H, d), 7.40 (2H, s), 3.67 (2H, d), 2.53 (3H, m), 1.79-1.89 (1H, m), 0.83 (6H, d).

Example 112.5

3-(5-Amino-6-(1H-1,2,4-triazol-1-yl)pyrazin-2-yl)-4-methyl-N-((tetrahydrofuran-3-yl)oxy)benzenesulfonamide

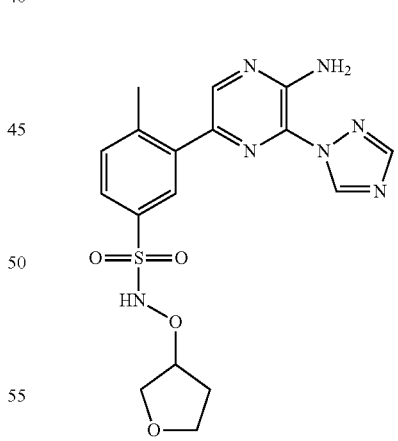

Prepared using 0-(Tetrahydrofuran-3-yl)hydroxylamine (intermediate F)

LCMS: Rt 3.60 min; MS m/z 418.3 [M+H]+; Method 10minLowpHv01

¹H NMR (400 MHz, DMSO-d6) δ 10.44 (1H, s), 9.32 (1H, s), 8.42 (1H, s), 8.39 (1H, s), 7.91 (1H, d), 7.77 (1H, dd), 7.60 (1H, d), 7.40 (2H, s), 4.68 (1H, m), 3.79 (1H, d), 3.63 (3H, m), 2.53 (3H, s), 1.97 (2H, m).

Example 113

5-(5-Amino-6-(2-methylthiazol-5-yl)pyrazin-2-yl)-2-fluoro-N-(3-hydroxypropyl)-4-methylbenzenesulfonamide

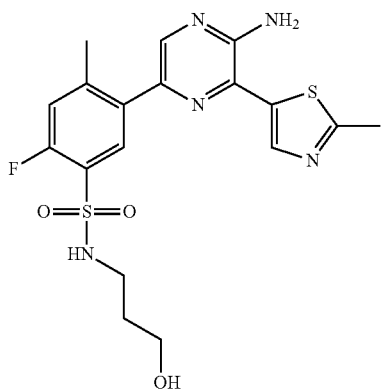 [SMILES: Cc1ncc(-c2nc(-c3cc(S(=O)(=O)NCCCO)c(F)cc3C)cnc2N)s1]

Prepared from 5-(5-amino-6-chloropyrazin-2-yl)-2-fluoro-N-(3-hydroxypropyl)-4-methylbenzenesulfonamide (Intermediate D5) and 2-methyl-5-(4,4,5,5-tetramethyl-1,3,2-dioxaborolan-2-yl)thiazole by analogy to Example 11. The resulting solid was crystallized from EtOAc/Et$_2$O (dissolving the compound in minimal hot EtOAc and diluting with Et$_2$O. The resulting solution was left to cool and solid was collected by filtration, washed with a small amount of Et$_2$O and dried to give the title compound as a yellow solid;

LCMS: Rt 0.83 mins; MS m/z 438.1 [M+H]+; Method: 2minLowpH $^1$H NMR (400 MHz, DMSO-d6) δ 8.27 (1H, s), 8.20 (1H, s), 7.81 (1H, br s), 7.78 (1H, d), 7.44 (1H, d), 6.72 (2H, s), 4.42 (1H, br m), 3.38 (2H, m), 2.93 (2H, m), 2.68 (3H, s), 2.47 (3H, s), 1.56 (2H, m).

Example 114

5-(5-Amino-6-(1-methyl-1H-pyrazol-4-yl)pyrazin-2-yl)-2-fluoro-N-(3-hydroxypropyl)-4-methylbenzenesulfonamide

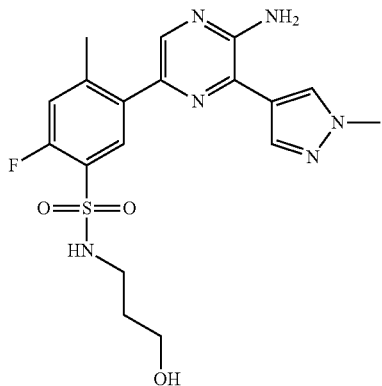 [SMILES: Cc1cc(F)c(S(=O)(=O)NCCCO)cc1-c1cnc(N)c(-c2cnn(C)c2)n1]

Prepared from 5-(5-amino-6-chloropyrazin-2-yl)-2-fluoro-N-(3-hydroxypropyl)-4-methylbenzenesulfonamide (Intermediate D5) and 1-methyl-4-(4,4,5,5-tetramethyl-1,3,2-dioxaborolan-2-yl)-1H-pyrazole by analogy to Example 11. The resulting solid was crystallized from EtOAc/Et$_2$O (dissolving the compound in minimal hot EtOAc and diluting with Et$_2$O. The resulting solution was left to cool and solid was collected by filtration, washed with a small amount of Et$_2$O and dried to give the title compound as a white solid;

LCMS: Rt 0.75 mins; MS m/z 421.2 [M+H]+; Method: 2minLowpH $^1$H NMR (400 MHz, DMSO-d6) δ 8.31 (1H, s), 8.06 (1H, s), 7.98 (1H, s), 7.80 (1H, br s), 7.77 (1H, d), 7.42 (1H, d), 6.31 (2H, s), 4.42 (1H, br s), 3.91 (3H, s), 3.38 (2H, t), 2.92 (2H, t), 2.46 (3H, s), 1.56 (2H, m).

Example 115

5-(5-Amino-6-(1-methyl-1H-pyrazol-4-yl)pyrazin-2-yl)-2-fluoro-N-(3-hydroxy-3-methylbutyl)-4-methylbenzenesulfonamide

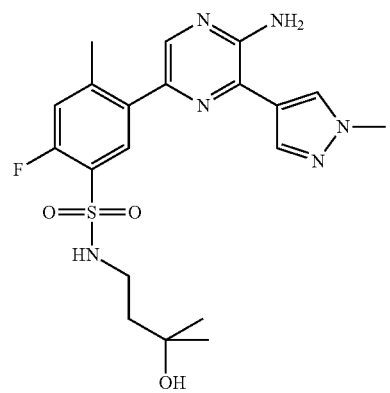 [SMILES: Cc1cc(F)c(S(=O)(=O)NCCC(C)(C)O)cc1-c1cnc(N)c(-c2cnn(C)c2)n1]

Prepared by analogy to Example 11 from 1-methyl-4-(4,4,5,5-tetramethyl-1,3,2-dioxaborolan-2-yl)-1H-pyrazole and 5-(5-amino-6-chloropyrazin-2-yl)-2-fluoro-N-(3-hydroxy-3-methylbutyl)-4-methylbenzenesulfonamide (prepared in two steps by analogy to Intermediate D5) The resulting solid was crystallized from EtOAc/Et$_2$O (dissolving the compound in minimal hot EtOAc and diluting with Et$_2$O. The resulting solution was left to cool and solid was collected by filtration, washed with a small amount of Et$_2$O and dried to give the title compound as a white solid;

LCMS; Rt 0.82 mins; MS m/z 449.2 [M+H]+; Method: 2minLowpH

Example 116

5-(5-Amino-6-(1H-1,2,4-triazol-1-yl)pyrazin-2-yl)-2-fluoro-N-(3-hydroxy-3-methylbutyl)-4-methylbenzenesulfonamide

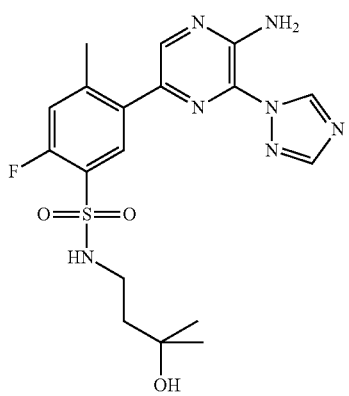 [SMILES: Cc1cc(F)c(S(=O)(=O)NCCC(C)(C)O)cc1-c1cnc(N)c(-n2cncn2)n1]

The title compound was prepared using 5-(5-amino-6-chloropyrazin-2-yl)-2-fluoro-N-(3-hydroxy-3-methylbutyl)-4-methylbenzenesulfonamide (prepared in two steps by analogy to Intermediate A12) and 5-chloro-3-(1H-1,2,4-triazol-1-yl)pyrazin-2-amine (Intermediate C5) under analogous conditions to those of Example 6. The resulting solid was crystallized from EtOAc/Et$_2$O (dissolving the compound in minimal hot EtOAc and diluting with Et$_2$O. The resulting solution was left to cool and solid was collected by filtration, washed with a small amount of Et$_2$O and dried to give the title compound as a white solid;

LCMS: Rt 0.84 mins; MS m/z 436.3 [M+H]+; Method: 2minLC_v003

Example 117

3-(5-Amino-6-(3-((dimethylamino)methyl)-1H-1,2,4-triazol-1-yl)pyrazin-2-yl)-N-(2-hydroxy-2-methylpropyl)-4-methylbenzenesulfonamide hydrochloride salt

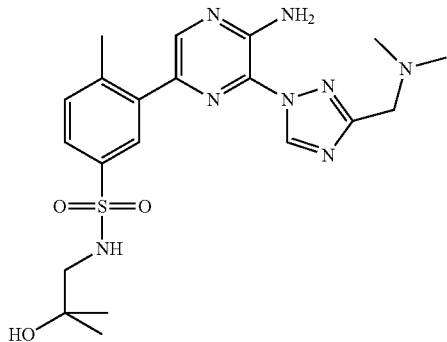 [SMILES: Cc1ccc(S(=O)(=O)NCC(C)(C)O)cc1-c1cnc(N)c(-n2cnc(CN(C)C)n2)n1]

Step 1: N,N-Dimethyl-1-(1H-1,2,4-triazol-3-yl)methanamine

To 3-(chloromethyl)-1H-1,2,4-triazole (400 mg, 2.60 mmol) was added dimethylamine (2.0M in THF) (51.900 ml, 10.38 mmol) and the reaction mixture was stirred for 24 hours at room temperature. The mixture was concentrated to dryness and crude product loaded onto 2×10 g Isolute® SCX-2 cartridges, flushed with MeOH (50 ml) and product eluted with 2.0M NH$_3$ in MeOH (50 ml). Concentration of the ammonia in methanol gave the title compound;

$^1$H NMR (400 MHz, DMSO-d6) δ 3.51 (2H, s), 2.16 (6H, s).

Step 2: 5-Bromo-3-(3-((dimethylamino)methyl)-1H-1,2,4-triazol-1-yl)pyrazin-2-amine A mixture of 5-bromo-3-chloropyrazin-2-amine (376 mg, 1.801 mmol), N,N-dimethyl-1-(1H-1,2,4-triazol-3-yl)methanamine (from Step 1) (250 mg, 1.982 mmol), Cs$_2$CO$_3$ (1174 mg, 3.60 mmol) in DMF (9007 µl) was heated to 60° C. for 16 hours. The mixture was concentrated to dryness, added to water (50 ml) and product extracted into EtOAc (4×40 ml). The organic extracts were washed brine, dried over MgSO$_4$ and concentrated under reduced pressure to give the title compound as a orange solid, which was taken onto the next step without further purification;

LCMS: Rt 0.84 mins; MS m/z 298.4 [M+H]+; Method: 2minLowpHv01

Step 3: 3-(5-Amino-6-(3-((dimethylamino)methyl)-1H-1,2,4-triazol-1-yl)pyrazin-2-yl)-N-(2-hydroxy-2-methylpropyl)-4-methylbenzenesulfonamide hydrochloride salt To a solution of N-(2-hydroxy-2-methylpropyl)-4-methyl-3-(4,4,5,5-tetramethyl-1,3,2-dioxaborolan-2-yl)benzenesulfonamide (Intermediate B2) (235 mg, 0.636 mmol) in DME (2652 µl) was added 5-bromo-3-(3-((dimethylamino)methyl)-1H-1,2,4-triazol-1-yl)pyrazin-2-amine (from Step 2) (158 mg, 0.530 mmol), bis(triphenylphosphine)palladium(II) chloride (18.61 mg, 0.027 mmol) and Na$_2$CO$_3$ (aq. 2.0M) (795 µl, 1.591 mmol). The reaction mixture was microwaved at 120° C. for 60 mins. The mixture was added to water (50 ml) and product extracted into EtOAc (2×50 ml). The organic extracts were washed with brine, dried over MgSO$_4$ and Si-TMT resin to remove Pd. The solids were removed by filtration, washed with EtOAc and concentrated under reduced pressure. The crude product was purified by flash column chromatography, eluting with 0-10% gradient of (2M NH$_3$ in MeOH) in DCM on a 12 g Si-column. The resulting oil was dissolved in a small amount of MeOH (1 ml) and 4.0M HCl in dioxane was added (1 ml). The mixture was concentrated to dryness and the resulting solid recrystallized from hot EtOH (~4 ml). Upon cooling a white solid crystallized. This was collected by filtration and dried to give the title compound as a pale yellow solid;

LCMS: Rt 0.66 mins; MS m/z 461.4 [M+H]+; Method: 2minLowpHv01

¹H NMR (400 MHz, DMSO-d6) δ 10.76 (1H, br s), 9.42 (1H, s), 8.45 (1H, s), 7.93 (1H, s), 7.73 (1H, d), 7.58-7.49 (2H, m), 7.46 (2H, s), 4.58 (2H, s), 4.44 (1H, br s), 2.89 (6H, s), 2.62 (1H, d), 2.51 (3H, s under DMSO), 1.07 (6H, s).

Example 118

5-(2-Methyl-5-(3-(trifluoromethyl)piperazin-1-ylsulfonyl)phenyl)-3-(2-methylthiazol-5-yl)pyrazin-2-amine

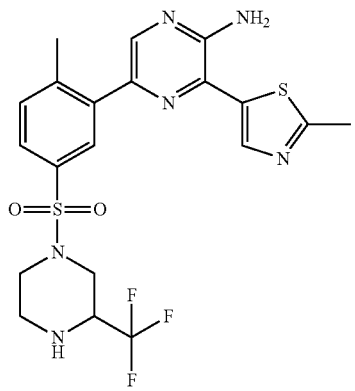 [SMILES: Cc1ncc(-c2nc(-c3cc(S(=O)(=O)N4CCNC(C(F)(F)F)C4)ccc3C)cnc2N)s1]

Prepared by analogy to Example 11 from 2-methyl-5-(4,4,5,5-tetramethyl-1,3,2-dioxaborolan-2-yl)thiazole and 3-chloro-5-(2-methyl-5-((3-(trifluoromethyl)piperazin-1-1)sulfonyl)phenyl)pyrazin-2-amine (prepared in two steps by analogy to Intermediate D5 from 3-bromo-4-methylbenzene-1-sulfonyl chloride, 5-bromo-3-chloropyrazin-2-amine and 2-(trifluoromethyl)piperazine)

LCMS: Rt 0.99 mins; MS m/z 499.2 [M+H]+; Method 2minLowpH.

Example 119

3-(5-Amino-6-(1-methyl-3-(trifluoromethyl)-1H-pyrazol-5-yl)pyrazin-2-yl)-N-(3-hydroxy-3-methylbutyl)-4-methylbenzenesulfonamide

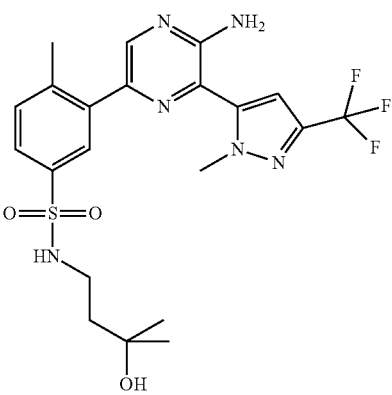 [SMILES: Cc1ccc(S(=O)(=O)NCCC(C)(C)O)cc1-c1cnc(N)c(-c2cc(C(F)(F)F)nn2C)n1]

To 1-methyl-3-trifluoromethylpyrazole-5-boronic acid (18 mg, 0.094 mmol) was added Pd(PPh₃)₂Cl₂ (2.74 mg, 3.9 μmol), sodium carbonate (2M aqueous solution, 0.117 mL, 0.234 mmol) and a solution of 3-(5-amino-6-chloropyrazin-2-yl)-N-(3-hydroxy-3-methylbutyl)-4-methylbenzenesulfonamide (Intermediate D3) (30 mg, 0.078 mmol) in acetonitrile (0.7 mL). The resulting mixture was heated in the microwave at 150° C. for 30 mins then filtered through a 500 mg IsoIte® Si-TMT cartridge, rinsing with acetonitrile (1 mL). After evaporation under reduced pressure, the residue was dissolved in DMSO and purified by HPLC (acetonitrile/water gradient, 0.1% TFA modifier). The product fractions were combined and evaporated to give the title compound;

LC-MS: Rt 1.00 mins; MS m/z 499.5 [M+H]+; Method 2minLowpH.

The following examples were prepared by analogous conditions to those described for the preparation of Example 119 starting from 3-(5-amino-6-chloropyrazin-2-yl)-N-(3-hydroxy-3-methylbutyl)-4-methylbenzenesulfonamide (Intermediate D3) and the appropriate boronic acid or ester obtained from a commercial supplier. The reactions were carried out in an appropriate solvent e.g. acetonitrile or DME. Final compounds were purified by appropriate techniques known in the art, for example preparative HPLC as described for Example 119. Compounds were isolated as trifluoroacetic acid salt (from TFA modifier in preparative HPLC) or free base, except for 119.32 and 119.41 for which hydrochloride salts were formed after purification using standard conditions e.g. HCl/dioxane. For 119.42 to 119.46 (PdCl₂(dppf)-CH₂Cl₂ adduct) catalyst was used in place of Pd(PPh₃)₂Cl₂.

| Ex | Name | Rt (min) | MS m/z | LCMS Method |
|---|---|---|---|---|
| 119.1 | 3-(5-amino-6-(2-fluoropyridin-3-yl)pyrazin-2-yl)-N-(3-hydroxy-3-methylbutyl)-4-methylbenzenesulfonamide | 0.87 | 446.3 | 2minLow pH_TFA |
| 119.2 | 3-(5-amino-6-(4-methoxypyridin-3-yl)pyrazin-2-yl)-N-(3-hydroxy-3-methylbutyl)-4-methylbenzenesulfonamide | 1.24 | 458.6 | 2minLow pH_TFA |
| 119.3 | 3-(5-amino-6-(2-methoxypyridin-4-yl)pyrazin-2-yl)-N-(3-hydroxy-3-methylbutyl)-4-methylbenzenesulfonamide | 1.23 | 458.6 | 2minLow pH_TFA |

-continued
| Ex | Name | Rt (min) | MS m/z | LCMS Method |
|---|---|---|---|---|
| 119.4 | 3-(5-amino-6-(2-methoxypyridin-3-yl)pyrazin-2-yl)-N-(3-hydroxy-3-methylbutyl)-4-methylbenzenesulfonamide | 1.05 | 458.6 | 2minLow pH_TFA |
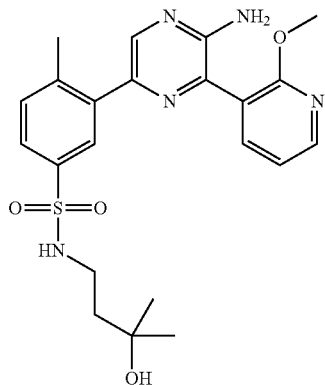
| | | | | |
|---|---|---|---|---|
| 119.5 | 3-(5-amino-6-(pyridin-3-yl)pyrazin-2-yl)-N-(3-hydroxy-3-methylbutyl)-4-methylbenzenesulfonamide | 0.99 | 428.5 | 2minLow pH_TFA |
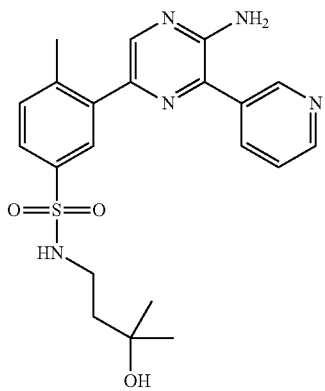
| | | | | |
|---|---|---|---|---|
| 119.6 | 3-(5-amino-6-(2-chloropyridin-3-yl)pyrazin-2-yl)-N-(3-hydroxy-3-methylbutyl)-4-methylbenzenesulfonamide | 1.21 | 462.6 | 2minLow pH_TFA |
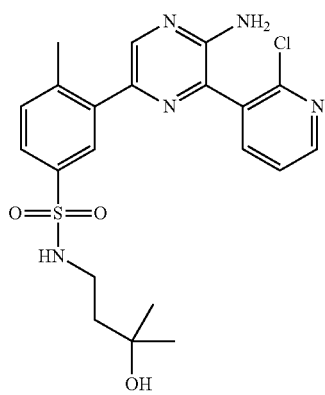

| Ex | Name | Rt (min) | MS m/z | LCMS Method |
|---|---|---|---|---|
| 119.7 | 3-(5-amino-6-(5-methylpyridin-3-yl)pyrazin-2-yl)-N-(3-hydroxy-3-methylbutyl)-4-methylbenzenesulfonamide | 1.21 | no ionisation | 2minLow pH_TFA |
| 119.8 | 3-(5-amino-6-(5-chloro-2-fluoropyridin-3-yl)pyrazin-2-yl)-N-(3-hydroxy-3-methylbutyl)-4-methylbenzenesulfonamide | 1.26 | no ionisation | 2minLow pH_TFA |
| 119.9 | 3-(5-amino-6-(6-chloro-4-methylpyridin-3-yl)pyrazin-2-yl)-N-(3-hydroxy-3-methylbutyl)-4-methylbenzenesulfonamide | 1.21 | 476.6 | 2minLow pH_TFA |

| Ex | Name | Rt (min) | MS m/z | LCMS Method |
|---|---|---|---|---|
| 119.10 | 3-(5-amino-6-(2-fluoropyridin-4-yl)pyrazin-2-yl)-N-(3-hydroxy-3-methylbutyl)-4-methylbenzenesulfonamide | 1.18 | no ionisation | 2minLow pH_TFA |
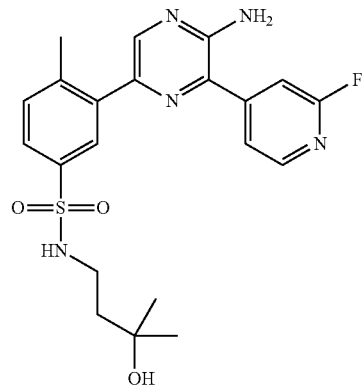
| Ex | Name | Rt (min) | MS m/z | LCMS Method |
|---|---|---|---|---|
| 119.11 | 3-(5-amino-6-(3-fluoropyridin-4-yl)pyrazin-2-yl)-N-(3-hydroxy-3-methylbutyl)-4-methylbenzenesulfonamide | 1.08 | no ionisation | 2minLow pH_TFA |
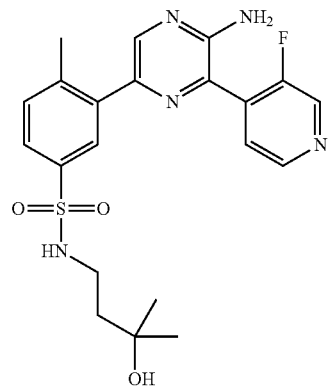

-continued

| Ex | Name | Rt (min) | MS m/z | LCMS Method |
|---|---|---|---|---|
| Reference example 119.12 | 3-(5-amino-6-(2-isopropoxypyridin-3-yl)pyrazin-2-yl)-N-(3-hydroxy-3-methylbutyl)-4-methylbenzenesulfonamide | 1.22 | 486.7 | 2minLow pH_TFA |
| 119.13 | 3-(5-amino-6-(6-ethoxypyridin-3-yl)pyrazin-2-yl)-N-(3-hydroxy-3-methylbutyl)-4-methylbenzenesulfonamide | 1.2 | 472.6 | 2minLow pH_TFA |
| 119.14 | 3-(5-amino-6-(6-methoxy-2-methylpyridin-3-yl)pyrazin-2-yl)-N-(3-hydroxy-3-methylbutyl)-4-methylbenzenesulfonamide | 1.12 | 472.6 | 2minLow pH_TFA |

-continued
| Ex | Name | Rt (min) | MS m/z | LCMS Method |
|---|---|---|---|---|
| 119.15 | 3-(5-amino-6-(furan-3-yl)pyrazin-2-yl)-N-(3-hydroxy-3-methylbutyl)-4-methylbenzenesulfonamide | 1.09 | 417.5 | 2minLow pH_TFA |
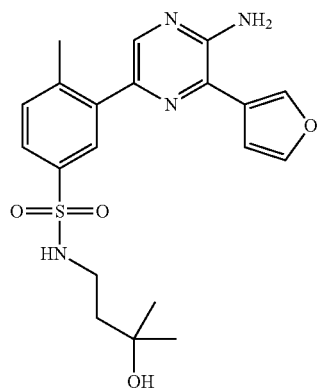
| | | | | |
|---|---|---|---|---|
| 119.16 | 3-(5-amino-6-(1-methyl-1H-pyrazol-4-yl)pyrazin-2-yl)-N-(3-hydroxy-3-methylbutyl)-4-methylbenzenesulfonamide | 0.81 | 431.4 | 2minLow pH_TFA |
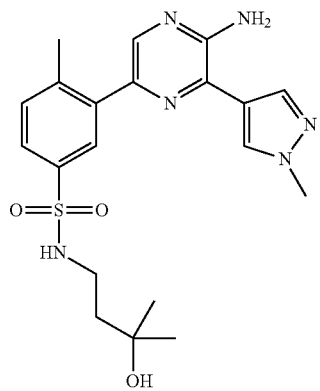
| | | | | |
|---|---|---|---|---|
| 119.17 | 3-(5-amino-6-(6-(pyrrolidin-1-yl)pyridin-3-yl)pyrazin-2-yl)-N-(3-hydroxy-3-methylbutyl)-4-methylbenzenesulfonamide | 1.00 | 497.7 | 2minLow pH_TFA |
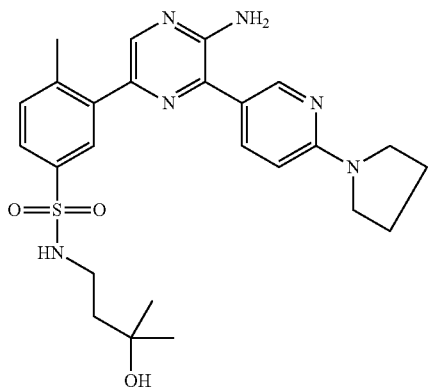

| Ex | Name | Rt (min) | MS m/z | LCMS Method |
|---|---|---|---|---|
| 119.18 | 3-(5-amino-6-(6-fluoropyridin-3-yl)pyrazin-2-yl)-N-(3-hydroxy-3-methylbutyl)-4-methylbenzenesulfonamide | 1.12 | 446.6 | 2minLow pH_TFA |
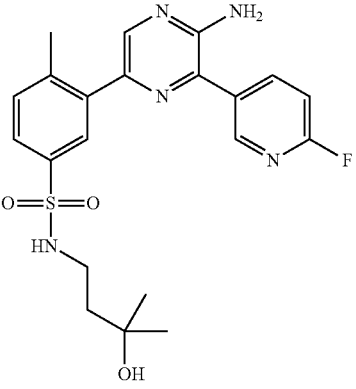
| 119.19 | 3-(5-amino-6-(1,5-dimethyl-1H-pyrazol-4-yl)pyrazin-2-yl)-N-(3-hydroxy-3-methylbutyl)-4-methylbenzenesulfonamide | 0.99 | no ionisation | 2minLow pH_TFA |
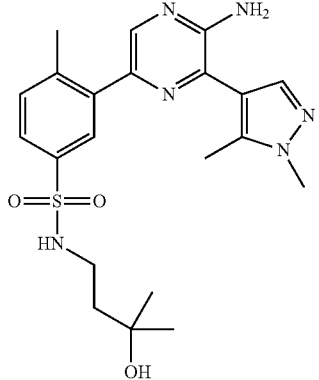
| 119.20 | 3-(5-amino-6-(pyrimidin-5-yl)pyrazin-2-yl)-N-(3-hydroxy-3-methylbutyl)-4-methylbenzenesulfonamide | 1.03 | 429.5 | 2minLow pH_TFA |
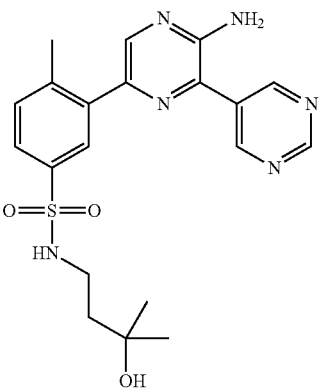

| Ex | Name | Rt (min) | MS m/z | LCMS Method |
| --- | --- | --- | --- | --- |
| 119.21 | 3-(5-amino-6-(6-morpholinopyridin-3-yl)pyrazin-2-yl)-N-(3-hydroxy-3-methylbutyl)-4-methylbenzenesulfonamide | 0.95 | 513.7 | 2minLow pH_TFA |
| 119.22 | 3-(5-amino-6-(3-methyl-1H-pyrazol-4-yl)pyrazin-2-yl)-N-(3-hydroxy-3-methylbutyl)-4-methylbenzenesulfonamide | 0.96 | 431.5 | 2minLow pH_TFA |
| 119.23 | 3-(5-amino-6-(6-(piperidin-1-yl)pyridin-3-yl)pyrazin-2-yl)-N-(3-hydroxy-3-methylbutyl)-4-methylbenzenesulfonamide | 1.02 | 511.6 | 2minLow pH_TFA |

-continued

| Ex | Name | Rt (min) | MS m/z | LCMS Method |
|---|---|---|---|---|
| 119.24 | 3-(5-amino-6-(6-(tetrahydro-2H-pyran-4-yloxy)pyridin-3-yl)pyrazin-2-yl)-N-(3-hydroxy-3-methylbutyl)-4-methylbenzenesulfonamide | 1.17 | 528.6 | 2minLow pH_TFA |
| 119.25 | 3-(5-amino-6-(1-propyl-1H-pyrazol-4-yl)pyrazin-2-yl)-N-(3-hydroxy-3-methylbutyl)-4-methylbenzenesulfonamide | 1.14 | 459.6 | 2minLow pH_TFA |
| 119.26 | 3-(5-amino-6-(1-isopentyl-1H-pyrazol-4-yl)pyrazin-2-yl)-N-(3-hydroxy-3-methylbutyl)-4-methylbenzenesulfonamide | 1.26 | 487.7 | 2minLow pH_TFA |

| Ex | Name | Rt (min) | MS m/z | LCMS Method |
|---|---|---|---|---|
| 119.27 | 3-(5-amino-6-(pyridin-4-yl)pyrazin-2-yl)-N-(3-hydroxy-3-methylbutyl)-4-methylbenzenesulfonamide | 0.68 | 428.4 | 2minLow pH |
| 119.28 | 3-(5-amino-6-(2-methylpyridin-4-yl)pyrazin-2-yl)-N-(3-hydroxy-3-methylbutyl)-4-methylbenzenesulfonamide | 0.65 | 442.0 | 2minLow pH |
| 119.29 | 3-(5-amino-6-(2-methylthiazol-5-yl)pyrazin-2-yl)-N-(3-hydroxy-3-methylbutyl)-4-methylbenzenesulfonamide | 0.9 | 448.3 | 2minLow pH |

-continued

| Ex | Name | Rt (min) | MS m/z | LCMS Method |
|---|---|---|---|---|
| 119.30 | 3-(5-amino-6-(2-methylthiazol-4-yl)pyrazin-2-yl)-N-(3-hydroxy-3-methylbutyl)-4-methylbenzenesulfonamide | 0.89 | 448.2 | 2minLow pH |
| 119.31 | 3-(5-amino-6-(1-isopropyl-1H-pyrazol-4-yl)pyrazin-2-yl)-N-(3-hydroxy-3-methylbutyl)-4-methylbenzenesulfonamide | 0.9 | 459.3 | 2minLow pH |
| 119.32 | 3-(5-amino-6-(1-isobutyl-1H-pyrazol-4-yl)pyrazin-2-yl)-N-(3-hydroxy-3-methylbutyl)-4-methylbenzenesulfonamide hydrochloride | 0.96 | 473.3 | 2minLow pH |

-continued

| Ex | Name | Rt (min) | MS m/z | LCMS Method |
|---|---|---|---|---|
| 119.33 | 3-(5-amino-6-(1H-pyrazol-4-yl)pyrazin-2-yl)-N-(3-hydroxy-3-methylbutyl)-4-methylbenzenesulfonamide | 0.76 | 417.2 | 2minLow pH |
| 119.34 | 3-(5-amino-6-(1H-ethyl-1H-pyrazol-4-yl)pyrazin-2-yl)-N-(3-hydroxy-3-methylbutyl)-4-methylbenzenesulfonamide | 0.86 | 445.3 | 2minLow pH |
| 119.35 | 3-(5-amino-6-(5-(hydroxymethyl)thiophen-2-yl)pyrazin-2-yl)-N-(3-hydroxy-3-methylbutyl)-4-methylbenzenesulfonamide | 0.86 | 463.4 | 2minLow pH |

-continued
| Ex | Name | Rt (min) | MS m/z | LCMS Method |
|---|---|---|---|---|
| 119.36 | 3-(5-amino-6-(1,3-dimethyl-1H-pyrazol-5-yl)pyrazin-2-yl)-N-(3-hydroxy-3-methylbutyl)-4-methylbenzenesulfonamide 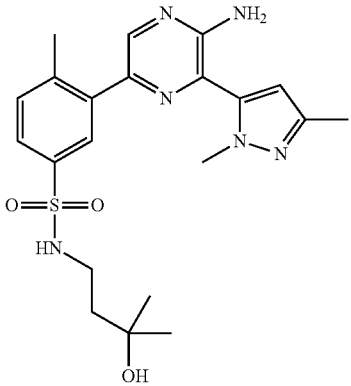 | 0.91 | 445.1 | 2minLow pHv01 |
| 119.37 | 3-(5-amino-6-(1-(pyridin-2-ylmethyl)-1H-pyrazol-4-yl)pyrazin-2-yl)-N-(3-hydroxy-3-methylbutyl)-4-methylbenzenesulfonamide 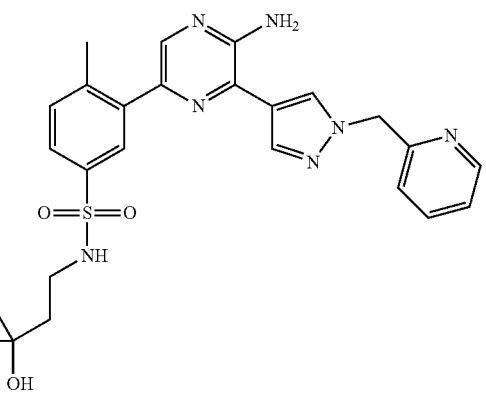 | 0.81 | 508.3 | 2minLow pH |
| 119.38 | 3-(5-amino-6-(1-(pyridin-3-ylmethyl)-1H-pyrazol-4-yl)pyrazin-2-yl)-N-(3-hydroxy-3-methylbutyl)-4-methylbenzenesulfonamide 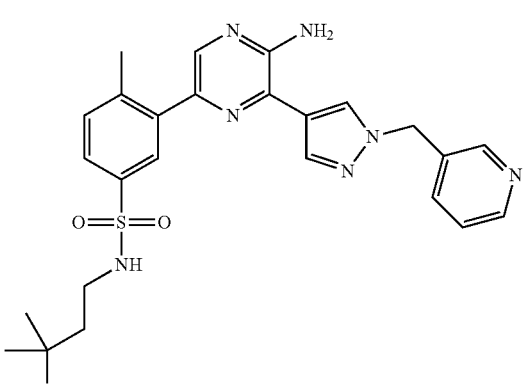 | 0.71 | 508.7 | 2minLow pH |

-continued

| Ex | Name | Rt (min) | MS m/z | LCMS Method |
|---|---|---|---|---|
| 119.39 | 3-(5-amino-6-(1-(pyridin-4-ylmethyl)-1H-pyrazol-4-yl)pyrazin-2-yl)-N-(3-hydroxy-3-methylbutyl)-4-methylbenzenesulfonamide | 0.67 | 508.7 | 2minLow pH |

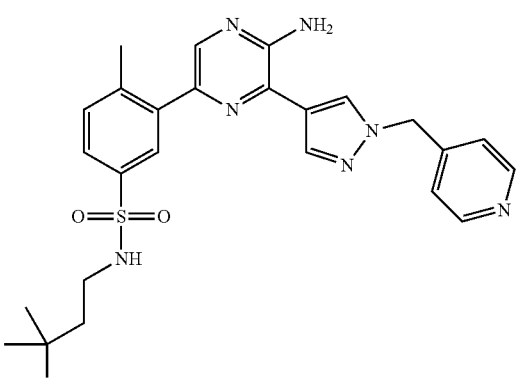

| 119.40 | 3-(5-amino-6-(2-methyloxazol-5-yl)pyrazin-2-yl)-N-(3-hydroxy-3-methylbutyl)-4-methylbenzenesulfonamide | 0.89 | 432.5 | 2minLow pHv01 |

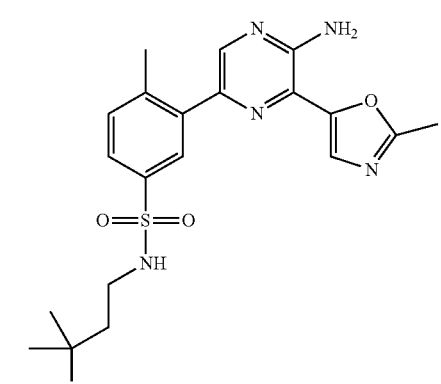

| 119.41 | 3-(5-amino-6-(1-(2-morpholinoethyl)-1H-pyrazol-4-yl)pyrazin-2-yl)-N-(3-hydroxy-3-methylbutyl)-4-methylbenzenesulfonamide hydrochloride | 0.63 | 530.5 | 2minLow pHv01 |

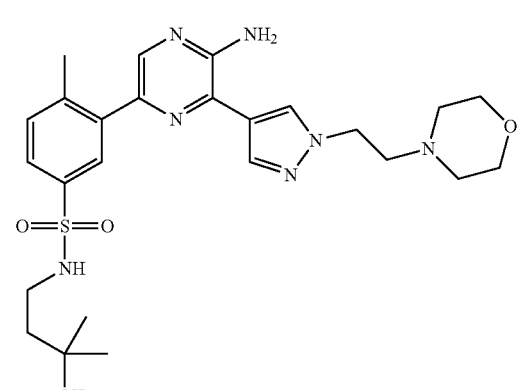

-continued

| Ex | Name | Rt (min) | MS m/z | LCMS Method |
|---|---|---|---|---|
| 119.42 | 3-(5-amino-6-(1H-pyrazol-3-yl)pyrazin-2-yl)-N-(3-hydroxy-3-methylbutyl)-4-methylbenzenesulfonamide | 0.96 | 417.2 | LowpH_v002 |
| 119.43 | 3-(5-amino-6-(4-methylthiophen-2-yl)pyrazin-2-yl)-N-(3-hydroxy-3-methylbutyl)-4-methylbenzenesulfonamide | 1 | 447.4 | LowpH_v002 |
| 119.44 | 3-(5-amino-6-(5-methylthiophen-2-yl)pyrazin-2-yl)-N-(3-hydroxy-3-methylbutyl)-4-methylbenzenesulfonamide | 0.99 | 447.5 | LowpH_v002 |

| Ex | Name | Rt (min) | MS m/z | LCMS Method |
|---|---|---|---|---|
| 119.45 | 3-(5-amino-6-(thiophen-2-yl)pyrazin-2-yl)-N-(3-hydroxy-3-methylbutyl)-4-methylbenzenesulfonamide | 0.95 | 433.5 | LowpH_v002 |
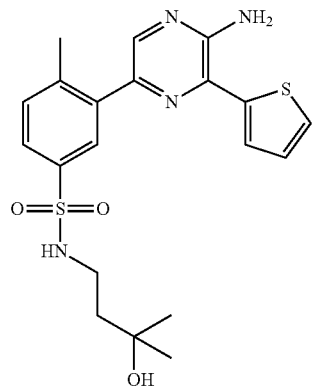
| 119.46 | 3-(5-amino-6-(5-cyclopropylthiophen-2-yl)pyrazin-2-yl)-N-(3-hydroxy-3-methylbutyl)-4-methylbenzenesulfonamide | 1.18 | 473.3 | LowpH_v002 |
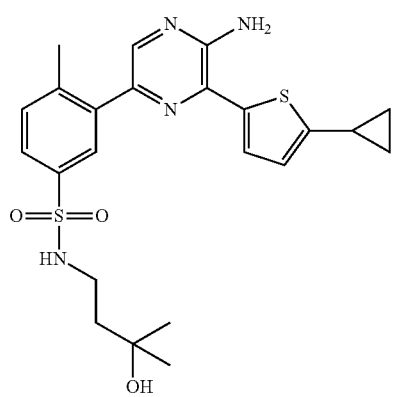

Example 120

3-(5-Amino-6-(2-methylthiazol-5-yl)pyrazin-2-yl)-4-methyl-N-((3-methyloxetan-3-yl)methyl)benzenesulfonamide

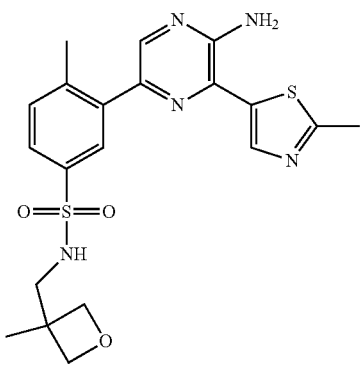

The title compound was prepared using 5-chloro-3-(2-methylthiazol-5-yl)pyrazin-2-amine (Intermediate C6) and 4-methyl-N-(3-methyl-oxetan-3-ylmethyl)-3-(4,4,5,5)tetramethyl-[1,3,2] dioxaborolan-2-yl)-benzenesulfonamide (Intermediate B4) under analogous conditions to those of Example 41;

LCMS: Rt 1.09 mins, MS m/z 446.2 [M+H]+; Method 2minLowpHv03.

Example 121

5-(5-Amino-6-(1H-1,2,4-triazol-1-yl)pyrazin-2-yl)-N-(2-hydroxy-2-methylpropyl)-2,4-dimethylbenzenesulfonamide

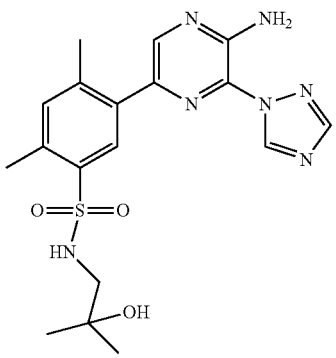 [SMILES: Cc1cc(C)c(S(=O)(=O)NCC(C)(C)O)cc1-c1cnc(N)c(-n2cncn2)n1]

Step 1: 5-Amino-6-(1H-1,2,4-triazol-1-yl)pyrazin-2-ylboronic acid

A mixture of bis(pinacolato)diboron (750 mg, 2.95 mmol), 5-bromo-3-(1H-1,2,4-triazol-1-yl)pyrazin-2-amine (Intermediate C11), potassium acetate (435 mg, 4.43 mmol) and PdCl$_2$(dppf).CH$_2$Cl$_2$ adduct (120 mg, 0.147 mmol) in 1,2-dimethoxyethane (14 mL) was heated in a microwave at 120° C. for 30 minutes. The resulting mixture was filtered through Celite®, washing with DCM and 5% methanol in DCM and the filtrate was evaporated under reduced pressure. The crude residue was dissolved in DCM (10 mL) and treated with pinacol (320 mg, 2.71 mmol) and stirred at room temperature. Hexane (20 mL) was added to the mixture and the resulting solid was collected by filtration, washed with water and dried in the vacuum oven to give the title compound as a grey solid;

LCMS: Rt 0.52 min; MS m/z 207.5 [M+H]+; Method: 2minLowpHv01

Step 2: 5-Bromo-N-(2-hydroxy-2-methylpropyl)-2,4-dimethylbenzenesulfonamide

To a stirring solution of 1-amino-2-methylpropan-2-ol (104 mg, 1.164 mmol) in DCM (5 mL), triethylamine (0.295 mL, 2.116 mmol) was added followed by 5-bromo-2,4-dimethylbenzene-1-sulfonyl chloride (300 mg, 1.058 mmol) and the reaction mixture was stirred for 30 minutes at room temperature. The resulting mixture was diluted in DCM and poured into a separating funnel. The solution was washed with 1M HCl and separated. The organic portion was washed with saturated brine, dried over MgSO$_4$ and filtered. The solvent was removed under reduced pressure to give a white solid;

LCMS: Rt 1.12 min; MS m/z 337.4 [M+H]+; Method: 2minLowpHv01

Step 3: 5-(5-Amino-6-(1H-1,2,4-triazol-1-yl)pyrazin-2-yl)-N-(2-hydroxy-2-methylpropyl)-2,4-dimethylbenzenesulfonamide 5-Bromo-N-(2-hydroxy-2-methylpropyl)-2,4-dimethylbenzenesulfonamide (from step 2) (176 mg, 0.523 mmol), 5-amino-6-(1H-1,2,4-triazol-1-yl)pyrazin-2-ylboronic acid (from step 1) (108 mg, 0.523 mmol), potassium phosphate (222 mg, 1.047 mmol) and [1,1'-bis(di-tert-butylphosphino)ferrocene]dichloropalladium(II) (17.06 mg, 0.026 mmol) were weighed out into the microwave vial. 1,4-Dioxane (2 ml) and water (0.500 ml) were added and the solution was placed in the microwave for 10 minutes at 100° C. The reaction mixture was diluted with water and ethyl acetate. The organic layer was extracted in a separating funnel by diluting with ethyl dried over magnesium sulphate and the solvent was removed under reduced pressure. The crude product was purified flash column chromatography, eluting in a 0% to 10% MeOH:DCM gradient, on a 12 g silica cartridge. The crude product was loaded on the column using DCM. The product fractions were combined and the solvent was removed to give a yellow solid.

LCMS: Rt 3.68 min; MS m/z 418.4 [M+H]+; Method: 10minLowpHv01

$^1$H NMR (400 MHz, DMSO-d6) δ 9.32 (1H, s), 8.42 (1H, s), 8.38 (1H, s), 7.89 (1H, s), 7.53 (1H, s), 7.37 (1H, s), 7.34 (1H, s), 5.76 (1H, s), 4.39 (1H, s), 2.72 (2H, s), 2.59 (3H, s), 2.47 (3H, s), 1.05 (6H, s)

Example 122

5-(5-Amino-6-(1H-1,2,4-triazol-1-yl)pyrazin-2-yl)-2-fluoro-N-(2-hydroxy-2-methylpropyl)-4-methyl-benzenesulfonamide

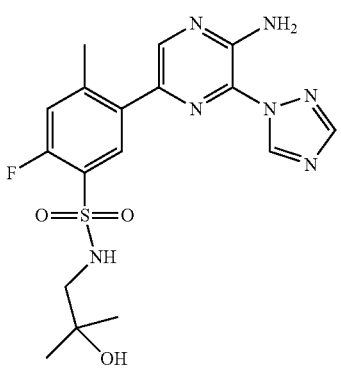 [SMILES: Cc1cc(F)c(S(=O)(=O)NCC(C)(C)O)cc1-c1cnc(N)c(-n2cncn2)n1]

Step 1: 5-bromo-2-fluoro-N-(2-hydroxy-2-methylpropyl)-4-methylbenzenesulfonamide To a stirring solution of 1-amino-2-methylpropan-2-ol (102 mg, 1.148 mmol) in DCM (10 ml), triethylamine (0.291 ml, 2.087 mmol) was added. 5-bromo-2-fluoro-4-methylbenzene-1-sulfonyl chloride (300 mg, 1.043 mmol) and stirring continued for 2 hrs. The reaction mixture was diluted with DCM and washed with 1M HCl and washed with saturated brine. The organic portion was dried over $MgSO_4$ and filtered. The solvent was removed under reduced pressure to afford the title compound;

LCMS: Rt 1.03 min; MS m/z 341.2 [M+H]+; Method: 2minLowpHv01

Step 2: 5-(5-Amino-6-(1H-1,2,4-triazol-1-yl)pyrazin-2-yl)-2-fluoro-N-(2-hydroxy-2-methylpropyl)-4-methylbenzenesulfonamide 5-Bromo-2-fluoro-N-(2-hydroxy-2-methylpropyl)-4-methylbenzenesulfonamide (step 1) (100 mg, 0.294 mmol), 5-amino-6-(1H-1,2,4-triazol-1-yl)pyrazin-2-ylboronic acid (see Example 121 step 1) (60.5 mg, 0.294 mmol), potassium phosphate (125 mg, 0.588 mmol) and [1,1'-bis(di-tert-butylphosphino)ferrocene]dichloropalladium(II) (9.58 mg, 0.015 mmol) were added to a microwave vial. 1,4-Dioxane (2 ml) and water (0.500 ml) were added and the reaction mixture was heated in the microwave at 100° C. for 10 minutes. The reaction mixture was diluted with ethyl acetate and washed with water and saturated brine. The organic portion was dried over $MgSO_4$, filtered and vacuum evaporated under reduced pressure. The crude product was purified by flash column chromatography, eluting in a 0% to 100% iso-hexane:EtOAc gradient, on a 12 g silica cartridge. The product fractions were combined and the solvent was removed to give the title compound as a yellow solid;

LCMS: Rt 3.44 min; MS m/z 422.2 [M+H]+; Method: 10minLowpHv01

$^1$H NMR (400 MHz, DMSO-d6) δ 9.32 (1H, s) 8.42 (1H, s) 8.38 (1H, s) 7.84 (1H, d) 7.72 (1H, s) 7.46 (1H, d) 7.37 (2H, s) 4.42 (1H, s) 2.80 (2H, s) 2.54 (3H, s), 1.07 (6H, s)

Example 123

3-(5-Amino-6-(1H-1,2,4-triazol-1-yl)pyrazin-2-yl)-N-(2-hydroxy-2-methylpropyl)benzenesulfonamide

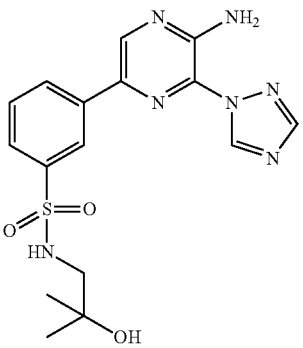 [SMILES: CC(C)(O)CNS(=O)(=O)c1cccc(-c2cnc(N)c(-n3cncn3)n2)c1]

Step 1: 3-Bromo-N-(2-hydroxy-2-methylpropyl)benzenesulfonamide

A mixture comprising 3-bromobenzene-1-sulfonyl chloride (300 mg, 1.174 mmol), 1-amino-2-methylpropan-2-ol (115 mg, 1.292 mmol), triethylamine (0.327 ml, 2.348 mmol) and DCM (10 ml) was stirred at room temperature for 1 hour. The resulting mixture was diluted with DCM and washed with 1M HCl, sat. sodium bicarbonate solution and dried over $MgSO_4$. The solution was then filtered and vacuum evaporated to remove the solvent. This gave the title compound as a yellow crystalline solid;

LCMS: Rt 0.92 min; MS m/z 308.1 [M+H]+; Method: 2minLowpHv01

Step 2: 3-(5-Amino-6-(1H-1,2,4-triazol-1-yl)pyrazin-2-yl)-N-(2-hydroxy-2-methylpropyl)benzenesulfonamide 3-Bromo-N-(2-hydroxy-2-methylpropyl)benzenesulfonamide (from step 1) (100 mg, 0.324 mmol), 5-amino-6-(1H-1,2,4-triazol-1-yl)pyrazin-2-ylboronic acid (see Example 121 step 1) (66.8 mg, 0.324 mmol), potassium phosphate (138 mg, 0.649 mmol) and [1,1'-bis(di-tert-butylphosphino)ferrocene]dichloropalladium(II) (10.57 mg, 0.016 mmol) was added to a microwave vial. 1,4-Dioxane (2 mL) and water (0.500 mL) were added and the mixture was heated using microwave radiation for 10 minutes. The reaction mixture was washed with ethyl acetate and water. The solution was washed with saturated brine and then separated. The solution was dried over $MgSO_4$, filtered and vacuum evaporated on a rotary evaporator to give a brown oil. The crude product was purified by flash column chromatography, eluting in a 0% to 100% iso-hexane:EtOAc gradient, on a 4 g silica cartridge, crude product was dry loaded on the column. The relevant fractions were combined and the solvent was removed to give a light green solid;

LCMS: Rt 3.28 min; MS m/z 390.5 [M+H]+; Method: 10minLowpHv01

$^1$H NMR (400 MHz, DMSO-d6) δ 9.56 (1H, s) 8.85 (1H, s) 8.48 (1H, s) 8.44 (1H, s) 8.34 (1H, d) 7.79 (1H, d) 7.68 (1H, t) 7.63 (1H, s) 7.46 (2H, s) 4.43 (1H, s) 2.65 (2H, s) 1.07 (6H, s)

Example 124

5-(5-Amino-6-(1H-1,2,4-triazol-1-yl)pyrazin-2-yl)-2-chloro-N-(2-hydroxy-2-methylpropyl)-4-methylbenzenesulfonamide

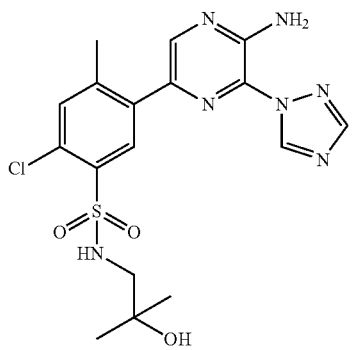 [SMILES: Cc1cc(Cl)c(S(=O)(=O)NCC(C)(C)O)cc1-c1cnc(N)c(-n2cncn2)n1]

Step 1: 5-Bromo-2-chloro-N-(2-hydroxy-2-methylpropyl)-4-methylbenzenesulfonamide To a round bottom flask was added 1-bromo-4-chloro-2-methylbenzene (300 mg, 1.460 mmol). At 0° C. was added chlorosulfonic acid (2.347 mL, 35.0 mmol) in CHCl₃ (10 mL). The reaction mixture was warmed to RT and stirred for 2 hours. The reaction mixture was added to ice cold water and DCM and was stirred. The organic layer was separated and treated with 1-amino-2-methylpropan-2-ol (143 mg, 1.606 mmol) and triethylamine (0.407 mL, 2.92 mmol) and stirring continued RT for 1 hr. The reaction mixture was washed with 1M HCl and saturated bicarbonate solution. The organic layer was separated, dried over MgSO₄ and filtered. The solvent was removed under reduced pressure to give a brown oil. The crude product was purified by flash column chromatography, eluting in a 0% to 40% iso-hexane:EtOAc gradient, on a 4 g silica cartridge, crude product was dry loaded on the column. The relevant fractions were combined and the solvent was removed to give a white solid;

LCMS: Rt 1.18 min; MS m/z 356.1 [M+H]+; Method: 2minLowpHv01

Step 2: 5-(5-Amino-6-(1H-1,2,4-triazol-1-yl)pyrazin-2-yl)-2-chloro-N-(2-hydroxy-2-methylpropyl)-4-methylbenzenesulfonamide To a microwave vial was added 5-bromo-2-chloro-N-(2-hydroxy-2-methylpropyl)-4-methylbenzenesulfonamide (step 1) (60 mg, 0.168 mmol), 5-amino-6-(1H-1,2,4-triazol-1-yl)pyrazin-2-ylboronic acid (see Example 121 step 1) (34.6 mg, 0.168 mmol), bis(triphenylphosphine)palladium dichloride (5.90 mg, 8.41 μmol), sodium carbonate (53.5 mg, 0.505 mmol) in DME (1 mL). The reaction mixture was placed in a microwave for 20 minutes at 70° C. and then 5 minutes at 100° C. The reaction mixture was washed with water and EtOAc. The organic layer was then separated, dried over MgSO₄ and then filtered. The solvent was removed under reduced pressure to give a brown solid. The crude product was purified by flash column chromatography, eluting in a 0% to 10% DCM:MeOH/NH₃ gradient, on a 4 g silica cartridge, crude product was dry loaded on the column. The relevant fractions were combined and the solvent was removed to give a yellow solid;

LCMS: Rt 3.61 min; MS m/z 438.3 [M+H]+; Method: 10minLowpHv01

¹H NMR (400 MHz, DMSO-d6) δ 9.33 (1H, s) 8.422 (1H, s) 8.419 (1H, s) 8.02 (1H, s) 7.67 (1H, s) 7.62 (1H, s) 7.42 (2H, s) 4.43 (1H, s) 2.50 (3H, s) 2.80 (2H, d) 1.07 (6H, s).

Example 125

3-(5-Amino-6-(1,3-dimethyl-1H-pyrazol-4-yl)pyrazin-2-yl)-N-(2-hydroxy-2-methylpropoxy)-4-methylbenzenesulfonamide

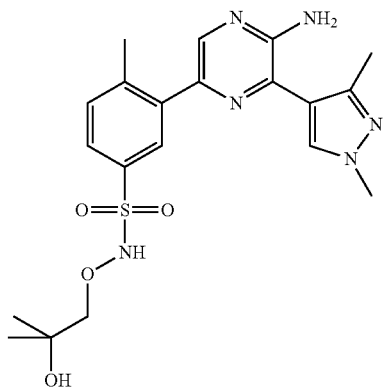 [SMILES: Cc1ccc(S(=O)(=O)NOCC(C)(C)O)cc1-c1cnc(N)c(-c2cn(C)nc2C)n1]

To 3-(5-amino-6-(1,3-dimethyl-1H-pyrazol-4-yl)pyrazin-2-yl)-4-methylbenzene-1-sulfonyl chloride (Intermediate E3) (338 mg, 0.895 mmol) in THF (6 mL) was added 1-(aminooxy)-2-methylpropan-2-ol (103 mg, 0.984 mmol) and pyridine (0.080 mL, 0.984 mmol). The reaction mixture was stirred at RT over the weekend. The solvent removed under reduced pressure to give a brown solid. The product was dissolved in 1 ml DMSO and purified by preparative HPLC. The product fractions were washed with saturated bicarbonate solution and dried over MgSO₄, filtered and the solvent removed under reduced pressure to give an oil which was triturated with diethyl ether to give a pale yellow solid;

LCMS: Rt 3.45 min; MS m/z 447.2 [M+H]+; Method: 10minLowpHv01

¹H NMR (400 MHz, MeOD-d4) δ 8.03 (1H, s) 7.97 (1H, s) 7.96 (1H, d) 7.83 (1H, d) 7.54 (1H, d) 3.91 (3H, s) 3.85 (2H, s) 2.51 (3H, s) 2.36 (3H, s) 1.15 (6H, s)

Example 126

3-(5-Amino-6-(2-methyloxazol-5-yl)pyrazin-2-yl)-N-(2-hydroxy-2-methylpropyl)-4-methylbenzenesulfonamide

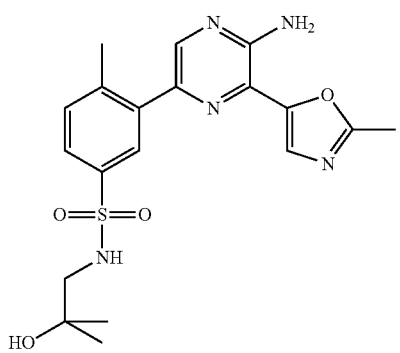 [SMILES: Cc1ncc(-c2nc(-c3cc(S(=O)(=O)NCC(C)(C)O)ccc3C)cnc2N)o1]

To 3-(5-amino-6-chloro-pyrazin-2-yl)-N-(2-hydroxy-2-methyl-propyl)-4-methyl-benzenesulfonamide (Intermediate D2) (140 mg, 0.378 mmol), 2-methyl-5-(4,4,5,5-tetramethyl-1,3,2-dioxaborolan-2-yl)oxazole (79 mg, 0.378 mmol), potassium phosphate (160 mg, 0.755 mmol) and [1,1'-bis(di-tert-butylphosphino)ferrocene]dichloropalladium(II) (24.60 mg, 0.038 mmol) in 1,4-dioxane (2 mL), water (0.500 mL) was added. The reaction mixture was stirred at 120° C. for 20 mins in the microwave. The reaction mixture was poured into water and the product was extracted using EtOAc. The organic layer was separated and washed with water and brine then dried over MgSO$_4$. Isolute® Si-TMT was added to the filtrate and this was stirred for 1 hr and filtered. The solvent was removed under reduced pressure. The crude product was purified by flash column chromatography, eluting in a 0% to 10% TBME:MeOH gradient, on a 12 g silica cartridge, the crude product was dry loaded on the column. The product fractions were combined and the solvent was removed under reduced pressure to afford the title compound;

LCMS: Rt 2.91 min; MS m/z 418.5 [M+H]+; Method: 8minLowpHv01

$^1$H NMR (400 MHz, DMSO-d6) δ 8.24 (1H, s), 7.87-7.83 (1H, m), 7.74-7.65 (2H, m), 7.56-7.43 (2H, m), 6.73 (2H, s), 4.40 (1H, s), 2.62 (2H, br. s.), 2.54 (3H, s), 2.46 (3H, s), 1.06 (6H, s)

Example 127

3-(5-Amino-6-(1H-1,2,4-triazol-1-yl)pyrazin-2-yl)-4-methyl-N-(2,2,2-trifluoroethyl)benzenesulfonamide

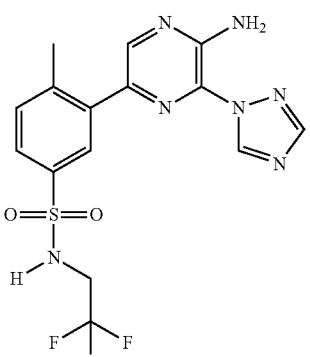

To 2,2,2-trifluoroethanamine (15 mg, 0.15 mmol) was added DMA (1 ml) followed by DIPEA (0.035 ml, 0.200 mmol). The reaction mixture was shaken at RT for 30 mins and then treated with 3-(5-amino-6-(1H-1,2,4-triazol-1-yl)pyrazin-2-yl)-4-methylbenzene-1-sulfonyl chloride (Intermediate E1) (0.1 mmol) and DMA (1 ml). The resulting mixture was shaken at RT for 3 hrs and then concentrated under reduced pressure. The crude product was purified by HPLC (acetonitrile/water gradient, 0.1% TFA modifier) and the product fractions were combined and evaporated to give the title compound;

LCMS: Rt 0.82 min; MS m/z 414.1 [M+H]+; Method: 2minLowpHv01

The following examples were prepared by analogous conditions to those described for the preparation of Example 127 starting from 3-(5-amino-6-(1H-1,2,4-triazol-1-yl)pyrazin-2-yl)-4-methylbenzene-1-sulfonyl chloride (Intermediate E1) and the appropriate commercially available amine. (Amines used in Examples 127.22 and 127.23 can be prepared according to the procedure described in patent application WO2011/113894 page 99). Final compounds were purified by appropriate techniques known in the art. Where trifluoroacetic acid salt formation is indicated, this was formed due to the presence of TFA as modifier in the reverse-phase purification and a basic centre in the molecule. LCMS Method 2minLowpHv01 used unless otherwise stated.

| Ex. | Name | Rt (min) | MS m/z (M + H)+ unless stated |
|---|---|---|---|
| 127.1 | 5-(5-(3,3-difluoropiperidin-1-ylsulfonyl)-2-methylphenyl)-3-(1H-1,2,4-triazol-1-yl)pyrazin-2-amine | 1.12 | 436.2 |
| 127.2 | 5-(5-(3-fluoropyrrolidin-1-ylsulfonyl)-2-methylphenyl)-3-(1H-1,2,4-triazol-1-yl)pyrazin-2-amine | 1.01 | 404.1 |
| 127.3 | 5-(5-(3,3-difluoropyrrolidin-1-ylsulfonyl)-2-methylphenyl)-3-(1H-1,2,4-triazol-1-yl)pyrazin-2-amine | 1.08 | 422.1 |

| Ex. | Name | Rt (min) | MS m/z (M + H)+ unless stated |
|---|---|---|---|
| 127.4 | 5-(5-(3,3-difluoroazetidin-1-ylsulfonyl)-2-methylphenyl)-3-(1H-1,2,4-triazol-1-yl)pyrazin-2-amine | 1.05 | 408.1 |
| 127.5 | 5-(5-(3-fluoroazetidin-1-ylsulfonyl)-2-methylphenyl)-3-(1H-1,2,4-triazol-1-yl)pyrazin-2-amine | 0.99 | 390.1 |
| 127.6 | 3-(5-amino-6-(1H-1,2,4-triazol-1-yl)pyrazin-2-yl)-N-(4-(hydroxymethyl)cyclohexyl)-4-methylbenzenesulfonamide | 0.93 | 444.2 |

| Ex. | Name | Rt (min) | MS m/z (M + H)+ unless stated |
|---|---|---|---|
| 127.7 | 3-(5-amino-6-(1H-1,2,4-triazol-1-yl)pyrazin-2-yl)-N-(3,3-difluorocyclobutyl)-4-methylbenzenesulfonamide | 1.05 | 422.2 |
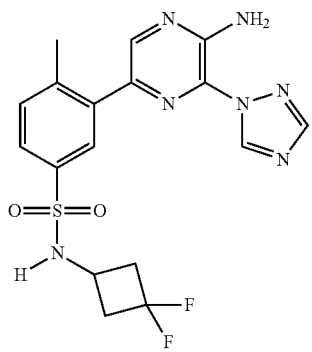
| 127.8 | 5-(2-methyl-5-(3,3,4,4-tetrafluoropyrrolidin-1-ylsulfonyl)phenyl)-3-(1H-1,2,4-triazol-1-yl)pyrazin-2-amine | 1.16 | 458.1 |
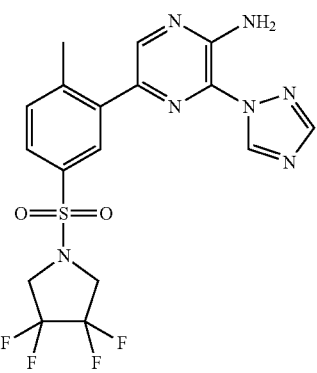
| 127.9 | 3-(5-amino-6-(1H-1,2,4-triazol-1-yl)pyrazin-2-yl)-N-(5-hydroxypentyl)-4-methylbenzenesulfonamide | 0.91 | 418.2 |
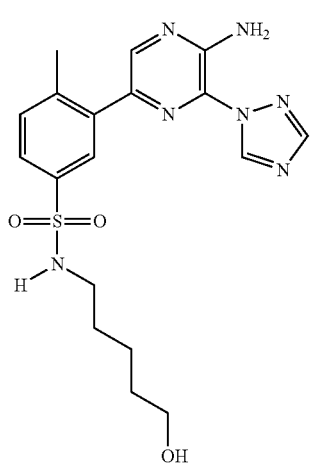

-continued
| Ex. | Name | Rt (min) | MS m/z (M + H)+ unless stated |
|---|---|---|---|
| 127.10 | 3-(5-amino-6-(1H-1,2,4-triazol-1-yl)pyrazin-2-yl)-N-(3-methoxypropyl)-4-methylbenzenesulfonamide | 0.96 | 404.2 |
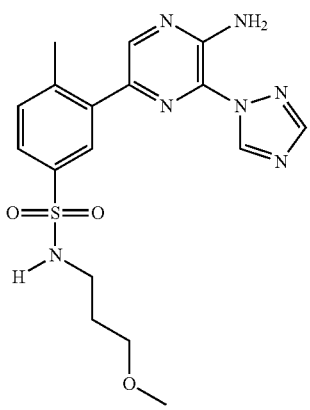
| 127.11 | 3-(5-amino-6-(1H-1,2,4-triazol-1-yl)pyrazin-2-yl)-N-((1-hydroxycyclohexyl)methyl)-4-methylbenzenesulfonamide | 1.04 | 426.2 (M-17) |
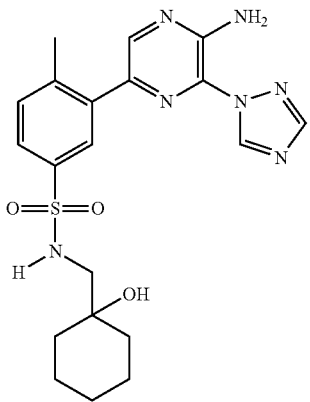
| 127.12 | (R)-3-(5-amino-6-(1H-1,2,4-triazol-1-yl)pyrazin-2-yl)-N-((1-ethylpyrrolidin-2-yl)methyl)-4-methylbenzenesulfonamide trifluoroacetic acid salt | 0.76 | 443.2 |
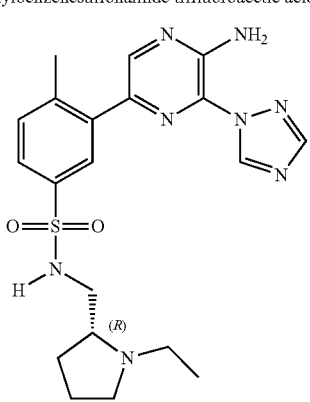

| Ex. | Name | Rt (min) | MS m/z (M + H)+ unless stated |
|---|---|---|---|
| 127.13 | (R)-3-(5-amino-6-(1H-1,2,4-triazol-1-yl)pyrazin-2-yl)-N-(2-hydroxypropyl)-4-methylbenzenesulfonamide | 0.87 | 390.1 |
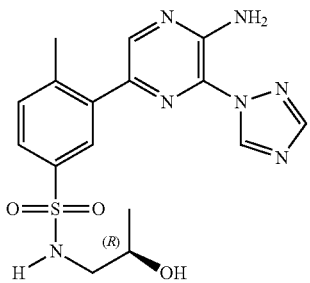
| 127.14 | (R)-3-(5-amino-6-(1H-1,2,4-triazol-1-yl)pyrazin-2-yl)-4-methyl-N-((tetrahydrofuran-2-yl)methyl)benzenesulfonamide | 0.97 | 416.1 |
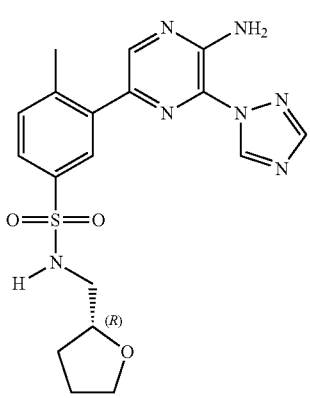
| 127.16 | 3-(5-amino-6-(1H-1,2,4-triazol-1-yl)pyrazin-2-yl)-N-((1-hydroxycyclobutyl)methyl)-4-methylbenzenesulfonamide | 0.95 | 416.1 |
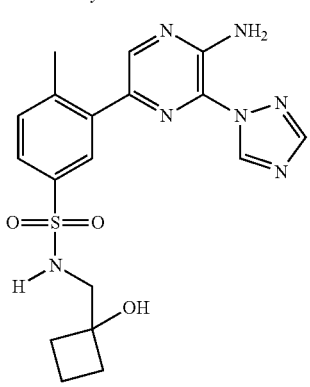

-continued
| Ex. | Name | Rt (min) | MS m/z (M + H)+ unless stated |
|---|---|---|---|
| 127.17 | 3-(5-amino-6-(1H-1,2,4-triazol-1-yl)pyrazin-2-yl)-4-methyl-N-((tetrahydro-2H-pyran-2-yl)methyl)benzenesulfonamide | 1.05 | 430.2 |
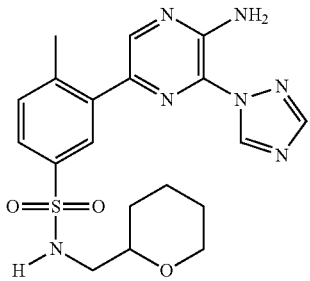
| 127.18 | 3-(5-amino-6-(1H-1,2,4-triazol-1-yl)pyrazin-2-yl)-4-methyl-N-((1-methylpyrrolidin-3-yl)methyl)benzenesulfonamide trifluoroacetic acid salt | 0.74 | 429.2 |
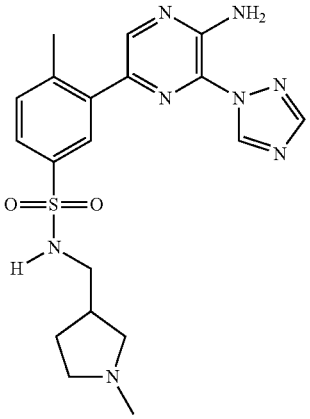
| 127.19 | 3-(5-amino-6-(1H-1,2,4-triazol-1-yl)pyrazin-2-yl)-4-methyl-N-((tetrahydro-2H-pyran-3-yl)methyl)benzenesulfonamide | 0.99 | 430.2 |
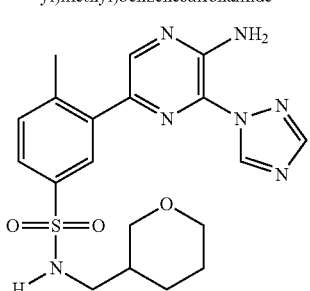

-continued

| Ex. | Name | Rt (min) | MS m/z (M + H)+ unless stated |
|---|---|---|---|
| 127.20 | (R)-3-(5-amino-6-(1H-1,2,4-triazol-1-yl)pyrazin-2-yl)-4-methyl-N-(tetrahydrofuran-3-yl)benzenesulfonamide | 0.91 | 402.1 |
| 127.21 | (S)-3-(5-amino-6-(1H-1,2,4-triazol-1-yl)pyrazin-2-yl)-4-methyl-N-(tetrahydrofuran-3-yl)benzenesulfonamide | 0.91 | 402.1 |
| 127.22 | (R)-3-(5-amino-6-(1H-1,2,4-triazol-1-yl)pyrazin-2-yl)-4-methyl-N-(3,3,3-trifluoro-2-hydroxy-2-methylpropyl)benzenesulfonamide | 1.01 | 458.2 |

| Ex. | Name | Rt (min) | MS m/z (M + H)+ unless stated |
|---|---|---|---|
| 127.23 | (S)-3-(5-amino-6-(1H-1,2,4-triazol-1-yl)pyrazin-2-yl)-4-methyl-N-(3,3,3-trifluoro-2-hydroxy-2-methylpropyl)benzenesulfonamide | 1.01 | 458.2 |
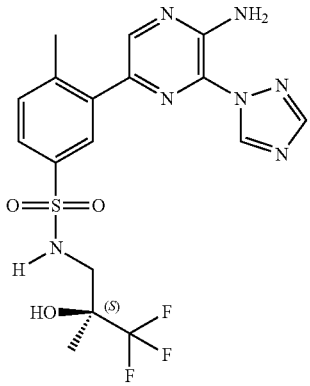
| 127.24 | 3-(5-amino-6-(1H-1,2,4-triazol-1-yl)pyrazin-2-yl)-4-methyl-N-(4,4,4-trifluoro-3-hydroxy-3-methylbutyl)benzenesulfonamide | 1.02 | 472.2 |
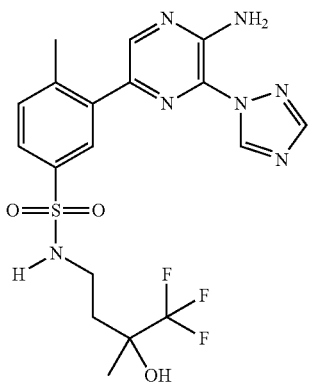
| 127.25 | 3-(5-amino-6-(1H-1,2,4-triazol-1-yl)pyrazin-2-yl)-N-((1-(hydroxymethyl)cyclopentyl)methyl)-4-methylbenzenesulfonamide | 0.91 | 444.2 |
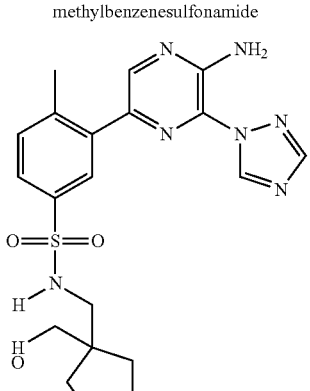

-continued
| Ex. | Name | Rt (min) | MS m/z (M + H)+ unless stated |
|---|---|---|---|
| 127.26 | (S)-3-(5-amino-6-(1H-1,2,4-triazol-1-yl)pyrazin-2-yl)-4-methyl-N-((tetrahydrofuran-3-yl)methyl)benzenesulfonamide 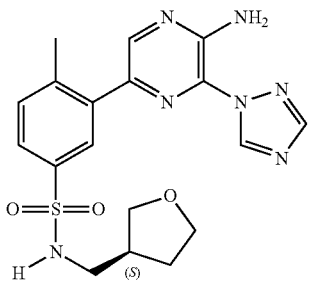 | 0.79 | 416.1 |
| 127.27 | (R)-3-(5-amino-6-(1H-1,2,4-triazol-1-yl)pyrazin-2-yl)-4-methyl-N-((tetrahydrofuran-3-yl)methyl)benzenesulfonamide 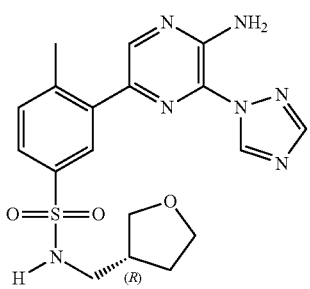 | 0.79 | 416.1 |
| 127.28 | 3-(5-amino-6-(1H-1,2,4-triazol-1-yl)pyrazin-2-yl)-N-(2-fluoroethyl)-4-methylbenzenesulfonamide 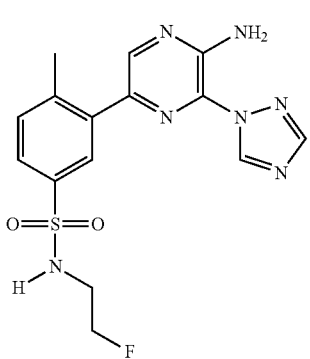 | 0.75 | 378.2 |

| Ex. | Name | Rt (min) | MS m/z (M + H)+ unless stated |
|---|---|---|---|
| 127.29 | 3-(5-amino-6-(1H-1,2,4-triazol-1-yl)pyrazin-2-yl)-N-(3-fluoropropyl)-4-methylbenzenesulfonamide | 0.81 | 392.1 |
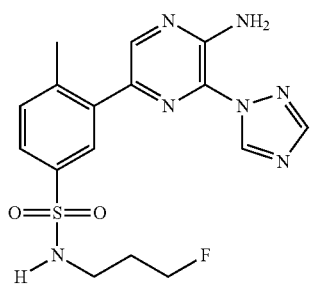
| 127.30 | 3-(5-amino-6-(1H-1,2,4-triazol-1-yl)pyrazin-2-yl)-4-methyl-N-(2-oxotetrahydrofuran-3-yl)benzenesulfonamide | 0.90 | 416.1 |
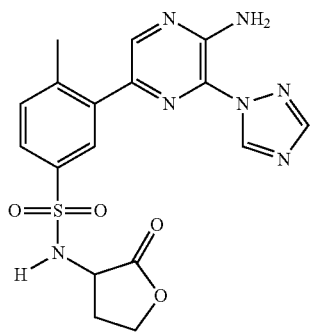
| 127.31 | 3-(5-amino-6-(1H-1,2,4-triazol-1-yl)pyrazin-2-yl)-4-methyl-N-(3,3,3-trifluoropropyl)benzenesulfonamide | 1.06 | 428.2 |
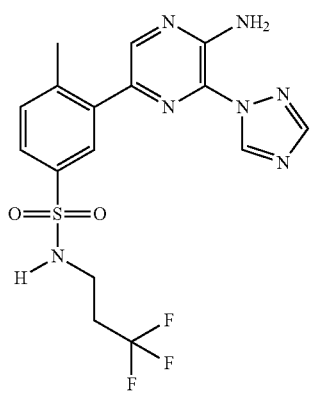

-continued
| Ex. | Name | Rt (min) | MS m/z (M + H)+ unless stated |
|---|---|---|---|
| 127.32 | 3-(5-amino-6-(1H-1,2,4-triazol-1-yl)pyrazin-2-yl)-4-methyl-N-(2-methyl-2-morpholinopropyl)benzenesulfonamide trifluoroacetic acid salt | 0.73 | 473.3 |
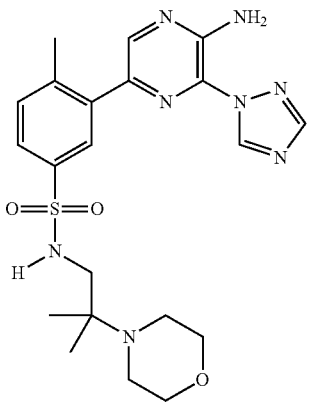
| 127.33 | 5-(5-(4,4-difluoropiperidin-1-ylsulfonyl)-2-methylphenyl)-3-(1H-1,2,4-triazol-1-yl)pyrazin-2-amine | 1.11 | 436.2 |
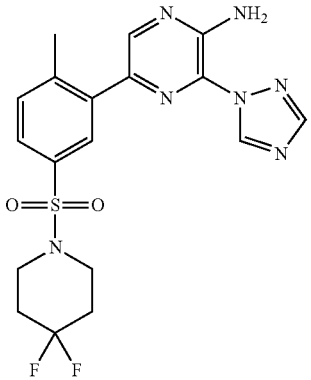
| 127.34 | 5-(5-(4-fluoropiperidin-1-ylsulfonyl)-2-methylphenyl)-3-(1H-1,2,4-triazol-1-yl)pyrazin-2-amine | 1.08 | 418.2 |
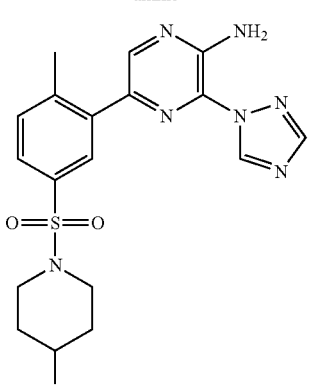

-continued
| Ex. | Name | Rt (min) | MS m/z (M + H)+ unless stated |
|---|---|---|---|
| 127.35 | 3-(5-amino-6-(1H-1,2,4-triazol-1-yl)pyrazin-2-yl)-N-((1-hydroxycyclopentyl)methyl)-4-methylbenzenesulfonamide | 0.99 | 412.2 (M-17) |
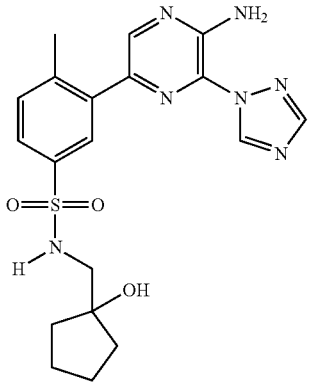
| 127.36 | 3-(5-amino-6-(1H-1,2,4-triazol-1-yl)pyrazin-2-yl)-N-(2-(1-hydroxycyclopentyl)ethyl)-4-methylbenzenesulfonamide | 1.02 | 426.2 (M-17) |
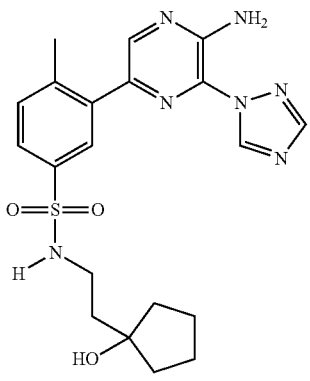
| 127.37 | 3-(5-amino-6-(1H-1,2,4-triazol-1-yl)pyrazin-2-yl)-N-(2-(1-hydroxycyclohexyl)ethyl)-4-methylbenzenesulfonamide | 1.06 | 440.2 (M-17) |
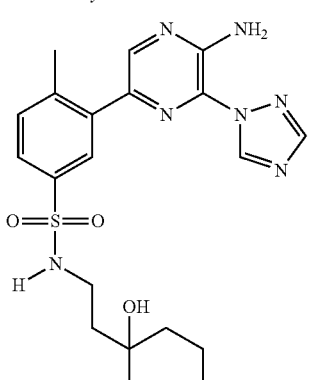

| Ex. | Name | Rt (min) | MS m/z (M + H)+ unless stated |
|---|---|---|---|
| 127.38 | 3-(5-amino-6-(1H-1,2,4-triazol-1-yl)pyrazin-2-yl)-N-((1-(hydroxymethyl)cyclopropyl)methyl)-4-methylbenzenesulfonamide | 0.92 | 398.1 (M-17) |
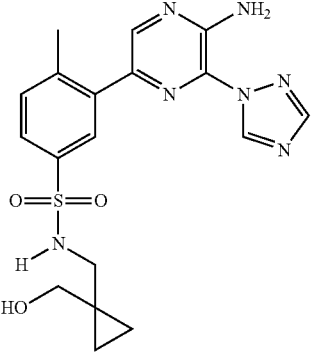
| 127.39 | (S)-3-(5-amino-6-(1H-1,2,4-triazol-1-yl)pyrazin-2-yl)-N-((5,5-dimethyltetrahydrofuran-2-yl)methyl)-4-methylbenzenesulfonamide | 1.1 | 444.2 |
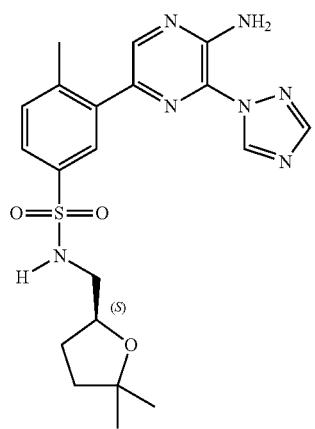
| 127.40 | (R)-3-(5-amino-6-(1H-1,2,4-triazol-1-yl)pyrazin-2-yl)-N-((5,5-dimethyltetrahydrofuran-2-yl)methyl)-4-methylbenzenesulfonamide | 1.07 | 444.2 |
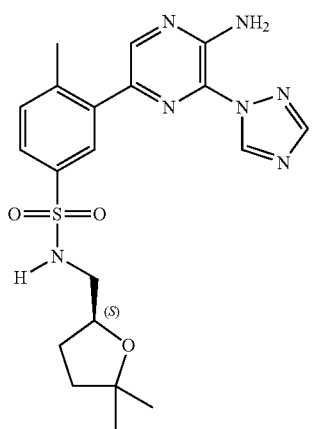

-continued
| Ex. | Name | Rt (min) | MS m/z (M + H)+ unless stated |
|---|---|---|---|
| 127.41 | (S)-3-(5-amino-6-(1H-1,2,4-triazol-1-yl)pyrazin-2-yl)-N-(1-hydroxypropan-2-yl)-4-methylbenzenesulfonamide | 0.87 | 390.1 |
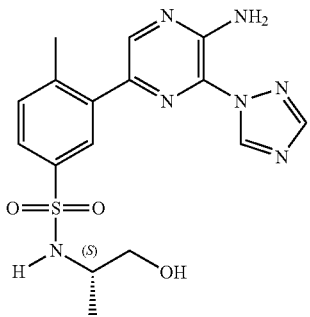
| 127.42 | 3-(5-amino-6-(1H-1,2,4-triazol-1-yl)pyrazin-2-yl)-N-(1-hydroxypropan-2-yl)-4-methylbenzenesulfonamide | 0.87 | 390.2 |
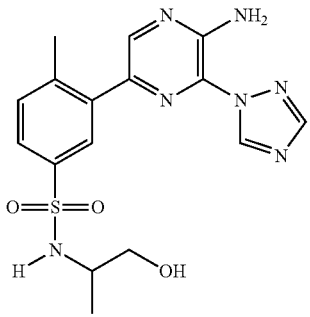
| 127.43 | 3-(5-amino-6-(1H-1,2,4-triazol-1-yl)pyrazin-2-yl)-N-(2,2-difluoropropyl)-4-methylbenzenesulfonamide | 1.02 | 410.2 |
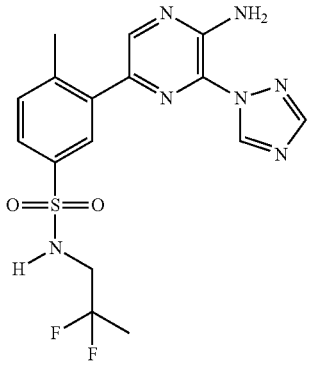 [SMILES: Cc1ccc(S(=O)(=O)NCC(F)(F)F)cc1-c1cnc(N)c(-n2cncn2)n1]

-continued

| Ex. | Name | Rt (min) | MS m/z (M + H)+ unless stated |
|---|---|---|---|
| 127.44 | 3-(5-amino-6-(1H-1,2,4-triazol-1-yl)pyrazin-2-yl)-4-methyl-N-(3-methylbutan-2-yl)benzenesulfonamide | 1.13 | 402.2 |
| 127.45 | (1-(3-(5-amino-6-(1H-1,2,4-triazol-1-yl)pyrazin-2-yl)-4-methylphenylsulfonyl)azetidin-3-yl)methanol | 0.88 | 402.1 |
| 127.46 | 1-(3-(5-amino-6-(1H-1,2,4-triazol-1-yl)pyrazin-2-yl)-4-methylphenylsulfonyl)-3-methylazetidin-3-ol | 0.83 | 402.4 |

-continued
| Ex. | Name | Rt (min) | MS m/z (M + H)+ unless stated |
|---|---|---|---|
| 127.47 | 3-(5-amino-6-(1H-1,2,4-triazol-1-yl)pyrazin-2-yl)-N-((3-hydroxyoxetan-3-yl)methyl)-4-methylbenzenesulfonamide | 0.81 | 418.5 |
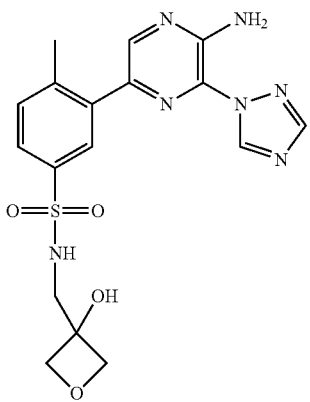
| 127.48 | (R)-3-(5-amino-6-(1H-1,2,4-triazol-1-yl)pyrazin-2-yl)-N-(1-cyano-2-hydroxyethyl)-4-methylbenzenesulfonamide | 0.85 | 401.1 |
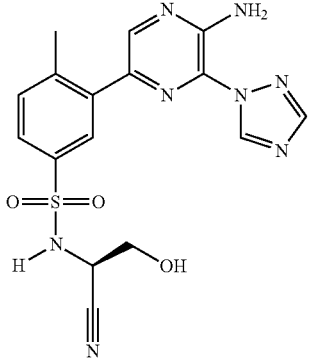
| 127.49 | 3-(5-amino-6-(1H-1,2,4-triazol-1-yl)pyrazin-2-yl)-N-((1-(hydroxymethyl)cyclobutyl)methyl)-4-methylbenzenesulfonamide | 0.94 | 430.2 |
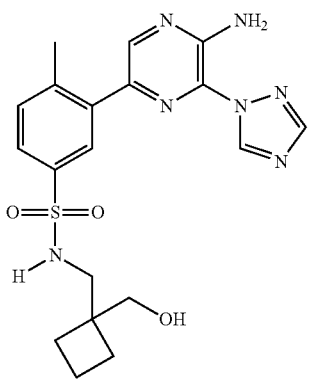

| Ex. | Name | Rt (min) | MS m/z (M + H)+ unless stated |
|---|---|---|---|
| 127.50 | 3-(5-amino-6-(1H-1,2,4-triazol-1-yl)pyrazin-2-yl)-N-((4-(hydroxymethyl)tetrahydro-2H-pyran-4-yl)methyl)-4-methylbenzenesulfonamide | 0.88 | 460.2 |
| 127.51 | 3-(5-amino-6-(1H-1,2,4-triazol-1-yl)pyrazin-2-yl)-4-methyl-N-(2-oxotetrahydrothiophen-3-yl)benzenesulfonamide | 0.98 | 432.1 |
| 127.52 | 3-(5-amino-6-(1H-1,2,4-triazol-1-yl)pyrazin-2-yl)-N-((1-(hydroxymethyl)cyclohexyl)methyl)-4-methylbenzenesulfonamide | 1.08 | 458.3 |

-continued
| Ex. | Name | Rt (min) | MS m/z (M + H)+ unless stated |
|---|---|---|---|
| 127.53 | 3-(5-amino-6-(1H-1,2,4-triazol-1-yl)pyrazin-2-yl)-N-cyclopropyl-4-methylbenzenesulfonamide | 0.97 | 372.7 |
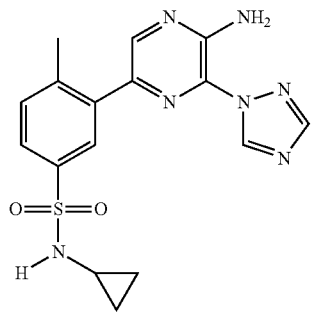
| 127.54 | 3-(5-amino-6-(1H-1,2,4-triazol-1-yl)pyrazin-2-yl)-N-cyclobutyl-4-methylbenzenesulfonamide | 1.03 | 386.2 |
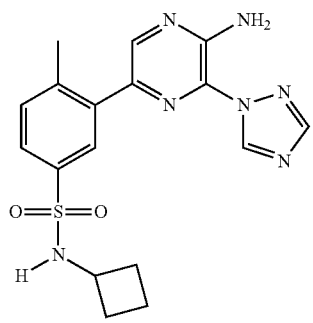
| 127.55 | 3-(5-amino-6-(1H-1,2,4-triazol-1-yl)pyrazin-2-yl)-N-cyclopentyl-4-methylbenzenesulfonamide | 1.08 | 400.2 |
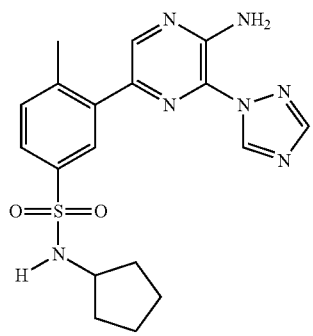

| Ex. | Name | Rt (min) | MS m/z (M + H)+ unless stated |
|---|---|---|---|
| 127.56 | 1-((3-(5-amino-6-(1H-1,2,4-triazol-1-yl)pyrazin-2-yl)-4-methyl phenylsulfonamido)methyl)cyclopropanecarboxamide | 0.88 | 429.2 |

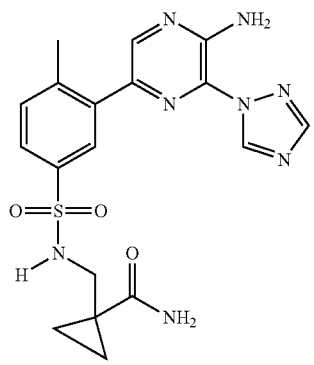

The following examples were prepared by analogous conditions to those described for the preparation of Example 127 starting from 3-(5-amino-6-(1H-1,2,4-triazol-1-yl)pyrazin-2-yl)-4-methylbenzene-1-sulfonyl chloride (Intermediate E1) and an appropriate mono-boc protected amine. The boc protecting group was removed from the final compounds by shaking a solution of each compound in DCM (2 mL) containing TFA (0.15 mL) for 3 hours, prior to purification.

| Ex. | Name | Rt (min) | MS m/z (M + H)+ |
|---|---|---|---|
| 127.57 | (R)-3-(5-amino-6-(1H-1,2,4-triazol-1-yl)pyrazin-2-yl)-4-methyl-N-(pyrrolidin-3-ylmethyl)benzenesulfonamide trifluoroacetic acid salt | 0.72 | 415.2 |

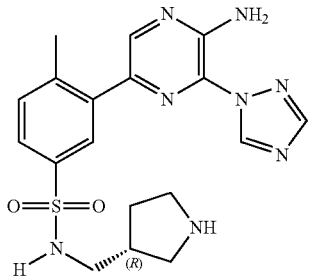

| Ex. | Name | Rt (min) | MS m/z (M + H)+ |
|---|---|---|---|
| 127.58 | (S)-3-(5-amino-6-(1H-1,2,4-triazol-1-yl)pyrazin-2-yl)-4-methyl-N-(pyrrolidin-3-ylmethyl)benzenesulfonamide trifluoroacetic acid salt | 0.72 | 415.2 |

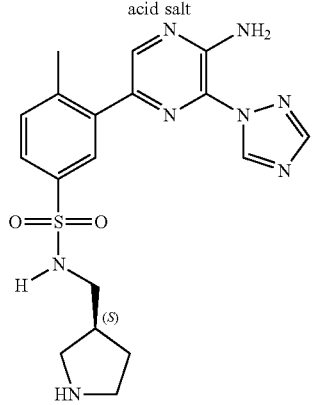

| 127.60 | 3-(5-amino-6-(1H-1,2,4-triazol-1-yl)pyrazin-2-yl)-N-((3R,4R)-4-hydroxypyrrolidin-3-yl)-4-methylbenzenesulfonamide trifluoroacetic acid salt | 1.01 | 417.2 |

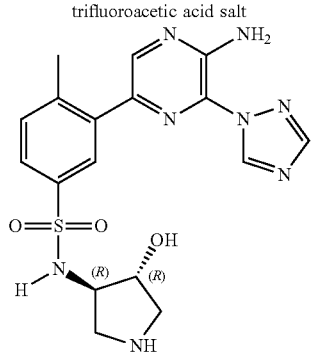

Example 128

3-(5-Amino-6-(1,3-dimethyl-1H-pyrazol-4-yl)
pyrazin-2-yl)-N-((3-(hydroxymethyl)oxetan-3-yl)
methyl)-4-methylbenzenesulfonamide

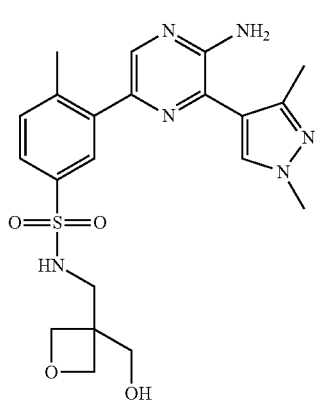 [SMILES: Cc1ccc(S(=O)(=O)NCC2(CO)COC2)cc1-c1cnc(N)c(-c2cn(C)nc2C)n1]

3-(5-Amino-6-(1,3-dimethyl-1H-pyrazol-4-yl)pyrazin-2-yl)-4-methylbenzene-1-sulfonyl chloride (Intermediate E3) (200 mg, 0.53 mmol) in DMA (2 ml) was added dropwise to a stirred solution of (3-(aminomethyl)oxetan-3-yl)methanol (68 mg, 0.58 mmol) and DIPEA (0.28 ml, 1.5 mmol) in DMA (2 ml) at 0° C. The reaction was allowed to warm to RT and stirred for 1 h when LCMS suggested a 1:1 mixture of product and sulfonic acid. The reaction mixture was diluted with EtOAc and washed with aq. NaHCO₃. The organic extract was separated, dried over MgSO₄, and the solvent removed to give a colourless oil. Chromatography on silica, eluting with EtOH, EtOH 1:1, gave the product as a white amorphous solid;

LCMS: Rt 0.84 mins; MS m/z 459.5 [M+H]+; Method 2minLowpH $^1$H NMR (400 MHz, DMSO-d6) δ 8.09 (2H, s), 7.88 (1H, s), 7.75 (1H, br s), 7.70 (1H, d), 7.52 (1H, d), 6.29 (2H, s), 4.85 (1H br s), 4.28 (4H, m), 3.82 (3H, s), 3.52 (2H, s), 2.95 (2H, s), 2.45 (3H, s), 2.29 (3H, s).

The following compounds were prepared in an analogous manner to that used for the synthesis of Example 128, starting from 3-(5-amino-6-(1,3-dimethyl-1H-pyrazol-4-yl)pyrazin-2-yl)-4-methylbenzene-1-sulfonyl chloride (Intermediate E3) and an appropriate amine.

Example 128.1

(S)-3-(5-Amino-6-(1,3-dimethyl-1H-pyrazol-4-yl)
pyrazin-2-yl)-N-((1-ethylpyrrolidin-2-yl)methyl)-4-
methylbenzenesulfonamide

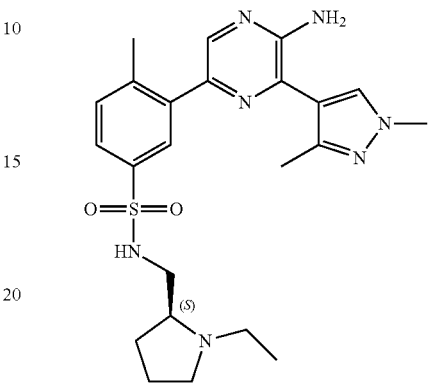

LCMS: Rt 0.6 mins; MS m/z 470.4 [M+H]+; Method 2minLowpH.

$^1$H NMR (400 MHz, DMSO-d6) δ 8.09 (1H, s), 8.05 (1H, s), 7.86 (1H, s), 7.67 (1H, d), 7.50 (1H, d), 7.46 (1H, br t), 6.29 (2H, s), 3.82 (3H, s), 2.95 (1H, m), 2.80 (1H, m), 2.60 (2H, m), 2.48 (3H, s), 2.38 (1H, m), 2.27 (3H, s), 2.13 (1H, m), 2.05 (1H, m), 1.74 (1H, m), 1.52 (3H, m), 0.92 (3H, t).

Example 128.2

3-(5-Amino-6-(1,3-dimethyl-1H-pyrazol-4-yl)
pyrazin-2-yl)-4-methyl-N-((4-methylmorpholin-3-yl)
methyl)benzenesulfonamide

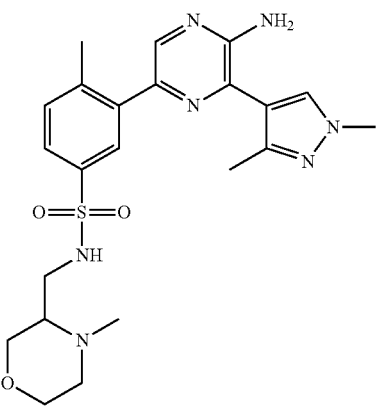 [SMILES: Cc1ccc(S(=O)(=O)NCC2COCCN2C)cc1-c1cnc(N)c(-c2cn(C)nc2C)n1]

LCMS: RT 0.67 mins; MS m/z 472.4 [M+H]+; Method 2minLowpH $^1$H NMR (400 MHz, DMSO-d6) δ 8.09 (1H, s), 8.07 (1H, s), 7.86 (1H, s), 7.58 (1H, d), 7.51 (2H, m), 6.28 (2H, s), 3.82 (3H, s), 3.62 (2H, m), 3.41 (1H, m), 3.19 (1H, m), 2.95 (1H, m), 2.69 (1H, m), 2.58 (1H, m), 2.45 (3H, s), 2.29 (3H, s), 2.11 (3H, s), 2.08 (2H, m).

Example 128.3a (R or S)-3-(5-Amino-6-(1,3-dimethyl-1H-pyrazol-4-yl)pyrazin-2-yl)-4-methyl-N-((4-methylmorpholin-3-yl)methyl)benzenesulfonamide and Example 128.3b: (R or S)-3-(5-Amino-6-(1,3-dimethyl-1H-pyrazol-4-yl)pyrazin-2-yl)-4-methyl-N-((4-methylmorpholin-3-yl)methyl)benzenesulfonamide

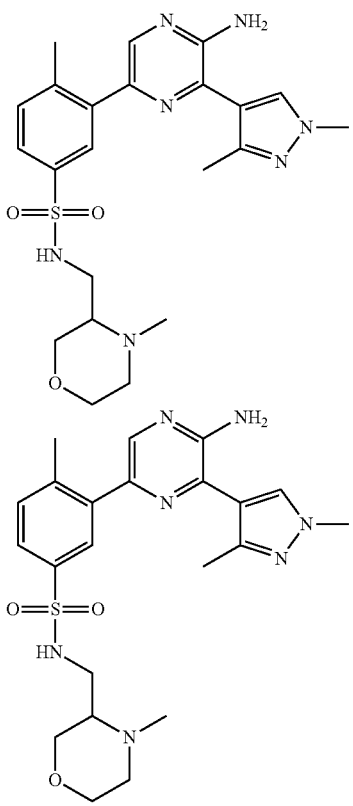

Racemic 3-(5-amino-6-(1,3-dimethyl-1H-pyrazol-4-yl)pyrazin-2-yl)-4-methyl-N-((4-methylmorpholin-3-yl)methyl)benzenesulfonamide was purified by chiral SFC. Method details: (Chiralpak AS-H, 250×10 mm, 5 um @ 35 deg C.) eluting with 50% Isopropanol+0.1% v/v diethylamine/50% CO2 with a flow rate of 10 ml/min. (Detection: UV @ 220 nm, System: Berger Minigram SFC1). Two peaks were collected Peak 1 RT 3.13 mins, Peak 2 RT 4.86 mins.

Example 128.3a

Peak 1 (First Eluted Peak)

SFC retention time=3.13 mins (R)-3-(5-Amino-6-(1,3-dimethyl-1H-pyrazol-4-yl)pyrazin-2-yl)-4-methyl-N-((4-methylmorpholin-3-yl)methyl)benzenesulfonamide or (S)-3-(5-Amino-6-(1,3-dimethyl-1H-pyrazol-4-yl)pyrazin-2-yl)-4-methyl-N-((4-methylmorpholin-3-yl)methyl)benzenesulfonamide LCMS: RT 0.94 mins; MS m/z 472.4 [M+H]+; Method 2minHighpH $^1$H NMR (400 MHz, DMSO-d6) δ 8.09 (1H, s), 8.07 (1H, s), 7.86 (1H, s), 7.58 (1H, d), 7.51 (2H, m), 6.28 (2H, s), 3.82 (3H, s), 3.62 (2H, m), 3.41 (1H, m), 3.19 (1H, m), 2.95 (1H, m), 2.69 (1H, m), 2.58 (1H, m), 2.45 (3H, s), 2.29 (3H, s), 2.11 (3H, s), 2.08 (2H, m).

Example 128.3b

Peak 2 (Second Eluted Peak)

SFC retention time=4.86 mins (R)-3-(5-Amino-6-(1,3-di methyl-1H-pyrazol-4-yl)pyrazin-2-yl)-4-methyl-N-((4-methylmorpholin-3-yl)methyl)benzenesulfonamide or (S)-3-(5-Amino-6-(1,3-dimethyl-1H-pyrazol-4-yl)pyrazin-2-yl)-4-methyl-N-((4-methylmorpholin-3-yl)methyl)benzenesulfonamide LCMS: RT 0.94 mins; MS m/z 472.4 [M+H]+ Method 2minHighpH.

$^1$H NMR (400 MHz, DMSO-d6) δ 8.09 (1H, s), 8.07 (1H, s), 7.86 (1H, s), 7.58 (1H, d), 7.51 (2H, m), 6.28 (2H, s), 3.82 (3H, s), 3.62 (2H, m), 3.41 (1H, m), 3.19 (1H, m), 2.95 (1H, m), 2.69 (1H, m), 2.58 (1H, m), 2.45 (3H, s), 2.29 (3H, s), 2.11 (3H, s), 2.08 (2H, m).

Example 128.4

3-(5-Amino-6-(1,3-di methyl-1H-pyrazol-4-yl)pyrazin-2-yl)-4-methyl-N-((2-methyltetrahydrofuran-2-yl)methyl)benzenesulfonamide

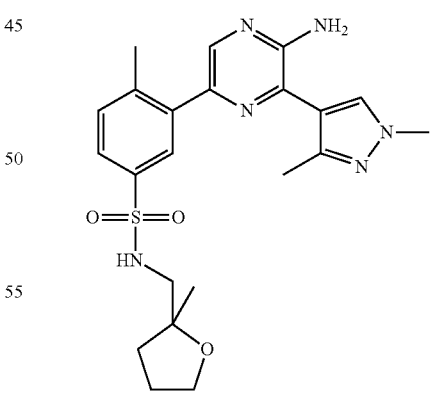

LCMS: RT 0.97 min; MS m/z 457.2 [M+H]+; Method 2minLowpH

Example 128.5

3-(5-Amino-6-(1,3-dimethyl-1H-pyrazol-4-yl)pyrazin-2-yl)-4-methyl-N-((4-methylmorpholin-2-yl)methyl)benzenesulfonamide

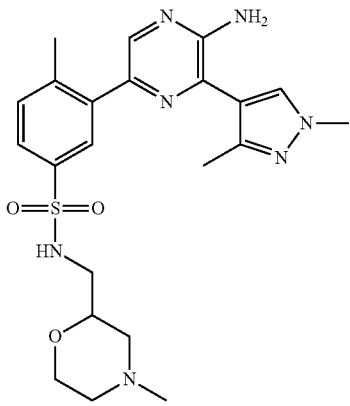 [SMILES: Cc1ccc(S(=O)(=O)NCC2CN(C)CCO2)cc1-c1cnc(N)c(-c2cn(C)nc2C)n1]

LCMS: RT 0.96 mins MS m/z 472.3 [M+H]+; Method 2minHighpH.

The following compounds were prepared in an analogous manner to that used for the synthesis of Example 128, starting from 3-(5-amino-6-(1,3-dimethyl-1H-pyrazol-4-yl)pyrazin-2-yl)-4-methylbenzene-1-sulfonyl chloride (Intermediate E3) and the appropriate amine protected with a Boc group. After sulfonamide formation, the Boc group was removed by treatment with DCM:TFA at room temperature prior to purification.

Example 128.6

(R)-3-(5-Amino-6-(1,3-dimethyl-1H-pyrazol-4-yl)pyrazin-2-yl)-4-methyl-N-(morpholin-3-ylmethyl)benzenesulfonamide

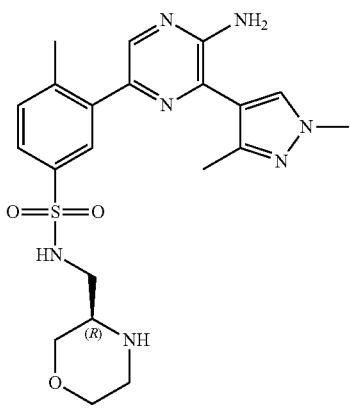

LCMS: Rt 0.60 mins; MS m/z 458.4 [M+H]+; Method 2minLowpH.

$^1$H NMR (400 MHz, DMSO-d6) δ 8.12 (2H, m), 7.89 (1H, s), 7.73 (1H, d), 7.60 (1H, br s), 7.50 (1H, d), 6.29 (2H, s), 3.82 (3H, s), 3.66 (1H, m), 3.58 (1H, m), 3.26 (2H, m), 2.99 (1H, m), 2.62 (5H, m), 2.45 (3H, s), 2.28 (3H, s).

Example 128.7

(S)-3-(5-Amino-6-(1,3-dimethyl-1H-pyrazol-4-yl)pyrazin-2-yl)-4-methyl-N-(morpholin-3-ylmethyl)benzenesulfonamide

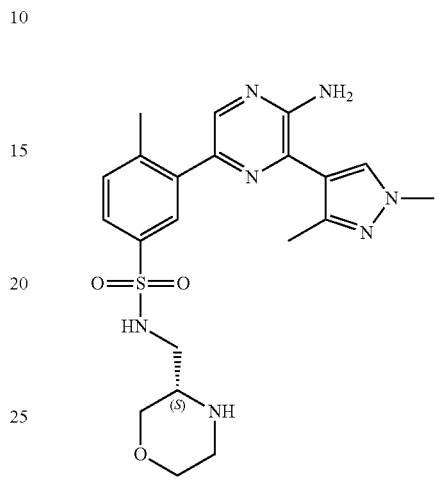

LCMS: RT 0.60 mins; MS m/z 458.3 [M+H]+; Method 2minLowpH.

$^1$H NMR (400 MHz, DMSO-d6) δ 8.09 (2H, m), 7.85 (1H, s), 7.65 (1H, d), 7.59 (1H, br s), 7.50 (1H, d), 6.29 (2H, s), 3.82 (3H, s), 3.65 (1H, d), 3.58 (1H, d), 3.28 (2H, m), 2.95 (1H, m), 2.60 (5H, m), 2.45 (3H, s), 2.28 (3H, s).

Example 128.8

3-(5-amino-6-(1,3-dimethyl-1H-pyrazol-4-yl)pyrazin-2-yl)-4-methyl-N-(morpholin-2-ylmethyl)benzenesulfonamide

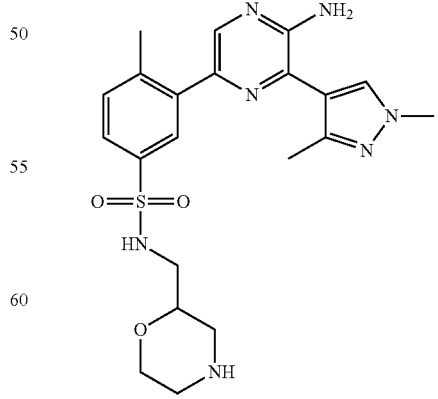

LCMS: Rt 0.84 mins; MS m/z 458.2 [M+H]+; Method 2minHighpHv03.

Example 129

(R)-3-(5-Amino-6-(2-methylpyridin-4-yl)pyrazin-2-yl)-N-(2-hydroxypropyl)-4-methyl benzene sulfonamide trifluoroacetic acid salt

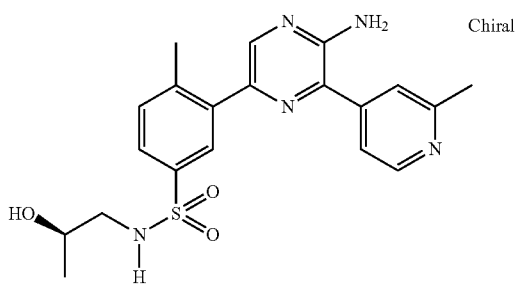 [SMILES: Cc1cc(-c2nc(-c3cc(S(=O)(=O)NC[C@@H](C)O)ccc3C)cnc2N)ccn1]

To a mixture of 2,4,6-trichlorophenyl 3-(5-amino-6-(2-methylpyridin-4-yl)pyrazin-2-yl)-4-methylbenzenesulfonate (Intermediate E4) (50 mg, 0.093 mmol), (2R)-1-aminopropan-2-ol (15 mg, 0.2 mmol), tetrabutylammonium chloride (41 mg, 1.6 eq) in acetonitrile (2 ml) was added triethylamine (100 μL, 7 eq). The reaction mixture was heated to 140° C. for 30 mins using microwave radiation. The solvent was evaporated under reduced pressure. The crude material was treated with DMSO (1 ml) and purified by HPLC (acetonitrile/water gradient, TFA modifier). The product fractions were combined and evaporated to give (R)-3-(5-amino-6-(2-methylpyridin-4-yl)pyrazin-2-yl)-N-(2-hydroxypropyl)-4-methylbenzenesulfonamide:trifluoroacetic acid (1:1)

LCMS: Rt 0.61 mins; MS m/z 412.2 [M−H]−; Method: 2minLowpH

The following examples were prepared by analogous conditions to those described for the preparation of Example 129 starting from 2,4,6-trichlorophenyl 3-(5-amino-6-(2-methylpyridin-4-yl)pyrazin-2-yl)-4-methylbenzenesulfonate (Intermediate E4) and the appropriate amine. Amines used are commercially available except for amine used in synthesis of Example 129.20 which can be prepared according to the procedure described in patent application WO2011/113894 page 99. All compounds were obtained as trifluoroacetic acid salt except 129.17 to 127.19 which were obtained as free base. LCMS Method: 2minLowpH unless stated.

| Example | Name | MS m/z [M + H]+ unless stated | Rt (min) |
|---|---|---|---|
| 129.1 | 3-(5-amino-6-(2-methylpyridin-4-yl)pyrazin-2-yl)-N-(4-(hydroxymethyl)cyclohexyl)-4-methylbenzenesulfonamide | 468.3 | 0.67 |

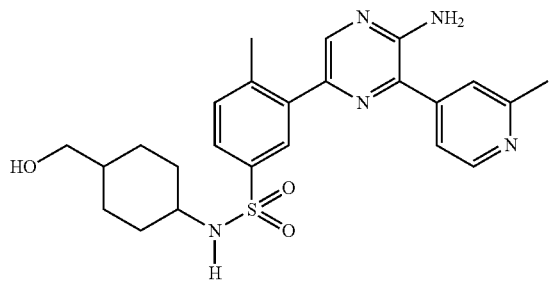 [SMILES: Cc1cc(-c2nc(-c3cc(S(=O)(=O)NC4CCC(CO)CC4)ccc3C)cnc2N)ccn1]

| 129.2 | 3-(5-amino-6-(2-methylpyridin-4-yl)pyrazin-2-yl)-N-(3,3-difluorocyclobutyl)-4-methylbenzenesulfonamide | 446.5 | 0.73 |

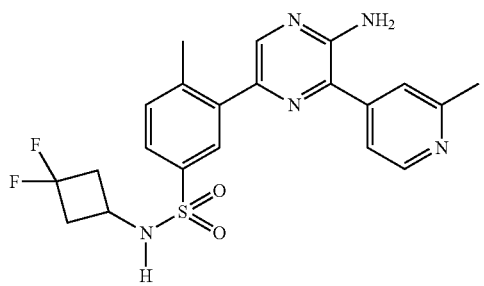 [SMILES: Cc1cc(-c2nc(-c3cc(S(=O)(=O)NC4CC(F)(F)C4)ccc3C)cnc2N)ccn1]

-continued
| Example | Name | MS m/z [M + H]+ unless stated | Rt (min) |
|---|---|---|---|
| 129.3 | 3-(5-amino-6-(2-methylpyridin-4-yl)pyrazin-2-yl)-N-(5-hydroxypentyl)-4-methylbenzenesulfonamide | 442.4 | 0.65 |
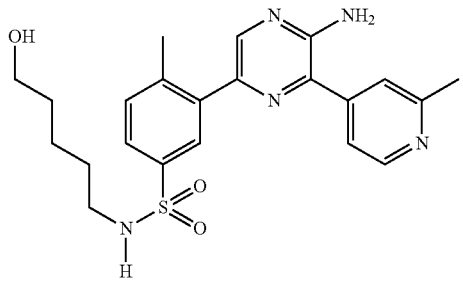 [SMILES: Cc1cc(-c2nc(-c3cc(S(=O)(=O)NCCCCCO)ccc3C)cnc2N)ccn1]
| | | | |
|---|---|---|---|
| 129.4 | 3-(5-amino-6-(2-methylpyridin-4-yl)pyrazin-2-yl)-N-((1-hydroxycyclohexyl)methyl)-4-methylbenzenesulfonamide | 468.3 | 0.74 |
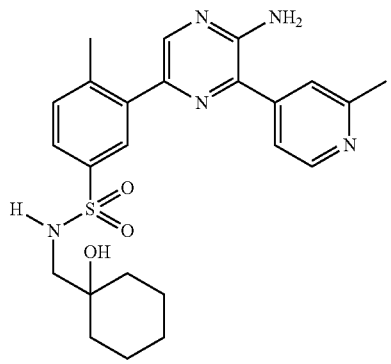 [SMILES: Cc1cc(-c2nc(-c3cc(S(=O)(=O)NCC4(O)CCCCC4)ccc3C)cnc2N)ccn1]
| | | | |
|---|---|---|---|
| 129.5 | 3-(5-amino-6-(2-methylpyridin-4-yl)pyrazin-2-yl)-N-((1-hydroxycyclobutyl)methyl)-4-methylbenzenesulfonamide | 438.3 [M − H]− | 0.67 |
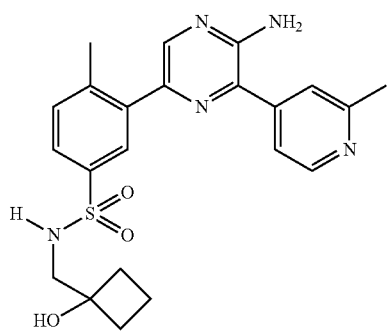 [SMILES: Cc1cc(-c2nc(-c3cc(S(=O)(=O)NCC4(O)CCC4)ccc3C)cnc2N)ccn1]

-continued

| Example | Name | MS m/z [M + H]+ unless stated | Rt (min) |
| --- | --- | --- | --- |
| 129.6 | (S)-3-(5-amino-6-(2-methylpyridin-4-yl)pyrazin-2-yl)-N-(1-hydroxybutan-2-yl)-4-methylbenzenesulfonamide | 426.4 [M − H]− | 0.64 |
| 129.7 | (R)-3-(5-amino-6-(2-methylpyridin-4-yl)pyrazin-2-yl)-N-(1-hydroxybutan-2-yl)-4-methylbenzenesulfonamide | 428.5 | 0.64 |
| 129.8 | 3-(5-amino-6-(2-methylpyridin-4-yl)pyrazin-2-yl)-N-(1-hydroxy-2-methylpropan-2-yl)-4-methylbenzenesulfonamide | 428.2 | 0.64 |
| 129.9 | (S)-3-(5-amino-6-(2-methylpyridin-4-yl)pyrazin-2-yl)-N-(2-hydroxypropyl)-4-methylbenzenesulfonamide | 414.2 | 0.61 |

| Example | Name | MS m/z [M + H]+ unless stated | Rt (min) |
|---|---|---|---|
| 129.10 | 3-(5-amino-6-(2-methylpyridin-4-yl)pyrazin-2-yl)-4-methyl-N-(tetrahydro-2H-pyran-4-yl)benzenesulfonamide | 440.2 | 0.65 |
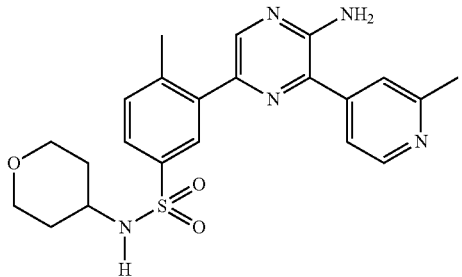 [SMILES: Cc1cc(-c2nc(-c3cc(S(=O)(=O)NC4CCOCC4)ccc3C)cnc2N)ccn1]
| | | | |
|---|---|---|---|
| 129.11 | 3-(5-amino-6-(2-methylpyridin-4-yl)pyrazin-2-yl)-N-(3-methoxypropyl)-4-methylbenzenesulfonamide | 426.3 [M − H]− | 0.67 |
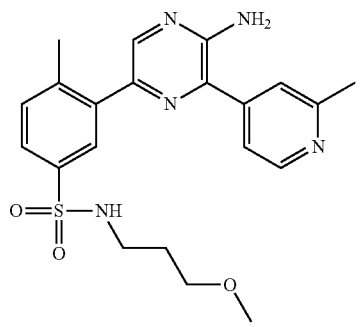 [SMILES: COCCCNS(=O)(=O)c1ccc(C)c(-c2cnc(N)c(-c3ccnc(C)c3)n2)c1]
| | | | |
|---|---|---|---|
| 129.12 | (R)-3-(5-amino-6-(2-methylpyridin-4-yl)pyrazin-2-yl)-4-methyl-N-((tetrahydrofuran-2-yl)methyl)benzenesulfonamide | 438.3 [M − H]− | 0.68 |
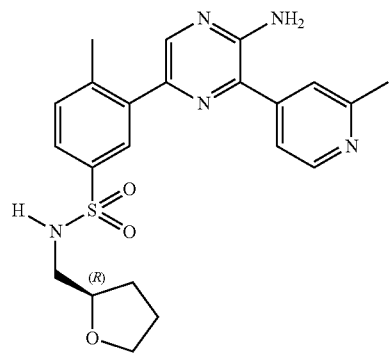

| Example | Name | MS m/z [M + H]+ unless stated | Rt (min) |
|---|---|---|---|
| 129.13 | 3-(5-amino-6-(2-methylpyridin-4-yl)pyrazin-2-yl)-4-methyl-N-(4,4,4-trifluoro-3-hydroxy-3-methylbutyl)benzenesulfonamide | 496.3 | 0.72 |
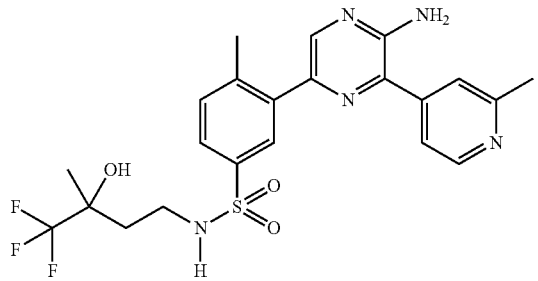 [SMILES: Cc1cc(-c2nc(-c3cc(S(=O)(=O)NCCC(C)(O)C(F)(F)F)ccc3C)cnc2N)ccn1]
| | | | |
|---|---|---|---|
| 129.14 | 3-(5-amino-6-(2-methylpyridin-4-yl)pyrazin-2-yl)-4-methyl-N-((tetrahydro-2H-pyran-3-yl)methyl)benzenesulfonamide | 454.5 | 0.70 |
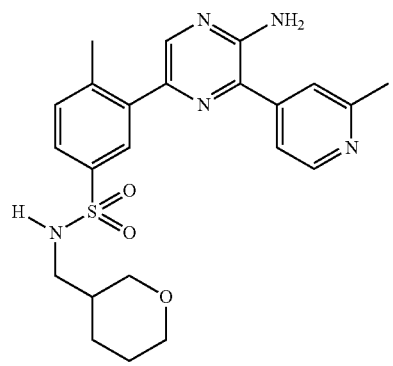 [SMILES: Cc1cc(-c2nc(-c3cc(S(=O)(=O)NCC4CCCOC4)ccc3C)cnc2N)ccn1]
| | | | |
|---|---|---|---|
| 129.15 | 3-(5-amino-6-(2-methylpyridin-4-yl)pyrazin-2-yl)-N-(2-methoxy-2-methylpropyl)-4-methylbenzenesulfonamide | 442.3 | 0.71 |
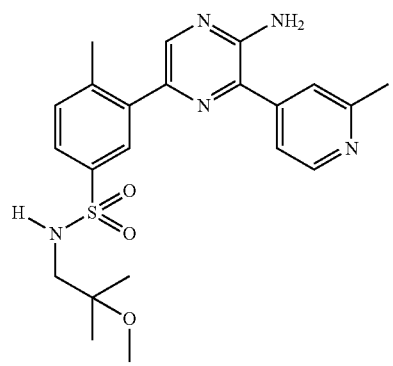 [SMILES: COC(C)(C)CNS(=O)(=O)c1ccc(C)c(-c2cnc(N)c(-c3ccnc(C)c3)n2)c1]

| Example | Name | MS m/z [M + H]+ unless stated | Rt (min) |
|---|---|---|---|
| 129.16 | 3-(5-amino-6-(2-methylpyridin-4-yl)pyrazin-2-yl)-4-methyl-N-((tetrahydro-2H-pyran-2-yl)methyl)benzenesulfonamide | 454.6 | 0.73 |
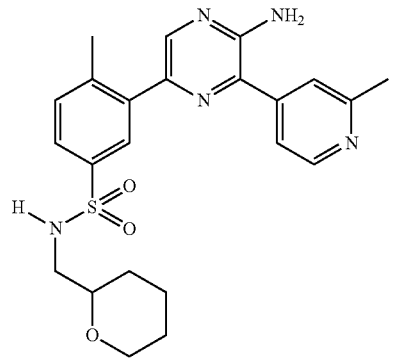 [SMILES: Cc1cc(-c2nc(-c3cc(S(=O)(=O)NCC4CCCCO4)ccc3C)cnc2N)ccn1]
| | | | |
|---|---|---|---|
| 129.17 | 3-(5-amino-6-(2-methylpyridin-4-yl)pyrazin-2-yl)-4-methyl-N-((tetrahydrofuran-2-yl)methyl)benzenesulfonamide | 440.2 | 0.67 |
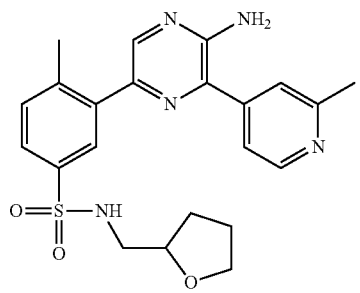 [SMILES: Cc1cc(-c2nc(-c3cc(S(=O)(=O)NCC4CCCO4)ccc3C)cnc2N)ccn1]
| | | | |
|---|---|---|---|
| 129.18 | 3-(5-amino-6-(2-methylpyridin-4-yl)pyrazin-2-yl)-4-methyl-N-((tetrahydrofuran-3-yl)methyl)benzenesulfonamide | 440.2 | 0.64 |
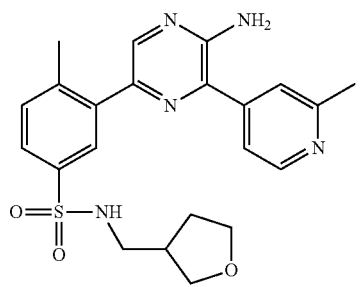 [SMILES: Cc1cc(-c2nc(-c3cc(S(=O)(=O)NCC4CCOC4)ccc3C)cnc2N)ccn1]

| Example | Name | MS m/z [M + H]+ unless stated | Rt (min) |
|---|---|---|---|
| 129.19 | 3-(5-amino-6-(2-methylpyridin-4-yl)pyrazin-2-yl)-N-(4-hydroxy-4-methylcyclohexyl)-4-methylbenzenesulfonamide | 468.2 | 0.68 |

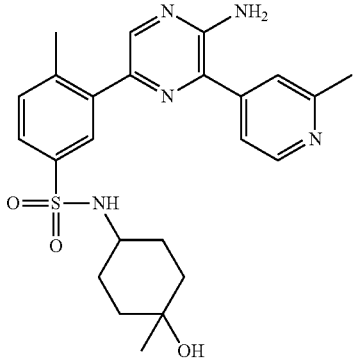 [SMILES: Cc1cc(-c2nc(-c3cc(S(=O)(=O)NC4CCC(C)(O)CC4)ccc3C)cnc2N)ccn1]

| 129.20 | (R)-3-(5-amino-6-(2-methylpyridin-4-yl)pyrazin-2-yl)-4-methyl-N-(3,3,3-trifluoro-2-hydroxy-2-methylpropyl)benzenesulfonamide | 482.5 | 0.71 |

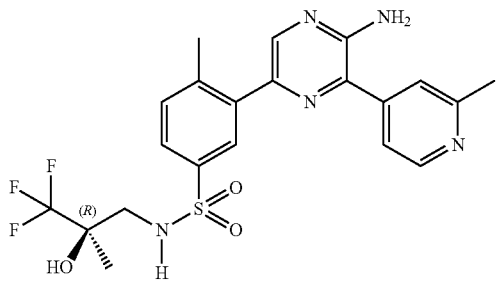

The following examples were prepared by analogous conditions to those described for the preparation of Example 129 starting from 2,4,6-trichlorophenyl 3-(5-amino-6-(2-methylpyridin-4-yl)pyrazin-2-yl)-4-methylbenzenesulfonate (Intermediate E4) and the appropriate commercially available amine. Following HPLC and evaporation, an additional purification step using solid phase extraction (Isolute® PE-AX) was required to remove sulfonic acid impurity. The products 129.21 to 129.31 were hence obtained as acetic acid salts.

| Example | Name | MS m/z [M + H]+ unless stated | LCMS Method: 2minLow pH unless stated Rt (min) |
|---|---|---|---|
| 129.21 | 3-(5-amino-6-(2-methylpyridin-4-yl)pyrazin-2-yl)-N-(1-isopropylpiperidin-4-yl)-4-methylbenzenesulfonamide | 481.3 | 0.51 |
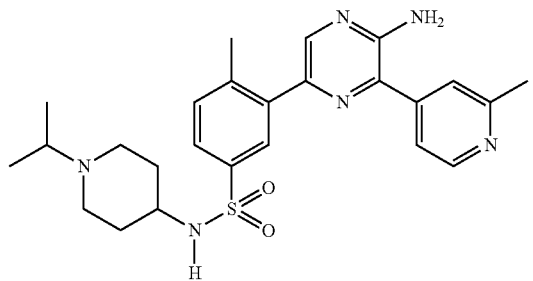 [SMILES: Cc1cc(-c2nc(-c3cc(S(=O)(=O)NC4CCN(C(C)C)CC4)ccc3C)cnc2N)ccn1]
| 129.22 | 3-(5-amino-6-(2-methylpyridin-4-yl)pyrazin-2-yl)-4-methyl-N-(1-methylpiperidin-4-yl)benzenesulfonamide | 453.3 | 0.45 |
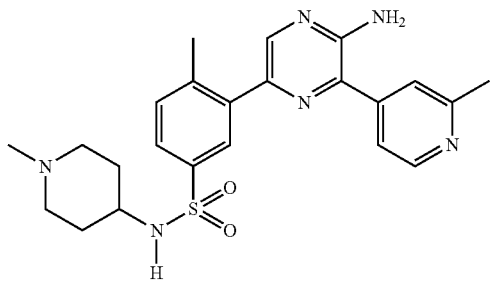
| 129.23 | 3-(5-amino-6-(2-methylpyridin-4-yl)pyrazin-2-yl)-N-(3-(diethylamino)propyl)-4-methylbenzenesulfonamide | 469.3 | 0.52 |
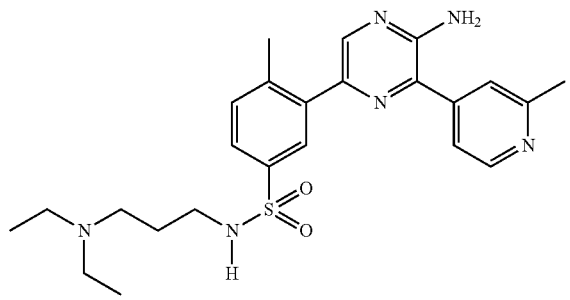 [SMILES: CCN(CC)CCCNS(=O)(=O)c1ccc(C)c(-c2cnc(N)c(-c3ccnc(C)c3)n2)c1]

| Example | Name | MS m/z [M + H]+ unless stated | LCMS Method: 2minLow pH unless stated Rt (min) |
|---|---|---|---|
| 129.24 | 3-(5-amino-6-(2-methylpyridin-4-yl)pyrazin-2-yl)-N-(3-(dimethylamino)-2,2-dimethylpropyl)-4-methylbenzenesulfonamide | 469.3 | 0.52 |
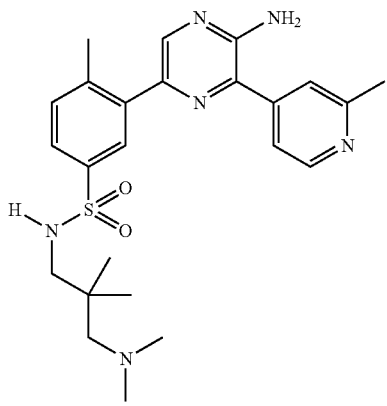 [SMILES: Cc1cc(-c2nc(-c3cc(S(=O)(=O)NCC(C)(C)CN(C)C)ccc3C)cnc2N)ccn1]
| 129.25 | (R)-3-(5-amino-6-(2-methylpyridin-4-yl)pyrazin-2-yl)-N-((1-ethylpyrrolidin-2-yl)methyl)-4-methylbenzenesulfonamide | 467.3 | 0.51 |
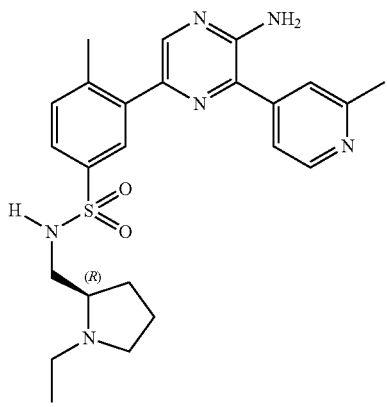
| 129.26 | 3-(5-amino-6-(2-methylpyridin-4-yl)pyrazin-2-yl)-N-(2-(dimethylamino)ethyl)-4-methylbenzenesulfonamide | 427.3 | 0.38 |
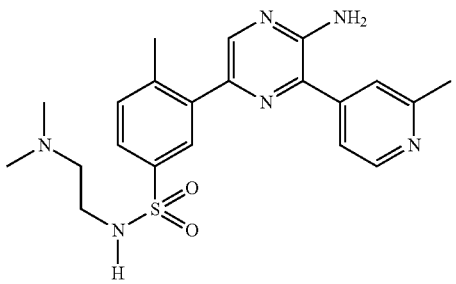

| Example | Name | MS m/z [M + H]+ unless stated | LCMS Method: 2minLow pH unless stated Rt (min) |
|---|---|---|---|
| 129.27 | 3-(5-amino-6-(2-methylpyridin-4-yl)pyrazin-2-yl)-4-methyl-N-(2-(pyrrolidin-1-yl)ethyl)benzenesulfonamide | 453.3 | 0.49 |
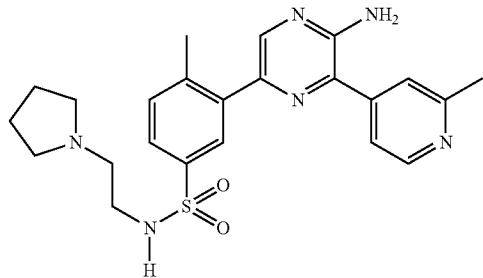 [SMILES: Cc1cc(-c2nc(-c3cc(S(=O)(=O)NCCN4CCCC4)ccc3C)cnc2N)ccn1]
| | | | |
|---|---|---|---|
| 129.28 | 3-(5-amino-6-(2-methylpyridin-4-yl)pyrazin-2-yl)-4-methyl-N-(2-morpholinoethyl)benzenesulfonamide | 469.3 | 0.46 |
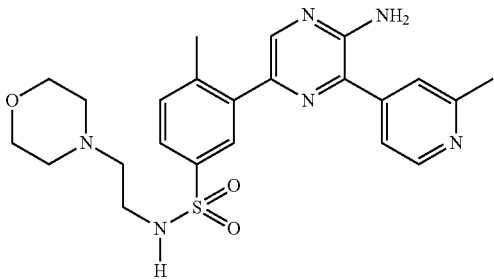 [SMILES: Cc1cc(-c2nc(-c3cc(S(=O)(=O)NCCN4CCOCC4)ccc3C)cnc2N)ccn1]
| | | | |
|---|---|---|---|
| 129.29 | 3-(5-amino-6-(2-methylpyridin-4-yl)pyrazin-2-yl)-4-methyl-N-(2-methyl-2-morpholinopropyl)benzenesulfonamide | 497.3 | 0.51 |
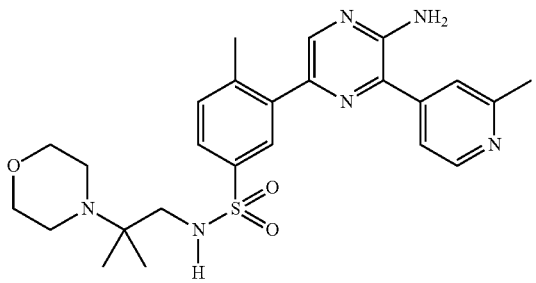 [SMILES: Cc1cc(-c2nc(-c3cc(S(=O)(=O)NCC(C)(C)N4CCOCC4)ccc3C)cnc2N)ccn1]

| Example | Name | MS m/z [M + H]+ unless stated | LCMS Method: 2minLow pH unless stated Rt (min) |
|---|---|---|---|
| 129.30 | 3-(5-amino-6-(2-methylpyridin-4-yl)pyrazin-2-yl)-4-methyl-N-((1-methylpyrrolidin-3-yl)methyl)benzenesulfonamide | 453.5 | 0.49 |

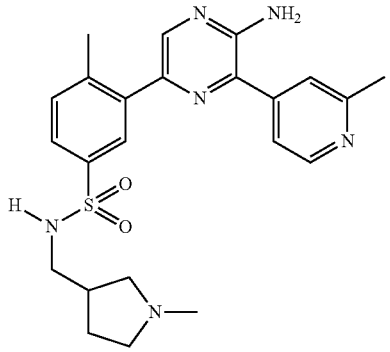 [SMILES: Cc1cc(-c2nc(-c3cc(S(=O)(=O)NCC4CCN(C)C4)ccc3C)cnc2N)ccn1]

| 129.31 | 4-((3-(5-amino-6-(2-methylpyridin-4-yl)pyrazin-2-yl)-4-methylphenylsulfonamido)methyl)tetrahydro-2H-pyran-4-carboxamide | 497.5 | 0.60 |

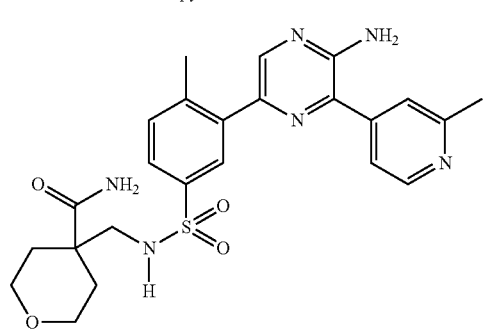

The following examples were prepared by analogous conditions to those described for the preparation of Example 129 starting from 2,4,6-trichlorophenyl 3-(5-amino-6-(2-methylpyridin-4-yl)pyrazin-2-yl)-4-methylbenzenesulfonate (Intermediate E4) and the appropriate boc-protected amine. Prior to HPLC purification, 20% TFA in DCM (2 mL) was added to the crude residue and the mixtures were shaken at RT for 30 mins to remove the Boc group. Mixtures were evaporated and re-dissolved in DMSO (1 mL), then purified by HPLC as previously to give trifluoroacetic acid salts.

| Example | Name | Rt (min) | MS m/z [M + H]+ unless stated |
|---|---|---|---|
| 129.32 | 3-(5-amino-6-(2-methylpyridin-4-yl)pyrazin-2-yl)-N-((3-hydroxyoxetan-3-yl)methyl)-4-methylbenzenesulfonamide | 0.59 | 442.3 |
| 129.33 | 3-(5-amino-6-(2-methylpyridin-4-yl)pyrazin-2-yl)-4-methyl-N-(2-(methylamino)ethyl)benzenesulfonamide | 0.60 | 413.2 |
| 129.34 | 3-(5-amino-6-(2-methylpyridin-4-yl)pyrazin-2-yl)-N-(2-aminoethyl)-4-methylbenzenesulfonamide | 0.60 | 399.2 |
| 129.35 | (R)-3-(5-amino-6-(2-methylpyridin-4-yl)pyrazin-2-yl)-4-methyl-N-(pyrrolidin-3-ylmethyl)benzenesulfonamide | 0.63 | 439.2 |

| Example | Name | Rt (min) | MS m/z [M + H]+ unless stated |
|---|---|---|---|
| 129.36 | (S)-3-(5-amino-6-(2-methylpyridin-4-yl)pyrazin-2-yl)-4-methyl-N-(pyrrolidin-3-ylmethyl)benzenesulfonamide | 0.63 | 439.3 |
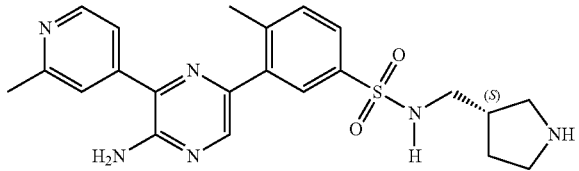
| 129.37 | 5-(5-(2,6-diazaspiro[3.3]heptan-2-ylsulfonyl)-2-methylphenyl)-3-(2-methylpyridin-4-yl)pyrazin-2-amine | 0.64 | 437.2 |
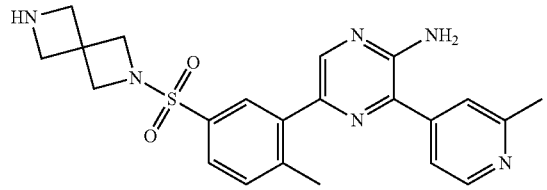 [SMILES: Cc1cc(-c2nc(-c3cc(S(=O)(=O)N4CC5(CNC5)C4)ccc3C)cnc2N)ccn1]
| 129.38 | 3-(5-amino-6-(2-methylpyridin-4-yl)pyrazin-2-yl)-N-((1S,2S)-2-aminocyclopentyl)-4-methylbenzenesulfonamide | 0.63 | 439.3 |
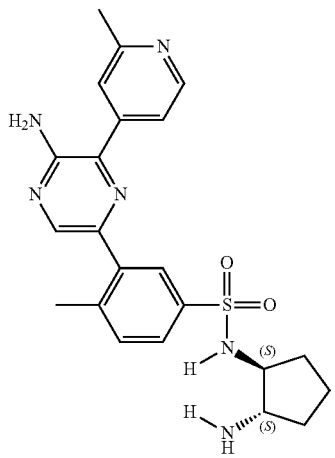

-continued
| Example | Name | Rt (min) | MS m/z [M + H]+ unless stated |
|---|---|---|---|
| 129.39 | 3-(5-amino-6-(2-methylpyridin-4-yl)pyrazin-2-yl)-N-((1R,2R)-2-aminocyclopentyl)-4-methylbenzenesulfonamide | 0.63 | 439.3 |
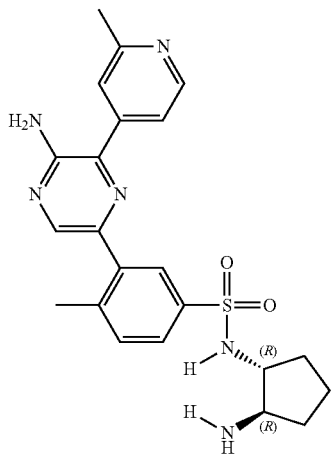
| 129.40 | (R)-5-(5-(3-aminopyrrolidin-1-ylsulfonyl)-2-methylphenyl)-3-(2-methylpyridin-4-yl)pyrazin-2-amine | 0.63 | 425.2 |
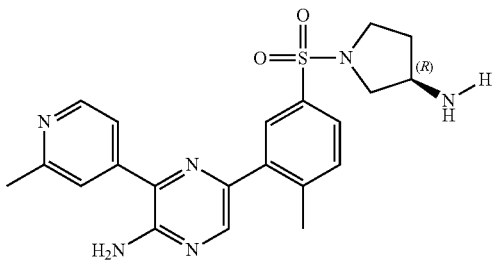
| 129.41 | 5-(5-(4-aminopiperidin-1-ylsulfonyl)-2-methylphenyl)-3-(2-methylpyridin-4-yl)pyrazin-2-amine | 0.65 | 439.3 |
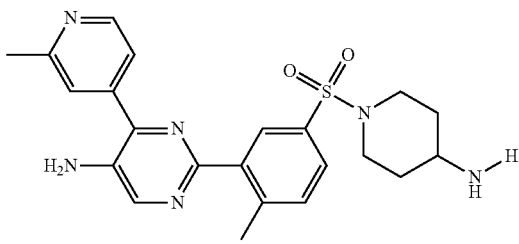 [SMILES: Cc1cc(-c2nc(-c3cc(S(=O)(=O)N4CCC(N)CC4)ccc3C)ncc2N)ccn1]

-continued
| Example | Name | Rt (min) | MS m/z [M + H]+ unless stated |
|---|---|---|---|
| 129.42 | 3-(5-amino-6-(2-methylpyridin-4-yl)pyrazin-2-yl)-N-(((1S,3R)-3-(aminomethyl)cyclohexyl)methyl)-4-methylbenzenesulfonamide | 0.71 | 481.3 |
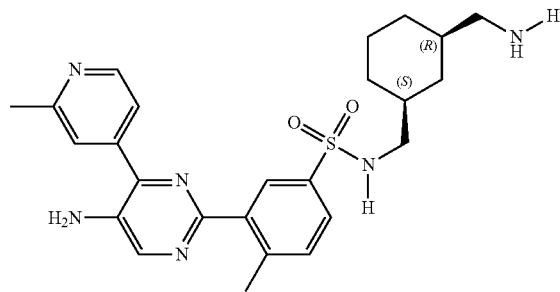
| 129.43 | 3-(5-amino-6-(2-methylpyridin-4-yl)pyrazin-2-yl)-N-((1r,4r)-4-aminocyclohexyl)-4-methylbenzenesulfonamide | 0.63 | 453.3 |
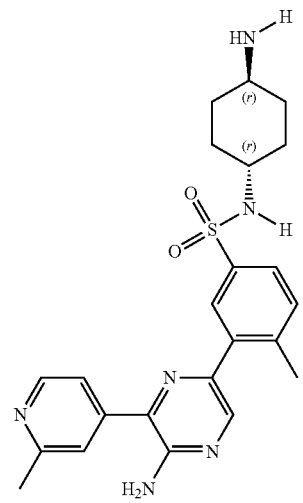 [SMILES: Cc1cc(-c2nc(-c3cc(S(=O)(=O)N[C@H]4CC[C@H](N)CC4)ccc3C)cnc2N)ccn1]

Example 130

3-(5-Amino-6-(1-(2,2,2-trifluoroethyl)-1H-pyrazol-4-yl)pyrazin-2-yl)-N-(3-hydroxy-3-methylbutyl)-4-methylbenzenesulfonamide

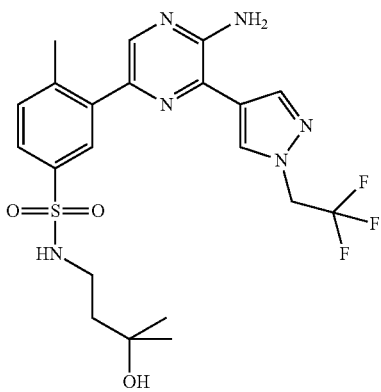 [SMILES: Cc1ccc(S(=O)(=O)NCCC(C)(C)O)cc1-c1cnc(N)c(-c2cnn(CC(F)(F)F)c2)n1]

Step 1: 4-(4,4,5,5-Tetramethyl-1,3,2-dioxaborolan-2-yl)-1-(2,2,2-trifluoroethyl)-1H-pyrazole Cesium carbonate (3.36 g, 10.31 mmol) was added to a stirred solution of 4-(4,4,5,5-tetramethyl-1,3,2-dioxaborolan-2-yl)-1H-pyrazole (1.0 g, 5.15 mmol) in dry DMF (12 ml). After stirring at RT for 10 min 2,2,2-trifluoroethyl trifluoromethanesulfonate (1.11 ml, 7.73 mmol) was added. The reaction was stirred for 2 days at RT then the solvent was removed and the residue was partitioned between diethyl ether and water. The organic extract was separated, dried over MgSO$_4$ and the solvent removed to give an oil;
LCMS: Rt 1.00 mins; MS MS m/z 277.4 [M+H]+; Method 2minLCv003

Step 2: 3-(5-Amino-6-(1-(2,2,2-trifluoroethyl)-1H-pyrazol-4-yl)pyrazin-2-yl)-N-(3-hydroxy-3-methylbutyl)-4-methylbenzenesulfonamide A mixture of 4-(4,4,5,5-tetramethyl-1,3,2-dioxaborolan-2-yl)-1-(2,2,2-trifluoroethyl)-1H-pyrazole (step 1) (115 mg, 0.417 mmol), 3-(5-Amino-6-chloropyrazin-2-yl)-N-(3-hydroxy-3-methylbutyl)-4-methyl benzenesulfonamide (Intermediate D3) (150 mg, 0.390 mmol), bis(triphenylphosphine) palladium dichloride (14 mg, 0.020 mmol) in sodium carbonate 2M aqueous solution (0.6 mL, 1.200 mmol), Ethanol (1.2 ml) and DME (1.8 mL) was heated to 120° C. for 30 minutes in the microwave, then partitioned between DCM/water, separated using a phase separator and organics evaporated under reduced pressure. The crude product was purified by flash column chromatography (12 g silica, 0-5% methanol in TBME). The product fractions were combined and evaporated, triturated with a mixture of ethyl acetate/diethyl ether and solid collected by filtration, washed with cold dry diethyl ether and dried in the vacuum oven overnight to give pale yellow solid;
$^1$H NMR (400 MHz, DMSO-d6) δ 8.49 (1H, s); 8.16 (1H, s); 8.13 (1H, s); 7.83 (1H, d, ~2 Hz); 7.68 (1H, dd, ~8 and 2 Hz); 7.53 (1H, d, ~8 Hz); 7.42 (1H, t); 6.37 (2H, s); 5.21 (2H, q); 4.27 (1H, s); 2.83 (2H, m); 2.48 (3H, s, partially overlapping with solvent); 1.51 (2H, m); 1.01 (6H, s).

LC-MS: Rt 0.92 min; MS m/z 499.2 [M+H]+; Method: 2minLowpH

Example 131

3-(5-Amino-6-(1H-1,2,4-triazol-1-yl)pyrazin-2-yl)-4-methyl-N-(oxetan-3-ylmethyl)benzenesulfonamide

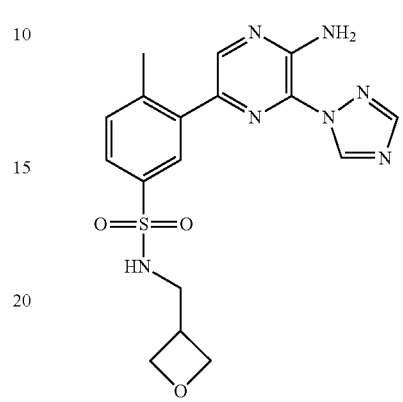

To a stirring solution of 3-(5-amino-6-(1H-1,2,4-triazol-1-yl)pyrazin-2-yl)-4-methylbenzene-1-sulfonyl chloride (Intermediate E1) (80 mg, 0.228 mmol) and triethylamine (0.035 ml, 0.251 mmol) in DCM (5 ml) was added oxetane-3-ylmethanamine (22 mg, 0.251 mmol). The reaction mixture was stirred at room temp for 30 mins then extracted into DCM, washed with water, brine, the organic layer separated, dried over MgSO$_4$, filtered and the solvent removed under reduced pressure. The yellow residue was dissolved in ethyl acetate and recrystallized overnight at room temperature to yield off white crystals;
LCMS: Rt 0.87 mins; MS m/z 402.3 [M+H]+; Method LowpH_v002
$^1$H NMR (400 MHz, DMSO-d6) δ (ppm) 9.34 (1H, s), 8.43 (1H, s), 8.42 (1H, s), 7.91 (1H, d), 7.79 (1H, t), 7.73 (1H, dd), 7.56 (1H, d), 7.39 (2H, br s), 4.54 (2H, mult), 4.20 (2H, mult), 3.05 (2H, mult), 2.99 (1H, mult). Tolyl methyl group not seen, likely obscured by DMSO peak.

Example 132

3-(5-Amino-6-(1-benzyl-1H-pyrazol-4-yl)pyrazin-2-yl)-N-(3-hydroxy-3-methylbutyl)-4-methylbenzenesulfonamide hydrochloride

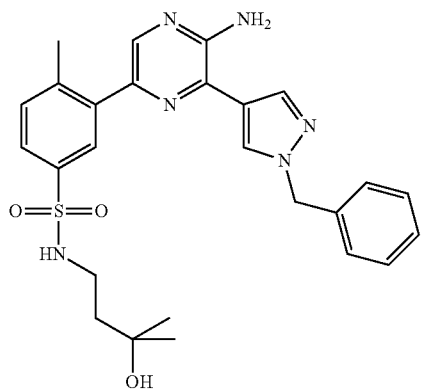 [SMILES: Cc1ccc(S(=O)(=O)NCCC(C)(C)O)cc1-c1cnc(N)c(-c2cnn(Cc3ccccc3)c2)n1]

The title compound was prepared from 3-(5-amino-6-chloropyrazin-2-yl)-N-(3-hydroxy-3-methylbutyl)-4-methyl benzenesulfonamide (Intermediate D3) and 1-benzyl-4-(4,4,5,5-tetramethyl-1,3,2-dioxaborolan-2-yl)-1H-pyrazole using analogous conditions to Example 11. Compound was treated with 1M hydrogen chloride in ether to form hydrochloride salt.

LC-MS: Rt 0.98 min; MS m/z 507.3 [M+H]+; Method: 2minLowpH

Example 133

2-(3-(5-Amino-6-(1H-1,2,4-triazol-1-yl)pyrazin-2-yl)-4-methylphenylsulfonamido)acetamide

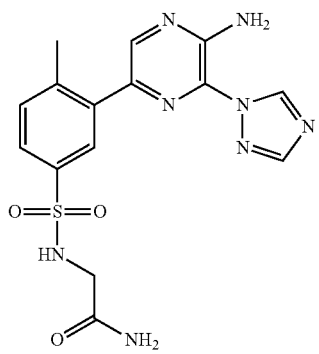 [SMILES: Cc1ccc(S(=O)(=O)NCC(N)=O)cc1-c1cnc(N)c(-n2cncn2)n1]

To 3-(5-amino-6-(1H-1,2,4-triazol-1-yl)pyrazin-2-yl)-4-methylbenzene-1-sulfonyl chloride (Intermediate E1) (50 mg, 0.143 mmol) in DCM (1.5 ml) was added 2-aminoacetamide hydrochloride (15.76 mg, 0.143 mmol) and TEA (0.040 ml, 0.285 mmol) and the resulting mixture stirred at room temperature. After 3 days, the mixture was diluted with sat. aq. NH$_4$Cl and DCM. A white solid precipitated from the aqueous phase which was collected by filtration and triturated with diethyl ether to give a white solid.

LC-MS: Rt 2.84 mins; MS m/z 389.3 [M+H]+; Method 10minLowpHv01

Example 134

3-(5-Amino-6-(2-methylpyridin-4-yl)pyrazin-2-yl)-4-methyl-N-(2-oxopiperidin-4-yl)benzenesulfonamide

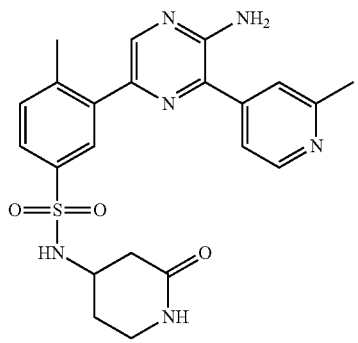 [SMILES: Cc1cc(-c2nc(-c3cc(S(=O)(=O)NC4CCNC(=O)C4)ccc3C)cnc2N)ccn1]

Step 1: 3-Bromo-4-methyl-N-(2-oxopiperidin-4-yl) benzenesulfonamide

To a stirring solution of 3-bromo-4-methylbenzene-1-sulfonyl chloride (685 mg, 2.54 mmol) and DIPEA (0.532 ml, 3.05 mmol) in DCM (12.700 ml) under nitrogen was added 4-aminopiperidin-2-one (290 mg, 2.54 mmol). The reaction mixture was stirred overnight at room temperature then diluted with DCM (100 ml). The organic phase was washed with sat. Na$_2$CO$_3$ (80 ml), 1M HCl (80 ml), brine, dried over MgSO$_4$, and concentrated to dryness. The crude product was purified by flash column chromatography (24 g silica, 0-100% ethyl acetate in hexane) to give an off-white solid;

LCMS: Rt 0.82 mins; MS m/z 349.1 [M+H]+; Method: 2minLowpH.

Step 2: 3-(5-Amino-6-(2-methylpyridin-4-yl)pyrazin-2-yl)-4-methyl-N-(2-oxopiperidin-4-yl)benzenesulfonamide A mixture of 3-bromo-4-methyl-N-(2-oxopiperidin-4-yl)benzenesulfonamide (step 1) (100 mg, 0.288 mmol), potassium acetate (42.4 mg, 0.432 mmol), PdCl$_2$(dppf).CH$_2$Cl$_2$ adduct (11.76 mg, 0.014 mmol) and bis(pinacolato)diboron (80 mg, 0.317 mmol) in DME (1440 µL), under nitrogen, was heated at 90° C. for 3 hours. To the mixture was added 5-chloro-3-(2-methylpyridin-4-yl)pyrazin-2-amine (prepared by analogy to Intermediate C6, starting from 2-methyl-4-(4,4,5,5-tetramethyl-1,3,2-dioxaborolan-2-yl)pyridine and 3-bromo-5-chloropyrazin-2-amine) (63.5 mg, 0.288 mmol), followed by Na$_2$CO$_3$ (2.0M) (432 µL, 0.864 mmol), PdCl$_2$(dppf).CH$_2$Cl$_2$ adduct (11.76 mg, 0.014 mmol) and reaction heated overnight at 90° C. The resulting mixture was added to sat. Na$_2$CO$_3$ (50 ml) and the product extracted into EtOAc (2×40 ml). The organic extracts were washed with brine, dried over MgSO$_4$ and concentrated under reduced pressure. The crude product was purified first by flash column chromatography (12 g silica, 0-10% 2M methanolic ammonia in DCM) then further by preparative HPLC to give the title compound as a yellow solid;

LCMS: Rt 0.57 mins; MS m/z 453.3 [M+H]+; Method: 2minLowpH

Example 135

3-(5-Amino-6-(2-methylpyridin-4-yl)pyrazin-2-yl)-N-((1r,4r)-4-hydroxycyclohexyl)-4-methylbenzenesulfonamide

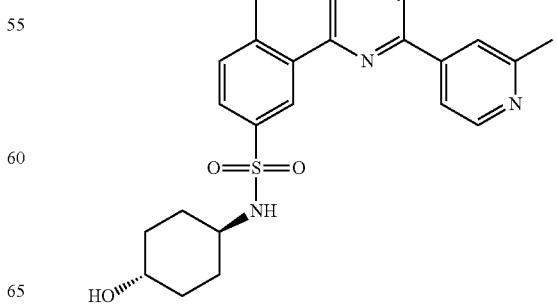

The title compound was prepared by analogy to Example 25 from N-(trans-4-hydroxycyclohexyl)-4-methyl-3-(4,4,5,5-tetramethyl-1,3,2-dioxaborolan-2-yl)benzenesulfonamide (Intermediate B5) and 5-chloro-3-(2-methylpyridin-4-yl)pyrazin-2-amine (itself prepared by analogy to intermediate C6, starting from 2-methyl-4-(4,4,5,5-tetramethyl-1,3,2-dioxaborolan-2-yl)pyridine and 3-bromo-5-chloropyrazin-2-amine).

LCMS: Rt 0.66 mins; MS m/z 454.4 [M+H]+; Method2minLowpHv01

Example 136

3-(5-Amino-6-(3-ethyl-1,2,4-oxadiazol-5-yl)pyrazin-2-yl)-N-(3-hydroxy-3-methylbutyl)-4-methylbenzenesulfonamide

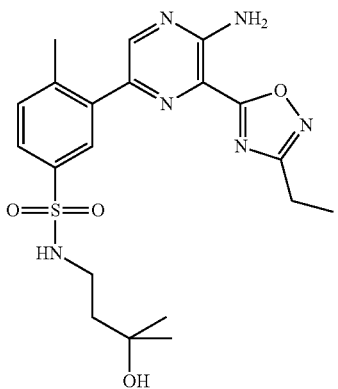 [SMILES: CCc1noc(-c2nc(-c3cc(S(=O)(=O)NCCC(C)(C)O)ccc3C)cnc2N)n1]

The title compound was prepared using 5-bromo-3-(3-ethyl-1,2,4-oxadiazol-5-yl)pyrazin-2-amine (Intermediate C2d) and N-(3-hydroxy-3-methyl-butyl)-4-methyl-benzenesulfonamide-3-boronic acid (Intermediate B3a) under analogous conditions to those of Example 1;

LC-MS: MS m/z 447.3 [M+H]+; Method A $^1$H NMR (400 MHz, DMSO-d6) δ 8.60 (1H, s), 7.91 (1H, s), 7.83 (1H, br s), 7.75 (1H, d), 7.57 (1H, d), 2.85 (4H, m), 2.50 (2H, m), 2.35 (3H, m), 1.00 (6H, s), OH, Me and NH2 not visible, may be obscured by DMSO and water peaks.

Example 137

3-(5-Amino-6-(3-ethyl-1,2,4-oxadiazol-5-yl)pyrazin-2-yl)-N-(azetidin-3-yl)-4-methylbenzenesulfonamide

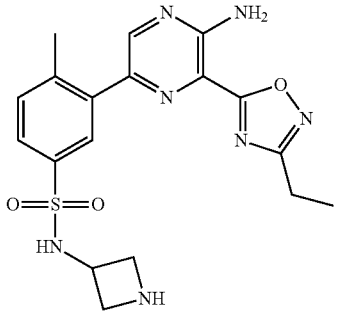 [SMILES: CCc1noc(-c2nc(-c3cc(S(=O)(=O)NC4CNC4)ccc3C)cnc2N)n1]

The title compound was prepared using 5-bromo-3-(3-ethyl-1,2,4-oxadiazol-5-yl)pyrazin-2-amine (Intermediate C2d) and tert-butyl 3-(4-methyl-3-(4,4,5,5-tetramethyl-1,3,2-dioxaborolan-2-yl)phenylsulfonamido)azetidine-1-carboxylate (prepared by analogy to intermediate B1) under analogous conditions to those of Example 1, followed by removal of the Boc protecting group using TFA/DCM;

LCMS Method:
Column: Cynergi2.5 um Max-RP100A (20×4.0) mm
Mobile Phase: A: 0.01M Ammonium acetate (Aq)B:ACN T
% B: 0/20, 1.0/20, 2.5/85, 4.0/95, 4.5/20, 5.0/20
Flow: 1.0 mL/min, Diluent: ACN LC-MS: MS m/z 416.2 [M+H]+

$^1$H NMR (400 MHz, DMSO-d6) δ 8.62 (1H, s), 7.90 (1H, s), 7.85 (1H, br s), 7.75 (1H, d), 7.57 (1H, d), 4.00 (1H, m), 3.25 (4H, m), 2.88 (2H, m), 1.75 (3H, s), 1.35 (2H, t). Two protons not visible, may be obscured by DMSO and/or water peaks.

Example 138

Trans-3-(5-Amino-6-(5-ethyl-1,3,4-oxadiazol-2-yl)pyrazin-2-yl)-N-((1r,4r)-4-hydroxycyclohexyl)-4-methylbenzenesulfonamide

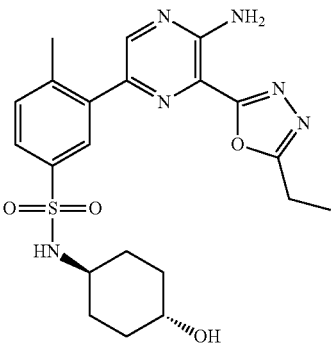 [SMILES: CCc1nnc(-c2nc(-c3cc(S(=O)(=O)N[C@H]4CC[C@H](O)CC4)ccc3C)cnc2N)o1]

The title compound prepared using 5-bromo-3-(5-ethyl-1,3,4-oxadiazol-2-yl)pyrazin-2-amine (Intermediate C1b) and Trans-N-(4-Hydroxy-cyclohexyl)-4-methyl-benzenesulfonamide 3-boronic acid (Intermediate B5a) under analogous conditions to those of Example 1;

LC-MS: MS m/z 459.3 [M+H]+;

$^1$H NMR (400 MHz, DMSO-d6) δ 8.50 (1H, s), 7.88 (1H, s), 7.75 (2H, m), 7.35 (1H, m), 4.45 (1H, br s), 3.30 (1H, br s), 3.00 (2H, m), 2.90 (1H, br s), 2.50 (1H, s), 2.48 (3H, s), 1.70 (4H, m), 1.32 (3H, m), 1.10 (4H, m). Two protons not visible, may be obscured by DMSO and/or water peaks.

Example 139

Trans-3-[5-Amino-6-(3-ethyl-[1,2,4]oxadiazol-5-yl)-pyrazin-2-yl]-N-(4-hydroxy-cyclohexyl)-4-methyl-benzene sulfonamide

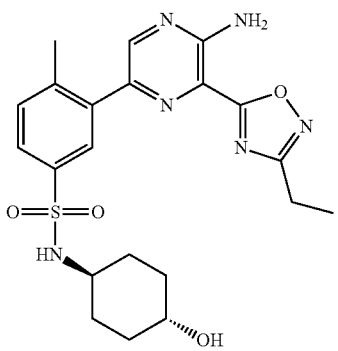 [SMILES: CCc1noc(-c2nc(-c3cc(S(=O)(=O)N[C@H]4CC[C@H](O)CC4)ccc3C)cnc2N)n1]

The title compound prepared using 5-bromo-3-(3-ethyl-1,2,4-oxadiazol-5-yl)pyrazin-2-amine (Intermediate C2d) and Trans-N-(4-Hydroxy-cyclohexyl)-4-methyl-benzene-sulfonamide 3-boronic acid (intermediate B5a) under analogous conditions to those of Example 1;

LCMS: Rt 1.91 mins MS m/z 459.3 [M+H]+:

$^1$H NMR (400 MHz, DMSO-d6) δ 8.60 (1H, s), 7.92 (1H, s), 7.82 (1H, br s), 7.75 (1H, d), 7.65 (1H, d), 7.57 (1H, d), 4.45 (1H, s), 3.30 (1H, m), 2.90 (1H, m), 2.85 (2H, q), 1.78-1.60 (4H, m), 1.43 (3H, t), 1.22-1.00 (4H, m). One proton not visible, may be obscured by DMSO and/or water peaks.

Example 140

Trans-3-[5-Amino-6-(3-propyl-[1,2,4] oxadiazol-5-yl)-pyrazin-2-yl]-N-(4-hydroxy-cyclohexyl)-4-methyl-benzene sulfonamide

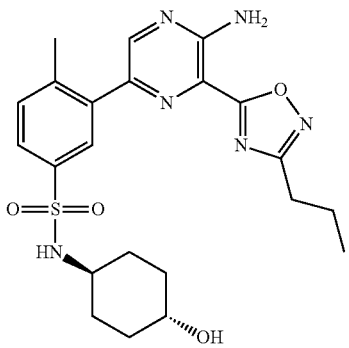 [SMILES: CCCc1noc(-c2nc(-c3cc(S(=O)(=O)N[C@H]4CC[C@H](O)CC4)ccc3C)cnc2N)n1]

The title compound prepared using 5-bromo-3-(3-propyl-1,2,4-oxadiazol-5-yl)pyrazin-2-amine (Intermediate C2e) and trans-N-(4-Hydroxy-cyclohexyl)-4-methyl-benzenesulfonamide 3-boronic acid (intermediate B5a) under analogous conditions to those of Example 1;

LCMS: Rt 2.03 mins MS m/z 473.3 [M+H]+

$^1$H NMR (400 MHz, DMSO-d6) δ 8.60 (1H, s), 7.92 (1H, s), 7.80 (2H, br s), 7.75 (1H, d), 7.65 (1H, d), 7.57 (1H, d), 4.45 (1H, s), 3.30 (1H, m), 2.90 (1H, m), 2.80 (2H, m), 2.47 (3H, s), 1.80 (2H, m), 1.60-1.78 (4H, m), 1.00-1.22 (4H, m), 0.95 (3H, t).

Example 141

(1-((3-(5-Amino-6-(3-ethyl-1,2,4-oxadiazol-5-yl)pyrazin-2-yl)-4-methylphenyl)sulfonyl) piperidin-4-yl)methanol

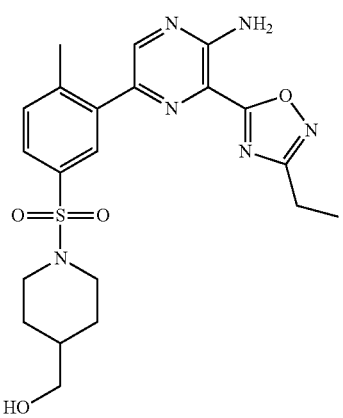 [SMILES: CCc1noc(-c2nc(-c3cc(S(=O)(=O)N4CCC(CO)CC4)ccc3C)cnc2N)n1]

The title compound prepared under analogous conditions to those of Example 1 using 5-bromo-3-(3-ethyl-1,2,4-oxadiazol-5-yl)pyrazin-2-amine (Intermediate C2d) and (5-((4-(hydroxymethyl)piperidin-1-yl)sulfonyl)-2-methylphenyl)boronic acid (prepared in two steps under analogous conditions to those of Intermediate B5a);

LC-MS: MS m/z 459.1 [M+H]+; Method A $^1$H NMR (400 MHz, DMSO-d6) δ 8.63 (1H, s), 7.81 (1H, br s), 7.80 (1H, s), 7.70 (1H, m), 7.60 (1H, m), 4.44 (1H, br s), 3.33 (2H, d), 3.22 (2H, d), 2.87 (2H, m), 2.45 (3H, s), 2.14 (2H, m), 1.70 (2H, m), 1.33 (3H, m), 1.20 (3H, m). One proton not visible, may be obscured by DMSO and/or water peaks.

Example 142

3-(5-Amino-6-(1-(2-(dimethylamino)ethyl)-1H-pyrazol-4-yl)pyrazin-2-yl)-N-(2-hydroxy-2-methylpropyl)-4-methylbenzenesulfonamide

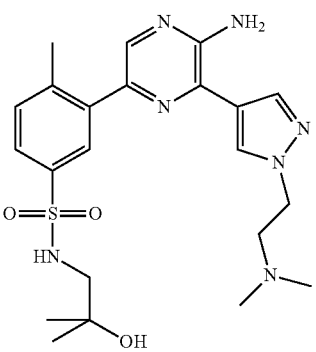 [SMILES: Cc1ccc(S(=O)(=O)NCC(C)(C)O)cc1-c1cnc(N)c(-c2cnn(CCN(C)C)c2)n1]

Step 1: 3-(5-Amino-6-(1-(2-hydroxyethyl)-1H-pyrazol-4-yl)pyrazin-2-yl)-N-(2-hydroxy-2-methylpropyl)-4-methylbenzenesulfonamide The title compound was prepared analogously to Example 13 from 2-(4-(4,4,5,5-tetramethyl-1,3,2-dioxaborolan-2-yl)-1H-pyrazol-1-yl)ethanol (Syntech solutions commercially available) and 3-(5-amino-6-chloro-pyrazin-2-yl)-N-(2-hydroxy-2-methyl-propyl)-4-methyl-benzenesulfonamide (Intermediate D2);

LCMS: Rt=0.84 mins; MS m/z 447.3 [M+H]+; Method 2minLowpHv03

Step 2: 2-(4-(3-Amino-6-(5-(N-(2-hydroxy-2-methylpropyl)sulfamoyl)-2-methylphenyl)pyrazin-2-yl)-1H-pyrazol-1-yl)ethyl 4-methylbenzenesulfonate Reference: Prepared according to Patent US 2002/0161004 (page. 44)

To a solution of 3-(5-amino-6-(1-(2-hydroxyethyl)-1H-pyrazol-4-yl)pyrazin-2-yl)-N-(2-hydroxy-2-methylpropyl)-4-methylbenzenesulfonamide (step 1) (190 mg, 0.426 mmol) in DCM (1064 µl) at 0° C., under an atmosphere of nitrogen, was added triethylamine (74.1 µl, 0.532 mmol). To this mixture was added a solution of p-toluenesulfonyl chloride (81 mg, 0.426 mmol) in DCM (1064 µl) dropwise over 5 minutes and the reaction mixture was stirred at 0° C. for 3.5 hours then allowed to warm to temperature overnight. Further portions of p-toluenesulfonyl chloride (81 mg, 0.426 mmol) and triethylamine (74.1 µl, 0.532 mmol) were added and stirring continued overnight. p-Toluenesulfonyl chloride (81 mg, 0.426 mmol) and triethylamine (74.1 µl, 0.532 mmol) were added and stirring continued overnight. The reaction mixture was added to water (50 ml) and the organic portion was separated, washed with 1M HCl (50 ml), saturated NaHCO₃ solution (50 ml) and saturated brine (20 ml). The organics were dried over MgSO₄, filtered and concentrated under reduced pressure to give a pale yellow oil. Purification by chromatography on silica eluting 0-10% MeOH in DCM afforded the title compound;

LCMS: Rt=1.15 mins; MS m/z 601.6 [M+H]+; Method 2minLowpHv03

Step 3: 3-(5-Amino-6-(1-(2-(dimethylamino)ethyl)-1H-pyrazol-4-yl)pyrazin-2-yl)-N-(2-hydroxy-2-methylpropyl)-4-methylbenzenesulfonamide To a stirring solution of 2-(4-(3-amino-6-(5-(N-(2-hydroxy-2-methylpropyl)sulfamoyl)-2-methylphenyl)pyrazin-2-yl)-1H-pyrazol-1-yl)ethyl 4-methylbenzenesulfonate (step 2)(25 mg, 0.042 mmol) in THF (416 µl) under N₂ was added DIPEA (14.54 µl, 0.083 mmol) and dimethylamine (2.0M in THF) (250 µl, 0.499 mmol). The reaction mixture was stirred for 16 hours at room temperature. A further portion of dimethylamine (2.0M in THF) (250 µl, 0.499 mmol) was added and stirring continued overnight. The resulting mixture was concentrated under reduced pressure. The crude product was purified by chromatography on silica eluting with 0-10% gradient of (2.0M NH₃ in MeOH) in DCM. The resulting residue was further purified by loading onto a 1 g Isolute®SCX-2 cartridge, flushing with MeOH and eluting the compound with 2.0M NH₃ in MeOH to afford the title compound;

LCMS: Rt=0.65 mins; MS m/z 474.6 [M−H]+; Method 2minLowpHv03

Example 143

3-(5-Amino-6-(3-cyclopropyl-1,2,4-oxadiazol-5-yl)pyrazin-2-yl)-N-(3-hydroxy-3-methylbutyl)-4-methylbenzenesulfonamide

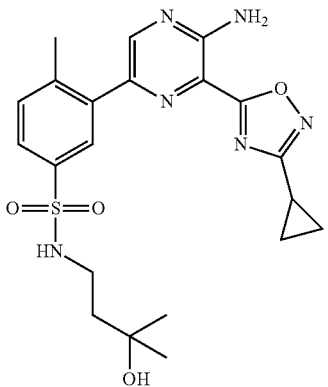 [SMILES: Cc1ccc(S(=O)(=O)NCCC(C)(C)O)cc1-c1cnc(N)c(-c2nc(C3CC3)no2)n1]

The title compound was prepared by conditions analogous to those used for the preparation of Example 18 from N-(3-hydroxy-3-methylbutyl)-4-methyl-3-(4,4,5,5-tetramethyl-1,3,2-dioxaborolan-2-yl)benzenesulfonamide (Intermediate B3) and 5-bromo-3-(3-cyclopropyl-[1,2,4]oxadiazol-5-yl)-pyrazin-2-ylamine (Intermediate C2c);

LCMS: Rt 1.01 mins; MS m/z 359.2 [M+H]+; Method 2minLC_v003

PREPARATION OF INTERMEDIATES

Bromides (A)

Intermediate A1

3-Bromo-N-(3-hydroxypropyl)-4-methylbenzenesulfonamide

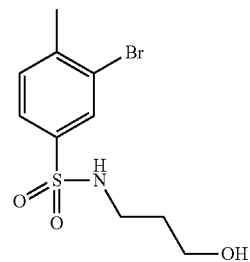 [SMILES: Cc1ccc(S(=O)(=O)NCCCO)cc1Br]

To a stirring solution of 3-bromo-4-methylbenzene-1-sulfonyl chloride (2 g, 7.42 mmol) in THF (37 mL) under N₂ was added 3-amino-1-propanol (0.568 ml, 7.42 mmol) and the resulting mixture was stirred at RT for 24 hours. The solvent was removed under reduced pressure and the crude material was added to 0.1M HCl (100 ml). The mixture was extracted with EtOAc (150 ml) and the organic extract was washed with sat. Na₂CO₃ (60 ml), brine, dried over MgSO₄ and concentrated under reduced pressure to afford the title compound;

LCMS: Rt 0.89 mins; MS m/z 310.1 [M+H]+; Method 2minLC_v003

Intermediate A2

3-Bromo-N-(2-hydroxy-2-methylpropyl)-4-methyl-benzenesulfonamide

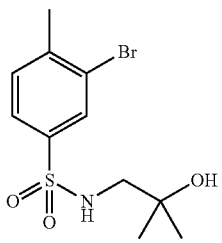 [SMILES: Cc1ccc(S(=O)(=O)NCC(C)(C)O)cc1Br]

To a stirring solution of 3-bromo-4-methylbenzene-1-sulfonyl chloride (3.02 g, 11.22 mmol) in pyridine (56.1 ml) under $N_2$ was added 1-amino-2-methylpropan-2-ol (1.0 g, 11.22 mmol) and the mixture was stirred at RT for 72 hours. The solvent was removed under reduced pressure and the resulting crude material was added to 0.1M HCl (100 ml). The mixture was extracted with EtOAc (150 ml) and the organic extract was washed with sat. $Na_2CO_3$ (100 ml), brine, dried over $MgSO_4$ and concentrated under reduced pressure to afford the title compound;

LCMS: Rt 1.01 mins; MS m/z 324.1 [M+H]+; Method 2minLC_v003

Intermediate A3

3-Bromo-N-(3-hydroxy-3-methyl-butyl)-4-methyl-benzenesulfonamide

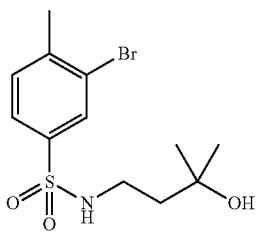 [SMILES: Cc1ccc(S(=O)(=O)NCCC(C)(C)O)cc1Br]

Prepared from 3-bromo-4-methylbenzene-1-sulfonyl chloride and 4-amino-2-methylbutan-2-ol analogously to Intermediate A2

LCMS: Rt 1.04 mins; MS m/z does not ionise [M+H]+; Method 2minLC_v003

Intermediate A4

3-Bromo-4-methyl-N-(3-methyl-oxetan-3-ylmethyl)-benzenesulfonamide

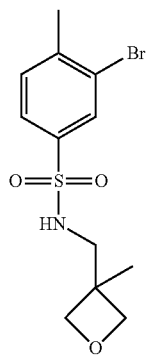 [SMILES: Cc1ccc(S(=O)(=O)NCC2(C)COC2)cc1Br]

To a solution of (3-methyloxetan-3-yl)methanamine (2.026 g, 20.03 mmol) in DMA (50 ml) was added DIPEA (4.37 ml, 25.04 mmol). The mixture was stirred at RT for 30 min before adding 3-bromo-4-methylbenzene-1-sulfonyl chloride (4.5 g, 16.70 mmol). The mixture was stirred at RT for 1 hr. The solvent was removed under reduced pressure and the residue was dissolved in EtOAc and washed with saturated aq. $NaHCO_3$ followed by 0.1M HCl then brine. The organic extract was dried over $MgSO_4$ and the solvent removed to give the product as a pale yellow powder (5.19 g)

LCMS: Rt 1.10 mins; MS m/z 336.1 [M+H]+; Method 2minLowpHv01

The following tabulated intermediates were prepared using methods analogous to those for Intermediates A1 to A4 starting from 3-bromo-4-methylbenzene-1-sulfonyl chloride and the appropriate amines. The amines are either commercially available or may be prepared according to known methods.

TABLE 1

| Int. | Structure | Name | [M + H]+/NMR |
|---|---|---|---|
| A5 | 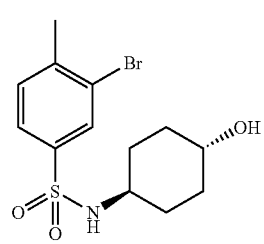 [SMILES: Cc1ccc(S(=O)(=O)N[C@H]2CC[C@H](O)CC2)cc1Br] | Trans-3-Bromo-N-(4-hydroxy-cyclohexyl)-4-methylbenzenesulfonamide | LCMS: Rt 1.01 mins; MS m/z 348.1 [M + H]+; Method 2minLC_v003 |

TABLE 1-continued

| Int. | Structure | Name | [M + H]⁺/NMR |
|---|---|---|---|
| A6 | 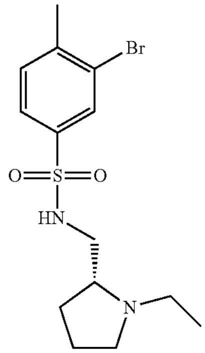 [SMILES: CCN1CCC[C@@H]1CNS(=O)(=O)c1ccc(C)c(Br)c1] | 3-Bromo-N-((R)-1-ethyl-pyrrolidin-2-ylmethyl)-4-methyl-benzenesulfonamide | LCMS: RT 0.64 mins; MS m/z 363.5 [M + H]+; Method 2minLowpHv01 |
| A7 | 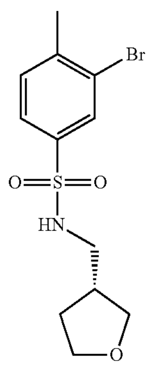 | 3-Bromo-4-methyl-N-[(R)-1-(tetrahydro-furan-3-yl)methyl]-benzenesulfon-amide | LCMS: Rt 1.09 mins; MS m/z 336.4 [M + H]+; Method 2minLowpHv01 |
| A8 | 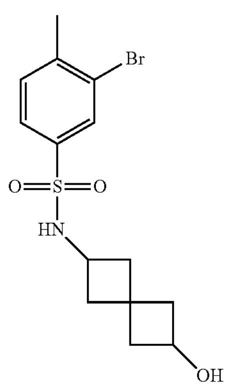 [SMILES: Cc1ccc(S(=O)(=O)NC2CC3(CC(O)C3)C2)cc1Br] | 3-Bromo-N-(6-hydroxy-spiro[3.3]hept-2-yl)-4-methyl-benzenesulfonamide | LCMS: Rt 1.01 mins; MS m/z 360.3 [M + H]+; Method 2minLowpHv01 |

TABLE 1-continued

| Int. | Structure | Name | [M + H]⁺/NMR |
|---|---|---|---|
| A9 | 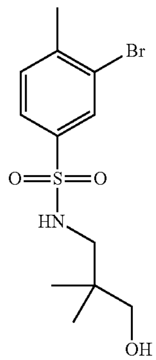 [SMILES: Cc1ccc(S(=O)(=O)NCC(C)(C)CO)cc1Br] | 3-Bromo-N-(3-hydroxy-2,2-dimethylpropyl)-4-methylbenzenesulfonamide | LCMS: Rt 0.98 mins; MS m/z 336.1 [M + H]+; Method 2minLC_v003 |
| A10 | 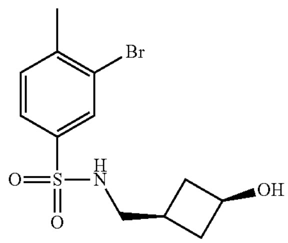 | Cis-3-Bromo-N-(3-hydroxy-cyclobutylmethyl)-4-methyl-benzenesulfonamide (approx. 20% trans isomer) | LCMS: RT 0.64 mins; MS m/z 363.5 [M + H]+; Method 2minLowpHv01 |
| A11 | 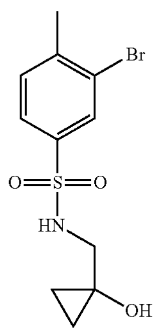 [SMILES: Cc1ccc(S(=O)(=O)NCC2(O)CC2)cc1Br] | 3-Bromo-N-(1-hydroxy-cyclopropylmethyl)-4-methyl-benzenesulfonamide | ¹H NMR (400 MHz, DMSO-d6) δ 7.97 (1H, d, J = 1.4 Hz), 7.77-7.74 (1H, m, J = 6.0 Hz), 7.71-7.69 (1H, dd, J = 1.4, 8.0 Hz), 7.58-7.56 (1H, d, J = 8.0 Hz), 5.32 (1H, s), 2.86-2.85 (2H, d, J = 6.1 Hz), 2.42 (3H, s), 0.52-0.49 (2H, m), 0.46-0.43 (2H, m). |

Intermediate A12

5-Bromo-2-fluoro-N-(3-hydroxypropyl)-4-methyl-benzenesulfonamide

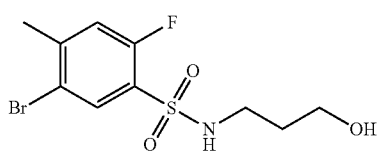 [SMILES: Cc1cc(F)c(S(=O)(=O)NCCCO)cc1Br]

The title compound was prepared from 5-bromo-2-fluoro-4-methylbenzene-1-sulfonyl chloride and 3-aminopropan-1-ol analogously to Intermediate A1.

LCMS: Rt 0.88 mins; MS m/z 328.1 [M+H]+; Method: 2minLC_v003

Boronic Esters (B)

Intermediate B1

N-(3-Hydroxypropyl)-4-methyl-3-(4,4,5,5-tetramethyl-1,3,2-dioxaborolan-2-yl)benzenesulfonamide

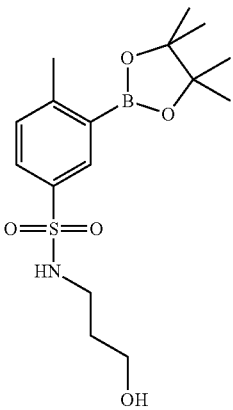 [SMILES: Cc1ccc(S(=O)(=O)NCCCO)cc1B1OC(C)(C)C(C)(C)O1]

A mixture comprising 3-bromo-N-(3-hydroxypropyl)-4-methylbenzenesulfonamide (Intermediate A1) (2.25 g, 7.30 mmol), KOAc (1.075 g, 10.95 mmol), PdCl$_2$(dppf).CH$_2$Cl$_2$ adduct (0.298 g, 0.365 mmol) and bis(pinicolato)diboron (2.039 g, 8.03 mmol) in DME (36.5 mL) under N$_2$ was stirred at 90° C. for 5 hours. The resulting mixture was added to water (100 ml) and extracted with EtOAc (2×100 ml). The combined organic extracts were washed with brine, dried over MgSO$_4$ and concentrated under reduced pressure.

Purification by chromatography on silica eluting with 0-100% gradient EtOAc in isohexane afforded the title compound;

LCMS: Rt 1.03 mins; MS m/z 356.5 [M+H]+; Method 2minLC_v003

The compounds of the following tabulated intermediates were prepared analogously to Intermediate B1 from the appropriate bromide starting compounds (see Intermediates A1-A11):

TABLE 2

| Int. | Structure | Name | [M + H]+/NMR |
|---|---|---|---|
| B2 | 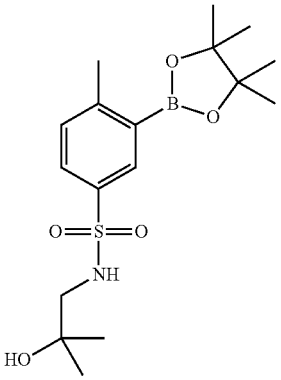 [SMILES: Cc1ccc(S(=O)(=O)NCC(C)(C)O)cc1B1OC(C)(C)C(C)(C)O1] | N-(2-Hydroxy-2-methyl-propyl)-4-methyl-3-(4,4,5,5-tetramethyl[1,3,2]dioxaborolan-2-yl)benzenesulfonamide | LCMS Rt 1.20 min. MS m/z 370.3 [M + H]+), Method: 2minLowpHv01 |
| B3 | 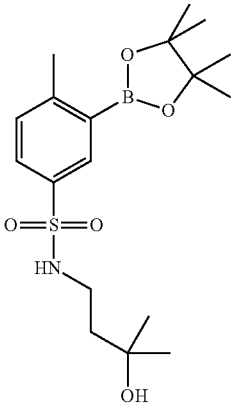 [SMILES: Cc1ccc(S(=O)(=O)NCCC(C)(C)O)cc1B1OC(C)(C)C(C)(C)O1] | N-(3-Hydroxy-3-methylbutyl)-4-methyl-3-(4,4,5,5-tetramethyl-1,3,2-dioxaborolan-2-yl)benzenesulfonamide | LCMS: Rt 1.10 mins; MS m/z 384.5 [M + H]+; Method 2minLC_v003 |
| B4 | 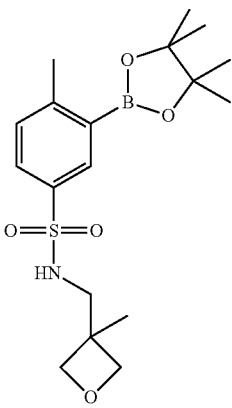 [SMILES: Cc1ccc(S(=O)(=O)NCC2(C)COC2)cc1B1OC(C)(C)C(C)(C)O1] | 4-Methyl-N-(3-methyl-oxetan-3-ylmethyl)-3-(4,4,5,5)tetramethyl-[1,3,2]dioxaborolan-2-yl)-benzenesulfonamide | LCMS: Rt 1.22 minsMS m/z 382.6 [M + H]+; Method 2minLC_v003 |

TABLE 2-continued

| Int. | Structure | Name | [M + H]+/NMR |
|---|---|---|---|
| B5 | 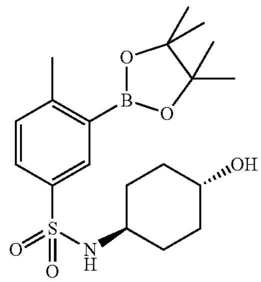 [SMILES: Cc1ccc(S(=O)(=O)N[C@H]2CC[C@H](O)CC2)cc1B1OC(C)(C)C(C)(C)O1] | N-(trans-4-Hydroxycyclohexyl)-4-methyl-3-(4,4,5,5-tetramethyl-1,3,2-dioxaborolan-2-yl)benzenesulfonamide | LCMS: Rt 1.14 mins; MS m/z 396.3 [M + H]+; Method 2minLC_v003 |
| B6 | 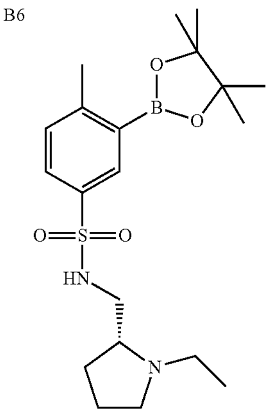 | N-((R)-1-Ethyl-pyrrolidin-2-ylmethyl)-4-methyl-3-(4,4,5,5-tetramethyl-[1,3,2]dioxaborolan-2-yl)-benzenesulfonamide | LCMS: RT 0.97 mins; MS m/z 409.3 [M + H]+; Method 2minLowpHv02 |
| B7 | 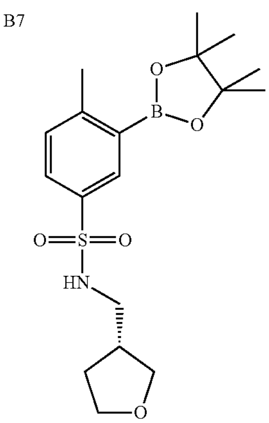 | 4-Methyl-N-[(R)-1-(tetrahydro-furan-3-yl)methyl]-3-(4,4,5,5-tetramethyl-[1,3,2]dioxaborolan-2-yl)-benzene-sulfonamide | LCMS: Rt 1.28 mins; MS m/z 382.3 [M + H]+; Method 2minLowpHv01 |
| B8 | 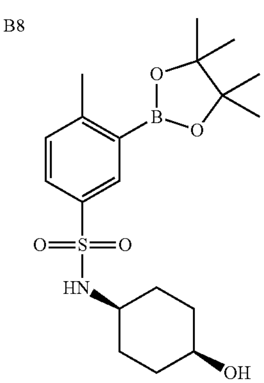 | N-((cis)-4-hydroxycyclohexyl)-4-methyl-3-(4,4,5,5-tetramethyl-1,3,2-dioxaborolan-2-yl)benzenesulfonamide | $^1$H NMR (400 MHz, DMSO) δ8.06 (1H, d, J = 2.1 Hz), 7.79-7.76 (1H, dd, J = 2.1, 8.0 Hz), 7.58-7.56 (1H, d, J = 6.8 Hz), 7.38-7.40 (1H, d, J = 8.1 Hz), 4.32 (1H, d, J = 3.0 Hz), 3.56 (1H, broad m), 2.93 (1H, broad m), 2.53 (3H, s), 1.56-1.48 (4H, m), 1.36-1.28 (4H, m), 1.33 (12H, s). |

Boronic Acids (B)

Intermediate B3a

N-(3-Hydroxy-3-methyl-butyl)-4-methyl-benzene-sulfonamide-3-boronic acid

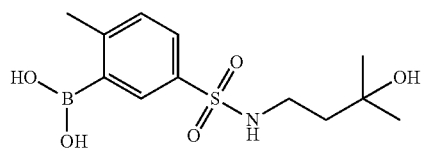 [SMILES: Cc1ccc(S(=O)(=O)NCCC(C)(C)O)cc1B(O)O]

To a stirred solution of 3-bromo-N-(3-hydroxy-3-methyl-butyl)-4-methyl-benzenesulfonamide (Intermediate A3)(1.0 g, 2.97 mmol) in THF (20 ml) was added n-BuLi (5.9 ml, 14.85 mmol, 2.5 M) dropwise at −78° C. The reaction was maintained at this temperature for 30 min before dropwise addition of triisopropyl borate (8.9 g, 47.6 mmol). The reaction mixture was allowed to warm slowly to RT then stirred for an additional 15 h. The reaction was quenched with 3N HCl (50 ml) and extracted with ethyl acetate (3×100 ml). The organic extract was separated, dried over sodium sulphate and concentrated under reduced pressure to afford the crude compound. The product was dissolved in ethyl acetate (100 ml) and extracted with sodium carbonate solution (3×150 ml) (pH 9). The aqueous extract was brought to 2 by adding conc HCl, and the product was extracted with ethyl acetate (3×200 ml). The organic extract was dried over sodium sulphate and concentrated under vacuum to afford the title compound (0.29 g).

Intermediate B5a

Trans-N-(4-Hydroxy-cyclohexyl)-4-methyl-benzene-sulfonamide 3-boronic acid

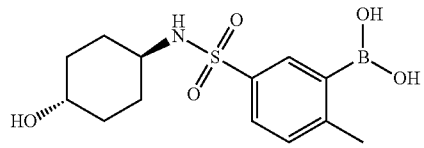 [SMILES: Cc1ccc(S(=O)(=O)N[C@H]2CC[C@H](O)CC2)cc1B(O)O]

To a stirred solution of trans-3-bromo-N-(4-hydroxy-cyclohexyl)-4-methylbenzenesulfonamide (Intermediate A5) (2.0 g, 5.77 mmol) in THF (60 ml) was added n-BuLi (11.5 ml, 28.8 mmol, 2.5 M) dropwise at −78° C. The reaction was maintained at this temperature for 30 min before dropwise addition of triisopropyl borate (17.35 g, 92.32 mmol). The reaction mixture was allowed to warm slowly to RT then stirred for an additional 15 h. The reaction was quenched with 3N HCl (200 ml) and extracted with ethyl acetate (3×250 ml). The organic extract was separated, dried over sodium sulphate and concentrated under vacuum to afford the crude product. The product was dissolved in ethyl acetate (500 ml) and extracted with sodium carbonate solution (3×150 ml) (pH 9). The aqueous extract was brought to pH 2 by adding conc. HCl and the product was extracted with ethyl acetate (3×250 ml). The organic extract was dried over sodium sulphate and concentrated under vacuum to afford the title compound.

Intermediate C1

5-Bromo-3-(5-methyl-[1,3,4]oxadiazol-2-yl)-pyrazin-2-ylamine

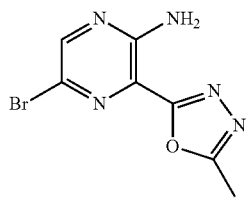

Step 1: 3-Amino-6-bromo-pyrazine-2-carboxylic acid N'-acetyl-hydrazide

HATU (3.4 g, 9.05 mmol) and triethylamine (1.2 g, 12.06 mmol) were added to a suspension of 2-Amino-5-bromopyrazine-3-carboxylic acid (1.40 g, 6.03 mmol) and acetohydrazide (0.44 g, 6.03 mmol) in DCM (100 ml) and the resultant solution was stirred at ambient temperature for 24 hr. The reaction was monitored by TLC. The reaction mixture was poured into water (200 ml) and the solid collected by filtration and dried under vacuum to afford 3-amino-6-bromo-pyrazine-2-carboxylic acid N'-acetyl-hydrazide;

LCMS: Rt 0.57 mins MS m/z 274.0 [M+H}+; Method 2minLowpHv01

Step 2: 5-Bromo-3-(5-methyl-[1,3,4]oxadiazol-2-yl)-pyrazin-2-ylamine

3-Amino-6-bromo-pyrazine-2-carboxylic acid N'-acetyl-hydrazide (step 1) (0.86 g, 3.15 mmol) was dissolved in DCM (40 ml) and triethylamine (0.95 g, 9.45 mmol) was added dropwise at room temperature under nitrogen followed by p-toluenesulfonyl chloride (1.79 g, 9.45 mmol). The reaction was stirred at room temperature for 24 hr. DCM (20 ml) was added and the solid was removed by filtration and washed with DCM (30 ml). The organic filtrate was washed with water (2×30 ml) and concentrated under vacuum to afford required compound. The product was purified by flash-chromatography on silica eluting with EtOAc-hexane (9:1) to give the product as a yellow solid:

LCMS: Rt 0.86 mins MS m/z 256.0 [M+H]+; Method 2minLowpHv01

Intermediate C1b

5-Bromo-3-(5-ethyl-1,3,4-oxadiazol-2-yl)pyrazin-2-amine

The title compound was prepared analogously to Intermediate C1

Intermediate C2a

5-Bromo-3-(3-methyl-[1,2,4]oxadiazol-5-yl)-pyrazin-2-ylamine

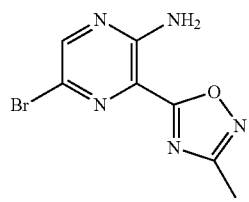

Step 1: 3-(3-Methyl-[1,2,4]oxadiazol-5-yl)-pyrazin-2-ylamine

DCC (1.39 g, 6.75 mmol) and HOBt.H$_2$O (1.03 g, 13.51 mmol) were added to a stirred suspension of N'-hydroxyacetimidamide (0.5 g, 10.12 mmol) and 3-amino pyrazine-2-carboxylic acid (0.94 g, 6.75 mmol) in DMF (15 ml). The reaction mixture was stirred at rt for 3 h followed by 100° C. for 2 h. When cool, the reaction mixture was poured in to water (100 ml) and diethyl ether (100 ml). The solid was removed by filtration and the filtrate was extracted with more diethyl ether (2×100 ml). The combined organic extracts was dried over Na$_2$SO$_4$ and concentrated under reduced pressure to afford the crude product. Purification by chromatography on silica, eluting with 10% EtOAc in hexane, gave the title compound as a white solid (0.35 g, 29%).

Step 2: 5-Bromo-3-(3-methyl-[1,2,4]oxadiazol-5-yl)-pyrazin-2-ylamine

A stirred solution of 3-(3-methyl-[1,2,4]oxadiazol-5-yl)-pyrazin-2-ylamine (step 1) (258 mg, 1.45 mmol) and NBS (259 mg, 1.45 mmol) in acetonitrile (10 ml) was heated at reflux for 5 h. The solvent was removed and the product was purified by chromatography on silica, eluting with 7% EtOAc in hexane, to give the product as a brown solid (240 mg, 64%).

Intermediate C2b

5-Bromo-3-(3-isopropyl-[1,2,4]oxadiazol-5-yl)-pyrazin-2-ylamine

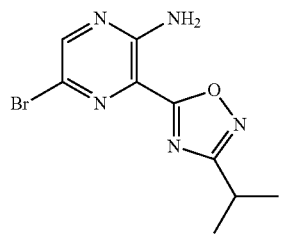 [SMILES: CC(C)c1noc(-c2nc(Br)cnc2N)n1]

The title compound was prepared analogously to Intermediate C2a starting from N'-hydroxyisobutyrimidamide

Intermediate C2c

5-Bromo-3-(3-cyclopropyl-[1,2,4]oxadiazol-5-yl)-pyrazin-2-ylamine

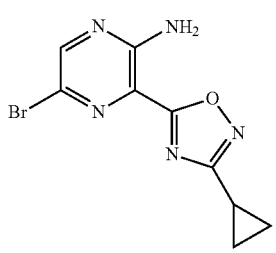 [SMILES: Nc1ncc(Br)nc1-c1nc(C2CC2)no1]

The title compound was prepared analogously to Intermediate C2a starting from N'-hydroxycyclopropanecarboximidamide

Intermediate C2d

5-Bromo-3-(3-ethyl-1,2,4-oxadiazol-5-yl)pyrazin-2-amine

The title compound was prepared analogously to Intermediate C2a, starting from N'-hydroxypropionimidamide

Intermediate C2e

5-Bromo-3-(3-propyl-1,2,4-oxadiazol-5-yl)pyrazin-2-amine

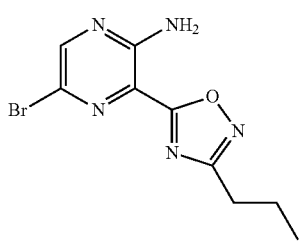 [SMILES: CCCc1noc(-c2nc(Br)cnc2N)n1]

The title compound was prepared analogously to Intermediate C2a starting from N'-hydroxybutyrimidamide

Intermediate C3

5-Bromo-3-(3-methyl-isoxazol-5-yl)-pyrazin-2-ylamine

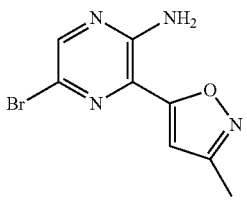

Step 1: 3-(3-Methyl-isoxazol-5-yl)-pyrazin-2-ylamine n-Butyllithium (7 ml, 9.8 mmol, 1.4 M in hexanes) was added to a solution of acetone oxime (0.36 g, 4.9 mmol) in dry THF (15 ml) under nitrogen at 0° C. The mixture was allowed to warm to RT and stirred for 30 min. A solution of 3-amino-pyrazine-2-carboxylic acid methyl ester (0.50 g, 3.26 mmol) in THF (5 ml) was added and the reaction was stirred at RT until the starting material was consumed. Sulfuric acid (2 ml) was added at 0° C. followed by stirring at room temperature for 1 h. The reaction mixture was basified with aq. Na$_2$CO$_3$ and the product was extracted with DCM (5×15 ml). The combined organic extracts were dried over Na$_2$SO$_4$ and the solvent removed. The residue was purified by chromatography on silica, eluting with EtOAc: hexane (2:8) to give the title compound.

Step 2: 5-Bromo-3-(3-methyl-isoxazol-5-yl)-pyrazin-2-ylamine

NBS (50 mg, 0.28 mmol) was added to a stirred solution of 3-(3-Methyl-isoxazol-5-yl)-pyrazin-2-ylamine (50 mg, 0.28 mmol) in chloroform and the reaction was stirred for 4 h at room temperature. The reaction was diluted with water and extracted with CHCl$_3$. The organic extract was dried over Na$_2$SO$_4$ and purified by chromatography on silica, eluting with hexane: EtOAc (3:1) to give the title compound.

LCMS: Rt 0.98 mins MS m/z 255.0 [M+H]+; Method 2minLowpHv01

Intermediate C4

5-Bromo-3-(1-methyl-1H-pyrazol-4-yl)-pyrazin-2-ylamine

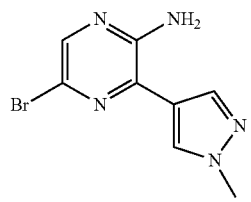

Step 1: 3-(1-Methyl-1H-pyrazol-4-yl)-pyrazin-2-ylamine

Sodium carbonate (17 ml of a 2M solution, 33 mmol) was added to a mixture of 3-chloropyrazin-2-amine (1.23 g, 9.47 mmol), 1-methyl-4-(4,4,5,5-tetramethyl-1,3,2-dioxoborolan-2-yl)-1H-pyrazole (1.97 g, 9.47 mmol) and PdCl$_2$(dppf).CH$_2$Cl$_2$ (0.387 g, 0.473 mmol) in DME (60 ml). The mixture was de-gassed several times under nitrogen then heated at 85° C. for 3 h. The solvent was removed and the residue was diluted with water and extracted several times with EtOAc. The organic extract was separated, dried over MgSO$_4$ and the solvent removed to give a dark oil. Chromatography on silica, eluting with EtOAc:MeOH (3:1), followed by trituration with EtOAc and diethyl ether gave the title compound as a grey powder (1.25 g)

LCMS: Rt 0.45 mins; MS m/z 176.4 [M+H]+; Method 2minLC_v003

$^1$H NMR (400 MHz, CDCl$_3$) 8.01 (2H, m), 7.93 (2H, s), 4.75 (2H, br s), 4.00 (3H, s)

Step 2: 5-Bromo-3-(1-methyl-1H-pyrazol-4-yl)-pyrazin-2-ylamine

A stirred solution of 3-(1-methyl-1H-pyrazol-4-yl)pyrazin-2-amine (step 1) (1.3 g, 7.42 mmol) and NBS (1.45 g, 8.16 mmol) in acetonitrile (15 ml) was heated at reflux under nitrogen for 5 hrs. The solvent was removed under reduced pressure and the residue was diluted with aq. NaHCO$_3$ and extracted several times with EtOAc. The organic extract was dried over MgSO$_4$ and concentrated under reduced pressure to give a dark oil. Chromatography on silica, eluting with EtOAc, gave the title compound as a solid (0.523 g, 26%)

LCMS: Rt 0.75 mins MS m/z 254.3 [M+H]+; Method 2minLC_v003

$^1$H NMR (400 MHz, CDCl$_3$) δ (ppm) 8.01 (2H, s), 7.96 (1H, s), 4.75 (2H, br s), 4.00 (3H, s).

Intermediate C5

5-Chloro-3-(1H-1,2,4-triazol-1-yl)pyrazin-2-amine

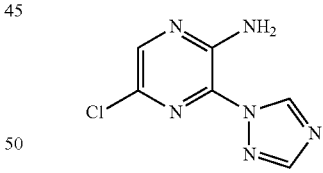

A mixture of 3-bromo-5-chloropyrazin-2-amine (5 g, 23.99 mmol), 1H-1,2,4-triazole (1.740 g, 25.2 mmol), N,N-dimethylglycine (0.247 g, 2.399 mmol), Cs$_2$CO$_3$ (23.45 g, 72.0 mmol) and CuI (0.457 g, 2.399 mmol) in dimethylaniline (120 ml) was heated at 150° C. for 4 hours. The resulting mixture was added to water (700 ml) and the product was extracted into EtOAc (2×500 ml). The combined organic extracts were washed with brine, dried over MgSO$_4$ and concentrated under reduced pressure. Purification by chromatography on silica eluting with a gradient of 0-10% [2M NH$_3$ in MeOH] in DCM afforded the title compound as a yellow solid; LCMS: Rt 0.74 mins; MS m/z 197.1 [M+H]+; Method 2minLowpH.

Intermediate C6

5-Chloro-3-(2-methylthiazol-5-yl)pyrazin-2-amine

A mixture of 2-methyl-5-(4,4,5,5-tetramethyl-1,3,2-dioxaborolan-2-yl)thiazole (1 g, 4.44 mmol), 3-bromo-5-chloropyrazin-2-amine (0.926 g, 4.44 mmol), PdCl$_2$(dppf).CH$_2$Cl$_2$ adduct (0.181 g, 0.222 mmol) and 2 M Na$_2$CO$_3$ (6.66 ml) in DME (22.21 ml) under N$_2$ was heated using microwave radiation at 120° C. for 45 mins. The mixture was added to water (100 ml) and extracted with EtOAc (2×90 ml). The organic extracts were washed with brine, dried over MgSO$_4$ and concentrated under reduced pressure. Purification by chromatography on silica eluting with 0-10% [2.0M NH$_3$ in MeOH] in TBME afforded the title compound as a brown solid;

LCMS: Rt 0.87 mins; MS m/z 227.1 [M+H]+; Method 2minLC_v003.

Intermediate C7

5-Chloro-3-(1,3-dimethyl-1H-pyrazol-4-yl)-pyrazin-2-ylamine

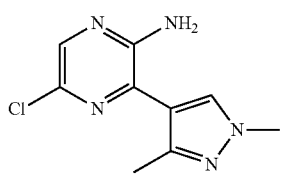

To a solution of 3-bromo-5-chloropyrazin-2-amine (3.75 g, 18.01 mmol) in DME (90 mL) was added 1,3-dimethyl-4-(4,4,5,5-tetramethyl-1,3,2-dioxaborolan-2-yl)-1H-pyrazole (4 g, 18.01 mmol), bis(triphenylphosphine)palladium (11) chloride (0.632 g, 0.901 mmol) and Na$_2$CO$_3$ (aq. 2.0M) (27.0 mL, 54.0 mmol). The reaction was heated to 90° C. overnight. The reaction was added to water (250 ml) and the product was extracted into EtOAc (2×230 ml). The organic phase was washed with brine, dried over MgSO$_4$. The solids were removed by filtration, washed with EtOAc and the filtrate concentrated under vacuum. The crude product was purified by flash column chromatography, eluting with 0-10% gradient of (2M NH$_3$ in MeOH) in DCM on a 80 g Si-column, loading with DCM to give the product (2.5 g)

LCMS: Rt 0.81 mins; MS m/z 224.0 [M+H]+; Method 2minLowpHv01

Intermediate C8

5-Bromo-3-(1H-[1,2,3]triazol-4-yl)-pyrazin-2-ylamine

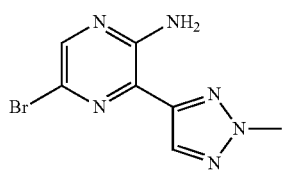

Step 1: 5-Bromo-3-trimethylsilanylethynyl-pyrazin-2-ylamine

To a 150 mL round-bottomed flask was added 3,5-dibromopyrazin-2-amine (3 g, 11.86 mmol) and triethylamine (16.53 ml, 119 mmol) in THF (60 ml) to give a yellow suspension. To the stirring solution was added bis(triphenylphosphine)palladium(11) chloride (833 mg, 1.186 mmol) and copper(I) iodide (452 mg, 2.373 mmol). Whilst maintaining the temperature below 10° C., ethynyltrimethylsilane (1.844 ml, 13.05 mmol) was added slowly and the reaction stirred at below 10° C. for 30 mins before warming to room temperature and stirring for a further 30 mins.

The reaction was concentrated under reduced pressure. After dilution with ethyl acetate the organics were washed with brine, the organic layer separated, dried over MgSO$_4$, filtered and the solvent removed under reduced pressure. The residue was loaded onto silica and purified by flash column chromatography, elution with iso hexane:ethyl acetate (0-30%) on an 80 g silica column. The required fractions were combined and the solvent removed under reduced pressure to yield the product as a light brown solid (2.5 g).

LCMS: Rt 1.26 mins MS m/z 272.3 [M+H]+; Method 2minLowpH $^1$H NMR (400 MHz, DMSO-d6) δ 8.12 (1H, s), 6.80 (2H, br s), 0.26 (9H, s).

Step 2: 5-Bromo-3-ethynyl-pyrazin-2-ylamine

To a 150 mL round-bottomed flask was added 5-bromo-3-((trimethylsilyl)ethynyl) pyrazin-2-amine (2.5 g, 9.25 mmol) and K$_2$CO$_3$ (1.279 g, 9.25 mmol) in MeOH (40 ml) to give a brown solution. The reaction was stirred at room temp for 30 mins. The reaction was extracted into DCM, washed with water, brine, the organic layer separated, dried over MgSO$_4$, filtered and the solvent removed under reduced pressure to yield the product as a brown solid (1.54 g).

LCMS; Rt 0.78 mins MS m/z 200.2. [M+H]+; Method 2minLowpH $^1$H NMR (400 MHz, DMSO-d6) δ 8.12 (1H, s), 6.86 (2H, broad s), 4.81 (1H, s).

Step 3: 5-Bromo-3-(1H-[1,2,3]triazol-4-yl)-pyrazin-2-ylamine

To a 100 mL round-bottomed flask was added 5-bromo-3-ethynylpyrazin-2-amine (800 mg, 4.04 mmol), Sodium ascorbate (0.404 ml, 0.404 mmol), and copper(II) sulfate pentahydrate (10.09 mg, 0.040 mmol) in tertiary butanol (10.00 ml) and water (20 ml) to give a brown suspension. To this was added trimethylsilyl azide (1.61 ml, 12.12 mmol) and the reaction heated at 90° C. for 4 hours. The reaction was extracted into ethyl acetate, washed with brine, the organic layer separated, dried over MgSO$_4$, filtered and the solvent removed under reduced pressure. The residue was loaded onto silica and purified by flash column chromatography, elution with iso hexane:ethyl acetate (0-70%) on a 40 g silica cartridge. The required fractions were combined and the solvent removed under reduced pressure to yield the product as a dark yellow solid (560 mg, 57%).

LCMS: Rt 0.82 mins MS m/z 243.2. [M+H]+; Method 2minLowpH $^1$H NMR (400 MHz, DMSO-d6) δ (ppm) 15.66 (1H br s), 8.52 (1H, br s), 8.14 (1H, s), 7.46 (2H, br s).

Step 4: 5-Bromo-3-(1H-[1,2,3]triazol-4-yl)-pyrazin-2-ylamine

To a 25 mL round-bottomed flask was added 5-bromo-3-(1H-1,2,3-triazol-4-yl)pyrazin-2-amine (250 mg, 1.037 mmol), potassium carbonate (430 mg, 3.11 mmol), and iodomethane (0.195 ml, 3.11 mmol) in THF (10 ml) to give a yellow suspension. The reaction was stirred at room temp for 1 hour whereupon a 1:1 mixture of two regioisomers had formed. The reaction was extracted into ethyl acetate, washed with brine, the organic layer separated, dried over MgSO$_4$, filtered and the solvent removed under reduced pressure. The crude mixture was taken up in DMSO and purified by mass directed preparative purification to give the title compound.

LCMS: Rt 0.95 mins MS m/z 255.2. [M+H]+; Method 2minLowpH $^1$H NMR (400 MHz, DMSO-d6), δ 8.27 (1H, s), 8.18 (1H, s), 7.30 (2H, br s), 4.29 (3H, s).

Intermediate C8a

5-Bromo-3-(1-ethyl-1H-1,2,3-triazol-4-yl)pyrazin-2-amine and

Intermediate C8b

5-Bromo-3-(2-ethyl-2H-1,2,3-triazol-4-yl)pyrazin-2-amine

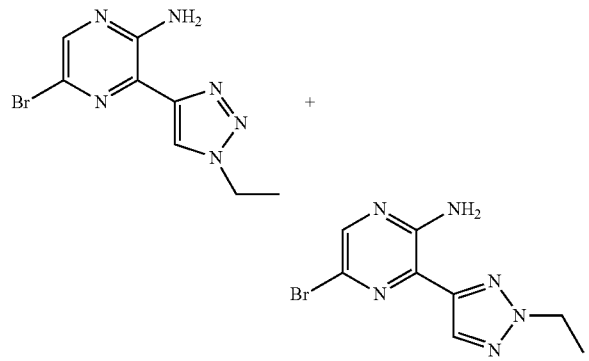

To a 25 mL round-bottomed flask was added 5-bromo-3-(1H-1,2,3-triazol-4-yl)pyrazin-2-amine (Intermediate C8 step 3) (300 mg, 1.245 mmol), potassium carbonate (516 mg, 3.73 mmol) and iodoethane (0.302 mL, 3.73 mmol) in THF (10 mL) to give a yellow suspension. The reaction mixture was heated at 70° C. for 4 hours. A 4:6 ratio of two regioisomers formed. The reaction was extracted into ethyl acetate, washed with water, brine, the organic layer separated dried over MgSO$_4$, filtered and the solvent removed under reduced pressure. The sample was dissolved in DMSO and purified by mass directed preparative chromatography. The required fractions were combined, extracted into DCM, washed with sat. sodium bicarbonate solution to remove all traces of TFA, the organic layer separated, dried over MgSO$_4$, filtered and the solvent removed under reduced pressure to afford the individual regioisomers:

First Eluted Peak:

Intermediate C8a

5-Bromo-3-(1-ethyl-1H-1,2,3-triazol-4-yl)pyrazin-2-amine

LCMS: Rt 0.99 mins MS m/z 269.4 [M+H]+; Method 2minLowpHv01.

$^1$H NMR (400 MHz, DMSO-d6) δ 8.79 (1H, s), 8.12 (1H, s), 7.54 (2H, broad), 4.49 (2H, mult), 1.50 (3H, t).

Second Eluted Peak:

Intermediate C8b

5-Bromo-3-(2-ethyl-2H-1,2,3-triazol-4-yl)pyrazin-2-amine

LCMS: Rt 1.07 mins MS m/z 269.3 [M+H]+; Method 2minLowpHv01.

$^1$H NMR (400 MHz, DMSO-d6) δ 8.29 (1H, s), 8.18 (1H, s), 7.30 (2H, broad), 4.57 (2H, mult), 1.52 (3H, t).

Intermediate C8c

5-Bromo-3-(2-(2,2,2-trifluoroethyl)-2H-1,2,3-triazol-4-yl)pyrazin-2-amine

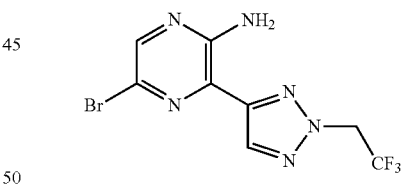

To a 25 mL round-bottomed flask was added 5-bromo-3-(1H-1,2,3-triazol-4-yl)pyrazin-2-amine (Intermediate C8 step 3) (300 mg, 1.245 mmol), cesium carbonate (1217 mg, 3.73 mmol), and 2,2,2-trifluoroethyl trifluoromethanesulfonate (0.359 mL, 2.489 mmol) in acetonitrile (10 mL) to give a yellow suspension. The reaction mixture was stirred at room temperature for 1 hour. The mixture was extracted into ethyl acetate, washed with water, brine, the organic layer separated dried over MgSO$_4$, filtered and the solvent removed under reduced pressure. The sample was dissolved in DMSO and purified by mass directed preparative chromatography.). The required fractions were combined, extracted into DCM, washed with sat. sodium bicarbonate to remove all traces of TFA, the organic layer separated, dried over MgSO$_4$, filtered and the solvent removed under reduced pressure to yield an off white solid;

LCMS: Rt 1.17 mins MS m/z 323.4 [M+H]+; Method 2minLowpHv01.
¹H NMR (400 MHz, DMSO-d6) δ 8.49 (1H, s), 8.24 (1H, s), 7.33 (2H, broad), 5.72 (2H, q).

Intermediate C9

5-Bromo-3-(2,5-dimethyl-2H-[1,2,3]triazol-4-yl)-pyrazin-2-ylamine

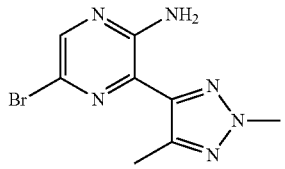

Step 1: 5-Bromo-3-(prop-1-ynyl)pyrazin-2-amine

To a 100 mL round-bottomed flask was added 3,5-dibromopyrazin-2-amine (2 g, 7.91 mmol) and bis(triphenylphosphine)palladium(II) chloride (0.278 g, 0.395 mmol) in toluene (30 ml) to give a yellow suspension. To the stirring solution was added tributyl(prop-1-ynyl)stannane (2.41 ml, 7.91 mmol) and the reaction heated at 60° C. for 1 hour. The crude reaction was loaded onto silica and the solvent removed under reduced pressure. The product was purified by flash column chromatography, elution with isohexane:ethyl acetate (0-50%) on an 40 g silica column. The required fractions were combined and the solvent removed under reduced pressure to yield the product as a light brown solid (1.3 g).
LCMS: Rt 0.87 mins MS m/z 212.0 [M+H]+; Method 2minLowpHv01
¹H NMR (400 MHz, DMSO-d6) δ 8.02 (1H, s), 6.80 (2H, br), 2.13 (3H, s).

Step 2: 5-Bromo-3-(5-methyl-1H-[1,2,3]triazol-4-yl)-pyrazin-2-ylamine

To a 25 mL round-bottomed flask was added 5-bromo-3-(prop-1-ynyl)pyrazin-2-amine (1.1 g, 5.19 mmol) and TMS azide (2.066 ml, 15.56 mmol) in DMF (25 ml) to give a brown solution. The reaction was heated at 120° C. for 2 hours followed by 150° C. for a further 4 hours. The reaction was extracted into ethyl acetate, washed with brine, the organic layer separated, dried over MgSO₄, filtered and the solvent removed under reduced pressure. The reddish brown residue was loaded onto silica and purified by flash column chromatography, elution with isohexane:ethyl acetate (0-50%) on a 40 g silica cartridge. The required fractions were combined and the solvent removed under reduced pressure to yield a dark yellow oil. DCM:isohexane (1:3) was added and the resulting yellow suspension filtered to yield a yellow solid (205 mg).
LCMS: Rt 0.95 mins; MS m/z 255.3 [M+H]+; Method 2minLowpHv01.
¹H NMR (400 MHz, DMSO-d6) δ 15.40 (1H, br s), 8.09 (1H, s), 7.51 (2H, br s), 2.58 (3H, s).

Step 3: 5-Bromo-3-(2,5-dimethyl-2H-[1,2,3]triazol-4-yl)-pyrazin-2-ylamine

To a 50 mL round-bottomed flask was added 5-bromo-3-(5-methyl-1H-1,2,3-triazol-4-yl)pyrazin-2-ylamine (205 mg, 0.804 mmol), potassium carbonate (333 mg, 2.411 mmol), and iodomethane (0.151 ml, 2.411 mmol) in THF (8 ml) to give a yellow suspension. The reaction was stirred at room temp for 1 hour then heated at 40° C. for 2 hours to give a 1:1 mixture of two regioisomers. The reaction was extracted into ethyl acetate, washed with brine, the organic layer separated, dried over MgSO₄, filtered and the solvent removed under reduced pressure. The crude product was purified by flash column chromatography, elution with iso hexane:ethyl acetate (0-50%) on a 12 g silica cartridge. The required fractions were combined and the solvent removed under reduced pressure to yield the product as a yellow solid (175 mg) containing an additional regioisomer.
LCMS: Rt 0.96 mins MS m/z 269.0 [M+H]+, 1.07 mins MS m/z 269.1 [M+H]+; Method 2minLowpHv01.

Intermediate C10

5-Chloro-3-(2-cyclopropyl-thiazol-5-yl)-pyrazin-2-ylamine

The title compound was prepared from 2-Cyclopropyl-5-(4,4,5,5-tetramethyl-[1,3,2]dioxaborolan-2-yl)-thiazole and 3-Bromo-5-chloro-pyrazin-2-ylamine analogously to Intermediate C7.
LCMS: Rt 1.06 mins; MS m/z 253.1 [M+H]+; Method: 2minLowpHv01

Intermediate C11

5-Bromo-3-(1H-1,2,4-triazol-1-yl)pyrazin-2-amine

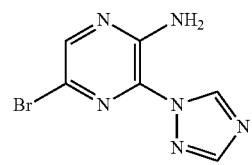 [SMILES: Nc1ncc(Br)nc1-n1cncn1]

A mixture of 5-bromo-3-chloropyrazin-2-amine (1.3 g, 6.24 mmol), 1H-1,2,4-triazole (0.5 g, 7.24 mmol) and cesium carbonate (3.5 g, 10.74 mmol) in DMF (25 ml) was heated to 60° C. overnight. After cooling to room temperature, the mixture was partitioned between ethyl acetate (150 mL) and water (75 mL). The organic portion was separated and the aqueous was extracted with ethyl acetate (2×75 mL). The combined organic extracts were washed with brine (50 mL), dried over anhydrous sodium sulfate, filtered and evaporated under reduced pressure. Purification of the crude product by chromatography on silica eluting with 10-25% ethyl acetate in iso-hexane afforded the title compound;
LCMS: Rt 2.86 min; m/z 241.1 and 243.3 [M+H]+ bromine isotopes; Method 2minLowpH
¹H NMR (400 MHz, DMSO-d6) δ 9.25 (1H, s), 8.40 (1H, s), 8.30 (1H, s), 7.34 (2H, s).

Intermediate C12

5-Bromo-3-(3-methyl-[1,2,4]triazol-1-yl)-pyrazin-2-ylamine

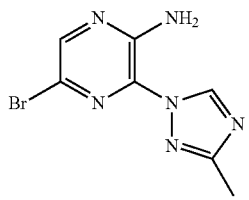

Prepared using 5-bromo-3-chloropyrazin-2-amine and 3-methyl-1H-[1,2,4]triazole by analogy to Intermediate C11.

LCMS: Rt 0.87 mins; MS m/z 355.0 [M+H]+; Method 2minLowpHv01

Intermediate C13

5-Chloro-3-(3-cyclopropylisoxazol-5-yl)pyrazin-2-amine

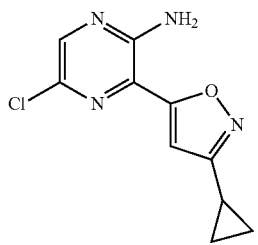 [SMILES: Nc1ncc(Cl)nc1-c1cc(C2CC2)no1]

Step 1: 5-Chloro-3-((trimethylsilyl)ethynyl)pyrazin-2-amine

To a 500 mL round-bottomed flask was added 3-bromo-5-chloropyrazin-2-amine (5 g, 23.99 mmol), ethynyltrimethylsilane (10.17 ml, 72.0 mmol), and triethylamine (33.4 ml, 240 mmol) in THF (100 ml) to give a brown solution. The reaction was degassed and purged with nitrogen. To the stirring solution was added bis(triphenylphosphine)palladium(II) chloride (1.684 g, 2.399 mmol) and copper(I) iodide (914 mg, 4.80 mmol). The reaction was stirred at room temperature for 30 mins. The reaction was extracted into ethyl acetate, washed with brine, the organic layer separated, dried over MgSO$_4$, filtered and the solvent removed under reduced pressure. The crude product loaded onto silica was purified by flash column chromatography elution with iso hexane:ethyl acetate (0-30%) using an 80 g silica cartridge. The required fractions were combined and the solvent removed under reduced pressure to yield a brown solid;

LCMS: Rt=1.29 mins MS m/z 226.2 [M+H]+; Method 2minLowpHv02.

$^1$H NMR (400 MHz, DMSO-d6) δ 8.08 (1H, s), 6.82 (2H, broad s), 0.27 (9H, s).

Step 2: 5-Chloro-3-ethynylpyrazin-2-amine

To a 250 mL round-bottomed flask was added 5-chloro-3-((trimethylsilyl)ethynyl)pyrazin-2-amine (step 1) (3.64 g, 16.12 mmol) and K$_2$CO$_3$ (2.228 g, 16.12 mmol) in MeOH (75 ml) to give a brown solution. The reaction was stirred at room temperature for 30 mins. The reaction was extracted into DCM, washed with water, brine, the organic layer separated, dried over MgSO$_4$, filtered and the solvent removed under reduced pressure to yield a brown solid;

LCMS: Rt=0.80 mins MS m/z 154.1 [M+H]+; Method 2minLowpHv02.

$^1$H NMR (400 MHz, DMSO-d6) δ 8.13 (1H, s), 6.92 (2H, broad s), 4.85 (1H, s).

Step 3: 5-Chloro-3-(3-cyclopropylisoxazol-5-yl)pyrazin-2-amine

To a 50 mL round-bottomed flask was added cyclopropanecarboxaldehyde (0.245 ml, 3.26 mmol), hydroxylamine hydrochloride (238 mg, 3.42 mmol) and NaOH (137 mg, 3.42 mmol) in t-BuOH (8 ml) and water (8 ml) to give a colorless solution. The reaction was stirred at room temperature for 30 mins. To the reaction was added chloramine-T (840 mg, 3.42 mmol), copper powder (9 mg, 0.140 mmol) and copper(II)sulfate pentahydrate (24 mg, 0.098 mmol) and the mixture was stirred for 15 mins. To the greenish brown solution was added 5-chloro-3-ethynylpyrazin-2-amine (from step 2) (500 mg, 3.26 mmol) and the reaction stirred at 50° C. for 2 hours. The mixture was extracted into ethyl acetate, washed with ammonium hydroxide, brine, the organic layer separated, dried over MgSO$_4$, filtered and the solvent removed under reduced pressure. The crude product was purified by flash column chromatography elution with iso-hexane:ethyl acetate (0-40%) on a 24 g silica cartridge. The required fractions were combined and the solvent removed under reduced pressure to yield a light brown solid. The solid was triturated in iso hexane:ethyl acetate (4:1) and the resulting suspension flittered to yield a yellow solid which was dissolved in DCM (20 mL) and PS-TBD (2896 mg, 3.19 mmol) added to give a yellow suspension. The reaction was stirred at room temperature for 2 hours. The suspension was filtered through Celite® cartridge to remove the polymer supported reagent. The filtrate was collected and the solvent removed under reduced pressure to yield a yellow solid;

LCMS: Rt=1.12 mins MS m/z 237.1 [M+H]+; Method 2minLowpHv02.

$^1$H NMR (400 MHz, DMSO-d6) δ 8.24 (1H, s), 6.94 (2H, broad s), 6.82 (1H, s), 2.12-2.05 (1H, m), 1.08-1.04 (2H, m), 0.92-0.88 (2H, m).

Intermediate D1

Trans-3-(5-Amino-6-chloropyrazin-2-yl)-N-(4-hydroxycyclohexyl)-4-methylbenzene sulfonamide

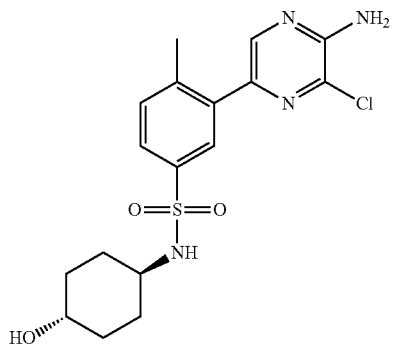 [SMILES: Cc1ccc(S(=O)(=O)N[C@H]2CC[C@H](O)CC2)cc1-c1cnc(N)c(Cl)n1]

A mixture comprising trans-N-(4-hydroxycyclohexyl)-4-methyl-3-(4,4,5,5-tetramethyl-1,3,2-dioxaborolan-2-yl)benzenesulfonamide (Intermediate A5) (9.48 mg, 2.40 mmol), 5-bromo-3-chloropyrazin-2-amine (500 mg, 2.399 mmol), PdCl$_2$(dppf).CH$_2$Cl$_2$ adduct (98 mg, 0.120 mmol) and Na$_2$CO$_3$ (6.00 ml, 11.99 mmol) in DME (11.400 ml) under N2 was heated using microwave irradiation at 120° C. for 45 mins. The mixture was added to water (100 ml) and extracted with EtOAc (2×100 ml). The organic extracts were washed with brine, dried over MgSO$_4$ and concentrated under reduced pressure. Purification by chromatography on silica eluting with 0-100% EtOAc in iso-hexane followed by sonication of the resulting solid afforded the title compound as an off-white solid;

LCMS: Rt 0.88 mins; MS m/z 438.2 [M+H]+; Method 2minLC_v003

Intermediate D2

3-(5-amino-6-chloropyrazin-2-yl)-N-(2-hydroxy-2-methylpropyl)-4-methyl benzenesulfonamide

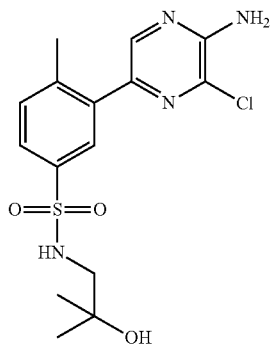 [SMILES: Cc1ccc(S(=O)(=O)NCC(C)(C)O)cc1-c1cnc(N)c(Cl)n1]

The title compound was prepared analogously to Intermediate D1 by replacing trans-N-(4-hydroxycyclohexyl)-4-methyl-3-(4,4,5,5-tetramethyl-1,3,2-dioxaborolan-2-yl)benzene sulfonamide (Intermediate A5) with N-(2-Hydroxy-2-methyl-propyl)-4-methyl-3-(4,4,5,5-tetramethyl[1,3,2]dioxaborolan-2-yl)benzenesulfonamide (Intermediate A2);

LC-MS: RT 0.93 mins; MS m/z 371.2 [M+H]$^+$; Method 2minLowpHv01

Intermediate D3

3-(5-Amino-6-chloropyrazin-2-yl)-N-(3-hydroxy-3-methylbutyl)-4-methyl benzenesulfonamide

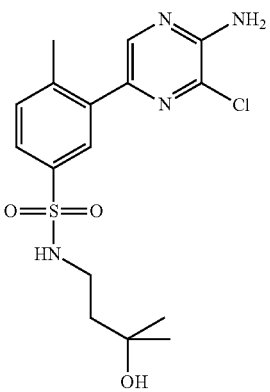 [SMILES: Cc1ccc(S(=O)(=O)NCCC(C)(C)O)cc1-c1cnc(N)c(Cl)n1]

The title compound was prepared analogously to Intermediate D1 by replacing trans-N-(4-hydroxycyclohexyl)-4-methyl-3-(4,4,5,5-tetramethyl-1,3,2-dioxaborolan-2-yl)benzene sulfonamide (Intermediate A5) with N-(3-hydroxy-3-methylbutyl)-4-methyl-3-(4,4,5,5-tetramethyl-1,3,2-dioxaborolan-2-yl)benzenesulfonamide (Intermediate A3);

LCMS: Rt 0.88 mins; MS m/z 385.2 [M+H]+; 2minLC_v003

Intermediate D4

3-(5-Amino-6-chloropyrazin-2-yl)-4-methyl-N-(4,4,4-trifluoro-3-hydroxybutyl) benzenesulfonamide

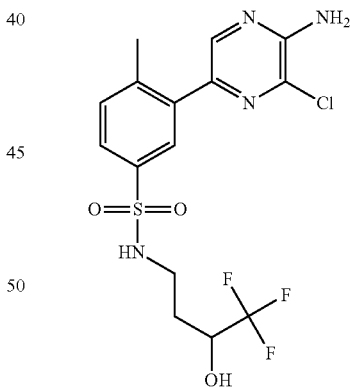

To a solution of 4-amino-1,1,1-trifluorobutan-2-ol hydrochloride (275 mg, 1.531 mmol) and 3-bromo-4-methylbenzene-1-sulfonyl chloride (425 mg, 1.577 mmol) in THF (7 mL) was added DIPEA (0.55 mL, 3.15 mmol). The resulting mixture was stirred at room temperature overnight then diluted with DCM, washed with 10% citric acid, then dried by passing through a phase separator. The organic phase was evaporated under reduced pressure and purified by flash column chromatography (24 g silica, 0-50% ethyl acetate in isohexane). The resulting material [3-bromo-4-methyl-N-(4,4,4-trifluoro-3-hydroxybutyl)benzenesulfonamide, 530 mg, estimated 80% purity] was dissolved in 1,2-dimethoxyethane (6 mL). Bis(pinacolato)diboron (340 mg, 1.339 mmol), bis(triphenylphosphine)palladium dichloride (40 mg, 0.057 mmol) and potassium acetate (175 mg, 1.783 mmol) were added and the reaction heated to reflux. After two hours further bis(pinacolato)diboron (100 mg) was added and the mixture refluxed again for three hours. 5Bromo-3-chloropyrazin-2-amine (260 mg, 1.247 mmol) and aq. 2M sodium carbonate (1.7 mL, 3.40 mmol) were added and the resulting mixture heated to 90° C. for 3 hours in the microwave. The resulting mixture was partitioned between DCM and water and separated using a phase separator cartridge. The organics were evaporated under reduced pressure, bound to silica and purified by flash column chromatography on 40 g silica, 10-70% ethyl acetate in isohexanes. The product fractions were combined and evaporated under reduced pressure to give title compound as a yellow oil;

LCMS: Rt 0.94 min; MS m/z 425.1 [M+H]+; Method Name: 2minLowpH

Chiral separation of 3-(5-amino-6-chloropyrazin-2-yl)-4-methyl-N-(4,4,4-trifluoro-3-hydroxybutyl) benzenesulfonamide using Supercritical Fluid Chromatography afforded the individual enantiomers (Intermediate D4a and D4b).
Method Details:
Column: Phenomenex LUX C4 250×10 mm, 5 um @ 35 deg C.
Mobile phase: 20% Isopropanol+0.1% v/v DEA/80% CO2
System: Berger Minigram SF02

Intermediate D4a and Intermediate D4b (R) and (S)-3-(5-Amino-6-chloropyrazin-2-yl)-4-methyl-N-(4,4,4-trifluoro-3-hydroxybutyl)benzene-sulfonamide

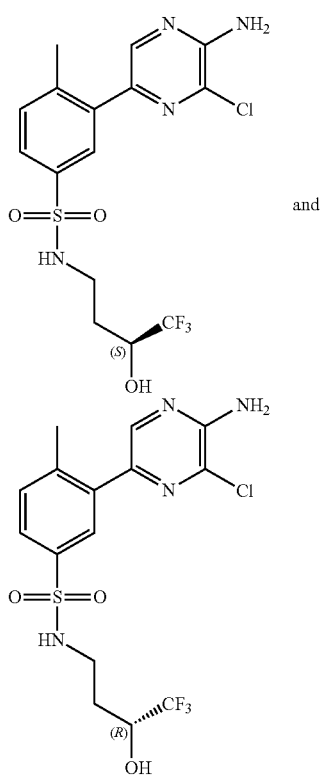

and

Chiral separation afforded two peaks which were analysed by analytical chiral SFC using the following method:
Column: Phenomenex LUX C4 250×10 mm, 5 um @ 35 deg C.
Mobile phase: 20% Isopropanol+0.1% v/v DEA/80% CO2
Flow: 10 ml/min; Run Time: 15.00 min
Detection: UV @ 220 nm
System: Berger Minigram SF02

Intermediate D4a

First eluted peak: SFC retention Time=10.5 min (S)-3-(5-amino-6-chloropyrazin-2-yl)-4-methyl-N-(4,4,4-trifluoro-3-hydroxybutyl)benzenesulfonamide or (R)-3-(5-Amino-6-chloropyrazin-2-yl)-4-methyl-N-(4,4,4-trifluoro-3-hydroxybutyl)benzenesulfonamide Intermediate D4b Second eluted peak: SFC retention Time=13.1 min (S)-3-(5-amino-6-chloropyrazin-2-yl)-4-methyl-N-(4,4,4-trifluoro-3-hydroxybutyl)benzenesulfonamide or (R)-3-(5-Amino-6-chloropyrazin-2-yl)-4-methyl-N-(4,4,4-trifluoro-3-hydroxybutyl)benzenesulfonamide Intermediate D5

5-(5-Amino-6-chloropyrazin-2-yl)-2-fluoro-N-(3-hydroxypropyl)-4-methyl benzene sulfonamide

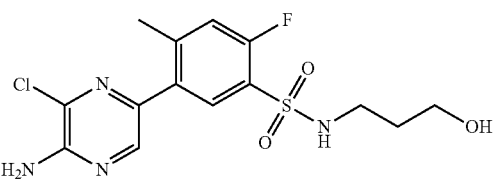 [SMILES: Cc1cc(F)c(S(=O)(=O)NCCCO)cc1-c1cnc(N)c(Cl)n1]

A mixture of 5-bromo-2-fluoro-N-(3-hydroxypropyl)-4-methylbenzenesulfonamide (Intermediate A12) (590 mg, 1.809 mmol), KOAc (266 mg, 2.71 mmol), PdCl$_2$(dppf).CH$_2$Cl$_2$ adduct (73.9 mg, 0.090 mmol) and bis(pinicolato)diboron (505 mg, 1.990 mmol) in DME (9043 µL), under N$_2$, was heated at 90° C. for 14 hours. 5-bromo-3-chloropyrazin-2-amine (377 mg, 1.809 mmol) was added to the reaction mixture, followed by Na$_2$CO$_3$ (2713 µL, 5.43 mmol) and PdCl$_2$(dppf).CH$_2$Cl$_2$ adduct (73.9 mg, 0.090 mmol) and the reaction mixture was microwaved at 120° C. for 45 mins. To the mixture was added to sat. Na$_2$CO$_3$ (100 ml) and the product extracted into EtOAc (2×90 ml). The organic extracts were washed with brine, dried over MgSO$_4$, and concentrated under reduced pressure. The crude product was purified by flash column chromatography, eluting with a 0-10% gradient of (2M NH$_3$ in MeOH) in TBME on a 40 g Si-column to give the title compound as a pale yellow solid;

LCMS: Rt 0.81 mins; MS m/z 375.1 [M+H]+; Method: 2minLowpH $^1$H NMR (400 MHz, DMSO-d6) δ 8.19 (1H, s), 7.81 (1H, br s), 7.73 (1H, d), 7.42 (1H, d), 7.02 (2H, s), 4.41 (1H, br s), 3.37 (2H, t), 2.91 (2H, t), 2.42 (3H, s), 1.54 (2H, m).

Intermediate E1

3-(5-Amino-6-(1H-1,2,4-triazol-1-yl)pyrazin-2-yl)-4-methylbenzene-1-sulfonyl chloride Step 1: 5-o-Tolyl-3-(1H-1,2,4-triazol-1-yl)pyrazin-2-amine

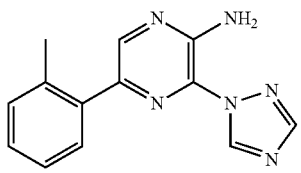 [SMILES: Cc1ccccc1-c1cnc(N)c(-n2cncn2)n1]

To a 20 ml microwave vial was added o-tolylboronic acid (0.169 g, 1.245 mmol), 5-bromo-3-(1H-1,2,4-triazol-1-yl)pyrazin-2-amine (Intermediate C11, 0.3 g, 1.245 mmol), PdCl$_2$(dppf)-CH$_2$Cl$_2$ adduct (50.8 mg, 0.062 mmol) and 2M sodium carbonate (1.556 ml, 3.11 mmol) in DME (3.5 ml) to give an orange suspension. The reaction was heated in the biotage initiator microwave at 120° C. for 60 mins. The reaction was extracted into ethyl acetate, washed with water, brine, the organic layer separated, dried over MgSO$_4$, filtered and the solvent removed under reduced pressure. Purified by flash column chromatography, elution with isohexane:ethyl acetate (0-100%) on a 12 g silica column. The required fractions were combined and the solvent removed under reduced pressure to yield the title compound as a brown solid (230 mg).

LCMS Rt 0.96 mins; MS m/z 253.2 [M+H]+; Method 2minLowpH $^1$H NMR (400 MHz, DMSO-d6) 9.33 (1H, s), 8.41 (1H, s), 8.35 (1H, s), 7.52 (1H, mult), 7.32 (3H, mult), 7.27 (2H, br), 2.42 (3H, s).

Step 2: 3-(5-Amino-6-(1H-1,2,4-triazol-1-yl)pyrazin-2-yl)-4-methylbenzene-1-sulfonyl chloride

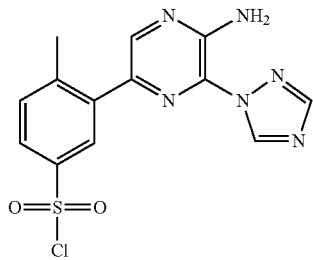 [SMILES: Cc1ccc(S(=O)(=O)Cl)cc1-c1cnc(N)c(-n2cncn2)n1]

To a 50 ml round bottom flask cooled to <5° C. was added 5-o-tolyl-3-(1H-1,2,4-triazol-1-yl)pyrazin-2-amine (step 1, 780 mg, 3.09 mmol) and chlorosulfonic acid (4.97 ml, 74.2 mmol) in CHCl$_3$ (15 ml) to give a brown solution. The solution became biphasic upon complete addition of the acid and was allowed to warm to room temperature with stirring overnight. The reaction was carefully added dropwise to a stirring solution of ice water and DCM (3:1). A suspension formed. The contents were transferred to a separating funnel, DCM added and the suspension shaken until it completely dissolved in the organic layer. The organics were separated, dried over MgSO$_4$, filtered and the solvent removed under reduced pressure to yield the title compound as a pale yellow solid (900 mg).

$^1$H NMR (400 MHz, CHCl$_3$) 9.21 (1H, s), 8.30 (1H, s), 8.22 (1H, s), 8.13 (1H, d), 8.01 (1H, dd), 7.59 (1H, d), 6.75 (2H, br), 2.61 (3H, s)

Intermediate E 3-(5-Amino-6-(2-methylthiazol-5-yl)pyrazin-2-yl)-4-methylbenzene-1-sulfonyl chloride

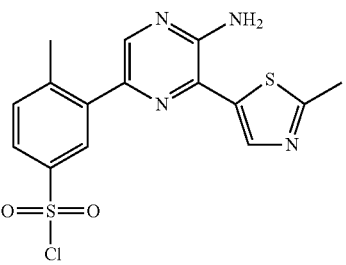 [SMILES: Cc1ncc(-c2nc(-c3cc(S(=O)(=O)Cl)ccc3C)cnc2N)s1]

Step 1: 3-(2-Methylthiazol-5-yl)-5-(o-tolyl)pyrazin-2-amine

Pd-118 (0.136 g, 0.221 mmol) was added to a mixture of 5-chloro-3-(2-methylthiazol-5-yl)pyrazin-2-amine (Intermediate C6) (1 g, 4.41 mmol), o-tolylboronic acid (0.660 g, 4.85 mmol), potassium phosphate (1.873 g, 8.82 mmol), 1,4-dioxane (17.65 ml) and water (4.41 ml). The reaction mixture was heated at 100° C. for 2.5 hours. The reaction mixture was added to water (100 ml) and extracted with EtOAc (2×100 ml). The organic phase was washed with brine (100 ml) and dried over MgSO$_4$. The solid was filtered off, washed with EtOAc and the solvent was concentrated under reduced pressure to give a dark grey residue. The residue was triturated with Et$_2$O to give a solid, which was filtered off, washed with Et$_2$O and dried in a vacuum oven at 50° C. for 5 hours to give the title compound as a dark grey solid.

LCMS: Rt 1.24 mins, MS m/z 283.2 [M+H]+; Method 2minLowpHv03.

$^1$H NMR (400 MHz, DMSO-d6) δ 8.26 (1H, s), 8.15 (1H, s), 7.44 (1H, m), 7.32-7.26 (3H, m), 6.57 (2H, br s), 2.67 (3H, s), 2.40 (3H, s).

Step 2: 3-(5-Amino-6-(2-methylthiazol-5-yl)pyrazin-2-yl)-4-methylbenzene-1-sulfonyl chloride Chlorosulfonic acid (4.50 mL, 67.1 mmol) was added dropwise to a stirring solution of 3-(2-methylthiazol-5-yl)-5-(o-tolyl)pyrazin-2-amine (step 1) (790 mg, 2.80 mmol) in CHCl$_3$ (14 ml) at 0° C. Upon complete addition, the reaction mixture was allowed to warm up to RT and was stirred overnight at RT. The reaction mixture was added dropwise to stirring ice water and the resulting mixture was extracted with CHCl$_3$ (125 ml). The organic phase was separated and washed with brine (100 ml) and dried over MgSO$_4$. The solid was filtered off, washed with CHCl$_3$ and the solvent was concentrated under reduced pressure to give a brown oil. The residue was triturated with Et$_2$O to give a solid, which was filtered off, washed with Et$_2$O and dried in a vacuum oven at 50° C. overnight to give the title compound as a brown solid which was used directly in the next step.

Intermediate E3

3-(5-Amino-6-(1,3-dimethyl-1H-pyrazol-4-yl)pyrazin-2-yl)-4-methylbenzene-1-sulfonyl chloride

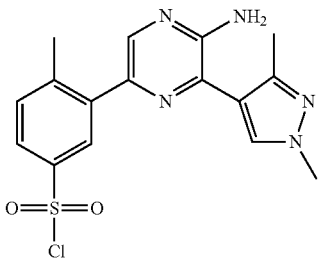 [SMILES: Cc1ccc(S(=O)(=O)Cl)cc1-c1cnc(N)c(-c2cn(C)nc2C)n1]

Step 1: 3-(1,3-Dimethyl-1H-pyrazol-4-yl)-5-(o-tolyl)pyrazin-2-amine

5-Chloro-3-(1,3-dimethyl-1H-pyrazol-4-yl)pyrazin-2-amine (Intermediate C7) (11.3 g, 50.5 mmol) and o-tolyl boronic acid (8.24 g, 60.6 mmol) were dissolved in dioxane (170 ml) with stirring and degassed with nitrogen. Potassium phosphate (21.45 g, 101 mmol) in water (45 ml) was added, followed by Pd-118 [PdCl$_2$(dtbpf)] (1.646 g, 2.53 mmol). The dark red slurry gradually darkened with stirring. This was heated to 100° C. overnight, internal temp 85° C. under nitrogen.

The reaction mixture was partitioned in ethyl acetate/water (1:1, 500 ml). The layers were separated and the mainly organic layer filtered through Celite®. The aqueous layer was re-extracted with ethyl acetate (100 ml). The organic extracts were bulked, washed with saturated sodium bicarbonate (400 ml), water (300 ml), brine (300 ml), then dried over MgSO$_4$ and charcoal. The desiccant was filtered off and the filtrate concentrated under reduced pressure to give a brown solid. This was slurried in diethyl ether (130 ml) and sonicated for 30 mins. The residual pale brown solid was removed by filtration and dried in vacuo to give the title compound;
LCMS: Rt 0.95 mins; MS m/z 280.3 & 281.4 [M+H]+; Method 2minLowpH.
$^1$H NMR (400 MHz, DMSO-d6) δ 8.1 (1H, s), 7.95 (1H, s), 7.4 (1H, m), 7.25 (3H, m), 6.1 (2H, br s), 3.8 (3H, s), 2.35 (3H, s), 2.25 (3H, s).

Step 2: 3-(5-Amino-6-(1,3-dimethyl-1H-pyrazol-4-yl)pyrazin-2-yl)-4-methylbenzene-1-sulfonyl chloride Chlorosulfonic acid (5.75 ml, 86 mmol) was added dropwise to a stirred solution of 3-(1,3-dimethyl-1H-pyrazol-4-yl)-5-(o-tolyl)pyrazin-2-amine (step 1) (1.0 g, 3.58 mmol) in chloroform (20 ml) at 0° C. When the addition was complete the reaction was allowed to warm to room temperature and stirred for 20 h. The reaction mixture was added dropwise to rapidly stirred ice water and the product precipitated as a pale yellow solid. When most of the ice had melted the mixture was filtered through a sinter funnel to collect the product which was washed with EtOAc and dried in a vacuum oven at RT to give the title compound;

LCMS: Rt 1.08 mins; MS m/z 378.3 [M+H]+; Method 2minLowpH
$^1$H NMR (400 MHz, CDCl$_3$) δ 8.18 (1H, s), 7.98 (1H, s), 7.69 (1H, s), 7.55 (1H, d), 7.26 (1H, d), 3.35 (3H, s), 3.27 (3H, s), 2.27 (3H, s).

Intermediate E4

2,4,6-Trichlorophenyl 3-(5-amino-6-(2-methylpyridin-4-yl)pyrazin-2-yl)-4-methyl benzenesulfonate

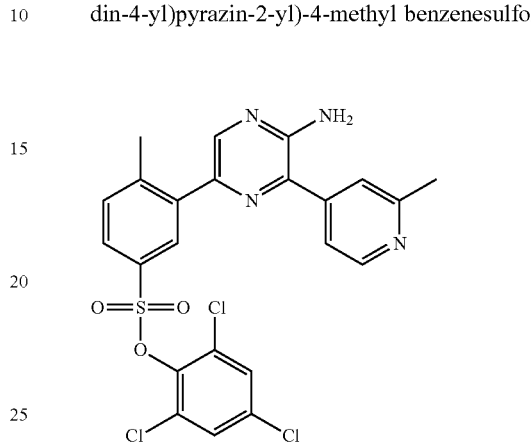

Step 1: 3-Chloro-5-o-tolylpyrazin-2-amine

A mixture comprising 5-bromo-3-chloropyrazin-2-amine (2 g, 9.59 mmol), o-tolylboronic acid (1.35 g, 9.93 mmol), PdCl$_2$(dppf).CH$_2$Cl$_2$ adduct (0.25 g, 0.306 mmol) and Na$_2$CO$_3$ (5 g, 47.2 mmol) in DME (30 ml) and water (6.00 ml), under nitrogen was heated at reflux for 3 hours. The resulting mixture was diluted with water (100 mL) and extracted with ethyl acetate. The combined organic extracts were dried over anhydrous magnesium sulfate, filtered and evaporated under reduced pressure. The resulting brown residue was bound to silica and purified by flash column chromatography (80 g silica, 0-25% ethyl acetate in iso-hexane) to give a pale yellow solid;
LCMS: Rt 1.00 min; MS m/z 220.1 [M+H]+; Method: 2minLowpH Step 2: 3-(2-Methylpyridin-4-yl)-5-o-tolylpyrazin-2-amine A mixture of Pd(PPh$_3$)$_2$Cl$_2$ (0.125 g, 0.178 mmol), 3-chloro-5-o-tolylpyrazin-2-amine (step 1) (0.78 g, 3.55 mmol), 2-methyl-4-(4,4,5,5-tetramethyl-1,3,2-dioxaborolan-2-yl)pyridine (0.8 g, 3.65 mmol), sodium carbonate (1.1 g, 10.38 mmol) in DME (7.5 mL), EtOH (5.00 mL) and water (2.5 mL) was heated to 120° C. in the microwave for 2 hours. The resulting mixture was diluted with ethyl acetate and water, using sonication to ensure all material was transferred from the microwave vial and evaporated under reduced pressure to remove organics. The remaining aqueous was extracted with ethyl acetate (2×50 mL), washed with saturated sodium bicarbonate (50 mL) and brine (25 mL), dried over anhydrous magnesium sulfate and filtered. The resulting dark brown solution was evaporated and bound to silica, then purified by flash column chromatography (80 g silica, 70-100% ethyl acetate in iso-hexane, then 5-10% 2M methanolic ammonia in TBME). The product fractions were evaporated to give the title compound as a yellow solid;

LC-MS: Rt 0.69 min; m/z 277.6 [M+H]+; Method: 2min-LowpH

Step 3: 2,4,6-Trichlorophenyl 3-(5-amino-6-(2-methylpyridin-4-yl)pyrazin-2-yl)-4-methyl benzenesulfonate To a solution of 3-(2-methylpyridin-4-yl)-5-o-tolylpyrazin-2-amine (step 2) (600 mg, 2.171 mmol) in chloroform (10 mL) at 0° C. (ice bath) under nitrogen was added dropwise chlorosulfonic acid (3.5 mL, 52.3 mmol) over 10 minutes. The resulting red solution was stirred and allowed to warm slowly to room temperature and stirring continued overnight at room temperature. The resulting mixture was added dropwise to an ice-cooled stirring mixture of DCM (90 mL) and saturated sodium bicarbonate (150 mL). This mixture was passed through a phase separator directly into a stirring mixture of 2,4,6-trichlorophenol (450 mg, 2.280 mmol) and triethylamine (0.75 mL, 5.38 mmol) in DCM (5 mL). The aqueous and precipitate were re-extracted with DCM (50 mL) and passed through a phase separator directly into the same stirring mixture. After four hours stirring, the reaction mixture was evaporated under reduced pressure, then triturated with ethyl acetate and dried in vacuum oven overnight to give a yellow solid (465 mg, batch 1). The remaining aqueous and solid was extracted again with DCM (100 mL), washed with 2M sodium carbonate and passed through a phase separator directly into a stirring mixture of 2,4,6-trichlorophenol (200 mg) and triethylamine (0.3 mL). After stirring overnight, this was evaporated under reduced pressure and washed with ethyl acetate to give pale yellow solid (480 mg, batch 2). Estimated 80% purity, contains triethylamine/triethylamine hydrochloride but used without further purification.

LCMS: Rt 1.00 min; m/z 533.0, 535.1 [M−H]−; Method: 2minLowpH

Intermediate F

O-(Tetrahydrofuran-3-yl)hydroxylamine

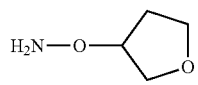

Step 1: 2-((Tetrahydrofuran-3-yl)oxy)isoindoline-1,3-dione

To a stirring solution of N-hydroxyphthalimide (5 g, 30.7 mmol) in THF (200 ml) at 0° C., PS-triphenylphosphine (loading 1.88 mmol/g) (19.56 g, 36.8 mmol) was added followed by tetrahydrofuran-3-ol (2.477 ml, 30.7 mmol) and di-tert-butyl azodicarboxylate (7.06 g, 30.7 mmol). The mixture was stirred at 0° C. for 10 mins, then for 21 hours at RT. The mixture was filtered, and solvent removed under reduced pressure. The resulting yellow solid was triturated with ether and the solid collected by filtration, washing with more ether to give a pale yellow solid. The mother liquors were evaporated under reduced pressure and triturated again with ether to give a pale yellow solid;

LCMS: Rt 0.82 min; MS m/z 234.4[M+H]+; Method: 2minLowpHv01.

Step 2: O-(Tetrahydrofuran-3-yl)hydroxylamine

To a stirred solution of 2-((tetrahydrofuran-3-yl)oxy)isoindoline-1,3-dione (step 1) (3.07 g, 13.16 mmol) in MeOH (60 mL) was added hydrazine hydrate (1.097 mL, 14.48 mmol). The resulting mixture was stirred at RT for 16 hours overnight, yielding a yellow solution with a suspension of a white solid. The white solid was removed by filtration and the filtrate was evaporated under reduced pressure. This was triturated with DCM and the solid again removed by filtration. The filtrate was evaporated under reduced pressure to give a yellow oil, which was used without further purification in the subsequent step.

Pharmaceutical Use and Assay

The compounds of the present invention and their pharmaceutically acceptable salts may be useful as pharmaceuticals. In particular, the compounds are suitable PI 3-kinase gamma isoform selective inhibitors and may be tested in the following assays.

Abbreviations:
ADP: Adenosine diphosphate
ATP: Adenosine triphosphate
BSA: Bovine serum albumin
DMEM: Dulbecco's modified Eagle's medium
DMSO: Dimethylsulfoxide
DTT: Dithiothreitol
CHAPS: 3-[(3-cholamidopropyl)dimethylammonio]-1-propanesulfonate
EDTA: Ethylenediaminetetraacetic acid
EGTA: Ethylene glycol tetraacetic acid
FACS: Fluorescence-activated cell sorting
FBS: Fetal bovine serum
HBSS: Hank's Balanced Salt Solution
HEPES: 4-(2-Hydroxyethyl)piperazine-1-ethanesulfonic acid
HTRF: Homogeneous Time Resolved Fluorescence
MIP1α: Macrophage Inflammatory Protein form 1α (also known as CCL3)
PBS: phosphate-buffered saline
RPM I: Roswell Park Memorial Institute medium
TR-FRET: Time-Resolved Fluorescence Resonance Energy Transfer Kinase Glo Luminescent Kinase Assay (Kglo) for Pb 3-Kinase Alpha (A), Pb 3-Kinase Beta (B), Vps34 (C), Pb 4-Kinase Beta (D)

The luminescence-based ATP detection reagent Kinase-Glo was obtained from Promega, (Cat. No. V6714, Lot No. 236161) through Catalys, Wallisellen, Switzerland. L-alpha-phosphatidylinositol (PI, liver, bovine) was obtained from Avanti Polar Lipid (Cat. No. 840042C, Lot#LPI-274), Phosphatidylinositol-4,5-bisphosphate (PIP(4,5)2) was also obtained from Avanti Polar Lipid (Cat. No. 840046X). L-α-Phosphatidylserine (PS) was obtained from Avanti Polar Lipid (Cat. No. 840032C), n-Octylglucoside from Avanti Polar Lipid (Cat. No. 10634425001). Luminescence is a well established readout to determine ATP concentrations and can thus be used to follow the activity of many kinases regardless of their substrate. The Kinase Glo Luminescent Kinase Assay (Promega, Madison/Wis., USA) is a homogeneous HTS method of measuring kinase activity by quantifying the amount of ATP remaining in solution following a kinase reaction.

50 nL of compound dilutions were dispensed onto black 384-well low volume Non Binding Styrene (NBS) plates (Costar Cat. No. NBS#3676). L-α-phosphatidylinositol (PI), provided as 10 mg/ml solution in methanol, was transferred into a glass tube and dried under a nitrogen beam. It was then resuspended in 3% OctylGlucoside (1-0-n-octyl-beta-D-glucopyranoside) by vortexing and stored at 4° C. 5 μL of a mix of PI/OctylGlucoside with the PI 3-kinase alpha and PI 3-kinase beta subtypes, or Vps34 or PI 4-kinase beta were added. Kinase reactions were started by the addition of 5 μl of an ATP-mix containing in a final volume 10 μL 10 mM TRIS-HCl pH 7.5, 3 mM $MgCl_2$, 50 mM NaCl, 0.05% CHAPS, 1 mM DTT and 1 μM ATP at room temperature. Reactions were stopped with 10 μl of KinaseGlo and plates were read 10 mins later in a Synergy2 reader using an integration time of 0.1 seconds per well. 2.5 μM of NVP-BGT226 (1-(3-(trifluoromethyl)-4-(piperazin-1-yl)phenyl)-8-(6-methoxypyridin-3-yl)-3-methyl-1H-imidazo[4,5-c]quinolin-2(3H)-one) was added to the assay plates to generate the 100% inhibition of the kinase reaction, and the 0% inhibition was given by the solvent vehicle (90% DMSO in water). (1-(3-(trifluoromethyl)-4-(piperazin-1-yl)phenyl)-8-(6-methoxypyridin-3-yl)-3-methyl-1H-imidazo[4,5-c]quinolin-2(3H)-one) was used as a reference compound and included in all assay plates in the form of 16 dilution points in duplicate.

$IC_{50}$ values of the percentage inhibition of each compound at 8 concentrations (10, 3.0, 1.0, 0.3, 0.1, 0.030, 0.010 and 0.003 μM) n=2 were derived by fitting a sigmoidal dose-response curve to a plot of assay readout over inhibitor concentration as described. All fits were performed with the program XLfit4 (ID Business Solutions, Guildford, UK).

TR-FRET Adapta Assay for PI 3-Kinase Gamma (E), PI 3-Kinase Delta (F)

The TR-FRET Adapta™ Universal Kinase Assay Kit was purchased from Invitrogen Corporation (Carlsbad/CA, USA) (Cat. No. PV5099). The kit contains the following reagents: Adapta Eu-anti-ADP Antibody (Europium labeled anti-ADP antibody in HEPES buffered saline, Cat. No. PV5097), Alexa Fluor® 647-labeled ADP tracer (Alexa Fluor® 647-labeled ADP tracer in HEPES buffered saline, Cat. No. PV5098), TR-FRET dilution buffer pH 7.5 (Cat. No. PV3574).

PIK3CD substrate phosphatidylinositol (PI) was obtained from Invitrogen (vesicles consisting of 2 mM phosphatidylinositol (PI) in 50 mM HEPES pH7.5; Cat. No. PV5371). PIK3CG substrate phosphatidylinositol-4,5-bisphosphate (PIP(4,5)2 was obtained from Invitrogen (PIP2:PS large unilamellar vesicules consisting of 1 mM PIP2: 19 mM PS in 50 mM HEPES pH7.5, 3 mM $MgCl_2$, 1 mM EGTA; Cat. No. PV5100).

Time-Resolved Fluorescence Resonance Energy Transfer (TR-FRET) is a technology based on energy transfer between two adjacent dyes, from an excited electron in one dye (the donor) to an electron of an adjacent dye (the acceptor) through resonance, then released as a photon. This energy transfer is detected by an increase in the fluorescence emission of the acceptor, and a decrease in the fluorescence emission of the donor. TR-FRET assays for protein kinases use a long-lifetime lanthanide Terbium or Europium chelates as the donor species which overcome interference from compound autofluorescence or light scatter from precipitated compounds, by introducing a delay after excitation by a flashlamp excitation source. Results are often expressed as a ratio of the intensities of the acceptor and donor fluorophores. The ratiometric nature of such a value corrects for differences in assay volumes between wells, as well as corrects for quenching effects due to colored compounds. The Adapta™ assay can be divided into two phases: a kinase reaction phase and an ADP detection phase. In the kinase reaction phase, all kinase reaction components are added to the well and the reaction is allowed to incubate for a set period of time specific for each kinase. After the reaction, a detection solution of Eu-labeled anti-ADP antibody, Alexa Fluor® 647-labeled ADP tracer, and EDTA (to stop the kinase reaction) are added to the assay well. ADP formed by the kinase reaction will displace the Alexa Fluor® 647-labeled ADP tracer from the antibody, resulting in a decrease in TR-FRET signal. In the presence of an inhibitor, the amount of ADP formed by the kinase reaction is reduced, and the resulting intact antibody-tracer interaction maintains a high TR-FRET signal. In the Adapta™ assay, the donor (Europium-anti-ADP antibody) is excited at 340 nm and will transfer its energy to the acceptor (Alexa Fluor® 647-labeled ADP tracer). The emission from the Alexa Fluor® 647 can be monitored with a filter centered at 665 nm because it is located between the emission peaks of the donor, which is measured at 615/620 nm.

50 nL of compound dilutions were dispensed onto white 384-well small volume polystyrene plate. Then 5 μL of either PI 3-kinase gamma or PI 3-kinase delta and lipid substrate (PI or PIP2:PS) followed by 5 μL of ATP (final assay volume 10 μL) are incubated at RT. The standard reaction buffer for the Adapta™ TR-FRET assay contained 10 mM Tris-HCl pH 7.5, 3 mM $MgCl_2$, 50 mM NaCl, 1 mM DTT, 0.05% CHAPS 3-[(3-cholamidopropyl)dimethylammonio]-1-propanesulfonate). Reactions were stopped with 5 μL of a mixture of EDTA containing the Eu-labeled anti-ADP antibody and the Alexa Fluor® 647-labeled ADP tracer in TR-FRET dilution buffer. Plates are read 15 to 60 mins later in a Synergy2 reader using an integration time of 0.4 seconds and a delay of 0.05 seconds. Control for the 100% inhibition of the kinase reaction was performed by replacing the PI 3-kinase by the standard reaction buffer. The control for the 0% inhibition was given by the solvent vehicle of the compounds (90% DMSO in $H_2O$). The standard compound 1-(3-(trifluoromethyl)-4-(piperazin-1-yl)phenyl)-8-(6-methoxypyridin-3-yl)-3-methyl-1H-imidazo[4,5-c]quinolin-2(3H)-one (NVP-BGT226) was used as a reference compound and included in all assay plates in the form of 16 dilution points in duplicate.

Data are analyzed using Excel fit software or Graphpad Prism. $IC_{50}$ values were derived by fitting a sigmoidal dose-response curve to a plot of assay readout over inhibitor concentration. All fits were performed with the program XLfit4 (ID Business Solutions, Guildford, UK). Determination of $IC_{50}$ values of the percentage inhibition of each compound at 8 concentrations (usually 10, 3.0, 1.0, 0.3, 0.1, 0.030, 0.010 and 0.003 μM) n were derived by fitting a sigmoidal dose-response curve to a plot of assay readout over inhibitor concentration. All fits were performed with the program XLfit4 (ID Business Solutions, Guildford, UK).

Lanthascreen™ Kinase Binding Assay for mTOR (G)

Binding Assays are based on the binding and displacement of an Alexa Fluor® 647-labeled, ATP-competitive kinase inhibitors to the kinase of interest. Invitrogen's "Kinase Tracers" have been developed to address a wide range of kinase targets and are based on ATP-competitive kinase inhibitors, making them suitable for detection of any compounds that bind to the ATP site or to an allosteric site altering the conformation of the ATP site. In the Lanthascreen™ kinase binding assay, the donor ($Eu^{3+}$-anti-GST (glutathione 5-transferase) antibody) is excited at 340 nm and will transfer its energy to the acceptor (Alexa Fluor® 647-labeled ATP-competitive kinase inhibitor=Tracer-314). The emission from the Tracer-314 (Alexa Fluor® 647 inhibitor) can be monitored with a filter centered at 665 nm because it is located between the emission peaks of the donor, which is measured at 615/620 nm. The binding of both, the Tracer-314 and Eu$^{3+}$-anti-GST antibody, to the kinase results in a high degree of FRET from the Eu$^{3+}$-donor fluorophore to the Alexa-Fluor® 647-acceptor fluorophore on the Tracer-314. Binding of an inhibitor to the kinase competes for binding with the tracer, resulting in a loss of FRET.

50 nL of compound dilutions were dispensed onto white 384-well small volume polystyrene plate. Then 5 µL of GST-mTOR and Europium-anti-GST antibody followed by 5 µL of tracer-314 (final assay volume 10 µL) are incubated at RT. The standard reaction buffer for the Lanthascreen™ kinase binding assay contained 50 mM HEPES pH 7.5, 5 mM MgCl2, 1 mM EGTA, 0.01% Pluronic F-127. Plates are read 60 mins later in a Synergy2 reader using an integration time of 0.2 microseconds and a delay of 0.1 microseconds.

To calculate the emission ratio, the signal emitted at 665 nm from the acceptor (Alexa Fluor® 647-labeled Tracer-314) is divided by the signal emitted at 620 nm from the donor (Eu$^{3+}$ anti-GST antibody).

Control for the 0% inhibition was given by the solvent vehicle of the compounds (90% DMSO in H$_2$O). Control for the relative 100% inhibition was performed by adding 10 µM in the mix containing GST-mTOR and Europium anti-GST antibody. An additional control for the absolute 0% inhibition is given by Eu$^{3+}$ anti-GST antibody without GST-mTOR. Standard compounds for the lipid kinase panel profiling were used as a reference and included in all assay plates in the form of 8 dilution points.

Cellular Assays for PI 3-Kinase Alpha (H1), Beta (I1) and Delta (J1): Surefire Format AlphaScreen (Amplified Luminescent Proximity Homogeneous Assay, ALPHA, Perkin Elmer) is a non-radioactive bead-based proximity assay technology to study biomolecular interactions in a homogenous microtiter plate format. The brand name SureFire denotes AlphaScreen assays that are adapted to quantify the phosphorylation of endogenous cellular proteins in cell lysates, by using matched antibody pairs, which consist of an anti-phospho-kinase and an anti-kinase antibody. The assay allows characterization of kinase signaling in cells as well as measurement of kinase inhibitor effects.

Rat-1 cell lines stably overexpressing activated PI 3-kinase class I isoforms Rat-1 pBABEpuro Myr-HA-hp110 delta clone 5 (Rat-1_PI3Kdelta) and Rat-1 pBABEpuro Myr-HA-hp110 alpha clone 6 (Rat-1_PI3Kalpha) and Rat-1 pBABEpuro Myr-HA-hp110 beta (Rat-1_PI3beta) were cultivated in complete growth medium (DMEM high glucose, 10% (v/v) fetal bovine serum, 1% (v/v) MEM NEAA, 10 mM HEPES, 2 mM L-glutamine, puromycin (10 µg/mL for Rat-1_PI3Kdelta and Rat-1_PI3Kalpha, 4 µg/mL for Rat-1_PI3beta), 1% (v/v) Pen/Strep) to 90% confluency at 37° C./5% CO$_2$/90% humidity in a humidified CO$_2$ incubator and were split twice a week.

The following materials were used for p-AKT(5473) detection in Rat-1 cell lysates: Dulbecco's modified Eagle's medium (DMEM) high glucose (Gibco Invitrogen, Basel, Switzerland, Cat. No. 41965), heat inactivated fetal bovine serum, qualified (HI FBS; Gibco Invitrogen, Basel, Switzerland, Lot. No. 16140), MEM non essential amino acids (NEAA; Gibco Invitrogen, Basel, Switzerland, Cat. No. 11140), HEPES (Gibco Invitrogen, Basel, Switzerland, Cat. No. 15630), penicillin/streptomycin (Pen/Strep, 100×; Gibco Invitrogen, Basel, Switzerland, Cat. No. 15140-122), L-glutamine (Gibco Invitrogen, Basel, Switzerland, Cat. No. 25030), puromycin (Sigma Aldrich, Buchs, Switzerland, Cat. No. P9620), DMSO (MERCK, Dietikon, Switzerland, Cat. No. 8.02912.2500), H$_2$O, MilliQ-H$_2$O unless otherwise stated (MILLIPORE QGARDOOR1, Millipore, Zug, Switzerland), bovine serum albumine (BSA; Sigma Aldrich, Buchs, Switzerland Cat. No. A8412), SureFire p-Akt ½ (Ser473) Assay Kit (PerkinElmer, Schwerzenbach, Switzerland, Cat. No. TGRAS50K).

The p-Akt (S473) SureFire assay measures the phosphorylation of endogenous cellular Akt ½ at Ser473 in cell lysates. Using Rat-1 cells stably expressing myr-HA-tagged versions of the human PI3Kdelta, PI3Kalpha, or PI3Kbeta p110 catalytic subunit isoforms, the assay was developed as a two-plate protocol in a 384-well format.

For compound testing, the cells were seeded at a density of 4000 (Rat-1_PI3Kdelta), 7500 (Rat-1_PI3Kalpha), or 6200 (Rat-1_PI3Kbeta) cells in 20 µl complete growth medium into cell culture treated 384-well plates and were grown at 37° C./5% CO$_2$/90% humidity for 24 h. Shortly before compound transfer, the complete medium was removed, 30 µl assay buffer (DMEM high glucose, 1×MEM NEAA, 10 mM HEPES, 2 mM L-glutamine, 0.1% (w/v) BSA) was added and 10 µl of the compound predilutions were transferred to the cells. After treatment with compound for 1 h, the cells were lysed by the addition of 20 µl lysis buffer supplemented with 0.24% (w/v) BSA. Detection of p-AKT (Ser473) was performed with the SureFire p-Akt ½ (Ser473) Assay Kit according to the manufacturer's instructions using 5 µl of cell lysate in a total detection volume of 12 µl.

IC$_{50}$ values of the percentage inhibition of each compound at 8 concentrations (usually 10, 3.0, 1.0, 0.3, 0.1, 0.030, 0.010 and 0.003 µM) n=2 were derived by fitting a sigmoidal dose-response curve to a plot of assay readout over inhibitor concentration as described. All fits were performed with the program XLfit4 (ID Business Solutions, Guildford, UK).

Cellular Assays for PI 3-Kinase Alpha (H2), Beta (I2) and Delta (J2): HTRF (Homogeneous Time Resolved Fluorescence) Format The following materials were used for p-AKT(5473) detection in Rat-1 cell lysates: Dulbecco's modified Eagle's medium (DMEM), high Glucose, GlutaMAX™, Pyruvate (Gibco Invitrogen, Basel, Switzerland, Cat. No. 31966), Dialyzed Fetal Bovine Serum (FBS) US origin (Gibco Invitrogen, Basel, Switzerland, Cat. No. 36400, Lot. No. 776683), MEM non essential amino acids (NEAA; Gibco Invitrogen, Basel, Switzerland, Cat. No. 11140), HEPES (Gibco Invitrogen, Basel, Switzerland, Cat. No. 15630), Penicillin/Streptomycin (Pen/Strep, 100×; Gibco Invitrogen, Basel, Switzerland, Cat. No. 15140-122), Puromycin (Sigma Aldrich, Buchs, Switzerland, Cat. No. P9620), DMSO (MERCK, Dietikon, Switzerland, Cat. No. 8.02912.2500), H2O, MilliQ-H2O unless otherwise stated (MILLIPORE QGARDOOR1, Millipore, Zug, Switzerland), HTRF Phospho-AKT (Ser473) Assay Kit (Cisbio, Codolet, France, Cat. No. 64AKSPEH)

The Rat-1 cell lines stably overexpressing activated PI3K class I isoforms Rat-1 pBABEpuro Myr-HA-hp110 delta clone 6 (Rat-1_PI3Kdelta) and Rat-1 pBABEpuro Myr-HA-hp110 alpha clone 6 (Rat-1_PI3Kalpha) and Rat-1 pBABEpuro Myr-HA-hp110 beta clone 1-E8 (Rat-1_PI3Kbeta) were used. All cell lines were cultivated in complete growth medium (DMEM high glucose GlutaMAX™ Pyruvate, 10% (v/v) fetal bovine serum, 0.1 mM MEM NEAA, 25 mM HEPES, puromycin 10 µg/mL, 100 U/ml Penicillin, 100 µg/ml Streptomycin) to 90% confluency at 37° C./5% CO2/90% humidity in a humidified CO2 incubator and were split twice a week.

Semi-automated preparation of cell lysates: For low (inhibited) controls, 0.9 mM NVP-BGT226-AF-1 in 90% (v/v) DMSO was added to the compound master plate. For compound testing, the cells were seeded at a density of 4000 (Rat-1_PI3Kdelta), 8000 (Rat-1_PI3Kalpha), or 6500 (Rat-1_PI3Kbeta) cells in 30 µl complete growth medium into cell culture treated 384-well plates and were grown at 37° C./5% CO2/90% humidity for 24 h. 10 µl of the compound predilutions were transferred to the cells. After treatment with compound for 1 h, medium was removed and cells were lysed by the addition of 20 µl lysis buffer supplemented with blocking buffer. Detection of p-AKT(Ser473) was performed with the HTRF pAKT (Ser473) assay kit according to the manufacturer's instructions using 16 µl of cell lysate in a total detection volume of 20 µl.

Cellular U937 AKT Assay for PI 3-Kinase Gamma (K1)

The U937 monocyte cell line is maintained in a basal medium of RPMI 1640 supplemented with 10% heat inactivated FBS, 100 U/ml Penicillin, 100 ug/ml streptomycin and 2 mM L-glutamine (Invitrogen). U937 suspension culture is maintained by seeding cells at a density of $0.125 \times 10^6$ cells per ml in fresh medium every three or four days. Cells are incubated at 37° C., 5% CO2. Three or four days prior to assay, cells are seeded at a density of $0.25 \times 10^6$ cells per ml in a total volume of 40 ml in a T162 culture flask.

Before beginning the cell manipulations described below, the MSD (Meso Scale Discovery) assay plate is blocked by addition of 150 µl/well blocking buffer supplied and incubated with shaking for a minimum of one hour at room temperature. All steps of the assay must be performed quickly, with accurately timed incubation periods and observing temperature controls where indicated.

Cells seeded at $0.25 \times 10^6$/ml 3 or 4 days prior to the assay are aspirated, transferred to a 50 ml falcon tube, counted and centrifuged for eight minutes at 300 g at room temperature. Supernatant is aspirated, the cell pellet resuspended and washed once in HBSS (Hank's Balanced Salt Solution) by centrifugation for eight minutes at 300 g at room temperature. The cell pellet is resuspended in HBSS to a concentration of $4 \times 10^6$ per ml, and 100 µL of cell suspension added to each well of a flat-bottomed 96-well tissue culture plate. Assay plates are incubated for 1.5 hours at 37° C., 5% $CO_2$ to allow background AKT phosphorylation to reduce before the compound stimulation step.

A 5 mM stock concentration of compound is prepared in 100% DMSO; from this a 1 in 125 dilution is made in HBSS giving a top compound concentration of 40 µM, 0.8% DMSO. Compound titrations are prepared in a fresh flat-bottomed, 96-well plate, by 10-fold serial dilution of 40 µM into HBSS 0.8% DMSO; pipette tips are replaced after each dilution is made. Compound concentrations at this stage are 4-times the final concentration required in the assay plate. Cells are stimulated with compound or HBSS 0.8% DMSO by direct transfer of 50 µl/well from the compound dilution plate. The assay plate containing compound-treated cells is then incubated for 30 minutes at 37° C. A standard plate layout is used for all experiments.

Compound-treated cells, in addition to positive control wells ("max MIP1α"), are stimulated with 50 µL per well of 40 ng/ml MIP1α (R&D Systems catalogue number 270-LD, lyophilized stock reconstituted to 50 µg/ml with PBS 0.1% BSA). Negative control wells ("min HBSS"), are stimulated with 50 µl/well of HBSS in the absence of MIP1α. Final compound concentrations are now diluted 4-fold giving a top concentration of 10 µM; where added, the final concentration of MIP1α is 10 ng/ml. Cells are incubated with MIP1α for 3 minutes, at 37° C., 5% CO2. After the three minute stimulation period, the assay plate is kept ice cold at all times. Assay plates are centrifuged for 2 minutes at 300 g, 4° C. and supernatant is removed by gently inverting, and then blotting the plate on tissue. Cells are then washed by gentle addition of 150 µL/well of ice cold HBSS and centrifugation at 300 g, for 5 minutes at 4° C. Supernatant is aspirated and the plate blotted as described above. The plate is placed on ice and cells are immediately treated with 35 µL per well of ice cold lysis buffer, prepared according to the kit instructions (per assay plate, to 5 ml of Tris lysis buffer add 100 µl of 50× protease inhibitor solution and 50 µl of each 100× phosphatase inhibitor solutions I and II). Plates are incubated on ice for 20 minutes before centrifugation at 841 g for 5 minutes, 4° C.

Block buffer is aspirated from the MSD plate, and the plate washed four times with 300 µl/well Tris wash buffer. 25 µL of cell lysate is then transferred from the assay plate to the washed MSD plate which is sealed and incubated at room temperature for one hour with shaking. The plate is washed four times with 300 µL per well of Tris wash buffer before addition of 25 µL per well of sulfo-tag anti-total AKT/pAKT detection antibody (60 µl of 50× antibody stock is diluted in 1 ml block buffer mixed with 2 ml wash buffer) and incubated at room temperature for one hour with shaking. The plate is washed four times with 300 µl per well of Tris wash buffer and 150 µl per well of Read buffer is added, taking care to avoid the introduction of bubbles. The plate is immediately read using an MSD SECTOR Imager 6000. Results are exported in Excel and the percentage of phosphorylated AKT is calculated using the equation: % Phosphoprotein=((2*Phospho signal)/(Phospho signal+Total signal))*100. Compound-mediated inhibition of AKT phosphorylation is analysed using Prizm V Graphpad software.

Cellular U937 AKT Assay for PI 3-Kinase Gamma (K2)

Materials used: Bio-Rad TC10TM automated cell counter, Bio-RAD counting slides (#145-0011), Trypan blue solution 0.4% (#T8154 Sigma), diluted 1:2 in PBS), Bioconcept Multidrop combi, Versette automated liquid handler (Thermo scientific), HTRF Phospho-AKT (Ser473) 10'000 tests assay kit (cisbio #64AKSPEH), ProxiPlate-384 Plus, White, TC treated (Perkin Elmer #6008239)

384-well tissue culture treated plate (BD Falcon #353289), RPMI+GlutaMAX (Life Technologies #61870-010), FBS dialyzed (Life Technologies #26400), Penicilin/Streptomycin (Life Technologies #15140), HBSS 1× (Life Technologies #14025-050), Wortmannin (Sigma-Aldrich # W1628), stock solution 10 mM in 90% DMSO, Recombinant Human CCL3/MIP1α (R&D Systems #270-LD) (stock solution 10 µg/ml), RUBYstar Microplate Reader (BMG Labtech #8)

U937 cells are split every 3-4 days: $5 \times 10^6$ cells/flask (175 cm$^2$) in 40 ml. 3-4 days before the assay, cells should be seeded: 4-5 flasks with 107 cells in 40 ml.

Semi-automated preparation of cell lysates: Cells were resuspended in HBSS, seeded (200'000 cells/well/60 µl) into a 384-well plate and incubated in a humidified 37° C., 5% CO2 incubator for 1.5 hours. The compounds were diluted with HBSS and 40 µl were added to the starved cells (except for wells 24 I-P). 10 µM Wortmanin was added to the negative control (wells 24 I-P). The cells were then incubated for 30 minutes at 37° C. and 5% CO2. Stimulation occurred during 3 minutes by addition of 20 µl MIP1α (final 10 ng/ml, diluted in HBSS) in the incubator. Wells 24 A-H were only stimulated with HBSS.

The stimulation was then stopped by putting the cell plates on ice (filled with cold water). The cells were then centrifuged at 1200 rpm and 4° C. for 3 minutes. 80 µl of supernatant was removed. The cells were again centrifuged at 1200 rpm and 4° C. for 3 minutes. The supernatant was then removed by turning plates upside down and 30 µl of lysis buffer were added. The plate was incubated at room temperature for 30 minutes under shaking. 16 µl were then transferred to a ProxiPlate Plus 384-well. 4 µl of the master mix (each conjugate diluted 1:20 with detection reagent) were added to each well and the plate was kept in the dark at room temperature for 4 hours. Fluorescence was measured at 665 nm and 620 nm with a RUBYstar Reader.

Whole Blood Neutrophil Shape Change Assay (L)

A flow cytometry based method used to measure the inhibition of IL-8 (interleukin-8)-induced neutrophil shape change in human whole blood.

Reagents, Material & Equipment

Sterile Distilled Water, Baxter # UKF117

10× CellFIX solution, BECTON DICKINSON Biosciences #340181

IL-8, R&D Systems #208-IL

DMSO, Hybri-Max, Sigma-Aldrich # D2650

Dulbecco's Phosphate Buffered Saline 1×[+]$CaCL_2$, $MgCL_2$, gibco by life technologies #14040

Albumin Solution from Bovine Serum (30%), Sigma Aldrich # A9576-50 ml

Ammonium Chloride $NH_4CL$, Sigma Aldrich # A0171

Potassium Bicarbonate $KHCO_3$, Sigma Aldrich # P9144

K2 EDTA Vacutainers, Becton Dickinson Vacutainer®#367525

96-well Polypropylene deep-well plates, VWR # PORV219009

96 well Plates, V-bottom with lid, Costar #3894

96 well Polypropylene Plates, Round Bottom, Greiner #650261 (for HIGH THROUGHPUT SAMPLER FACS)

120 µl pre-sterilized Biohit Filter Tips, Biohit #790101F

350 µl pre-sterilized Biohit Tips, Biohit #790350

1200 µl pre-sterilized Biohit Tips, Biohit #791202

Biohit e1200 Electronic 8-channel Pipette

Biohit e120 Electronic 8-channel Pipette

Eppendorf Research Plus 100-1000 µl Pipette

Eppendorf Research Plus 20-200 µl Pipette

Becton Dickinson Biosciences FACS Canto 11 Flow Cytometer with HIGH THROUGHPUT SAMPLER IL-8 was made up to 2 µM stocks in 0.1% bovine serum albumin/PBS and stored at −80° C. On the day IL-8 was diluted in PBS (phosphate buffered saline) 10 minutes before use. IL-8 was used at final concentration of 2 nM and a concentration range from 0.003 to 200 nM for the donor dose response curve.

Assay fixative solution was prepared fresh each day from 10× concentrated CellFIX™ solution diluted 1:10 in sterile distilled water and then 1:4 with PBS. Assay fixative solution was kept on ice prior to use.

A 10× lysis buffer was prepared in advance by dissolving 20.75 g $NH_4Cl$ and 2.5 g $KHCO_3$ in 250 ml sterile $H_2O$. This 10× lysis buffer was filtered under sterile conditions and stored for up to two weeks at 4° C. On the day a 1× lysis solution was prepared with sterile distilled $H_2O$ and kept on ice prior to use.

The test compounds were prepared as 10 mM stock solutions in 100% DMSO and were stored at 4° C. Once in use for an assay 10 mM stock compounds were thawed and stored at RT protected from light. Compound dilutions were prepared fresh on the day. The first series of dilutions in 100% DMSO were done first thing in the morning. Only once blood had been collected and arrived in laboratory was the next set of dilutions into PBS carried out (1:10 PBS, 10% DMSO). This limited the exposure of diluted compound to plastic and made sure the exposure timing was consistent between assays. Compounds were added to the deep 96 well plates at 10× the final desired concentration (with addition of blood final [DMSO]=1%).

Table 3 illustrates the compound dilution series used in human whole blood neutrophil shape change assay.

TABLE 3

| 100% DMSO Serial Dil'n 1 in 4 | 10% DMSO 1 in 10 PBS | 1% DMSO Assay Plate | $_{example}$Well ID* |
|---|---|---|---|
| 10000 µM | 1000 µM | 100 µM | B2; CPD + IL-8 |
| 2500 | 250 | 25 | B3; CPD + IL-8 |
| 625 | 62.5 | 6.25 | B4; CPD + IL-8 |
| 156.25 | 15.62 | 1.56 | B5; CPD + IL-8 |
| 39.0625 | 3.9 | 0.39 | B6; CPD + IL-8 |
| 9.765625 | 0.97 | 0.097 | B7; CPD + IL-8 |
| 2.441406 | 0.24 | 0.024 | B8; CPD + IL-8 |
| 0.610352 | 0.06 | 0.006 | B9; CPD + IL-8 |
| 100% DMSO | 10% DMSO | 1% DMSO | B10; + IL-8 |
| 100% DMSO | 10% DMSO | 1% DMSO | B11; + PBS |

On the day of running the assay, assay fixative buffer and 1× lysis solutions were prepared and stored on ice. Compound dilutions in 100% DMSO were prepared as described previously. Human whole blood was collected in K2 EDTA Vacutainers. Once blood was in the laboratory, compound dilutions into PBS were carried out as described previously and depicted in Table 1.

10 µl of 10× final compound concentration was added to appropriate wells of a deep 96-well plate except controls where 10 µl of 10% DMSO was added in place of compound, as outlined in the dilution series in Table 1. The outer wells of the deep well assay plate were filled with 1200 µl of sterile distilled $H_2O$ in an effort to limit edge effects (rows A1-H1, A1-A12, A12-H12).

An IL-8 dose response was determined for each blood donor examined, to monitor the donor response to IL-8. At this step in assay preparation for the IL-8 dose response samples 10 µl of PBS was added to designated wells. In addition the assay window without DMSO was also assessed each day. For such samples at this step in assay preparation 10 µl of PBS was added in the place of 10% DMSO.

80 µl of whole blood was added to compound/10% DMSO/PBS and mixed once gently upon addition. Lids were placed on the 96 well plates and samples were incubated for 15 minutes at 37° C. in a water-bath.

Following the compound pre-incubation 10× final IL-8 was added to appropriate wells (10 µl of 20 nM working stock IL-8, final IL-8 concentration in blood=2 nM) and 10 µl of PBS was added to the un-stimulated controls. 10× final dose response range IL-8 was also added to designated wells (final concentration range on assay plate was 200 nM to 0.0005 nM, 1:5 serial dilution in PBS). The IL-8 and PBS were added to appropriate wells across all assay plates in the same sequence as the blood to compound addition. Once added to all assay plates, samples were mixed quickly once to ensure even distribution of IL-8. Samples were incubated for 5 minutes at 37° C. in a water-bath. Following the incubation sample plates were transferred to ice where 250 µl of chilled Assay Fixative Buffer was added promptly to all wells.

Samples were incubated on ice for 7 minutes (no mixing). Following fixation 1.2 ml of 1× Lysis Solution was then added promptly to each well. Once added samples were mixed once and incubated on ice for 30 minutes to achieve uniform red blood cells lysis. After lysis, 200 µl of sample was transferred to a 96 well microplate on ice. Samples were acquired using the HTS on high throughput mode on a Becton Dickinson FACS Canto II. Granulocytes were identified based on differential side scatter (SSC) and forward scatter (FSC) characteristics. Neutrophils were distinguished from eosinophils using the phycoerythrin channel, as the latter have higher auto-fluorescence.

The mean FSC value for the neutrophil population was taken as measure of cell shape change (the greater the FSC value meant the greater the degree of shape change). Data was presented as % shape change over basal for the IL-8 dose response curve and assay window controls and presented as % inhibition of shape change for compound treated samples.

% Shape Change Above Basal

Subtract the un-stimulated control FSC reading from agonist FSC readings, divide results by the un-stimulated FSC value and multiply by 100 to give % shape change above basal.

% inhibition

% inhibition=$(X-Y)/X*100$(FIG. 2. for sample values)

X=IL-8 FSC response minus the un-stimulated control (basal) FSC.

(120,984−86,163=34821=X)

Y=IL-8 FSC response in compound treated samples minus the un-stimulated control (basal) FSC.

(89,841−86,163=3678=Y)

(34821−3678)/34821*100=89% inhibition of shape change

The % inhibition values were plotted on the Y-axis against compound concentration on the x-axis, to give $IC_{50}$ values.

Microsomal Clearance Assay (M)

The experiments were performed in 96-well glass plates at 37° C. on an automated Tecan EVO platform. Test compounds at a concentration of 10 mM in pure DMSO were diluted 1:1000 in water to 10 µM. This solution (30 µL) was added to 120 µL of rat liver microsomal protein (1.25 mg/mL) suspended in phosphate buffer (pH 7.4). Reactions were initiated by the addition of 150 µL of a cofactor solution containing 2 mM NADPH. At specific reaction time points (0, 5, 20, and 30 min), aliquots (50 µL) were removed and reactions were terminated by the addition to acetonitrile (100 µL) containing the analytical internal standards (1 µM alprenolol and 1.6 µM chlorzoxazone) and stored at −20° C. for at least 1 h to allow complete precipitation of proteins. The samples were then centrifuged at 5000 g at 4° C. for 35 min, and 20 µL of the supernatants were analyzed by LC-MS/MS for quantitation of the remaining test article. The percentage of test compound remaining, relative to time zero minute incubation, is used to estimate the in vitro elimination-rate constant ($k_{mic}$), which is used to calculate the in vitro metabolic clearance rates.

The biochemical assay data for examples 1-143 is provided in the following Table 4:

TABLE 4

| Example | Assay A PI3Kα IC50 (µM) | Assay B PI3Kβ IC50 (µM) | Assay C VPS34 IC50 (µM) | Assay D PI4Kβ IC50 (µM) | Assay E PI3Kγ IC50 (µM) | Assay F PI3Kδ IC50 (µM) | Assay G mTOR IC50 (µM) |
|---|---|---|---|---|---|---|---|
| 1 | 1.30 | 5.86 | >9.1 | >9.1 | 0.015 | 1.01 | |
| 2 | 0.82 | 7.60 | >9.1 | >9.1 | 0.003 | 0.39 | >9.1 |
| 3 | 0.60 | 5.88 | >9.1 | >9.1 | 0.046 | 0.14 | >9.1 |
| 4 | 0.51 | 3.24 | >9.1 | 3.70 | 0.026 | 0.30 | 6.51 |
| 5 | 0.68 | 0.69 | >10 | 6.70 | 0.012 | 1.00 | >10 |
| 6 | 0.52 | 2.31 | >9.4 | 7.12 | 0.039 | 0.95 | 9.01 |
| 7 | 0.06 | 0.99 | 0.39 | 1.95 | 0.006 | 0.07 | 0.92 |
| 8 | 0.04 | 1.52 | 0.41 | 1.96 | <0.003 | 0.02 | 0.27 |
| 9a | 0.12 | 0.54 | >10 | 9.60 | 0.015 | 0.20 | 8.10 |
| 9b | 0.21 | 1.20 | >10 | 9.10 | 0.012 | 0.24 | >10 |
| 10 | 0.04 | 0.89 | 0.21 | 1.89 | 0.013 | 0.06 | 1.88 |
| 11 | 0.14 | 2.62 | >9.1 | 3.58 | 0.010 | 0.13 | 5.89 |
| 12 | 0.14 | 2.65 | >9.1 | >9.1 | 0.041 | 0.24 | >9.1 |
| 13 | 0.20 | 1.09 | >10 | 6.50 | 0.034 | 0.33 | >10 |
| 14 | 0.09 | 0.62 | 0.42 | 1.57 | 0.014 | 0.04 | 0.88 |
| 15 | 0.16 | 1.93 | >9.1 | 5.68 | 0.018 | 0.15 | >9.1 |
| 16 | 0.14 | 1.02 | >10 | 6.40 | 0.009 | 0.25 | 5.30 |
| 17 | 0.22 | 0.90 | >10 | 8.30 | 0.010 | 0.59 | 6.10 |
| 18 | 0.29 | 2.80 | >10 | 8.60 | 0.031 | 0.62 | 5.55 |
| 19 | 0.04 | 0.14 | 9.40 | 3.85 | 0.005 | 0.02 | 0.42 |
| 20a | 0.03 | 1.06 | >9.1 | 5.28 | 0.007 | 0.05 | 1.88 |
| 20b | 0.05 | 0.88 | 0.40 | 4.98 | 0.011 | 0.05 | 3.31 |
| 21 | 0.04 | 0.15 | 1.40 | 1.50 | 0.006 | 0.08 | 0.69 |
| 22 | 0.76 | 5.71 | >9.1 | 7.08 | 0.044 | 0.42 | 8.02 |
| 23 | 0.39 | >9.10 | >9.1 | >9.1 | 0.010 | 0.09 | 6.45 |
| 24 | 0.20 | 6.06 | >9.1 | >9.1 | 0.007 | 0.06 | 7.91 |
| 25 | 0.62 | 3.15 | >10 | >10 | 0.079 | 1.03 | 0.21 |
| 26 | 0.31 | 6.38 | >9.1 | 5.47 | 0.003 | 0.07 | >9.1 |
| 27 | 0.21 | 0.87 | >10 | 6.65 | 0.047 | 0.07 | 7.40 |
| 28 | 0.68 | 4.30 | >9.1 | 8.90 | 0.026 | 0.56 | >9.1 |
| 29 | 1.30 | 6.80 | >9.1 | 5.20 | 0.009 | 0.91 | >9.1 |
| 30 | 0.30 | 5.21 | >9.1 | 7.89 | 0.024 | 0.05 | 6.99 |
| 31 | 0.16 | 2.00 | >9.55 | 4.40 | 0.027 | 0.12 | 3.80 |
| 32 | 0.66 | 1.46 | >10 | 4.05 | 0.094 | 1.50 | >10 |
| 33 | 0.21 | 0.38 | >10 | 0.91 | 0.047 | 0.78 | 1.50 |
| 34 | 0.70 | 2.50 | >10 | 3.80 | 0.074 | 2.90 | 2.50 |

TABLE 4-continued

Biochemical assay data

| Example | Assay A PI3Kα IC50 (μM) | Assay B PI3Kβ IC50 (μM) | Assay C VPS34 IC50 (μM) | Assay D PI4Kβ IC50 (μM) | Assay E PI3Kγ IC50 (μM) | Assay F PI3Kδ IC50 (μM) | Assay G mTOR IC50 (μM) |
|---|---|---|---|---|---|---|---|
| 35 | 0.63 | 1.90 | >10 | 3.70 | 0.025 | 0.99 | 5.60 |
| 36 | 0.16 | 0.85 | >10 | 8.00 | 0.017 | 0.11 | 0.25 |
| 37 | 1.00 | 3.50 | >9.1 | 3.50 | 0.083 | 0.73 | 5.90 |
| 38 | 0.92 | 3.50 | >9.1 | 4.20 | 0.025 | 0.14 | 8.40 |
| 39 | 0.79 | 3.95 | >9.55 | 7.05 | 0.067 | 1.07 | >9.55 |
| 40 | 0.76 | 1.40 | >10 | >10 | 0.036 | 0.84 | 3.80 |
| 41 | 0.11 | 0.25 | 7.70 | 9.40 | 0.010 | 0.02 | |
| 42 | 0.03 | 0.66 | 4.65 | 3.50 | 0.007 | 0.03 | |
| 43 | 0.05 | 0.20 | 0.90 | 1.40 | 0.006 | 0.22 | |
| 43a | 0.1 | 0.69 | 2.5 | 2.3 | 0.026 | 0.67 | |
| 43b | 0.23 | 1.5 | 5.5 | 4.8 | 0.042 | 2.2 | |
| 44 | 0.06 | 0.24 | 2.30 | 1.60 | 0.005 | 0.15 | |
| 45 | 0.06 | 0.53 | 1.10 | 1.60 | 0.014 | 0.23 | |
| 45.1 | 0.05 | 0.20 | 1.90 | 3.00 | 0.011 | 0.08 | |
| 45.2 | 0.04 | 0.37 | 6.00 | 5.80 | 0.018 | 0.05 | |
| 45.3 | 0.04 | 0.24 | 1.60 | 1.60 | 0.013 | 0.10 | |
| 45.4 | 0.11 | 0.88 | 3.00 | 1.80 | 0.009 | 0.10 | |
| 45.5 | 0.04 | 0.99 | 0.65 | 0.78 | 0.005 | 0.04 | |
| 45.6a | 0.07 | 0.29 | 1.5 | 4.1 | 0.009 | 0.11 | |
| 45.6b | 0.38 | 2.5 | 4.5 | >10 | 0.042 | 1.1 | |
| 45.7a | 0.28 | 0.68 | 1.1 | 3.4 | 0.027 | 0.42 | |
| 45.7b | 0.16 | 0.31 | 1.1 | 1.3 | 0.010 | 0.16 | |
| 45.8 | 0.09 | 0.59 | 2.00 | 3.30 | 0.130 | 0.32 | |
| 45.9 | 0.03 | 0.32 | 9.40 | 4.90 | 0.039 | 0.10 | |
| 45.10 | 0.02 | 0.34 | 3.90 | 1.90 | 0.010 | 0.15 | |
| 45.11 | 0.04 | 0.29 | 1.60 | 1.20 | 0.005 | 0.13 | |
| 45.12 | 0.05 | 0.39 | 2.60 | 1.40 | 0.015 | 0.10 | |
| 46 | 0.22 | 0.82 | >10 | >10 | 0.026 | 0.45 | >10 |
| 46.1 | 1.40 | >10 | >10 | >10 | 0.210 | 2.60 | >10 |
| 46.2 | 0.48 | 2.00 | >10 | 6.20 | 0.054 | 0.73 | 9.70 |
| 47 | 0.33 | 6.00 | >10 | 8.70 | 0.049 | 0.53 | >10 |
| 48 | 2.60 | 7.30 | >10 | >10 | 0.081 | 0.92 | >10 |
| 49 | 0.62 | 5.30 | >10 | >10 | 0.049 | 1.70 | >10 |
| 50 | 2.50 | 2.80 | >10 | >10 | 0.850 | >10 | >10 |
| 51 | 0.37 | 4.19 | 7.15 | >9.1 | 0.042 | 0.49 | >9.1 |
| 52a | 0.17 | 1.10 | >10 | 5.50 | 0.016 | 0.15 | 2.00 |
| 52b | 0.23 | 2.10 | >10 | 4.20 | 0.026 | 0.53 | >10 |
| 53 | 1.70 | 7.00 | >10 | >10 | 0.690 | 3.70 | |
| 54 | 0.19 | 0.77 | >9.1 | >9.1 | 0.017 | 0.11 | 4.81 |
| 55 | 0.04 | 0.12 | 0.64 | 3.74 | 0.026 | 0.03 | 0.62 |
| 56 | 0.29 | 1.75 | 3.52 | 7.27 | 0.019 | 0.08 | 2.38 |
| 57 | 0.32 | 6.48 | >9.1 | >9.1 | 0.057 | 0.58 | >9.1 |
| 58 | 0.49 | 2.93 | 3.10 | 5.85 | 0.019 | 0.10 | >9.1 |
| 59 | 0.91 | 5.29 | >9.1 | >9.1 | 0.105 | 0.41 | 6.02 |
| 60 | 0.11 | 4.57 | >9.1 | 3.63 | 0.040 | 0.22 | 8.35 |
| 61 | 5.47 | >9.10 | >9.1 | >9.1 | 1.823 | 5.81 | >9.1 |
| 62 | 0.68 | 1.01 | >9.1 | 3.68 | 0.056 | 0.21 | >9.1 |
| 63 | 0.33 | 3.93 | >9.1 | 7.85 | 0.068 | 0.42 | 6.50 |
| 64 | 0.37 | 3.85 | 8.49 | 6.61 | 0.046 | 0.25 | >9.1 |
| 65 | 0.44 | 4.03 | >9.1 | >9.1 | 0.022 | 0.24 | >9.1 |
| 66 | 0.19 | >9.10 | >9.1 | 7.94 | 0.006 | 0.08 | 5.98 |
| 67 | 0.09 | 0.86 | 1.80 | 7.40 | 0.003 | 0.16 | 2.20 |
| 68 | 0.64 | 2.55 | >10 | 4.40 | 0.072 | 1.50 | 8.75 |
| 69a | 0.39 | 3.50 | >10 | >10 | 0.038 | 0.53 | 9.20 |
| 69b | 0.39 | 1.40 | >10 | >10 | 0.057 | 0.69 | 9.60 |
| 70a | 0.11 | 0.75 | >10 | 4.60 | 0.025 | 0.29 | 2.00 |
| 70b | 0.84 | 2.50 | >10 | >10 | 0.004 | 1.10 | 5.90 |
| 71a | 0.33 | 1.10 | >10 | 2.80 | 0.013 | 1.00 | >10 |
| 71b | 0.76 | 1.90 | >10 | 4.60 | 0.021 | 1.30 | >10 |
| 72 | 0.58 | 2.67 | >9.1 | >9.1 | 0.034 | 0.39 | >9.1 |
| 73 | 0.35 | 1.83 | >9.1 | >9.1 | 0.015 | 0.39 | >9.1 |
| 74 | 0.19 | 0.83 | >10 | 6.20 | 0.041 | 0.38 | 3.50 |
| 75 | 0.47 | 2.48 | 7.49 | 7.97 | 0.056 | 0.24 | 4.51 |
| 76 | 0.18 | 3.71 | >9.1 | 4.47 | 0.064 | 0.48 | 4.19 |
| 77 | 0.23 | 4.20 | >9.1 | >9.1 | 0.034 | 0.30 | 5.47 |
| 78 | 0.24 | 2.20 | >9.55 | 1.55 | 0.013 | 0.18 | 2.35 |
| 79 | 0.28 | 1.20 | 7.60 | 3.90 | 0.022 | 0.37 | 6.50 |
| 80 | 0.25 | 1.70 | >10 | 4.55 | 0.077 | 0.40 | >10 |
| 81 | 2.60 | 6.30 | >10 | 9.00 | 0.077 | 2.50 | >10 |
| 82 | 0.18 | 5.50 | >10 | >10 | 0.041 | 0.54 | >10 |
| 83 | 1.90 | 5.20 | >10 | 4.30 | 0.085 | 0.70 | >10 |
| 84 | 0.12 | 2.30 | >10 | 7.05 | 0.042 | 0.21 | >10 |
| 85 | 0.09 | 1.20 | >10 | >10 | 0.021 | 0.12 | 7.90 |
| 87 | 0.06 | 0.27 | 0.32 | 1.57 | 0.006 | 0.03 | 1.84 |

TABLE 4-continued

Biochemical assay data

| Example | Assay A PI3Kα IC50 (μM) | Assay B PI3Kβ IC50 (μM) | Assay C VPS34 IC50 (μM) | Assay D PI4Kβ IC50 (μM) | Assay E PI3Kγ IC50 (μM) | Assay F PI3Kδ IC50 (μM) | Assay G mTOR IC50 (μM) |
|---|---|---|---|---|---|---|---|
| 88 | 0.52 | 2.20 | 9.10 | 6.10 | 0.014 | 1.10 | 9.10 |
| 89 | 0.42 | 1.30 | 3.40 | 7.00 | 0.018 | 0.84 | >10 |
| 90 | 2.10 | 0.94 | >10 | >10 | 0.078 | 2.00 | >10 |
| 91 | 2.35 | 2.55 | >9.55 | >9.55 | 0.270 | 2.10 | >9.55 |
| 92 | 1.40 | 8.20 | >9.1 | >9.1 | 0.073 | 0.69 | >9.1 |
| 93 | 1.10 | >9.10 | >9.1 | >9.1 | 0.081 | 0.33 | >9.1 |
| 94 | 1.70 | >9.10 | >9.1 | >9.1 | 0.014 | 0.57 | 8.90 |
| 95 | 0.90 | 4.10 | >9.55 | >9.55 | 0.036 | 0.73 | 7.40 |
| 96 | 0.55 | 3.35 | >9.55 | >9.55 | 0.092 | 0.55 | 8.80 |
| 97 | 1.20 | >10.00 | >10 | >10 | 0.061 | 1.70 | >10 |
| 98 | 1.70 | 1.40 | >9.1 | 2.50 | 0.038 | 0.31 | >9.1 |
| 99 | 0.74 | 1.65 | 2.95 | 2.70 | 0.014 | 0.14 | 4.95 |
| 100 | 0.50 | 5.30 | 7.20 | 5.75 | 0.003 | 0.68 | >9.55 |
| 101 | 2.00 | 1.70 | >10 | 2.40 | 0.210 | 3.00 | >10 |
| 102 | 0.55 | 1.80 | >10 | 5.90 | 0.150 | 0.90 | 2.90 |
| 103 | 0.39 | 1.88 | >9.1 | 2.74 | 0.013 | 0.15 | >9.1 |
| 105 | 0.12 | 0.16 | 9.40 | 2.60 | 0.014 | 0.01 | |
| 106 | 0.10 | 0.75 | >10 | 5.60 | 0.025 | 0.14 | |
| 107 | 0.08 | 2.09 | 3.10 | 0.94 | 0.006 | 0.06 | 1.39 |
| 108 | 0.31 | 0.26 | >10 | 0.64 | 0.038 | 0.33 | >10 |
| 109 | 0.44 | 3.00 | >10 | 8.60 | 0.028 | 0.69 | |
| 110 | 0.09 | 0.52 | >10 | >10 | 0.010 | 0.32 | >10 |
| 111 | 0.18 | 1.98 | >9.1 | 1.96 | 0.018 | 0.06 | >9.1 |
| 112 | 0.86 | 3.30 | >10 | 3.15 | 0.019 | 0.50 | 6.30 |
| 112.1 | 0.29 | 1.70 | >10 | 1.80 | 0.033 | 0.21 | 6.00 |
| 112.2 | 0.86 | 1.30 | >10 | 5.40 | 0.104 | 1.20 | >10 |
| 112.3 | 0.36 | 1.10 | >10 | 1.20 | | 0.26 | 1.36 |
| 112.4 | 0.08 | 0.56 | >10 | 1.10 | 0.093 | 0.19 | >10 |
| 112.5 | 0.12 | 2.25 | >10 | 3.00 | | 0.53 | 1.83 |
| 113 | 0.05 | 0.44 | 0.47 | 1.48 | 0.008 | 0.32 | 3.45 |
| 114 | 0.29 | 3.70 | 7.83 | 5.90 | 0.044 | 1.19 | >9.1 |
| 115 | 0.32 | 2.35 | 8.99 | 5.64 | 0.039 | 0.48 | 8.64 |
| 116 | 1.20 | >9.10 | >9.1 | 8.10 | 0.028 | 0.30 | >9.1 |
| 117 | 0.90 | >10.00 | >10 | >10 | 0.036 | | >10 |
| 118 | 0.03 | 0.47 | 1.46 | 4.72 | 0.011 | 0.13 | 0.46 |
| 119 | 0.60 | >9.10 | >9.1 | >9.1 | 0.118 | 0.71 | 4.31 |
| 119.1 | 0.61 | >9.10 | >9.1 | 6.20 | 1.003 | 2.30 | 4.91 |
| 119.2 | 0.45 | >9.10 | >9.1 | >9.1 | 0.050 | 0.25 | >9.1 |
| 119.3 | 0.09 | 7.49 | >9.1 | 7.46 | 0.044 | 0.13 | 3.70 |
| 119.4 | 2.83 | >9.10 | >9.1 | >9.1 | 3.117 | 5.70 | >9.1 |
| 119.5 | 0.75 | >9.10 | >9.1 | 8.00 | 0.082 | 0.55 | >9.1 |
| 119.6 | 0.82 | >9.10 | 7.99 | 7.70 | 0.161 | 0.38 | 5.61 |
| 119.7 | 2.98 | >9.10 | >9.1 | 7.96 | 0.278 | 0.72 | 4.32 |
| 119.8 | 1.05 | >9.10 | >9.1 | 4.53 | 0.167 | 0.20 | 5.94 |
| 119.9 | 0.33 | 7.78 | >9.1 | 0.69 | 0.178 | 0.90 | >9.1 |
| 119.10 | 0.12 | 6.47 | >9.1 | >9.1 | 0.030 | 0.10 | 6.40 |
| 119.11 | 0.45 | >9.10 | >9.1 | >9.1 | 0.303 | 1.10 | >9.1 |
| 119.13 | 0.58 | >9.10 | >9.1 | 4.14 | 0.098 | 0.45 | >9.1 |
| 119.14 | 1.16 | >9.10 | >9.1 | 7.35 | 0.667 | 1.44 | 8.53 |
| 119.15 | 1.66 | 8.81 | >9.1 | 4.86 | 0.162 | 0.96 | >9.1 |
| 119.16 | 0.39 | 3.79 | 6.23 | 6.61 | 0.022 | 0.19 | >9.1 |
| 119.17 | 1.45 | >9.10 | >9.1 | 1.56 | 0.362 | 2.54 | >9.1 |
| 119.18 | 0.49 | 8.04 | >9.1 | 8.19 | 0.248 | 0.58 | >9.1 |
| 119.19 | >9.10 | >9.10 | >9.1 | >9.1 | 3.468 | >9.1 | >9.1 |
| 119.20 | 1.48 | >9.10 | >9.1 | >9.1 | 0.508 | 2.08 | 4.82 |
| 119.21 | 1.73 | >9.10 | >9.1 | 3.83 | 0.401 | 2.18 | >9.1 |
| 119.22 | 0.57 | 1.93 | >9.1 | 2.19 | 0.157 | 0.53 | 2.34 |
| 119.23 | 1.34 | >9.10 | >9.1 | 0.94 | 0.525 | 2.04 | 7.60 |
| 119.24 | 1.09 | >9.10 | >9.1 | 3.40 | 0.761 | 1.67 | 9.02 |
| 119.25 | 0.40 | 5.78 | >9.1 | 4.05 | 0.031 | 0.29 | 8.74 |
| 119.26 | 0.25 | 3.90 | >9.1 | 1.79 | 0.037 | 0.04 | 5.87 |
| 119.27 | 0.17 | 4.97 | >9.1 | 5.75 | 0.035 | 0.12 | 4.78 |
| 119.28 | 0.23 | 7.38 | >9.1 | 4.41 | 0.049 | 0.19 | 6.00 |
| 119.29 | 0.17 | 0.92 | 0.57 | 2.64 | 0.009 | 0.07 | 0.59 |
| 119.30 | 0.17 | 1.50 | >9.1 | 4.71 | 0.013 | 0.11 | 2.88 |
| 119.31 | 0.16 | 7.85 | >9.1 | 3.74 | 0.007 | 0.11 | 2.23 |
| 119.32 | 0.26 | 3.22 | >9.1 | 2.67 | 0.011 | 0.20 | 6.04 |
| 119.33 | 0.16 | 0.69 | >9.1 | 1.00 | 0.014 | 0.26 | >9.1 |
| 119.34 | 0.18 | 3.51 | >9.1 | 4.25 | 0.013 | 0.22 | 6.59 |
| 119.35 | 0.08 | 0.94 | >9.1 | 0.74 | 0.013 | 0.07 | 3.90 |
| 119.36 | 0.22 | 4.41 | >9.1 | >9.1 | 0.034 | 0.17 | >9.1 |
| 119.37 | 0.18 | 3.00 | >9.1 | 5.30 | 0.024 | 0.04 | >9.1 |
| 119.38 | 0.09 | 3.50 | >9.1 | 6.30 | 0.012 | 0.03 | 4.60 |
| 119.39 | 0.10 | 2.80 | >9.1 | 6.50 | 0.006 | 0.04 | 6.90 |

TABLE 4-continued

Biochemical assay data

| Example | Assay A PI3Kα IC50 (μM) | Assay B PI3Kβ IC50 (μM) | Assay C VPS34 IC50 (μM) | Assay D PI4Kβ IC50 (μM) | Assay E PI3Kγ IC50 (μM) | Assay F PI3Kδ IC50 (μM) | Assay G mTOR IC50 (μM) |
|---|---|---|---|---|---|---|---|
| 119.40 | 0.15 | 3.50 | >10 | 6.20 | 0.023 | 0.18 | >10 |
| 119.41 | 0.42 | 3.25 | >10 | 6.00 | 0.025 | 0.03 | >10 |
| 119.42 | 0.71 | 2.34 | >9.1 | 0.88 | 0.069 | 0.36 | >9.1 |
| 119.43 | 0.25 | 1.78 | >9.1 | >9.1 | 0.054 | 0.10 | 3.37 |
| 119.44 | 0.12 | 1.37 | >9.1 | 0.76 | 0.099 | 0.04 | 3.99 |
| 119.45 | 0.15 | 3.60 | >9.1 | 2.46 | 0.012 | 0.10 | 8.69 |
| 119.46 | 0.25 | | >9.1 | 0.61 | 0.110 | 0.07 | 6.70 |
| 120 | 0.02 | 1.00 | 1.30 | 2.50 | 0.004 | 0.06 | |
| 121 | 0.12 | 1.20 | >10 | 0.51 | 0.092 | 0.96 | 5.20 |
| 122 | 0.49 | 2.20 | >10 | 1.90 | 0.085 | 1.60 | 6.60 |
| 123 | 2.90 | 5.50 | >10 | 2.50 | 2.100 | 4.70 | 9.00 |
| 124 | 0.04 | 0.10 | >10 | 0.42 | 0.022 | 0.16 | 0.71 |
| 125 | 0.28 | 6.00 | >10 | 7.60 | 0.100 | 0.13 | >10 |
| 126 | 0.28 | 3.1 | >10 | >10 | 0.057 | 1 | |
| 127 | 0.30 | 1.10 | >10 | 4.40 | 0.024 | 0.88 | 2.60 |
| 127.1 | 0.29 | 1.20 | >10 | 1.50 | 0.011 | 0.56 | 1.10 |
| 127.2 | 0.32 | 1.00 | >10 | 1.70 | 0.073 | 0.85 | 9.40 |
| 127.3 | 0.38 | 3.20 | >10 | 3.40 | 0.160 | >10 | >10 |
| 127.4 | 2.55 | 6.55 | >9.55 | 4.20 | 0.260 | 2.50 | >9.55 |
| 127.5 | 0.40 | 3.10 | >10 | >10 | 0.100 | 3.90 | 1.80 |
| 127.6 | 0.39 | 2.20 | >10 | >10 | 0.160 | 1.50 | >10 |
| 127.7 | 0.26 | 1.30 | >10 | 6.30 | 0.040 | 1.10 | 1.50 |
| 127.8 | 6.00 | >10.00 | >10 | >10 | 1.000 | >10 | >10 |
| 127.9 | 2.30 | >10.00 | >10 | >10 | 1.600 | 3.00 | >10 |
| 127.10 | 1.70 | 9.20 | >10 | >10 | 0.320 | 5.50 | >10 |
| 127.11 | 0.98 | 1.30 | >10 | >10 | 0.270 | 0.76 | >10 |
| 127.12 | 3.50 | 1.50 | >10 | >10 | 0.091 | 0.57 | >10 |
| 127.13 | 0.28 | 0.53 | >10 | 3.80 | 0.026 | 1.10 | 6.10 |
| 127.14 | 0.92 | 2.60 | >10 | 8.45 | 0.069 | 0.90 | 9.00 |
| 127.16 | 0.33 | 0.81 | >10 | 5.00 | 0.045 | 1.10 | 8.70 |
| 127.17 | 0.89 | 1.20 | >10 | 7.40 | 0.038 | 1.10 | >10 |
| 127.18 | 1.90 | 2.40 | >10 | >10 | 1.300 | 0.38 | >10 |
| 127.19 | 0.26 | 1.30 | >10 | 3.90 | 0.061 | 0.62 | >10 |
| 127.20 | 0.97 | 5.10 | >10 | 5.30 | 0.130 | 1.70 | >10 |
| 127.21 | 0.36 | 1.90 | >10 | >10 | 0.098 | 1.20 | 3.00 |
| 127.22 | 0.27 | 0.97 | >10 | 8.30 | 0.040 | 0.50 | 3.90 |
| 127.23 | 0.18 | 0.58 | >10 | 2.90 | 0.023 | 0.36 | 9.10 |
| 127.24 | 0.20 | 0.79 | >10 | 1.80 | 0.027 | 0.32 | 4.70 |
| 127.25 | 0.13 | 0.65 | >10 | 4.40 | 0.031 | 0.34 | 3.30 |
| 127.26 | 0.57 | 2.00 | >10 | 5.20 | 0.150 | 0.23 | 5.90 |
| 127.27 | 0.20 | 1.80 | >10 | 8.70 | 0.026 | 0.79 | 9.60 |
| 127.28 | 0.45 | 5.10 | >10 | 8.40 | 0.160 | 3.50 | >10 |
| 127.29 | 0.24 | 1.80 | >10 | 3.90 | 0.124 | 0.64 | >10 |
| 127.30 | 1.90 | 5.30 | >10 | 7.70 | 0.130 | 1.60 | >10 |
| 127.31 | 0.19 | 1.55 | >10 | 4.87 | 0.067 | 0.45 | 7.95 |
| 127.32 | 1.80 | 4.60 | >10 | >10 | 0.140 | 1.20 | 6.70 |
| 127.33 | 0.74 | >10.00 | >10 | >10 | 0.170 | 8.70 | >10 |
| 127.34 | 1.50 | 5.30 | >10 | 3.00 | 0.180 | 3.20 | >10 |
| 127.35 | 0.33 | 1.10 | >10 | 6.30 | 0.050 | 0.81 | 7.10 |
| 127.36 | 0.19 | 1.90 | >10 | 5.30 | 0.024 | 0.79 | 7.60 |
| 127.37 | 0.65 | 1.40 | >10 | 8.00 | 0.034 | 1.50 | >10 |
| 127.38 | 0.54 | 3.50 | >10 | 6.70 | 0.100 | 2.80 | >10 |
| 127.39 | 1.40 | 2.30 | >10 | >10 | 0.100 | 2.10 | 9.30 |
| 127.40 | 0.77 | 1.50 | >10 | 7.60 | 0.140 | 1.40 | >10 |
| 127.41 | 1.70 | 3.50 | >10 | 4.20 | 0.270 | 6.60 | >10 |
| 127.42 | 1.70 | 5.90 | >10 | 7.10 | 0.800 | >10 | >10 |
| 127.43 | 0.56 | 1.70 | >10 | 2.90 | 0.095 | 3.40 | 8.80 |
| 127.44 | 0.73 | 2.20 | >10 | 6.10 | 0.120 | 1.40 | 3.70 |
| 127.45 | 0.42 | 6.20 | >9.1 | 3.40 | 0.060 | 1.50 | >9.1 |
| 127.46 | 1.30 | >9.10 | >9.1 | 6.90 | 0.073 | 0.72 | >9.1 |
| 127.47 | 1.10 | 2.20 | >10 | 6.60 | 0.060 | 3.20 | >10 |
| 127.48 | 1.20 | 6.20 | >10 | 5.90 | 0.060 | 3.20 | |
| 127.49 | 0.10 | 0.46 | >10 | 4.00 | 0.013 | 0.32 | 7.00 |
| 127.50 | 0.84 | 1.40 | >10 | >10 | 0.032 | 2.10 | 5.60 |
| 127.51 | 0.60 | 1.90 | >10 | 5.30 | 0.065 | 0.58 | 5.90 |
| 127.52 | 0.14 | 0.34 | >10 | 3.10 | 0.009 | 0.33 | 3.60 |
| 127.53 | 0.43 | 1.40 | >10 | 1.70 | 0.025 | 1.40 | 3.90 |
| 127.54 | 0.18 | 1.10 | >10 | 2.60 | 0.032 | 1.10 | 1.80 |
| 127.56 | 0.42 | 1.20 | >10 | >10 | 0.073 | 1.40 | 7.40 |
| 127.57 | 1.40 | 0.73 | >10 | 5.90 | 0.050 | 0.76 | 5.00 |
| 127.58 | 1.30 | 1.30 | >10 | >10 | 0.042 | 0.46 | 1.20 |
| 127.60 | 0.96 | 0.73 | >10 | 3.30 | 0.140 | 2.40 | >10 |
| 128 | 0.15 | 0.50 | >10 | 6.80 | 0.014 | 0.10 | |
| 128.1 | 1.00 | 3.00 | >10 | >10 | | 0.25 | |

TABLE 4-continued

Biochemical assay data

| Example | Assay A PI3Kα IC50 (μM) | Assay B PI3Kβ IC50 (μM) | Assay C VPS34 IC50 (μM) | Assay D PI4Kβ IC50 (μM) | Assay E PI3Kγ IC50 (μM) | Assay F PI3Kδ IC50 (μM) | Assay G mTOR IC50 (μM) |
|---|---|---|---|---|---|---|---|
| 128.2 | 0.27 | 2.90 | >10 | >10 | 0.049 | 0.45 | |
| 128.3a | 0.23 | 1.90 | >10 | >10 | 0.027 | 0.57 | |
| 128.3b | 0.37 | 2.50 | >10 | 4.60 | 0.055 | 0.54 | |
| 128.4 | 0.10 | 1.70 | >10 | >10 | 0.045 | 0.50 | |
| 128.5 | 2.30 | 9.60 | >10 | >10 | 0.370 | 2.20 | |
| 128.6 | 0.19 | 7.70 | >10 | >10 | 0.190 | 0.30 | |
| 128.7 | 0.22 | 1.90 | >10 | >10 | 0.079 | 0.69 | |
| 128.8 | 0.59 | 1.80 | >10 | >10 | 0.021 | 0.10 | |
| 129 | 0.13 | 7.30 | >9.1 | >9.1 | 0.024 | 0.55 | >9.1 |
| 129.1 | 0.19 | 6.30 | >9.1 | 6.50 | 0.023 | 0.25 | 6.30 |
| 129.2 | 0.28 | 4.30 | >9.1 | 7.00 | 0.022 | 1.20 | 6.10 |
| 129.3 | 0.49 | 7.10 | >9.1 | >9.1 | 0.016 | 0.34 | >9.1 |
| 129.4 | 0.19 | >9.10 | >9.1 | >9.1 | 0.069 | 0.43 | 5.00 |
| 129.5 | 0.27 | >9.10 | >9.1 | 5.00 | 0.038 | 0.57 | 6.50 |
| 129.6 | 0.74 | >9.10 | >9.1 | >9.1 | 0.270 | 2.80 | >9.1 |
| 129.7 | 0.90 | >9.10 | >9.1 | >9.1 | 0.270 | 3.30 | 7.80 |
| 129.9 | 0.42 | 6.90 | >9.1 | >9.1 | 0.045 | 0.94 | >9.1 |
| 129.10 | 0.55 | >9.10 | >9.1 | 6.20 | 0.027 | 0.94 | >9.1 |
| 129.11 | 0.64 | >9.10 | >9.1 | >9.1 | 0.173 | 0.79 | >9.1 |
| 129.12 | 1.20 | >9.10 | >9.1 | >9.1 | 0.058 | 0.91 | 8.70 |
| 129.13 | 0.30 | >9.10 | >9.1 | >9.1 | 0.028 | 0.26 | >9.1 |
| 129.14 | 0.21 | 4.50 | >9.1 | >9.1 | 0.059 | 0.48 | 5.70 |
| 129.15 | 1.90 | >9.10 | >9.1 | >9.1 | 0.240 | 2.10 | >9.1 |
| 129.16 | 0.63 | >9.10 | >9.1 | >9.1 | 0.066 | 2.00 | >9.1 |
| 129.17 | 0.35 | 5.50 | >9.1 | >9.1 | 0.056 | 0.42 | >9.1 |
| 129.18 | 0.69 | 8.11 | >9.1 | >9.1 | 0.064 | 0.40 | >9.1 |
| 129.19 | 0.33 | 5.11 | >9.1 | 7.20 | 0.066 | 0.47 | 3.02 |
| 129.20 | 0.32 | 8.50 | >9.1 | >9.1 | 0.110 | 0.29 | >9.1 |
| 129.21 | 2.90 | >9.10 | >9.1 | >9.1 | 0.053 | 1.00 | >9.1 |
| 129.22 | 1.50 | >9.10 | >9.1 | >9.1 | 0.280 | 7.50 | >9.1 |
| 129.23 | 2.80 | 3.30 | >9.1 | >9.1 | 0.380 | 1.90 | >9.1 |
| 129.24 | >9.10 | >9.10 | >9.1 | >9.1 | 0.200 | 6.60 | >9.1 |
| 129.25 | 0.54 | 2.30 | >9.1 | >9.1 | 0.042 | 0.38 | >9.1 |
| 129.26 | 1.60 | 1.70 | >9.1 | >9.1 | 0.590 | 1.60 | >9.1 |
| 129.27 | 9.00 | >9.10 | >9.1 | >9.1 | 0.760 | 2.10 | >9.1 |
| 129.28 | 0.26 | 5.30 | >9.1 | >9.1 | 0.140 | 1.10 | >9.1 |
| 129.29 | 0.69 | 5.40 | >9.1 | >9.1 | 0.140 | 1.20 | 6.00 |
| 129.30 | 5.40 | >9.10 | >9.1 | >9.1 | 0.041 | 1.20 | >9.1 |
| 129.31 | 0.29 | 1.80 | >9.1 | 6.70 | 0.120 | 0.80 | >9.1 |
| 129.32 | 2.00 | 7.00 | >9.1 | >9.1 | 0.039 | 1.80 | >9.1 |
| 129.33 | 2.30 | >9.10 | >9.1 | >9.1 | 0.260 | 2.00 | >9.1 |
| 129.34 | 0.70 | >9.10 | >9.1 | >9.1 | 0.110 | 1.20 | >9.1 |
| 129.35 | 2.10 | >9.10 | >9.1 | >9.1 | 0.089 | 1.20 | >9.1 |
| 129.36 | 1.30 | 6.90 | >9.1 | >9.1 | 0.110 | 0.96 | >9.1 |
| 129.37 | 1.30 | >9.10 | >9.1 | 8.30 | 0.540 | 2.80 | >9.1 |
| 129.38 | 1.60 | 2.70 | >9.1 | >9.1 | 0.820 | 4.50 | >9.1 |
| 129.39 | 0.73 | 7.50 | >9.1 | >9.1 | 0.110 | 0.91 | >9.1 |
| 129.40 | 0.67 | 6.40 | >9.1 | >9.1 | 1.100 | 4.00 | >9.1 |
| 129.41 | 1.60 | 4.00 | >9.1 | >9.1 | 0.320 | 2.30 | >9.1 |
| 129.42 | 2.00 | 6.60 | >9.1 | >9.1 | 0.150 | 1.70 | >9.1 |
| 129.43 | 3.00 | 5.70 | >9.1 | >9.1 | 1.000 | 2.30 | >9.1 |
| 130 | 0.15 | 2.83 | >9.1 | 7.01 | 0.012 | 0.18 | 5.11 |
| 131 | 0.37 | 2.45 | 4.30 | 4.95 | 0.042 | 0.76 | 3.70 |
| 132 | 0.18 | >9.10 | >9.1 | 2.26 | 0.017 | 0.05 | >9.1 |
| 133 | 1.02 | 7.80 | >9.55 | 8.90 | 0.110 | 1.14 | >9.55 |
| 134 | 0.40 | 4.33 | >9.1 | 7.17 | 0.055 | 0.35 | >9.1 |
| 135 | 0.18 | 5.22 | >9.55 | 4.16 | 0.051 | 1.70 | 4.37 |
| 136 | 0.44 | >9.10 | >9.1 | >9.1 | 0.012 | 0.13 | >9.1 |
| 137 | 1.74 | >9.10 | >9.1 | >9.1 | 0.058 | 0.33 | 0.95 |
| 138 | 2.70 | >9.10 | >9.1 | 8.54 | 0.004 | 0.86 | >9.1 |
| 139 | 0.54 | 8.39 | >9.1 | >9.1 | 0.016 | 0.16 | 8.30 |
| 140 | 0.24 | 7.16 | >9.1 | >9.1 | 0.016 | 0.09 | 8.82 |
| 141 | 1.77 | >9.10 | >9.1 | >9.1 | 0.054 | 0.34 | >9.1 |
| 142 | 1.00 | 6.00 | >10 | >10 | 0.270 | 1.00 | |
| 143 | 0.2 | >9.10 | >9.1 | >9.1 | 0.012 | 0.292 | 2.19 |

Compound 3-(5-amino-6-(2-isopropoxypyridin-3-yl)pyrazin-2-yl)-N-(3-hydroxy-3-methylbutyl)-4-methylbenzenesulfonamide (Reference example 119.12) has not shown any activity in assay E.

The cellular assay data and whole blood shape change functional assay data for examples 1-143 is provided in the following table:

TABLE 5

Cellular data in isoform-specific assays (Assays H, I, J, K1, K2), whole blood neutrophil shape change data (WBSC, Assay L) and intrinsic clearance data in rat liver microsomes (RLM, Assay M).

| Ex. | Assay H PI3Kα IC50 (µM) | Assay I PI3Kβ IC50 (µM) | Assay J PI3Kδ IC50 (µM) | Assay K1 PI3Kγ IC50 (µM) | Assay K2 PI3Kγ IC50 (µM) | Assay L WBSC IC50 (µM) | Assay M RLM Cl(int) (µL · min$^{-1}$ · mg$^{-1}$) |
|---|---|---|---|---|---|---|---|
| 1 | 9.36 | >10 | 7.42 | 0.504 | | 0.803 | <3.4 |
| 2 | 3.18 | >10 | 1.07 | 0.147 | | 0.687 | 25 |
| 3 | 1.04 | 8.33 | 1.17 | 0.394 | | 1.107 | |
| 4 | 2.55 | 4.46 | 0.91 | 0.038 | | 0.675 | 27 |
| 5 | >10 | >10 | 3.45 | 0.078 | 0.261 | 0.696 | 26 |
| 6 | 4.38 | 7.28 | 4.14 | 0.366 | 0.215 | 0.47 | 14 |
| 7 | 0.84 | 3.46 | 0.38 | 0.029 | | 0.188 | 48 |
| 8 | 0.75 | 6.03 | 0.37 | 0.021 | | 0.169 | 50 |
| 9a | >10 | >10 | 3.53 | 0.04 | | 0.327 | 34 |
| 9b | >10 | >10 | 7.64 | | | 0.335 | 27 |
| 10 | 0.73 | 6.31 | 0.6 | 0.025 | | 0.045 | 44 |
| 11 | 2.57 | 6.91 | 3.52 | 0.057 | | 0.157 | 78 |
| 12 | 4.7 | >10 | 3.41 | 0.117 | | 0.2 | |
| 13 | >10 | >10 | 1.57 | 0.062 | | 0.211 | 9 |
| 14 | 1 | 1.79 | 0.31 | 0.008 | | 0.044 | 39 |
| 15 | 1.93 | 2.01 | 1.45 | 0.061 | | 0.166 | 24 |
| 16 | 0.9 | 1.86 | 0.62 | 0.043 | | 0.154 | 47 |
| 17 | 2.8 | 8.25 | 1.92 | 0.051 | | 0.166 | 34 |
| 18 | 1.69 | 2.6 | 0.79 | 0.145 | 0.207 | 0.568 | 29 |
| 19 | 0.09 | 0.28 | 0.07 | 0.009 | 0.076 | 0.21 | 65 |
| 20a | 0.72 | 1.43 | 0.42 | 0.011 | 0.023 | 0.232 | 55 |
| 20b | 0.66 | 1.73 | 0.61 | 0.014 | 0.024 | 0.106 | 30 |
| 21 | 0.51 | 0.59 | 0.46 | 0.018 | 0.09 | 0.244 | 109 |
| 22 | 6.67 | >10 | 4.69 | 0.164 | 0.1 | 0.256 | 47 |
| 23 | 3.01 | 6.46 | 1.01 | 0.106 | | 0.447 | |
| 24 | 1.06 | 6.25 | 0.66 | 0.053 | | 0.561 | 43 |
| 25 | 2.19 | 1.7 | 1.39 | 0.153 | 2.335 | 0.742 | 71 |
| 26 | 1.1 | 2.03 | 0.76 | 0.054 | | 0.683 | 223 |
| 27 | >10 | >10 | 1.02 | 0.058 | | 0.562 | 60 |
| 28 | | | | 0.28 | | 0.759 | 34 |
| 29 | 4.63 | 8.08 | 6.61 | 0.206 | 0.314 | 0.956 | 62 |
| 30 | 3.81 | 1.65 | 0.48 | 0.098 | | 0.407 | 116 |
| 31 | 1.04 | 2.51 | 1.03 | 0.04 | | 0.917 | 37 |
| 32 | | | | 0.387 | | 0.668 | 28 |
| 33 | | | | 1.976 | 0.622 | 0.742 | 12 |
| 34 | | | | 0.137 | | 0.805 | 52 |
| 35 | >10 | >10 | >10 | 0.418 | | 0.669 | 25 |
| 36 | | | | 0.051 | | 0.478 | 710 |
| 37 | 7.91 | 1.89 | 5.92 | | | 1.548 | 33 |
| 38 | 3.02 | 2.11 | 2.36 | | | 3.375 | 89 |
| 39 | | | | 0.192 | 0.999 | | 88 |
| 40 | | | | 0.04 | | | 92 |
| 41 | >3 | 0.98 | <0.003 | 0.039 | 0.024 | | 314 |
| 42 | 0.13 | 0.79 | 0.16 | 0.014 | 0.018 | | 160 |
| 43 | 1.39 | >10 | 1.19 | 0.015 | | | 55 |
| 43a | 2.14* | 4.56* | 0.97* | | 0.068 | 0.992 | 63 |
| 43b | 5.44* | 2.95* | 2.18* | | 0.18 | | 45 |
| 44 | 7.04 | >10 | >10 | 0.022 | 0.059 | 0.413 | 37 |
| 45 | | | | | 0.089 | | 83 |
| 45.1 | | | | | | 0.306 | 70 |
| 45.2 | | | | | | | 194 |
| 45.3 | | | | | 0.494 | | 78 |
| 45.4 | 1.23* | 2.13* | 0.58* | | | | 502 |
| 45.5 | | | | | | | 147 |
| 45.6a | 0.82* | 1.56* | 0.27* | | | | 228 |
| 45.6b | 1.76* | 1.2* | 0.96* | | | | 237 |
| 45.7a | 1.05* | 2.20* | 0.55* | | | | 151 |
| 45.7b | 0.31* | 1.32* | 0.37* | | 0.001 | | 135 |
| 45.8 | | | | | 0.317 | | 67 |
| 45.9 | 0.35* | 0.88* | 0.28* | | 0.033 | | 83 |
| 45.10 | | | | | 0.03 | 0.662 | 32 |
| 45.11 | | | | 0.012 | 0.026 | 0.079 | 43 |
| 46 | | | | 0.145 | 0.331 | 0.73 | 24 |
| 46.1 | | | | | | | 16 |
| 46.2 | | | | | | 0.597 | 49 |
| 47 | | | | | | 3.138 | 140 |

TABLE 5-continued

Cellular data in isoform-specific assays (Assays H, I, J, K1, K2), whole blood
neutrophil shape change data (WBSC, Assay L) and intrinsic clearance
data in rat liver microsomes (RLM, Assay M).

| Ex. | Assay H PI3Kα IC50 (μM) | Assay I PI3Kβ IC50 (μM) | Assay J PI3Kδ IC50 (μM) | Assay K1 PI3Kγ IC50 (μM) | Assay K2 PI3Kγ IC50 (μM) | Assay L WBSC IC50 (μM) | Assay M RLM Cl(int) (μL · min$^{-1}$ · mg$^{-1}$) |
|---|---|---|---|---|---|---|---|
| 48 | | | | 0.487 | | 1.526 | 59 |
| 49 | | | | | | 0.856 | 20 |
| 50 | | | | | | | 28 |
| 51 | 6.17 | 6.6 | 3.95 | 0.068 | | | 55 |
| 52a | | | | | | 0.806 | 60 |
| 52b | | | | 0.06 | 0.337 | 0.55 | 43 |
| 53 | >10 | >10 | >10 | | | | 29 |
| 54 | 1.69 | 7.41 | 2.03 | 0.14 | | 2.011 | 141 |
| 55 | 1.04 | 2.67 | 1.24 | 0.065 | | 0.893 | 237 |
| 56 | 4.4 | 5.88 | 3.12 | 0.129 | | 0.211 | 24 |
| 57 | >10 | >10 | >10 | 0.329 | | 1.269 | 17 |
| 58 | 8.58 | 6.13 | 2.46 | 0.073 | | 0.385 | 14 |
| 59 | 8.47 | >10 | 6.42 | | | 0.801 | |
| 60 | 1.54 | 3.08 | 1.3 | 0.093 | | | 24 |
| 61 | 8.97 | >10 | 8.18 | 0.479 | | | 56 |
| 62 | 1.44 | >10 | 0.97 | 0.11 | | 7.906 | 155 |
| 63 | 2.97 | >10 | 3.25 | 0.163 | | 0.626 | 44 |
| 64 | 1.24 | 4.37 | 1.19 | 0.189 | | 0.543 | 61 |
| 65 | 1.45 | >10 | 1.44 | 0.155 | | 0.802 | 87 |
| 66 | 0.99 | 5.92 | 0.73 | 0.109 | | | 311 |
| 67 | 1.33 | 2.93 | 0.92 | 0.068 | | 0.249 | 36 |
| 68 | 2.84 | 6.25 | 3.11 | 0.43 | | 1.791 | 54 |
| 69a | 3.3 | 4.42 | 2.66 | 0.103 | | 1.153 | 49 |
| 69b | 6.68 | 8.47 | 5.18 | 0.135 | | 1.952 | 227 |
| 70a | 1.92 | 2.64 | 1.41 | | | 0.185 | 58 |
| 70b | 4.06 | >10 | 3.98 | | | 0.687 | 57 |
| 71a | 3.06 | 8.02 | 3.65 | | | 0.763 | 18 |
| 71b | 6.91 | >10 | 5.86 | | | 1.622 | 26 |
| 72 | 3.11 | 6.03 | 2.64 | 0.293 | | 0.723 | 41 |
| 73 | 2.26 | 5.38 | 2 | 0.177 | | 0.803 | 64 |
| 74 | >10 | >10 | 6.86 | | | | 30 |
| 75 | >10 | >10 | 7.8 | 0.091 | | 0.83 | 13 |
| 76 | 3.37 | >10 | 3.52 | 0.203 | | | 48 |
| 77 | | | | 0.134 | | 0.881 | 45 |
| 78 | | | | 0.066 | | | 152 |
| 79 | | | | 0.053 | | 3.212 | 63 |
| 80 | | | | 0.098 | | 2.879 | 106 |
| 81 | >10 | >10 | 4.04 | | | | 29 |
| 82 | 0.86 | 2.98 | 0.61 | | | 0.825 | 25 |
| 83 | >10 | 8.75 | 4.05 | | | | 45 |
| 84 | 0.45 | >3 | 0.44 | | | 1.01 | 64 |
| 85 | | | | 0.041 | 0.065 | 0.497 | 73 |
| 86 | | | | | | | 62 |
| 87 | 1.34 | 3.4 | 1.22 | 0.018 | | 0.447 | 61 |
| 88 | | | | 0.152 | | 1.641 | 27 |
| 89 | | | | | | 3.699 | 46 |
| 90 | | | | | | | 19 |
| 91 | | | | | | | 46 |
| 92 | | | | | | 1.158 | 64 |
| 94 | 2.98 | 8.96 | 2.09 | | | 3.781 | |
| 95 | | | | 0.262 | | 1.589 | 53 |
| 96 | | | | 0.276 | | | 62 |
| 97 | | | | | | 2.146 | 60 |
| 98 | | | | 0.2 | | 4.172 | 31 |
| 99 | | | | 0.059 | | 3.518 | 74 |
| 100 | | | | 0.074 | | | 95 |
| 101 | | | | | | | 39 |
| 102 | 4.53 | 5.3 | 1.33 | | 0.211 | | 75 |
| 103 | 2.25 | 3.25 | 0.85 | 0.028 | | 0.515 | 29 |
| 106 | >10 | >10 | >10 | 2.276 | | | 29 |
| 107 | 0.79 | 1.29 | 0.96 | | | | 119 |
| 108 | 5.78 | 3.01 | 0.41 | 0.058 | 0.163 | 5.563 | 112 |
| 109 | 2.61 | >10 | 1.9 | | | 0.935 | <3.4 |
| 110 | 0.48 | 1.73 | 0.69 | | | | 254 |
| 111 | 1.47 | >10 | 0.46 | 0.02 | | 0.637 | 74 |
| 112 | 0.79 | 1.14 | 0.31 | 0.095 | 0.172 | 0.586 | 62 |
| 112.1 | 0.8 | 1.47 | 0.38 | 0.091 | 0.063 | 1.326 | |
| 112.2 | | >10 | >10 | 0.137 | | | |
| 112.3 | 0.4 | >3 | 0.86 | | | | 123 |
| 112.4 | 0.07 | >3 | 0.4 | | | | |
| 112.5 | 0.13 | >10 | 0.83 | 0.036 | | 0.97 | 40 |

TABLE 5-continued

Cellular data in isoform-specific assays (Assays H, I, J, K1, K2), whole blood neutrophil shape change data (WBSC, Assay L) and intrinsic clearance data in rat liver microsomes (RLM, Assay M).

| Ex. | Assay H PI3Kα IC50 (μM) | Assay I PI3Kβ IC50 (μM) | Assay J PI3Kδ IC50 (μM) | Assay K1 PI3Kγ IC50 (μM) | Assay K2 PI3Kγ IC50 (μM) | Assay L WBSC IC50 (μM) | Assay M RLM Cl(int) (μL·min⁻¹·mg⁻¹) |
|---|---|---|---|---|---|---|---|
| 113 | 1.08 | 3.57 | 1.08 | 0.055 | 0.024 | 0.143 | 39 |
| 114 | 5.43 | >3 | 7.99 | 0.177 | | 0.499 | 17 |
| 115 | 2.98 | 3.53 | 2.21 | 0.117 | | 1.109 | 38 |
| 116 | 2.31 | 4.75 | 2.12 | 0.197 | | | 35 |
| 117 | >10 | >3 | >10 | 0.577 | 0.945 | 0.727 | 85 |
| 118 | 0.63 | 1.59 | 0.53 | 0.102 | | 0.898 | 264 |
| 119 | 1.64 | 3.06 | 1.76 | | | | |
| 119.1 | 2.69 | 3.81 | 2.82 | | | | |
| 119.2 | 2.74 | 4.07 | 2.38 | 0.333 | | 2.184 | 101 |
| 119.3 | 0.49 | 1.77 | 0.87 | 3.641 | | | 81 |
| 119.4 | >10 | >10 | >10 | | | | |
| 119.5 | 4.9 | 1.66 | 4.85 | 0.575 | | | 118 |
| 119.6 | 4.07 | 1.72 | 2.88 | 0.86 | | | |
| 119.7 | 6.97 | 4.05 | 5.93 | | | | |
| 119.8 | 3.85 | 4.64 | 5.2 | | | | |
| 119.9 | 1.92 | 3.07 | 4.23 | | | | |
| 119.1 | 0.63 | 2.59 | 1.04 | 0.172 | | | |
| 119.11 | 2.54 | 3.56 | 6.94 | | | | |
| 119.12 | >10 | >10 | >10 | | | | |
| 119.13 | 2.45 | 6.75 | 3.26 | >10 | | | 98 |
| 119.14 | 3.14 | 4.39 | 4.96 | | | | |
| 119.15 | 1.48 | 7.33 | 1.65 | | | | |
| 119.16 | 4.01 | 3.7 | 2.35 | 0.081 | | 1.244 | 21 |
| 119.17 | 2.81 | 6.17 | 7.16 | | | | |
| 119.18 | 1.32 | 4.48 | 1.3 | | | | |
| 119.19 | >10 | >10 | >10 | | | | |
| 119.2 | 4.95 | 4.86 | 7.03 | | | | |
| 119.21 | 5.16 | >10 | 7.48 | | | | |
| 119.22 | 4.41 | >10 | >10 | | | | |
| 119.23 | 1.97 | 8.49 | 3.53 | | | | |
| 119.24 | 2.6 | 9.22 | 3.17 | | | | |
| 119.25 | 1.28 | 4.1 | 1.2 | 0.065 | | 2.092 | |
| 119.26 | 0.7 | 1.8 | 0.51 | | | | 380 |
| 119.27 | 0.47 | 9.24 | 0.91 | 0.128 | | 0.726 | 87 |
| 119.28 | 1.25 | >10 | 2.15 | 0.179 | | 0.963 | 44 |
| 119.29 | 0.58 | 9.08 | 0.47 | 0.057 | | 1.464 | 68 |
| 119.3 | 0.69 | 6.99 | 0.63 | 0.042 | | 1.145 | 77 |
| 119.31 | 2.83 | 6.99 | 1.24 | 0.046 | | 1.664 | 79 |
| 119.32 | 1.68 | 6.04 | 0.79 | | | | 191 |
| 119.33 | 5.51 | >10 | 3.59 | 0.73 | | 0.601 | 50 |
| 119.34 | 2.27 | 7.42 | 1.27 | 0.041 | | 1.491 | 49 |
| 119.35 | | | | 0.018 | | 1.017 | 78 |
| 119.36 | | | | 1.283 | | | 48 |
| 119.37 | 3.02 | 2.87 | 1.14 | 0.093 | | 0.581 | 78 |
| 119.38 | 6.57 | 2.21 | 1.03 | 0.034 | | | 167 |
| 119.39 | 5.04 | 2.15 | 1.61 | 0.034 | | | 203 |
| 119.4 | 1.1 | 8.16 | 1.04 | | 0.047 | | 56 |
| 119.41 | >10 | 3.2 | 6.49 | 0.091 | | | 73 |
| 119.42 | | | | 0.2 | | 2.238 | 41 |
| 119.43 | | | | 0.06 | | | 136 |
| 119.44 | | | | 0.042 | | 7.078 | 137 |
| 119.45 | | | | 0.085 | | | 188 |
| 119.46 | | | | 0.081 | | 9.194 | 122 |
| 120 | | | | | | | 95 |
| 121 | | | | | | | 31 |
| 122 | 2.28 | 1.49 | 1.19 | 0.151 | 0.296 | 0.988 | 26 |
| 123 | >10 | >10 | 3.63 | | | 85.09 | 62 |
| 124 | 0.25 | 0.81 | 0.29 | 0.038 | | | 79 |
| 125 | 2.81 | 3.47 | 0.23 | 0.051 | | 0.879 | 8 |
| 126 | 4* | >10* | 4.24* | | | | 20 |
| 127 | | | | | | 1.496 | |
| 127.1 | 1.57 | >10 | 1.14 | | | 2.471 | 907 |
| 127.2 | | | | | 0.084 | 3.565 | 375 |
| 127.3 | | | | 0.371 | | | |
| 127.4 | | | | 1.968 | 1.491 | | 85 |
| 127.5 | | | | | 0.419 | 9.682 | 72 |
| 127.7 | | | | | | 3.986 | |
| 127.12 | 6.56 | 1.54 | 0.8 | 0.359 | | 1.21 | 233 |
| 127.13 | | | | 0.21 | | | |
| 127.14 | | | | 0.645 | | 1.793 | |
| 127.16 | | | | | | 1.725 | |

TABLE 5-continued

Cellular data in isoform-specific assays (Assays H, I, J, K1, K2), whole blood neutrophil shape change data (WBSC, Assay L) and intrinsic clearance data in rat liver microsomes (RLM, Assay M).

| Ex. | Assay H PI3Kα IC50 (μM) | Assay I PI3Kβ IC50 (μM) | Assay J PI3Kδ IC50 (μM) | Assay K1 PI3Kγ IC50 (μM) | Assay K2 PI3Kγ IC50 (μM) | Assay L WBSC IC50 (μM) | Assay M RLM Cl(int) (μL · min$^{-1}$ · mg$^{-1}$) |
|---|---|---|---|---|---|---|---|
| 127.17 | | | | 0.392 | | | |
| 127.19 | | | | 0.153 | | 1.618 | |
| 127.2 | | | | 0.85 | | | |
| 127.21 | | | | 0.32 | | | |
| 127.22 | | | | 0.156 | | | |
| 127.23 | | | | 0.082 | | | |
| 127.24 | | | | 0.168 | | | |
| 127.25 | | | | 0.066 | | | 493 |
| 127.26 | | | | | | 1.79 | |
| 127.27 | | | | 0.242 | | 1.087 | |
| 127.28 | | | | 0.29 | | | |
| 127.29 | | | | 0.131 | | | |
| 127.31 | 0.85 | 1.71 | 1.05 | 0.103 | | | 192 |
| 127.32 | | | | 1.878 | | | |
| 127.33 | | | | | | | 560 |
| 127.34 | | | | | | | 641 |
| 127.35 | >10 | 2.05 | >10 | 0.085 | 0.391 | 0.847 | 202 |
| 127.36 | | | | 0.126 | | 3.849 | |
| 127.37 | | | | 0.23 | 0.408 | 6.223 | |
| 127.39 | | | | | | 6.285 | |
| 127.4 | | | | 0.411 | | | |
| 127.43 | | | | 0.275 | | 1.64 | |
| 127.45 | 6.11 | 9.05 | 7.27 | | 0.323 | 2.645 | 26 |
| 127.46 | | | | 0.708 | 0.546 | 3.766 | 34 |
| 127.47 | | | | 0.266 | | 2.185 | |
| 127.48 | | | | | | 2.489 | |
| 127.5 | | | | 0.179 | | 1.074 | |
| 127.52 | 0.97 | 6.28 | 1.1 | 0.052 | | 1.772 | >924 |
| 127.53 | 0.65 | >3 | 6.51 | 0.172 | 0.198 | 1.865 | 129 |
| 127.54 | | | | | | >100 | |
| 127.56 | 9.61 | 3.56 | 6 | | | 0.715 | 25 |
| 127.57 | >10 | >10 | >10 | | | 13.765 | 21 |
| 127.58 | | | | | | 23.59 | |
| 127.6 | | | | | | | 20 |
| 128 | >10 | 9.91 | >10 | 0.209 | 0.201 | 2.987 | 22 |
| 128.1 | >10 | >10 | 1.64 | | 0.332 | | |
| 128.2 | 1.91 | >10 | 1.57 | 0.09 | | | 27 |
| 128.3a | 5.15 | >10 | 2.1 | | 0.241 | | |
| 128.3b | 4.97 | >10 | 3.82 | | | | |
| 128.4 | 1.51 | 1.55 | 0.78 | 0.104 | 0.28 | | 134 |
| 128.5 | >10 | >10 | >10 | | | | |
| 128.6 | >10 | >10 | >10 | | 0.193 | 2.175 | 20 |
| 128.7 | >10 | >10 | >10 | 0.249 | 0.117 | 0.826 | 20 |
| 128.8 | >3 | >10 | >10 | 0.751 | 0.421 | 1.671 | <3.4 |
| 129 | | | | | | | 28 |
| 129.1 | | | | | | 0.721 | |
| 129.2 | | | | | | 2.418 | 130 |
| 129.3 | 7.6 | >10 | 6.84 | | | | 139 |
| 129.5 | | | | | | 1.167 | 79 |
| 129.9 | | | | | | | 20 |
| 129.1 | | | | | | 1.607 | 78 |
| 129.11 | 2.73 | 8.38 | 3.33 | | | 5.682 | 105 |
| 129.12 | 4.29 | >10 | 4.97 | 0.804 | 1.602 | | 99 |
| 129.13 | 3 | >10 | 5.86 | 0.144 | | | 170 |
| 129.14 | 2.96 | 5.15 | 2.96 | | | | 347 |
| 129.17 | 2.5 | 3.72 | 1.94 | 0.354 | | | 104 |
| 129.18 | 4.92 | >10 | 5.63 | 0.528 | | | 97 |
| 129.19 | 8.58 | >10 | 4.37 | 0.251 | | 3.428 | 21 |
| 129.21 | | | | | | 8.953 | |
| 129.24 | | | | | | | 755 |
| 129.25 | | | | | | 2.954 | |
| 129.28 | | | | | | | 159 |
| 129.29 | | | | | | | >924 |
| 129.3 | >10 | >10 | >10 | >10 | | | |
| 129.32 | >10 | >10 | >10 | 0.8 | | 1.996 | 18 |
| 129.35 | | | | | >10 | | |
| 129.36 | >10 | >3 | | 6.208 | >10 | | 15 |
| 129.39 | | | | | | | >924 |
| 129.41 | | | | | | | 13 |
| 130 | 1.63 | 4.52 | 1.2 | 0.065 | | 0.735 | 62 |
| 131 | | | | 0.493 | | | 42 |

TABLE 5-continued

Cellular data in isoform-specific assays (Assays H, I, J, K1, K2), whole blood neutrophil shape change data (WBSC, Assay L) and intrinsic clearance data in rat liver microsomes (RLM, Assay M).

| Ex. | Assay H PI3Kα IC50 (μM) | Assay I PI3Kβ IC50 (μM) | Assay J PI3Kδ IC50 (μM) | Assay K1 PI3Kγ IC50 (μM) | Assay K2 PI3Kγ IC50 (μM) | Assay L WBSC IC50 (μM) | Assay M RLM Cl(int) (μL · min$^{-1}$ · mg$^{-1}$) |
|---|---|---|---|---|---|---|---|
| 132 | 1.28 | 6.05 | 0.35 | 0.074 | | 0.449 | |
| 133 | | | | | | | 19 |
| 134 | >10 | >10 | >10 | | | | |
| 135 | 7.84 | 8.75 | 9.39 | 0.063 | | 0.359 | 30 |
| 136 | 0.99 | >10 | 1.12 | 0.124 | | 1.298 | |
| 137 | >10 | >10 | 8.58 | | | | 28 |
| 138 | 8.8 | >10 | 3.55 | 0.26 | | 4.83 | 31 |
| 139 | 1.08 | 7.96 | 0.97 | 0.102 | | 0.565 | |
| 140 | 1.11 | 6.38 | 0.84 | 0.051 | | 0.817 | 82 |
| 141 | 4.7 | 8.75 | 5.31 | 0.947 | | | |
| 142 | >10 | >10 | >10 | | | | 34 |
| 143 | 2.35 | 6.03 | 1.01 | 0.129 | | 1.701 | 134 |

For assays H, I and J, non-asterisked data denotes data generated in versions H1, I1, J1 (Surefire format) of these assays and asterisked data denotes data generated in versions H2, I2, J2 (HTRF format) of these assays. Two closely related assay formats were used to generate PI3K gamma isoform cellular activities (IC50s). The table includes all data from both formats (Assays K1 and K2).

The following tables 6 and 7 give data generated in the above assays for compounds disclosed in the prior art.

TABLE 6

| Compound | Assay A PI3Kα | Assay B PI3Kβ | Assay C VPS34 | Assay D PI4Kβ | Assay E PI3Kγ | Assay F PI3Kδ | Assay G mTOR |
|---|---|---|---|---|---|---|---|
| 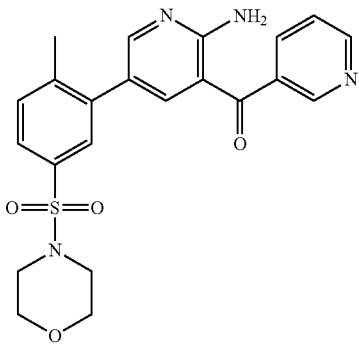 (i) | 0.25 | 1.24 | >9.4 | 3.16 | 0.064 | 0.63 | — |
| 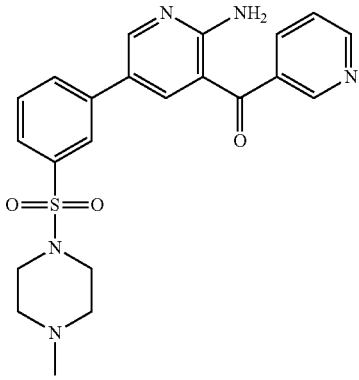 (ii) | 1.50 | 2.00 | >10 | 3.00 | 2.00 | >10 | — |

TABLE 6-continued

| Compound | Assay A PI3Kα | Assay B PI3Kβ | Assay C VPS34 | Assay D PI4Kβ | Assay E PI3Kγ | Assay F PI3Kδ | Assay G mTOR |
|---|---|---|---|---|---|---|---|
| (iii) | 0.02 | 1.70 | 0.70 | 0.30 | 1.200 | 2.30 | — |
| (iv) | 0.49 | 1.27 | 1.76 | 3.76 | 0.060 | 1.50 | — |
| (v) | 0.07 | 0.14 | 0.91 | 0.16 | 0.247 | 1.97 | — |

TABLE 6-continued
| Compound | Assay A PI3Kα | Assay B PI3Kβ | Assay C VPS34 | Assay D PI4Kβ | Assay E PI3Kγ | Assay F PI3Kδ | Assay G mTOR |
|---|---|---|---|---|---|---|---|
| 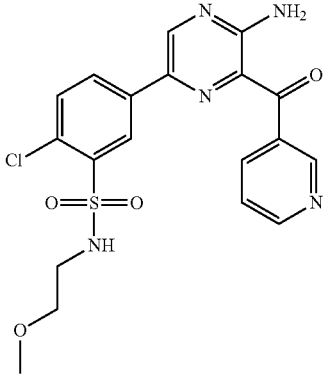 (vi) | 0.09 | 0.19 | 2.38 | 0.61 | 0.034 | 0.45 | — |
| 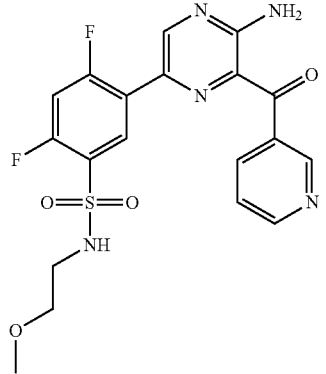 (vii) | — | — | — | — | — | — | — |
| 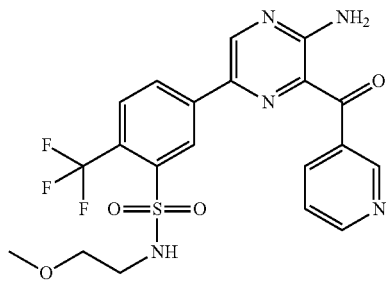 (viii) | 0.06 | 0.46 | — | 0.29 | — | — | — |

TABLE 6-continued

| Compound | Assay A PI3Kα | Assay B PI3Kβ | Assay C VPS34 | Assay D PI4Kβ | Assay E PI3Kγ | Assay F PI3Kδ | Assay G mTOR |
|---|---|---|---|---|---|---|---|
| (ix) | 0.78 | 0.63 | 6.31 | 4.01 | 0.007 | 0.08 | — |
| (x) | 0.46 | 0.70 | 1.80 | 0.54 | 0.110 | 1.40 | 2.50 |
| (xi) | 1.20 | 1.60 | 1.60 | 0.41 | 0.031 | 1.00 | 4.50 |

TABLE 6-continued

| Compound | Assay A PI3Kα | Assay B PI3Kβ | Assay C VPS34 | Assay D PI4Kβ | Assay E PI3Kγ | Assay F PI3Kδ | Assay G mTOR |
|---|---|---|---|---|---|---|---|
| 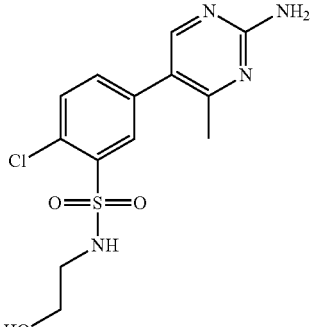 (xii) | 3.32 | 1.19 | — | — | 0.753 | 6.01 | — |

Compounds (i)-(ix) are disclosed in WO09/115517, compounds (x) and (xi) are disclosed in Leahy et al., *J. Med. Chem.*, 2012, 55 (11), pp 5467-5482 and compound (xii) is disclosed in WO09/013348.

TABLE 7

| Compound | Assay H PI3Kα | Assay I PI3Kβ | Assay J PI3Kδ | Assay K1 PI3Kγ | Assay K2 PI3Kγ | Assay L WBSC | Assay M RLM CI (int) |
|---|---|---|---|---|---|---|---|
| (i) | 0.97 | 3.77 | 1.10 | 0.526 | 0.838 | 2.39 | 47 |
| (ii) | >10* | >10* | 0.58* | — | 9.48 | 11.32 | 233 |
| (iii) | — | — | — | — | — | — | 219 |
| (iv) | 0.93 | 3.96 | 1.36 | 0.128 | 0.264 | 2.06 | 465 |
| (v) | 0.18 | 0.23 | 0.15 | — | — | 0.71 | 173 |
| (vi) | 0.17 | 0.26 | 0.17 | 0.182 | — | — | 630 |
| (vii) | — | — | — | — | — | — | 283 |
| (viii) | — | — | — | — | — | — | — |
| (ix) | 0.85 | 2.29 | 1.26 | 0.020 | — | 2.34 | 267 |
| (x) | >10 | >10 | 2.87 | 0.352 | — | >100 | — |
| (xi) | 5.41 | 5.58 | 5.87 | 0.539 | — | >44 | 271 |
| (xii) | >10* | 4.37* | 5.55* | — | — | 15.12 | 9 |

The numbering (i)-(xii) refers to the compounds in Table 6. For assays H, 1 and J, non-asterisked data denotes data generated in versions H1, I1, J1 of these assays and asterisked data denotes data generated in versions H2, I2, J2 of these assays.

The invention claimed is:

1. A compound of formula (I)

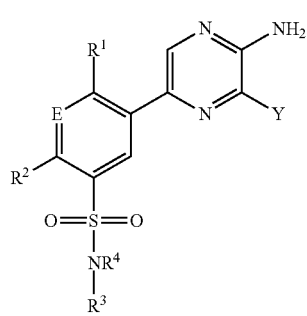

(I)

wherein
E is selected from N and $CR^E$;
$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy, $C_{1-4}$ hydroxyalkyl and $C_{3-7}$ cycloalkyl;
$R^3$ is selected from
(i) $C_{1-4}$ alkyl which is unsubstituted or substituted with 1 or more substituents independently selected from hydroxy, $C_{1-4}$ hydroxyalkyl, halogen, $C_{1-4}$ haloalkyl, $C_{1-4}$ alkoxy, $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;
(ii) $C_{1-4}$ alkoxy which is unsubstituted or substituted with 1 or more substituents independently selected from hydroxy, $C_{1-4}$ hydroxyalkyl, halogen, $C_{1-4}$ haloalkyl, $C_{1-4}$ alkoxy $C_{1-4}$ alkyl, oxo, CN, —($C_{0-3}$ alkyl)-$NR^{3a}R^{3b}$, $C_{3-7}$ cycloalkyl and $C_{3-7}$ heterocyclyl, and wherein the $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iii) —$C_{3-7}$ cycloalkyl or —O—$C_{3-7}$ cycloalkyl wherein the $C_{3-7}$ cycloalkyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(iv) —($C_{0-3}$ alkyl)-$C_{3-7}$ cycloalkyl or —O—($C_{0-3}$ alkyl)-$C_{3-7}$ cycloalkyl wherein the $C_{3-7}$ cycloalkyl is spiro fused to a second $C_{3-7}$ cycloalkyl or $C_{3-7}$ heterocyclyl by one single carbon atom, and wherein the $C_{3-7}$ cycloalkyl or $C_{3-7}$ heterocyclyl is unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

(v) —($C_{0-3}$ alkyl)-$C_{3-7}$ heterocyclyl or —O—($C_{0-3}$ alkyl)-$C_{3-7}$ heterocyclyl, and wherein said $C_{3-7}$ heterocyclyl is unsubstituted or substituted with 1 to 3 substituents independently selected from hydroxy, $C_{1-4}$ hydroxyalkyl, halogen, $C_{1-4}$ alkyl $C_{1-4}$ alkoxy, $C_{1-4}$ haloalkyl, oxo and —($C_{0-3}$ alkyl)-$NR^{3a}R^{3b}$;

(vi) —($C_{0-3}$ alkyl)-$C_{3-7}$ heterocyclyl or —(O—$C_{0-3}$ alkyl)-$C_{3-7}$ heterocyclyl, and wherein said $C_{3-7}$ heterocyclyl is spiro fused to a second $C_{3-7}$ heterocyclyl or a $C_{3-7}$ cycloalkyl by one single carbon atom, and wherein the $C_{3-7}$ heterocyclyl or $C_{3-7}$ cycloalkyl is unsubstituted or substituted with 1 to 3 substituents independently selected from hydroxy, $C_{1-4}$ hydroxyalkyl, halogen, $C_{1-4}$ alkyl $C_{1-4}$ alkoxy, $C_{1-4}$ haloalkyl, oxo and —($C_{0-3}$ alkyl)-$NR^{3a}R^{3b}$; and (vii) H;

$R^4$ is selected from H and $C_{1-4}$ alkyl; or $R^3$ and $R^4$ together with the nitrogen atom to which they are attached form a $C_{3-7}$ heterocyclyl, which $C_{3-7}$ heterocyclyl is optionally spiro fused to a second $C_{3-7}$ heterocyclyl or a $C_{3-7}$ cycloalkyl by one single carbon atom, and which $C_{3-7}$ heterocyclyl and $C_{3-7}$ cycloalkyl are unsubstituted or substituted with 1 to 3 substituents independently selected from hydroxy, $C_{1-4}$ hydroxyalkyl, halogen, $C_{1-4}$ alkyl, $C_{1-4}$ alkoxy, $C_{1-4}$ haloalkyl, oxo and —($C_{0-3}$ alkyl)-$NR^{3a}R^{3b}$;

$R^{3a}$ and $R^{3b}$ are independently selected from H, $C_{1-4}$ alkyl and $C_{1-4}$ haloalkyl; and Y is selected from the group consisting of

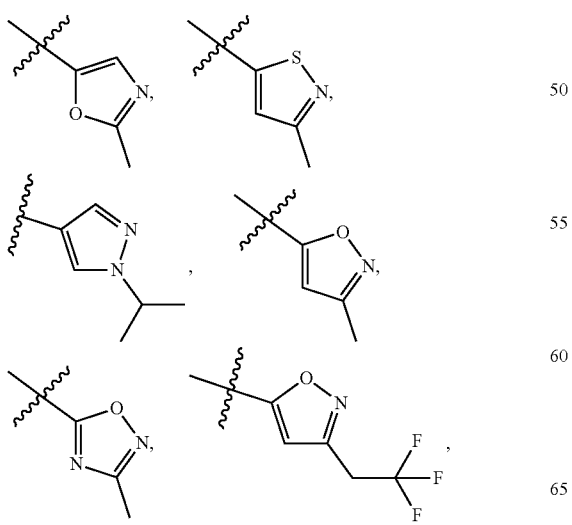

-continued

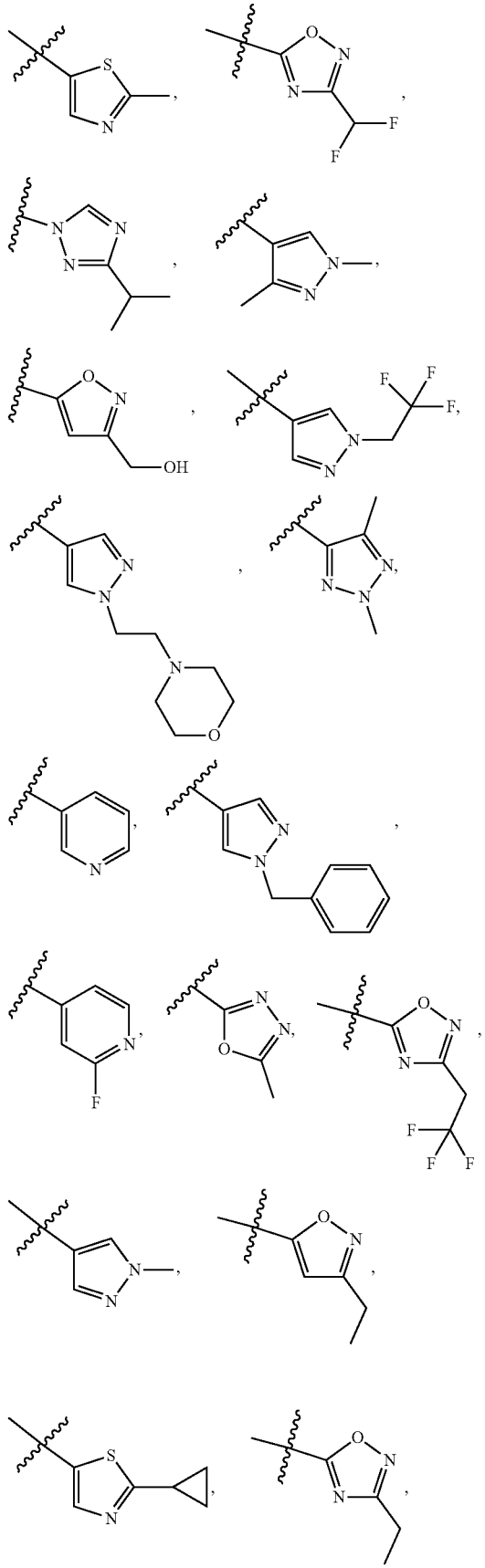

401
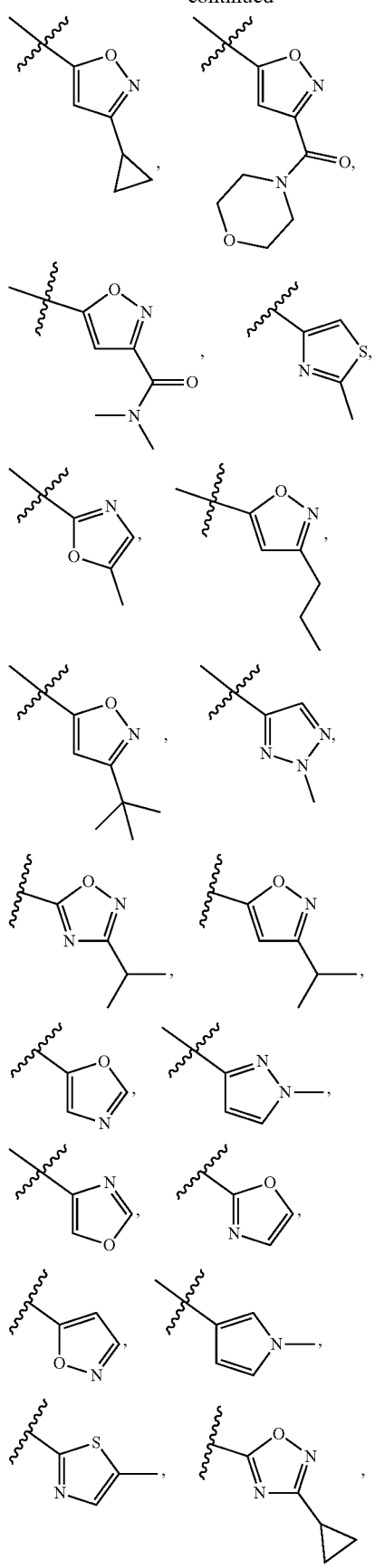
402
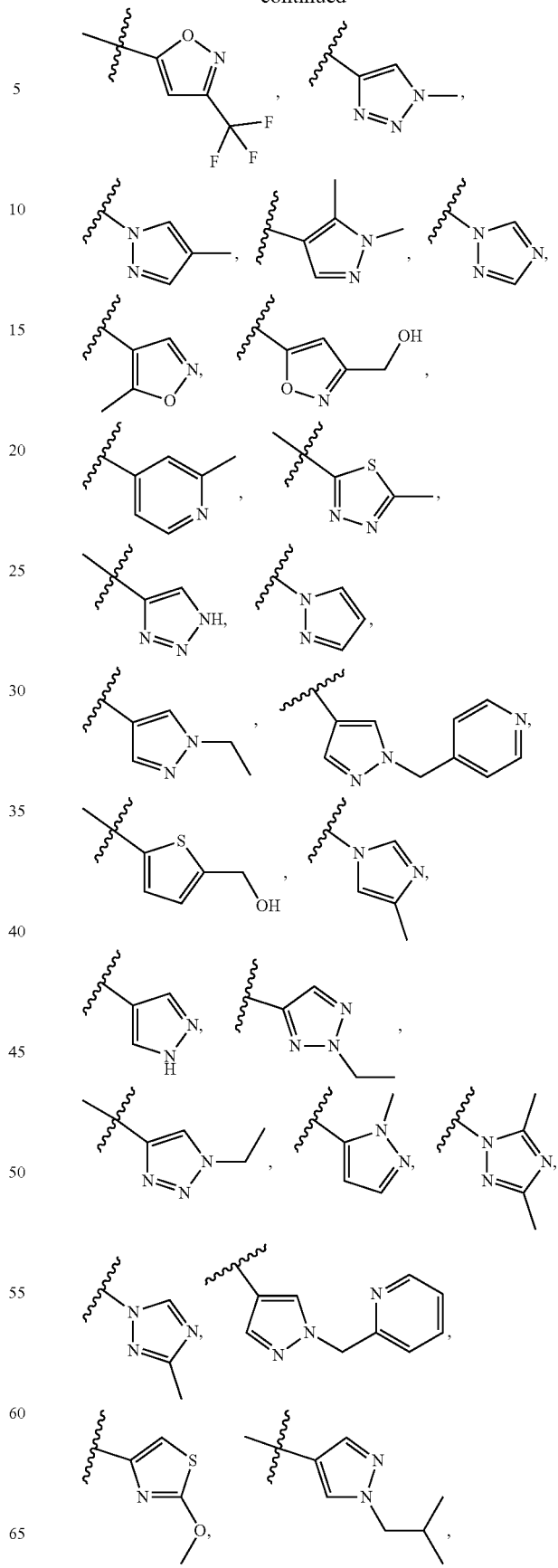

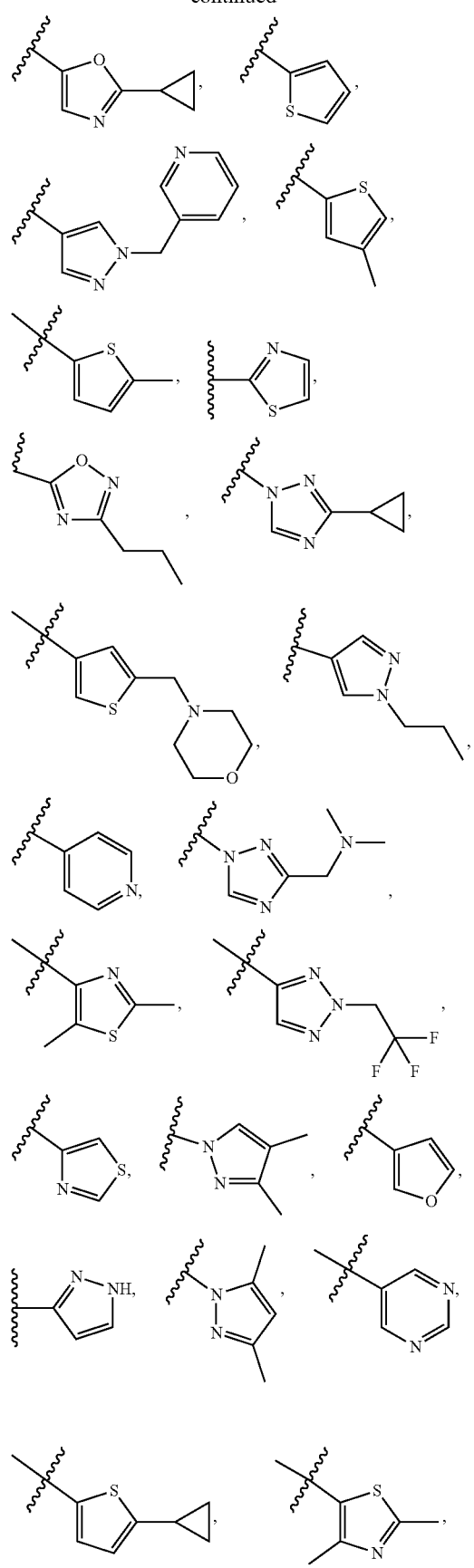
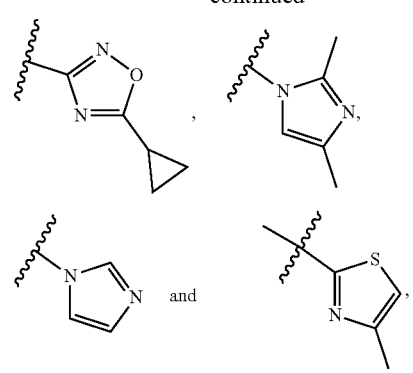
and
or a pharmaceutically acceptable salt thereof.
2. The compound according to claim 1, wherein $R^3$ is selected from
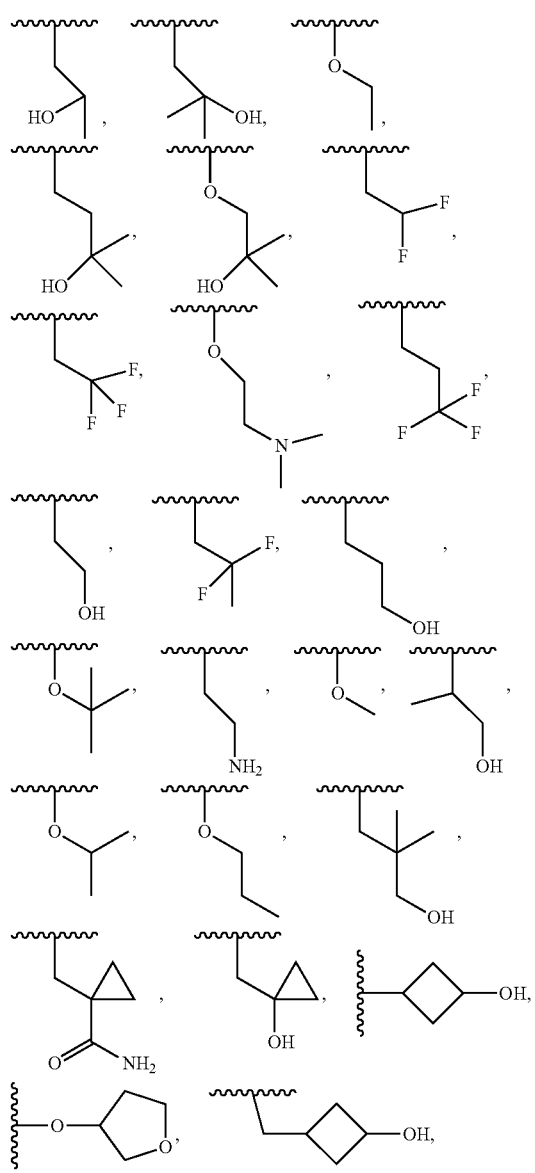

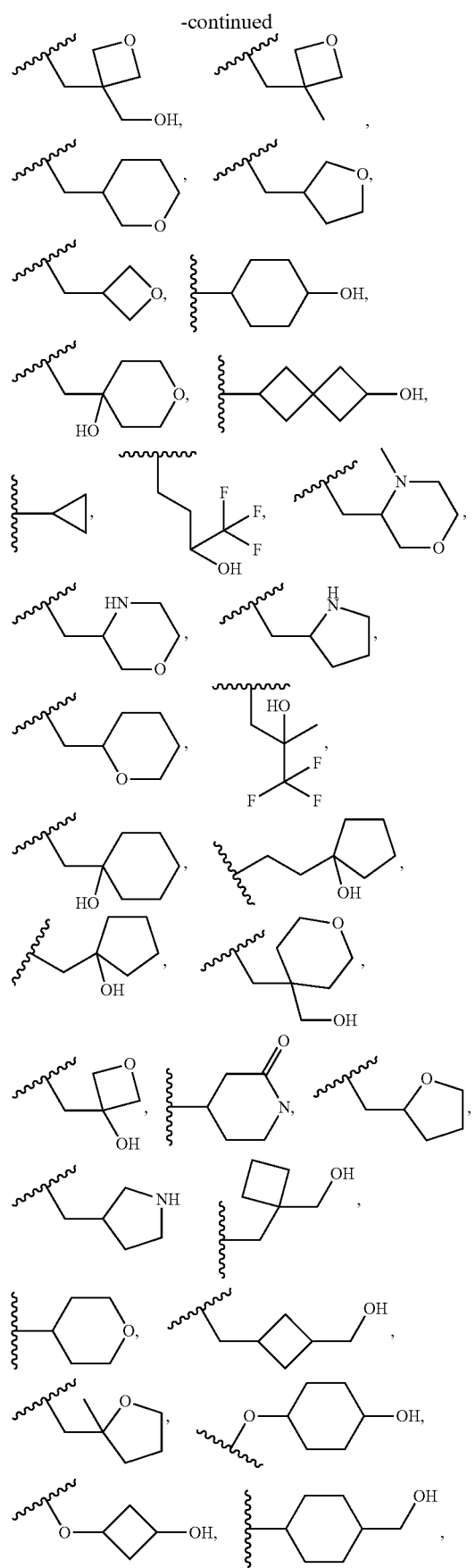
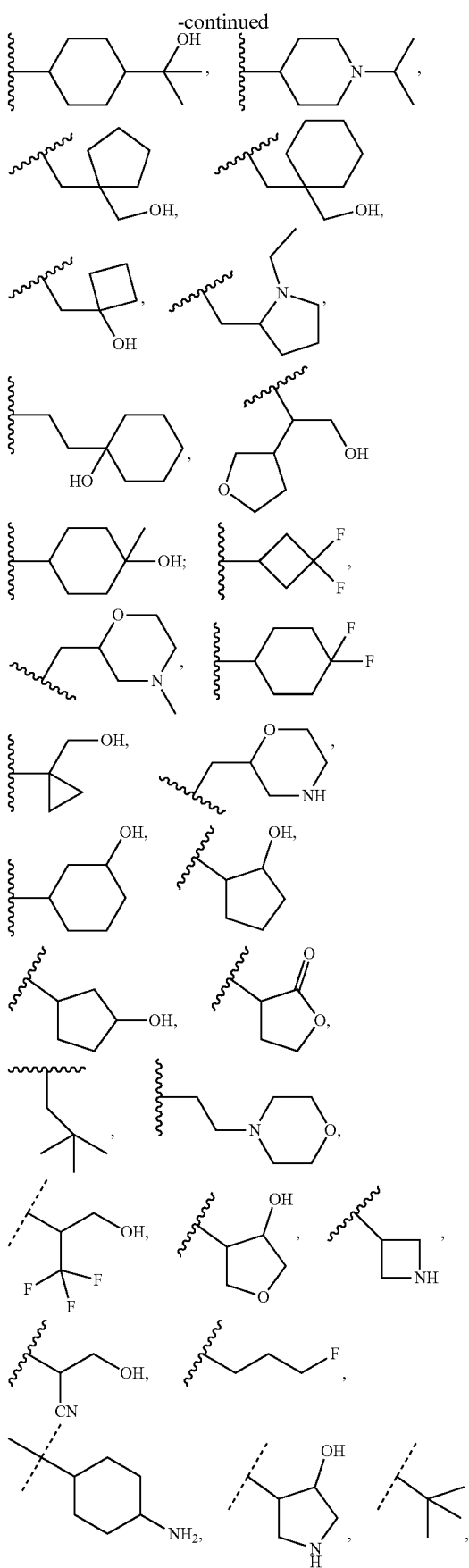

407
-continued

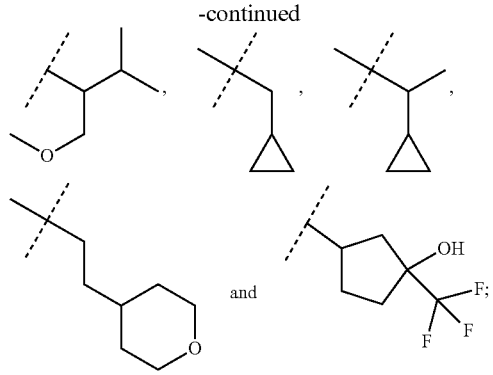

or R³ and R⁴ together with the nitrogen atom to which they are attached form a ring selected from

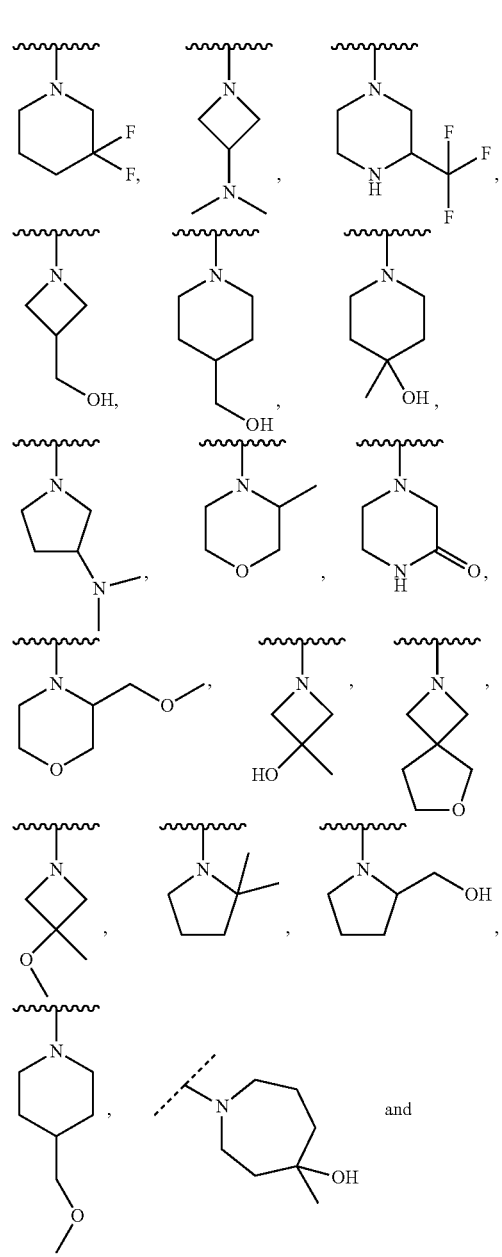

408
-continued

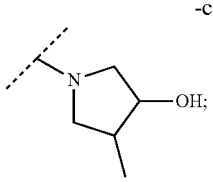

or a pharmaceutically acceptable salt thereof.

3. A compound of formula (I)

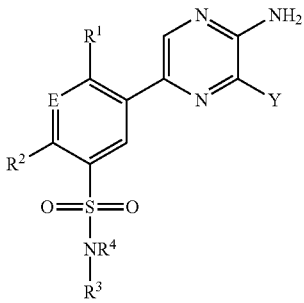

wherein

E is selected from N and $CR^E$;

$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy, $C_{1-4}$ hydroxyalkyl and $C_{3-7}$ cycloalkyl;

Y is selected from the group consisting of

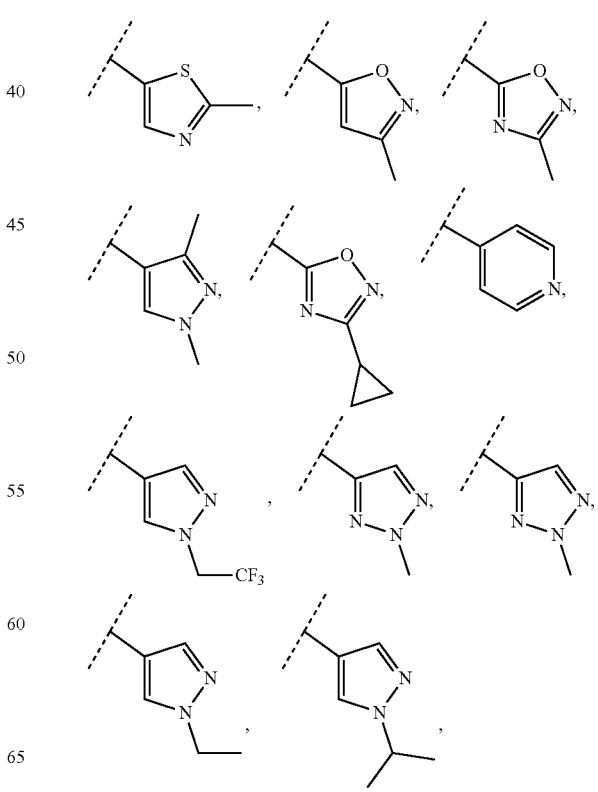

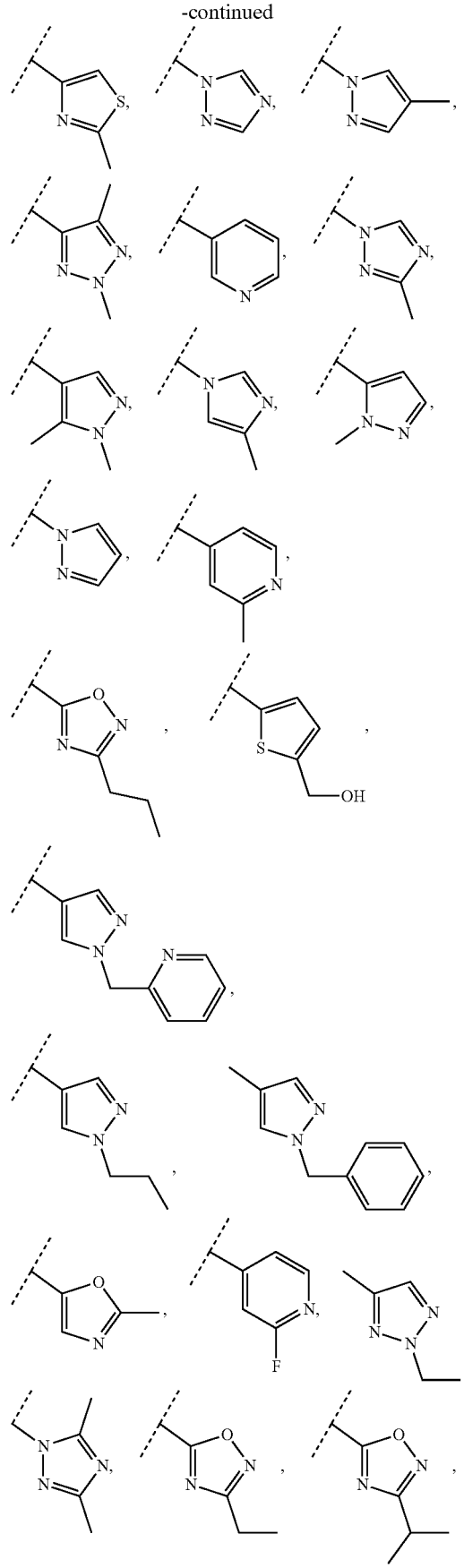
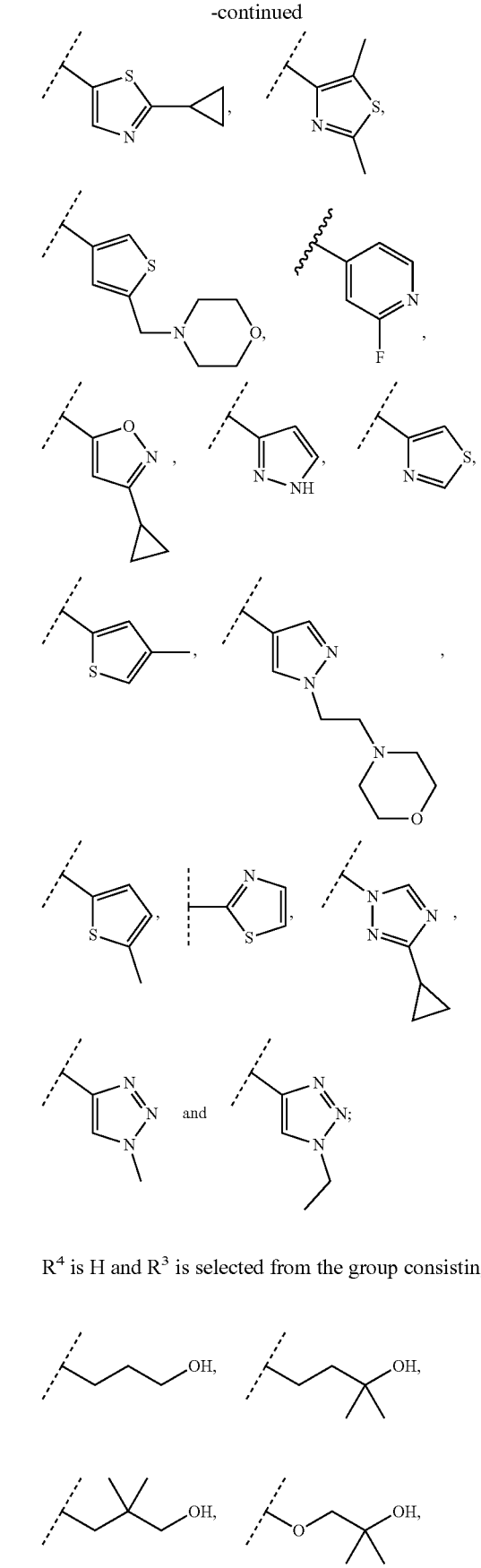
R⁴ is H and R³ is selected from the group consisting of
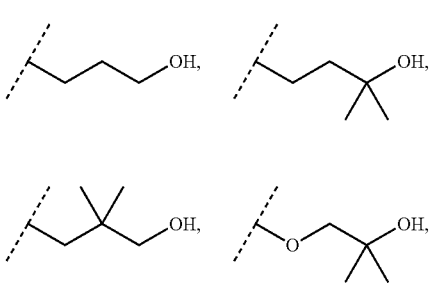

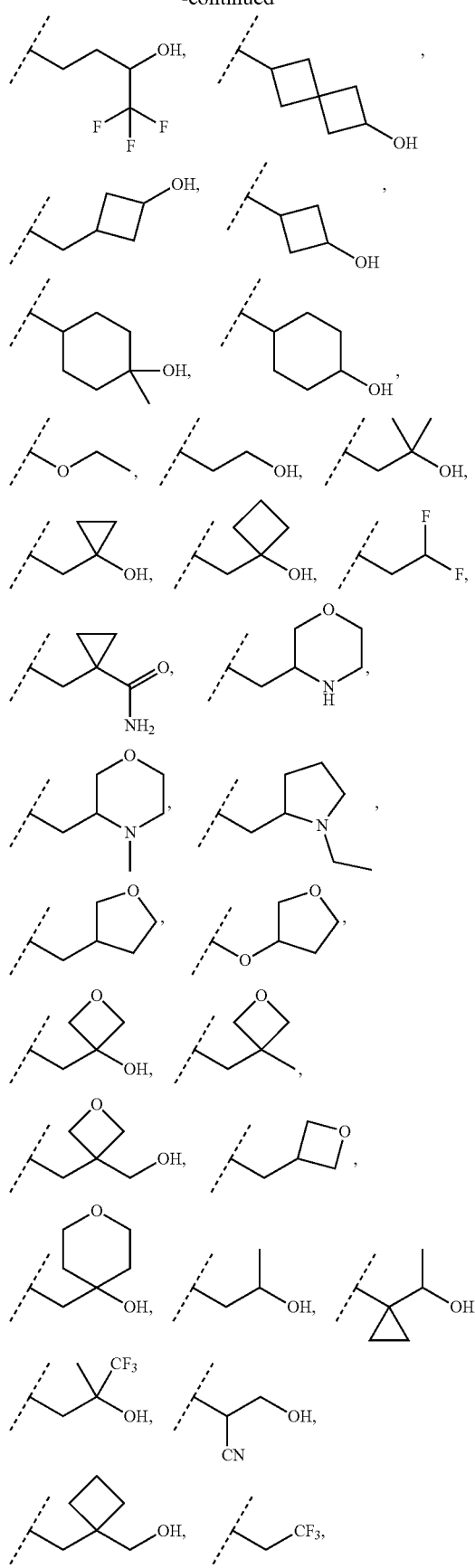
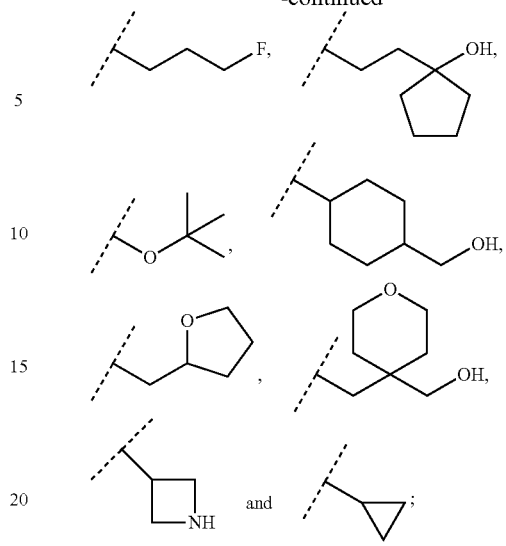

or R³ and R⁴ together with the nitrogen atom to which they are attached form a $C_{3-7}$ heterocyclyl selected from the group consisting of

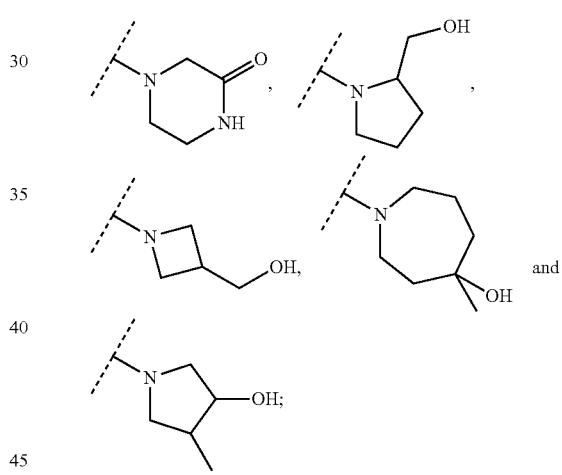

or a pharmaceutically acceptable salt thereof.

4. The compound according to claim 1 selected from
3-[5-amino-6-(5-methyl-[1,3,4]oxadiazol-2-yl)-pyrazin-2-yl]-N-(4-hydroxy-cyclohexyl)-4-methyl-benzenesulfonamide;
3-[5-amino-6-(3-methyl-[1,2,4]oxadiazol-5-yl)-pyrazin-2-yl]-N-(4-hydroxy-cyclohexyl)-4-methyl-benzenesulfonamide;
3-[5-amino-6-(3-methyl-[1,2,4]oxadiazol-5-yl)-pyrazin-2-yl]-N-(3-hydroxy-3-methyl-butyl)-4-methyl-benzenesulfonamide;
3-[5-amino-6-(3-methyl-isoxazol-5-yl)-pyrazin-2-yl]-N-(4-hydroxy-cyclohexyl)-4-methyl-benzenesulfonamide;
3-[5-amino-6-(1-methyl-1H-pyrazol-4-yl)-pyrazin-2-yl]-4-methyl-N-(3-methyl-oxetan-3-ylmethyl)-benzenesulfonamide;
3-(5-amino-6-(1H-1,2,4-triazol-1-yl)pyrazin-2-yl)-N-(2-hydroxy-2-methylpropyl)-4-methylbenzenesulfonamide;

3-(5-amino-6-(2-methylthiazol-5-yl)pyrazin-2-yl)-N-(2-hydroxy-2-methylpropyl)-4-methylbenzenesulfonamide;

3-[5-amino-6-(2-methyl-thiazol-5-yl)-pyrazin-2-yl]-N-(3-hydroxy-2,2-dimethyl-propyl)-4-methyl-benzenesulfonamide;

3-[5-amino-6-(1,3-dimethyl-1H-pyrazol-4-yl)-pyrazin-2-yl]-N-(6-hydroxy-spiro[3.3]hept-2-yl)-4-methyl-benzenesulfonamide;

3-(5-amino-6-(2-methylthiazol-5-yl)pyrazin-2-yl)-N-(3-hydroxypropyl)-4-methylbenzenesulfonamide;

3-(5-amino-6-(pyridin-4-yl)pyrazin-2-yl)-N-(4-hydroxycyclohexyl)-4-methylbenzenesulfonamide;

3-(5-amino-6-(1,3-dimethyl-1H-pyrazol-4-yl)pyrazin-2-yl)-N-(3-hydroxy-3-methylbutyl)-4-methylbenzenesulfonamide;

3-[5-amino-6-(1,3-dimethyl-1H-pyrazol-4-yl)-pyrazin-2-yl]-N-(3-hydroxy-3-methyl-butyl)-4-methyl-benzenesulfonamide;

3-(5-amino-6-(2-methylthiazol-5-yl)pyrazin-2-yl)-N-(4-hydroxycyclohexyl)-4-methylbenzenesulfonamide;

3-(5-amino-6-(1H-1,2,4-triazol-1-yl)pyrazin-2-yl)-N-(4-hydroxycyclohexyl)-4-methylbenzenesulfonamide;

3-[5-amino-6-(1,3-dimethyl-1H-pyrazol-4-yl)-pyrazin-2-yl]-4-methyl-N—[(R)-1-(tetrahydrofuran-3-yl)methyl]-benzenesulfonamide;

3-[5-amino-6-(1,3-dimethyl-1H-pyrazol-4-yl)-pyrazin-2-yl]-4-methyl-N-(3-methyl-oxetan-3-ylmethyl)-benzenesulfonamide;

3-[5-amino-6-(2-methyl-2H-[1,2,3]triazol-4-yl)-pyrazin-2-yl]-N-(2-hydroxy-2-methyl-propyl)-4-methyl-benzenesulfonamide;

3-[5-amino-6-(2,5-dimethyl-2H-[1,2,3]triazol-4-yl)-pyrazin-2-yl]-N-(2-hydroxy-2-methyl-propyl)-4-methyl-benzenesulfonamide;

3-[5-amino-6-(2-methyl-thiazol-5-yl)-pyrazin-2-yl]-N-(3-hydroxy-cyclobutylmethyl)-4-methyl-benzenesulfonamide;

3-[5-amino-6-(2-cyclopropyl-thiazol-5-yl)-pyrazin-2-yl]-N-(2-hydroxy-2-methyl-propyl)-4-methyl-benzenesulfonamide;

3-(5-amino-6-pyridin-3-yl-pyrazin-2-yl)-N-(4-hydroxy-cyclohexyl)-4-methyl-benzenesulfonamide;

3-[5-amino-6-(3-isopropyl-[1,2,4]oxadiazol-5-yl)-pyrazin-2-yl]-N-(4-hydroxy-cyclohexyl)-4-methyl-benzene sulfonamide;

3-[5-amino-6-(3-cyclopropyl-[1,2,4]oxadiazol-5-yl)-pyrazin-2-yl]-N-(4-hydroxy-cyclohexyl)-4-methyl-benzene sulfonamide;

3-[5-amino-6-(3-methyl-[1,2,4]triazol-1-yl)-pyrazin-2-yl]-N-(2-hydroxy-2-methyl-propyl)-4-methyl-benzenesulfonamide;

3-[5-amino-6-(3-cyclopropyl-[1,2,4]triazol-1-yl)-pyrazin-2-yl]-N-(3-hydroxy-3-methyl-butyl)-4-methyl-benzenesulfonamide;

3-[5-amino-6-(1,3-dimethyl-1H-pyrazol-4-yl)-pyrazin-2-yl]-N—((R)-1-ethyl-pyrrolidin-2-ylmethyl)-4-methyl-benzenesulfonamide;

3-(5-amino-6-[1,2,4]triazol-1-yl-pyrazin-2-yl)-N-(1-hydroxy-cyclopropylmethyl)-4-methyl-benzenesulfonamide;

3-(5-amino-6-[1,2,4]triazol-1-yl-pyrazin-2-yl)-4-methyl-N-(3-methyl-oxetan-3-ylmethyl)-benzenesulfonamide;

3-[5-amino-6-(5-morpholin-4-ylmethyl-thiophen-3-yl)-pyrazin-2-yl]-N-(3-hydroxy-3-methyl-butyl)-4-methyl-benzenesulfonamide;

3-(5-amino-6-[1,2,4]triazol-1-yl-pyrazin-2-yl)-N-(2-hydroxy-2-methyl-propoxy)-4-methyl-benzenesulfonamide;

3-(5-amino-6-[1,2,4]triazol-1-yl-pyrazin-2-yl)-N-(4-hydroxy-tetrahydropyran-4-ylmethyl)-4-methylbenzenesulfonamide;

N-(2-amino-ethyl)-3-(5-amino-6-[1,2,4]triazol-1-yl-pyrazin-2-yl)-4-methyl-benzenesulfonamide;

3-(5-amino-6-[1,2,4]triazol-1-yl-pyrazin-2-yl)-N-(2,2-difluoro-ethyl)-4-methyl-benzenesulfonamide;

3-(5-amino-6-[1,2,4]triazol-1-yl-pyrazin-2-yl)-N-(3-hydroxymethyl-oxetan-3-ylmethyl)-4-methyl-benzenesulfonamide;

3-(5-amino-6-[1,2,4]triazol-1-yl-pyrazin-2-yl)-N-(3,3-dimethyl-2-oxo-butyl)-4-methyl-benzenesulfonamide;

3-(5-amino-6-(1H-1,2,4-triazol-1-yl)pyrazin-2-yl)-4-chloro-N-(2-hydroxy-2-methylpropyl)benzenesulfonamide;

3-(5-amino-6-(1H-1,2,4-triazol-1-yl)pyrazin-2-yl)-4-chloro-N-(3-hydroxy-3-methylbutyl)benzenesulfonamide;

3-(5-amino-6-(furan-3-yl)pyrazin-2-yl)-N-(2-hydroxy-2-methylpropyl)-4-methylbenzenesulfonamide;

3-(5-amino-6-(2,5-dimethylthiazol-4-yl)pyrazin-2-yl)-N-(2-hydroxy-2-methylpropyl)-4-methylbenzenesulfonamide;

(R)-3-(5-amino-6-(2-methylthiazol-5-yl)pyrazin-2-yl)-N-((1-ethylpyrrolidin-2-yl)methyl)-4-methylbenzenesulfonamide;

(R)-3-(5-amino-6-(2-methylthiazol-5-yl)pyrazin-2-yl)-4-methyl-N-((tetrahydrofuran-3-yl)methyl)benzenesulfonamide;

3-(5-amino-6-(2-methylthiazol-5-yl)pyrazin-2-yl)-N-(3-hydroxycyclobutyl)-4-methylbenzenesulfonamide;

3-(5-amino-6-(2-methylthiazol-5-yl)pyrazin-2-yl)-N-((3-(hydroxymethyl)oxetan-3-yl)methyl)-4-methylbenzenesulfonamide;

3-(5-amino-6-(2-methylthiazol-5-yl)pyrazin-2-yl)-N-(2-hydroxyethyl)-4-methylbenzenesulfonamide;

3-(5-amino-6-(2-methylthiazol-5-yl)pyrazin-2-yl)-4-methyl-N-(oxetan-3-ylmethyl)benzenesulfonamide;

3-(5-amino-6-(2-methylthiazol-5-yl)pyrazin-2-yl)-4-methyl-N-((tetrahydro-2H-pyran-4-yl)methyl)benzenesulfonamide;

3-(5-amino-6-(2-methylthiazol-5-yl)pyrazin-2-yl)-4-methyl-N-(tetrahydro-2H-pyran-4-yl)benzenesulfonamide;

3-(5-amino-6-(2-methylthiazol-5-yl)pyrazin-2-yl)-4-methyl-N-((tetrahydro-2H-pyran-2-yl)methyl)benzenesulfonamide;

3-(5-amino-6-(2-methylthiazol-5-yl)pyrazin-2-yl)-4-methyl-N-(2,2,2-trifluoroethyl)benzenesulfonamide;

3-(5-amino-6-(2-methylthiazol-5-yl)pyrazin-2-yl)-4-methyl-N-((tetrahydrofuran-2-yl)methyl)benzenesulfonamide;

3-(5-amino-6-(2-methylthiazol-5-yl)pyrazin-2-yl)-4-methyl-N-(tetrahydrofuran-3-yl)benzenesulfonamide;

(1-(3-(5-amino-6-(2-methylthiazol-5-yl)pyrazin-2-yl)-4-methylphenylsulfonyl)azetidin-3-yl)methanol;

3-(5-amino-6-(2-methylthiazol-5-yl)pyrazin-2-yl)-N-((4-(hydroxymethyl)tetrahydro-2H-pyran-4-yl)methyl)-4-methylbenzenesulfonamide;

3-(5-amino-6-(2-methylthiazol-5-yl)pyrazin-2-yl)-N-((4-hydroxytetrahydro-2H-pyran-4-yl)methyl)-4-methyl-benzenesulfonamide;

3-(5-amino-6-(2-methylthiazol-5-yl)pyrazin-2-yl)-N-((3-hydroxyoxetan-3-yl)methyl)-4-methylbenzenesulfonamide;

3-(5-amino-6-(2-methylthiazol-5-yl)pyrazin-2-yl)-4-methyl-N-((4-methylmorpholin-3-yl)methyl)benzenesulfonamide;

3-(5-amino-6-(1,5-dimethyl-1H-pyrazol-4-yl)pyrazin-2-yl)-N-(2-hydroxy-2-methylpropyl)-4-methylbenzenesulfonamide;

3-(5-amino-6-(2,4-dimethylthiazol-5-yl)pyrazin-2-yl)-N-(2-hydroxy-2-methylpropyl)-4-methylbenzenesulfonamide;

3-(5-amino-6-(1-methyl-1H-pyrazol-4-yl)pyrazin-2-yl)-N-(2-hydroxy-2-methylpropyl)-4-methylbenzenesulfonamide;

3-(5-amino-6-(3,4-dimethyl-1H-pyrazol-1-yl)pyrazin-2-yl)-N-(2-hydroxy-2-methylpropyl)-4-methylbenzenesulfonamide;

3-(5-amino-6-(3,5-dimethyl-1H-pyrazol-1-yl)pyrazin-2-yl)-N-(2-hydroxy-2-methylpropyl)-4-methylbenzenesulfonamide;

3-(5-amino-6-(3,5-dimethyl-1H-1,2,4-triazol-1-yl)pyrazin-2-yl)-N-(2-hydroxy-2-methylpropyl)-4-methylbenzenesulfonamide;

3-(5-amino-6-(2,4-dimethyl-1H-imidazol-1-yl)pyrazin-2-yl)-N-(2-hydroxy-2-methylpropyl)-4-methylbenzenesulfonamide;

3-(5-amino-6-(1-methyl-H-pyrazol-4-yl)pyrazin-2-yl)-4-methyl-N-(4,4,4-trifluoro-3-hydroxybutyl)benzenesulfonamide;

3-(5-amino-6-(1,3-dimethyl-1H-pyrazol-4-yl)pyrazin-2-yl)-4-methyl-N-(4,4,4-trifluoro-3-hydroxybutyl)benzenesulfonamide;

3-(5-amino-6-(1,3-dimethyl-1H-pyrazol-4-yl)pyrazin-2-yl)-4-methyl-N-(4,4,4-trifluoro-3-hydroxybutyl)benzenesulfonamide;

5-(5-amino-6-(1H-1,2,4-triazol-1-yl)pyrazin-2-yl)-N-(2-hydroxy-2-methylpropyl)-6-methylpyridine-3-sulfonamide;

3-(5-amino-6-(1-methyl-1H-pyrazol-4-yl)pyrazin-2-yl)-N-(4,4-difluorocyclohexyl)-4-methylbenzenesulfonamide;

3-(5-amino-6-(2-methylthiazol-5-yl)pyrazin-2-yl)-N-(4,4-difluorocyclohexyl)-4-methylbenzenesulfonamide;

3-(5-amino-6-(4-methyl-1H-imidazol-1-yl)pyrazin-2-yl)-N-((1r,4r)-4-hydroxycyclohexyl)-4-methylbenzenesulfonamide;

3-(5-amino-6-(4-methyl-1H-imidazol-1-yl)pyrazin-2-yl)-N-(3-hydroxypropyl)-4-methylbenzenesulfonamide;

3-(5-amino-6-(1-methyl-1H-pyrazol-4-yl)pyrazin-2-yl)-N-((1r,4r)-4-hydroxycyclohexyl)-4-methylbenzenesulfonamide;

3-(5-amino-6-(pyrimidin-5-yl)pyrazin-2-yl)-N-((1r,4r)-4-hydroxycyclohexyl)-4-methylbenzenesulfonamide;

3-(5-amino-6-(2-fluoropyridin-4-yl)pyrazin-2-yl)-N-((1r,4r)-4-hydroxycyclohexyl)-4-methylbenzenesulfonamide;

3-(5-amino-6-(1H-imidazol-1-yl)pyrazin-2-yl)-N-(3-hydroxy-3-methylbutyl)-4-methylbenzenesulfonamide;

3-(5-amino-6-(1H-pyrazol-1-yl)pyrazin-2-yl)-N-(3-hydroxy-3-methylbutyl)-4-methylbenzenesulfonamide;

3-(5-amino-6-(4-methyl-1H-imidazol-1-yl)pyrazin-2-yl)-N-(3-hydroxy-3-methylbutyl)-4-methylbenzenesulfonamide;

3-(5-amino-6-(1H-1,2,4-triazol-1-yl)pyrazin-2-yl)-N-(3-hydroxy-3-methylbutyl)-4-methylbenzenesulfonamide;

3-(5-amino-6-(3-methyl-1H-1,2,4-triazol-1-yl)pyrazin-2-yl)-N-(3-hydroxy-3-methylbutyl)-4-methylbenzenesulfonamide;

3-(5-amino-6-(3-isopropyl-1H-1,2,4-triazol-1-yl)pyrazin-2-yl)-N-(3-hydroxy-3-methylbutyl)-4-methylbenzenesulfonamide;

3-(5-amino-6-(1H-1,2,4-triazol-1-yl)pyrazin-2-yl)-N-(6-hydroxyspiro[3.3]heptan-2-yl)-4-methylbenzenesulfonamide;

3-(5-amino-6-(1H-1,2,4-triazol-1-yl)pyrazin-2-yl)-4-methyl-N-(tetrahydro-2H-pyran-4-yl)benzenesulfonamide;

3-(5-amino-6-(1H-1,2,4-triazol-1-yl)pyrazin-2-yl)-N-((1r,4r)-4-hydroxy-4-methylcyclohexyl)-4-methylbenzenesulfonamide;

3-(5-amino-6-(1H-1,2,4-triazol-1-yl)pyrazin-2-yl)-N-((1s,4s)-4-hydroxy-4-methylcyclohexyl)-4-methylbenzenesulfonamide;

3-(5-amino-6-(1H-1,2,4-triazol-1-yl)pyrazin-2-yl)-N-(6-hydroxyspiro[3.3]heptan-2-yl)-4-methylbenzenesulfonamide;

3-(5-amino-6-(1H-1,2,4-triazol-1-yl)pyrazin-2-yl)-N-(6-hydroxyspiro[3.3]heptan-2-yl)-4-methylbenzenesulfonamide;

3-(5-amino-6-(1H-1,2,4-triazol-1-yl)pyrazin-2-yl)-N-((1r,3r)-3-hydroxycyclobutyl)-4-methylbenzenesulfonamide;

3-(5-amino-6-(1H-1,2,4-triazol-1-yl)pyrazin-2-yl)-N-((1s,3s)-3-hydroxycyclobutyl)-4-methylbenzenesulfonamide;

3-(5-amino-6-(1H-1,2,4-triazol-1-yl)pyrazin-2-yl)-N-(((1s,3s)-3-hydroxycyclobutyl)methyl)-4-methylbenzenesulfonamide;

3-(5-amino-6-(1H-1,2,4-triazol-1-yl)pyrazin-2-yl)-N-(3-hydroxy-2,2-dimethylpropyl)-4-methylbenzenesulfonamide;

3-(5-amino-6-(1,3-dimethyl-1H-pyrazol-4-yl)pyrazin-2-yl)-N-(6-hydroxyspiro[3.3]heptan-2-yl)-4-methylbenzenesulfonamide;

3-(5-amino-6-(1-methyl-1H-pyrazol-4-yl)pyrazin-2-yl)-N-((1s,4s)-4-hydroxycyclohexyl)-4-methylbenzenesulfonamide;

3-(5-amino-6-(2-methylpyridin-4-yl)pyrazin-2-yl)-N-((1s,4s)-4-hydroxycyclohexyl)-4-methylbenzenesulfonamide;

3-(5-amino-6-(1-methyl-1H-pyrazol-5-yl)pyrazin-2-yl)-N-(3-hydroxy-3-methylbutyl)-4-methylbenzenesulfonamide;

3-(5-amino-6-(3-cyclopropylisoxazol-5-yl)pyrazin-2-yl)-N-(3-hydroxy-3-methylbutyl)-4-methylbenzenesulfonamide;

3-(5-amino-6-(3-cyclopropylisoxazol-5-yl)pyrazin-2-yl)-N-(2-hydroxy-2-methylpropyl)-4-methylbenzenesulfonamide;

3-(5-amino-6-(4-methylthiazol-2-yl)pyrazin-2-yl)-N-(2-hydroxy-2-methylpropyl)-4-methylbenzenesulfonamide;

3-(5-amino-6-(1-methyl-1H-1,2,3-triazol-4-yl)pyrazin-2-yl)-N-(2-hydroxy-2-methylpropyl)-4-methylbenzenesulfonamide;

3-(5-amino-6-(2-ethyl-2H-1,2,3-triazol-4-yl)pyrazin-2-yl)-N-(2-hydroxy-2-methylpropyl)-4-methylbenzenesulfonamide;

3-(5-amino-6-(1-ethyl-1H-1,2,3-triazol-4-yl)pyrazin-2-yl)-N-(2-hydroxy-2-methylpropyl)-4-methylbenzenesulfonamide;

3-(5-amino-6-(2-(2,2,2-trifluoroethyl)-2H-1,2,3-triazol-4-yl)pyrazin-2-yl)-N-(2-hydroxy-2-methylpropyl)-4-methylbenzenesulfonamide;
3-(5-amino-6-(2-methyl-2H-1,2,3-triazol-4-yl)pyrazin-2-yl)-N-(3-hydroxy-3-methylbutyl)-4-methylbenzenesulfonamide;
3-(5-amino-6-(2-methylthiazol-5-yl)pyrazin-2-yl)-N-((1s,4s)-4-hydroxycyclohexyl)-4-methylbenzenesulfonamide;
3-(5-amino-6-(3-methylisoxazol-5-yl)pyrazin-2-yl)-N-(2-hydroxy-2-methylpropyl)-4-methylbenzenesulfonamide;
3-(5-amino-6-(3-methylisoxazol-5-yl)pyrazin-2-yl)-N-(3-hydroxy-3-methylbutyl)-4-methylbenzenesulfonamide;
3-(5-amino-6-(5-methyl-1,3,4-oxadiazol-2-yl)pyrazin-2-yl)-N-(2-hydroxy-2-methylpropyl)-4-methylbenzenesulfonamide;
3-(5-amino-6-(5-cyclopropyl-1,2,4-oxadiazol-3-yl)pyrazin-2-yl)-N-(2-hydroxy-2-methylpropyl)-4-methylbenzenesulfonamide;
3-(5-amino-6-(3-methyl-1,2,4-oxadiazol-5-yl)pyrazin-2-yl)-N-(3-hydroxy-2,2-dimethylpropyl)-4-methylbenzenesulfonamide;
3-(5-amino-6-(3-cyclopropyl-1,2,4-oxadiazol-5-yl)pyrazin-2-yl)-N-(3-hydroxy-2,2-dimethylpropyl)-4-methylbenzenesulfonamide;
3-(5-amino-6-(3-cyclopropyl-1,2,4-oxadiazol-5-yl)pyrazin-2-yl)-N-(((1s,3s)-3-hydroxycyclobutyl)methyl)-4-methylbenzenesulfonamide;
3-(5-amino-6-(3-cyclopropyl-1,2,4-oxadiazol-5-yl)pyrazin-2-yl)-N-(2-hydroxy-2-methylpropyl)-4-methylbenzenesulfonamide;
3-(5-amino-6-(3-methyl-1,2,4-oxadiazol-5-yl)pyrazin-2-yl)-N-(((1s,3s)-3-hydroxycyclobutyl)methyl)-4-methylbenzenesulfonamide;
3-(5-amino-6-(3-isopropyl-1,2,4-oxadiazol-5-yl)pyrazin-2-yl)-N-(2-hydroxy-2-methylpropyl)-4-methylbenzenesulfonamide;
3-(5-amino-6-(1H-1,2,4-triazol-1-yl)pyrazin-2-yl)-N-(1-(hydroxymethyl)cyclopropyl)-4-methylbenzenesulfonamide;
3-(5-amino-6-(3-cyclopropylisoxazol-5-yl)pyrazin-2-yl)-N-(3-hydroxy-2,2-dimethylpropyl)-4-methylbenzenesulfonamide;
3-(5-amino-6-(3-cyclopropylisoxazol-5-yl)pyrazin-2-yl)-N-(1s,3s)-3-hydroxycyclobutyl)methyl)-4-methylbenzenesulfonamide;
2-(3-(5-amino-6-(1H-1,2,4-triazol-1-yl)pyrazin-2-yl)-4-methylphenylsulfonyl)-2-azaspiro[3.3]heptan-6-ol;
3-(1,3-dimethyl-1H-pyrazol-4-yl)-5-(5-(3-methoxy-3-methylazetidin-1-ylsulfonyl)-2-methylphenyl)pyrazin-2-amine;
3-(5-amino-6-(1H-pyrazol-1-yl)pyrazin-2-yl)-N-((1r,4r)-4-hydroxycyclohexyl)-4-methylbenzenesulfonamide;
(R)-3-(5-amino-6-(1,3-dimethyl-1H-pyrazol-4-yl)pyrazin-2-yl)-4-methyl-N-(pyrrolidin-2-ylmethyl)benzenesulfonamide;
3-(5-amino-6-(2-cyclopropylthiazol-5-yl)pyrazin-2-yl)-N-(3-hydroxy-3-methylbutyl)-4-methylbenzenesulfonamide;
3-(5-amino-6-(thiazol-4-yl)pyrazin-2-yl)-N-(3-hydroxy-3-methylbutyl)-4-methylbenzenesulfonamide;
3-(5-amino-6-(3-cyclopropyl-1H-1,2,4-triazol-1-yl)pyrazin-2-yl)-N-(2-hydroxy-2-methylpropyl)-4-methylbenzenesulfonamide;
3-(5-amino-6-(2-methoxythiazol-4-yl)pyrazin-2-yl)-N-(3-hydroxy-3-methylbutyl)-4-methylbenzenesulfonamide;
3-(5-amino-6-(4-methyl-1H-pyrazol-1-yl)pyrazin-2-yl)-N-((1r,4r)-4-hydroxycyclohexyl)-4-methylbenzenesulfonamide;
3-(5-amino-6-(1H-1,2,4-triazol-1-yl)pyrazin-2-yl)-N-ethoxy-4-methylbenzenesulfonamide;
3-(5-amino-6-(1H-1,2,4-triazol-1-yl)pyrazin-2-yl)-N-tert-butoxy-4-methylbenzenesulfonamide;
3-(5-amino-6-(1H-1,2,4-triazol-1-yl)pyrazin-2-yl)-N-(2-(dimethylamino)ethoxy)-4-methylbenzenesulfonamide;
3-(5-amino-6-(1H-1,2,4-triazol-1-yl)pyrazin-2-yl)-N-isopropoxy-4-methylbenzenesulfonamide;
3-(5-amino-6-(1H-1,2,4-triazol-1-yl)pyrazin-2-yl)-N-isobutoxy-4-methylbenzenesulfonamide;
3-(5-amino-6-(1H-1,2,4-triazol-1-yl)pyrazin-2-yl)-4-methyl-N-(tetrahydrofuran-3-yloxy)benzenesulfonamide;
5-(5-amino-6-(2-methylthiazol-5-yl)pyrazin-2-yl)-2-fluoro-N-(3-hydroxypropyl)-4-methylbenzenesulfonamide;
5-(5-amino-6-(1-methyl-1H-pyrazol-4-yl)pyrazin-2-yl)-2-fluoro-N-(3-hydroxypropyl)-4-methylbenzenesulfonamide;
5-(5-amino-6-(1-methyl-1H-pyrazol-4-yl)pyrazin-2-yl)-2-fluoro-N-(3-hydroxy-3-methylbutyl)-4-methylbenzenesulfonamide;
5-(5-amino-6-(1H-1,2,4-triazol-1-yl)pyrazin-2-yl)-2-fluoro-N-(3-hydroxy-3-methylbutyl)-4-methylbenzenesulfonamide;
3-(5-amino-6-(3-((dimethylamino)methyl)-1H-1,2,4-triazol-1-yl)pyrazin-2-yl)-N-(2-hydroxy-2-methylpropyl)-4-methylbenzenesulfonamide;
5-(2-methyl-5-(3-(trifluoromethyl)piperazin-1-ylsulfonyl)phenyl)-3-(2-methylthiazol-5-yl)pyrazin-2-amine;
3-(5-amino-6-(1-methyl-3-(trifluoromethyl)-1H-pyrazol-5-yl)pyrazin-2-yl)-N-(3-hydroxy-3-methylbutyl)-4-methylbenzenesulfonamide;
3-(5-amino-6-(2-fluoropyridin-3-yl)pyrazin-2-yl)-N-(3-hydroxy-3-methylbutyl)-4-methylbenzenesulfonamide;
3-(5-amino-6-(4-methoxypyridin-3-yl)pyrazin-2-yl)-N-(3-hydroxy-3-methylbutyl)-4-methylbenzenesulfonamide;
3-(5-amino-6-(2-methoxypyridin-4-yl)pyrazin-2-yl)-N-(3-hydroxy-3-methylbutyl)-4-methylbenzenesulfonamide;
3-(5-amino-6-(2-methoxypyridin-3-yl)pyrazin-2-yl)-N-(3-hydroxy-3-methylbutyl)-4-methylbenzenesulfonamide;
3-(5-amino-6-(pyridin-3-yl)pyrazin-2-yl)-N-(3-hydroxy-3-methylbutyl)-4-methylbenzenesulfonamide;
3-(5-amino-6-(2-chloropyridin-3-yl)pyrazin-2-yl)-N-(3-hydroxy-3-methylbutyl)-4-methylbenzenesulfonamide;
3-(5-amino-6-(5-methylpyridin-3-yl)pyrazin-2-yl)-N-(3-hydroxy-3-methylbutyl)-4-methylbenzenesulfonamide;
3-(5-amino-6-(5-chloro-2-fluoropyridin-3-yl)pyrazin-2-yl)-N-(3-hydroxy-3-methylbutyl)-4-methylbenzenesulfonamide;
3-(5-amino-6-(6-chloro-4-methylpyridin-3-yl)pyrazin-2-yl)-N-(3-hydroxy-3-methylbutyl)-4-methylbenzenesulfonamide;

3-(5-amino-6-(2-fluoropyridin-4-yl)pyrazin-2-yl)-N-(3-hydroxy-3-methylbutyl)-4-methylbenzenesulfonamide;

3-(5-amino-6-(3-fluoropyridin-4-yl)pyrazin-2-yl)-N-(3-hydroxy-3-methylbutyl)-4-methylbenzenesulfonamide;

3-(5-amino-6-(2-isopropoxypyridin-3-yl)pyrazin-2-yl)-N-(3-hydroxy-3-meth t)-4-methylbenzenesulfonamide;

3-(5-amino-6-(6-ethoxypyridin-3-yl)pyrazin-2-yl)-N-(3-hydroxy-3-methylbutyl)-4-methylbenzenesulfonamide;

3-(5-amino-6-(6-methoxy-2-methylpyridin-3-yl)pyrazin-2-yl)-N-(3-hydroxy-3-methylbutyl)-4-methylbenzenesulfonamide;

3-(5-amino-6-(furan-3-yl)pyrazin-2-yl)-N-(3-hydroxy-3-methylbutyl)-4-methylbenzenesulfonamide;

3-(5-amino-6-(1-methyl-1H-pyrazol-4-yl)pyrazin-2-yl)-N-(3-hydroxy-3-meth t)-4-methylbenzenesulfonamide;

3-(5-amino-6-(6-(pyrrolidin-1-yl)pyridin-3-yl)pyrazin-2-yl)-N-(3-hydroxy-3-methylbutyl)-4-methylbenzenesulfonamide;

3-(5-amino-6-(6-fluoropyridin-3-yl)pyrazin-2-yl)-N-(3-hydroxy-3-methylbutyl)-4-methylbenzenesulfonamide;

3-(5-amino-6-(1,5-dimethyl-1H-pyrazol-4-yl)pyrazin-2-yl)-N-(3-hydroxy-3-methylbutyl)-4-methylbenzenesulfonamide;

3-(5-amino-6-(pyrimidin-5-yl)pyrazin-2-yl)-N-(3-hydroxy-3-methylbutyl)-4-methylbenzenesulfonamide;

3-(5-amino-6-(6-morpholinopyridin-3-yl)pyrazin-2-yl)-N-(3-hydroxy-3-methylbutyl)-4-methylbenzenesulfonamide;

3-(5-amino-6-(3-methyl-1H-pyrazol-4-yl)pyrazin-2-yl)-N-(3-hydroxy-3-methylbutyl)-4-methylbenzenesulfonamide;

3-(5-amino-6-(6-(piperidin-1-yl)pyridin-3-yl)pyrazin-2-yl)-N-(3-hydroxy-3-methylbut)-4-methylbenzenesulfonamide;

3-(5-amino-6-(6-(tetrahydro-2H-pyran-4-yloxy)pyridin-3-yl)pyrazin-2-yl)-N-(3-hydroxy-3-methylbutyl)-4-methylbenzenesulfonamide;

3-(5-amino-6-(1-propyl-H-pyrazol-4-yl)pyrazin-2-yl)-N-(3-hydroxy-3-methylbutyl)-4-methylbenzenesulfonamide;

3-(5-amino-6-(1-isopentyl-1H-pyrazol-4-yl)pyrazin-2-yl)-N-(3-hydroxy-3-methylbutyl)-4-methylbenzenesulfonamide;

3-(5-amino-6-(pyridin-4-yl)pyrazin-2-yl)-N-(3-hydroxy-3-methylbutyl)-4-methylbenzenesulfonamide;

3-(5-amino-6-(2-methylpyridin-4-yl)pyrazin-2-yl)-N-(3-hydroxy-3-methylbutyl)-4-methylbenzenesulfonamide;

3-(5-amino-6-(2-methylthiazol-5-yl)pyrazin-2-yl)-N-(3-hydroxy-3-methylbutyl)-4-methylbenzenesulfonamide;

3-(5-amino-6-(2-methylthiazol-4-yl)pyrazin-2-yl)-N-(3-hydroxy-3-methylbutyl)-4-methylbenzenesulfonamide;

3-(5-amino-6-(1-isopropyl-1H-pyrazol-4-yl)pyrazin-2-yl)-N-(3-hydroxy-3-methylbutyl)-4-methylbenzenesulfonamide;

3-(5-amino-6-(1-isobutyl-1H-pyrazol-4-yl)pyrazin-2-yl)-N-(3-hydroxy-3-methylbutyl)-4-methylbenzenesulfonamide;

3-(5-amino-6-(1H-pyrazol-4-ylpyrazin-2-yl)-N-(3-hydroxy-3-meth 1 butyl)-4-methylbenzenesulfonamide;

3-(5-amino-6-(1-ethyl-1H-pyrazol-4-yl)pyrazin-2-yl)-N-(3-hydroxy-3-methylbutyl)-4-methylbenzenesulfonamide;

3-(5-amino-6-(5-(hydroxymethyl)thiophen-2-yl)pyrazin-2-yl)-N-(3-hydroxy-3-methylbutyl)-4-methylbenzenesulfonamide;

3-(5-amino-6-(1,3-dimethyl-1H-pyrazol-5-yl)pyrazin-2-yl)-N-(3-hydroxy-3-methylbutyl)-4-methylbenzenesulfonamide;

3-(5-amino-6-(1-(pyridin-2-ylmethyl)-1H-pyrazol-4-yl)pyrazin-2-yl)-N-(3-hydroxy-methylbutyl)-4-methylbenzenesulfonamide;

3-(5-amino-6-(1-(pyridin-3-ylmethyl)-1H-pyrazol-4-yl)pyrazin-2-yl)-N-(3-hydroxy-methylbutyl)-4-methylbenzenesulfonamide;

3-(5-amino-6-(1-(pyridin-4-ylmethyl)-1H-pyrazol-4-yl)pyrazin-2-yl)-N-(3-hydroxy-methylbutyl)-4-methylbenzenesulfonamide;

3-(5-amino-6-(2-methyloxazol-5-yl)pyrazin-2-yl)-N-(3-hydroxy-3-methylbutyl)-4-methylbenzenesulfonamide;

3-(5-amino-6-(1-(2-morpholinoethyl)-1H-pyrazol-4-yl)pyrazin-2-yl)-N-(3-hydroxy-methylbutyl)-4-methylbenzenesulfonamide;

3-(5-amino-6-(1H-pyrazol-3-yl)pyrazin-2-yl)-N-(3-hydroxy-3-methylbutyl)-4-methylbenzenesulfonamide;

3-(5-amino-6-(4-methylthiophen-2-yl)pyrazin-2-yl)-N-(3-hydroxy-3-methylbutyl)-4-methylbenzenesulfonamide;

3-(5-amino-6-(5-methylthiophen-2-yl)pyrazin-2-yl)-N-(3-hydroxy-3-methylbutyl)-4-methylbenzenesulfonamide;

3-(5-amino-6-(thiophen-2-yl)pyrazin-2-yl)-N-(3-hydroxy-3-methylbutyl)-4-methylbenzenesulfonamide;

3-(5-amino-6-(5-cyclopropylthiophen-2-yl)pyrazin-2-yl)-N-(3-hydroxy-3-methylbutyl)-4-methylbenzenesulfonamide;

3-(5-amino-6-(2-methylthiazol-5-yl)pyrazin-2-yl)-4-methyl-N-((3-methyloxetan-3-yl)methyl)benzenesulfonamide;

5-(5-amino-6-(1H-1,2,4-triazol-1-yl)pyrazin-2-yl)-N-(2-hydroxy-2-methylpropyl)-2,4-dimethylbenzenesulfonamide;

5-(5-amino-6-(1H-1,2,4-triazol-1-yl)pyrazin-2-yl)-2-fluoro-N-(2-hydroxy-2-methylpropyl) 4-methylbenzenesulfonamide;

3-(5-amino-6-(1H-1,2,4-triazol-1-yl)pyrazin-2-yl)-N-(2-hydroxy-2-methylpropyl)benzenesulfonamide;

5-(5-amino-6-(1H-1,2,4-triazol-1-yl)pyrazin-2-yl)-2-chloro-N-(2-hydroxy-2-methylpropyl) 4-methylbenzenesulfonamide;

3-(5-amino-6-(1,3-dimethyl-1H-pyrazol-4-yl)pyrazin-2-yl)-N-(2-hydroxy-2-methylpropoxy) 4-methylbenzenesulfonamide;

3-(5-amino-6-(2-methyloxazol-5-yl)pyrazin-2-yl)-N-(2-hydroxy-2-methylpropyl)-4-methylbenzenesulfonamide;

3-(5-amino-6-(1H-1,2,4-triazol-1-yl)pyrazin-2-yl)-4-methyl-N-(222-trifluoroethyl)benzenesulfonamide;

5-(5-(3,3-difluoropiperidin-1-ylsulfonyl)-2-methylphenyl)-3-(1H-1,2,4-triazol-1-yl)pyrazin-2-amine;

5-(5-(3-fluoropyrrolidin-1-ylsulfonyl)-2-methylphenyl)-3-(1H-1,2,4-triazol-1-yl)pyrazin-2-amine;

5-(5-(3,3-difluoropyrrolidin-1-ylsulfonyl)-2-methylphenyl)-3-(1H-1,2,4-triazol-1-yl)pyrazin 2-amine;

5-(5-(3,3-difluoroazetidin-1-ylsulfonyl)-2-methylphenyl)-3-(1H-1,2,4-triazol-1-yl)pyrazin-2-amine;

5-(5-(3-fluoroazetidin-1-ylsulfonyl)-2-methylphenyl)-3-(1H-1,2,4-triazol-1-yl)pyrazin-2-amine;

3-(5-amino-6-(1H-1,2,4-triazol-1-yl)pyrazin-2-yl)-N-(4-(hydroxymethyl)cyclohexyl)-4-methylbenzenesulfonamide;

3-(5-amino-6-(1H-1,2,4-triazol-1-yl)pyrazin-2-yl)-N-(3,3-difluorocyclobutyl)-4-methylbenzenesulfonamide;

5-(2-methyl-5-(3,3,4,4-tetrafluoropyrrolidin-1-ylsulfonyl)phenyl)-3-(1H-1,2,4-triazol-1-yl)pyrazin-2-amine;

3-(5-amino-6-(1H-1,2,4-triazol-1-yl)pyrazin-2-yl)-N-(5-hydroxypentyl)-4-methylbenzenesulfonamide;

3-(5-amino-6-(1H-1,2,4-triazol-1-yl)pyrazin-2-yl)-N-(3-methoxypropyl)-4-methylbenzenesulfonamide;

3-(5-amino-6-(1H-1,2,4-triazol-1-yl)pyrazin-2-yl)-N-((1-hydroxycyclohexyl)methyl)-4-methylbenzenesulfonamide;

(R)-3-(5-amino-6-(1H-1,2,4-triazol-1-yl)pyrazin-2-yl)-N-((1-ethylpyrrolidin-2-yl)methyl)-4-methylbenzenesulfonamide;

(R)-3-(5-amino-6-(1H-1,2,4-triazol-1-yl)pyrazin-2-yl)-N-(2-hydroxypropyl)-4-methylbenzenesulfonamide;

(R)-3-(5-amino-6-(1H-1,2,4-triazol-1-yl)pyrazin-2-yl)-4-methyl-N-((tetrahydrofuran-2-yl)methyl)benzenesulfonamide;

3-(5-amino-6-(1H-1,2,4-triazol-1-yl)pyrazin-2-yl)-N-((1-hydroxycyclobutyl)methyl)-4-methylbenzenesulfonamide;

3-(5-amino-6-(1H-1,2,4-triazol-1-yl)pyrazin-2-yl)-4-methyl-N-((tetrahydro-2H-pyran-2-yl)methyl)benzenesulfonamide;

3-(5-amino-6-(1H-1,2,4-triazol-1-yl)pyrazin-2-yl)-4-methyl-N-((1-methylpyrrolidin-3-yl)methyl)benzenesulfonamide;

3-(5-amino-6-(1H-1,2,4-triazol-1-yl)pyrazin-2-yl)-4-methyl-N-((tetrahydro-2H-pyran-3-yl)methyl)benzenesulfonamide;

(R)-3-(5-amino-6-(1H-1,2,4-triazol-1-yl)pyrazin-2-yl)-4-methyl-N-(tetrahydrofuran-3-yl)benzenesulfonamide;

(S)-3-(5-amino-6-(1H-1,2,4-triazol-1-yl)pyrazin-2-yl)-4-methyl-N-(tetrahydrofuran-3-yl)benzenesulfonamide;

(R)-3-(5-amino-6-(1H-1,2,4-triazol-1-yl)pyrazin-2-yl)-4-methyl-N-(3,3,3-trifluoro-2-hydroxy-2-methylpropyl)benzenesulfonamide;

(S)-3-(5-amino-6-(1H-1,2,4-triazol-1-yl)pyrazin-2-yl)-4-methyl-N-(3,3,3-trifluoro-2-hydroxy-2-methylpropyl)benzenesulfonamide;

3-(5-amino-6-(1H-1,2,4-triazol-1-yl)pyrazin-2-yl)-4-methyl-N-(4,4,4-trifluoro-3-hydroxy-3-methylbutyl)benzenesulfonamide;

3-(5-amino-6-(1H-1,2,4-triazol-1-yl)pyrazin-2-yl)-N-((1-(hydroxymethyl)cyclopentyl)methyl)-4-methylbenzenesulfonamide;

(S)-3-(5-amino-6-(1H-1,2,4-triazol-1-yl)pyrazin-2-yl)-4-methyl-N-((tetrahydrofuran-3-yl)methyl)benzenesulfonamide;

(R)-3-(5-amino-6-(1H-1,2,4-triazol-1-yl)pyrazin-2-yl)-4-methyl-N-((tetrahydrofuran-3-yl)methyl)benzenesulfonamide;

3-(5-amino-6-(1H-1,2,4-triazol-1-yl)pyrazin-2-yl)-N-(2-fluoroethyl)-4-methylbenzenesulfonamide;

3-(5-amino-6-(1H-1,2,4-triazol-1-yl)pyrazin-2-yl)-N-(3-fluoropropyl)-4-methylbenzenesulfonamide;

3-(5-amino-6-(1H-1,2,4-triazol-1-yl)pyrazin-2-yl)-4-methyl-N-(2-oxotetrahydrofuran-3-yl)benzenesulfonamide;

3-(5-amino-6-(1H-1,2,4-triazol-1-yl)pyrazin-2-yl)-4-methyl-N-(3,3,3-trifluoropropyl)benzenesulfonamide;

3-(5-amino-6-(1H-1,2,4-triazol-1-yl)pyrazin-2-yl)-4-methyl-N-(2-methyl-2-morpholinopropyl)benzenesulfonamide;

5-(5-(4,4-difluoropiperidin-1-ylsulfonyl)-2-methylphenyl)-3-(1H-1,2,4-triazol-1-yl)pyrazin-2-amine;

5-(5-(4-fluoropiperidin-1-ylsulfonyl)-2-methylphenyl)-3-(1H-1,2,4-triazol-1-yl)pyrazin-2-amine;

3-(5-amino-6-(1H-1,2,4-triazol-1-yl)pyrazin-2-yl)-N-((1-hydroxycyclopentyl)methyl)-4-methylbenzenesulfonamide;

3-(5-amino-6-(1H-1,2,4-triazol-1-yl)pyrazin-2-yl)-N-(2-(1-hydroxycyclopentyl)ethyl)-4-methylbenzenesulfonamide;

3-(5-amino-6-(1H-1,2,4-triazol-1-yl)pyrazin-2-yl)-N-(2-(1-hydroxycyclohexyl)ethyl)-4-methylbenzenesulfonamide;

3-(5-amino-6-(1H-1,2,4-triazol-1-yl)pyrazin-2-yl)-N-((1-(hydroxymethyl)cyclopropyl)methyl)-4-methylbenzenesulfonamide;

(S)-3-(5-amino-6-(1H-1,2,4-triazol-1-yl)pyrazin-2-yl)-N-((5,5-dimethyltetrahydrofuran-2-yl)methyl)-4-methylbenzenesulfonamide;

(R)-3-(5-amino-6-(1H-1,2,4-triazol-1-yl)pyrazin-2-yl)-N-((5,5-dimethyltetrahydrofuran-2-yl)methyl)-4-methylbenzenesulfonamide;

(S)-3-(5-amino-6-(1H-1,2,4-triazol-1-yl)pyrazin-2-yl)-N-(1-hydroxypropan-2-yl)-4-methylbenzenesulfonamide;

3-(5-amino-6-(1H-1,2,4-triazol-1-yl)pyrazin-2-yl)-N-(1-hydroxypropan-2-yl)-4-methylbenzenesulfonamide;

3-(5-amino-6-(1H-1,2,4-triazol-1-yl)pyrazin-2-yl)-N-(2,2-difluoropropyl)-4-methylbenzenesulfonamide;

3-(5-amino-6-(1H-1,2,4-triazol-1-yl)pyrazin-2-yl)-4-methyl-N-(3-methylbutan-2-yl)benzenesulfonamide;

(1-(3-(5-amino-6-(1H-1,2,4-triazol-1-yl)pyrazin-2-yl)-4-methylphenylsulfonyl)azetidin-3-yl)methanol;

1-(3-(5-amino-6-(1H-1,2,4-triazol-1-yl)pyrazin-2-yl)-4-methylphenylsulfonyl)-3-methylazetidin-3-ol;

3-(5-amino-6-(1H-1,2,4-triazol-1-yl)pyrazin-2-yl)-N-((3-hydroxyoxetan-3-yl)methyl)-4-methylbenzenesulfonamide;

(R)-3-(5-amino-6-(1H-1,2,4-triazol-1-yl)pyrazin-2-yl)-N-(1-cyano-2-hydroxyethyl)-4-methylbenzenesulfonamide;

3-(5-amino-6-(1H-1,2,4-triazol-1-yl)pyrazin-2-yl)-N-((1-(hydroxymethyl)cyclobutyl)methyl)-4-methylbenzenesulfonamide;

3-(5-amino-6-(1H-1,2,4-triazol-1-yl)pyrazin-2-yl)-N-((4-(hydroxymethyl)tetrahydro-2H-pyran-4-yl)methyl)-4-methylbenzenesulfonamide;

3-(5-amino-6-(1H-1,2,4-triazol-1-yl)pyrazin-2-yl)-4-methyl-N-(2-oxotetrahydrothiophen-3-yl)benzenesulfonamide;

3-(5-amino-6-(1H-1,2,4-triazol-1-yl)pyrazin-2-yl)-N-((1-(hydroxymethyl)cyclohexyl)methyl)-4-methylbenzenesulfonamide;

3-(5-amino-6-(1H-1,2,4-triazol-1-yl)pyrazin-2-yl)-N-cyclopropyl-4-methylbenzenesulfonamide;

3-(5-amino-6-(1H-1,2,4-triazol-1-yl)pyrazin-2-yl)-N-cyclobutyl-4-methylbenzenesulfonamide;

3-(5-amino-6-(1H-1,2,4-triazol-1-yl)pyrazin-2-yl)-N-cyclopentyl-4-methylbenzenesulfonamide;

(R)-3-(5-amino-6-(1H-1,2,4-triazol-1-yl)pyrazin-2-yl)-4-methyl-N-(pyrrolidin-3-ylmethyl)benzenesulfonamide;

(S)-3-(5-amino-6-(1H-1,2,4-triazol-1-yl)pyrazin-2-yl)-4-methyl-N-(pyrrolidin-3-ylmethyl)benzenesulfonamide;

3-(5-amino-6-(1H-1,2,4-triazol-1-yl)pyrazin-2-yl)-N-((3R,4R)-4-hydroxypyrrolidin-3-yl)-4-methylbenzenesulfonamide;
3-(5-amino-6-(1,3-dimethyl-1H-pyrazol-4-yl)pyrazin-2-yl)-N-((3-(hydroxymethyl)oxetan-3-yl)methyl)-4-methylbenzenesulfonamide;
(S)-3-(5-amino-6-(1,3-dimethyl-1H-pyrazol-4-yl)pyrazin-2-yl)-N-((1-ethylpyrrolidin-2-yl)methyl)-4-methylbenzenesulfonamide;
3-(5-amino-6-(1,3-dimethyl-1H-pyrazol-4-yl)pyrazin-2-yl)-4-methyl-N-((4-methylmorpholin-3-yl)methyl)benzenesulfonamide;
3-(5-amino-6-(1,3-dimethyl-1H-pyrazol-4-yl)pyrazin-2-yl)-4-methyl-N-((4-methylmorpholin-3-yl)methyl)benzenesulfonamide;
3-(5-amino-6-(1,3-dimethyl-1H-pyrazol-4-yl)pyrazin-2-yl)-4-methyl-N-((2-methyltetrahydrofuran-2-yl)methyl)benzenesulfonamide;
3-(5-amino-6-(1,3-dimethyl-1H-pyrazol-4-yl)pyrazin-2-yl)-4-methyl-N-((4-methylmorpholin-2-yl)methyl)benzenesulfonamide;
(R)-3-(5-amino-6-(1,3-dimethyl-1H-pyrazol-4-yl)pyrazin-2-yl)-4-methyl-N-(morpholin-3-ylmethyl)benzenesulfonamide;
(S)-3-(5-amino-6-(1,3-dimethyl-1H-pyrazol-4-yl)pyrazin-2-yl)-4-methyl-N-(morpholin-3-ylmethyl)benzenesulfonamide;
3-(5-amino-6-(1,3-dimethyl-1H-pyrazol-4-yl)pyrazin-2-yl)-4-methyl-N-(morpholin-2-ylmethyl)benzenesulfonamide;
(R)-3-(5-amino-6-(2-methylpyridin-4-yl)pyrazin-2-yl)-N-(2-hydroxypropyl)-4-methylbenzenesulfonamide;
3-(5-amino-6-(2-methylpyridin-4-yl)pyrazin-2-yl)-N-(4-(hydroxymethyl)cyclohexyl)-4-methylbenzenesulfonamide;
3-(5-amino-6-(2-methylpyridin-4-yl)pyrazin-2-yl)-N-(3,3-difluorocyclobutyl)-4-methylbenzenesulfonamide;
3-(5-amino-6-(2-methylpyridin-4-yl)pyrazin-2-yl)-N-(5-hydroxypentyl)-4-methylbenzenesulfonamide;
3-(5-amino-6-(2-methylpyridin-4-yl)pyrazin-2-yl)-N-((1-hydroxycyclohexyl)methyl)-4-methylbenzenesulfonamide;
3-(5-amino-6-(2-methylpyridin-4-yl)pyrazin-2-yl)-N-((1-hydroxycyclobutyl)methyl)-4-methylbenzenesulfonamide;
(S)-3-(5-amino-6-(2-methylpyridin-4-yl)pyrazin-2-yl)-N-(1-hydroxybutan-2-yl)-4-methylbenzenesulfonamide;
(R)-3-(5-amino-6-(2-methylpyridin-4-yl)pyrazin-2-yl)-N-(1-hydroxybutan-2-yl)-4-methylbenzenesulfonamide;
3-(5-amino-6-(2-methylpyridin-4-yl)pyrazin-2-yl)-N-(1-hydroxy-2-methylpropan-2-yl)-4-methylbenzenesulfonamide;
(S)-3-(5-amino-6-(2-methylpyridin-4-yl)pyrazin-2-yl)-N-(2-hydroxypropyl)-4-methylbenzenesulfonamide;
3-(5-amino-6-(2-methylpyridin-4-yl)pyrazin-2-yl)-4-methyl-N-(tetrahydro-2H-pyran-4-yl)benzenesulfonamide;
3-(5-amino-6-(2-methylpyridin-4-yl)pyrazin-2-yl)-N-(3-methoxypropyl)-4-methylbenzenesulfonamide;
(R)-3-(5-amino-6-(2-methylpyridin-4-yl)pyrazin-2-yl)-4-methyl-N-((tetrahydrofuran-2-yl)methyl)benzenesulfonamide;
3-(5-amino-6-(2-methylpyridin-4-yl)pyrazin-2-yl)-4-methyl-N-(4,4,4-trifluoro-3-hydroxy-3-methylbutyl)benzenesulfonamide;
3-(5-amino-6-(2-methylpyridin-4-yl)pyrazin-2-yl)-4-methyl-N-((tetrahydro-2H-pyran-3-yl)methyl)benzenesulfonamide;
3-(5-amino-6-(2-methylpyridin-4-yl)pyrazin-2-yl)-N-(2-methoxy-2-methylpropyl)-4-methylbenzenesulfonamide;
3-(5-amino-6-(2-methylpyridin-4-yl)pyrazin-2-yl)-4-methyl-N-((tetrahydro-2H-pyran-2-yl)methyl)benzenesulfonamide;
3-(5-amino-6-(2-methylpyridin-4-yl)pyrazin-2-yl)-4-methyl-N-((tetrahydrofuran-2-yl)methyl)benzenesulfonamide;
3-(5-amino-6-(2-methylpyridin-4-yl)pyrazin-2-yl)-4-methyl-N-((tetrahydrofuran-3-yl)methyl)benzenesulfonamide;
3-(5-amino-6-(2-methylpyridin-4-yl)pyrazin-2-yl)-N-(4-hydroxy-4-methylcyclohexyl)-4-methylbenzenesulfonamide;
(R)-3-(5-amino-6-(2-methylpyridin-4-yl)pyrazin-2-yl)-4-methyl-N-(3,3,3-trifluoro-2-hydroxy-2-methylpropyl)benzenesulfonamide;
3-(5-amino-6-(2-methylpyridin-4-yl)pyrazin-2-yl)-N-(1-isopropylpiperidin-4-yl)-4-methylbenzenesulfonamide;
3-(5-amino-6-(2-methylpyridin-4-yl)pyrazin-2-yl)-4-methyl-N-(1-methylpiperidin-4-yl)benzenesulfonamide;
3-(5-amino-6-(2-methylpyridin-4-yl)pyrazin-2-yl)-N-(3-(diethylamino)propyl)-4-methylbenzenesulfonamide;
3-(5-amino-6-(2-methylpyridin-4-yl)pyrazin-2-yl)-N-(3-(dimethylamino)-2,2-dimethylpropyl)-4-methylbenzenesulfonamide;
(R)-3-(5-amino-6-(2-methylpyridin-4-yl)pyrazin-2-yl)-N-((1-ethylpyrrolidin-2-yl)methyl)-4-methylbenzenesulfonamide;
3-(5-amino-6-(2-methylpyridin-4-yl)pyrazin-2-yl)-N-(2-(dimethylamino)ethyl)-4-methylbenzenesulfonamide;
3-(5-amino-6-(2-methylpyridin-4-yl)pyrazin-2-yl)-4-methyl-N-(2-(pyrrolidin-1-yl)ethyl)benzenesulfonamide;
3-(5-amino-6-(2-methylpyridin-4-yl)pyrazin-2-yl)-4-methyl-N-(2-morpholinoethyl)benzenesulfonamide;
3-(5-amino-6-(2-methylpyridin-4-yl)pyrazin-2-yl)-4-methyl-N-(2-methyl-2-morpholinopropyl)benzenesulfonamide;
3-(5-amino-6-(2-methylpyridin-4-yl)pyrazin-2-yl)-4-methyl-N-((1-methylpyrrolidin-3-yl)methyl)benzenesulfonamide;
4-((3-(5-amino-6-(2-methylpyridin-4-yl)pyrazin-2-yl)-4-methylphenylsulfonamido)methyl)tetrahydro-2H-pyran-4-carboxamide;
3-(5-amino-6-(2-methylpyridin-4-yl)pyrazin-2-yl)-N-((3-hydroxyoxetan-3-yl)methyl)-4-methylbenzenesulfonamide;
3-(5-amino-6-(2-methylpyridin-4-yl)pyrazin-2-yl)-4-methyl-N-(2-(methylamino)ethyl)benzenesulfonamide;
3-(5-amino-6-(2-methylpyridin-4-yl)pyrazin-2-yl)-N-(2-aminoethyl)-4-methylbenzenesulfonamide;
(R)-3-(5-amino-6-(2-methylpyridin-4-yl)pyrazin-2-yl)-4-methyl-N-(pyrrolidin-3-ylmethyl)benzenesulfonamide;

(S)-3-(5-amino-6-(2-methylpyridin-4-yl)pyrazin-2-yl)-4-methyl-N-(pyrrolidin-3-ylmethyl)benzenesulfonamide;

5-(5-(2,6-diazaspiro[3.3]heptan-2-ylsulfonyl)-2-methylphenyl)-3-(2-methylpyridin-4-yl)pyrazin-2-amine;

3-(5-amino-6-(2-methylpyridin-4-yl)pyrazin-2-yl)-N-((1S,2S)-2-aminocyclopentyl)-4-methylbenzenesulfonamide;

3-(5-amino-6-(2-methylpyridin-4-ylpyrazin-2-yl)-N-((1R,2R)-2-aminocyclopentyl)-4-methylbenzenesulfonamide;

(R)-5-(5-(3-aminopyrrolidin-1-ylsulfonyl)-2-methylphenyl)-3-(2-methylpyridin-4-yl)pyrazin-2-amine;

5-(5-(4-aminopiperidin-1-ylsulfonyl)-2-methylphenyl)-3-(2-methylpyridin-4-yl)pyrazin-2-amine;

3-(5-amino-6-(2-methylpyridin-4-yl)pyrazin-2-yl)-N-(((1S,3R)-3-(aminomethyl)cyclohexyl)methyl)-4-methylbenzenesulfonamide;

3-(5-amino-6-(2-methylpyridin-4-yl)pyrazin-2-yl)-N-((1r,4r)-4-aminocyclohexyl)-4-methylbenzenesulfonamide;

3-(5-amino-6-(1-(2,22-trifluoroethyl)-1H-pyrazol-4-yl)pyrazin-2-yl)-N-(3-hydroxy-methylbutyl)-4-methylbenzenesulfonamide;

3-(5-amino-6-(1H-1,2,4-triazol-1-yl)pyrazin-2-yl)-4-methyl-N-(oxetan-3-ylmethyl)benzenesulfonamide;

3-(5-amino-6-(1-benzyl-1H-pyrazol-4-yl)pyrazin-2-yl)-N-(3-hydroxy-3-methylbutyl)-4-methylbenzenesulfonamide;

2-(3-(5-amino-6-(1H-1,2,4-triazol-1-yl)pyrazin-2-yl)-4-methylphenylsulfonamido)acetamide;

3-(5-amino-6-(2-methylpyridin-4-yl)pyrazin-2-yl)-4-methyl-N-(2-oxopiperidin-4-yl)benzenesulfonamide;

3-(5-amino-6-(2-methylpyridin-4-yl)pyrazin-2-yl)-N-((1r,4r)-4-hydroxycyclohexyl)-4-methylbenzenesulfonamide;

3-(5-amino-6-(3-ethyl-1,2,4-oxadiazol-5-yl)pyrazin-2-yl)-N-(3-hydroxy-3-methylbutyl)-4-methylbenzenesulfonamide;

3-(5-amino-6-(3-ethyl-1,2,4-oxadiazol-5-yl)pyrazin-2-yl)-N-(azetidin-3-yl)-4-methylbenzenesulfonamide;

3-(5-amino-6-(5-ethyl-1,3,4-oxadiazol-2-yl)pyrazin-2-yl)-N-((1r,4r)-4-hydroxycyclohexyl-4-methylbenzenesulfonamide;

3-(5-amino-6-(3-ethyl-1,2,4-oxadiazol-5-yl)pyrazin-2-yl)-N-((1r,4r)-4-hydroxycyclohexyl)-4-methylbenzenesulfonamide;

3-(5-amino-6-(3-propyl-1,2,4-oxadiazol-5-yl)pyrazin-2-yl)-N-((1r,4r)-4-hydroxycyclohexyl)-4-methylbenzenesulfonamide;

(1-(3-(5-amino-6-(3-ethyl-1,2,4-oxadiazol-5-yl)pyrazin-2-yl)-4-methylphenylsulfonyl)piperidin-4-yl)methanol;

cis-3-(5-Amino-6-(2-methylthiazol-5-yl)pyrazin-2-yl)-N-(3-hydroxycyclobutyl)-4-methylbenzenesulfonamide;

trans-3-(5-Amino-6-(2-methylthiazol-5-yl)pyrazin-2-yl)-N-(3-hydroxycyclobutyl)-4-methylbenzenesulfonamide;

(R)-3-(5-Amino-6-(2-methylthiazol-5-yl)pyrazin-2-yl)-4-methyl-N-((tetrahydrofuran-2-yl)methyl)benzenesulfonamide;

(S)-3-(5-Amino-6-(2-methylthiazol-5-yl)pyrazin-2-yl)-4-methyl-N-((tetrahydrofuran-2-yl)methyl)benzenesulfonamide;

(R)-3-(5-Amino-6-(2-methylthiazol-5-yl)pyrazin-2-yl)-4-methyl-N-(tetrahydrofuran-3-yl)benzenesulfonamide;

(S)-3-(5-Amino-6-(2-methylthiazol-5-yl)pyrazin-2-yl)-4-methyl-N-(tetrahydrofuran-3-yl)benzenesulfonamide;

3-(5-Amino-6-(1-(2-(dimethylamino)ethyl)-1H-pyrazol-4-yl)pyrazin-2-yl)-N-(2-hydroxy-2-methylpropyl)-4-methylbenzenesulfonamide; and 3-(5-Amino-6-(3-cyclopropyl-1,2,4-oxadiazol-5-yl)pyrazin-2-yl)-N-(3-hydroxy-3-methylbutyl)-4-methylbenzenesulfonamide;

or a pharmaceutically acceptable salt thereof.

5. A pharmaceutical composition, comprising:
a therapeutically effective amount of the compound or salt according claim 1 and one or more pharmaceutically acceptable carriers.

6. A pharmaceutical combination, comprising:
a therapeutically effective amount of the compound or salt according to claim 1 and a second active agent.

7. A method of treating a disorder or disease mediated by the activation of PI 3-kinase gamma isoform, comprising administering to a subject having said disorder or disease a therapeutically effective amount of a compound or salt according to claim 1.

8. The method of claim 7, wherein the disorder or disease is selected from the group consisting of respiratory diseases, allergies, rheumatoid arthritis, osteoarthritis, rheumatic disorders, psoriasis, ulcerative colitis, Crohn's disease, septic shock, cancer, atherosclerosis, allograft rejection following transplantation, diabetes, stroke, obesity and restenosis.

9. A pharmaceutical composition, comprising a compound or salt according to claim 1 and one or more pharmaceutically acceptable carriers.

10. A pharmaceutical combination, comprising a compound or salt according to claim 1 and a second active agent.

11. A pharmaceutical composition, comprising a compound or salt according to claim 3 and one or more pharmaceutically acceptable carriers.

12. A pharmaceutical combination, comprising a compound or salt according to claim 3 and a second active agent.

13. A pharmaceutical composition, comprising a compound or salt according to claim 4 and one or more pharmaceutically acceptable carriers.

14. A pharmaceutical combination, comprising a compound or salt according to claim 4 and a second active agent.

* * * * *